US011718628B2

(12) United States Patent
Green et al.

(10) Patent No.: US 11,718,628 B2
(45) Date of Patent: Aug. 8, 2023

(54) SREBP INHIBITORS COMPRISING A 6-MEMBERED CENTRAL RING

(71) Applicant: Capulus Therapeutics, LLC, San Francisco, CA (US)

(72) Inventors: Michael John Green, Half Moon Bay, CA (US); Barry Patrick Hart, Palo Alto, CA (US)

(73) Assignee: CAPULUS THERAPEUTICS, LLC, San Francisco, CA (US)

( * ) Notice: Subject to any disclaimer, the term of this patent is extended or adjusted under 35 U.S.C. 154(b) by 0 days.

(21) Appl. No.: 16/940,212

(22) Filed: Jul. 27, 2020

(65) Prior Publication Data
US 2021/0047340 A1 Feb. 18, 2021

Related U.S. Application Data

(63) Continuation of application No. PCT/US2019/015458, filed on Jan. 28, 2019.

(60) Provisional application No. 62/744,397, filed on Oct. 11, 2018, provisional application No. 62/623,405, filed on Jan. 29, 2018.

(51) Int. Cl.
| C07D 491/056 | (2006.01) |
| C07D 401/04 | (2006.01) |
| C07D 401/10 | (2006.01) |
| C07D 401/14 | (2006.01) |
| C07D 405/14 | (2006.01) |
| C07D 471/08 | (2006.01) |
| C07D 491/048 | (2006.01) |
| C07D 491/052 | (2006.01) |

(52) U.S. Cl.
CPC ....... *C07D 491/056* (2013.01); *C07D 401/04* (2013.01); *C07D 401/10* (2013.01); *C07D 401/14* (2013.01); *C07D 405/14* (2013.01); *C07D 471/08* (2013.01); *C07D 491/048* (2013.01); *C07D 491/052* (2013.01)

(58) Field of Classification Search
CPC .............. C07D 491/056; C07D 401/04; C07D 401/10; C07D 401/14; C07D 405/14; C07D 471/08; C07D 491/048; C07D 491/052
See application file for complete search history.

(56) References Cited

U.S. PATENT DOCUMENTS

| 8,207,196 B2 | 6/2012 | Uesugi et al. |
| 8,343,966 B2 | 1/2013 | Adcock et al. |
| 8,563,583 B2 | 10/2013 | Ahmad et al. |
| 8,703,805 B2 | 4/2014 | Busch et al. |
| 8,778,976 B2 | 7/2014 | Uesugi et al. |
| 9,212,179 B2 | 12/2015 | Uesugi et al. |
| 9,233,941 B2 | 1/2016 | Uesugi et al. |
| 9,242,996 B2 | 1/2016 | Bagdanoff et al. |
| 2001/0031781 A1 | 10/2001 | Illig et al. |
| 2009/0042908 A1 | 2/2009 | Zhou et al. |
| 2011/0098325 A1 | 4/2011 | Raynham et al. |
| 2013/0281428 A1 | 10/2013 | Ohki et al. |
| 2015/0249215 A1 | 9/2015 | Ono et al. |
| 2016/0257675 A1 | 9/2016 | Uesugi et al. |
| 2018/0028518 A1 | 2/2018 | Bernales et al. |
| 2018/0051013 A1 | 2/2018 | Pujala et al. |
| 2022/0056018 A1 | 2/2022 | Green et al. |
| 2022/0356170 A1 | 11/2022 | Green et al. |

FOREIGN PATENT DOCUMENTS

| CN | 1791580 A | 6/2006 |
| CN | 101541751 A | 9/2009 |
| CN | 102015660 A | 4/2011 |
| CN | 103405429 A | 11/2013 |
| CN | 104185627 A | 12/2014 |
| CN | 106458980 A | 2/2017 |
| CN | 106604920 A | 4/2017 |
| EP | 2 269 993 A1 | 1/2011 |
| EP | 3 168 219 A1 | 5/2017 |
| JP | 2010-506954 A | 3/2010 |
| WO | WO-2004/084824 A2 | 10/2004 |
| WO | WO-2004/084824 A3 | 10/2004 |
| WO | WO 2008/049047 * | 4/2008 |
| WO | WO-2008/049047 A2 | 4/2008 |
| WO | WO-2008/049047 A3 | 4/2008 |

(Continued)

OTHER PUBLICATIONS

PubChem SID 226703021 (Year: 2015).*
Ullrich et al. in Bioorganic & Medicinal Chemistry Letters 20 (2010) 2903-2907 (Year: 2010).*
Extended European Search Report dated Aug. 2, 2021, for EP Application No. 19 743 447.5, filed on Jan. 28, 2019, 17 pages.
Ullrich, J.W. et al. (2010). "Synthesis of 4-(3-biaryl)quinoline sulfones as potent liver X receptor agonists," Bioorg. Med. Chem. Lett. 20:2903-2907.
Younis, Y. et al. (2012). "3,5-Diaryl-2-aminopyridines as a Novel Class of Orally Active Antimalarials Demonstrating Single Dose Cure in Mice and Clinical Candidate Potential," J. Med. Chem. 55:3479-3487.

(Continued)

*Primary Examiner* — Theodore R. Howell
(74) *Attorney, Agent, or Firm* — Cooley LLP

(57) ABSTRACT

Provided herein are compounds comprising a three-ring core, such as compounds of Formula (X), Formula (X-A), Formula (X-Ai), Formula (X-B), Formula (X-Bi), Formula (Z), Formula (Z-A), Formula (Z-Ai), Formula (Z-B), Formula (Z-Bi), Formula (I), Formula (I-A), Formula (I-Ai), Formula (I-B), and Formula (I-Bi), and pharmaceutically acceptable salts, solvates, tautomers, isotopes, or isomers thereof. Also provided herein are methods of inhibiting a component of the sterol regulatory element binding protein (SREBP) pathway, such as an SREBP or SREBP cleavage activating protein (SCAP), using these compounds, or pharmaceutically acceptable salts, solvates, tautomers, isotopes, or isomers thereof. Further provided are methods of treating a disorder in a subject in need thereof, such as liver disease, non-alcoholic steatohepatitis, insulin resistance, or cancer.

20 Claims, 2 Drawing Sheets

(56) References Cited

FOREIGN PATENT DOCUMENTS

| WO | WO-2008097835 A2 | 8/2008 |
| WO | WO-2012/121939 A2 | 9/2012 |
| WO | WO-2013/162061 A1 | 10/2013 |
| WO | WO-2015/031650 A1 | 3/2015 |
| WO | WO-2015/162456 A1 | 10/2015 |
| WO | WO-2016073826 A1 | 5/2016 |
| WO | WO-2016/105491 A1 | 6/2016 |
| WO | WO-2016/141159 A1 | 9/2016 |
| WO | WO-2016/141258 A1 | 9/2016 |
| WO | WO-2017/190086 A1 | 11/2017 |
| WO | WO-2018/111315 A1 | 6/2018 |
| WO | WO-2019084681 A1 | 5/2019 |
| WO | WO-2019/126733 A1 | 6/2019 |
| WO | WO-2019148125 A1 | 8/2019 |
| WO | WO-2020132700 A1 | 6/2020 |
| WO | WO-2020159889 A1 | 8/2020 |
| WO | WO-2020165062 A1 | 8/2020 |

OTHER PUBLICATIONS

PubChem SID 226703021 (2015). Located at https://pubchem.ncbi.nlm.nih.gov/substance/226703021, 7 total pages.

International Search Report dated May 3, 2019, for PCT Application No. PCT/US2019/015458, filed on Jan. 28, 2019, 4 pages.

Written Opinion of the International Searching Authority dated May 3, 2019, for PCT Application No. PCT/US2019/015458, filed on Jan. 28, 2019, 5 pages.

Extended European Search Report dated Oct. 11, 2022, for EP Application No. 20 747 729.0, filed on Jan. 27, 2020, 9 pages.

International Search Report dated Feb. 17, 2021, for PCT Application No. PCT/US2020/060276, filed on Nov. 12, 2020, 3 pages.

International Search Report dated Jun. 4, 2021, for PCT Application No. PCT/US2021/015101, filed on Jan. 26, 2021, 4 pages.

International Search Report dated Mar. 18, 2021, for PCT Application No. PCT/US2020/060277, filed on Nov. 12, 2020, 5 pages.

International Search Report dated May 15, 2020, for PCT Application No. PCT/US2020/015260, filed on Jan. 27, 2020, 4 pages.

International Search Report dated Sep. 17, 2021, for PCT Application No. PCT/US2021/043007, filed on Jul. 23, 2021, 4 pages.

Pubmed Compound Record for CID 134263555, 'C(C)(C)(C)C1=NC=CC(=C1)C=1C=C(SC=1)C1=C(C=C(C(=O)N2CC(CCC2)0)C=C1)CJ', U.S.National Library of Medicine, Jun. 23, 2018 (Jun. 23, 2018), pp. 1-8, URL: https://pubchem.ncbi.nlm.nih.gov/compound/134263555.

Pubmed Compound Record for CID 134273211,'C(C)(C)(C)C 1=NC=CC(=C 1 )C=1C=C(SC=1 )C1=C(C=C(C(=O)N2CCC(CC2)0)C=C1 )CI', U.S.National Library of Medicine, Jun. 23, 2018 (Jun. 23, 2018), pp. 1-8. URL: https://pubchem.ncbi.nlm.nih.gov/compound/134273211.

Written Opinion of the International Searching Authority dated Feb. 17, 2021, for PCT Application No. PCT/US2020/060276, filed on Nov. 12, 2020, 4 pages.

Written Opinion of the International Searching Authority dated Jul. 24, 2020, for PCT Application No. PCT/US2020/015260, filed on Jan. 27, 2020, 7 pages.

Written Opinion of the International Searching Authority dated Jun. 4, 2021, for PCT Application No. PCT/US2021/015101, filed on Jan. 26, 2021, 5 pages.

Written Opinion of the International Searching Authority dated Mar. 18, 2021, for PCT Application No. PCT/US2020/060277, filed on Nov. 12, 2020, 6 pages.

Written Opinion of the International Searching Authority dated Sep. 17, 2021, for PCT Application No. PCT/US2021/043007, filed on Jul. 23, 2021, 5 pages.

* cited by examiner

HepG2 nuclear extracts after
48 hours treatment at 500nM

SREBP INHIBITORS COMPRISING A 6-MEMBERED CENTRAL RING

CROSS-REFERENCE TO RELATED APPLICATIONS

This application is a continuation of International Patent Application No. PCT/US2019/015458, filed Jan. 28, 2019, which claims the benefit of U.S. Provisional Application No. 62/623,405, filed Jan. 29, 2018; and U.S. Provisional Application No. 62/744,397, filed Oct. 11, 2018, the disclosures of which are hereby incorporated by reference in their entireties.

FIELD OF THE INVENTION

The present disclosure relates to compounds comprising a three-ring core, their use for inhibiting components of the sterol regulatory element binding protein (SREBP) pathway, such as SREBP or SREBP cleavage activating protein (SCAP), and their use in therapeutic methods of treating conditions and disorders.

BACKGROUND

SREBPs are membrane-bound transcription factors that regulate cholesterol, fatty acid, and triglyceride biosynthesis, and lipid uptake. Fatty acids and lipids are a source of energy and important components of many biological structures, such as lipid membranes of cells. Cholesterol is an important component of biological processes and structures. In mammals, there are three known SREBP isoforms: SREBP-1a, SREBP-1c, and SREBP-2. SREBP-1a controls a broad range of target genes that are involved in the production of fatty acids, triglycerides, phospholipids, and cholesterol. SREBP-1c primarily activates genes which control fatty acid and triglyceride synthesis. SREBP-2 activates genes involved in the synthesis of regulators of cholesterol metabolism, which has been demonstrated in mouse, human, and *Drosophila* studies. The activity of SREBPs is regulated by SREBP cleavage activating protein (SCAP), which transports SREBP(s) from the endoplasmic reticulum to the Golgi apparatus where the SREBP(s) are proteolytically cleaved, releasing the transcription factor domain.

The pathways regulated by SREBPs and SCAP have been implicated in disorders of metabolism, such as hypertension, dyslipidemia, obesity, type 2 diabetes, insulin resistance, fatty liver, and nonalcoholic steatohepatitis (NASH). NASH, for example, is liver inflammation and hepatocyte ballooning as a result of fat building up in the liver, which can lead to liver damage, such as cirrhosis. NASH can also be associated with other metabolism disorders, such as insulin resistance and metabolic syndrome.

The metabolism of fatty acids, cholesterol, and triglycerides may also be linked to hyperproliferative disorders, such as cancer. One characteristic of the oncogenic transformation of cancer cells is the shift of metabolism from catabolic to anabolic processes. Many cancers require synthesis of fatty acids and other lipids (such as cholesterol), and steroids (such as androgens). Thus, components of the SREBP pathway may play a role in hyperproliferative disorders, such as prostate cancer. SREBP-1c is the major transcriptional regulator of the biosynthesis of fatty acids, and expression of this transcription factor can be stimulated by androgens and epidermal growth factor in prostate cancer cells. Overexpression of SREBP-1c may drive tumorigenicity and invasion of prostate cancer cells. In addition to regulating androgen synthesis, SREBP-2 itself is also regulated by androgens in a direct feedback circuit of androgen production. However, prostate cancer cells have dysfunctional cholesterol homeostasis, resulting in accumulation of cholesterol and increased proliferation. This increase in cholesterol levels has been shown to be driven by regulated by increased SREBP-2 activity. SREBP-2 expression increases during disease progression, and is significantly higher after castration compared to prior.

Regulating components of the SREBP pathway, such as SCAP or SREBPs, is an important therapeutic approach for treating disorders, such as metabolic diseases and cancer. Thus, there is a need for compounds that can inhibit components of the SREBP pathway, such as SREBPs and SCAP.

BRIEF SUMMARY

In some aspects, provided herein is a compound of Formula (X):

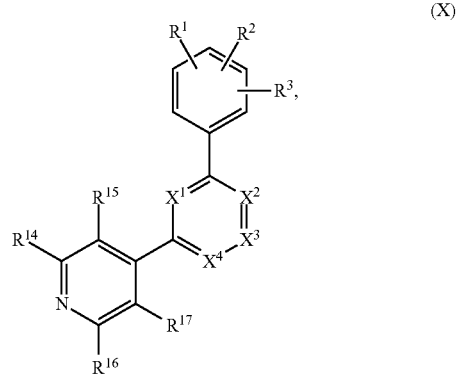

or a pharmaceutically acceptable salt, solvate, tautomer, isotope, or isomer thereof, wherein:

$R^1$ is —C(O)$R^9$, —C(O)NR$^8$R$^9$, —S(O)$_2$NR$^8$R$^9$, —NR$^{10}$C(O)NR$^8$R$^9$, —NR$^{10}$C(O)R$^9$, —NR$^{10}$S(O)$_2$R$^9$, —OR$^{26}$, —SR$^9$, —S(O)R$^9$, —S(O)$_2$R$^9$, —NR$^8$R$^9$, —NR$^{10}$C(O)OR$^9$, —C(O)R$^{26}$, —NR$^{10}$S(O)$_2$NR$^8$R$^9$, —C(O)NR$^{10}$S(O)$_2$R$^9$, or —C(O)NR$^{10}$NR$^8$R$^9$;

wherein each of $R^8$, $R^9$, and $R^{10}$ is independently selected from the group consisting of hydrogen, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl, $R^{26}$ is (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, or heteroaryl-alkyl, each (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl of $R^8$, $R^9$, $R^{10}$, and $R^{26}$ is independently unsubstituted or substituted with one or more substituents independently selected from the group consisting of halo, (C$_{1-10}$)alkyl, (C$_{1-10}$)haloalkyl, cyano, oxo, —OR$^{19}$, —C(O)NR$^{19}$R$^{19}$, —NR$^{19}$C(O)R$^{19}$, —NR$^{19}$C(O)NR$^{19}$R$^{19}$, —NR$^{19}$R$^{19}$, —S(O)$_2$NR$^{19}$R$^{19}$, —NR$^{19}$S(O)$_2$R$^{19}$, —S(O)$_{n4}$R$^{20}$, —C(O)OR$^{19}$, —C(O)R$^{20}$, and —(OR$^{38}$)$_{n15}$OR$^{19}$, each $R^{19}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{20}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, each $R^{38}$ is independently $(C_{1-10})$alkylene or $(C_{1-10})$haloalkylene, each n15 is independently an integer from 1 to 5; and n4 is 0, 1, or 2;

or $R^8$ and $R^9$, together with the nitrogen atom to which they are attached, form a heterocycloalkyl, wherein the heterocycloalkyl is unsubstituted or substituted with one or more substituents independently selected from the group consisting of halo, cyano, oxo, $(C_{1-10})$alkyl, $(C_{2-10})$alkenyl, $(C_{2-10})$alkynyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, heteroaryl-alkyl, —$OR^{23}$, —$C(O)NR^{23}R^{23}$, —$NR^{23}C(O)R^{23}$, —$NR^{23}C(O)OR^{23}$, —$NR^{23}C(O)NR^{23}R^{23}$, —$NR^{23}R^{23}$, —$S(O)_2NR^{23}R^{23}$, —$NR^{23}S(O)_2R^{24}$, —$S(O)_{n6}R^{24}$, —$C(O)OR^{23}$, —$C(O)R^{24}$, and —$(OR^{39})_{n16}OR^{23}$, wherein each alkyl, alkenyl, alkynyl, cycloalkyl, cycloalkyl-alkyl, heterocycloalkyl, heterocycloalkyl-alkyl, aryl, aryl-alkyl, heteroaryl, and heteroaryl-alkyl is independently unsubstituted or substituted with one or more substituents independently selected from the group consisting of halo, oxo, alkyl, haloalkyl, —$OR^{31}$, —$C(O)NR^{31}R^{31}$, —$NR^{31}C(O)R^{31}$, —$NR^{31}C(O)OR^{31}$, —$NR^{31}C(O)NR^{31}R^{31}$, —$NR^{31}S(O)_2R^{31}$, and —$S(O)_{n9}R^{31}$, wherein each $R^{31}$ is independently hydrogen, alkyl, or haloalkyl, and each n9 is independently 0, 1, or 2, each $R^{23}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{24}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, each $R^{39}$ is independently $(C_{1-10})$alkylene or $(C_{1-10})$haloalkylene, each n16 is independently an integer from 1 to 5; and n6 is 0, 1, or 2;

$R^2$ and $R^3$ are independently selected from the group consisting of hydrogen, halo, cyano, $(C_{1-10})$alkyl, $(C_{3-10})$cycloalkyl, $(C_{3-10})$cycloalkyl$(C_{1-10})$alkyl, —$OR^{25}$, —$C(O)NR^{25}R^{25}$, —$NR^{25}C(O)R^{25}$, —$NR^{25}C(O)NR^{25}R^{25}$, —$NR^{25}R^{25}$, —$S(O)_2NR^{25}R^{25}$, —$NR^{25}S(O)_2R^{25}$, —$S(O)_{n7}R^{30}$, —$NR^{25}C(O)OR^{25}R^{25}$, —$C(O)OR^{25}$, and —$C(O)R^{30}$, wherein each $(C_{1-10})$alkyl, $(C_{3-10})$cycloalkyl, and $(C_{3-10})$cycloalkyl$(C_{1-10})$alkyl is independently unsubstituted or substituted with one or more halo, each $R^{25}$ is independently hydrogen $(C_{1-10})$alkyl, $(C_{3-10})$cycloalkyl, $(C_{3-10})$cycloalkyl$(C_{1-10})$alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{30}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n7 is 0, 1, or 2;

$X^1$, $X^2$, $X^3$ and $X^4$ are independently $CR^4$ or N, wherein $X^2$, $X^3$ and $X^4$ may not all be N;

when at least one of $X^1$, $X^2$, $X^3$ and $X^4$ is N, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, n8 is 0, 1 or 2; or when each of $X^1$, $X^2$, $X^3$ and $X^4$ is $CR^4$, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$NR^{27}S(O)_2R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^1$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n8 is 0, 1, or 2; or two $R^4$ on adjacent annular carbon atoms together with the carbon atoms to which they are attached may form a carbocyclyl or heterocyclyl, wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —C(O)NR$^{27}$R$^{27}$, —NR$^{27}$C(O)R$^{27}$, —NR$^{27}$R$^{27}$, —S(O)$_2$NR$^{27}$R$^{27}$, —NR$^{27}$S(O)$_2$R$^{27}$, —S(O)$_{n8}$R$^{28}$, and —C(O)R$^{28}$, or the heterocyclyl is unsubstituted or substituted with one or more substituents independently selected from the group consisting of halo, cyano, (C$_{1-10}$)alkyl, (C$_{3-10}$)cycloalkyl, (C$_{3-10}$)cycloalkyl(C$_{1-10}$)alkyl, heterocycloalkyl connected by an annular carbon atom, heterocycloalkyl-alkyl, —OR$^{27}$, —C(O)NR$^{27}$R$^{27}$, —S(O)$_2$NR$^{27}$R$^{27}$, —S(O)$_{n8}$R$^{28}$, and —C(O)R$^{28}$, each R$^{27}$ is independently hydrogen, (C$_{1-10}$)alkyl, (C$_{3-10}$)cycloalkyl, (C$_{3-10}$)cycloalkyl(C$_{1-10}$)alkyl; or two R$^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each R$^{28}$ is independently (C$_{1-10}$)alkyl, (C$_{3-10}$)cycloalkyl, (C$_{3-10}$)cycloalkyl(C$_{1-10}$)alkyl, wherein each of the foregoing is independently unsubstituted or substituted with one or more halo, and n8 is 0, 1, or 2;

R$^{15}$ and R$^{17}$ are independently hydrogen, halo, alkyl, or —OR$^{29}$, wherein each R$^{29}$ is independently hydrogen, (C$_{1-10}$)alkyl, (C$_{3-10}$)cycloalkyl, or (C$_{3-10}$)cycloalkyl(C$_{1-10}$)alkyl, and each alkyl or cycloalkyl in R$^{15}$ or R$^{17}$, if present, is independently unsubstituted or substituted with one or more halo;

R$^{14}$ is (C$_{1-10}$)alkyl, (C$_{3-10}$)alkenyl, (C$_{3-10}$)cycloalkyl, (C$_{3-10}$)cycloalkenyl, (C$_{3-10}$)cycloalkyl(C$_{1-10}$)alkyl, heterocycloalkyl connected through an annular carbon atom, heterocycloalkenyl connected through an annular carbon atom, heterocycloalkyl-alkyl, —OR$^5$, —C(O)NR$^5$R$^5$, —R$^5$C(O)NR$^5$R$^5$, —S(O)$_2$NR$^5$R$^5$, —S(O)$_{n1}$R$^6$, or —C(O)R$^6$;

R$^{16}$ is hydrogen, fluoro, (C$_{1-10}$)alkyl, (C$_{3-10}$)cycloalkyl, (C$_{3-10}$)cycloalkyl(C$_{1-10}$)alkyl, heterocycloalkyl connected through an annular carbon atom, heterocycloalkyl-alkyl, —OR$^5$, —C(O)NR$^5$R$^5$, —R$^5$C(O)NR$^5$R$^5$, —S(O)$_2$NR$^5$R$^5$, —S(O)$_{n1}$R$^6$, or —C(O)R$^6$;

wherein the (C$_{1-10}$)alkyl, (C$_{1-10}$)alkenyl, (C$_{3-10}$)cycloalkyl, (C$_{3-10}$)cycloalkenyl, (C$_{3-10}$)cycloalkyl(C$_{1-10}$)alkyl, heterocycloalkyl, heterocycloalkenyl, or heterocycloalkyl-alkyl of R$^{14}$ or R$^{16}$ is independently unsubstituted or substituted with one or more substituents independently selected from the group consisting of (C$_{1-10}$)alkyl, cycloalkyl, heterocycloalkyl, halo, cyano, oxo, —OR$^7$, —C(O)OR$^7$, —C(O)NR$^7$R$^7$, —NR$^7$C(O)R$^7$, —NR$^7$C(O)NR$^7$R$^7$, —NR$^7$R$^7$, —S(O)$_2$NR$^7$R$^7$, —NR$^7$S(O)$_2$R$^7$, —S(O)$_{n2}$R$^{13}$, and —C(O)R$^{13}$;

wherein each alkyl, cycloalkyl, and heterocycloalkyl is independently unsubstituted or substituted with one or more substituents selected from the group consisting of halo, cycloalkyl, halocycloalkyl, heterocycloalkyl, haloheterocycloalkyl, and —(OR$^{33}$)$_{n10}$OR$^{32}$, wherein each n10 is independently an integer from 0 to 5, each R$^{32}$ is independently hydrogen, (C$_{1-10}$)alkyl or (C$_{1-10}$)haloalkyl, and each R$^{33}$ is independently (C$_{1-10}$)alkylene or (C$_{1-10}$)haloalkylene;

each R$^5$ is independently hydrogen, (C$_{1-10}$)alkyl, or (C$_{3-10}$)cycloalkyl; or two R$^5$, together with the nitrogen atom to which they are attached, form a heterocycloalkyl; wherein each alkyl, cycloalkyl, or heterocycloalkyl is independently unsubstituted or substituted with one or more substituents selected from the group consisting of halo, cyano, oxo, alkyl, haloalkyl, —C(O)OR$^{34}$, —C(O)NR$^{34}$R$^{34}$, —NR$^{34}$C(O)R$^{34}$, —NR$^{34}$C(O)NR$^{34}$R$^{34}$, —NR$^{34}$R$^{34}$, —S(O)$_2$NR$^{34}$R$^{34}$, —NR$^{34}$S(O)$_2$R$^{34}$, —S(O)$_{n11}$R$^{34}$, —C(O)R$^{34}$, and —(OR$^{35}$)$_{n12}$OR$^{34}$, wherein each R$^{34}$ is independently hydrogen, (C$_{1-10}$)alkyl, or (C$_{1-10}$)haloalkyl; each n11 is independently 0, 1, or 2; each n12 is independently an integer from 0 to 5; and each R$^{35}$ is independently (C$_{1-10}$)alkylene or (C$_{1-10}$)haloalkylene;

each R$^6$ is independently (C$_{1-10}$)alkyl or (C$_{3-10}$)cycloalkyl, wherein each alkyl or cycloalkyl is independently unsubstituted or substituted with one or more halo;

each n1 is independently 0, 1, or 2;

each R$^7$ is independently hydrogen, unsubstituted (C$_{1-10}$)alkyl, or (C$_{1-10}$)alkyl substituted with one or more halo;

each n2 is independently 0, 1, or 2, and each R$^{13}$ is independently unsubstituted (C$_{1-10}$)alkyl or (C$_{1-10}$)alkyl substituted with one or more halo;

or R$^{14}$ and R$^{15}$, together with the atoms to which they are attached, form a carbocyclyl or heterocyclyl, wherein the carbocyclyl or heterocyclyl is unsubstituted or substituted with one or more substituents independently selected from the group consisting of halo, cyano, oxo, (C$_{1-10}$)alkyl, (C$_{3-10}$)cycloalkyl, (C$_{3-10}$)cycloalkyl(C$_{1-10}$)alkyl, —OR$^{18}$, —C(O)NR$^{18}$R$^{18}$, —NR$^{18}$C(O)R$^{18}$, —NR$^{18}$C(O)NR$^{18}$R$^{18}$, —NR$^{18}$R$^{18}$, —S(O)$_2$NR$^{18}$R$^{18}$, —NR$^{18}$S(O)$_2$R$^{18}$, —S(O)$_{n3}$R$^{21}$, —C(O)OR$^{18}$, and —C(O)R$^{21}$, wherein each (C$_{1-10}$)alkyl, (C$_{3-10}$)cycloalkyl, and (C$_{3-10}$)cycloalkyl(C$_{1-10}$)alkyl is independently unsubstituted or substituted with one or more substituents independently selected from the group consisting of halo, alkyl, haloalkyl, cyano, oxo, —C(O)OR$^{36}$, —C(O)NR$^{36}$R$^{36}$, —NR$^{36}$C(O)R$^{36}$, —NR$^{36}$C(O)NR$^{36}$R$^{36}$, —NR$^{36}$R$^{36}$, —S(O)$_2$NR$^{36}$R$^{36}$, —NR$^{36}$S(O)$_2$R$^{36}$, —S(O)$_{n13}$R$^{36}$, —C(O)R$^{36}$, and —(OR$^{37}$)$_{n14}$OR$^{36}$, wherein each R$^{36}$ is independently hydrogen, (C$_{1-10}$)alkyl, or (C$_{1-10}$)haloalkyl; each n13 is independently 0, 1, or 2; each n14 is independently an integer from 0 to 5; and each R$^{37}$ is independently (C$_{1-10}$)alkylene or (C$_{1-10}$)haloalkylene;

wherein each R$^{18}$ is independently hydrogen, (C$_{1-10}$)alkyl, or (C$_{3-10}$)cycloalkyl; or two R$^{18}$, together with the nitrogen atom to which they are attached, form a heterocycloalkyl; wherein each alkyl, cycloalkyl, or heterocycloalkyl is independently unsubstituted or substituted with one or more halo;

each R$^{21}$ is independently (C$_{1-10}$)alkyl or (C$_{3-10}$)cycloalkyl, wherein each alkyl or cycloalkyl is independently unsubstituted or substituted with one or more halo; and each n3 is independently 0, 1, or 2.

In some variations, the compound of Formula (X) is a compound of Formula (X-A):

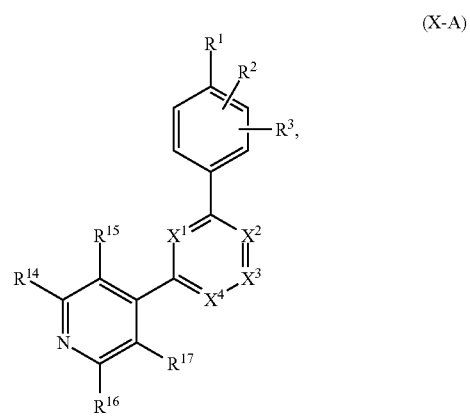

(X-A)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In other variations, the compound of Formula (X) or Formula (X-A) is a compound of Formula (X-Ai):

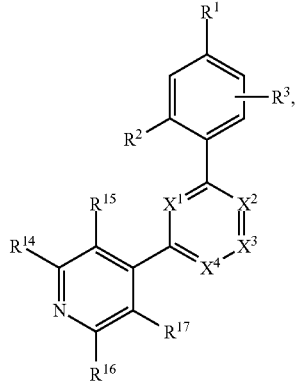

(X-Ai)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In other variations, the compound of Formula (X) is a compound of Formula (X-B):

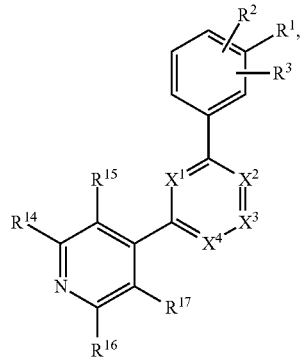

(X-B)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In certain variations, the compound of Formula (X) or Formula (X-B) is a compound of Formula (X-Bi):

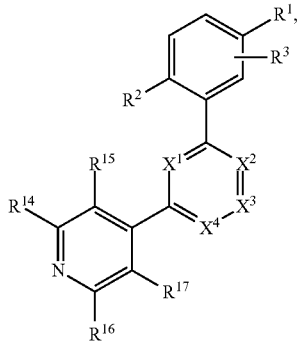

(X-Bi)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In some variations of any of the compounds disclosed herein, or a pharmaceutically acceptable salt, solvate, tautomer, isotope, or isomer thereof, $R^{17}$ is hydrogen. In certain variations of any of the compounds disclosed herein, or a pharmaceutically acceptable salt, solvate, tautomer, isotope, or isomer thereof, $R^1$ is —C(O)$NR^8R^9$, —S(O)$_2NR^8R^9$, —$NR^{10}$C(O)$NR^8R^9$, —$NR^{10}$C(O)$R^9$, —$NR^{10}$C(O)$OR^9$, or —$NR^{10}$(SO)$_2R^9$. In certain of these variations, $R^{10}$ is hydrogen. In some variations, $R^1$ is —C(O)$NR^8R^9$, and the $R^8$ and $R^9$ together with the nitrogen to which they are attached form an unsubstituted or substituted heterocycloalkyl.

In some variations of any of the disclosed variations, $R^2$ is halo. In certain variations, $R^4$ is independently selected from the group consisting of hydrogen, halo, cyano, ($C_{1-10}$) alkyl, and —$OR^{27}$. In some variations, $R^3$ is hydrogen.

In some embodiments of the compound of Formula (X-A), (X-B), (X-Ai), or (X-Bi), $R^1$ is —C(O)$R^9$, —C(O)$NR^8R^9$, —S(O)$_2NR^8R^9$, —$NR^{10}$C(O)$NR^8R^9$, —$NR^{10}$C(O)$R^9$, —$NR^{10}$S(O)$_2R^9$, —$OR^{26}$, —$SR^9$, —S(O)$R^9$, —S(O)$_2R^9$, —$NR^8R^9$, or —$NR^{10}$C(O)$OR^9$.

In other aspects, provided herein is a pharmaceutical composition which comprises a compound of Formula (X), such as a compound of Formula (X-A), (X-B), (X-Ai), or (X-Bi), or a pharmaceutically acceptable salt, solvate, tautomer, isotope, or isomer of any of the foregoing, and a pharmaceutically acceptable excipient.

In yet other aspects, provided herein is a method of inhibiting a sterol regulatory element-binding protein (SREBP) by contacting the SREBP or contacting an SREBP cleavage activating-protein (SCAP) with a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In still further aspects, provided herein is a method of inhibiting the proteolytic activation of a sterol regulatory element-binding protein (SREBP) by contacting an SREBP cleavage activating-protein (SCAP) with a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In other aspects, provided herein is a method of treating a disorder in a subject in need thereof by administering to the subject in need thereof an effective amount of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In some aspects, provided herein is a method of treating a disorder in a subject in need thereof, wherein the disorder is mediated by a sterol regulatory element-binding protein (SREBP), by administering to the subject in need thereof an effective amount of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In further aspects, provided herein is the use of compound of Formula (X), such as a compound of Formula (X-A), (X-B), (X-Ai), or (X-Bi), or a pharmaceutically acceptable salt, solvate, tautomer, isotope, or isomer of any of these, in the manufacture of a medicament for use in inhibiting a sterol regulatory element-binding protein (SREBP) in a subject in need thereof.

In yet other aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these, in the manufacture of a medicament for use in inhibiting the proteolytic activation of a sterol regulatory element-binding protein (SREBP) in a subject in need thereof.

In some aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these, in the manufacture of a medicament for use in treating a disorder in a subject in need thereof.

In other aspects, provided herein is the use of a compound of Formula (X), such as a compound of Formula (X-A), (X-B), (X-Ai), or (Z-Bi), or a pharmaceutically acceptable salt, solvate, tautomer, isotope, or isomer of any of these, in the manufacture of a medicament for use in treating a disorder in a subject in need thereof, wherein the disorder is mediated by a sterol regulatory element-binding protein (SREBP).

In still further aspects, provided herein is the use of a compound of Formula (X), such as a compound of Formula (X-A), (X-B), (X-Ai), or (Z-Bi), or a pharmaceutically acceptable salt, solvate, tautomer, isotope, or isomer of any of these; or a pharmaceutical composition comprising any of the foregoing and a pharmaceutically acceptable excipient, for inhibiting a sterol regulatory element-binding protein (SREBP).

In still further aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient, for use in inhibiting the proteolytic activation of a sterol regulatory element-binding protein (SREBP).

In further aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient, for treating a disorder in a subject in need thereof.

In some aspects, provided herein is a the use of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient, for treating a disorder in a subject in need thereof, wherein the disorder is mediated by a sterol regulatory element-binding protein (SREBP).

In some variations of the aspects herein, the SREBP is an SREBP-1. In certain variations, the SREBP is SREBP-1a. In other variations, the SREBP is SREBP-1c. In still further embodiments, the SREBP is SREBP-2. In some variations, the disorder is Metabolic Syndrome, type 2 diabetes, obesity, fatty liver disease, insulin resistance, adiposopathy, or dyslipidemia. In other variations, the disorder is a hyperproliferative disorder, such as cancer. In still further variations, the disorder is endotoxic shock, systemic inflammation, or atherosclerosis.

In some aspects, provided herein is a method of treating fatty liver disease in a subject in need thereof, by administering to the subject in need thereof an effective amount of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In further aspects, provided herein is the use of a compound of Formula (X), such as a compound of Formula (X-A), (X-B), (X-Ai), or (Z-Bi), or a pharmaceutically acceptable salt, solvate, tautomer, isotope, or isomer thereof; or a pharmaceutical composition comprising any of the foregoing and a pharmaceutically acceptable excipient, for treating fatty liver disease in a subject in need thereof.

In yet other aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these, in the manufacture of a medicament for use in treating fatty liver disease in a subject in need thereof.

In some aspects, provided herein is a method of treating non-alcoholic steatohepatitis (NASH) in a subject in need thereof, by administering to the subject in need thereof an effective amount of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In further aspects, provided herein is the use of a compound of Formula (X), such as a compound of Formula (X-A), (X-B), (X-Ai), or (X-Bi), or a pharmaceutically acceptable salt, solvate, tautomer, isotope, or isomer thereof; or a pharmaceutical composition comprising any of the foregoing and a pharmaceutically acceptable excipient, for treating non-alcoholic steatohepatitis (NASH) in a subject in need thereof.

In yet other aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these, in the manufacture of a medicament for use in treating non-alcoholic steatohepatitis (NASH) in a subject in need thereof.

In some aspects, provided herein is a method of treating a hyperproliferative disorder in a subject in need thereof, by administering to the subject in need thereof an effective amount of a compound of Formula (X), such as a compound of Formula (X-A), (X-B), (X-Ai), or (X-Bi), or a pharmaceutically acceptable salt, solvate, tautomer, isotope, or isomer of any of these; or a pharmaceutical composition comprising any of the foregoing and a pharmaceutically acceptable excipient.

In still further aspects, provided herein is the use of a compound of Formula (X), such as a compound of Formula (X-A), (X-B), (X-Ai), or (X-Bi), or a pharmaceutically acceptable salt, solvate, tautomer, isotope, or isomer thereof; or a pharmaceutical composition comprising any of the foregoing and a pharmaceutically acceptable excipient, for treating a hyperproliferative disorder in a subject in need thereof.

In other aspects, provided herein is the use of a compound of Formula (X), such as a compound of Formula (X-A), (X-B), (X-Ai), or (X-Bi), or a pharmaceutically acceptable salt, solvate, tautomer, isotope, or isomer of any of these, in the manufacture of a medicament for use in treating a hyperproliferative disorder in a subject in need thereof.

DETAILED DESCRIPTION

Figure 1:
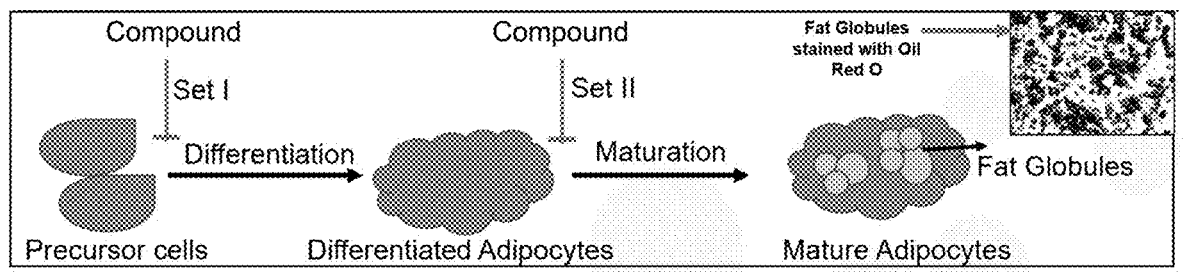
FIG. 1 is a diagram depicting the procedure to evaluate the effect of compounds on differentiation and maturation of adipocytes.

The following description sets forth numerous exemplary configurations, methods, parameters, and the like. It should be recognized, however, that such description is not intended as a limitation on the scope of the present disclosure, but is instead provided as a description of exemplary embodiments.

I. Compounds of Formula (X)

In some aspects, provided herein are compounds of Formula (X):

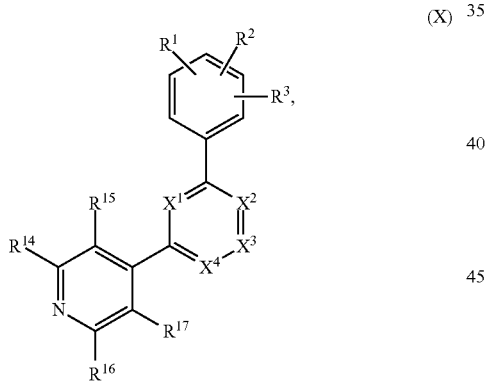

or a pharmaceutically acceptable salt, solvate, tautomer, isotope, or isomer thereof, wherein:

$R^1$ is —C(O)OR$^9$, —C(O)NR$^8$R$^9$, —S(O)$_2$NR$^8$R$^9$, —NR$^{10}$C(O)NR$^8$R$^9$, —NR$^{10}$C(O)R$^9$, —NR$^{10}$S(O)$_2$R$^9$, —OR$^{26}$, —SR$^9$, —S(O)R$^9$, —S(O)$_2$R$^9$, —NR$^8$R$^9$, —NR$^{10}$C(O)OR$^9$, —C(O)R$^{26}$, —NR$^{10}$S(O)$_2$NR$^8$R$^9$, —C(O)NR$^{10}$S(O)$_2$R$^9$, or —C(O)NR$^{10}$NR$^8$R$^9$;

wherein each of R$^8$, R$^9$, and R$^{10}$ is independently selected from the group consisting of hydrogen, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl, R$^{26}$ is (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, or heteroaryl-alkyl, each (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl of R$^8$, R$^9$, R$^{10}$, and R$^{26}$ is independently unsubstituted or substituted with one or more substituents independently selected from the group consisting of halo, (C$_{1-10}$)alkyl, (C$_{1-10}$)haloalkyl, cyano, oxo, —OR$^{19}$, —C(O)NR$^{19}$R$^{19}$, —NR$^{19}$C(O)R$^{19}$, —NR$^{19}$C(O)NR$^{19}$R$^{19}$, —NR$^{19}$R$^{19}$, —S(O)$_2$NR$^{19}$R$^{19}$, —NR$^{19}$S(O)$_2$R$^{19}$, —S(O)$_{n4}$R$^{20}$, —C(O)OR$^{19}$, —C(O)R$^{20}$, and —(OR$^{38}$)$_{n15}$OR$^{19}$, each R$^{19}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two R$^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo, each R$^{20}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, each R$^{38}$ is independently (C$_{1-10}$)alkylene or (C$_{1-10}$) haloalkylene, each n15 is independently an integer from 1 to 5; and n4 is 0, 1, or 2;

or R$^8$ and R$^9$, together with the nitrogen atom to which they are attached, form a heterocycloalkyl, wherein the heterocycloalkyl is unsubstituted or substituted with one or more substituents independently selected from the group consisting of halo, cyano, oxo, (C$_{1-10}$)alkyl, (C$_{2-10}$)alkenyl, (C$_{2-10}$)alkynyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, heteroaryl-alkyl, —OR$^{23}$, —C(O)NR$^{23}$R$^{23}$, —NR$^{23}$C(O)R$^{23}$, —NR$^{23}$C(O)OR$^{23}$, —NR$^{23}$C(O)NR$^{23}$R$^{23}$, —NR$^{23}$, —S(O)$_2$NR$^{23}$R$^{23}$, —NR$^{23}$S(O)$_2$R$^{24}$, —S(O)$_{n6}$R$^{24}$, —C(O)OR$^{23}$, —C(O)R$^{24}$, and —(OR$^{39}$)$_{n16}$OR$^{23}$, wherein each alkyl, alkenyl, alkynyl, cycloalkyl, cycloalkyl-alkyl, heterocycloalkyl, heterocycloalkyl-alkyl, aryl, aryl-alkyl, heteroaryl, and heteroaryl-alkyl is independently unsubstituted or substituted with one or more substituents independently selected from the group consisting of halo, oxo, alkyl, haloalkyl, —OR$^{31}$, —C(O)NR$^{31}$R$^{31}$, —NR$^{31}$C(O)R$^{31}$, —NR$^{31}$C(O)OR$^{31}$, —NR$^{31}$C(O)NR$^{31}$R$^{31}$, —NR$^{31}$S(O)$_2$R$^{31}$, and —S(O)$_{n9}$R$^{31}$, wherein each R$^{31}$ is independently hydrogen, alkyl, or haloalkyl, and each n9 is independently 0, 1, or 2, each R$^{23}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two R$^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo, each R$^{24}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, each R$^{39}$ is independently (C$_{1-10}$)alkylene or (C$_{1-10}$) haloalkylene, each n16 is independently an integer from 1 to 5; and n6 is 0, 1, or 2;

$R^2$ and $R^3$ are independently selected from the group consisting of hydrogen, halo, cyano, $(C_{1-10})$alkyl, $(C_{3-10})$cycloalkyl, $(C_{3-10})$cycloalkyl$(C_{1-10})$alkyl, $-OR^{25}$, $-C(O)NR^{25}R^{25}$, $-NR^{25}C(O)R^{25}$, $-NR^{25}C(O)NR^{25}R^{25}$, $-NR^{25}R^{25}$, $-S(O)_2NR^{25}R^{25}$, $-NR^{25}S(O)_2R^{25}$, $-S(O)_{n7}R^{30}$, $-NR^{25}C(O)OR^{25}R^{25}$, $-C(O)OR^{25}$, and $-C(O)R^{30}$,
  wherein each $(C_{1-10})$alkyl, $(C_{3-10})$cycloalkyl, and $(C_{3-10})$cycloalkyl$(C_{1-10})$alkyl is independently unsubstituted or substituted with one or more halo,
  each $R^{25}$ is independently hydrogen $(C_{1-10})$alkyl, $(C_{3-10})$cycloalkyl, $(C_{3-10})$cycloalkyl$(C_{1-10})$alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo,
  each $R^{30}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and
  n7 is 0, 1, or 2;
$X^1$, $X^2$, $X^3$ and $X^4$ are independently $CR^4$ or N, wherein $X^2$, $X^3$ and $X^4$ may not all be N;
when at least one of $X^1$, $X^2$, $X^3$ and $X^4$ is N, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, $-OR^{27}$, $-C(O)NR^{27}R^{27}$, $-S(O)_2NR^{27}R^{27}$, $-S(O)_{n8}R^{28}$, $-C(O)OR^{27}$, and $-C(O)R^{28}$,
  wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo,
  each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
  each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and
  n8 is 0, 1 or 2; or
when each of $X^1$, $X^2$, $X^3$ and $X^4$ is $CR^4$, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $-OR^{27}$, $-C(O)NR^{27}R^{27}$, $-NR^{27}C(O)R^{27}$, $-NR^{27}R^{27}$, $-NR^{27}S(O)_2R^{27}$, $-S(O)_2NR^{27}R^{27}$, $-S(O)_{n8}R^{28}$, $-C(O)OR^{27}$, and $-C(O)R^{28}$,
  wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo,
  each $R^{27}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
  each $R^{28}$ is independently $(C_{1-10})$alkyl, $(C_{3-10})$cycloalkyl, $(C_{3-10})$cycloalkyl$(C_{1-10})$alkyl, or heterocycloalkyl,
    wherein each of the foregoing is independently unsubstituted or substituted with one or more halo, and
  n8 is 0, 1, or 2; or
two $R^4$ on adjacent annular carbon atoms together with the carbon atoms to which they are attached may form a carbocyclyl or heterocyclyl,
  wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $-OR^{27}$, $-C(O)NR^{27}R^{27}$, $-NR^{27}C(O)R^{27}$, $-NR^{27}R^{27}$, $-S(O)_2NR^{27}R^{27}$, $-NR^{27}S(O)_2R^{27}$, $-S(O)_{n8}R^{28}$, and $-C(O)R^{28}$,
  or the heterocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, $-OR^{27}$, $-C(O)NR^{27}R^{27}$, $-S(O)_2NR^{27}R^{27}$, $-S(O)_{n8}R^{28}$, and $-C(O)R^{28}$,
  each $R^{27}$ is independently hydrogen, $(C_{1-10})$alkyl, $(C_{3-10})$cycloalkyl, $(C_{3-10})$cycloalkyl$(C_{1-10})$alkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
  each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and
  n8 is 0, 1, or 2;
$R^{15}$ and $R^{17}$ are independently hydrogen, halo, alkyl, or $-OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;
$R^{14}$ is $(C_{1-10})$alkyl, $(C_{3-10})$alkenyl, $(C_{3-10})$cycloalkyl, $(C_{3-10})$cycloalkenyl, $(C_{3-10})$cycloalkyl$(C_{1-10})$alkyl, heterocycloalkyl connected through an annular carbon atom, heterocycloalkenyl connected through an annular carbon atom, heterocycloalkyl-alkyl, $-OR^5$, $-C(O)NR^5R^5$, $-R^5C(O)NR^5R^5$, $-S(O)_2NR^5R^5$, $-S(O)_{n1}R^6$, or $-C(O)R^6$;
$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, $-OR^5$, $-C(O)NR^5R^5$, $-R^5C(O)NR^5R^5$, $-S(O)_2NR^5R^5$, $-S(O)_{n1}R^6$, or $-C(O)R^6$;
wherein the $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl, heterocycloalkenyl, or heterocycloalkyl-alkyl of $R^{14}$ or $R^{16}$ is independently unsubstituted or substituted with one or more substituents independently selected from the group consisting of $(C_{1-10})$alkyl, cycloalkyl, heterocycloalkyl, halo, cyano, oxo, $-OR^7$, $-C(O)OR^7$, $-C(O)NR^7R^7$, $-NR^7C(O)R^7$, $-NR^7C(O)NR^7R^7$, $-NR^7R^7$, $-S(O)_2NR^7R^7$, $-NR^7S(O)_2R^7$, $-S(O)_{n2}R^{13}$, and $-C(O)R^{13}$;
  wherein each alkyl, cycloalkyl, and heterocycloalkyl is independently unsubstituted or substituted with one or more substituents selected from the group consisting of halo, cycloalkyl, halocycloalkyl, heterocycloalkyl, haloheterocycloalkyl, and $-(OR^{33})_{n10}OR^{32}$, wherein each n10 is independently an integer from 0 to 5, each R[32] is independently hydrogen, $(C_{1-10})$alkyl or $(C_{1-10})$haloalkyl, and each R[33] is independently $(C_{1-10})$alkylene or $(C_{1-10})$haloalkylene;

each R[5] is independently hydrogen, $(C_{1-10})$alkyl, or $(C_{3-10})$cycloalkyl; or two R[5], together with the nitrogen atom to which they are attached, form a heterocycloalkyl; wherein each alkyl, cycloalkyl, or heterocycloalkyl is independently unsubstituted or substituted with one or more substituents selected from the group consisting of halo, cyano, oxo, alkyl, haloalkyl, —C(O)OR[34], —C(O)NR[34]R[34], —NR[34]C(O)R[34], —NR[34]C(O)NR[34]R[34], —NR[34]R[34], —S(O)$_2$NR[34]R[34], —NR[34]S(O)$_2$R[34], —S(O)$_{n11}$R[34], —C(O)R[34], and —(OR[35])$_{n12}$OR[34], wherein each R[34] is independently hydrogen, $(C_{1-10})$alkyl, or $(C_{1-10})$haloalkyl; each n11 is independently 0, 1, or 2; each n12 is independently an integer from 0 to 5; and each R[35] is independently $(C_{1-10})$alkylene or $(C_{1-10})$haloalkylene;

each R[6] is independently $(C_{1-10})$alkyl or $(C_{3-10})$cycloalkyl, wherein each alkyl or cycloalkyl is independently unsubstituted or substituted with one or more halo;

each n1 is independently 0, 1, or 2;

each R[7] is independently hydrogen, unsubstituted $(C_{1-10})$alkyl, or $(C_{1-10})$alkyl substituted with one or more halo;

each n2 is independently 0, 1, or 2, and each R[13] is independently unsubstituted $(C_{1-10})$alkyl or $(C_{1-10})$alkyl substituted with one or more halo;

or R[14] and R[15], together with the atoms to which they are attached, form a carbocyclyl or heterocyclyl, wherein the carbocyclyl or heterocyclyl is unsubstituted or substituted with one or more substituents independently selected from the group consisting of halo, cyano, oxo, $(C_{1-10})$alkyl, $(C_{3-10})$cycloalkyl, $(C_{3-10})$cycloalkyl$(C_{1-10})$alkyl, —OR[18], —C(O)NR[18]R[18], —NR[18]C(O)R[18], —NR[18]C(O)NR[18]R[18], —NR[18]R[18], —S(O)$_2$NR[18]R[18], —NR[18]S(O)$_2$R[18], —S(O)$_{n3}$R[21], —C(O)OR[18], and —C(O)R[21], wherein each $(C_{1-10})$alkyl, $(C_{3-10})$cycloalkyl, and $(C_{3-10})$cycloalkyl$(C_{1-10})$alkyl is independently unsubstituted or substituted with one or more substituents independently selected from the group consisting of halo, alkyl, haloalkyl, cyano, oxo, —C(O)OR[36], —C(O)NR[36]R[36], —NR[36]C(O)R[36], —NR[36]C(O)NR[36]R[36], —NR[36]R[36], —S(O)$_2$NR[36]R[36], —NR[36]S(O)$_2$R[36], —S(O)$_{n13}$R[36], —C(O)R[36], and —(OR[37])$_{n14}$OR[36], wherein each R[36] is independently hydrogen, $(C_{1-10})$alkyl, or $(C_{1-10})$haloalkyl; each n13 is independently 0, 1, or 2; each n14 is independently an integer from 0 to 5; and each R[37] is independently $(C_{1-10})$alkylene or $(C_{1-10})$haloalkylene;

wherein each R[18] is independently hydrogen, $(C_{1-10})$alkyl, or $(C_{3-10})$cycloalkyl; or two R[18], together with the nitrogen atom to which they are attached, form a heterocycloalkyl; wherein each alkyl, cycloalkyl, or heterocycloalkyl is independently unsubstituted or substituted with one or more halo;

each R[21] is independently $(C_{1-10})$alkyl or $(C_{3-10})$cycloalkyl, wherein each alkyl or cycloalkyl is independently unsubstituted or substituted with one or more halo; and each n3 is independently 0, 1, or 2.

In some embodiments, the compound of Formula (X) is a compound of Formula (Z):

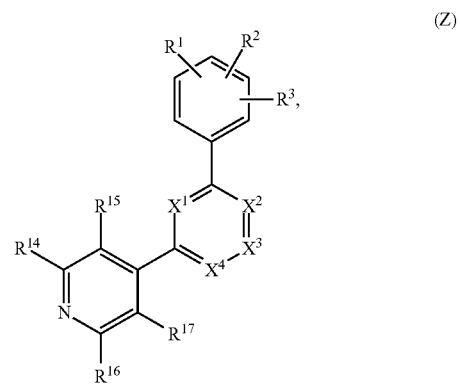

(Z)

or a pharmaceutically acceptable salt, solvate, tautomer, isotope, or isomer thereof, wherein:

R[1] is —C(O)R[9], —C(O)NR[8]R[9], —S(O)$_2$NR[8]R[9], —NR[10]C(O)NR[8]R[9], —NR[10]C(O)R[9], —NR[10]S(O)$_2$R[9], —OR[26], —SR[9], —S(O)R[9], —S(O)$_2$R[9], —NR[8]R[9], —NR[10]C(O)OR[9], —C(O)R[26], —NR[10]S(O)$_2$NR[8]R[9], or —C(O)NR[10]S(O)$_2$R[9];

wherein each of R[8], R[9], and R[10] is independently selected from the group consisting of hydrogen, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, and heteroaryl-alkyl, R[26] is $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, or heteroaryl-alkyl, each $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, and heteroaryl-alkyl of R[8], R[9], R[10], and R[26] is independently unsubstituted or substituted with one or more substituents independently selected from the group consisting of halo, cyano, oxo, —OR[19], —C(O)NR[19]R[19], —NR[19]C(O)R[19], —NR[19]C(O)NR[19]R[19], —NR[19]R[19], —S(O)$_2$NR[19]R[19], —NR[19]S(O)$_2$R[19], —S(O)$_{n4}$R[20], —C(O)OR[19], and —C(O)R[20], each R[19] is independently hydrogen, $(C_{1-10})$alkyl, $(C_{3-10})$cycloalkyl, $(C_{3-10})$cycloalkyl$(C_{1-10})$alkyl, or heterocycloalkyl; or two R[19], together with the nitrogen atom to which they are attached, form a heterocycloalkyl; wherein each of the foregoing alkyl, cycloalkyl, or heterocycloalkyl moieties is independently unsubstituted or substituted with one or more halo, each R[20] is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n4 is 0, 1, or 2;

or R[8] and R[9], together with the nitrogen atom to which they are attached, form a heterocycloalkyl, wherein the heterocycloalkyl is unsubstituted or substituted with 1 to 3 substituents independently selected from the group consisting of halo, cyano, oxo, $(C_{1-10})$alkyl, $(C_{2-10})$alkenyl, $(C_{2-10})$alkynyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, heteroaryl-alkyl, —OR[23], —C(O)NR[23]R[23], —NR[23]C(O)R[23], —NR[23]C(O)OR[23], —NR[23]C(O)

$NR^{23}R^{23}$, $-NR^{23}R^{23}$, $-S(O)_2NR^{23}R^{23}$, $-NR^{23}S(O)_2R^{24}$, $-S(O)_{n6}R^{24}$, $-C(O)OR^{23}$, and $-C(O)R^{24}$,
- wherein each $R^{23}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each $R^{24}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and
- n6 is 0, 1, or 2;

$R^2$ and $R^3$ are independently selected from the group consisting of hydrogen, halo, cyano, $(C_{1-10})$alkyl, $(C_{3-10})$cycloalkyl, $(C_{3-10})$cycloalkyl$(C_{1-10})$alkyl, $-OR^{25}$, $-C(O)NR^{25}R^{25}$, $-NR^{25}C(O)R^{25}$, $-NR^{25}C(O)NR^{25}R^{25}$, $-NR^{25}R^{25}$, $-S(O)_2NR^{25}R^{25}$, $-NR^{25}S(O)_2R^{25}$, $-S(O)_{n7}R^{30}$, $-NR^{25}C(O)OR^{25}R^{25}$, $-C(O)OR^{25}$, or $-C(O)R^{30}$,
- wherein each $(C_{1-10})$alkyl, $(C_{3-10})$cycloalkyl, and $(C_{3-10})$cycloalkyl$(C_{1-10})$alkyl is independently unsubstituted or substituted with one or more halo,
- each $R^{25}$ is independently hydrogen $(C_{1-10})$alkyl, $(C_{3-10})$cycloalkyl, $(C_{3-10})$cycloalkyl$(C_{1-10})$alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each $R^{30}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and
- n7 is 0, 1, or 2;

$X^1$, $X^2$, $X^3$ and $X^4$ are independently $CR^4$ or N, wherein $X^2$, $X^3$ and $X^4$ may not all be N;

when at least one of $X^1$, $X^2$, $X^3$ and $X^4$ is N, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, $-OR^{27}$, $-C(O)NR^{27}R^{27}$, $-S(O)_2NR^{27}R^{27}$, $-S(O)_{n8}R^{28}$, $-C(O)OR^{27}$, and $-C(O)R^{28}$,
- wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo,
- each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo,
- n8 is 0, 1 or 2; or when each of $X^1$, $X^2$, $X^3$ and $X^4$ is $CR^4$, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $-OR^{27}$, $-C(O)NR^{27}R^{27}$, $-NR^{27}C(O)R^{27}$, $-NR^{27}R^{27}$, $-NR^{27}S(O)_2R^{27}$, $-S(O)_2NR^{27}R^{27}$, $-S(O)_{n8}R^{28}$, $-C(O)OR^{27}$, and $-C(O)R^{28}$,
- wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo,
- each $R^{27}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and
- n8 is 0, 1, or 2; or two $R^4$ on adjacent annular carbon atoms together with the carbon atoms to which they are attached may form a carbocyclyl or heterocyclyl,
- wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $-OR^{27}$, $-C(O)NR^{27}R^{27}$, $-NR^{27}C(O)R^{27}$, $-NR^{27}R^{27}$, $-S(O)_2NR^{27}R^{27}$, $-NR^{27}S(O)_2R^{27}$, $-S(O)_{n8}R^{28}$, and $-C(O)R^{28}$,
- or the heterocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, $-OR^{27}$, $-C(O)NR^{27}R^{27}$, $-S(O)_2NR^{27}R^{27}$, $-S(O)_{n8}R^{28}$, and $-C(O)R^{28}$,
- each $R^{27}$ is independently hydrogen, $(C_{1-10})$alkyl, $(C_{3-10})$cycloalkyl, $(C_{3-10})$cycloalkyl$(C_{1-10})$alkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and
- n8 is 0, 1, or 2;

$R^{15}$ and $R^{17}$ are independently hydrogen, halo, alkyl, or $-OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;

$R^{14}$ is $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl connected through an annular carbon atom, heterocycloalkenyl connected through an annular carbon atom, heterocycloalkyl-alkyl, $-OR^5$, $-C(O)NR^5R^5$, $-RC(O)NR^5R^5$, $-S(O)_2NR^5R^5$, $-S(O)_{n1}R^6$, or $-C(O)R^6$;

$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, $-OR^5$, $-C(O)NR^5R^5$, $-R^5C(O)NR^5R^5$, $-S(O)_2NR^5R^5$, $-S(O)_{n1}R^6$, or $-C(O)R^6$;

the $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl, heterocycloalkenyl, or heterocycloalkyl-alkyl, of $R^{14}$ or $R^{16}$ is independently unsubstituted or substituted with 1 to 3 substituents independently selected from the group consisting of $(C_{1-10})$alkyl, halo, cyano, oxo, —$OR^7$, —$C(O)OR^7$, —$C(O)NR^7R^7$, —$NR^7C(O)R^7$, —$NR^7C(O)NR^7R^7$, —$NR^7R^7$, —$S(O)_2NR^7R^7$, —$NR^7S(O)_2R^7$, —$S(O)_{n2}R^{13}$, and —$C(O)R^{13}$;

each $R^5$ is independently hydrogen, $(C_{1-10})$alkyl, or $(C_{3-10})$cycloalkyl; or two $R^5$, together with the nitrogen atom to which they are attached, form a heterocycloalkyl; wherein each alkyl, cycloalkyl, or heterocycloalkyl is independently unsubstituted or substituted with one or more halo;

each $R^6$ is independently $(C_{1-10})$alkyl or $(C_{3-10})$cycloalkyl, wherein each alkyl or cycloalkyl is independently unsubstituted or substituted with one or more halo;

each n1 is independently 0, 1, or 2;

each $R^7$ is independently hydrogen, unsubstituted $(C_{1-10})$alkyl, or $(C_{1-10})$alkyl substituted with one or more halo;

each n2 is independently 0, 1, or 2, and each $R^{13}$ is independently unsubstituted $(C_{1-10})$alkyl or $(C_{1-10})$alkyl substituted with one or more halo;

or $R^{14}$ and $R^{15}$, together with the atoms to which they are attached, form a carbocyclyl or heterocyclyl, wherein the carbocyclyl or heterocyclyl is unsubstituted or substituted with one or two substituents independently selected from the group consisting of halo, cyano, oxo, $(C_{1-10})$alkyl, $(C_{3-10})$cycloalkyl, $(C_{3-10})$cycloalkyl$(C_{1-10})$alkyl, —$OR^{18}$, —$C(O)NR^{18}R^{18}$, —$NR^{18}C(O)R^{18}$, —$NR^{18}C(O)NR^{18}R^{18}$, —$NR^{18}R^{18}$, —$S(O)_2NR^{18}R^{18}$, —$NR^{18}S(O)_2R^{18}$, —$S(O)_{n3}R^{21}$, —$C(O)OR^{18}$, and —$C(O)R^{21}$, wherein each $R^{18}$ is independently hydrogen, $(C_{1-10})$alkyl, or $(C_{3-10})$cycloalkyl; or two $R^{18}$, together with the nitrogen atom to which they are attached, form a heterocycloalkyl; wherein each alkyl, cycloalkyl, or heterocycloalkyl is independently unsubstituted or substituted with one or more halo, each $R^{21}$ is independently $(C_{1-10})$alkyl or $(C_{3-10})$cycloalkyl, wherein each alkyl or cycloalkyl is independently unsubstituted or substituted with one or more halo, and each n3 is independently 0, 1, or 2.

In some embodiments, the compound of Formula (Z) is a compound of Formula (I), or a pharmaceutically acceptable salt, solvate, tautomer, isotope, or isomer thereof, wherein $R^1$ is —$C(O)OR^9$, —$C(O)NR^8R^9$, —$S(O)_2NR^8R^9$, —$NR^{10}C(O)NR^8R^9$, —$NR^{10}C(O)R^9$, —$NR^{10}S(O)_2R^9$, —$OR^{26}$, —$SR^9$, —$S(O)R^9$, —$S(O)_2R^9$, —$NR^8R^9$, or —$NR^{10}C(O)OR^9$.

Thus, in some aspects, provided herein are compounds of Formula (I):

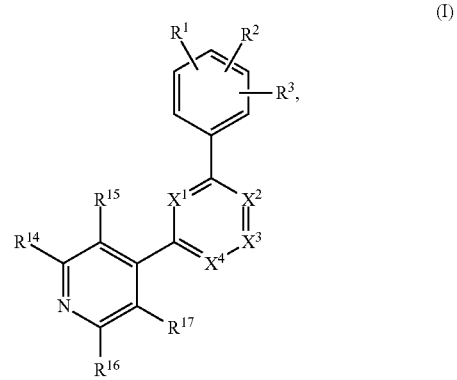

or a pharmaceutically acceptable salt, solvate, tautomer, isotope, or isomer thereof, wherein:

$R^1$ is —$C(O)R^9$, —$C(O)NR^8R^9$, —$S(O)_2NR^8R^9$, —$NR^{10}C(O)NR^8R^9$, —$NR^{10}C(O)R^9$, —$NR^{10}S(O)_2R^9$, —$OR^{26}$, —$SR^9$, —$S(O)R^9$, —$S(O)_2R^9$, —$NR^8R^9$, or —$NR^{10}C(O)OR^9$, wherein each of $R^8$, $R^9$, and $R^{10}$ is independently selected from the group consisting of hydrogen, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, and heteroaryl-alkyl, $R^{26}$ is $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, or heteroaryl-alkyl, each $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, and heteroaryl-alkyl is independently unsubstituted or substituted with one or more substituents independently selected from the group consisting of halo, cyano, oxo, —$OR^{19}$, —$C(O)NR^{19}R^{19}$, —$NR^{19}C(O)R^{19}$, —$NR^{19}C(O)NR^{19}R^{19}$, —$NR^{19}R^{19}$, —$S(O)_2NR^{19}R^{19}$, —$NR^{19}S(O)_2R^{19}$, —$S(O)_{n4}R^{20}$, —$C(O)OR^{19}$, and —$C(O)R^{20}$, each $R^{19}$ is independently hydrogen, $(C_{1-10})$alkyl, $(C_{1-10})$cycloalkyl, $(C_{3-10})$cycloalkyl$(C_{1-10})$alkyl, or heterocycloalkyl; or two $R^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{20}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n4 is 0, 1, or 2;

or $R^8$ and $R^9$, together with the nitrogen atom to which they are attached, form a heterocycloalkyl, wherein the heterocycloalkyl is unsubstituted or substituted with 1 to 3 substituents independently selected from the group consisting of halo, cyano, oxo, $(C_{1-10})$alkyl, $(C_{2-10})$alkenyl, $(C_{2-10})$alkynyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, heteroaryl-alkyl, —$OR^{23}$, —$C(O)NR^{23}R^{23}$, —$NR^{23}C(O)R^{23}$, —$NR^{23}C(O)OR^{23}$, —$NR^{23}C(O)NR^{23}R^{23}$, —$NR^{23}R^{23}$, —$S(O)_2NR^{23}R^{23}$, —$NR^{23}S(O)_2R^{24}$, —$S(O)_{n6}R^{24}$, —$C(O)OR^{23}$, and —$C(O)R^{24}$, wherein each $R^{23}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{24}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n6 is 0, 1, or 2;

$R^2$ and $R^3$ are independently selected from the group consisting of hydrogen, halo, cyano, $(C_{1-10})$alkyl, $(C_{3-10})$cycloalkyl, $(C_{3-10})$cycloalkyl$(C_{1-10})$alkyl, —$OR^{25}$, —$C(O)NR^{25}R^{25}$, —$NR^{25}C(O)R^{25}$, —$NR^{25}C(O)NR^{25}R^{25}$, —$NR^{25}R^{25}$, —$S(O)_2NR^{25}R^{25}$, —$NR^{25}S(O)_2R^{25}$, —$S(O)_{n7}R^{30}$, —$NR^{25}C(O)OR^{25}R^{25}$, —$C(O)OR^{25}$, or —$C(O)R^{30}$, wherein each $(C_{1-10})$alkyl, $(C_{3-10})$cycloalkyl, and $(C_{3-10})$cycloalkyl$(C_{1-10})$alkyl is independently unsubstituted or substituted with one or more halo, each $R^{25}$ is independently hydrogen $(C_{1-10})$alkyl, $(C_{3-10})$cycloalkyl, $(C_{3-10})$cycloalkyl$(C_{1-10})$alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{30}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n7 is 0, 1, or 2;

$X^1$, $X^2$, $X^3$ and $X^4$ are independently $CR^4$ or N, wherein $X^2$, $X^3$ and $X^4$ may not all be N;

when at least one of $X^1$, $X^2$, $X^3$ and $X^4$ is N, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, n8 is 0, 1 or 2; or when each of $X^1$, $X^2$, $X^3$ and $X^4$ is $CR^4$, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$NR^{27}S(O)_2R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^{27}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n8 is 0, 1, or 2;

two $R^4$ on adjacent annular carbon atoms together with the carbon atoms to which they are attached may form a carbocyclyl or heterocyclyl, wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$S(O)_2NR^{27}R^{27}$, —$NR^{27}S(O)_2R^{27}$, —$S(O)_{n8}R^{28}$, and —$C(O)R^{28}$, or the heterocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, and —$C(O)R^{28}$, each $R^{27}$ is independently hydrogen, $(C_{1-10})$alkyl, $(C_{3-10})$cycloalkyl, $(C_{3-10})$cycloalkyl$(C_{1-10})$alkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and n8 is 0, 1, or 2;

$R^{15}$ and $R^{17}$ are independently hydrogen, halo, alkyl, or —$OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;

$R^{14}$ is $(C_{1-10})$alkyl, $(C_{3-10})$alkenyl, $(C_{3-10})$cycloalkyl, $(C_{3-10}$ cycloalkenyl, $(C_{3-10})$cycloalkyl$(C_{1-10})$alkyl, heterocycloalkyl connected through an annular carbon atom, heterocycloalkenyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;

$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;

the $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl, heterocycloalkenyl, or heterocycloalkyl-alkyl, of $R^{14}$ or $R^{16}$ is independently unsubstituted or substituted with 1 to 3 substituents independently selected from the group consisting of $(C_{1-10})$alkyl, halo, cyano, oxo, —$OR^7$, —$C(O)R^7$, —$C(O)NR^7R^7$, —$NR^7C(O)R^7$, —$NR^7C(O)NR^7R^7$, —$NR^7R^7$, —$S(O)_2NR^7R^7$, —$NR^7S(O)_2R^7$, —$S(O)_2R^{13}$, and —$C(O)R^{13}$;

each $R^5$ is independently hydrogen, $(C_{1-10})$alkyl, or $(C_{3-10})$cycloalkyl; or two $R^5$, together with the nitrogen atom to which they are attached, form a heterocycloalkyl; wherein each alkyl, cycloalkyl, or heterocycloalkyl is independently unsubstituted or substituted with one or more halo;

each $R^6$ is independently $(C_{1-10})$alkyl or $(C_{3-10})$cycloalkyl, wherein each alkyl or cycloalkyl is independently unsubstituted or substituted with one or more halo;

each n1 is independently 0, 1, or 2;

each $R^7$ is independently hydrogen, unsubstituted $(C_{1-10})$alkyl, or $(C_{1-10})$alkyl substituted with one or more halo;

each n2 is independently 0, 1, or 2, and each $R^{13}$ is independently unsubstituted $(C_{1-10})$alkyl or $(C_{1-10})$alkyl substituted with one or more halo;

or $R^{14}$ and $R^{15}$, together with the atoms to which they are attached, form a carbocyclyl or heterocyclyl, wherein the carbocyclyl or heterocyclyl is unsubstituted or substituted with one or two substituents independently selected from the group consisting of halo, cyano, oxo, $(C_{1-10})$alkyl, $(C_{3-10})$cycloalkyl, $(C_{3-10})$cycloalkyl$(C_{1-10})$alkyl, —$OR^{18}$, —$C(O)NR^{18}R^{18}$, —$NR^{18}C(O)R^{18}$, —$NR^{18}C(O)NR^{18}R^{18}$, —$NR^{18}R^{18}$, —$S(O)_2NR^{18}R^{18}$, —$NR^{18}S(O)_2R^{18}$, —$S(O)_{n3}R^{21}$, —$C(O)OR^{18}$, and —$C(O)R^{21}$, wherein each $R^{18}$ is independently hydrogen, $(C_{1-10})$alkyl, or $(C_{3-10})$cycloalkyl; or two $R^{18}$, together with the nitrogen atom to which they are attached, form a heterocycloalkyl; wherein each alkyl, cycloalkyl, or heterocycloalkyl is independently unsubstituted or substituted with one or more halo each $R^{21}$ is independently $(C_{1-10})$alkyl or $(C_{3-10})$cycloalkyl, wherein each alkyl or cycloalkyl is independently unsubstituted or substituted with one or more halo, and each n3 is independently 0, 1, or 2.

In some embodiments, the compound of Formula (X) is a compound of Formula (X-A):

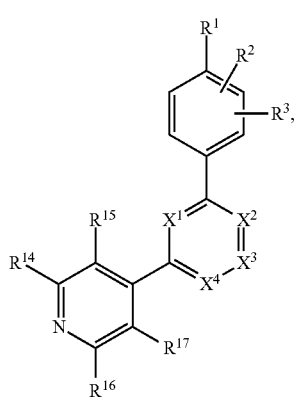

(X-A)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In some embodiments, the compound of Formula (Z) is a compound of Formula (Z-A):

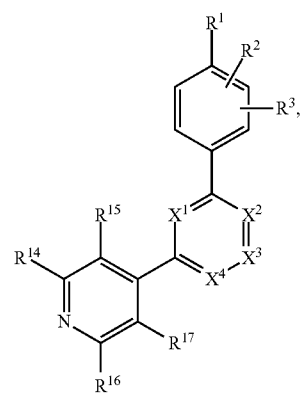

(Z-A)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (Z) above.

In some embodiments, the compound of Formula (I) is a compound of Formula (I-A):

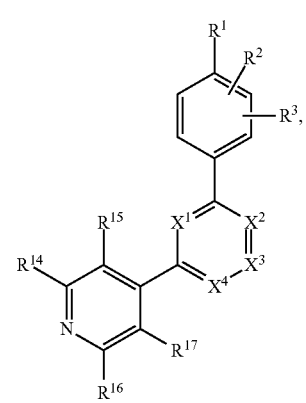

(I-A)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (I) above.

In some embodiments, the compound of Formula (X) or Formula (X-A) is a compound of Formula (X-Ai):

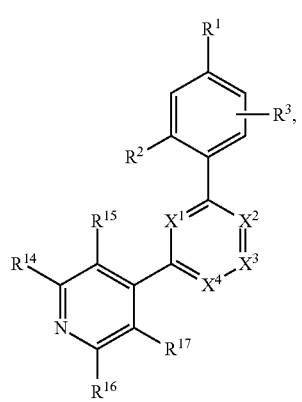

(X-Ai)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In some embodiments, the compound of Formula (Z) or Formula (Z-A) is a compound of Formula (Z-Ai):

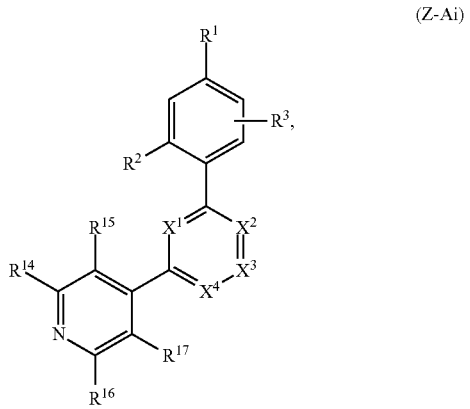

(Z-Ai)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (Z) above.

In some embodiments, the compound of Formula (I) or Formula (I-A) is a compound of Formula (I-Ai):

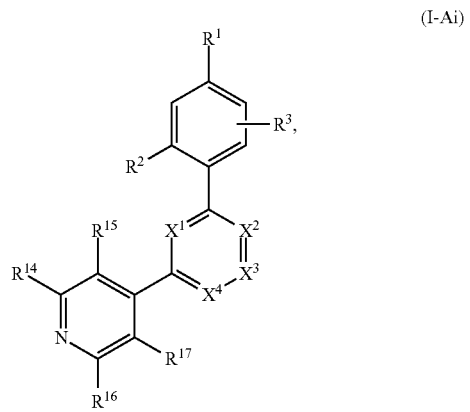

(I-Ai)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (I) above.

In other embodiments, the compound of Formula (X) is a compound of Formula (X-B):

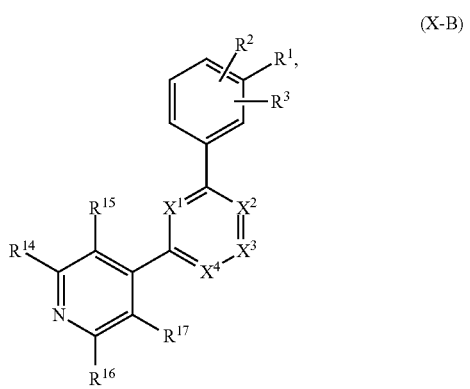

(X-B)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In other embodiments, the compound of Formula (Z) is a compound of Formula (Z-B):

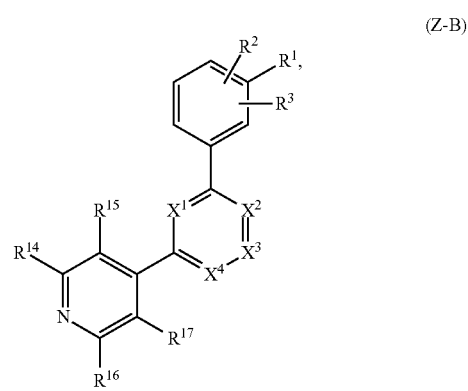

(Z-B)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (Z) above.

In other embodiments, the compound of Formula (I) is a compound of Formula (I-B):

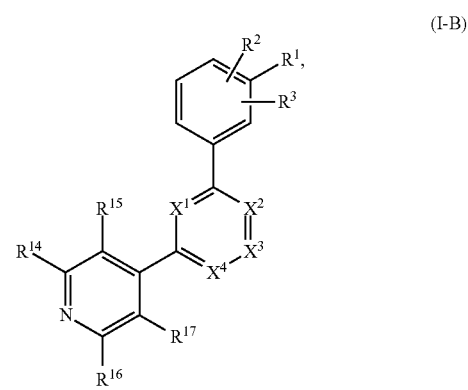

(I-B)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (I) above.

In certain embodiments, the compound of Formula (X) or Formula (X-B) is a compound of Formula (X-Bi):

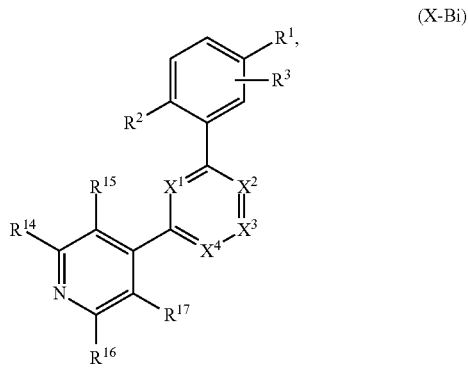

(X-Bi)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (X) above.

In certain embodiments, the compound of Formula (Z) or Formula (Z-B) is a compound of Formula (Z-Bi):

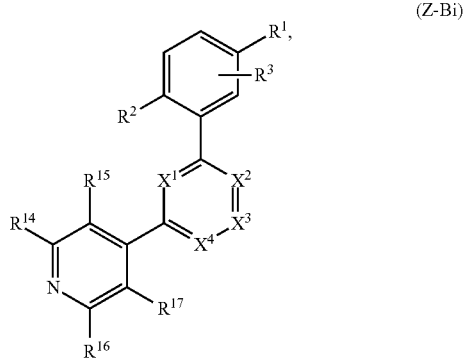

(Z-Bi)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (Z) above.

In certain embodiments, the compound of Formula (I) or Formula (I-B) is a compound of Formula (I-Bi):

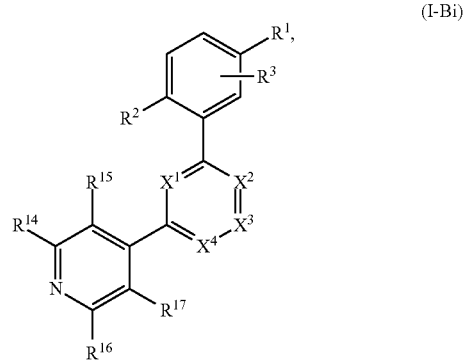

(I-Bi)

or a pharmaceutically acceptable salt, solvate, tautomer, isotope, or isomer thereof, where $R^1$, $R^2$, $R^3$, $R^{14}$, $R^{15}$, $R^{16}$, $R^{17}$, $X^1$, $X^2$, $X^3$, and $X^4$ are as described for Formula (I) above.

Thus, in some embodiments, the compound of Formula (Z-A), (Z-B), (Z-Ai), or (Z-Bi) is a compound of Formula (I-A), (I-B), (I-Ai), or (I-Bi), respectively, wherein $R^1$ is —C(O)O$R^9$, —C(O)NR$^8$R$^9$, —S(O)$_2$NR$^8$R$^9$, —NR$^{10}$C(O)NR$^8$R$^9$, —NR$^{10}$C(O)R$^9$, —NR$^{10}$S(O)$_2$R$^9$, —OR$^{26}$, —SR$^9$, —S(O)R$^9$, —S(O)$_2$R$^9$, —NR$^8$R$^9$, or —NR$^{10}$C(O)OR$^9$.

"Alkyl", as used herein, refers to an unbranched or branched saturated hydrocarbon chain. Alkyl can be used alone, or as part of another radical, such as cycloalkyl-alkyl. In some embodiments, alkyl as used herein has 1 to 50 carbon atoms (($C_{1-50}$)alkyl), 1 to 20 carbon atoms (($C_{1-20}$)alkyl), 1 to 12 carbon atoms (($C_{1-12}$)alkyl), 1 to 10 carbon atoms (($C_{1-10}$)alkyl), 1 to 8 carbon atoms (($C_{1-8}$)alkyl), 1 to 6 carbon atoms (($C_{1-6}$)alkyl), or 1 to 4 carbon atoms (($C_{1-4}$)alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methyl pentyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

"Haloalkyl", as used herein, refers to an alkyl group substituted with one or more independently selected halo groups (e.g., 1, 2, 3, 4, 5, 6, 7, 8, 9, 10, or more).

"Alkenyl", as used herein, refers to an unbranched or branched hydrocarbon chain containing at least one carbon-carbon double bond. Alkenyl can be used alone, or as part of another radical, such as cycloalkyl-alkenyl. In some embodiments, alkenyl as used herein has 1 to 50 carbon atoms (($C_{1-50}$)alkenyl), 1 to 20 carbon atoms (($C_{1-20}$)alkenyl), 1 to 12 carbon atoms (($C_{1-12}$)alkenyl), 1 to 10 carbon atoms (($C_{1-10}$)alkenyl), 1 to 8 carbon atoms (($C_{1-8}$)alkenyl), 1 to 6 carbon atoms (($C_{1-6}$)alkenyl), or 1 to 4 carbon atoms (($C_{1-4}$)alkenyl). Alkenyl may have one, two, three, four, five, or more carbon-carbon double bonds, as valency permits. When an alkenyl residue having a specific number of carbons is named, all geometric isomers having that number of carbons may be encompassed.

"Cycloalkyl", as used herein, refers to a monocyclic or polycyclic saturated hydrocarbon. In some embodiments, cycloalkyl has 3 to 50 carbon atoms (($C_{3-50}$)cycloalkyl), 3 to 20 carbon atoms (($C_{3-20}$)cycloalkyl), 3 to 12 carbon atoms (($C_{3-12}$)cycloalkyl), 3 to 10 carbon atoms (($C_{3-10}$)cycloalkyl), 3 to 8 carbon atoms (($C_{3-8}$)cycloalkyl), 3 to 6 carbon atoms (($C_{3-6}$)cycloalkyl), or 3 to 5 carbon atoms (($C_{3-4}$)cycloalkyl). Cycloalkyl includes monocyclic and polycyclic groups, such as fused bicycles and spirocycles. In some embodiments, polycyclic groups include fused bicycles, bridged cyclic groups, and spirocycles. Examples of cycloalkyl groups include cyclopropyl, cyclobutyl, cyclopentyl, cyclohexyl, octahydropentalenyl, octahydro-1H-indene, decahydronaphthalene, cubane, bicyclo[3.1.0]hexane, and bicyclo[1.1.1]pentane.

"Halocycloalkyl", as used herein, refers to a cycloalkyl group substituted with one or more independently selected halo groups (e.g., 1, 2, 3, 4, 5, 6, 7, 8, 9, 10, or more).

"Cycloalkenyl", as used herein, refers to a non-aromatic monocyclic or polycyclic hydrocarbon containing at least one carbon-carbon double bond. In some embodiments, cycloalkenyl has 3 to 50 carbon atoms (($C_{3-50}$)cycloalkenyl), 3 to 20 carbon atoms (($C_{3-20}$)cycloalkenyl), 3 to 12 carbon atoms (($C_{3-12}$)cycloalkenyl), 3 to 10 carbon atoms (($C_{3-10}$)cycloalkenyl), 3 to 8 carbon atoms (($C_{3-8}$)cycloalkenyl), 3 to 6 carbon atoms (($C_{3-6}$)cycloalkenyl), or 3 to 5 carbon atoms (($C_{3-4}$)cycloalkenyl). Cycloalkenyl includes monocyclic and polycyclic groups (including fused, bridged, and spirocycles), and may have one, two, three, four, five, or more carbon-carbon double bonds, as valency permits.

"Cycloalkyl-alkyl" refers to a cycloalkyl group (as defined above) connected to an alkyl group (as defined above), wherein the alkyl group is attached to another moiety (such as the core structure of the molecule). Substituted cycloalkyl-alkyl can include one or more additional attachments to substituents at any point of the cycloalkyl or alkyl, as valency permits. The cycloalkyl-alkyl may comprise any combination of cycloalkyl and alkyl groups. In some embodiments, the cycloalkyl has 3 to 50 carbon atoms (($C_{3-50}$)cycloalkyl-alkyl), 3 to 20 carbon atoms (($C_{3-20}$)cycloalkyl-alkyl), 3 to 12 carbon atoms (($C_{3-12}$)cycloalkyl-alkyl), 3 to 10 carbon atoms (($C_{3-10}$)cycloalkyl-alkyl), 3 to 8 carbon atoms ((C$_{3-8}$)cycloalkyl-alkyl), 3 to 6 carbon atoms ((C$_{3-6}$)cycloalkyl-alkyl), or 3 to 5 carbon atoms ((C$_{3-4}$)cycloalkyl-alkyl). In some embodiments, the alkyl has 1 to 50 carbon atoms (cycloalkyl-(C$_{1-50}$)alkyl), 1 to 20 carbon atoms (cycloalkyl-(C$_{1-20}$)alkyl), 1 to 12 carbon atoms (cycloalkyl-(C$_{1-12}$)alkyl), 1 to 10 carbon atoms (cycloalkyl-(C$_{1-10}$)alkyl), 1 to 8 carbon atoms (cycloalkyl-(C$_{1-8}$)alkyl), 1 to 6 carbon atoms (cycloalkyl-(C$_{1-6}$)alkyl), or 1 to 4 carbon atoms (cycloalkyl-(C$_{1-4}$)alkyl). In certain embodiments, the cycloalkyl-alkyl is a (C$_{3-20}$)cycloalkyl(C$_{1-20}$)alkyl, (C$_{3-12}$)cycloalkyl(C$_{1-12}$)alkyl, (C$_{3-10}$)cycloalkyl(C$_{1-10}$)alkyl, (C$_{3-10}$)cycloalkyl(C$_{1-8}$)alkyl, (C$_{3-10}$)cycloalkyl(C$_{1-6}$)alkyl, (C$_{3-6}$)cycloalkyl(C$_{1-8}$)alkyl, (C$_{3-6}$)cycloalkyl(C$_{1-6}$)alkyl, or (C$_{3-6}$)cycloalkyl(C$_{1-4}$)alkyl.

"Carbocyclyl" refers to a monocyclic or polycyclic saturated or unsaturated hydrocarbon. Carbocyclyl includes cycloalkyl, aryl, and non-aromatic unsaturated carbocyclic groups such as cycloalkenyl. In some embodiments, carbocyclyl has 3 to 50 carbon atoms ((C$_{3-50}$)carbocyclyl), 3 to 20 carbon atoms ((C$_{3-20}$)carbocyclyl), 3 to 12 carbon atoms ((C$_{3-12}$)carbocyclyl), 3 to 10 carbon atoms ((C$_{3-10}$)carbocyclyl), 3 to 8 carbon atoms ((C$_{3-8}$)carbocyclyl), 3 to 6 carbon atoms ((C$_{3-6}$)carbocyclyl), or 3 to 5 carbon atoms ((C$_{3-4}$)carbocyclyl).

"Heterocycloalkyl", as used herein, refers to a saturated monocyclic or polycyclic ring containing carbon and at least one heteroatom selected from the group consisting of O, N, and S. The heterocycloalkyl group may comprise 3, 4, 5, 6, 7, 8, 9, 10, 11, 12, or more ring atoms (e.g., be a 3-membered, 4-membered, 5-membered, 6-membered, 7-membered, 8-membered, 9-membered, 10-membered, 11-membered, or 12-membered heterocycloalkyl). The ring atoms may be, for example, atoms of a single ring or atoms of two or more fused rings, a bridged ring, or a spirocycle. Heterocycloalkyl may include groups comprising 1 to 5 ring heteroatoms, 1 to 4 heteroatoms, 1 to 3 ring heteroatoms, 1 or 2 ring heteroatoms, or 1 ring heteroatom, wherein each heteroatom is independently selected from the group consisting of N, O, and S. Each ring S atom, where present, may independently be unoxidized sulfur (e.g., —S—) or a sulfur oxide, such as —S(O)—, or —S(O)$_2$—. In certain examples, a heterocycloalkyl has 2 to 8 ring carbon atoms and with 1 to 3 ring heteroatoms independently selected from N, O, and S. Heterocycloalkyl may include, for example, saturated bridged cyclic structures comprising at least one ring heteroatom (for example, one ring with one heteroatom and a hydrocarbon bridge), and saturated spirocycles comprising at least one ring heteroatom (for example, a two-ring spirocycle with one hydrocarbon ring and one ring comprising one heteroatom). In some embodiments, heterocycloalkyl is connected through an annular carbon atom, wherein the point of attachment of the heterocycloalkyl to another group is a ring carbon atom of the heterocycloalkyl. Examples of heterocycloalkyl include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxinyl, piperidinyl, morpholinyl, thiomorpholinyl, thiomorpholinyl S-oxide, thiomorpholinyl S-dioxide, piperazinyl, azepinyl, oxepinyl, diazepinyl, and tropanyl.

"Haloheterocycloalkyl", as used herein, refers to a heterocycloalkyl group substituted with one or more independently selected halo groups (e.g., 1, 2, 3, 4, 5, 6, 7, 8, 9, 10, or more).

"Heterocycloalkenyl", as used herein, refers to a non-aromatic monocyclic or polycyclic ring containing carbon, at least one heteroatom selected from the group consisting of O, N, and S, and at least one double bond. Each ring S atom, where present, may independently be a sulfur oxide, such as —S(O)—, or —S(O)$_2$—. The heterocycloalkenyl group may comprise 3, 4, 5, 6, 7, 8, 9, 10, 11, 12, or more ring atoms (e.g., be a 3-membered, 4-membered, 5-membered, 6-membered, 7-membered, 8-membered, 9-membered, 10-membered, 11-membered, or 12-membered heterocycloalkenyl). Heterocycloalkenyl may include groups comprising 1 to 5 ring heteroatoms, 1 to 4 heteroatoms, 1 to 3 ring heteroatoms, 1 or 2 ring heteroatoms, or 1 ring heteroatom, wherein each heteroatom is independently selected from the group consisting of N, O, and S. In certain examples, a heterocycloalkenyl has 2 to 8 ring carbon atoms and with 1 to 3 ring heteroatoms independently selected from N, O, and S. In some embodiments, heterocycloalkenyl is connected through an annular carbon atom, wherein the point of attachment of the heterocycloalkenyl to another group is a ring carbon atom of the heterocycloalkenyl. Heterocycloalkenyl may have one, two, three, four, five, or more double bonds, as valency permits, and each double bond independently may be between two ring carbon atoms, two ring heteroatoms, or one ring carbon atom and one ring heteroatom, as valency permits.

"Heterocyclyl" refers to a saturated or unsaturated monocyclic or polycyclic ring containing carbon and at least one heteroatom selected from the group consisting of O, N, and S. Each ring S atom, where present, may independently be a sulfur oxide, such as —S(O)—, or —S(O)$_2$—. Heterocyclyl includes heterocycloalkyl, heteroaryl, and non-aromatic unsaturated heterocyclic groups such as heterocycloalkenyl. The heterocyclyl group may comprise 3, 4, 5, 6, 7, 8, 9, 10, 11, 12, or more ring atoms (e.g., be a 3-membered, 4-membered, 5-membered, 6-membered, 7-membered, 8-membered, 9-membered, 10-membered, 11-membered, or 12-membered heterocyclyl), and may include groups comprising 1 to 5 ring heteroatoms, 1 to 4 heteroatoms, 1 to 3 ring heteroatoms, 1 or 2 ring heteroatoms, or 1 ring heteroatom, wherein each heteroatom is independently selected from the group consisting of N, O, and S. In some embodiments, heterocyclyl is connected through an annular carbon atom, wherein the point of attachment of the heterocyclyl to another group is a ring carbon atom of the heterocyclyl.

"Heterocycloalkyl-alkyl" refers to a heterocycloalkyl group (as defined above) connected to an alkyl group (as defined above), wherein the alkyl group is attached to another moiety (such as the core structure of the molecule). The alkyl group may be attached to the heterocycloalkyl through an annular carbon atom of the heterocycloalkyl, or through an annular heteroatom of the heterocycloalkyl (such as through a ring N atom). Substituted heterocycloalkyl-alkyl can include one or more additional attachments to substituents at any point of the heterocycloalkyl or alkyl, as valency permits. The heterocycloalkyl-alkyl may comprise any combination of heterocycloalkyl and alkyl groups. In some embodiments, the heterocycloalkyl comprises 3, 4, 5, 6, 7, 8, 9, 10, 11, 12, or more ring atoms. The heterocycloalkyl may include groups comprising 1 to 5 ring heteroatoms, 1 to 4 heteroatoms, 1 to 3 ring heteroatoms, 1 or 2 ring heteroatoms, or 1 ring heteroatom, wherein each heteroatom is independently selected from the group consisting of N, O, and S. In some embodiments, the alkyl has 1 to 50 carbon atoms (heterocycloalkyl-(C$_{1-50}$)alkyl), 1 to 20 carbon atoms (heterocycloalkyl-(C$_{1-20}$)alkyl), 1 to 12 carbon atoms (heterocycloalkyl-(C$_{1-12}$)alkyl), 1 to 10 carbon atoms (heterocycloalkyl-(C$_{1-10}$)alkyl), 1 to 8 carbon atoms (heterocycloalkyl-($C_{1-8}$)alkyl), 1 to 6 carbon atoms (heterocycloalkyl-($C_{1-6}$)alkyl), or 1 to 4 carbon atoms (heterocycloalkyl-($C_{1-4}$)alkyl). In certain embodiments, the heterocycloalkyl-alkyl is a (3-20 membered)heterocycloalkyl($C_{1-20}$)alkyl, (3-12 membered)heterocycloalkyl($C_{1-12}$)alkyl, (3-12 membered)heterocycloalkyl($C_{1-10}$)alkyl, (3-10 membered)heterocycloalkyl($C_{1-8}$)alkyl, (3-10 membered)heterocycloalkyl ($C_{1-6}$)alkyl, (3-6 membered)heterocycloalkyl($C_{1-8}$)alkyl, (3-6 membered)heterocycloalkyl($C_{1-6}$)alkyl, or (3-6 membered)heterocycloalkyl($C_{1-4}$)alkyl.

"Aryl", as used herein, refers to a monocyclic or polycyclic radical comprising at least one aromatic hydrocarbon ring. Aryl may include an aromatic hydrocarbon monocyclic or polycyclic radical. Aryl may include groups with a single aromatic ring (e.g., phenyl) and multiple fused aromatic rings (e.g., naphthyl, anthryl). Aryl may also include, for example, a single aromatic hydrocarbon ring fused to a non-aromatic hydrocarbon ring (e.g., 1,2,3,4-tetrahydronaphthalene), or a single aromatic hydrocarbon fused to a non-aromatic ring comprising at least one heteroatom (e.g., 1,2,3,4-tetrahydroisoquinoline). In some embodiments, aryl as used herein has from 6 to 14 annular carbon atoms (($C_{6-14}$)aryl), or 6 to 10 annular carbon atoms (($C_{6-10}$)aryl).

"Aryl-alkyl" refers to an aryl group (as defined above) connected to an alkyl group (as defined above), wherein the alkyl group is attached to another moiety (such as the core structure of the molecule). Substituted aryl-alkyl can include one or more additional attachments to substituents at any point of the aryl or alkyl, as valency permits. The aryl-alkyl may comprise any combination of aryl and alkyl groups. In some embodiments, the aryl has from 6 to 14 annular carbon atoms (($C_{6-14}$)aryl-alkyl), or 6 to 10 annular carbon atoms (($C_{6-10}$)aryl-alkyl). In some embodiments, the alkyl has 1 to 50 carbon atoms (aryl-($C_{1-50}$)alkyl), 1 to 20 carbon atoms (aryl-($C_{1-20}$)alkyl), 1 to 12 carbon atoms (aryl-($C_{1-12}$)alkyl), 1 to 10 carbon atoms (aryl-($C_{1-10}$)alkyl), 1 to 8 carbon atoms (aryl-($C_{1-8}$)alkyl), 1 to 6 carbon atoms (aryl-($C_{1-6}$)alkyl), or 1 to 4 carbon atoms (aryl-($C_{1-4}$)alkyl). In certain embodiments, the aryl-alkyl is a ($C_{6-14}$)aryl($C_{1-20}$)alkyl, ($C_{6-14}$)aryl ($C_{1-12}$)alkyl, ($C_{6-14}$)aryl($C_{1-10}$)alkyl, ($C_{6-14}$)aryl($C_{1-8}$)alkyl, ($C_{6-14}$)aryl($C_{1-6}$)alkyl, ($C_{6-10}$)aryl($C_{1-10}$)alkyl, ($C_{6-10}$)aryl ($C_{1-8}$)alkyl, ($C_{6-10}$)aryl($C_{1-6}$)alkyl, or ($C_{6-10}$)aryl($C_{1-4}$)alkyl.

"Heteroaryl", as used herein, refers to a monocyclic or polycyclic radical comprising at least one aromatic ring, wherein the aromatic ring comprises at least one ring heteroatom independently selected from the group consisting of N, O, and S, (e.g., pyridine, pyrazine, furan, thiophene, quinoline). Each ring S atom, where present, may independently be unoxidized sulfur (e.g., —S—) or a sulfur oxide, such as —S(O)—, or —S(O)$_2$—. Heteroaryl includes polycyclic systems comprising two or more aromatic rings, wherein at least one aromatic ring comprises at least one ring heteroatom selected from N, O, and S. Heteroaryl may include groups comprising 1 to 5 ring heteroatoms, 1 to 4 heteroatoms, 1 to 3 ring heteroatoms, 1 or 2 ring heteroatoms, or 1 ring heteroatom, wherein each heteroatom is independently selected from the group consisting of N, O, and S. In certain examples, a heteroaryl has 3 to 8 ring carbon atoms, with 1 to 3 ring heteroatoms independently selected from N, O, and S. Heteroaryl may comprise 5, 6, 7, 8, 9, 10, 11, 12, or more annular atoms (e.g., be a 3-membered, 4-membered, 5-membered, 6-membered, 7-membered, 8-membered, 9-membered, 10-membered, 11-membered, or 12-membered heteroaryl), wherein the annular atoms are present in one or more rings. Heteroaryl may comprise, for example, 1 to 14 annular carbon atoms (($C_{1-14}$)heteroaryl), 1 to 10 annular carbon atoms (($C_{1-10}$) heteroaryl), 1 to 6 annular carbon atoms (($C_{1-6}$)heteroaryl), 1 to 5 annular carbon atoms (($C_{1-5}$)heteroaryl), or 2 to 5 annular carbon atoms (($C_{2-5}$)heteroaryl). In some embodiments, heteroaryl is connected through an annular carbon atom, wherein the point of attachment of the heteroaryl to another group is a ring carbon atom of the heteroaryl. Examples of heteroaryl groups include pyridyl, pyridazinyl, pyrimidinyl, benzothiazolyl, furanyl, and pyrazolyl.

"Heteroaryl-alkyl" refers to a heteroaryl group (as defined above) connected to an alkyl group (as defined above), wherein the alkyl group is attached to another moiety (such as the core structure of the molecule). Substituted heteroaryl-alkyl can include one or more additional attachments to substituents at any point of the heteroaryl or alkyl, as valency permits. The alkyl group may be attached to the heteroaryl through an annular carbon atom of the heteroaryl, or through an annular heteroatom of the heteroaryl. The heteroaryl-alkyl may comprise any combination of heteroaryl and alkyl groups. The heteroaryl may have 3 to 8 ring carbon atoms, with 1 to 3 ring heteroatoms independently selected from N, O, and S. Heteroaryl may comprise 5, 6, 7, 8, 9, 10, 11, 12, or more annular atoms (e.g., be a 3-membered, 4-membered, 5-membered, 6-membered, 7-membered, 8-membered, 9-membered, 10-membered, 11-membered, or 12-membered heteroaryl), wherein the annular atoms are present in one or more rings. In some embodiments, the alkyl has 1 to 50 carbon atoms (heteroaryl-($C_{1-50}$)alkyl), 1 to 20 carbon atoms (heteroaryl-($C_{1-20}$)alkyl), 1 to 12 carbon atoms (heteroaryl-($C_{1-12}$)alkyl), 1 to 10 carbon atoms (heteroaryl-($C_{1-10}$)alkyl), 1 to 8 carbon atoms (heteroaryl-($C_{1-8}$)alkyl), 1 to 6 carbon atoms (heteroaryl-($C_{1-6}$)alkyl), or 1 to 4 carbon atoms (heteroaryl-($C_{1-4}$)alkyl). In certain embodiments, the heteroaryl-alkyl is a ($C_{1-14}$)heteroaryl($C_{1-20}$)alkyl, ($C_{1-10}$)heteroaryl($C_{1-12}$)alkyl, ($C_{1-6}$)heteroaryl($C_{1-10}$)alkyl, ($C_{1-5}$)heteroaryl($C_{1-8}$)alkyl, ($C_{1-5}$)heteroaryl($C_{1-6}$)alkyl, ($C_{1-5}$)heteroaryl ($C_{1-8}$)alkyl, ($C_{1-5}$)heteroaryl($C_{1-6}$)alkyl, or ($C_{1-5}$)heteroaryl($C_{1-4}$) alkyl.

It should be understood that when a range of values is listed, it is intended to encompass each value and sub-range within the range. For example, "($C_{1-6}$)alkyl" (which may also be referred to as C1-C6 alkyl, $C_1$-$C_6$ alkyl, or C1-6 alkyl) is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Hydroxy", as used herein, refers to the radical —OH.

"Halo", as used herein, refers to fluoro, chloro, bromo, or iodo radicals.

"Cyano" means the radical —CN.

"Oxo", as used herein, refers to the radical =O.

"Optional" or "optionally" means that the subsequently described event or circumstance may or may not occur, and that the description includes instances where the event or circumstance occurs and instances in which it does not.

In some embodiments of the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), is a solvate. In some embodiments, the solvate is a hydrate.

In some embodiments, provided is a pharmaceutically acceptable salt of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi).

"Pharmaceutically acceptable" includes that which is useful in preparing a pharmaceutical composition that is generally safe, non-toxic and not biologically or otherwise undesirable, and includes that which is acceptable for veterinary use as well as human pharmaceutical use. For example, provided herein is a pharmaceutical composition comprising a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, and a pharmaceutically acceptable excipient.

"Pharmaceutically acceptable salt" includes a salt which is generally safe, non-toxic and not biologically or otherwise undesirable, and includes that which is acceptable for veterinary use as well as human pharmaceutical use. Such salts may include acid addition salts and base addition salts. Acid addition salts may be formed with inorganic acid such as, but not limited to, hydrochloric acid, hydrobromic acid, sulfuric acid, nitric acid, phosphoric acid and the like; or an organic acid such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, or undecylenic acid. Salts derived from inorganic bases may include, but are not limited to, sodium, potassium, lithium, ammonium, calcium, magnesium, iron, zinc, copper, manganese, and aluminum salts. Salts derived from organic bases may include, but are not limited to, salts of primary, secondary, or tertiary amines; substituted amines including naturally occurring substituted amines; cyclic amines; ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, or N-ethylpiperidine.

In some embodiments, provided is an isotope of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi).

Unless otherwise stated, structures depicted herein, such as compounds of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, or isomer thereof, are also meant to include compounds which differ only in the presence of one or more isotopically enriched atoms. The compounds herein may contain unnatural proportions of atomic isotopes at one or more of the atoms that constitute such compounds. In some embodiments, the compound is isotopically-labeled, such as an isotopically-labeled compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, or isomer thereof, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{35}S$, $^{18}F$, $^{36}Cl$. Certain isotope labeled compounds (e.g. $^{3}H$ and $^{14}C$) may be useful in compound or substrate tissue distribution study. Incorporation of heavier isotopes such as deuterium ($^{2}H$) may, in some embodiments, afford certain therapeutic advantages resulting from greater metabolic stability, for example, increased in vivo half-life, or reduced dosage requirements.

The compounds disclosed herein, such as compounds of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, or isotope thereof, may contain one or more asymmetric centers and thus may give rise to one or more isomers.

In some embodiments, provided is a tautomer of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi).

In some embodiments of the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, each of $R^8$, $R^9$, and $R^{10}$ is independently selected from the group consisting of hydrogen, $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl, or $R^8$ and $R^9$, together with the nitrogen atom to which they are attached, form a heterocycloalkyl. Each $(C_{1-10})$alkyl, $(C_{3-10})$cycloalkyl, $(C_{3-10})$cycloalkyl$(C_{1-10})$alkyl, heterocycloalkyl (including a heterocycloalkyl formed by $R^8$ and $R^9$) and heterocycloalkyl-alkyl is independently unsubstituted or substituted with one or more substituents independently selected from the group consisting of halo, cyano, oxo, —$OR^{19}$, —$C(O)NR^{19}R^{19}$, —$NR^{19}C(O)R^{19}$, —$NR^{19}C(O)NR^{91}R^{19}$, —$NR^{19}R^{19}$, —$S(O)_2NR^{19}R^{19}$, —$NR^{19}S(O)_2R^{19}$, —$S(O)_{n4}R^{20}$, —$C(O)OR^{19}$, and —$C(O)R^{20}$. In certain embodiments, the one or more substituents are independently selected from the group consisting of halo, —OH, —$O(C_{1-10})$alkyl, —$NR^{19}R^{19}$, and —$C(O)NR^{19}R^{19}$. In some embodiments, the halo is fluoro. In certain embodiments, each $R^{19}$ is independently H or $(C_{1-10})$alkyl, or two $R^{19}$, together with the nitrogen to which they are attached, form a heterocycloalkyl. In certain embodiments, the heterocycloalkyl is a 5-6 membered heterocycloalkyl comprising 1 to 4 heteroatoms independently selected from N, O, and S. In certain embodiments, the heterocycloalkyl of the heterocycloalkyl-alkyl is a 5-6 membered heterocycloalkyl comprising 1 to 4 heteroatoms independently selected from N, O, and S. In other embodiments, $R^8$ and $R^9$, together with the nitrogen atom to which they are attached, form a 5-6 membered heterocycloalkyl comprising 1 to 4 heteroatoms independently selected from N, O, and S. In certain embodiments, each of $R^8$, $R^9$, and $R^{10}$ is independently selected from the group consisting of hydrogen, $(C_{1-10})$alkyl, $(C_{3-6})$cycloalkyl, $(C_{3-6})$cycloalkyl$(C_{1-10})$alkyl, (5-6 membered) heterocycloalkyl, and (5-6 membered) heterocycloalkyl-$(C_{1-10})$alkyl, or $R^8$ and $R^9$, together with the nitrogen atom to which they are attached, form a 5-6 membered heterocycloalkyl comprising 1 to 4 heteroatoms independently selected from N, O, and S.

In some embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, each R is independently hydrogen or $(C_{1-10})$alkyl, such as $(C_{1-8})$alkyl, ($C_{1-6}$)alkyl, or ($C_{1-4}$)alkyl. In other embodiments, each $R^{24}$ is independently ($C_{1-10}$)alkyl, such as ($C_{1-8}$)alkyl, ($C_{1-6}$)alkyl, or ($C_{1-4}$)alkyl. In other embodiments, each $R^{25}$ is independently hydrogen or ($C_{1-10}$)alkyl, such as ($C_{1-8}$)alkyl, ($C_{1-6}$)alkyl, or ($C_{1-4}$)alkyl. In further embodiments, each $R^{30}$ is independently ($C_{1-10}$)alkyl, such as ($C_{1-8}$)alkyl, ($C_{1-6}$)alkyl, or ($C_{1-4}$)alkyl. In certain embodiments, each $R^{27}$ is independently hydrogen or ($C_{1-10}$)alkyl, such as ($C_{1-8}$)alkyl, ($C_{1-6}$)alkyl, or ($C_{1-4}$)alkyl. In other embodiments, each $R^{28}$ is independently ($C_{1-10}$)alkyl, such as ($C_{1-8}$)alkyl, ($C_{1-6}$)alkyl, or ($C_{1-4}$)alkyl. In some embodiments, each $R^{29}$ is independently hydrogen or ($C_{1-10}$)alkyl, such as ($C_{1-8}$)alkyl, ($C_{1-6}$)alkyl, or ($C_{1-4}$)alkyl. In other embodiments, each $R^5$ is independently hydrogen or ($C_{1-10}$)alkyl, such as ($C_{1-8}$)alkyl, ($C_{1-6}$)alkyl, or ($C_{1-4}$)alkyl. In still further embodiments, each $R^6$ is independently ($C_{1-10}$)alkyl, such as ($C_{1-8}$)alkyl, ($C_{1-6}$)alkyl, or ($C_{1-4}$)alkyl. In other embodiments, each $R^7$ is independently hydrogen or ($C_{1-10}$)alkyl, such as ($C_{1-8}$)alkyl, ($C_{1-6}$)alkyl, or ($C_{1-4}$)alkyl. In certain embodiments, any of the foregoing alkyl are independently unsubstituted or substituted with one or more halo. For example, in some embodiments any of the foregoing alkyl are independently unsubstituted or substituted with one, two, or three halo. In some embodiments, the halo is independently fluoro or chloro.

In some embodiments of Formula (X), (X-A), (X-Ai), (X-B), (X-Bi), (Z), (Z-A), (Z-Ai), (Z-B), or (Z-Bi), or a pharmaceutically acceptable salt, solvate, tautomer, isotope, or isomer thereof, $R^1$ is —C(O)OR$^9$, —C(O)NR$^8$R$^9$, —S(O)$_2$ NR$^8$R$^9$, —NR$^{10}$C(O)NR$^8$R$^9$, —NR$^{10}$C(O)R$^9$, —NR$^{10}$S(O)$_2$R$^9$, —OR$^{26}$, —SR$^9$, —S(O)R$^9$, —S(O)$_2$R$^9$, —NR$^8$R$^9$, —NR$^{10}$C(O)OR$^9$, —C(O)R$^{26}$, —NR$^{10}$S(O)$_2$NR$^8$R$^9$, or —C(O)NR$^{10}$S(O)$_2$R$^9$. In some embodiments, $R^1$ is —C(O)R$^{26}$, —NR$^{10}$S(O)$_2$NR$^8$R$^9$, or —C(O)NR$^{10}$S(O)$_2$R$^9$.

In some embodiments of Formula (X), (X-A), (X-Ai), (X-B), (X-Bi), (Z), (Z-A), (Z-Ai), (Z-B), or (Z-Bi), or a pharmaceutically acceptable salt, solvate, tautomer, isotope, or isomer thereof, $R^1$ is —NR$^{10}$S(O)$_2$NR$^8$R$^9$. In some embodiments, $R^{10}$ is hydrogen. In certain embodiments, $R^8$ and $R^9$ are independently hydrogen or ($C_{1-10}$)alkyl. In some embodiments, $R^8$ is hydrogen and $R^9$ is ($C_{1-10}$)alkyl, for example isopropyl. In other embodiments, $R^9$ is —C(O)NR$^{10}$S(O)$_2$R$^9$. In certain embodiments, $R^{10}$ is hydrogen. In certain embodiments, $R^9$ is hydrogen, ($C_{1-10}$)alkyl, or ($C_{3-10}$)cycloalkyl. In some embodiments, $R^{10}$ is hydrogen and $R^9$ is ($C_{3-10}$)cycloalkyl, for example cyclopropyl. In still other embodiments, $R^1$ is —C(O)R$^{26}$. In certain of these embodiments, $R^{26}$ is ($C_{1-10}$)alkyl or ($C_{3-10}$)cycloalkyl, wherein the alkyl or cycloalkyl is unsubstituted or substituted as described in Formula (X). In certain embodiments, $R^1$ is —C(O)R$^{26}$, wherein $R^{26}$ is ($C_{3-10}$)cycloalkyl, such as cyclohexyl.

Thus, in some embodiments, $R^1$ is:

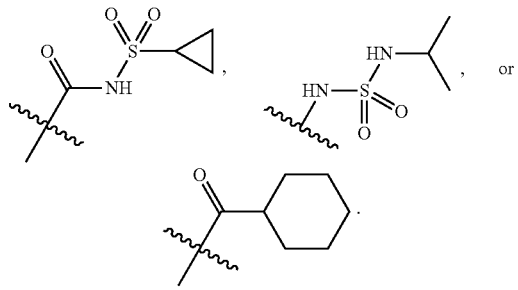

In some embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^1$ is —C(O)NR$^8$R$^9$, —S(O)$_2$NR$^8$R$^9$, —NR$^{10}$C(O)NR$^8$R$^9$, —NR$^{10}$C(O)R, —NR$^{10}$C(O)OR$^9$, or —NR$^{10}$S(O)$_2$R$^9$. In some embodiments, $R^1$ is —NR$^{10}$C(O)NR$^8$R$^9$. In other embodiments, $R^1$ is —NR$^{10}$C(O)OR$^9$. In still further embodiments, $R^1$ is —NR$^{10}$S(O)$_2$R$^9$. In any of these embodiments, $R^{10}$ may be H. Thus, in some embodiments, $R^1$ is —NHC(O)NR$^8$R$^9$, —NHC(O)R$^9$, —NHC(O)OR$^9$, or —NHS(O)$_2$R$^9$.

In certain embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^8$ and $R^9$, together with the nitrogen atom to which they are attached, form an unsubstituted or substituted heterocycloalkyl. In certain embodiments, the heterocycloalkyl is a 5-membered or 6-membered ring. In particular embodiments, $R^8$ and $R^9$, together with the nitrogen atom to which they are attached form an unsubstituted or substituted piperidinyl. In some of these embodiments, $R^1$ is —C(O)NR$^8$R$^9$, —S(O)$_2$NR$^8$R$^9$, or —NR$^{10}$C(O)NR$^8$R$^9$.

In certain embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, R is —C(O)NR$^8$R$^9$, and $R^8$ and $R^9$, together with the nitrogen atom to which they are attached, form an unsubstituted or substituted heterocycloalkyl. In some embodiments, the heterocycloalkyl is a 4-membered to 8-membered heterocycloalkyl, which is unsubstituted or substituted with one or more substituents selected from the group consisting of halo, oxo, —OR$^{23}$, ($C_{1-10}$)alkyl, —NR$^{23}$C(O)OR$^{23}$, —NR$^{23}$R$^{23}$, —C(O)OR$^{23}$, and —C(O)NR$^{23}$R$^{23}$. For example, in some embodiments the heterocycloalkyl is a substituted or unsubstituted ring, spirocycle, or bridged ring. In some embodiments, the heterocycloalkyl comprises, in addition to the nitrogen atom to which R$^8$ and R$^9$ are both connected, one or two additional heteroatoms selected from the group consisting of O, N, and S. In some embodiments, the heterocycloalkyl is a 5-membered or 6-membered ring, which is unsubstituted or substituted with one or more substituents selected from the group consisting of halo, —OR$^{23}$, ($C_{1-10}$)alkyl, —NR$^{23}$C(O)OR$^{23}$, —NR$^{23}$R$^{23}$, —C(O)OR$^{23}$, and —C(O)NR$^{23}$R$^{23}$. In some embodiments, the halo is fluoro. In certain embodiments, each ($C_{1-10}$)alkyl is independently unsubstituted or substituted with one or more substituents independently selected from the group consisting of halo and —OR$^{31}$. In some embodiments, each $R^{31}$ is independently hydrogen or alkyl. In some embodiments, the ($C_{1-10}$)alkyl is substituted with —OH. In certain embodiments, each $R^{23}$ is independently H or ($C_{1-10}$)alkyl, or two $R^{23}$, together with the nitrogen atom to which they are attached, form a heterocycloalkyl group. In some embodiments, $R^8$ and $R^9$, together with the nitrogen atom to which they are attached form an unsubstituted or substituted piperidinyl. In certain embodiments, the piperidinyl is unsubstituted. In other embodiments, the piperidinyl is substituted with one or more substituents independently selected from the group consisting of —OR$^{23}$, ($C_{1-10}$)alkyl, —C(O)OR$^{23}$, and —NR$^{23}$C(O)OR$^{23}$. For example, the piperidinyl may be substituted with one or two substituents independently selected from the group consisting of —OR$^{23}$, ($C_{1-10}$)alkyl, and —NR$^{23}$C(O)OR$^{23}$. In some embodiments, $R^{23}$ is independently H or ($C_{1-10}$)alkyl, such as ($C_{1-8}$)alkyl, ($C_{1-6}$)alkyl, or ($C_{1-4}$)alkyl. In certain embodiments, the piperidinyl is substituted with one or two substituents independently selected from the group consisting of —O(C$_{1-10}$)alkyl, —OH, (C$_{1-10}$)alkyl, —C(O)OH, and —NHC(O)O(C$_{1-10}$) alkyl. In some embodiments, the piperidinyl is substituted with one or two substituents independently selected from the group consisting of —OH, methyl, ethyl, propyl, butyl, —C(O)OH, and —NHC(O)O-tert-butyl. In some embodiments, the piperidinyl is substituted with one —OH. In still further embodiments, R$^8$ and R$^9$, together with the nitrogen atom to which they are attached form a 4-, 5-, 6-, 7-, or 8-membered heterocycloalkyl comprising one nitrogen ring atom, wherein the heterocycloalkyl is unsubstituted or substituted. In some embodiments, the heterocycloalkyl is substituted with one or more substituents (such as one to five) independently selected from the group consisting of halo, oxo, —OR$^{23}$, (C$_{1-10}$)alkyl, —C(O)OR$^{23}$, and —NR$^{23}$C(O)OR$^{23}$. In some embodiments, each halo is fluoro. In some embodiments, each (C$_{1-10}$)alkyl is independently unsubstituted or substituted with one or more —OH. In some embodiments the heterocycloalkyl is substituted with one or more substituents (such as one to five) independently selected from the group consisting of fluoro, —OH, and (C$_{1-10}$)alkyl, wherein each (C$_{1-10}$)alkyl is independently unsubstituted or substituted with one or more —OH. In still further embodiments, each (C$_{1-10}$)alkyl is independently methyl, ethyl, propyl, or butyl, each of which is independently unsubstituted or substituted with one or two —OH.

Thus, for example, R$^1$ may be:

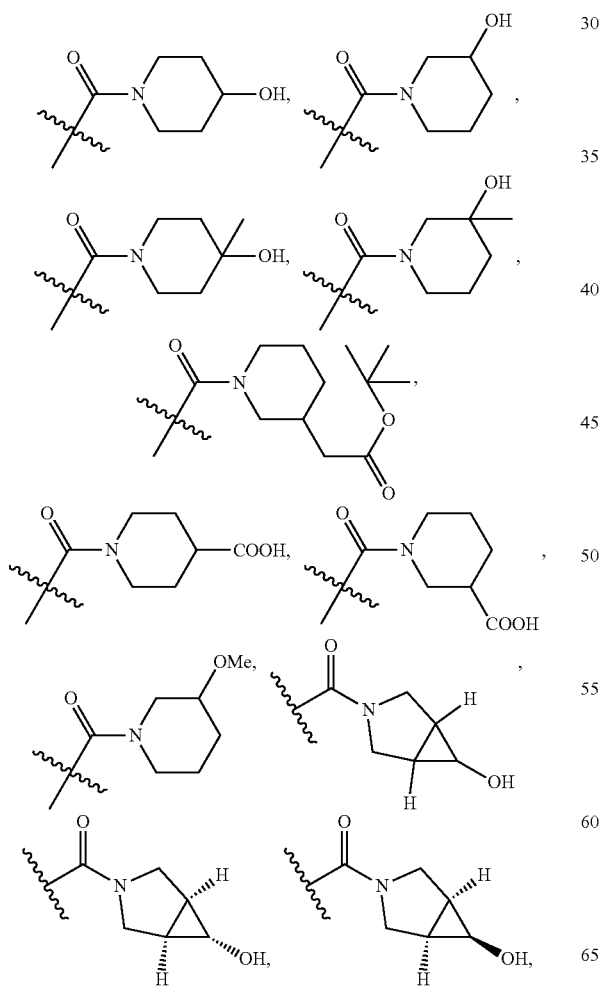

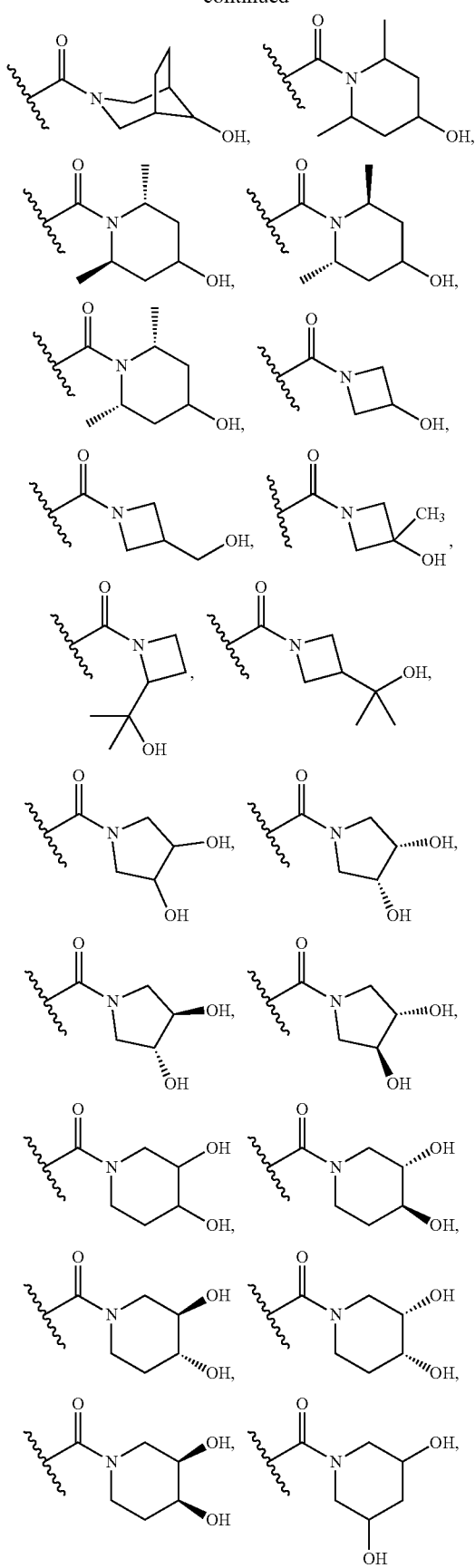

-continued

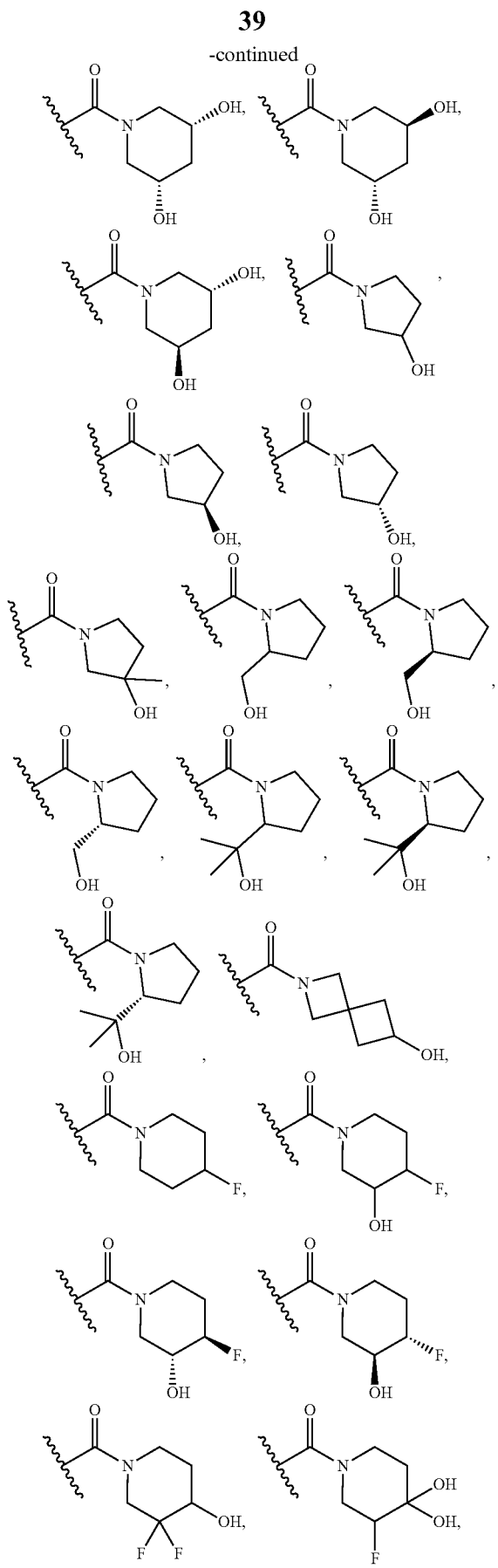

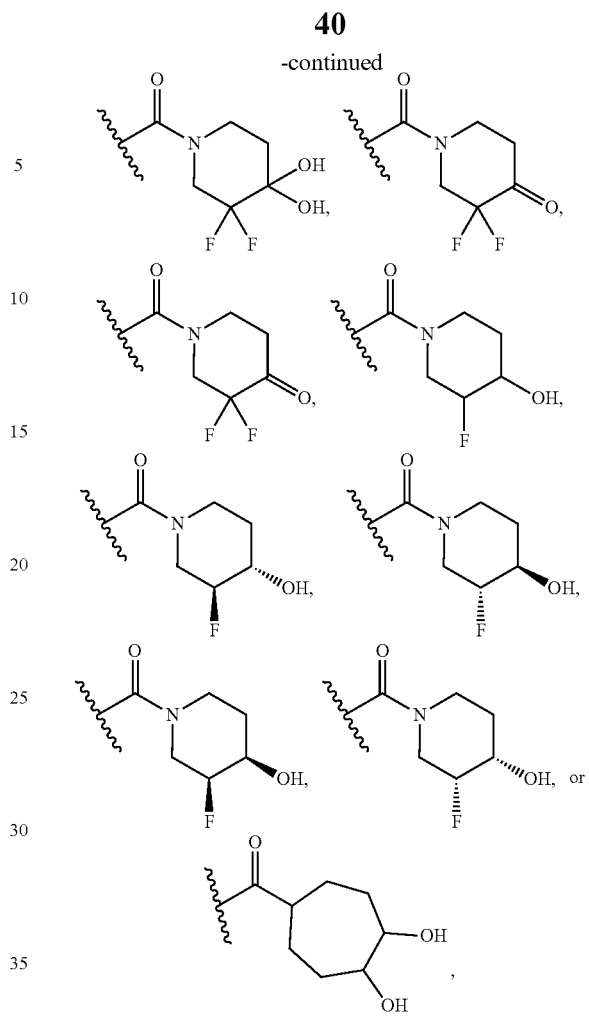

In other embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^1$ is —C(O)NR$^8$R$^9$, and $R^8$ and $R^9$ are both hydrogen. In still further embodiments, $R^8$ is hydrogen, and $R^9$ is $(C_{1-10})$alkyl, wherein the alkyl is unsubstituted or substituted. For example, in some embodiments the alkyl is unsubstituted or substituted with one or more substituents independently selected from the group consisting of halo, cyano, oxo, —OR$^{19}$, —NR$^{19}$R$^{19}$, —S(O)$_{n4}$R$^{20}$, —C(O)OR$^{19}$, and —C(O)R$^{20}$. In some embodiments, the alkyl is unsubstituted or substituted with one or more substituents selected from the group consisting of —OH, —NH, and —C(O)OH. Thus, in certain embodiments, $R^1$ is:

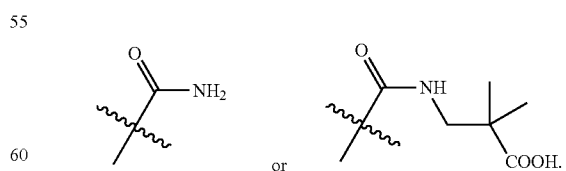

In certain embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^1$ is —NR$^{10}$C(O)NR$^8$R$^9$, wherein $R^8$ and $R^9$ are independently selected from the group consisting of hydrogen, $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl; or $R^8$ and $R^9$, together with the nitrogen atom to which they are attached, form a heterocycloalkyl. In some embodiments, the heterocycloalkyl is a 5-membered or 6-membered ring. In some embodiments, $R^8$ and $R^9$, together with the nitrogen atom to which they are attached form an unsubstituted or substituted piperidinyl. In some embodiments, $R^8$ is hydrogen and $R^9$ is hydrogen, $(C_{1-10})$alkyl, $(C_{3-10})$cycloalkyl, $(C_{3-10})$cycloalkyl$(C_{1-10})$alkyl, heterocycloalkyl, or heterocycloalkyl-alkyl. In some embodiments, the heterocycloalkyl is a 5- to 7-membered heterocycloalkyl, or the heterocycloalkyl-alkyl is a (5- to 7-membered)heterocycloalkyl-$(C_{1-10})$alkyl. The $(C_{1-10})$alkyl, $(C_{3-10})$cycloalkyl, $(C_{3-10})$cycloalkyl$(C_{1-10})$alkyl, heterocycloalkyl, or heterocycloalkyl-alkyl of $R^9$, or the heterocycloalkyl formed by $R^8$ and $R^9$, may be unsubstituted or substituted, for example with one or more substituents independently selected from the group consisting of —$OR^{23}$, $(C_{1-10})$alkyl, and —$NR^{23}C(O)OR^{23}$. In certain embodiments, one or two substituents are independently selected from the group consisting of —$OR^{23}$, $(C_{1-10})$alkyl, and —$NR^{23}C(O)OR^{23}$. In some embodiments, $R^{23}$ is independently H or $(C_{1-10})$alkyl, such as $(C_{1-8})$alkyl, $(C_{1-6})$alkyl, or $(C_{1-4})$alkyl. In certain embodiments, the piperidinyl is substituted with one or two —OH or —$CH_3$. In some embodiments, the piperidinyl is substituted with one —OH.

Thus, for example, $R^1$ may be:

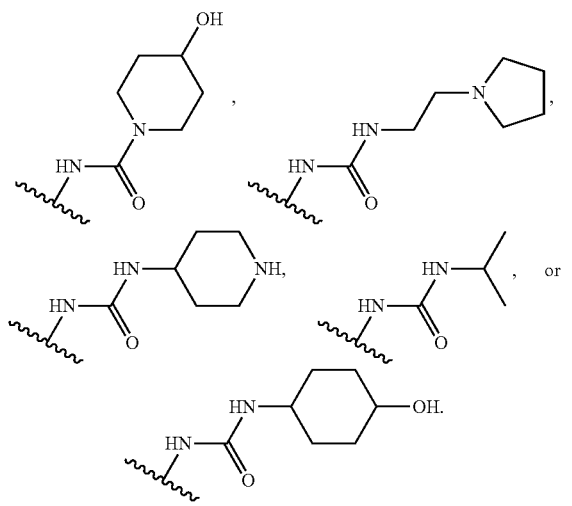

In certain embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^1$ is —$NR^{10}C(O)OR^9$, wherein $R^9$ is hydrogen, $(C_{1-10})$alkyl, $(C_{3-10})$cycloalkyl, $(C_{3-10})$cycloalkyl$(C_{1-10})$alkyl, heterocycloalkyl, or heterocycloalkyl-alkyl. In some embodiments, the heterocycloalkyl is a 5- to 7-membered heterocycloalkyl, or the heterocycloalkyl-alkyl is a (5- to 7-membered)heterocycloalkyl-$(C_{1-10})$alkyl. The $(C_{1-10})$alkyl, $(C_{3-10})$cycloalkyl, $(C_{3-10})$cycloalkyl$(C_{1-10})$alkyl, heterocycloalkyl, or heterocycloalkyl-alkyl of $R^9$, may be unsubstituted or substituted, for example with one or more substituents independently selected from the group consisting of —$OR^{23}$, $(C_{1-10})$alkyl, and —$NR^{23}C(O)OR^{23}$. In certain embodiments, $R^9$ is substituted with one or two substituents independently selected from the group consisting of —$OR^{23}$, $(C_{1-10})$alkyl, and —$NR^{23}C(O)OR^{23}$. In some embodiments, $R^{23}$ is independently H or $(C_{1-10})$alkyl, such as $(C_{1-8})$alkyl, $(C_{1-6})$alkyl, or $(C_{1-4})$alkyl. In certain embodiments, the piperidinyl is substituted with one or two —OH or —$CH_3$. In some embodiments, the piperidinyl is substituted with one —OH. In some embodiments, $R^{10}$ is hydrogen or $(C_{1-10})$alkyl, such as methyl, ethyl, propyl, or butyl.

Thus, for example, in some embodiments, $R^1$ is:

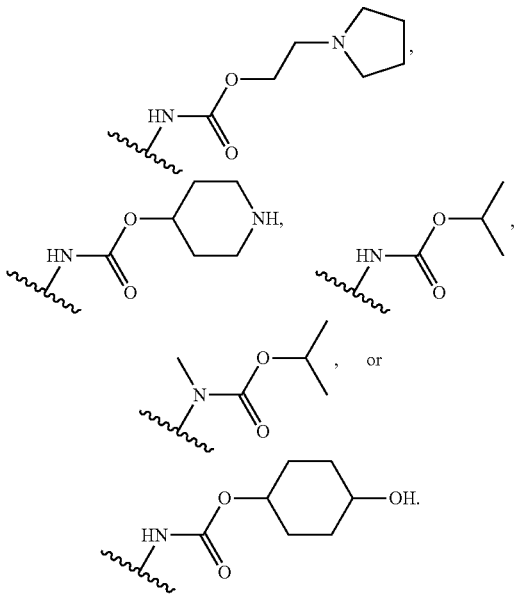

In certain embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^1$ is —$S(O)_2NR^8R^9$. In some embodiments, $R^8$ and $R^9$ are independently selected from the group consisting of hydrogen, $(C_{1-10})$alkyl, and $(C_{3-10})$cycloalkyl; or $R^8$ and $R^9$, together with the nitrogen atom to which they are attached, form a heterocycloalkyl. In some embodiments, the alkyl, cycloalkyl, or heterocycloalkyl are independently substituted with one or more —$OR^{23}$, halo, oxo, or —$NR^{19}R^{19}$ substituents. In some embodiments, the alkyl, cycloalkyl, or heterocycloalkyl are independently substituted with one or more —$OR^{23}$ or halo substituents. In other embodiments, $R^1$ is —$NR^{10}S(O)_2R^9$. In some embodiments, $R^{10}$ and $R^9$ are selected from the group consisting of hydrogen, $(C_{1-10})$alkyl, and $(C_{3-10})$cycloalkyl. In certain embodiments, $R^{10}$ is hydrogen. In some embodiments, the alkyl, cycloalkyl, or heterocycloalkyl are independently substituted with one or more —$OR^{23}$ or halo substituents. In other embodiments, $R^8$ and $R^9$ are both hydrogen. In still further embodiments, $R^{10}$ is $(C_{1-10})$alkyl, such as $(C_{1-6})$alkyl, or $(C_{1-4})$alkyl, such as methyl, ethyl, or propyl.

Thus, for example, in some embodiments, $R^1$ is:

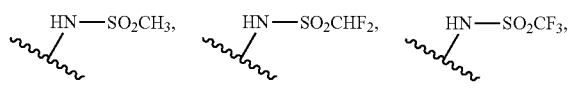

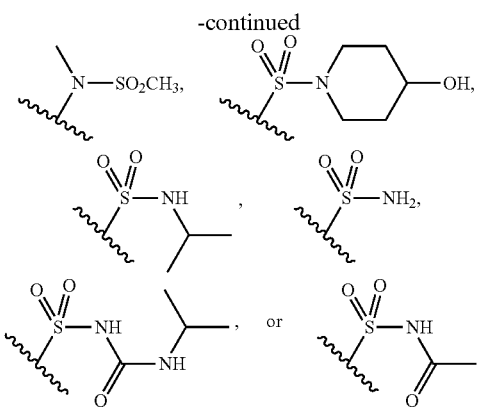

In still further embodiments of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $R^1$ is —C(O)OR$^9$. In some embodiments, $R^9$ is hydrogen, $(C_{1-10})$alkyl, or $(C_{3-10})$cycloalkyl. In some embodiments, $R^1$ is —C(O)OH, or —C(O)OCH$_3$.

In still other embodiments of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, $R^1$ is —NR$^8$R$^9$. In some embodiments, each $R^8$ and $R^9$ are independently hydrogen, $(C_{1-10})$alkyl, or $(C_{3-10})$cycloalkyl, wherein each alkyl and cycloalkyl is independently unsubstituted or substituted. In other embodiments, $R^8$ and $R^9$, together with the nitrogen atom to which they are attached, form a substituted or unsubstituted heterocycloalkyl. In some embodiments, the heterocycloalkyl is a 4- to 10-membered, 4- to 8-membered, 4- to 6-membered, or 5- or 6-membered heterocycloalkyl. In certain embodiments, the heterocycloalkyl comprises, in addition to the nitrogen atom to which $R^8$ and $R^9$ are attached, one or two heteroatoms independently selected from the group consisting of O, S, and N. For example, in some embodiments $R^8$ and $R^9$ form a 5- or 6-membered heterocycloalkyl comprising, in addition to the nitrogen to which $R^8$ and $R^9$ are attached, one O or one S ring atom. In some embodiments, wherein the heterocycloalkyl comprises an S ring atom, the S is in an oxidized state and forms —SO$_2$. In certain embodiments, the heterocycloalkyl is unsubstituted. In other embodiments, the heterocycloalkyl is substituted with one or more substituents selected from the group consisting of halo, oxo, and $(C_{1-10})$alkyl, wherein each alkyl is independently unsubstituted or substituted with one or more substituents selected from the group consisting of halo, —OH, —O(C$_{1-10}$)alkyl, and —O(C$_{1-10}$)haloalkyl. Thus, in some embodiments, $R^1$ is:

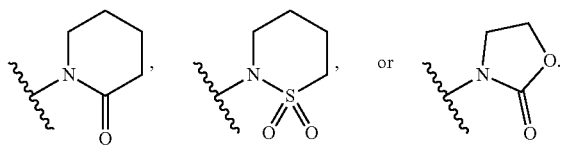 [SMILES: *N1CCCCC1=O ; *N1CCCCS1(=O)=O ; *N1CCOC1=O]

In still further embodiments of a compound of Formula (X), (X-A), (X-Ai), (X-B), or (X-Bi), or a pharmaceutically acceptable salt, solvate, tautomer, isotope, or isomer thereof, $R^1$ is —C(O)NR$^{10}$NR$^8$R$^9$. In some embodiments, $R^{10}$ is hydrogen or $(C_{1-10})$alkyl. In certain embodiments, $R^{10}$ is hydrogen. In other embodiments, $R^{10}$ is $(C_{1-10})$alkyl, such as $(C_{1-4})$alkyl, for example methyl or ethyl. In some embodiments, each of $R^8$ and $R^9$ are independently hydrogen, $(C_{1-10})$alkyl, or $(C_{3-10})$cycloalkyl, wherein each alkyl or cycloalkyl is unsubstituted or substituted. In some embodiments, the $(C_{1-10})$alkyl is $(C_{1-6})$alkyl, or $(C_{1-4})$alkyl. In certain embodiments, the $(C_{3-10})$cycloalkyl is $(C_{3-6})$cycloalkyl, such as cyclopropyl, cyclobutyl, cyclopentyl, or cyclohexyl. In some embodiments, the $(C_{1-10})$alkyl is methyl, ethyl, or propyl (such as isopropyl or n-propyl). In certain embodiments, each alkyl and cycloalkyl is independently unsubstituted or substituted with one or more substituents. In some embodiments, the substituents are selected from the group consisting of $(C_{1-10})$alkyl, halo, oxo, and —OR$^{19}$. In some embodiments, each $R^{19}$ is independently hydrogen, $(C_{1-10})$alkyl (such as $(C_{1-6})$alkyl, or $(C_{1-4})$alkyl), or $(C_{1-10})$haloalkyl (such as $(C_{1-6})$haloalkyl, or $(C_{1-4})$haloalkyl). In other embodiments, $R^8$ and $R^9$ together with the nitrogen with which they are attached form a heterocycloalkyl, which may be unsubstituted or substituted. In some embodiments, the heterocycloalkyl is a 5- to 8-membered heterocycloalkyl. In some embodiments, the heterocycloalkyl comprises one to three heteroatoms, in addition to the nitrogen attached to $R^8$ and $R^9$, selected from the group consisting of O, N, and S. In certain embodiments, the heterocycloalkyl is substituted with one or more substituents selected from the group consisting of $(C_{1-10})$alkyl (such as $(C_{1-6})$alkyl, or $(C_{1-4})$alkyl), halo, and —OR$^{23}$. In some embodiments, each $(C_{1-10})$alkyl is unsubstituted or substituted, for example with one or more halo or —OH, or a combination thereof. In some embodiments, each $R^{23}$ is independently hydrogen or $(C_{1-10})$alkyl (such as $(C_{1-6})$alkyl, or $(C_{1-4})$alkyl). Thus, in certain embodiments, $R^1$ is:

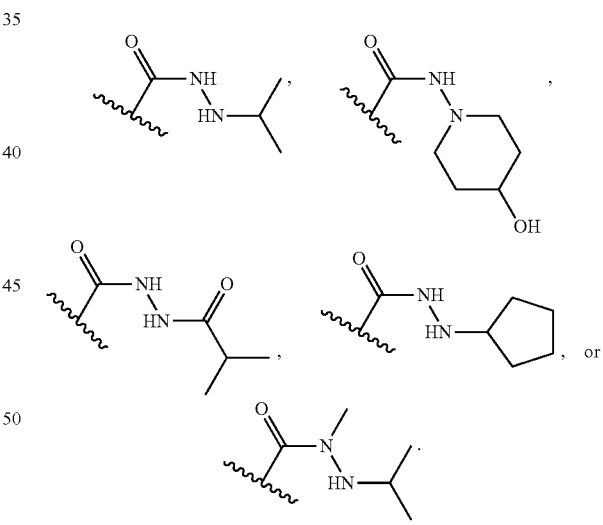

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $R^3$ is hydrogen, $(C_{1-10})$alkyl, or $(C_{3-10})$cycloalkyl. In certain embodiments, the $(C_{1-10})$alkyl or $(C_{3-10})$cycloalkyl is substituted with one or more halo. In some embodiments, the one or more halo is one, two, or three halo. In certain embodiments, the one or more halo is two or three halo. In some embodiments, $R^3$ is hydrogen or cyclopropyl. In certain embodiments, $R^3$ is hydrogen. In other embodiments, $R^3$ is methyl. In some embodiments, $R^3$ is halo, for example chloro or fluoro. In some embodiments, $R^2$ is hydrogen, halo, $(C_{1-10})$alkyl, $(C_{3-10})$cycloalkyl, or —$OR^{25}$. In certain embodiments, the $(C_{1-10})$alkyl or $(C_{3-10})$cycloalkyl is substituted with one or more halo. In some embodiments, the $(C_{1-10})$alkyl or $(C_{3-10})$cycloalkyl is substituted with one, two, or three halo. In some embodiments, the $(C_{1-10})$alkyl or $(C_{3-10})$cycloalkyl is substituted with two or three halo. In some embodiments, $R^2$ is chloro, fluoro, or propyl. In some embodiments, $R^2$ is methyl. In some embodiments, $R^2$ is chloro or fluoro. In certain embodiments, $R^3$ is hydrogen and $R^2$ is chloro. In certain embodiments, both of $R^2$ and $R^3$ are independently halo. In certain embodiments, $R^2$ and $R^3$ are independently hydrogen, halo, or $(C_{1-10})$alkyl, wherein the alkyl is unsubstituted or substituted with one or more halo. In certain embodiments, $R^2$ and $R^3$ are independently hydrogen, halo, or unsubstituted $(C_{1-10})$alkyl. In certain embodiments, $R^2$ and $R^3$ are independently hydrogen, chloro, or methyl. In some embodiments, $R^3$ is hydrogen, and $R^2$ is halo or $(C_{1-10})$alkyl, wherein the alkyl is unsubstituted or substituted with one or more halo. In other embodiments, $R^3$ is hydrogen, and $R^2$ is chloro or methyl.

In certain embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, wherein one or both of $R^2$ and $R^3$ is —$OR^{25}$, the $R^{25}$ is independently selected from the group consisting of $(C_{1-10})$alkyl, $(C_{3-10})$cycloalkyl, $(C_{3-10})$cycloalkyl$(C_{1-10})$alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo.

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, each of $X^1$, $X^2$, $X^3$, and $X^4$ are $CR^4$, and

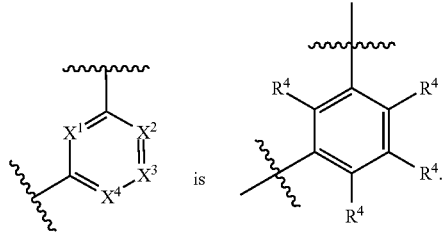

In other embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, each of $X^2$, $X^3$ and $X^4$ are $CR^4$; $X^1$ is N; and

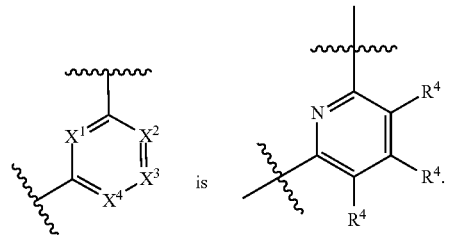

In certain embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, each of $X^1$, $X^3$ and $X^4$ are $CR^4$; $X^2$ is N; and

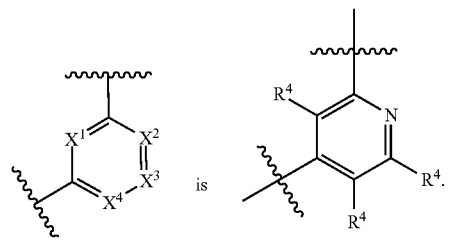

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, each of $X^1$, $X^2$, and $X^4$ are $CR^4$; $X^3$ is N; and

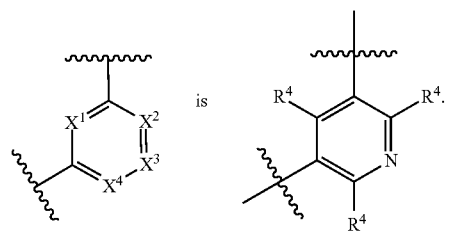

In other embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (—Bi), or a pharmaceutically acceptable salt, solvate, tautomer, isotope, or isomer thereof, each of $X^1$, $X^2$, and $X^3$ are $CR^4$; $X^4$ is N; and

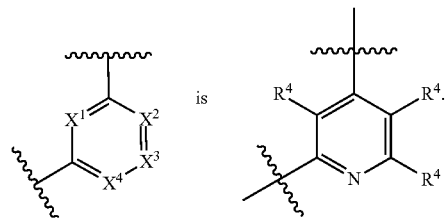

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^1$ and $X^4$ are $CR^4$, $X^2$ and $X^3$ are N; and

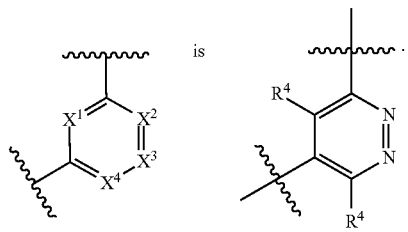

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^1$ and $X^2$ are $CR^4$, $X^3$ and $X^4$ are N, and

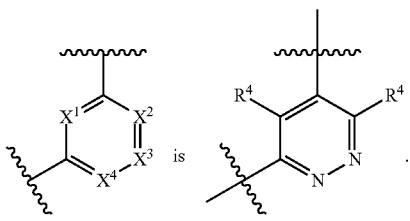

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^2$ and $X^3$ are $CR^4$, $X^1$ and $X^4$ are N, and

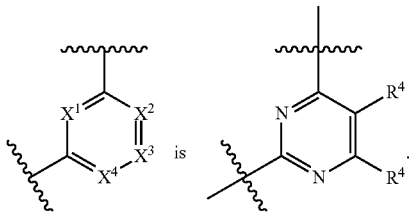

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^3$ and $X^4$ are $CR^4$, $X^1$ and $X^2$ are N, and

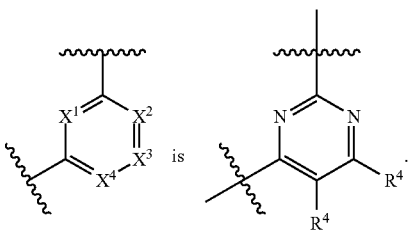

In other embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^1$ and $X^3$ are $CR^4$, $X^2$ and $X^4$ are N, and

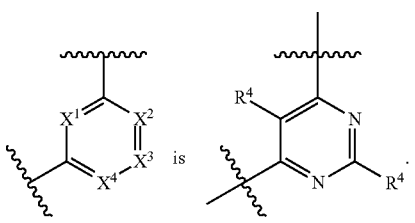

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^2$ and $X^4$ are $CR^4$, $X^1$ and $X^3$ are N, and

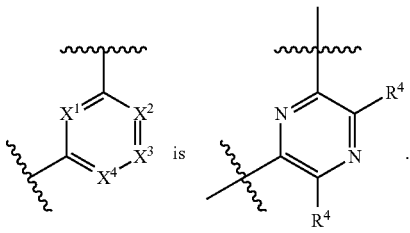

In some embodiments of any of the compounds provided herein, such as a compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, $X^3$ is $CR^4$; each of $X^1$, $X^2$, and $X^4$ are N; and

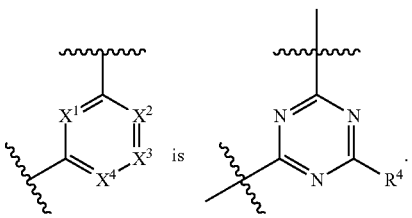

In some embodiments, when at least one of $X^1$, $X^2$, $X^3$ and $X^4$ is N, each $R^4$ is independently selected from the group consisting of hydrogen, halo, cyano, $(C_{1-10})$alkyl, and ($C_{3-10}$)cycloalkyl. In certain embodiments, the ($C_{1-10}$)alkyl or ($C_{3-10}$)cycloalkyl are independently unsubstituted or substituted with one or more halo. In some embodiments, the ($C_{1-10}$)alkyl or ($C_{3-10}$)cycloalkyl are substituted with one, two, or three halo. In some embodiments, the ($C_{1-10}$)alkyl or ($C_{3-10}$)cycloalkyl are substituted with two or three halo. In some embodiments, the ($C_{1-10}$)alkyl is substituted with one or more halo. In certain embodiments, the ($C_{1-10}$)alkyl is substituted with one, two, or three halo. In some embodiments, ($C_{1-10}$)alkyl is substituted with one halo. In certain embodiments, each $R^4$ is independently hydrogen, fluoro, chloro, cyano, methyl, ethyl, or propyl.

In some embodiments, when each of $X^1$, $X^2$, $X^3$ and $X^4$ is $CR^4$, each $R^4$ is independently selected from the group consisting of hydrogen, halo, cyano, ($C_{1-10}$)alkyl, —$NR^{27}R^{27}$, and ($C_{3-10}$)cycloalkyl. In certain embodiments, the ($C_{1-10}$)alkyl or ($C_{3-10}$)cycloalkyl are independently unsubstituted or substituted with one or more halo. In certain embodiments, the ($C_{1-10}$)alkyl or ($C_{3-10}$)cycloalkyl are independently unsubstituted or substituted with one, two, or three halo. In some embodiments, the ($C_{1-10}$)alkyl is substituted with one or more halo. In certain embodiments, the ($C_{1-10}$)alkyl is substituted with one, two, or three halo. In certain embodiments, halo is fluoro or chloro. In other embodiments, each $R^{27}$ is H or ($C_{1-10}$)alkyl, such as ($C_{1-8}$)alkyl, ($C_{1-6}$)alkyl, or ($C_{1-4}$)alkyl; or two $R^{27}$, together with the nitrogen atom to which they are attached, form heterocycloalkyl. In certain embodiments, each $R^4$ is independently hydrogen, fluoro, chloro, cyano, methyl, ethyl, propyl, —$NH_2$, or —$N(CH_3)_2$.

In certain embodiments, wherein at least one of $X^2$, $X^3$ and $X^4$ is N, an adjacent annular carbon is bonded to $R^4$, and the $R^4$ is halo, the halo is iodo or fluoro. In certain embodiments, the halo is fluoro. In some embodiments, wherein at least one of $X^2$, $X^3$ and $X^4$ is N, and an adjacent annular carbon is bonded to $R^4$, the $R^4$ is independently hydrogen, fluoro, cyano, ($C_{1-10}$)alkyl, or —$OR^{27}$.

In still further embodiments, two $R^4$ on adjacent annular carbon atoms together with the carbon atoms to which they are attached form a carbocyclyl, wherein the carbocyclyl is unsubstituted or substituted with one or more substituents independently selected from the group consisting of halo, cyano, ($C_{1-10}$)alkyl, ($C_{3-10}$)cycloalkyl, ($C_{3-10}$)cycloalkyl($C_{1-10}$)alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$S(O)_2NR^{27}R^{27}$, —$NR^{27}S(O)_2R^{27}$, —$S(O)_{n8}R^{28}$, and —$C(O)R^{28}$. For example, two $R^4$ on adjacent annular carbon atoms together with the carbon atoms to which they are attached may form a 5-membered or 6-membered carbocyclyl which is fused to the 6-membered ring formed by $X^1$, $X^2$, $X^3$, and $X^4$, wherein the carbocyclyl is unsubstituted or substituted. In some embodiments, the carbocyclyl is aromatic. In other embodiments, the carbocyclyl is not aromatic.

In other embodiments, two $R^4$ on adjacent annular carbon atoms together with the carbon atoms to which they are attached form a heterocarbocyclyl, wherein the heterocarbocyclyl is unsubstituted or substituted with one or more substituents independently selected from the group consisting of halo, cyano, ($C_{1-10}$)alkyl, ($C_{3-10}$)cycloalkyl, ($C_{3-10}$)cycloalkyl($C_{1-10}$)alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, and —$C(O)R^{28}$. For example, two $R^4$ on adjacent annular carbon atoms together with the carbon atoms to which they are attached may form a 5-membered or 6-membered heterocyclyl which is fused to the 6-membered ring formed by $X^1$, $X^2$, $X^3$, and $X^4$, wherein the heterocarbocyclyl is unsubstituted or substituted. In some embodiments, the heterocyclyl is aromatic. In other embodiments, the heterocyclyl is not aromatic. In certain embodiments, the heterocyclyl is comprises 1 to 3 heteroatoms independently selected from the group consisting of O, N, and S. In certain embodiments, the heterocyclyl is a 5- or 6-membered heterocyclyl comprising 1 to 2 heteroatoms independently selected from the group consisting of O and N.

Thus, for example, in some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof:

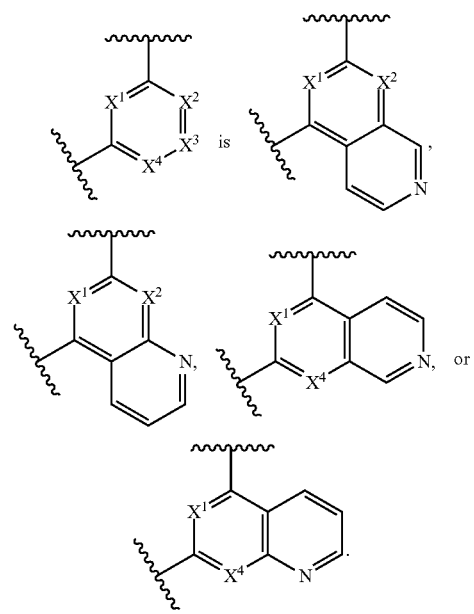

In certain embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof:

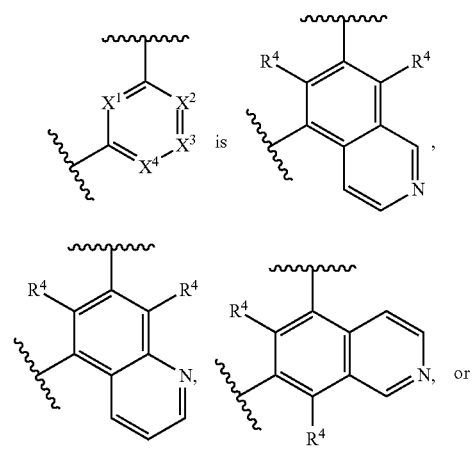

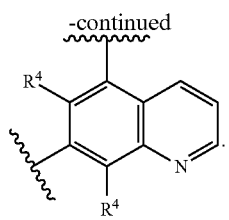

In certain embodiments, each $R^4$ is H.

In some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, such as any of the embodiments described above, $R^{15}$ and $R^{17}$ are independently hydrogen, halo, or alkyl. In some embodiments, the alkyl is independently unsubstituted or substituted with one or more halo. In some embodiments, the alkyl is independently unsubstituted or substituted with one, two, or three halo. In certain embodiments, the alkyl is independently unsubstituted or substituted with two or three halo. In certain embodiments, $R^{15}$ and $R^{17}$ are independently hydrogen, fluoro, chloro, methyl, ethyl, or propyl.

In some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, such as any of the embodiments described above, $R^{14}$ is $(C_{1-10})$alkyl, $(C_{1-10})$alkenyl, $(C_{3-10})$cycloalkyl, $(C_{3-10})$cycloalkenyl, heterocycloalkyl connected through an annular carbon atom, or heterocycloalkenyl connected through an annular carbon atom. In certain embodiments, $R^{14}$ is $(C_{1-10})$alkyl, $(C_{1-10})$alkenyl, $(C_{3-10})$cycloalkyl, heterocycloalkyl connected through an annular carbon atom, or heterocycloalkenyl connected through an annular carbon atom. In still further embodiments, $R^{14}$ is $(C_{1-10})$alkyl, $(C_{3-10})$cycloalkyl, or heterocycloalkyl connected through an annular carbon atom. In some embodiments, $R^{14}$ is $(C_{1-8})$akyl, $(C_{1-6})$alkyl, or $(C_{1-4})$alkyl, such as hexyl, pentyl, butyl, propyl, ethyl, or methyl, which may be unsubstituted or substituted. In some embodiments, $R^{14}$ is unsubstituted or substituted tert-butyl, or unsubstituted or substituted isopropyl. In some embodiments, $R^{14}$ is $(C_{1-8})$alkenyl, $(C_{1-6})$alkenyl, or $(C_{1-4})$alkenyl, wherein the alkenyl comprises one or two C—C double bonds, and wherein the alkenyl may be unsubstituted or substituted. For example, in some embodiments $R^{14}$ is isopropenyl. In other embodiments, $R^{14}$ is a 4-, 5-, or 6-membered heterocycloalkyl comprising one to three heteroatoms independently selected from O and N, wherein the heterocycloalkyl is connected through an annular carbon atom. For example, $R^{14}$ may be a $(C_{3-5})$heterocycloalkyl comprising one or two O atoms. In still further embodiments, $R^{14}$ is a 5- or 6-membered heterocycloalkenyl comprising one to three heteroatoms independently selected from O and N, wherein the heterocycloalkenyl is connected through an annular carbon atom. In still further embodiments, $R^{14}$ is $(C_{3-10})$cycloalkyl, for example $(C_{3-8})$cycloalkyl, $(C_{3-6})$cycloalkyl, or $(C_{4-6})$cycloalkyl. In some embodiments, $R^{14}$ is cyclobutyl or cyclopropyl, unsubstituted or substituted with halo, —$OR^7$ (such as —OH or —O$(C_{1-10})$alkyl) or a combination thereof.

In certain embodiments, the alkyl, alkenyl, cycloalkyl, cycloalkenyl, heterocycloalkyl, or heterocycloalkenyl of $R^{14}$ is substituted with one or more substituents as described in Formula (X). In some embodiments, the alkyl, alkenyl, cycloalkyl, cycloalkenyl, heterocycloalkyl, or heterocycloalkenyl of $R^{14}$ may be unsubstituted or substituted with 1 to 3 substituents independently selected from the group consisting of $(C_{1-10})$alkyl, halo, —$OR^7$, and —$C(O)OR^7$. Each $R^7$ may be hydrogen or $(C_{1-10})$alkyl, such as $(C_{1-8})$alkyl, $(C_{1-6})$alkyl, or $(C_{1-4})$alkyl, for example hexyl, pentyl, butyl, propyl, ethyl, or methyl, wherein the alkyl is independently unsubstituted or substituted with one or more halo. In some embodiments, the alkyl, cycloalkyl, heterocycloalkyl, or heterocycloalkenyl is independently unsubstituted or substituted with one, two, or three halo. In certain embodiments, the alkyl, cycloalkyl, heterocycloalkyl, or heterocycloalkenyl is substituted with two or three halo. In some embodiments, the alkyl is substituted with one, two, or three alkyl. In some embodiments, $R^{14}$ is $(C_{1-10})$alkyl wherein the alkyl is unsubstituted or substituted with oxo. In still other embodiments, $R^{14}$ is $(C_{1-10})$alkyl substituted with —$NR^7R^7$. In some embodiments, each $R^7$ is independently hydrogen or $(C_{1-10})$alkyl.

In other embodiments, $R^{14}$ is —$OR^5$, wherein $R^5$ is hydrogen, $(C_{1-10})$alkyl, or $(C_{3-10})$cycloalkyl, wherein the alkyl or cycloalkyl is unsubstituted or substituted as described in Formula (X). In some embodiments, one or more substituents are selected from the group consisting of halo, haloalkyl, and —$(OR^{35})_{n12}OR^{34}$. In some embodiments, $R^5$ is $(C_{1-10})$alkyl, such as $(C_{1-4})$alkyl or $(C_{1-2})$alkyl, or $(C_{3-10})$cycloalkyl, such as $(C_{3-6})$cycloalkyl, each of which may be unsubstituted or substituted with halo or —$(OR^{35})_{n12}OR^{34}$, or a combination thereof. In some embodiments of —$(OR^{35})_{n12}OR^{34}$, n12 is 0, 1, 2, or 3. In some embodiments, each $R^{35}$ is independently $(C_{1-10})$alkyl or $(C_{1-10})$haloalkyl alkyl, such as $(C_{1-4})$alkyl, $(C_{1-4})$haloalkyl, $(C_{1-3})$alkyl, or $(C_{1-3})$haloalkyl. In still further embodiments, $R^{34}$ is hydrogen or $(C_{1-10})$alkyl, such as $(C_{1-4})$alkyl or $(C_{1-3})$alkyl. In certain embodiments, n12 is 0 or 1, $R^{35}$ is methyl, ethyl, or propyl, and $R^{34}$ is hydrogen, methyl, ethyl, or propyl.

Thus, in some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, such as embodiments described above, $R^{14}$ is:

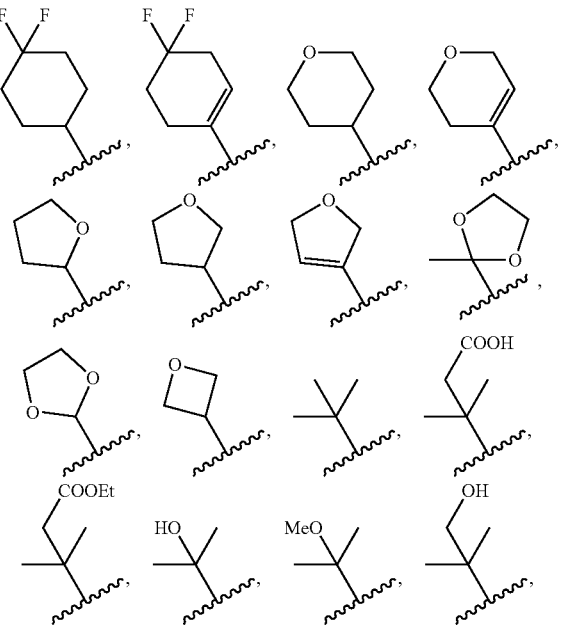

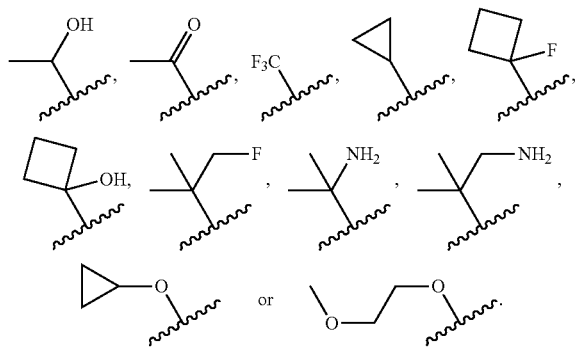

In some embodiments, R$^{15}$ is hydrogen. In other embodiments, R$^{15}$ is —OR$^{29}$. In some embodiments, R$^{29}$ is hydrogen, (C$_{1-10}$)alkyl, (C$_{1-10}$)haloalkyl, (C$_{3-10}$)cycloalkyl, or (C$_{3-10}$)halocycloalkyl.

Alternatively, in some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, R$^{14}$ and R$^{15}$, together with the atoms to which they are attached, form a carbocyclyl or heterocyclyl. The carbocyclyl or heterocyclyl may be unsubstituted or substituted with one or two substituents independently selected from the group consisting of halo, cyano, oxo, (C$_{1-10}$)alkyl, (C$_{3-10}$)cycloalkyl, (C$_{3-10}$)cycloalkyl(C$_{1-10}$)alkyl, —OR$^{18}$, —C(O)NR$^{18}$R$^{18}$, —NR$^{18}$C(O)R$^{18}$, —NR$^{18}$C(O)NR$^{18}$R$^{18}$, —NR$^{18}$R$^{18}$, —S(O)$_2$NR$^{18}$R$^{18}$, —NR$^{18}$S(O)$_2$R$^{18}$, —S(O)$_{n3}$R$^{21}$, —C(O)OR$^{18}$, and —C(O)R$^{21}$. In certain embodiments, R$^{14}$ and R$^{15}$, together with the atoms to which they are attached, form a C$_5$ or C$_6$ carbocyclyl. In other embodiments, R$^{14}$ and R$^{15}$, together with the atoms to which they are attached, form a 5- or 6-membered heterocyclyl. For example, in some embodiments, the heterocyclyl is a 5- or 6-membered heterocyclyl comprising one to three heteroatoms independently selected from O and N, such as a C$_{3-5}$ cycloalkyl comprising one or two O atoms. In some embodiments, the heterocyclyl is a 5- or 6-membered heterocyclyl comprising one or two N atoms, or one O atom and one N atom. In some embodiments, the carbocyclyl or heterocyclyl is unsubstituted or substituted with one or two substituents independently selected from the group consisting of (C$_{1-10}$)alkyl, (C$_{3-10}$)cycloalkyl, or (C$_{3-10}$)cycloalkyl(C$_{1-10}$)alkyl substituents, such as (C$_{1-8}$)alkyl, (C$_{1-6}$)alkyl, (C$_{1-4}$)alkyl, (C$_{3-8}$)cycloalkyl, (C$_{3-6}$)cycloalkyl, (C$_{5-6}$)cycloalkyl, (C$_{3-8}$)cycloalkyl(C$_{1-8}$)alkyl, (C$_{3-6}$)cycloalkyl(C$_{1-6}$)alkyl, and (C$_{4-6}$)cycloalkyl(C$_{1-4}$)alkyl. For example, in certain embodiments, the carbocyclyl or heterocyclyl is unsubstituted or substituted with one or two substituents independently selected from the group consisting of methyl, ethyl, propyl, butyl, pentyl, cyclopropyl, cyclobutyl, cyclopropyl-methyl, and cyclobutyl-methyl. In some embodiments, the butyl is tert-butyl. In some embodiments, the carbocyclyl or heterocyclyl is substituted with one or more halo.

Thus, in some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof:

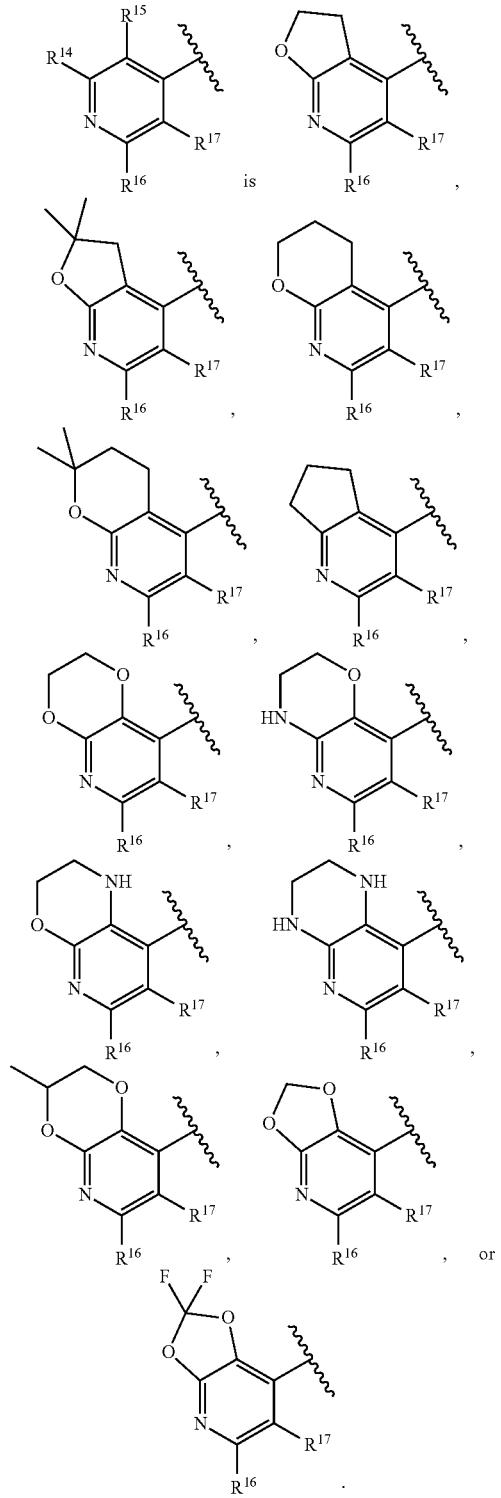

In some variations, R$^{16}$ and R$^{17}$ are both H. In other embodiments, R$^{16}$ is (C$_{1-10}$)alkyl, such as (C$_{1-6}$)alkyl or (C$_{1-4}$)alkyl. In some embodiments, the alkyl is unsubstituted, while in other embodiments, the alkyl is substituted. In yet other embodiments, R$^{16}$ is —OR$^5$. In some embodiments, R$^5$ is hydrogen or (C$_{1-10}$)alkyl. In certain embodiments, the alkyl is substituted with halo or —(OR$^{35}$)$_{n12}$OR$^{34}$. In some embodiments, R$^{17}$ is hydrogen.

In some embodiments of the compound of Formula (X), (X-A), (X-Ai), (X-B), (X-Bi), (Z), (Z-A), (Z-Ai), (Z-B), (Z-Bi), (I), (I-A), (I-B), (I-Ai), or (I-Bi), or a pharmaceutically acceptable salt, solvate, tautomer, isotope, or isomer thereof, which may include any of the embodiments described above, $R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, —OR$^5$, —C(O)NR$^5$R$^5$, —RC(O)NR$^5$R$^5$, —S(O)$_2$NR$^5$R$^5$, —S(O)$_{n1}$R$^6$, or —C(O)R$^6$, wherein the $(C_{1-10})$alkyl, $(C_{3-10})$cycloalkyl, $(C_{3-10})$cycloalkyl$(C_{1-10})$alkyl, heterocycloalkyl, or heterocycloalkyl-alkyl is independently unsubstituted or substituted with 1 to 3 substituents independently selected from the group consisting of $(C_{1-10})$alkyl, halo, cyano, oxo, —OR$^7$, —C(O)OR$^7$, —C(O)NR$^7$R$^7$, —NR$^7$C(O)R$^7$, —NR$^7$C(O)NR$^7$R$^7$, —NR$^7$R$^7$, —S(O)$_2$NR$^7$R$^7$, —NR$^7$S(O)$_2$R$^7$, —S(O)$_{n2}$R$^{13}$, and —C(O)R$^{13}$. In some embodiments, $R^{16}$ is hydrogen or fluoro. In some embodiments, $R^{16}$ is hydrogen.

In certain embodiments, the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi) is:

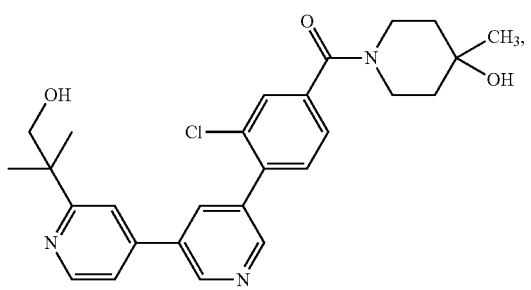

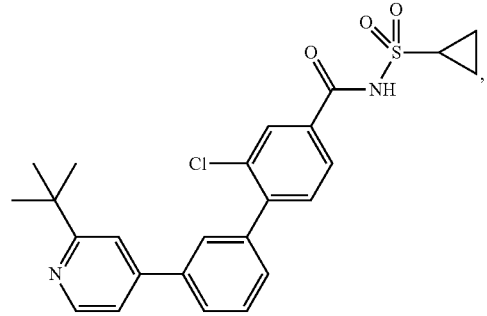

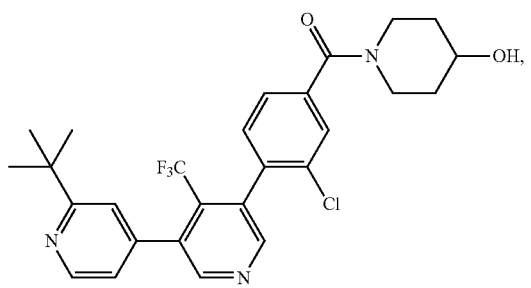

-continued

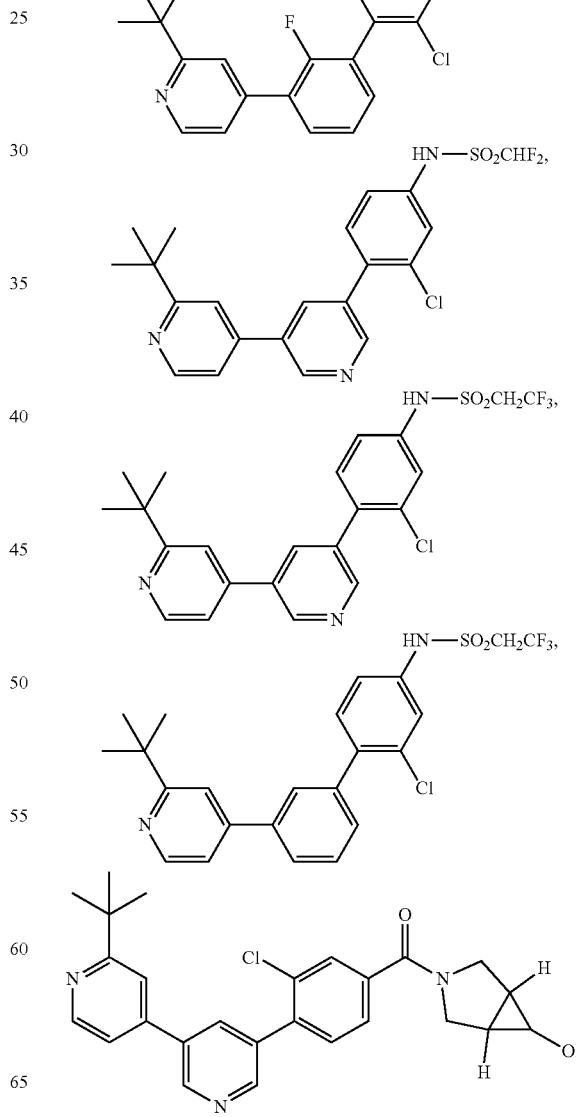

57
-continued
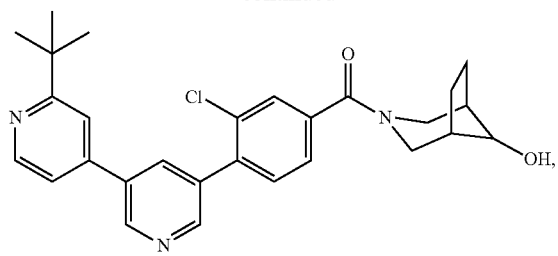
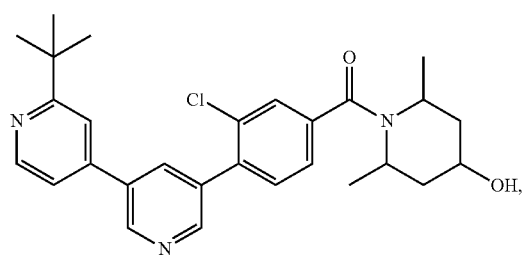
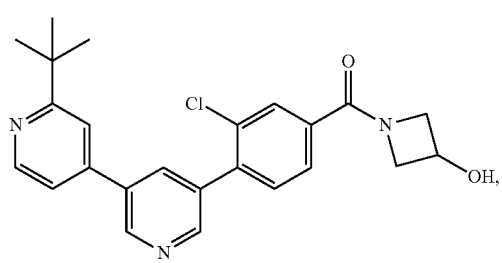
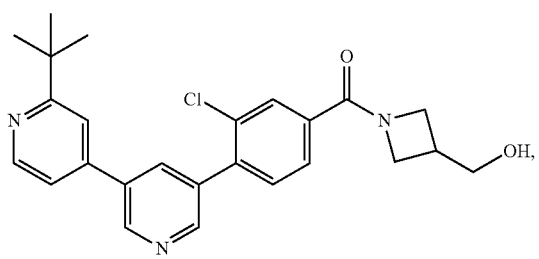
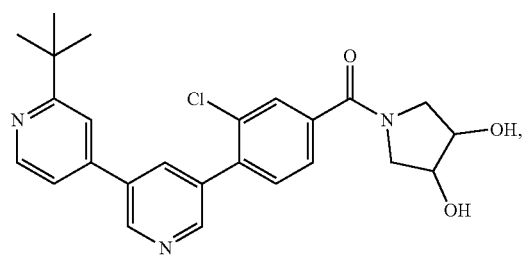
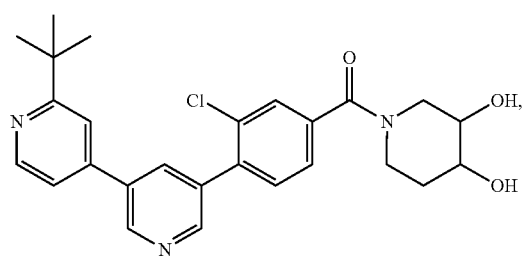
58
-continued
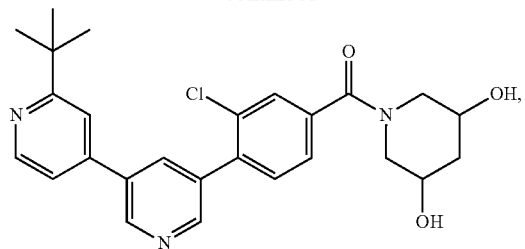
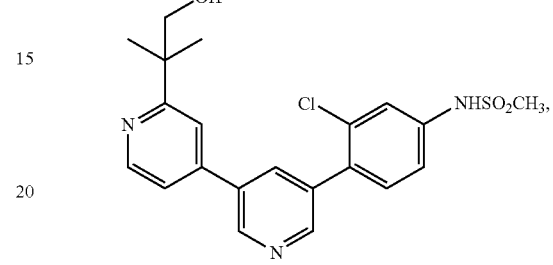
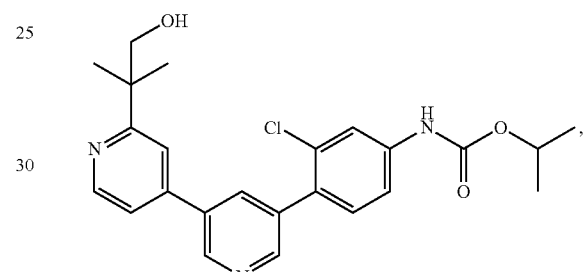
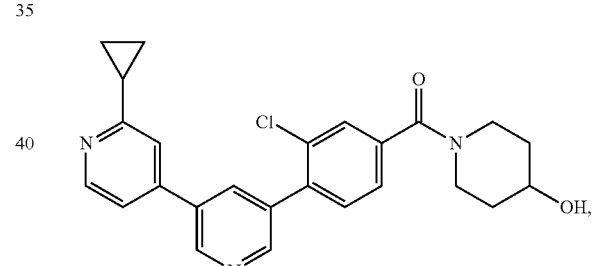
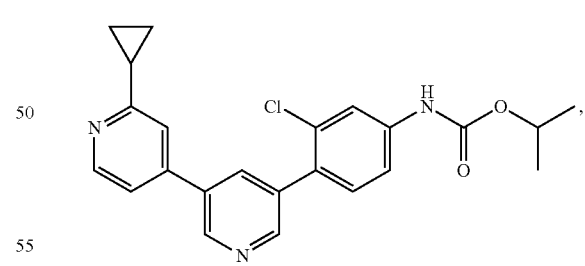
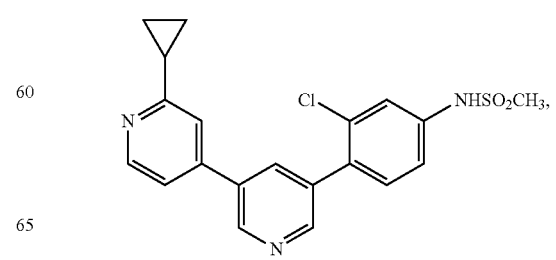

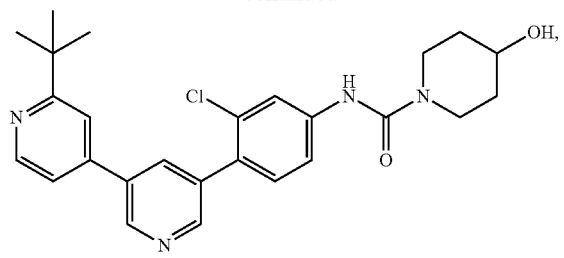
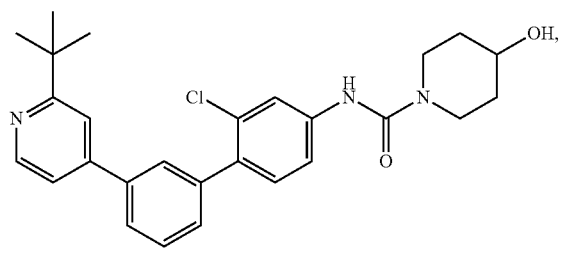
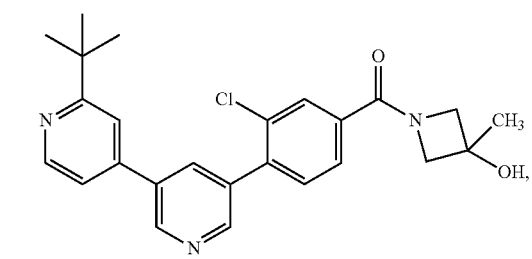
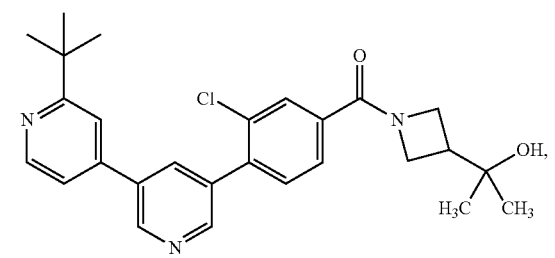
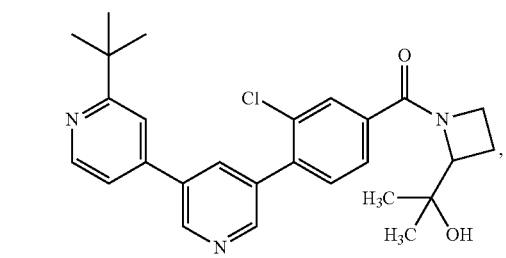
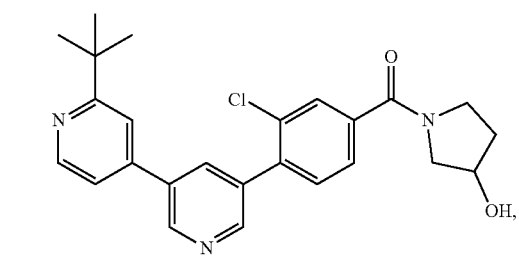
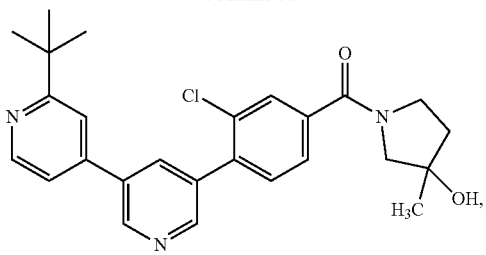
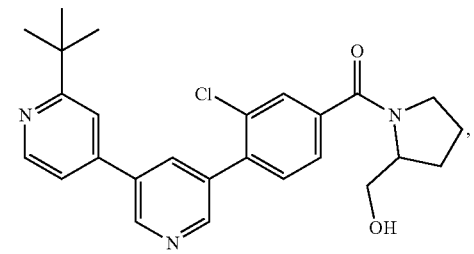
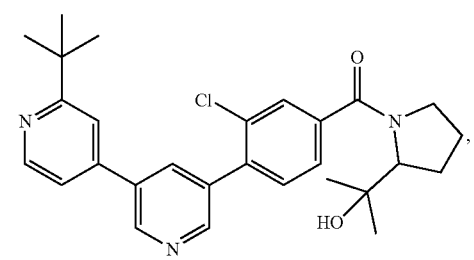
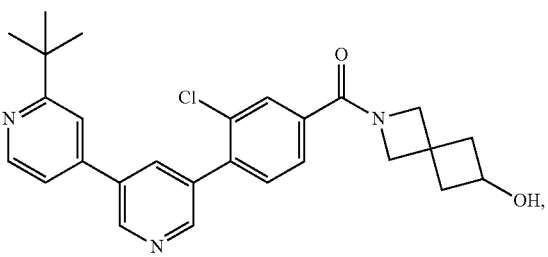
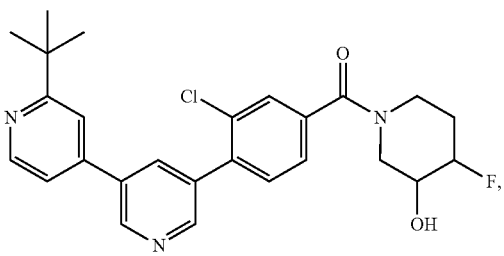
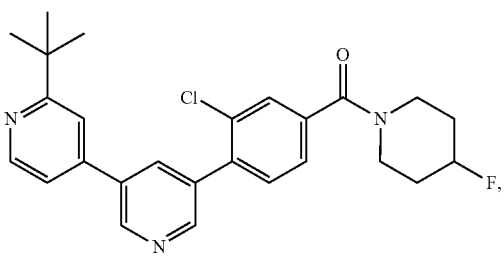

61
-continued
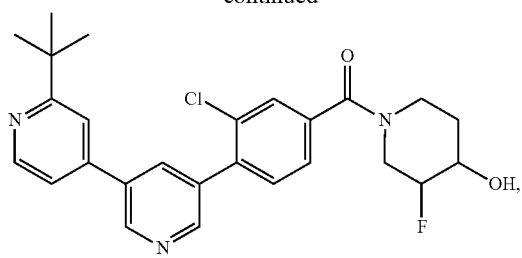
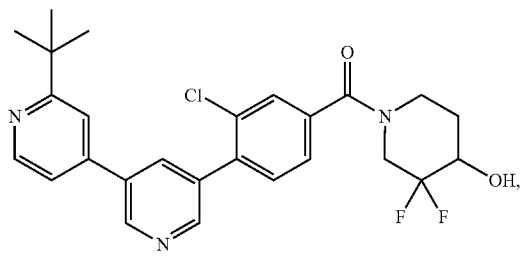
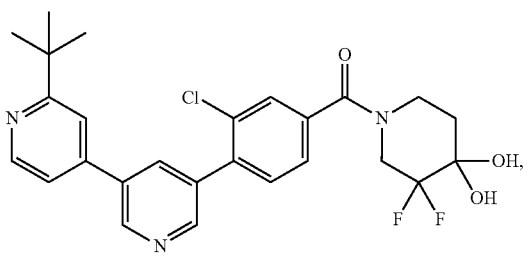
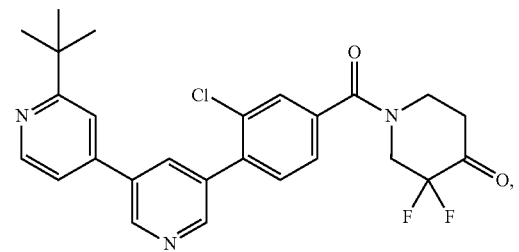
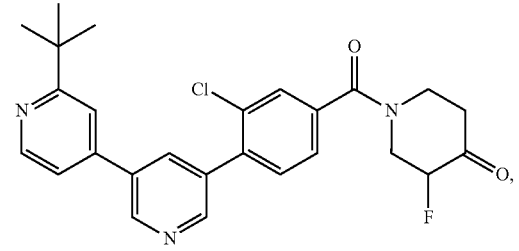
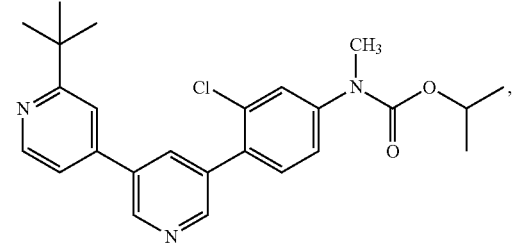
62
-continued
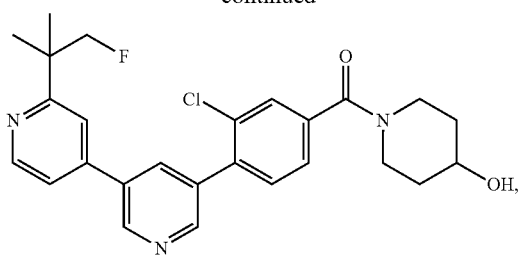
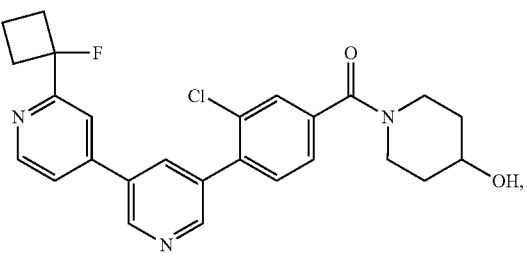
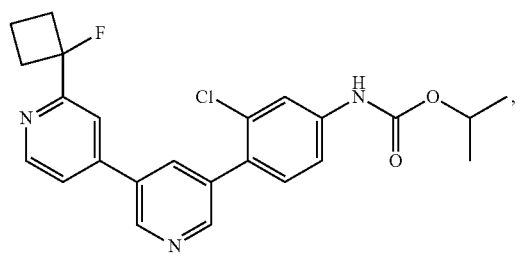
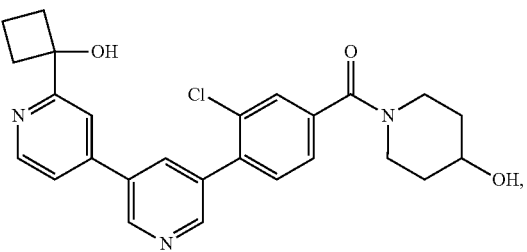
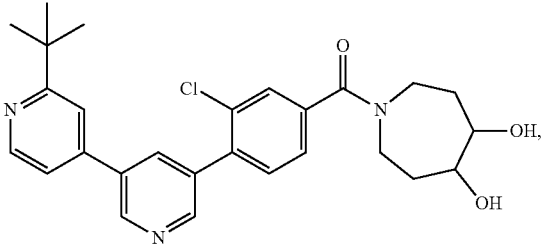
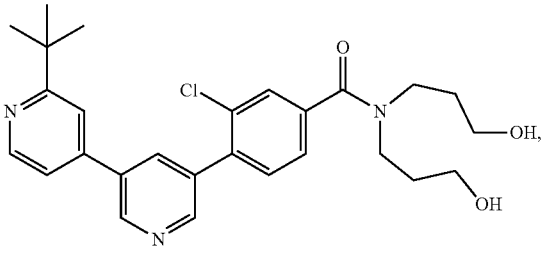

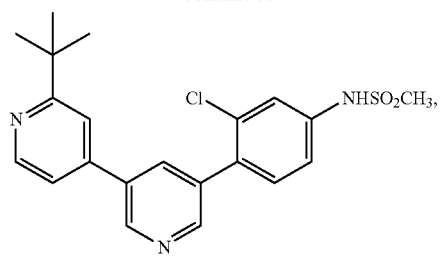
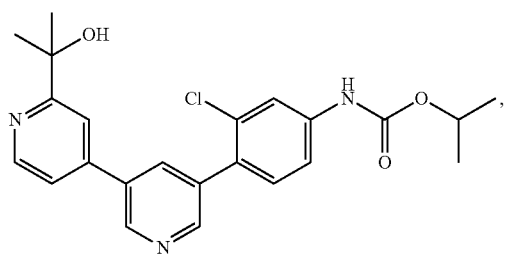
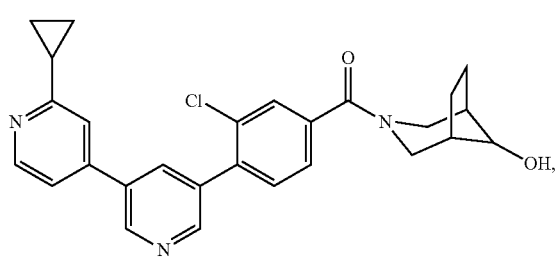
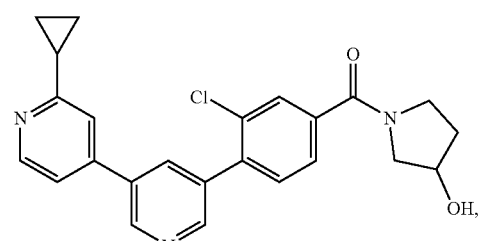
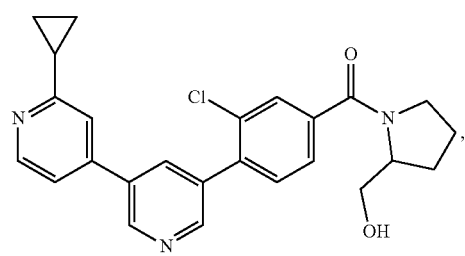
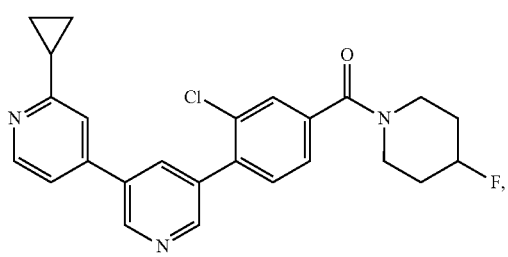
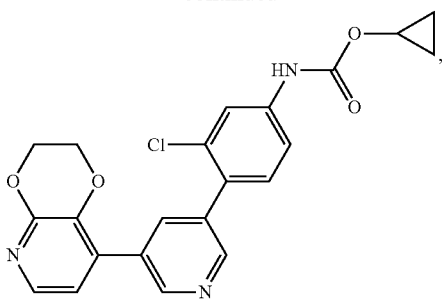
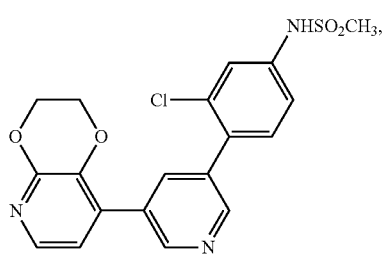
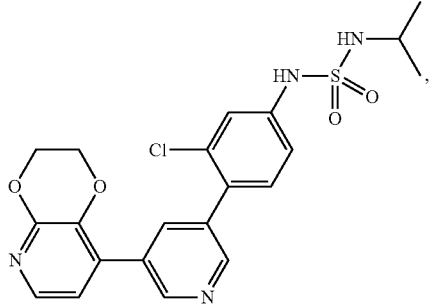
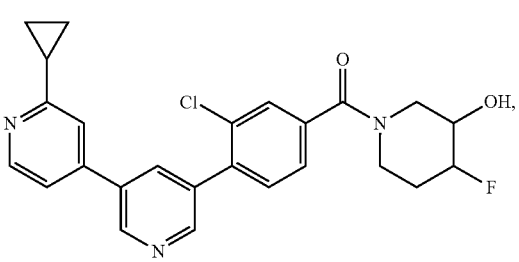
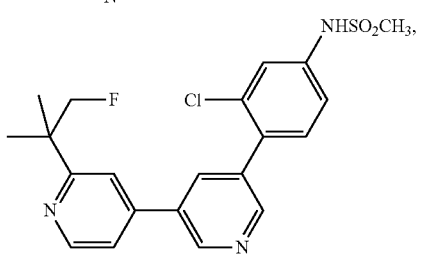
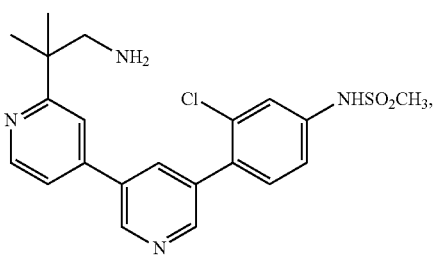

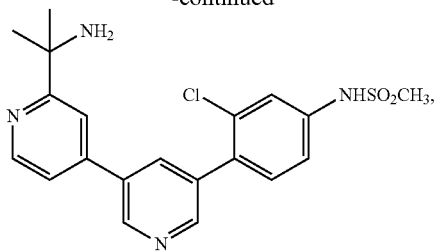
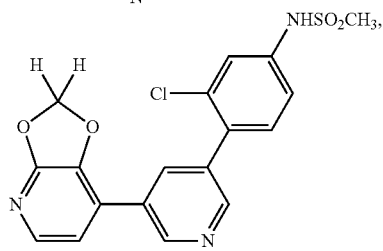
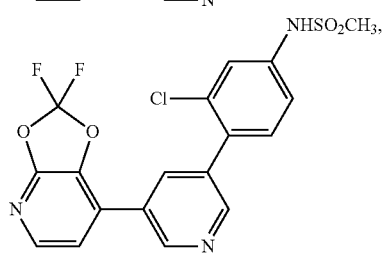
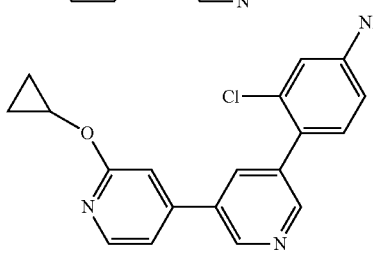
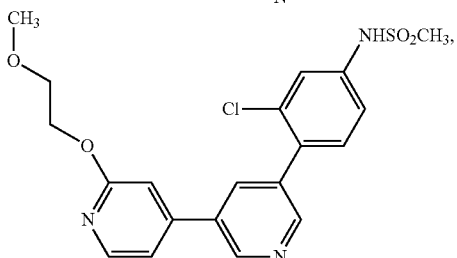
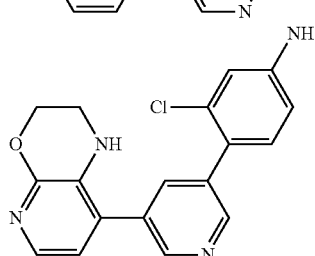
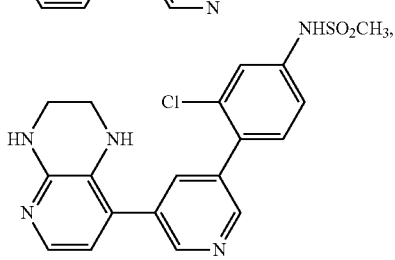
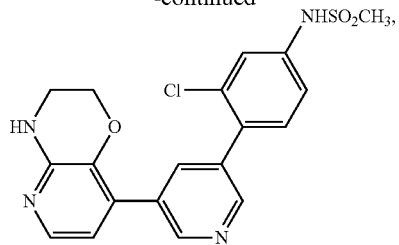
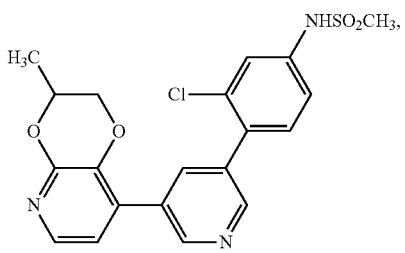
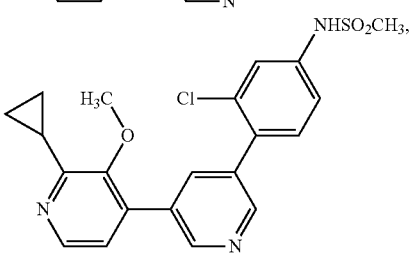
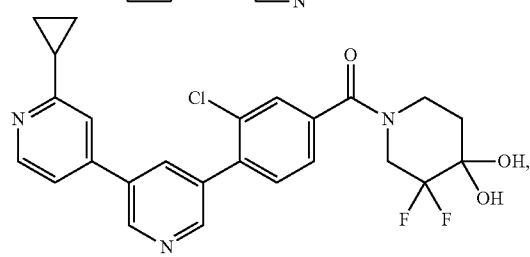
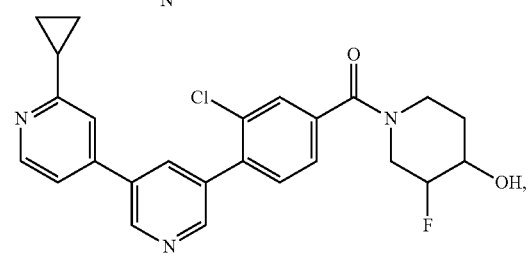
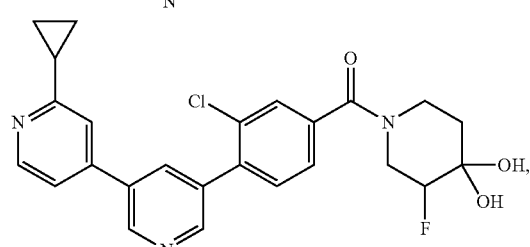
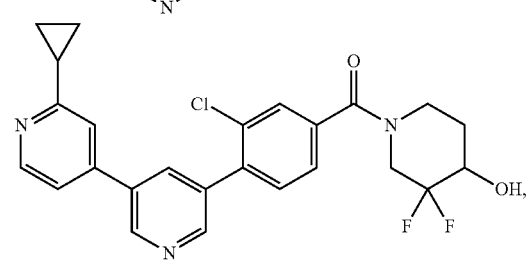

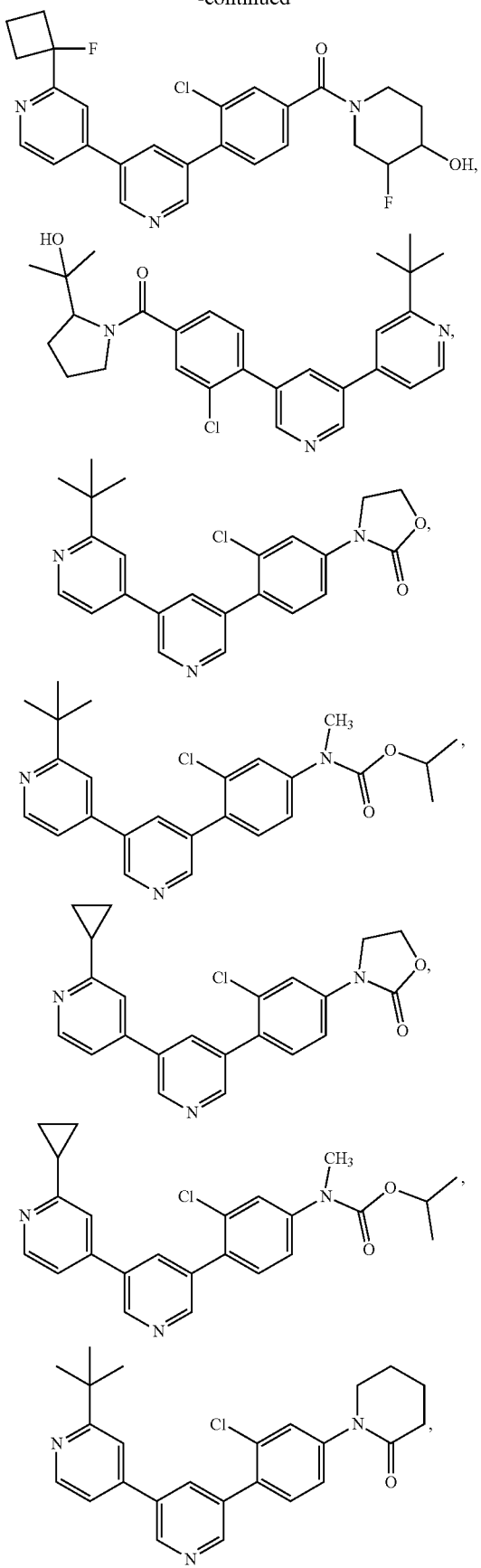
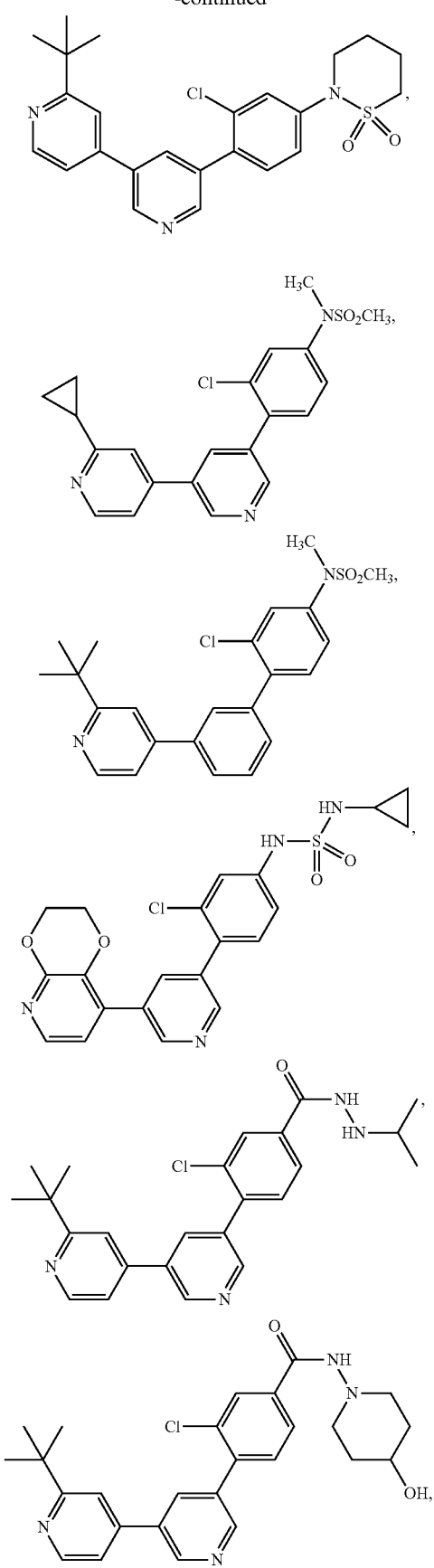

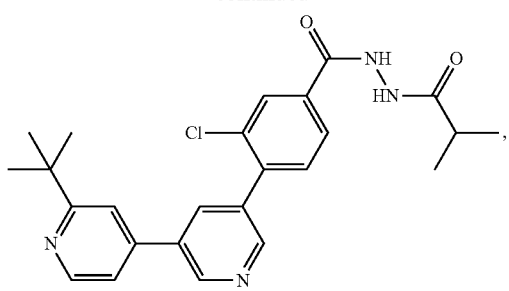
or a pharmaceutically acceptable salt, solvate, tautomer, isotope, or isomer of any of the foregoing.
In some embodiments,
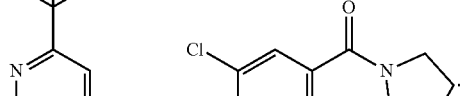
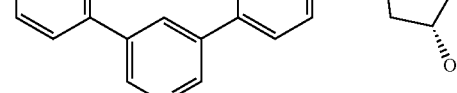
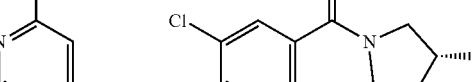

71
-continued
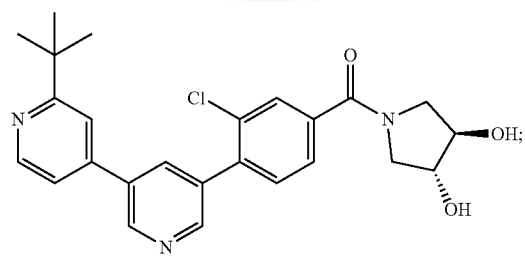
72
-continued
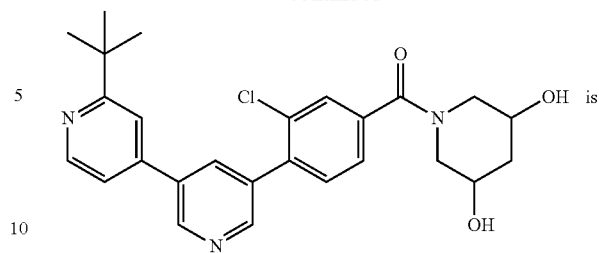
is
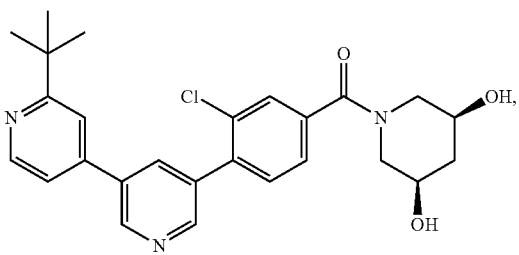
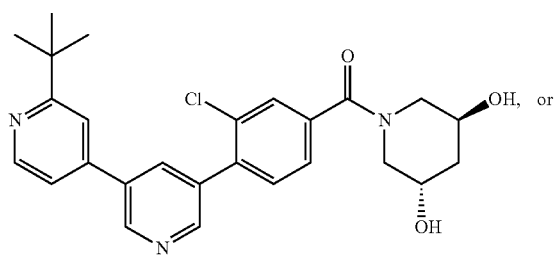
, or
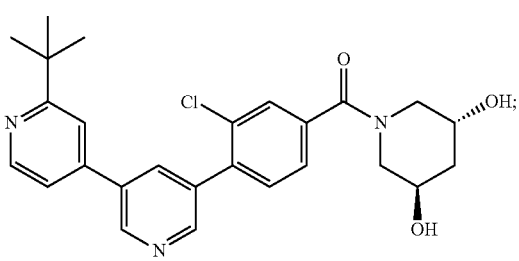
;
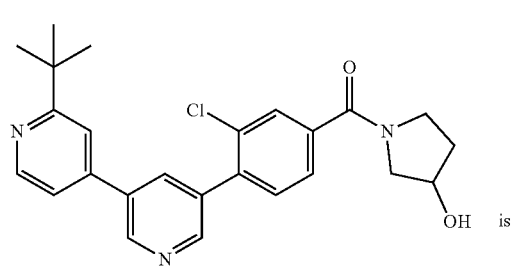
is
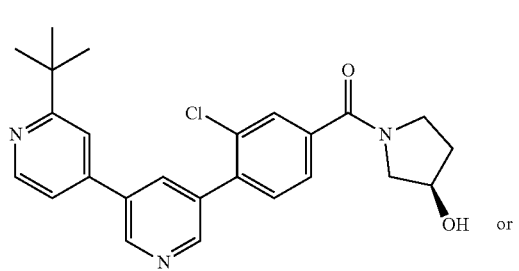
or

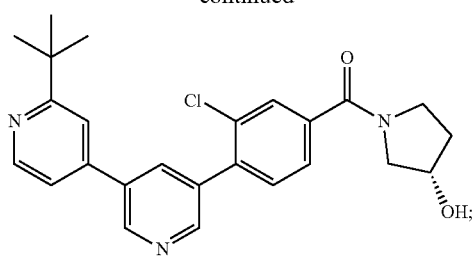 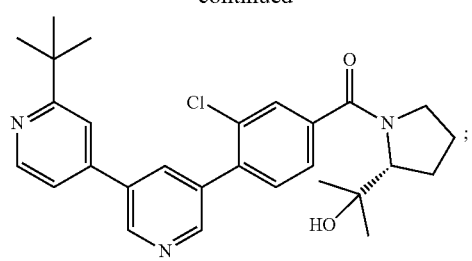

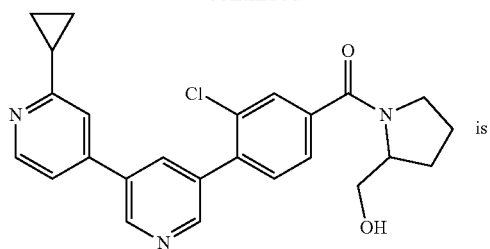
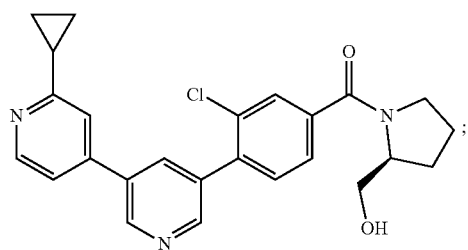
is
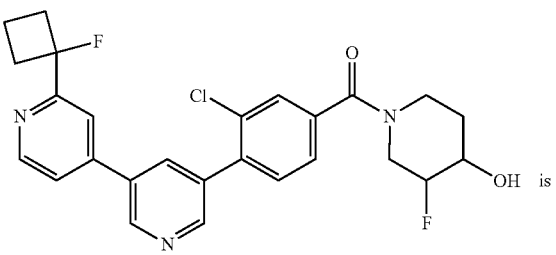
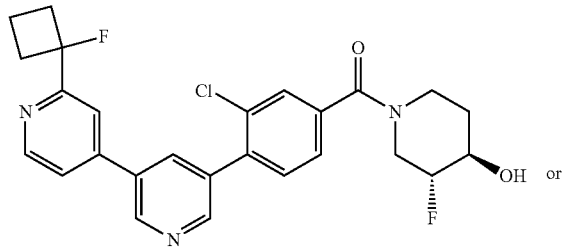
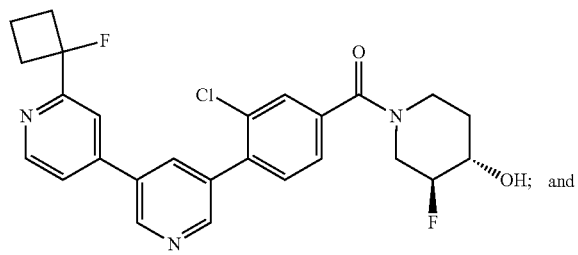
or
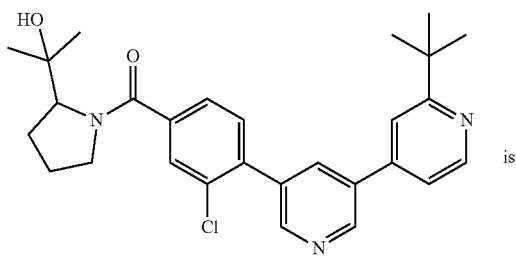
and
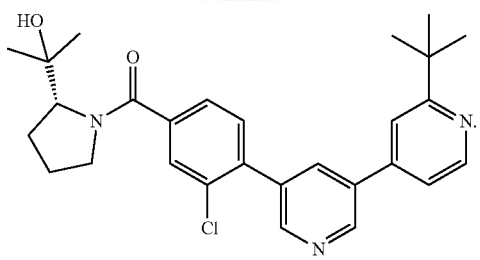
is
In certain embodiments, the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi) is:
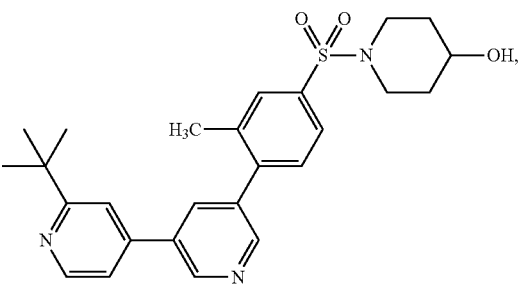
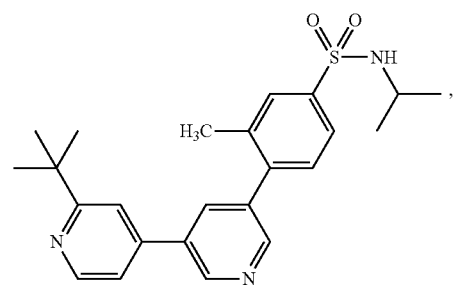
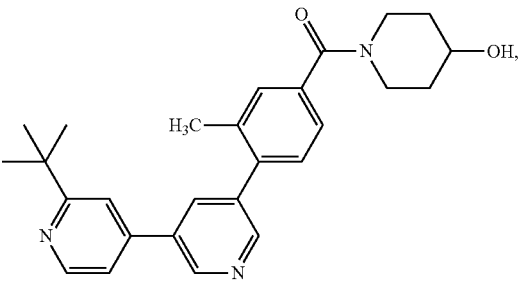
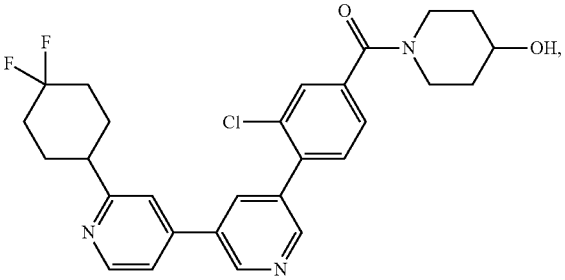

77
-continued
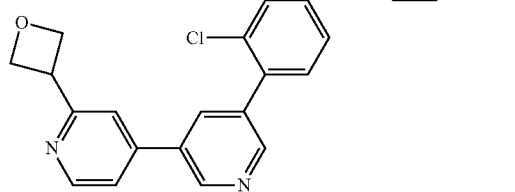
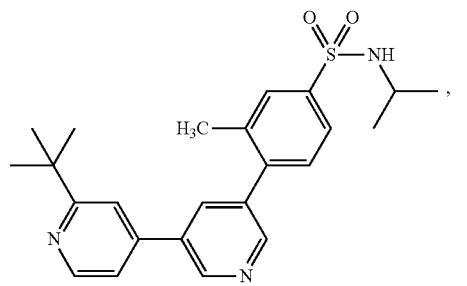
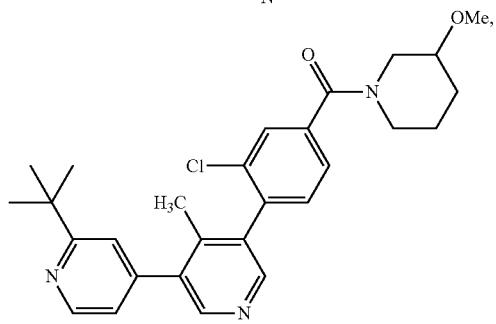
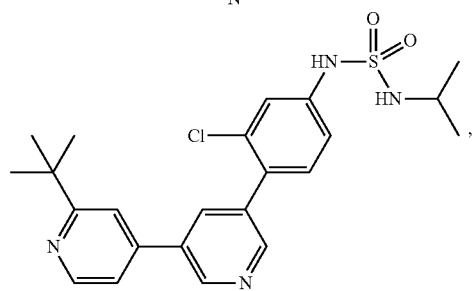
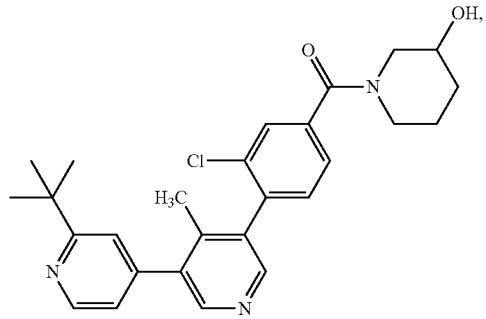
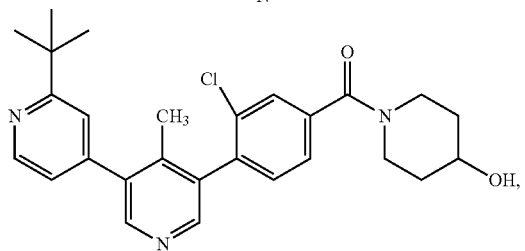
78
-continued
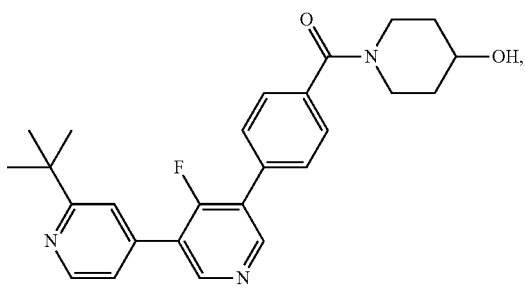
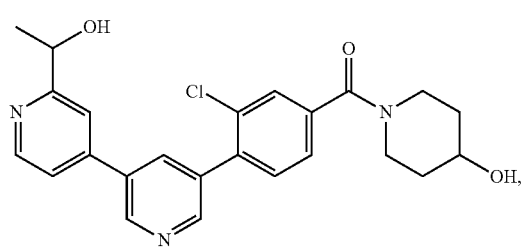
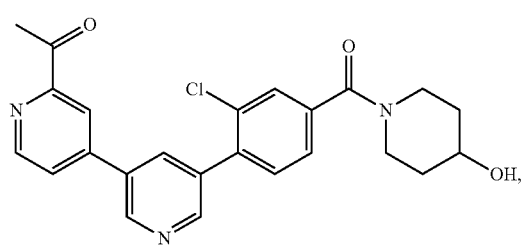
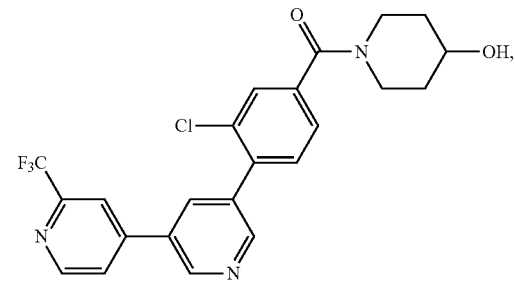
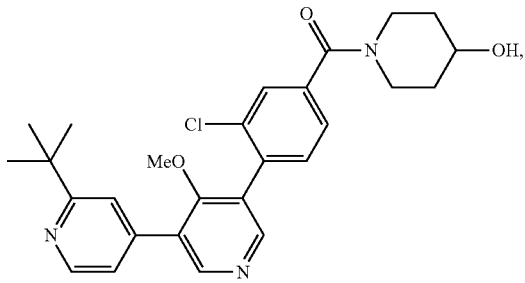
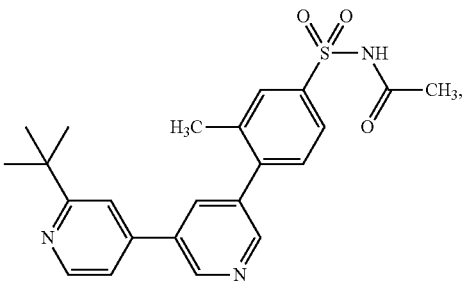

79
-continued
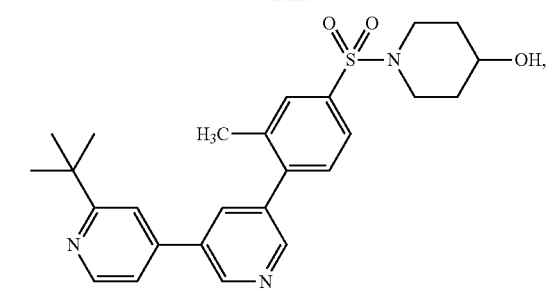
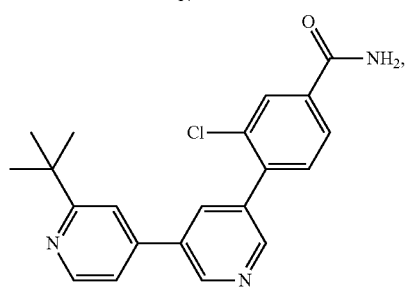
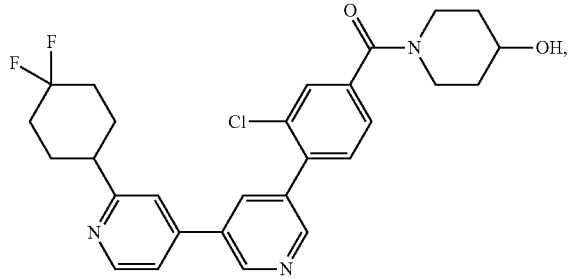
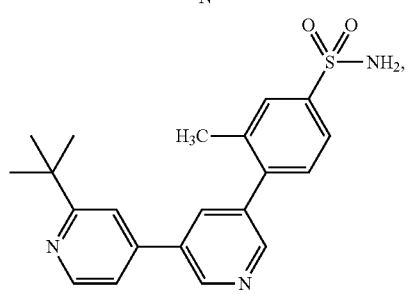
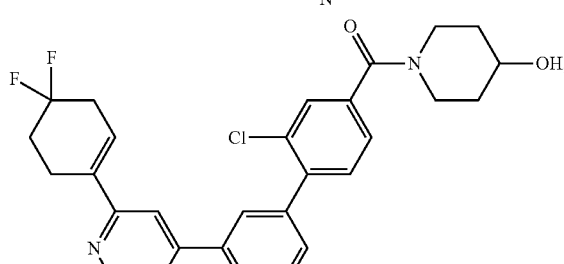
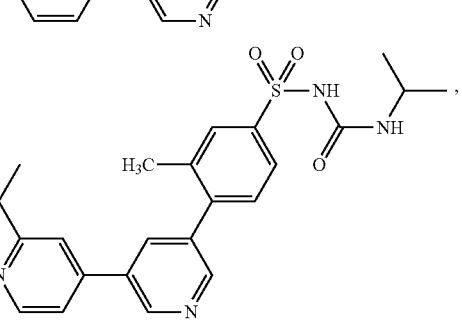
80
-continued
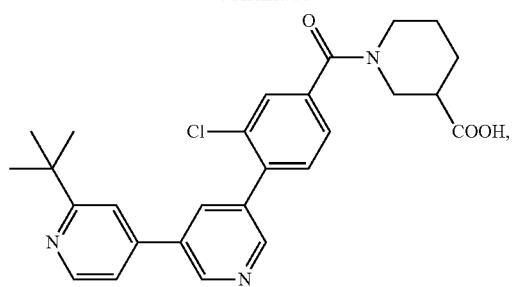
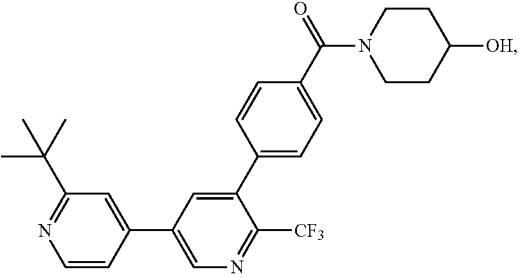
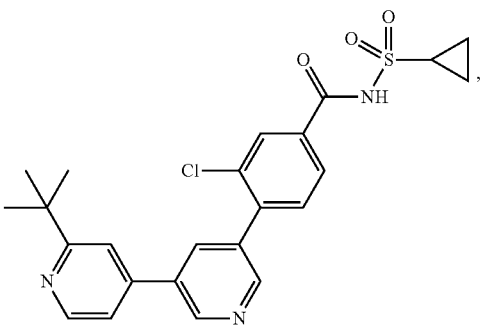
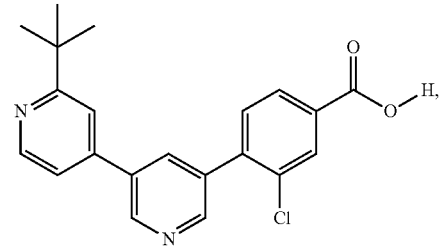
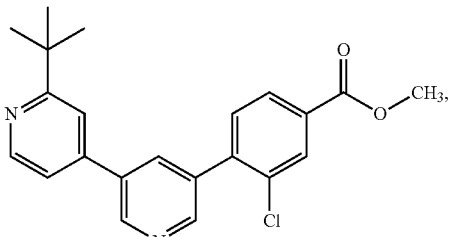
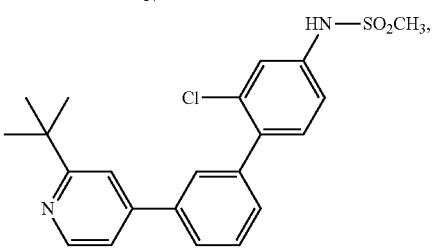

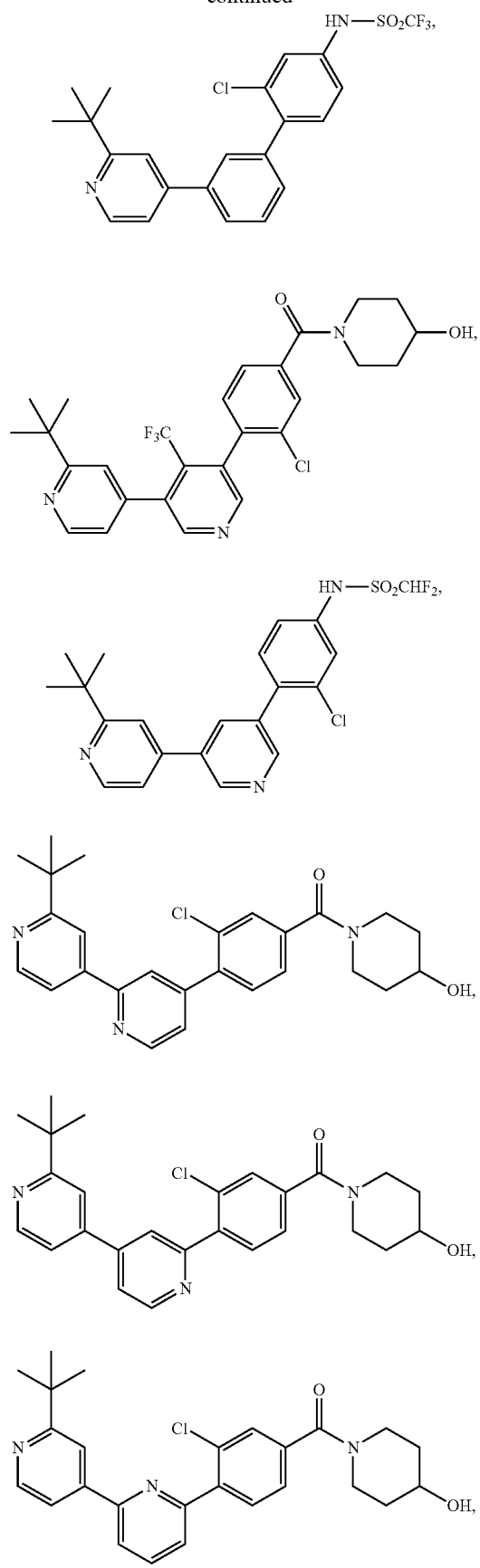
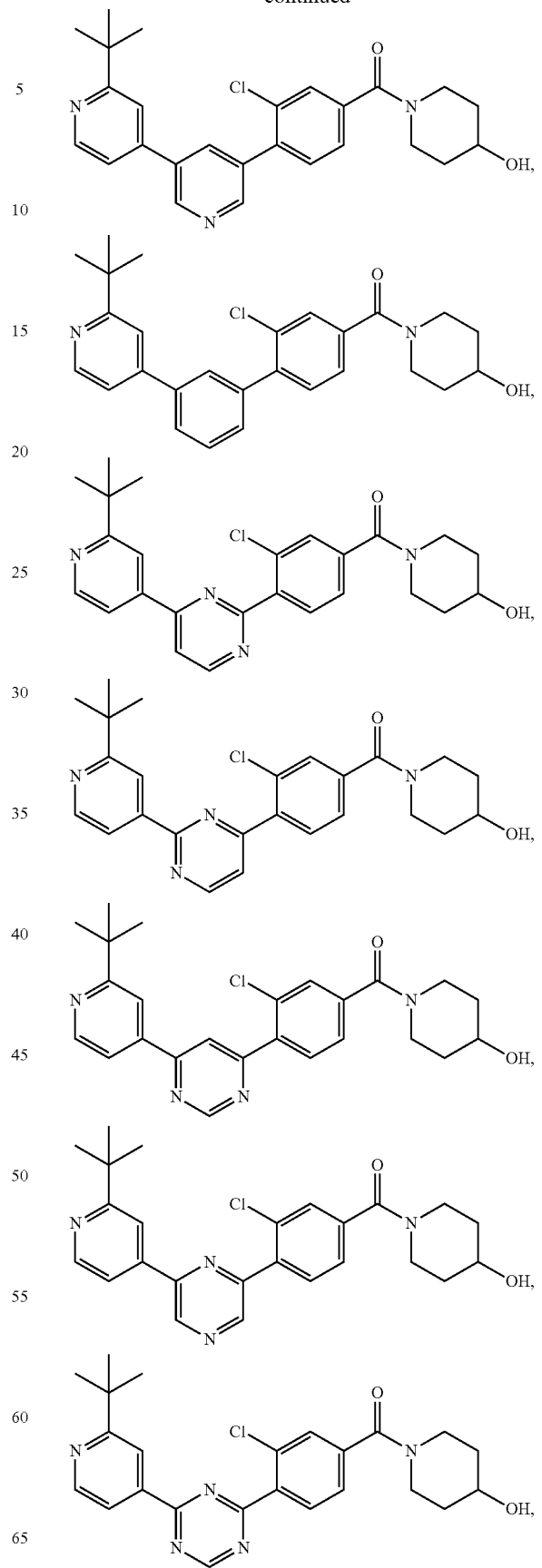

83
-continued
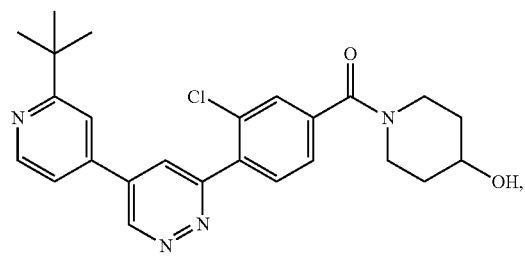
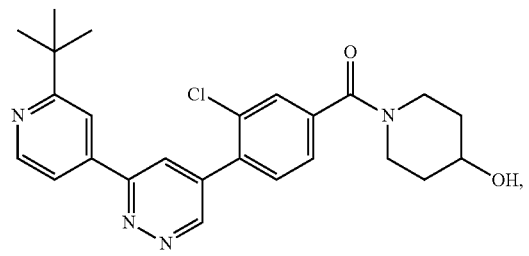
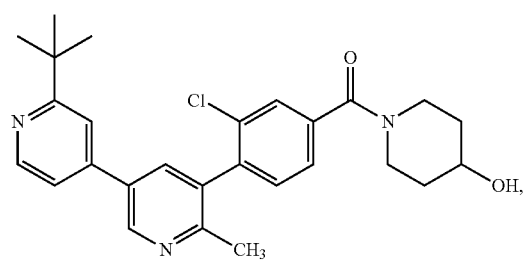
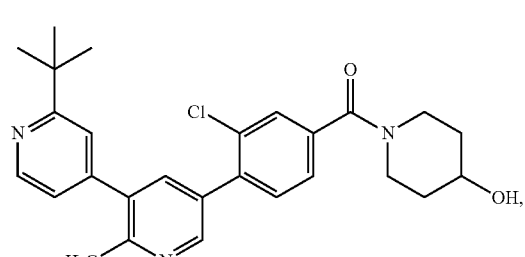
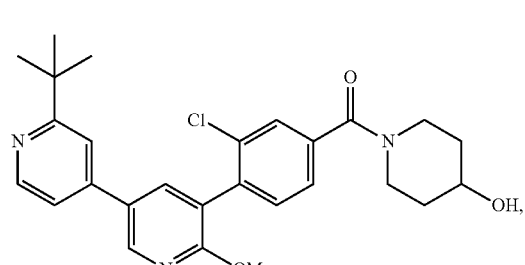
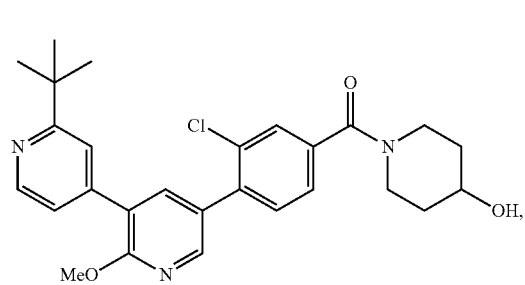
84
-continued
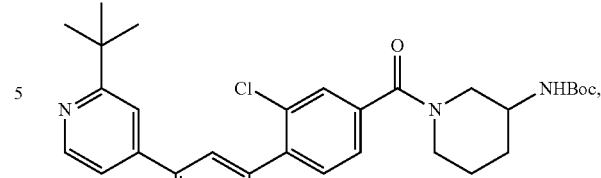
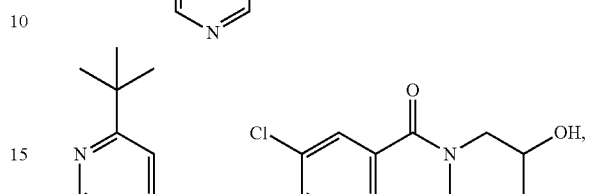
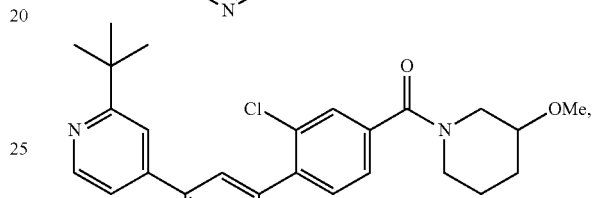
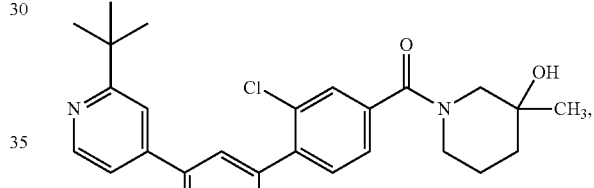
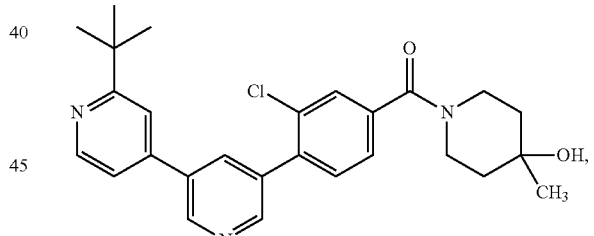
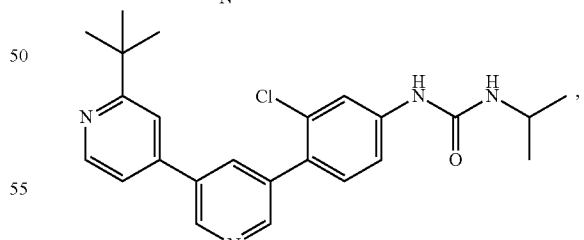
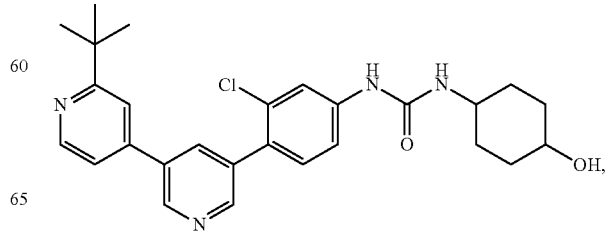

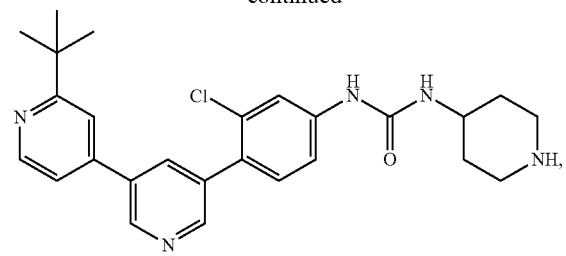
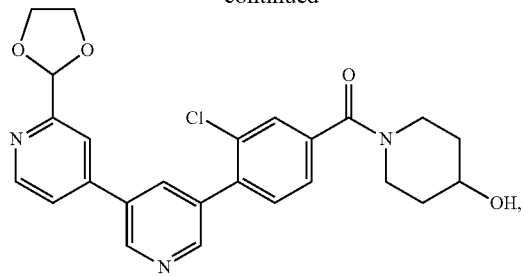
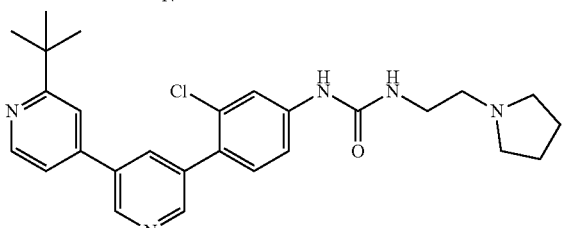
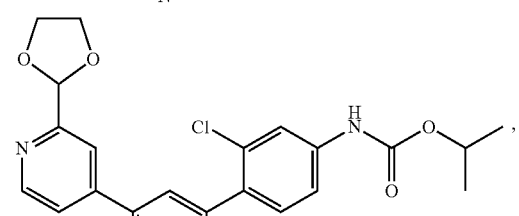
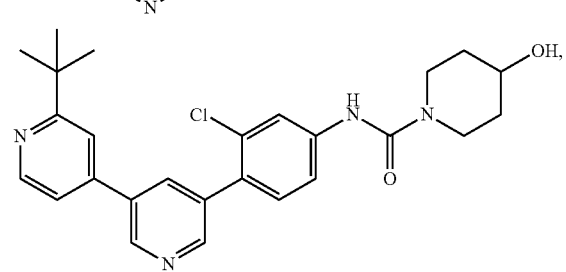
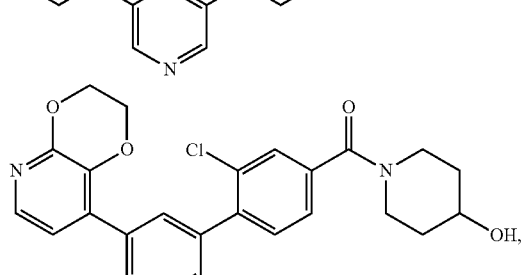
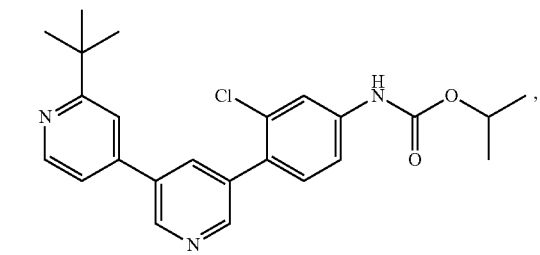
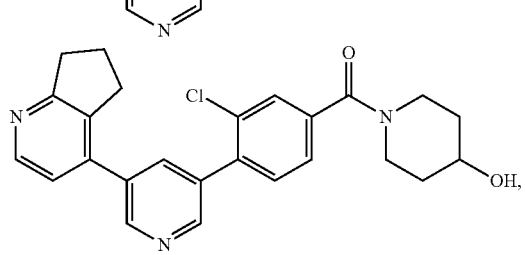
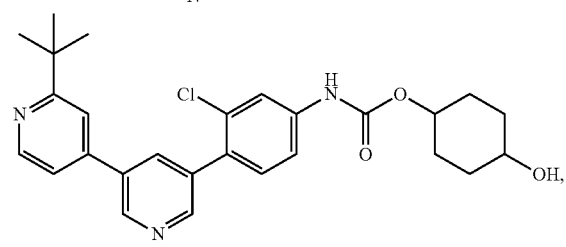
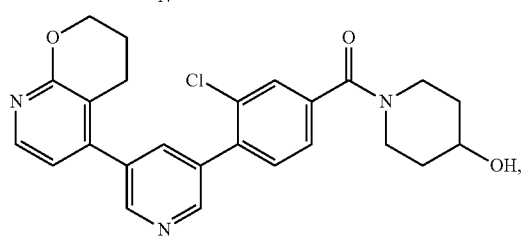
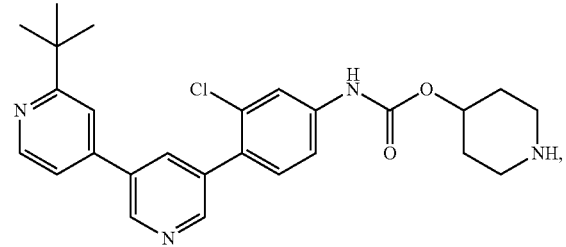
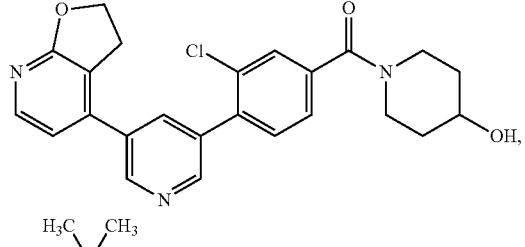
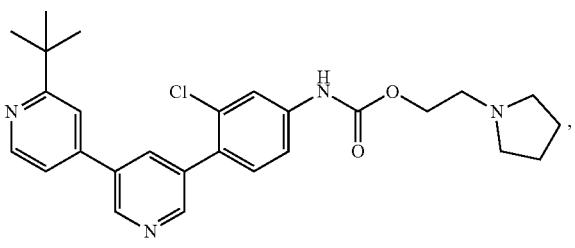
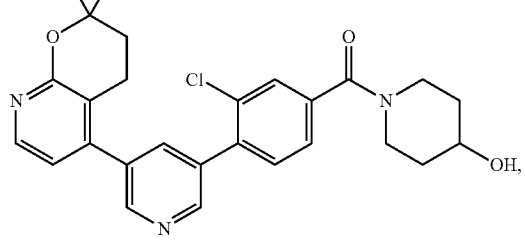

-continued
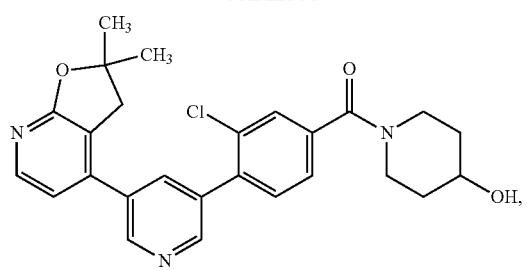
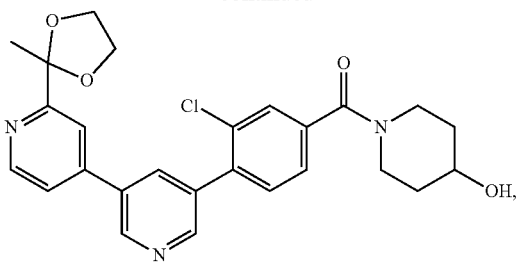
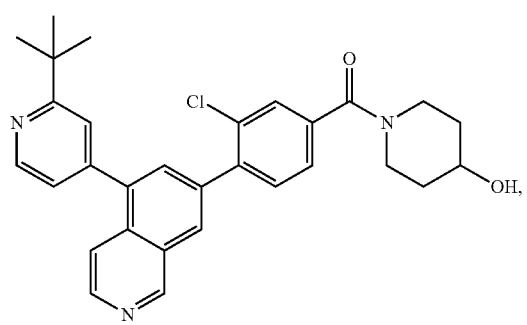
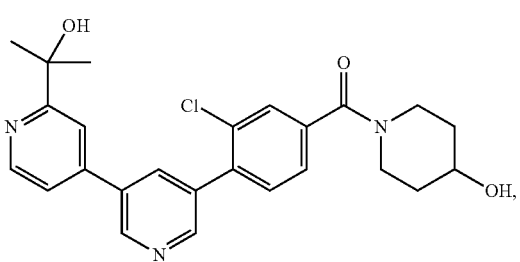
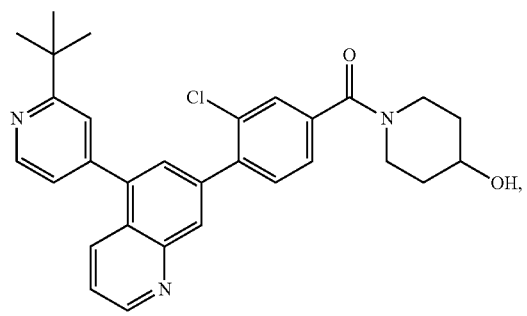
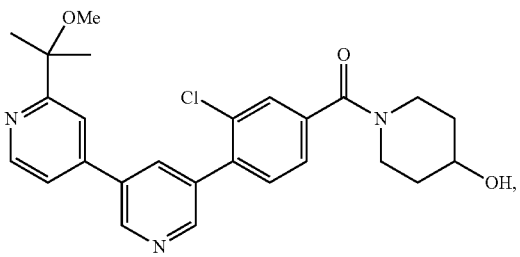
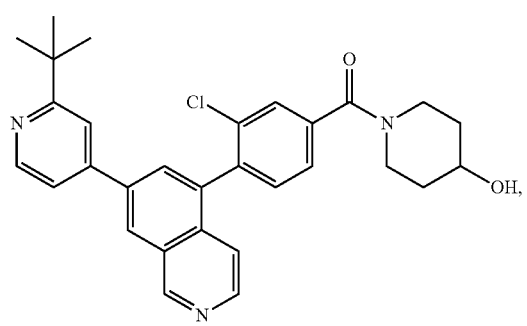
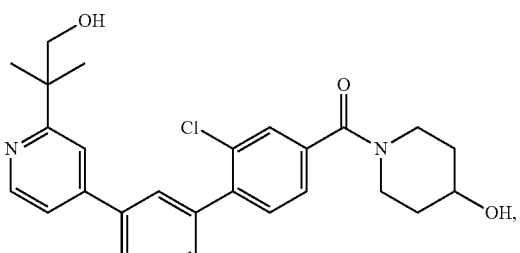
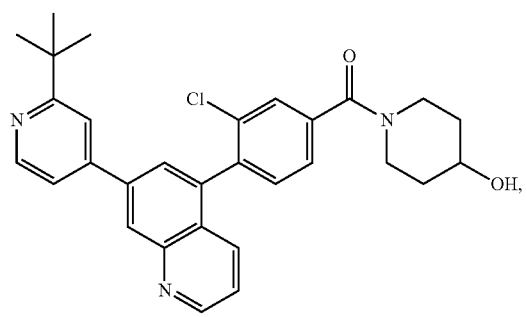
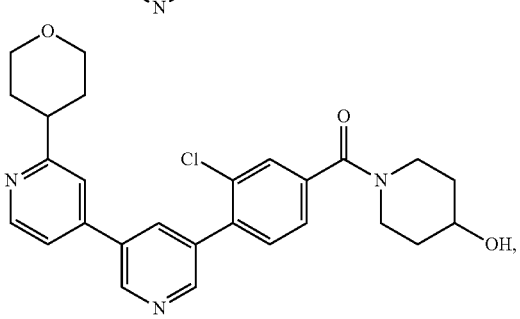

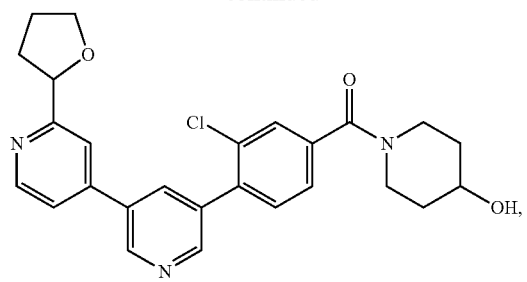
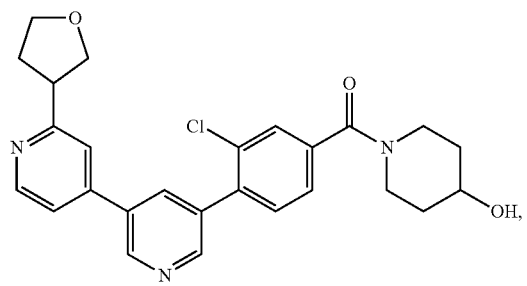
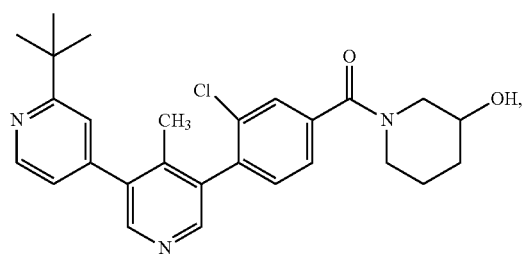
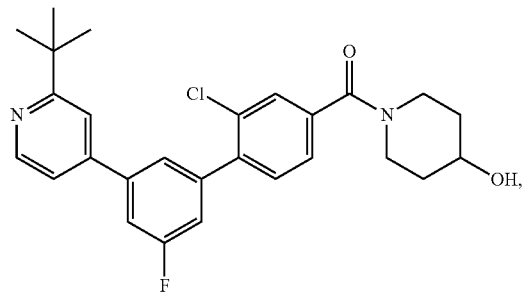
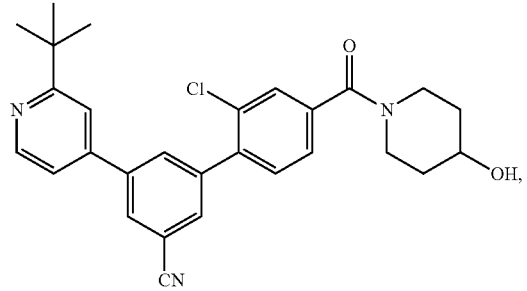
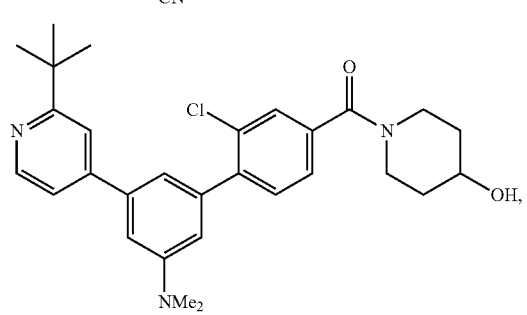
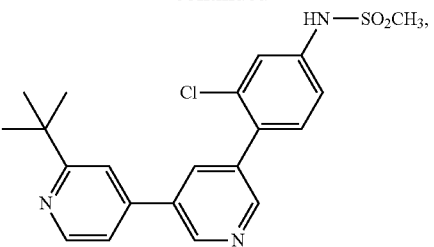
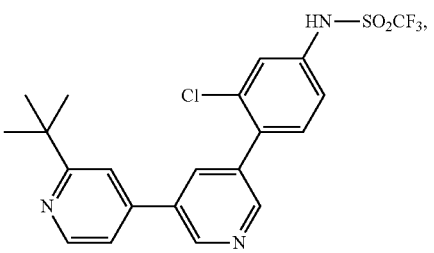
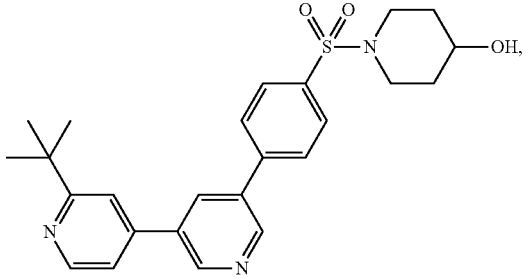
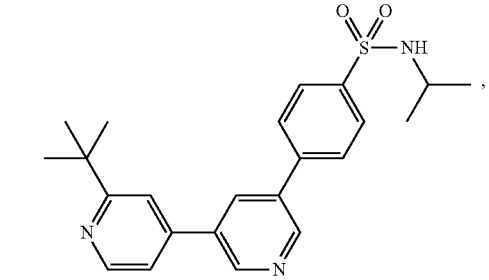
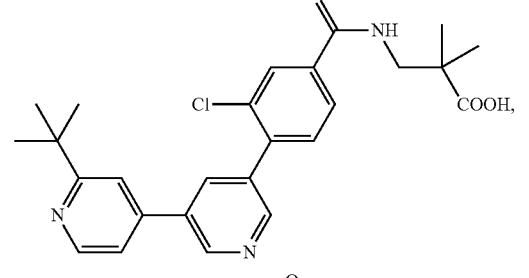
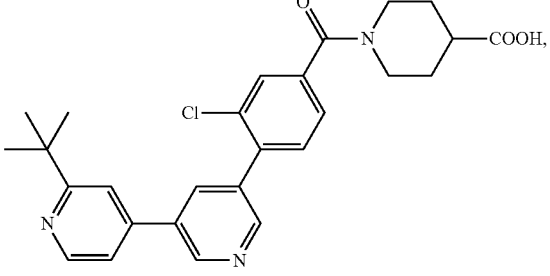

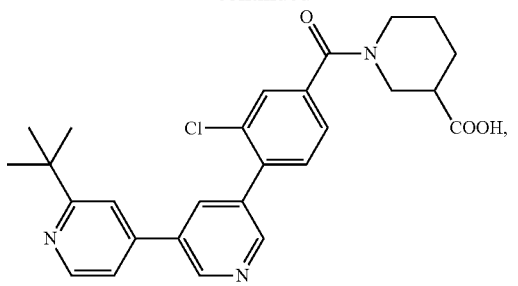
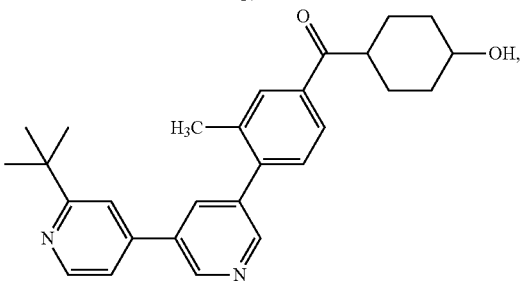
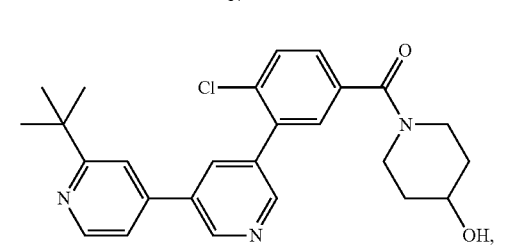
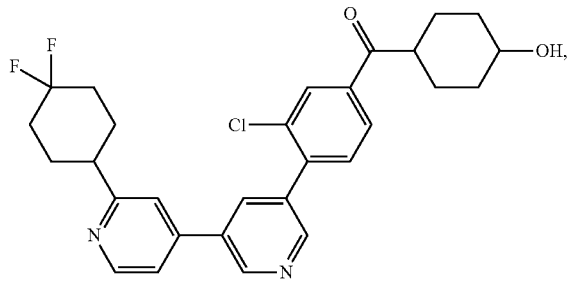
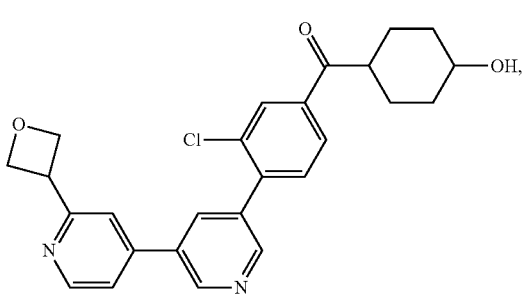
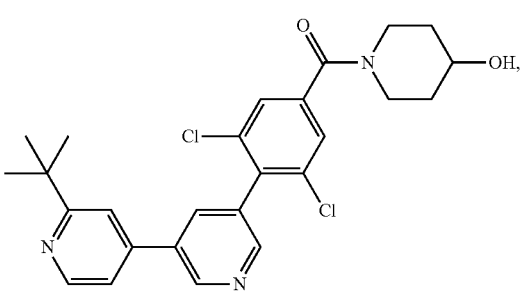
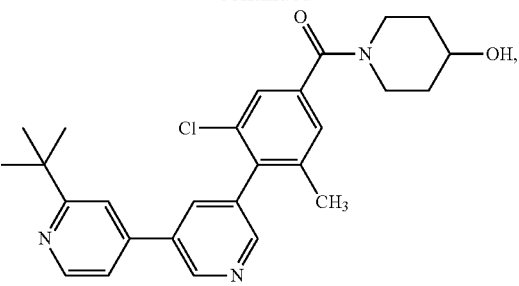
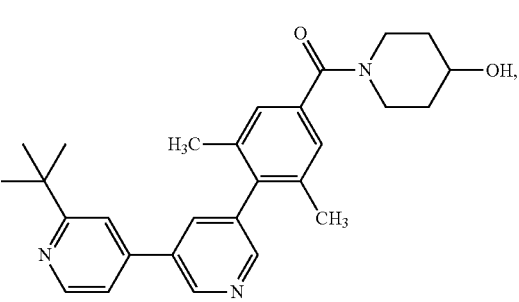
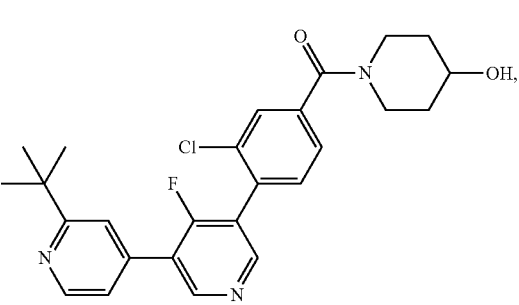
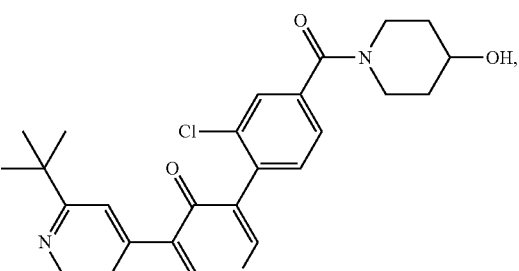
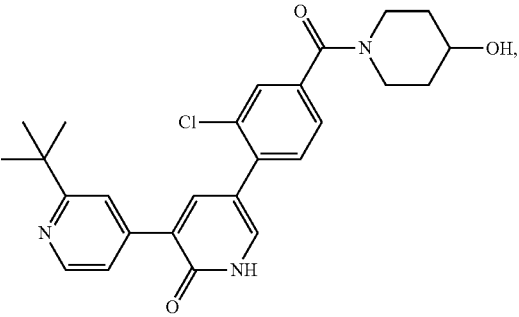

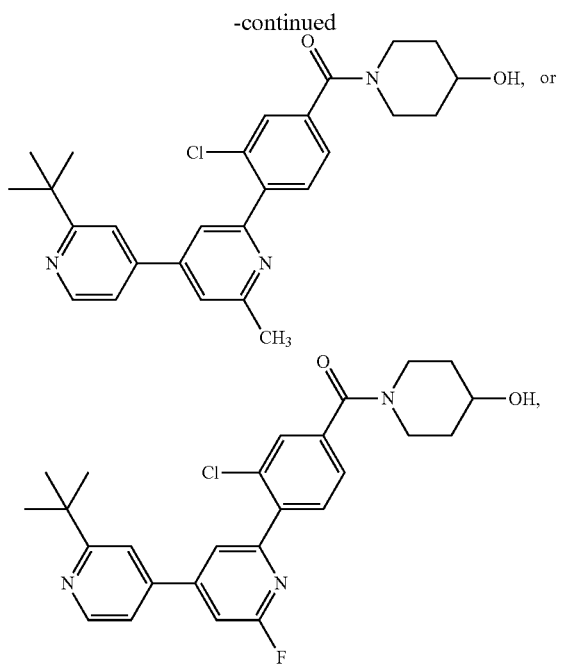
or a pharmaceutically acceptable salt, solvate, tautomer, isotope, or isomer of any of the foregoing.
In some embodiments, compound
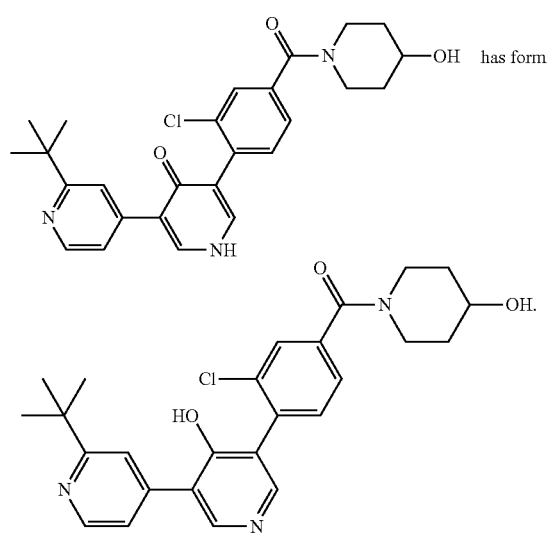
has form
In certain embodiments, compound
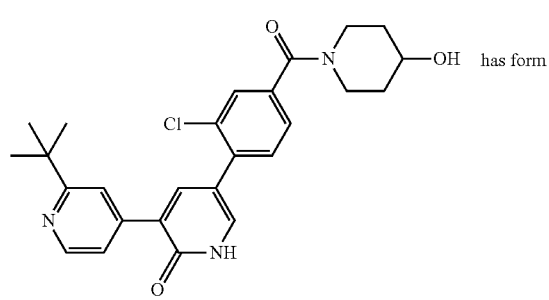
has form
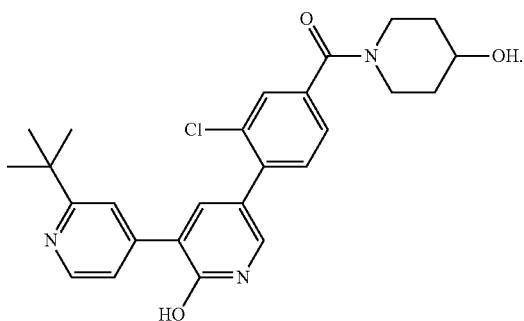
In certain embodiments, the compound of Formula (X), (X-A), (X-Ai), (X-B), (X-Bi), (Z), (Z-A), (Z-Ai), (Z-B), (Z-Bi), (I), (I-A), (I-Ai), (Z-B), or (Z-Bi) is:
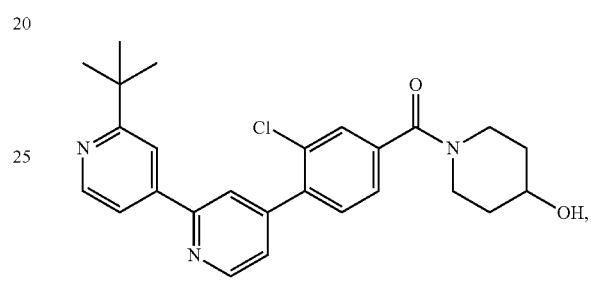

95
-continued
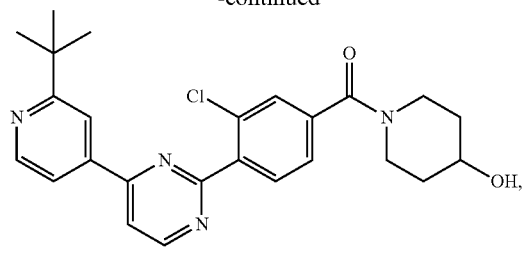
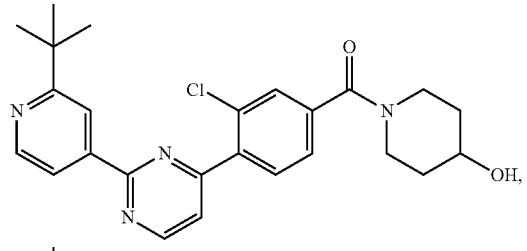
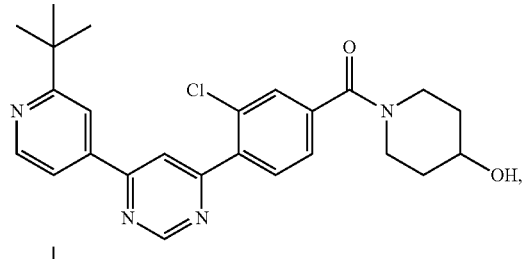
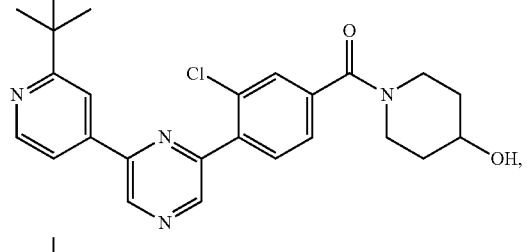
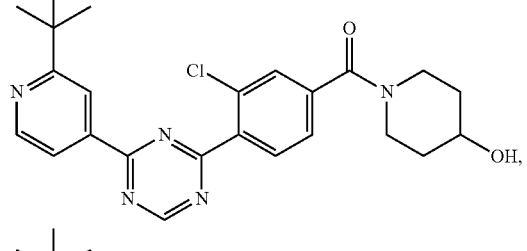
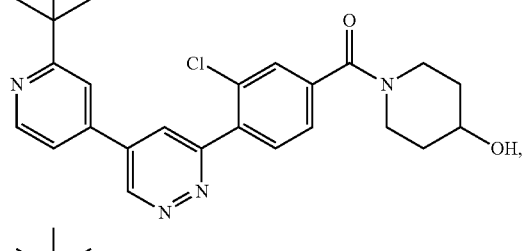
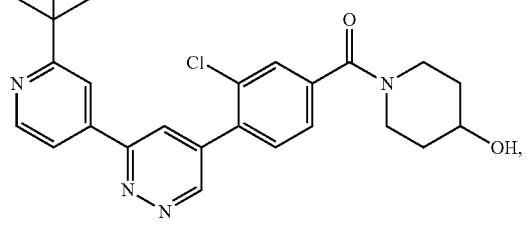
96
-continued
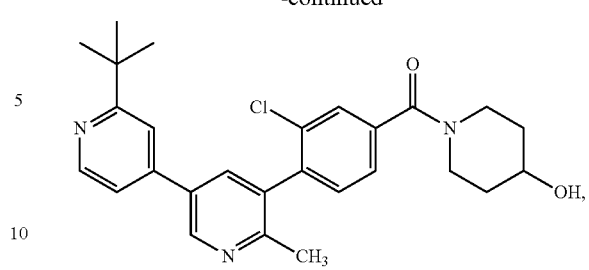
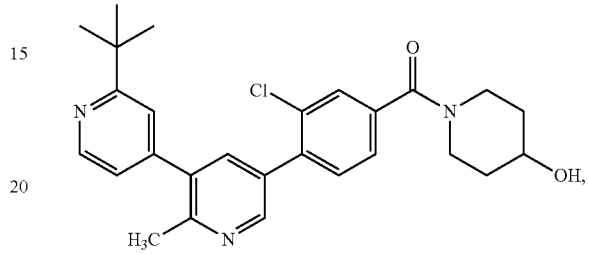
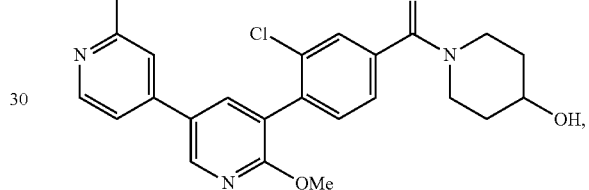
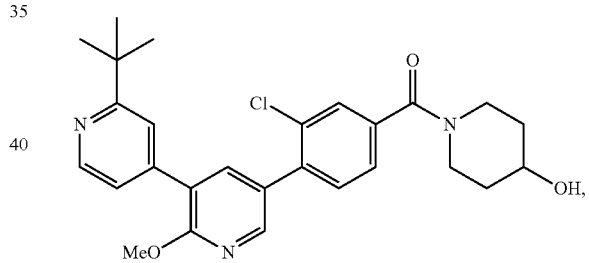

97
-continued
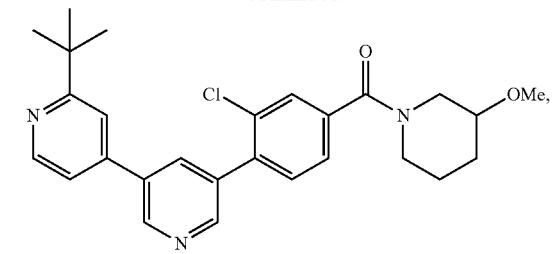
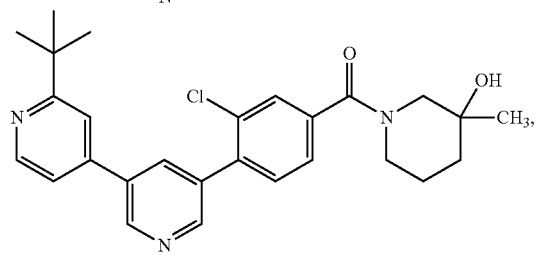
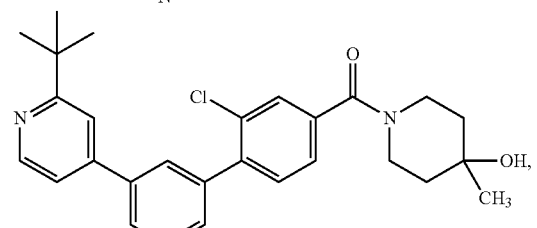
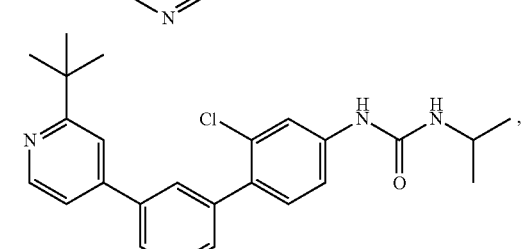
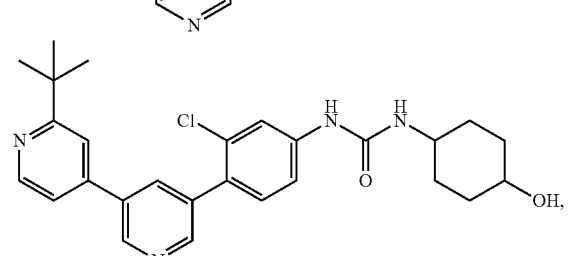
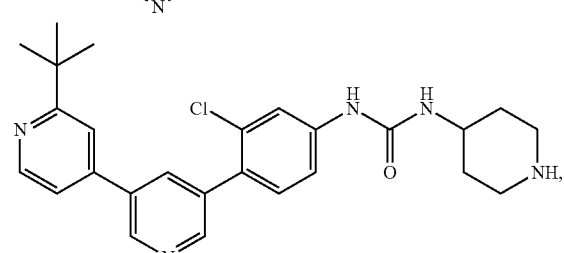
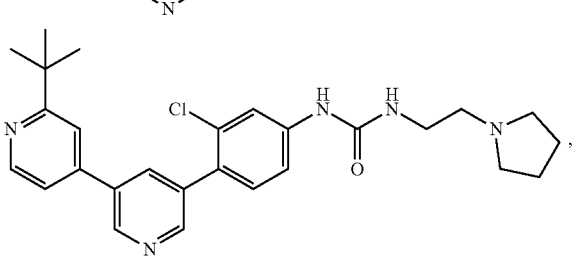
98
-continued
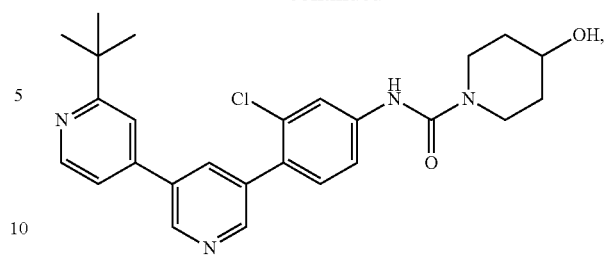
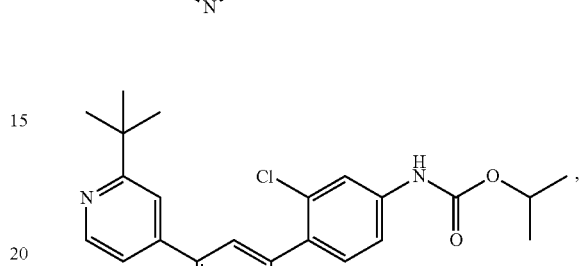
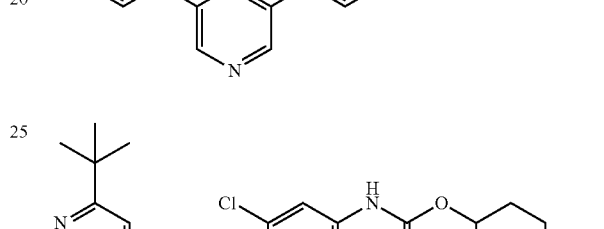
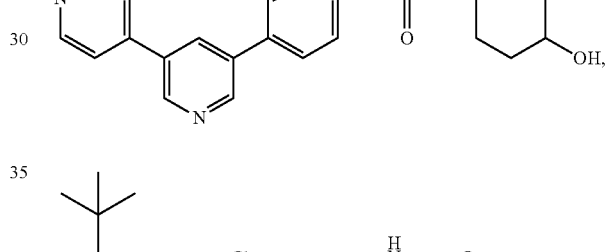
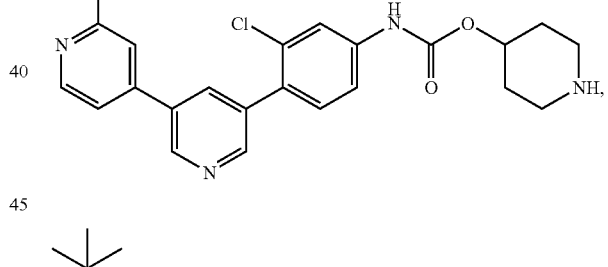
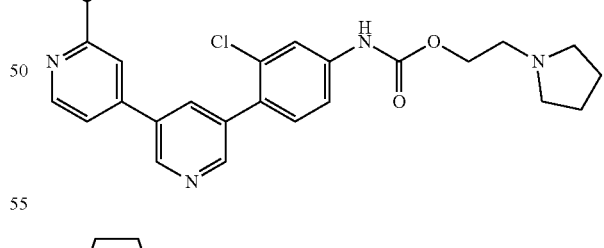
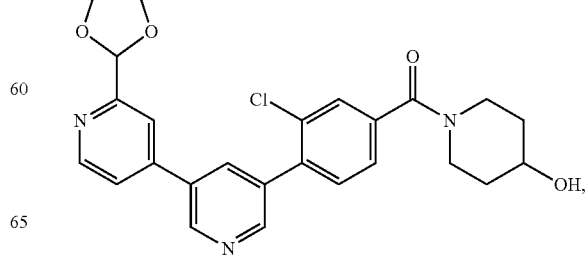

99
-continued
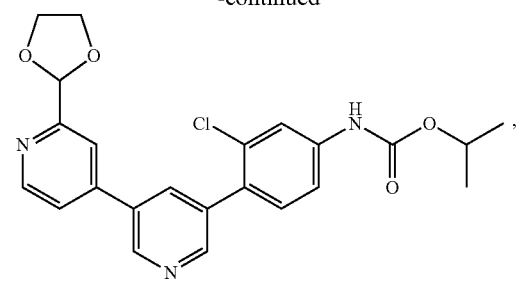
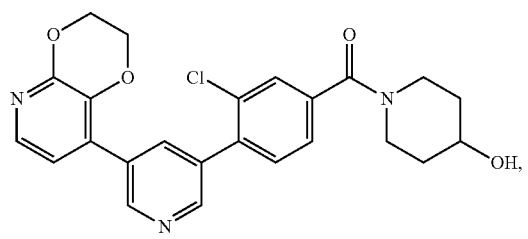
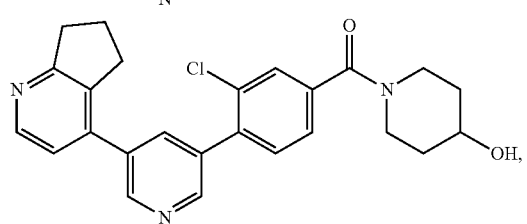
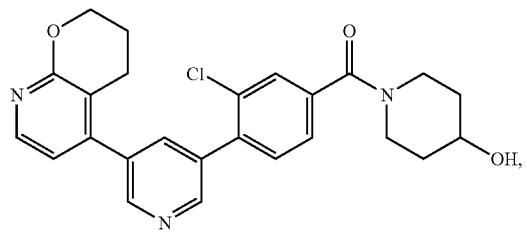
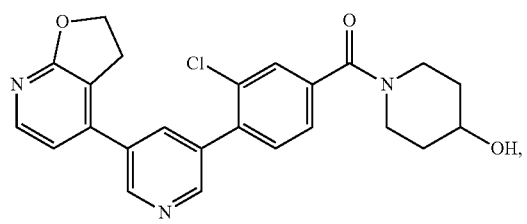
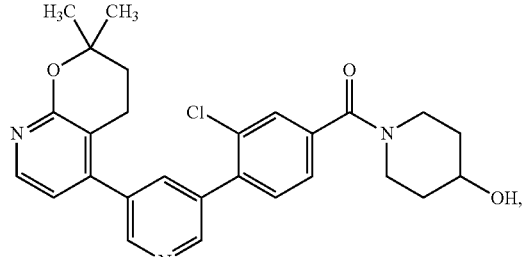
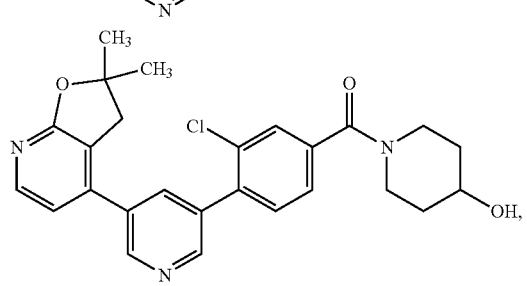
100
-continued
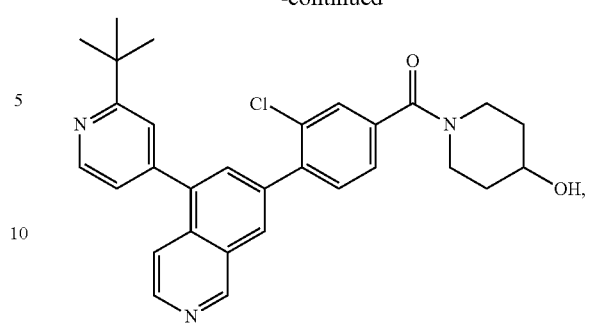
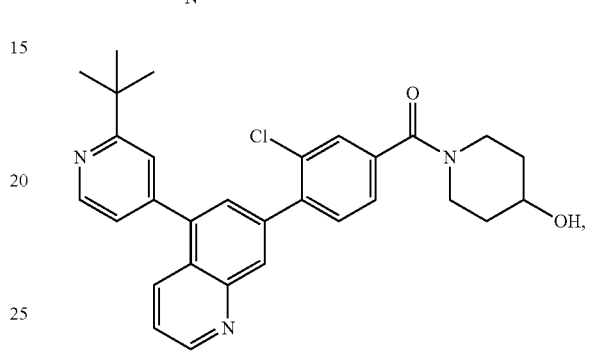
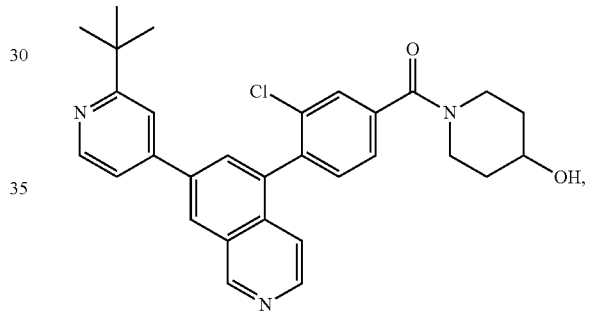
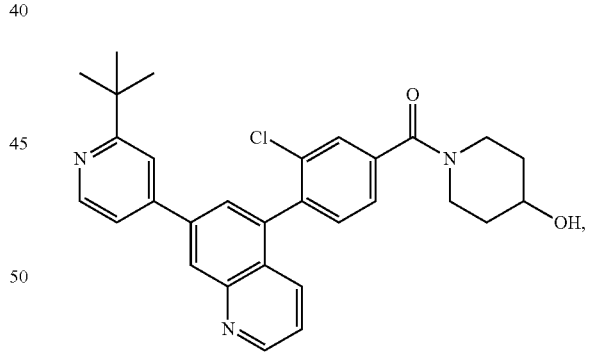
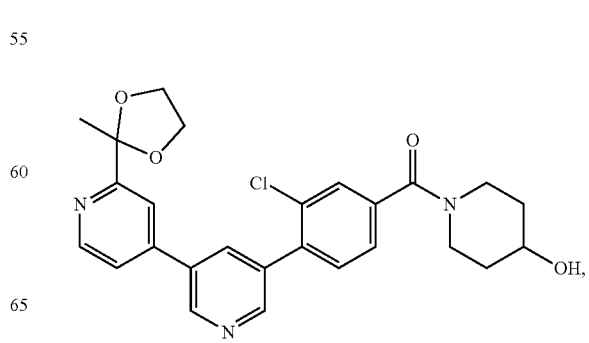

101
-continued
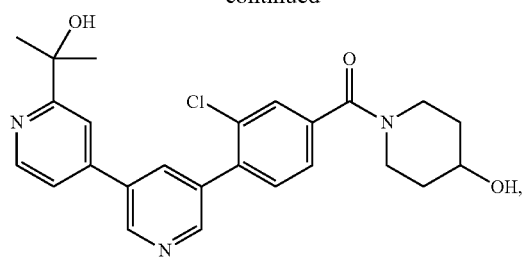
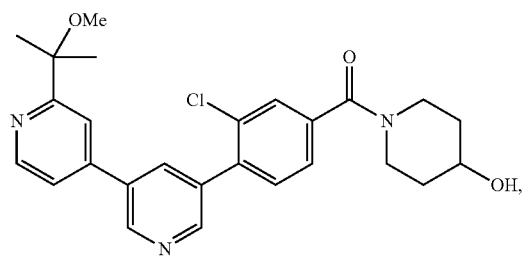
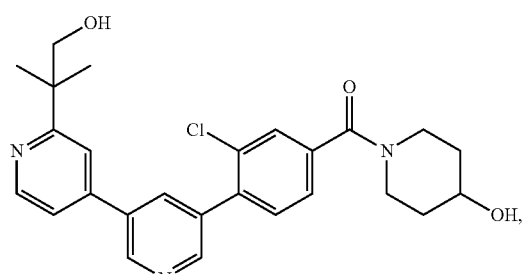
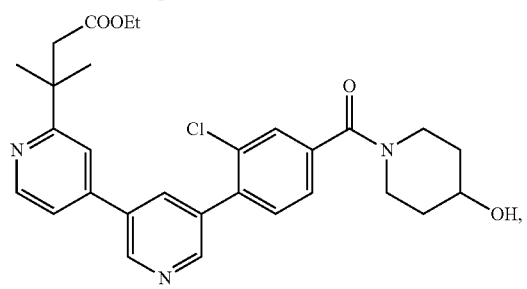
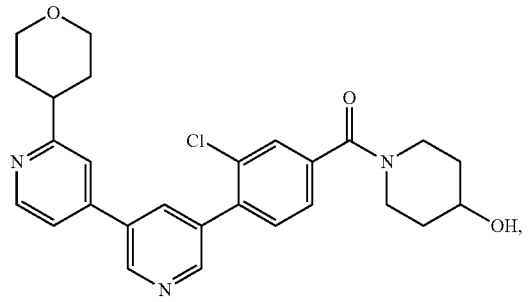
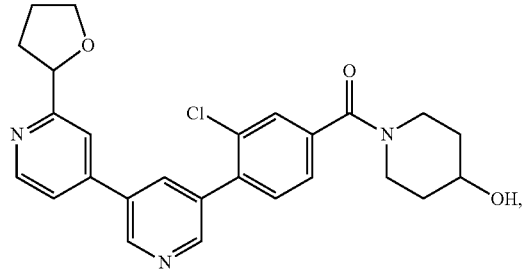
102
-continued
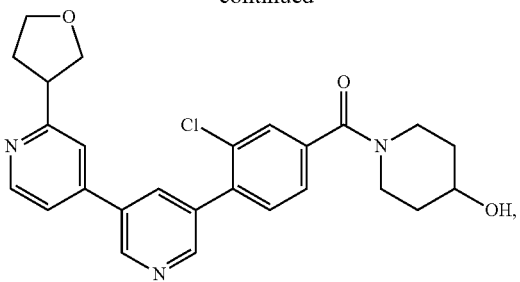
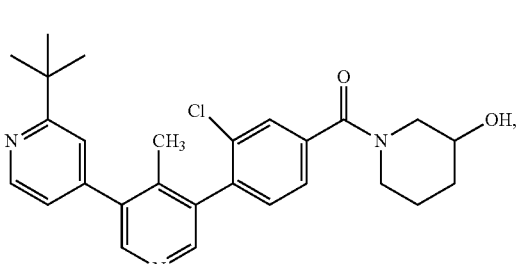
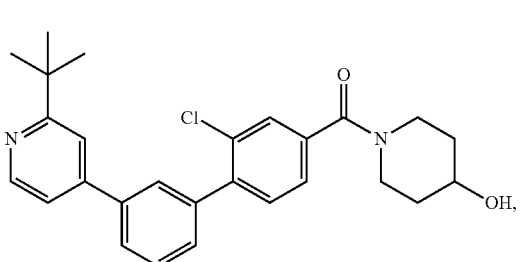
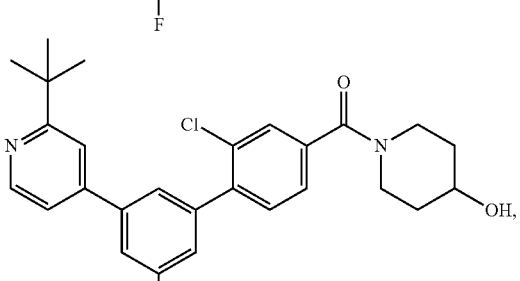
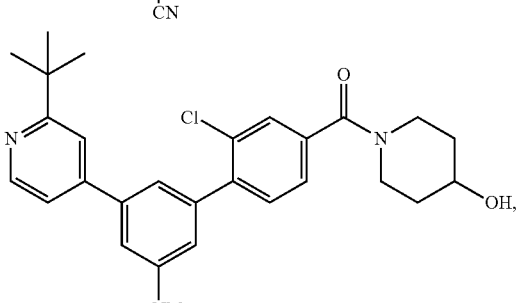
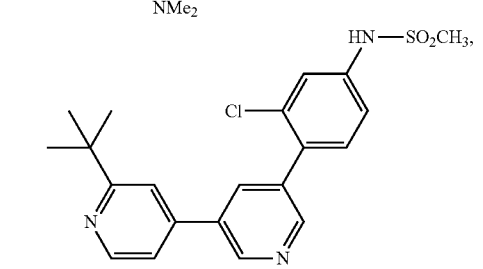

103
-continued
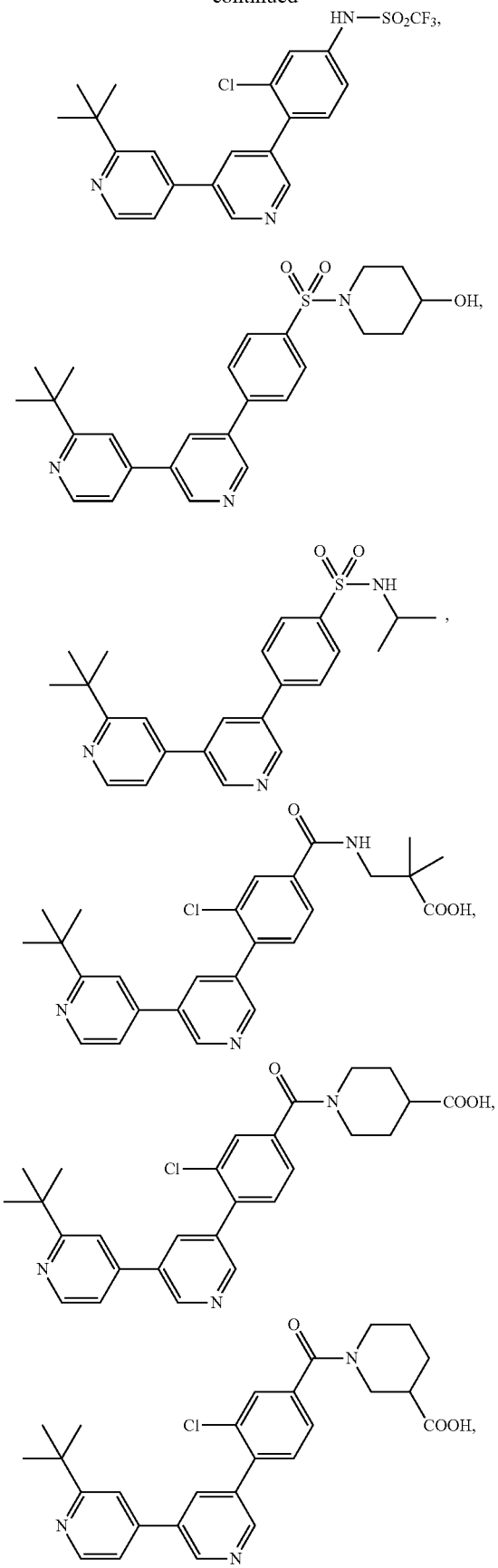
104
-continued
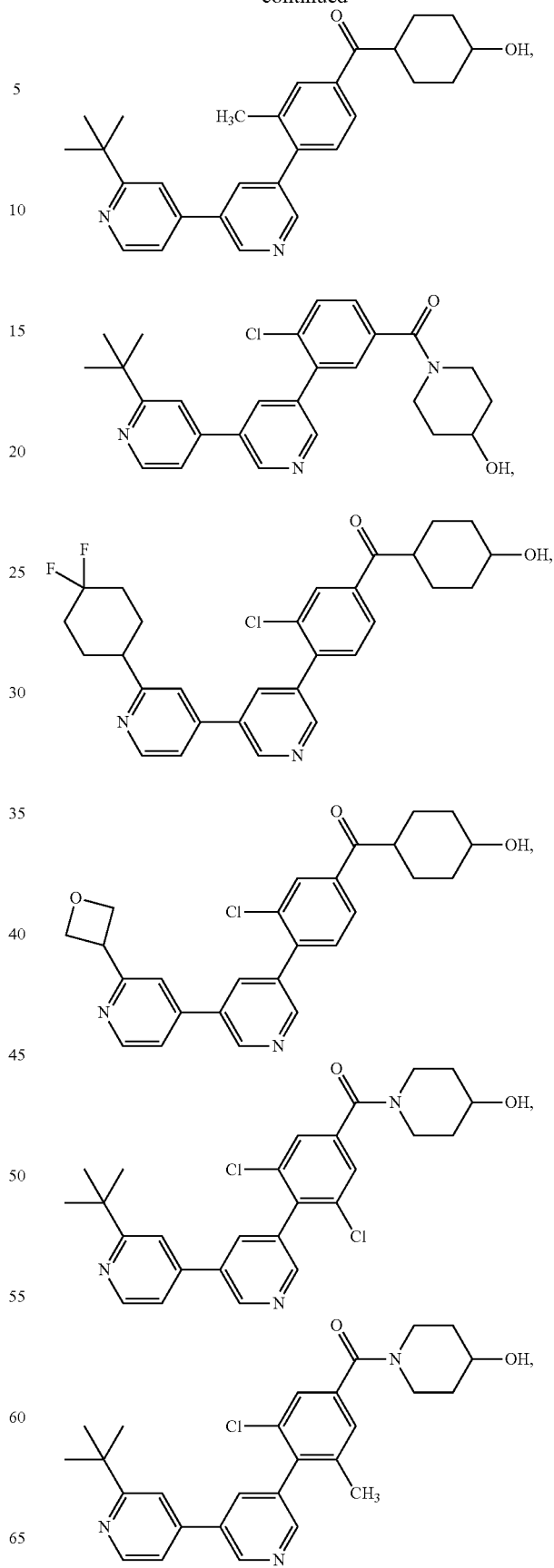

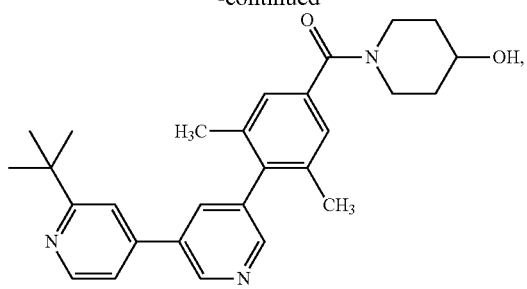
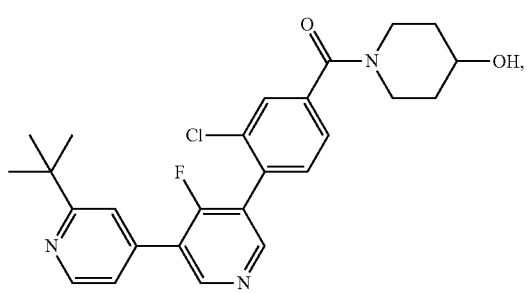
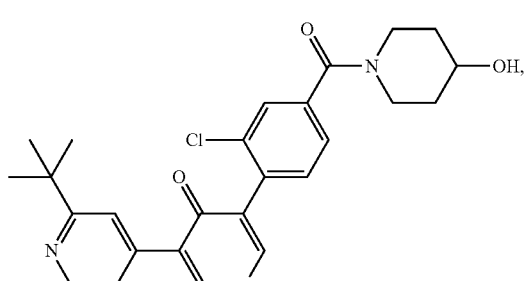
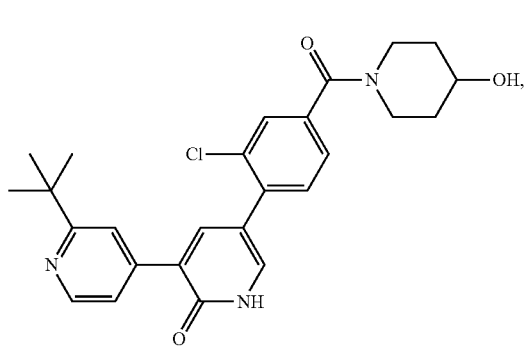
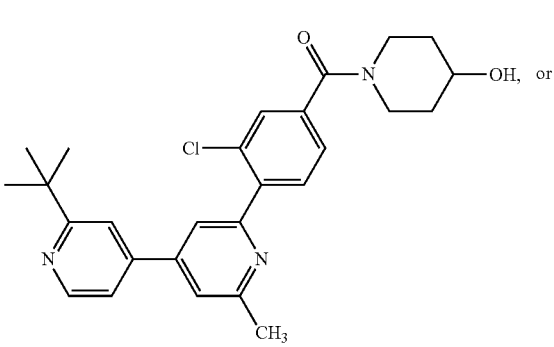
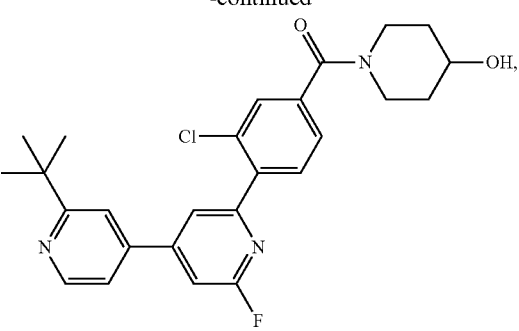
or a pharmaceutically acceptable salt, solvate, tautomer, isotope, or isomer of any of the foregoing.
In certain embodiments, the compound of Formula (X), (X-A), (X-Ai), (X-B), (X-Bi), (Z), (Z-A), (Z-Ai), (Z-B), (Z-Bi), (I), (I-A), (I-Ai), (Z-B), or (Z-Bi) is:
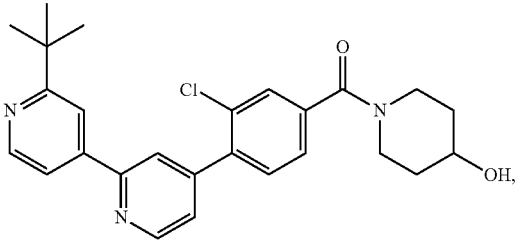
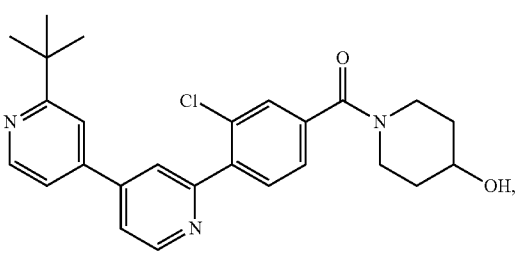
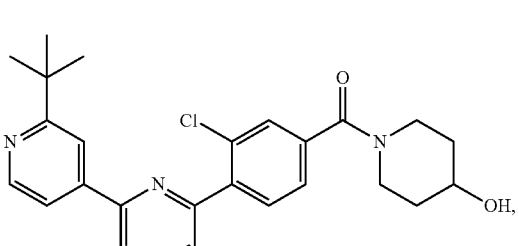

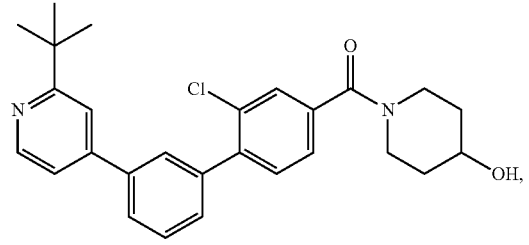
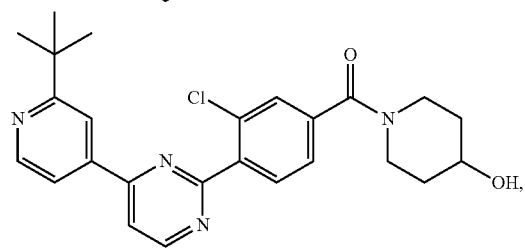
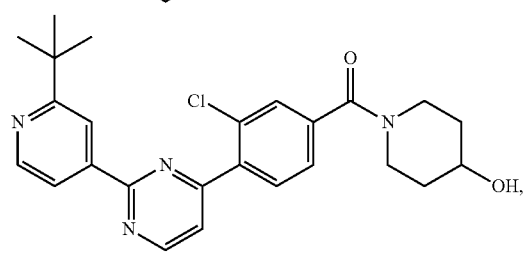
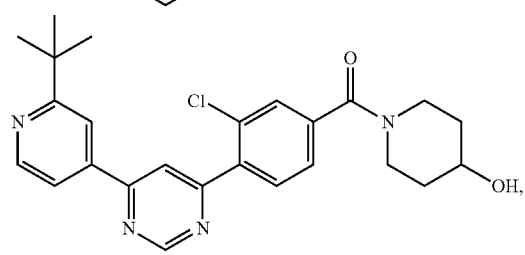
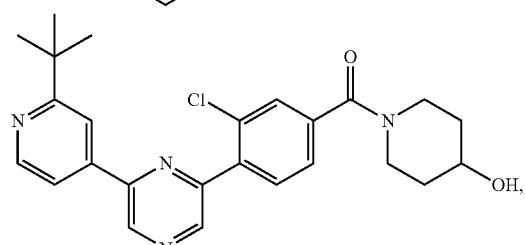
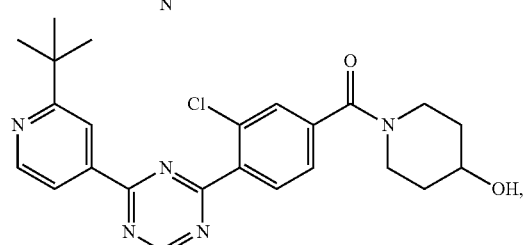
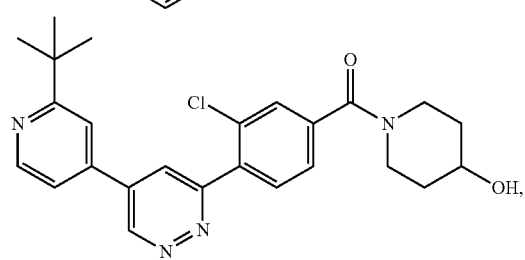
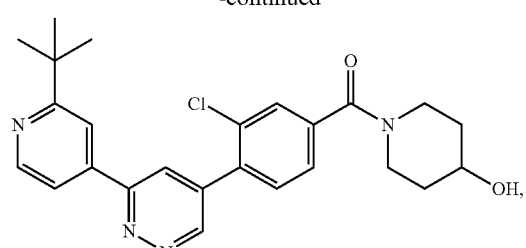
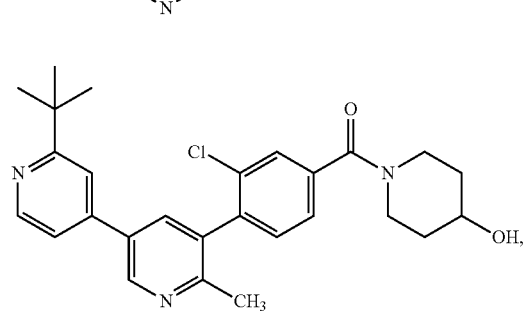
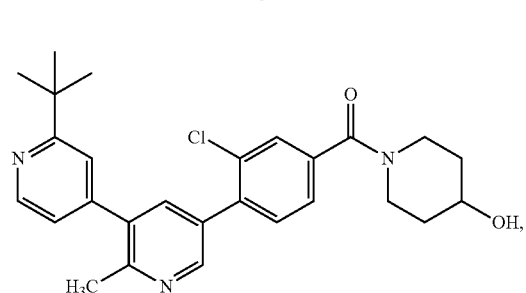
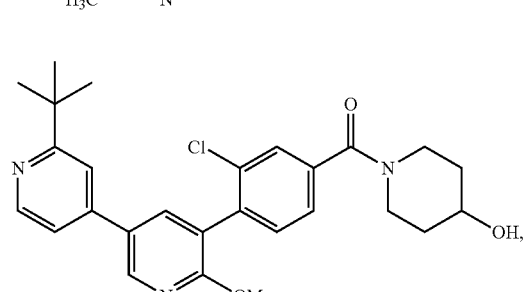
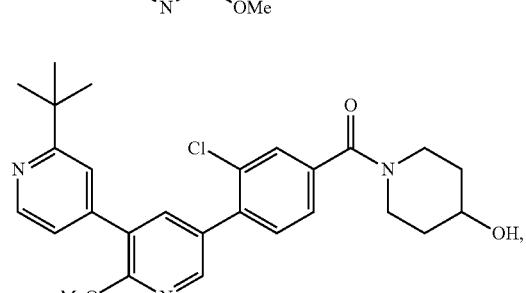
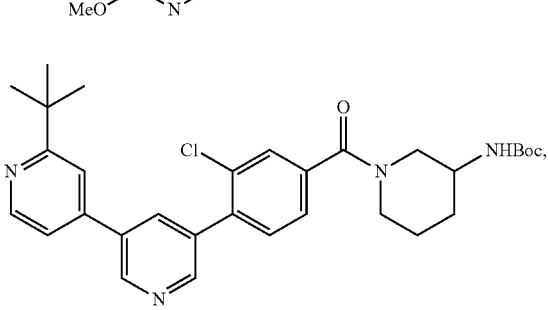

-continued
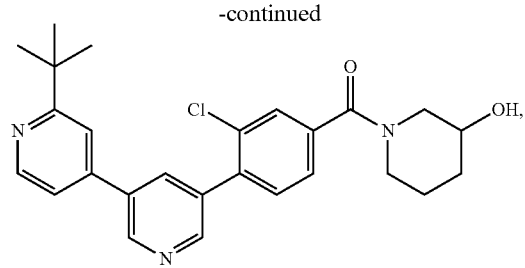
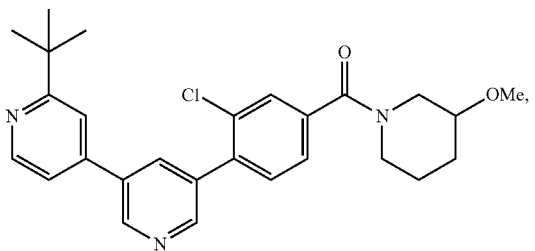
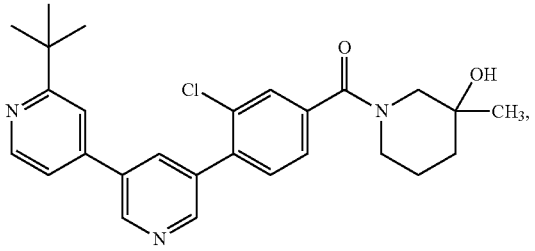
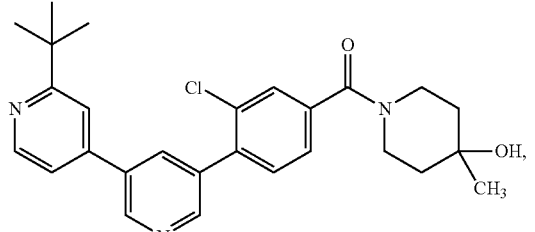
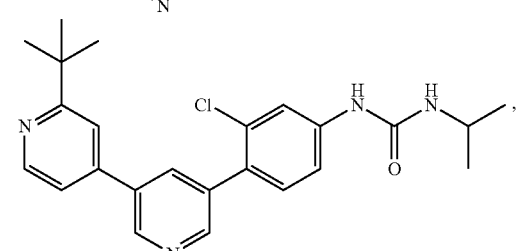
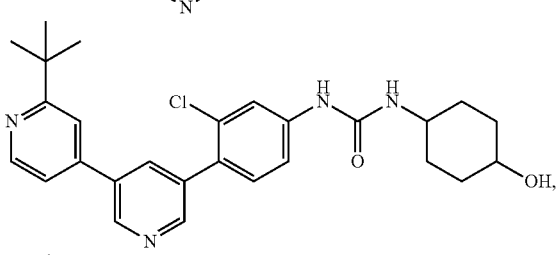
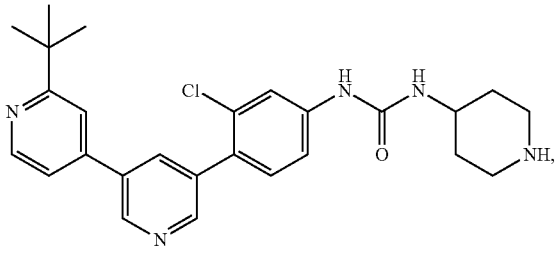
-continued
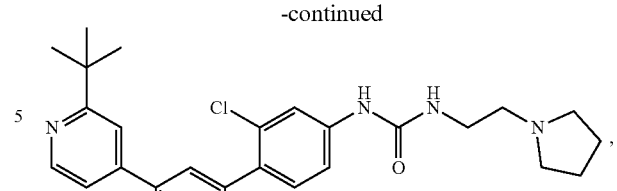
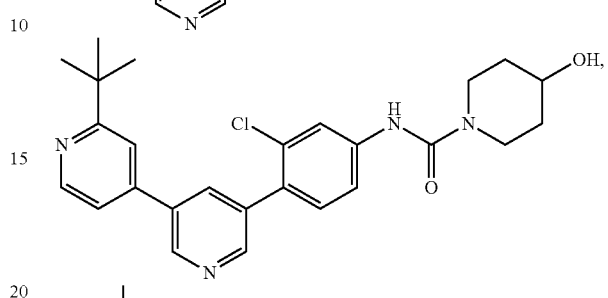
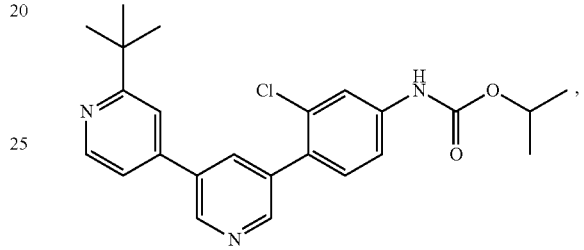
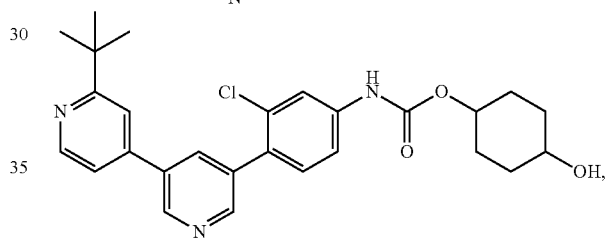
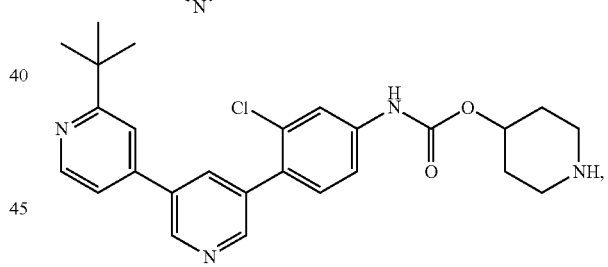
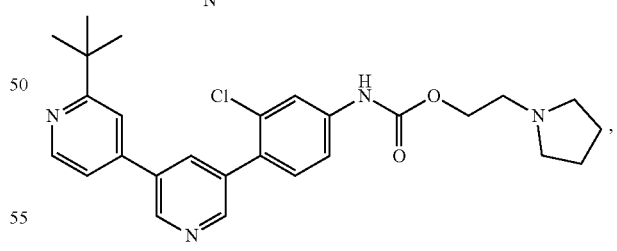
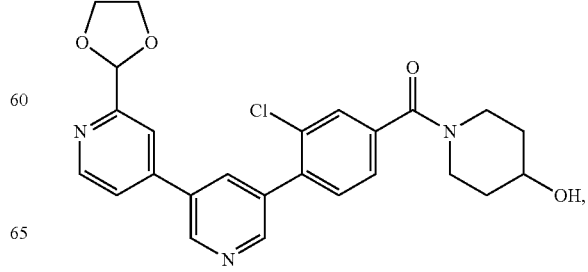

111
-continued
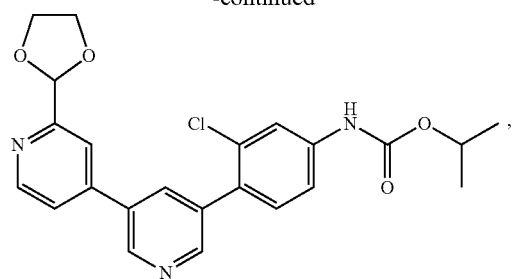
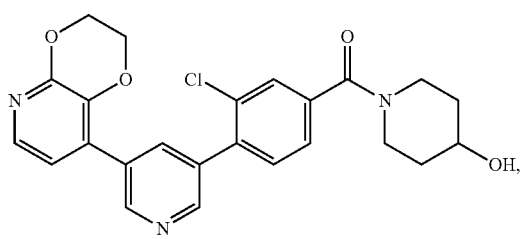
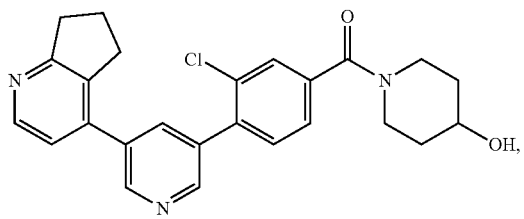
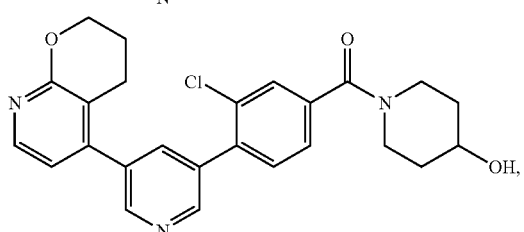
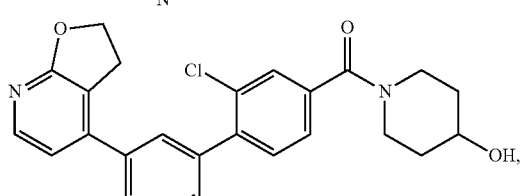
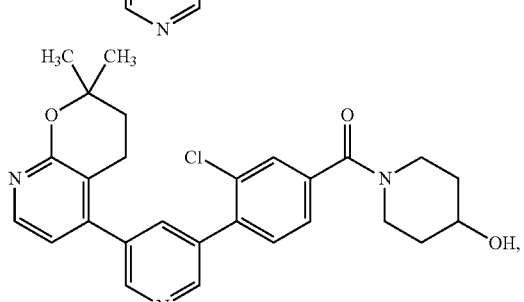
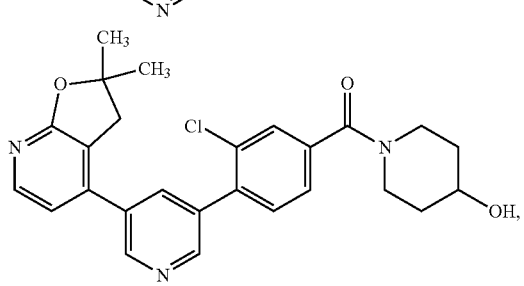
112
-continued
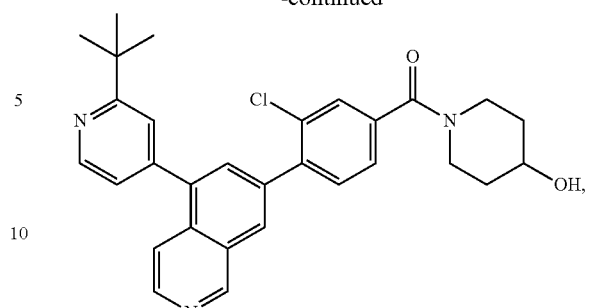
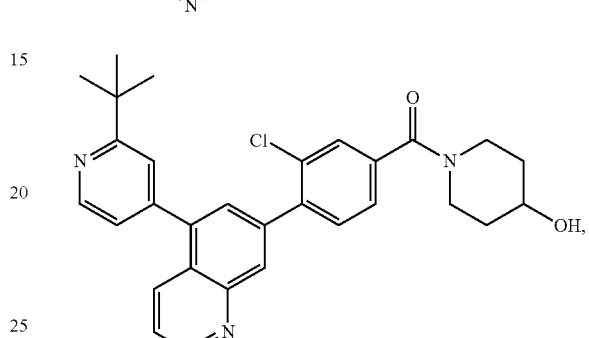
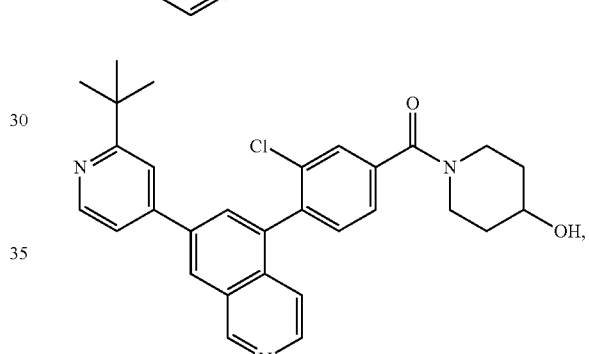
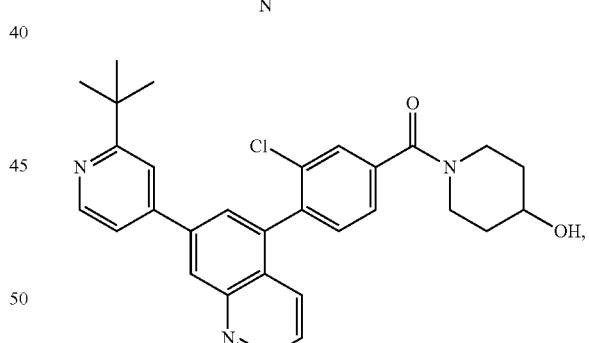
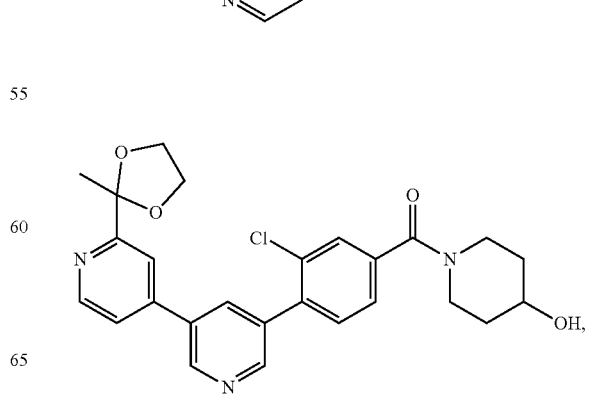

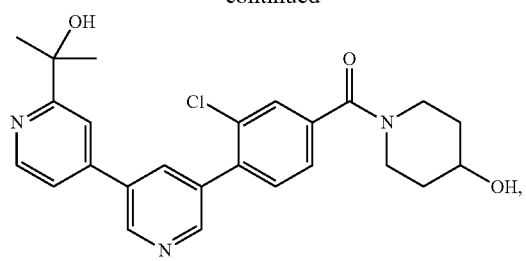
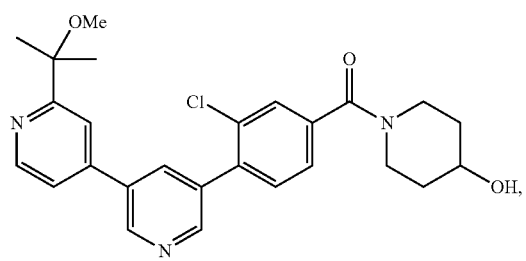
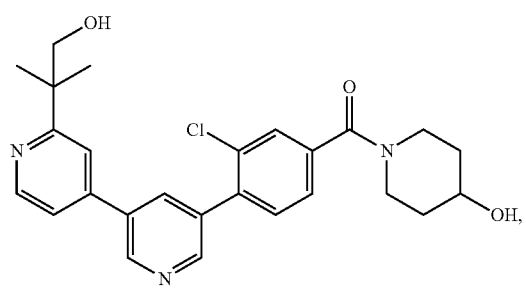
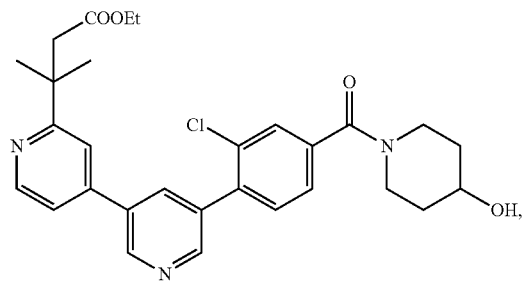
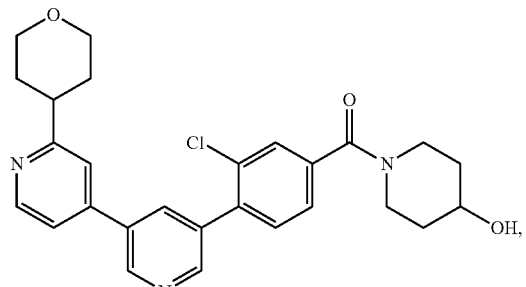
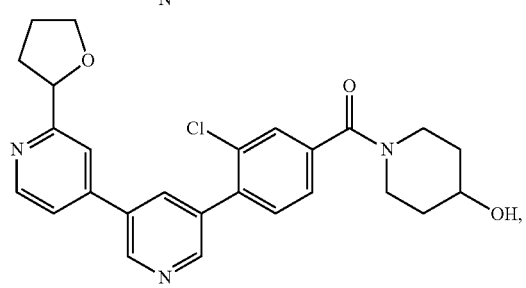
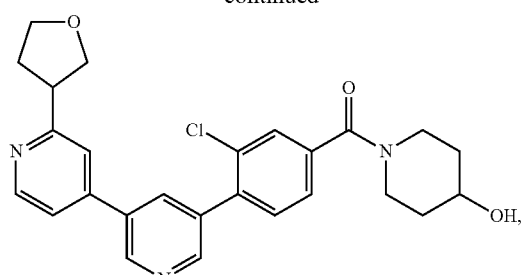
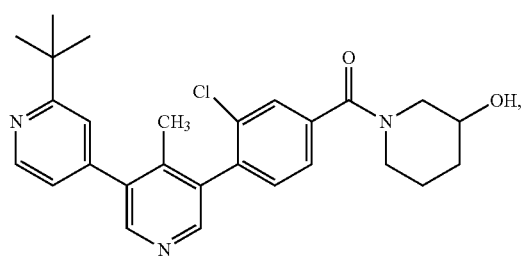
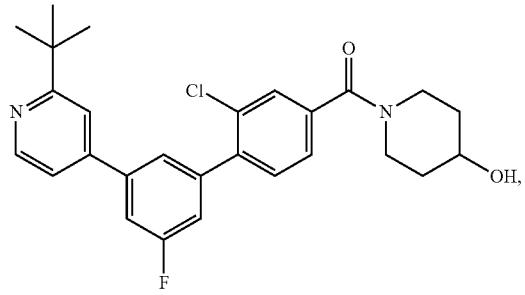
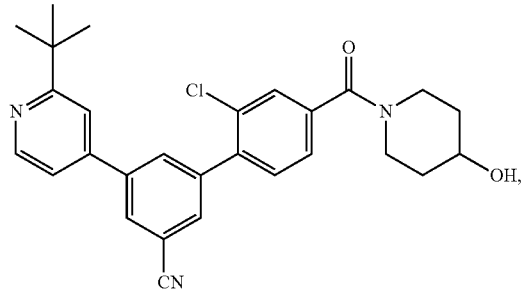
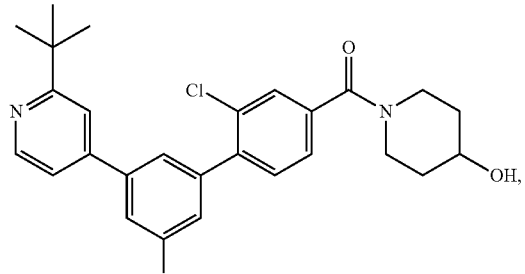
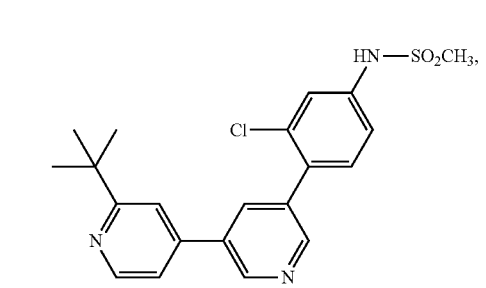

115
-continued
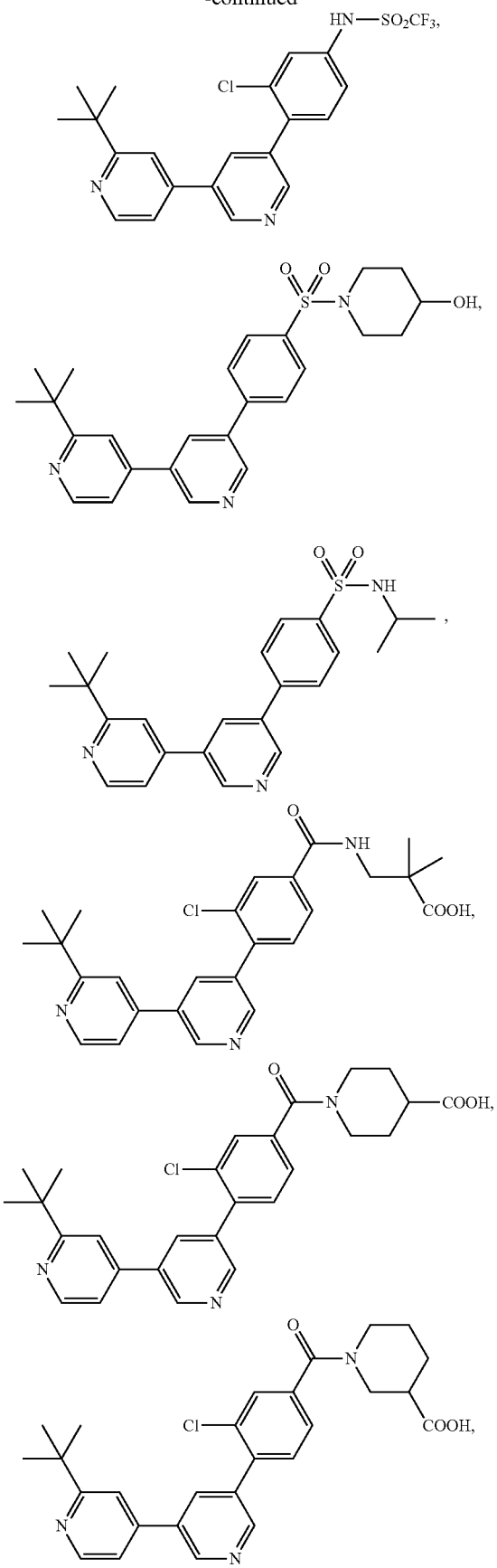
116
-continued
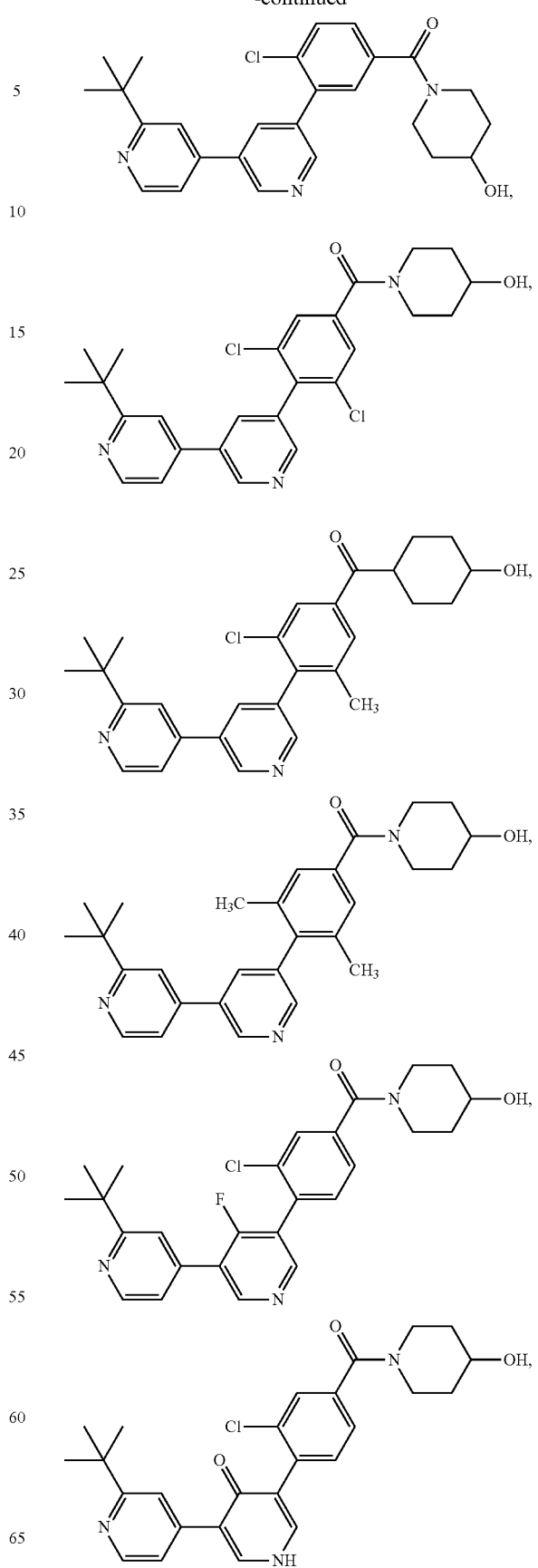

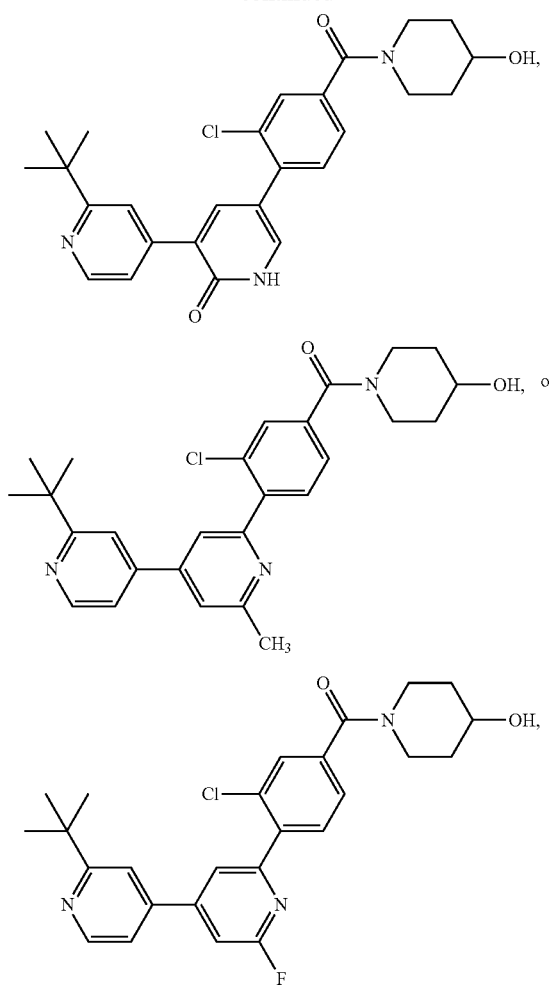
or a pharmaceutically acceptable salt, solvate, tautomer, isotope, or isomer of any of the foregoing.
In some embodiments, the compound of Formula (X), (X-A), (X-Ai), (X-B), (X-Bi), (Z), (Z-A), (Z-Ai), (I), (I-A), or (I-Ai) is:
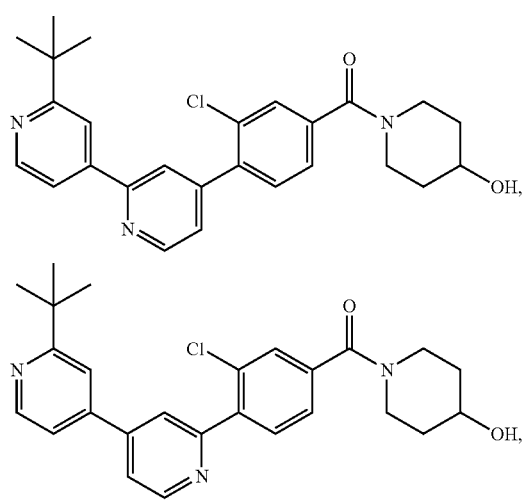
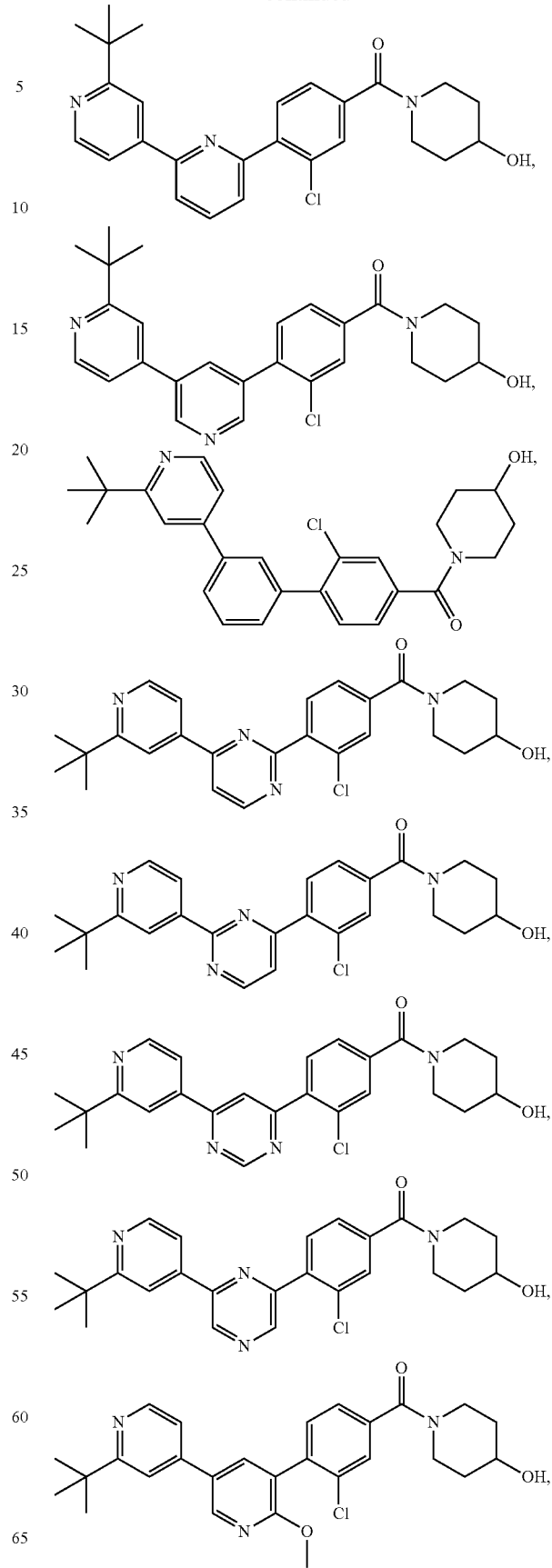

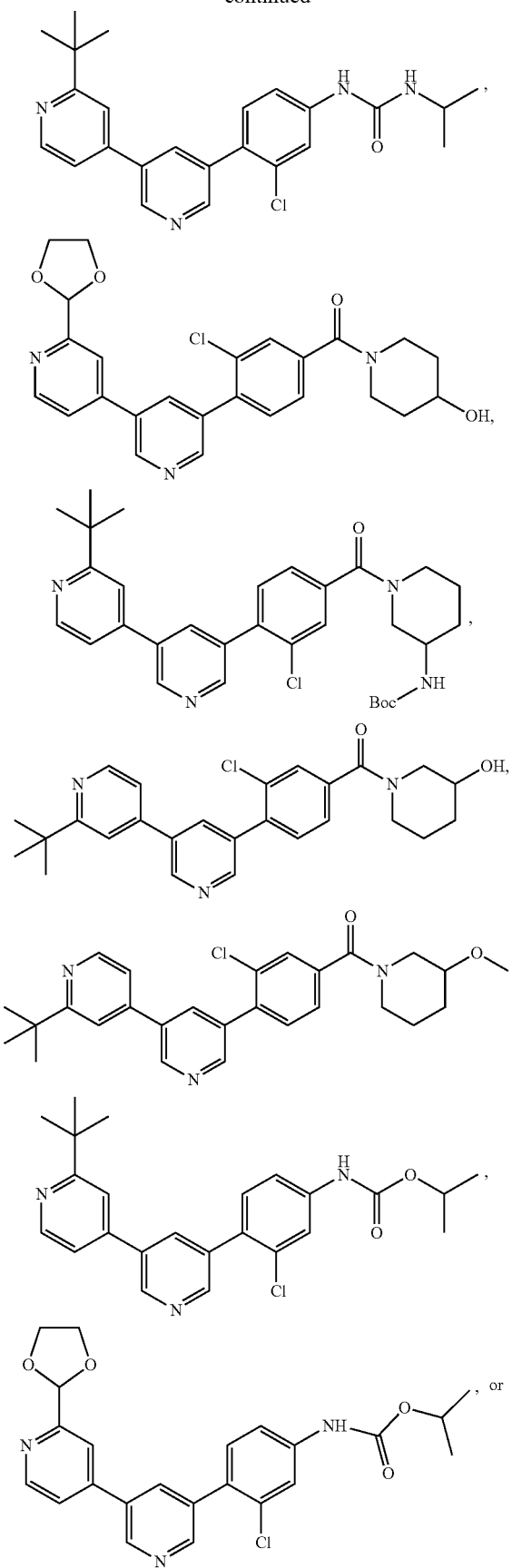
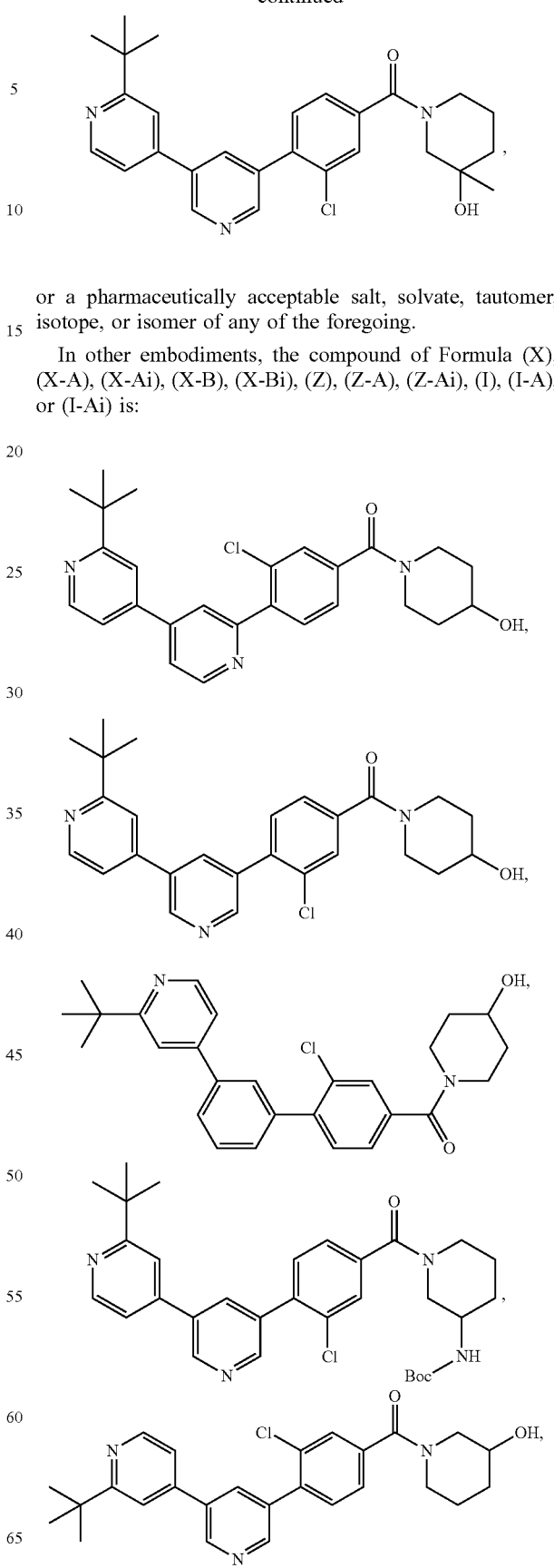
or a pharmaceutically acceptable salt, solvate, tautomer, isotope, or isomer of any of the foregoing.
In other embodiments, the compound of Formula (X), (X-A), (X-Ai), (X-B), (X-Bi), (Z), (Z-A), (Z-Ai), (I), (I-A), or (I-Ai) is:

-continued
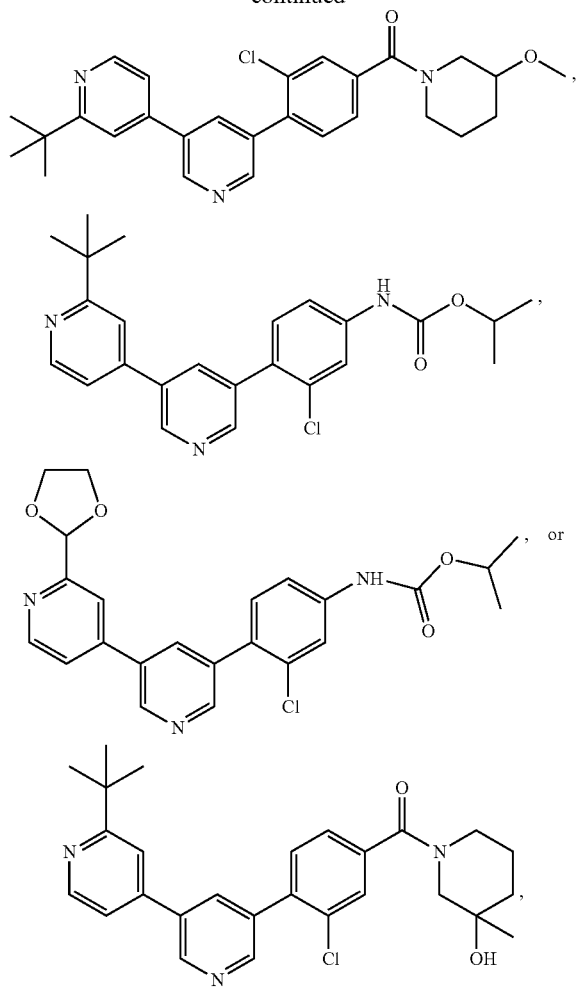
or a pharmaceutically acceptable salt, solvate, tautomer, isotope, or isomer of any of the foregoing.
In certain embodiments, the compound of Formula (X), (X-A), (X-Ai), (X-B), (X-Bi), (Z), (Z-A), (Z-Ai), (I), (I-A), or (I-Ai) is:
-continued
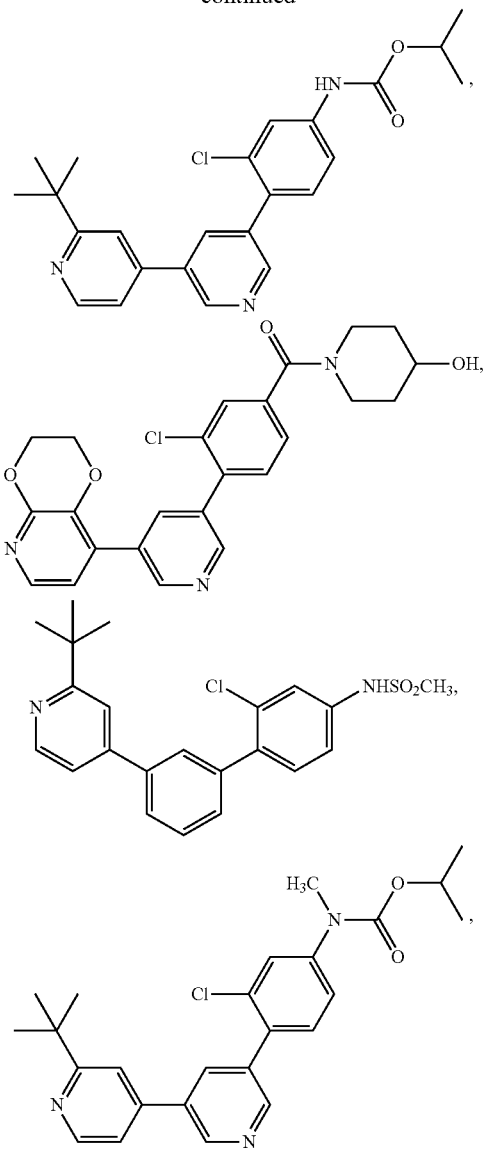
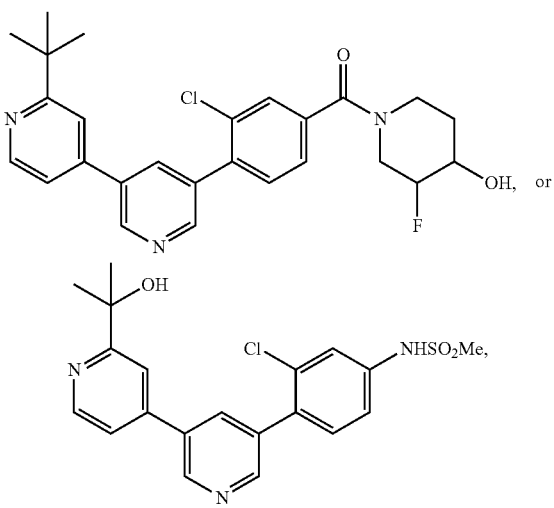
or a pharmaceutically acceptable salt, solvate, tautomer, isotope, or isomer of any of the foregoing In still further embodiments, the compound of Formula (X), (X-A), (X-Ai), (X-B), (X-Bi), (Z), (Z-A), (Z-Ai), (I), (I-A), or (I-Ai) is:

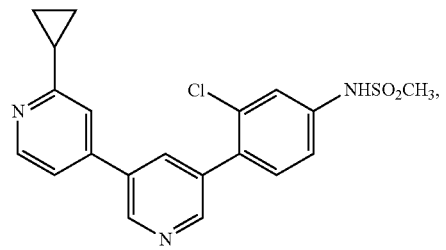

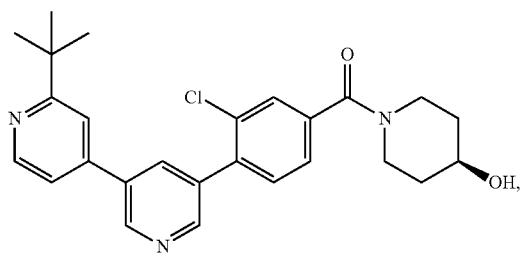

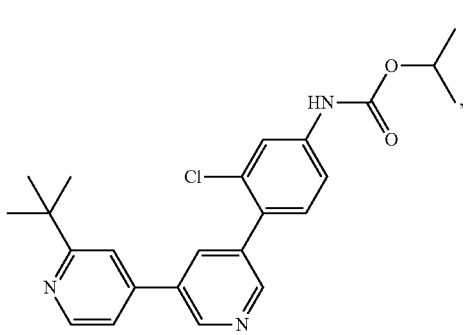

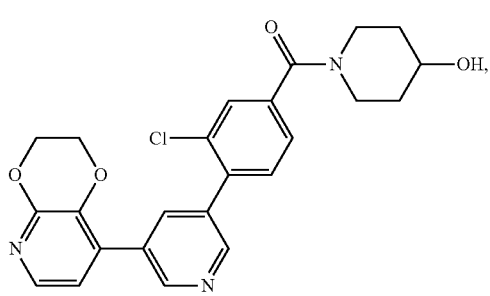

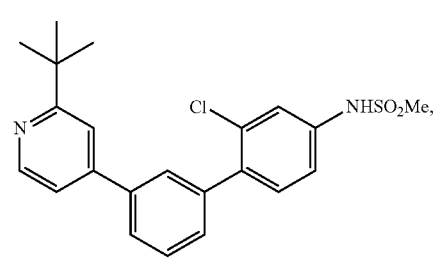

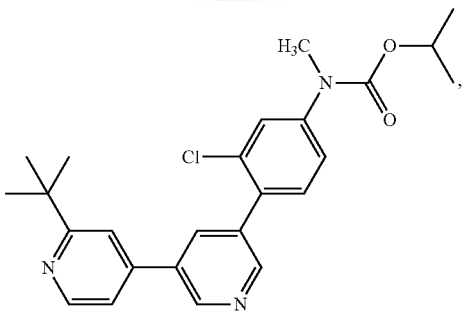

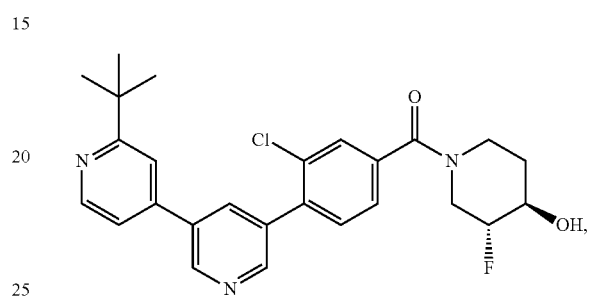

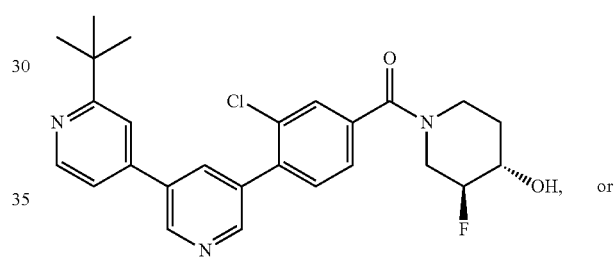

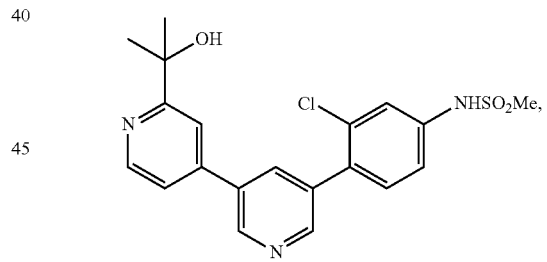

or a pharmaceutically acceptable salt, solvate, tautomer, isotope, or isomer of any of the foregoing Further provided are pharmaceutical compositions comprising any of the compounds disclosed herein, such as a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, and a pharmaceutically acceptable excipient.

The compounds disclosed herein, such as a compound of Formula (X), (X-A), (X-Ai), (X-B), (X-Bi), (Z), (Z-A), (Z-Ai), (I), (I-A), or (I-Ai), or a pharmaceutically acceptable salt, solvate, tautomer, isotope, or isomer thereof, may be prepared, for example, through the reaction routes depicted in General Schemes 1-III.

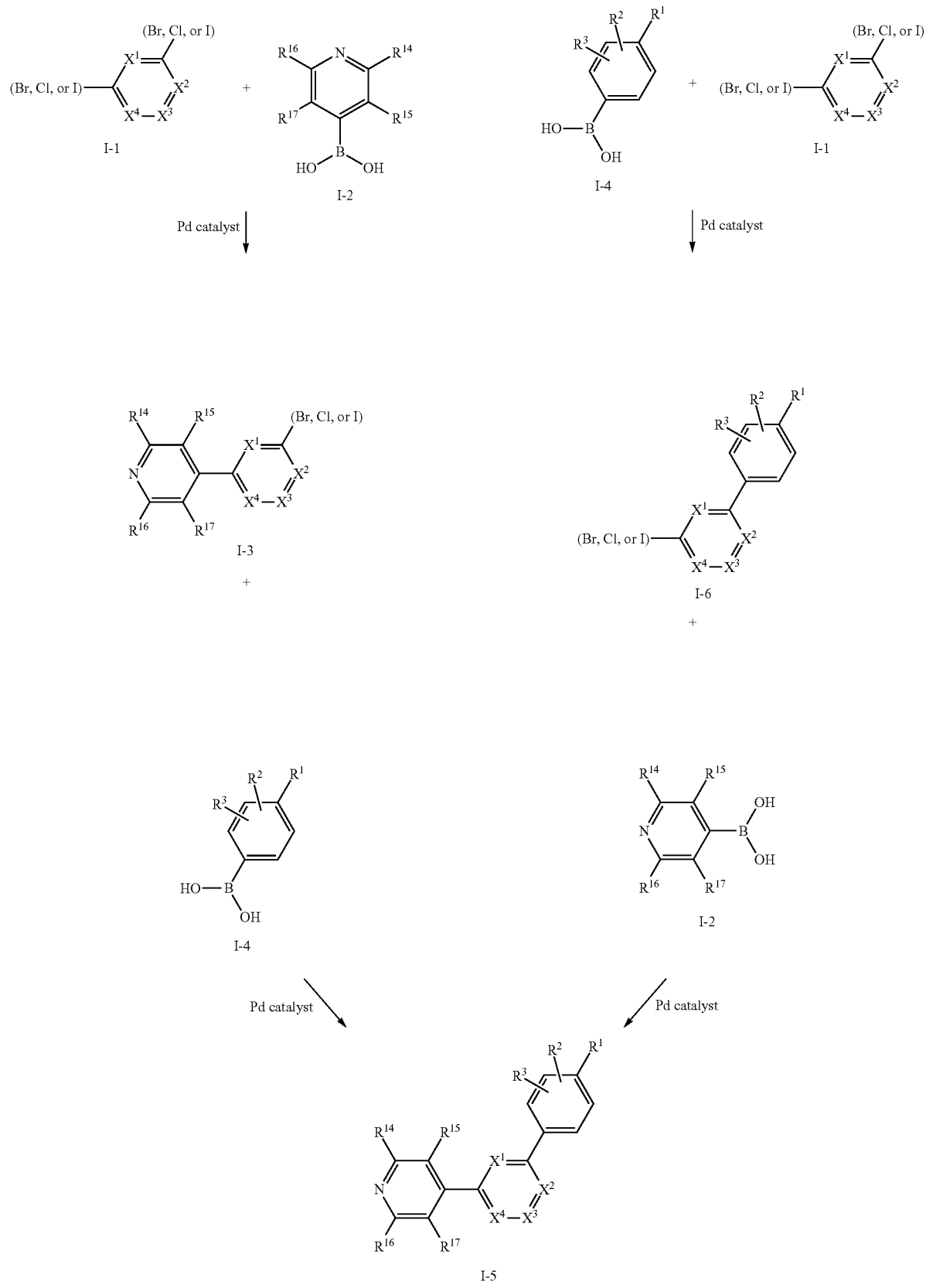
General Reaction Scheme I

General Reaction Scheme I provides two routes to compound I-5, which is an example of a compound of Formula (X), or a pharmaceutically acceptable salt, solvate, tautomer, isotope, or isomer thereof as described herein. In one route, compound I-1 is coupled with compound I-2 in the presence of a palladium catalyst and base to produce compound I-3. Suitable palladium catalysts may include, for example, tetrakis(triphenylphosphine)palladium(0), and suitable bases may include, for example, aqueous sodium carbonate or potassium carbonate. In the next step, compound I-3 is reacted with compound I-4 in the presence of a coupling reagent and a base. Suitable coupling reagents may include bis(di-tert-butyl(4-dimethylaminophenyl)phosphine) dichloropalladium(II) or [1,1'-bis(diphenylphosphino) ferrocene]dichloropalladium(II) or tetrakis(triphenylphosphine) palladium(0). Suitable bases may include aqueous sodium carbonate or potassium carbonate. Either of the two coupling reactions may be carried out using a solvent, for example, dioxane or dimethoxyethane. In some embodiments, the reactions are carried out between 60° C. to 120° C., for between 8 h to 24 h. In the second route provided in General Reaction Scheme I, compound I-4 is coupled with compound I-1 to produce compound I-6, which is next coupled with compound I-2 to produce compound I-5. Similar coupling reagents and conditions may be used as were previously described for the first route.

In certain embodiments, compounds of Formula (X), (X-A), (X-Ai), (Z), (Z-A), (Z-Ai), (I), (I-A), or (I-Ai), or a pharmaceutically acceptable salt, solvate, tautomer, isotope, or isomer thereof, wherein $R^1$ is —C(O)NR$^8$R$^9$ may be prepared according to General Reaction Scheme II.

General Reaction Scheme II

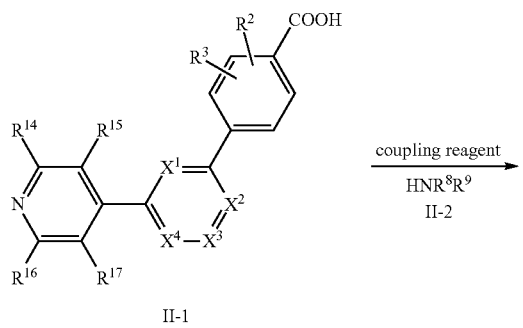

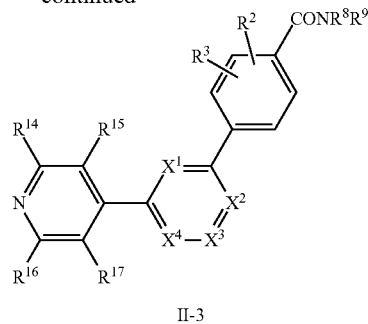

II-3

In General Reaction Scheme II, compound II-1 is combined with an amine II-2 in the presence of a coupling reagent, for example HATU ((1-[Bis(dimethylamino)methylene]-1H-1,2,3-triazolo[4,5-b]pyridinium 3-oxid hexafluorophosphate)) or EDC (1-ethyl-3-(3-dimethylaminopropyl) carbodiimide). The base DIPEA (N,N-diisopropylethylamine) may also be added. In some embodiments, the reaction is carried out in a dipolar aprotic solvent, such as DMF or dioxane, and may be performed, for example, at room temperature until the reaction has gone to completion, such as for 8 h to 48 h. The compound II-1 may be prepared as described in General Reaction Scheme I above, wherein $R^1$ is —COOH.

In certain embodiments, compounds of Formula (X), (X-A), (X-Ai), (Z), (Z-A), (Z-Ai), (I), (I-A), or (I-Ai), or a pharmaceutically acceptable salt, solvate, tautomer, isotope, or isomer thereof, wherein $R^1$ is —NR$^{10}$C(O)R$^9$, —NR$^{10}$SO$_2$R$^9$, —NR$^{10}$C(O)NR$^8$R$^9$, or —NR$^{10}$C(O)OR$^9$ may be prepared by proceeding as shown in General Reaction Scheme III:

General Reaction Scheme III

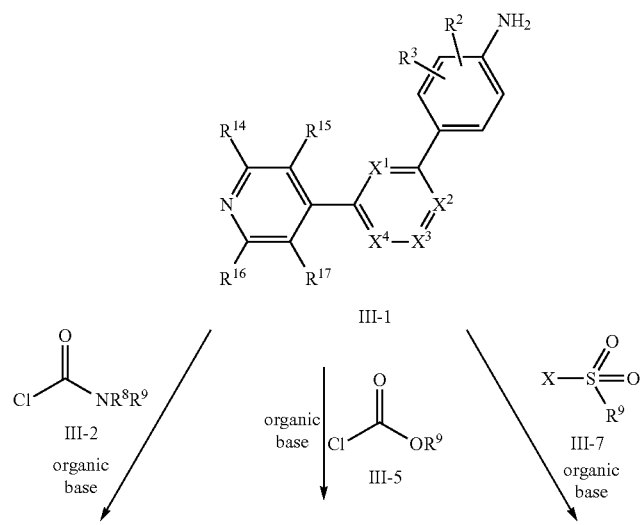

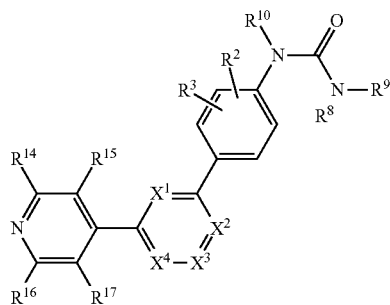
III-4

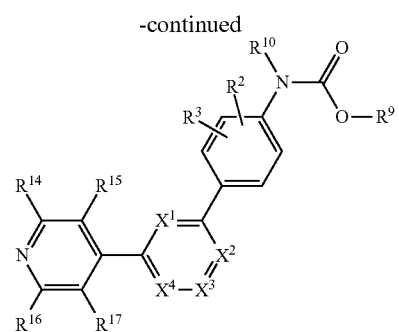
III-6

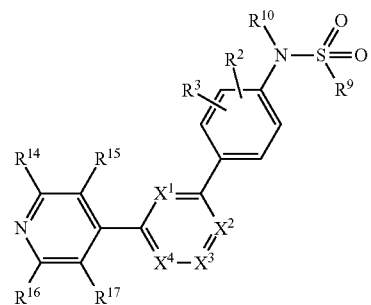
III-8

Compound III-4 may be prepared, for example, by reacting compound III-1 with a carbamoyl chloride compound III-2 in the presence of an organic base, such as diisopropylethyl amine or triethylamine. The reaction may be carried out in a solvent, such as dichloromethane, at room temperature for 4 h to 24 h. Alternatively, compound III-4 may be prepared by reacting compound III-1 with phenylchloroformate in dichloromethane in the presence of triethylamine for approximately 16 h at room temperature, and then treating resulting phenylcarbamate with an amine $HNR^8R^9$ in tetrahydrofuran at 0° C. to room temperature for 4 h to 24 h. Compound III-6 may be prepared, for example, by reacting compound III-1 with a chloroformate compound III-5, in the presence of an organic base, such as diisopropylethyl amine or triethylamine. The reaction may be carried out in a solvent, such as dichloromethane, at room temperature for 4 h to 24 h. Compound III-8 may be prepared, for example, by reacting compound III-1 with a sulfonyl halide compound III-7 wherein X is chlorine or fluorine. This reaction may be carried out in the presence of an organic base, such as triethylamine, and in solvent such as pyridine for 4 h to 24 h at room temperature. Compound III-1 may be prepared, for example, as described in General Reaction Scheme I above, wherein $R^1$ is —$NH_2$.

Synthesis of the compounds of described herein may, in some embodiments, be accomplished by methods analogous to those described in the synthetic schemes above or the specific examples below.

The variables $X^1$, $X^2$, $X^3$, $X^4$, $R^1$, $R^2$, $R^3$, $R^8$, $R^9$, $R^{10}$, $R^{14}$, $R^{15}$, $R^{16}$, and $R^{17}$ in the compounds of General Reaction Schemes I-III are as described for Formula (X), Formula (Z), and Formula (I) herein. While General Reaction Schemes I-III depict the preparation of compounds of Formula (X), (X-A), (X-Ai), (Z), (Z-A), (Z-Ai), (I), (I-A), or (I-Ai), or a pharmaceutically acceptable salt, solvate, tautomer, isotope, or isomer thereof, compounds of Formula (X-B), (X-Bi), (Z-B), (Z-Bi), (I-B), or (I-Bi), or a pharmaceutically acceptable salt, solvate, tautomer, isotope, or isomer thereof, may also in some embodiments be prepared following analogous reaction schemes. The reactants, solvents, coupling agents, catalysts, and other compounds used to prepare compounds of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, by following General Reaction Schemes I-III or by another route, may be commercially available may be prepared following organic chemical techniques.

II. Methods of Using Compounds of Formula (X) and Pharmaceutical Compositions Comprising Compounds of Formula (X)

Provided herein are methods of using the compounds disclosed herein, such as compounds of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, or a pharmaceutical composition comprising any of the foregoing and a pharmaceutically acceptable excipient. These include methods of inhibiting a component of the SREBP pathway, such as an SREBP or SCAP; and methods of treating a disorder in a subject in need thereof. In some embodiments, the disorder is mediated by an SREBP or SCAP.

The terms "treat," "treating," or "treatment" refers to any indicia of success in the amelioration of an injury, disease, disorder, pathology, or condition, including any objective or subjective parameter such as abatement; remission; diminishing of symptoms or making the injury, disease, disorder, pathology, or condition more tolerable to the subject; slowing or stopping the rate of degeneration, decline, or development; slowing the progression of injury, disease, disorder, pathology, or condition; making the final point of degeneration less debilitating; improving a subject's physical or mental well-being; or relieving or causing regression of the injury, disease, disorder, pathology, or condition. The treatment of symptoms, including the amelioration of symptoms, can be based on objective or subjective parameters, which may include the results of a physical examination, a neuropsychiatric exam, and/or a psychiatric evaluation. Certain methods and uses disclosed herein may treat cancer by, for example, decreasing the incidence of cancer, causing remission of cancer, slowing the rate of growth of cancer cells, slowing the rate of spread of cancer cells, reducing metastasis, or reducing the growth of metastatic tumors, reducing the size of one or more tumors, reducing the number of one or more tumors, or any combinations thereof.

The embodiments described herein for methods of treatment should also be considered to apply to the use of compounds of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, for the treatment of disorders; and the use of compounds of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, for inhibiting an SREBP or inhibiting the proteolytic activation of an SREBP; and other uses of compounds of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, as described herein; and the use of compounds of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, in the manufacture of medicaments.

A. Inhibiting SREBP or SCAP

Provided herein are uses and methods of inhibiting a component of the SREBP pathway, such as an SREBP or SCAP. In some embodiments, a combination of an SREBP and SCAP is inhibited. Such methods may include contacting an SREBP with a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, or a pharmaceutical composition comprising any of the forgoing and a pharmaceutically acceptable excipient. Such uses and methods may also include contacting SCAP with a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, or a pharmaceutical composition comprising any of the forgoing and a pharmaceutically acceptable excipient.

In certain embodiments, a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof is administered to a subject in need thereof to inhibit a component of the SREBP pathway. In other embodiments, a pharmaceutical composition comprising a pharmaceutically acceptable excipient and a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, is administered to the subject in need thereof. In certain embodiments, the amount of the compound or pharmaceutically acceptable salt, solvate, tautomer, isotope, or isomer thereof, relative to the subject's body mass, is between about 0.01 mg/kg to about 100 mg/kg. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof is administered to a subject in need thereof to inhibit a component of the SREBP pathway. In certain embodiments, the compound or pharmaceutically acceptable salt, solvate, tautomer, isotope, or isomer thereof, is administered as a pharmaceutical composition, as described herein.

The component of the SREBP pathway that is inhibited by the methods and uses described herein may be an SREBP or SCAP. In some embodiments, an SREBP is inhibited. The SREBP may be, for example, an SREBP-1 (such as SREBP-1a or SREBP-1c) or SREBP-2. In certain variations, two or three of SREBP-1a, SREBP-1c, and SREBP-2 are inhibited. In some embodiments, the component is an SREBP-1. In other embodiments, the SREBP is SREBP-1a. In certain embodiments, the component is SREBP-1c. In still other embodiments, the SREBP is SREBP-2. In other embodiments, the component of the SREBP pathway is SCAP. In some embodiments, both an SREBP and SCAP are inhibited. In certain embodiments, two or three of SREBP-1a, SREBP-1c, and SREBP-2 are inhibited, and SCAP is inhibited.

Inhibition of a component of the SREBP pathway, such as an SREBP or SCAP, may include partial inhibition or full inhibition. Partial inhibition may include reducing the activity of a component of the SREBP pathway to a level that is still detectable. Full inhibition may include stopping all activity of a component of the SREBP pathway (such as stopping the activity of an SREBP or SCAP), or reducing the activity of a component of the SREBP pathway to a level below detection. Inhibition of a component of the SREBP pathway may be measured directly or indirectly, using any methods known in the art.

In some embodiments, inhibition of a component of the SREBP pathway is measured directly, for example by measuring the product of a reaction catalyzed by an SREBP pathway component. Inhibition of SREBP activation (for example, by inhibiting SCAP) may in some embodiments be demonstrated by western blotting and quantitatively assessing the levels of full-length and cleaved SREBP-1 and/or SREBP-2 proteins from a cell line (such as a hepatic cell lines) or primary cells (such as primary hepatocytes of mouse, rat or human origin).

In some embodiments, inhibition of a component of the SREBP pathway is measured indirectly, for example by measuring the level of expression of one or more genes that are regulated by SREBP. The inhibition of a component of the SREBP pathway, such as an SREBP or SCAP, may reduce the expression of one or more genes that are regulated by an SREBP, for example an SREBP-1 (such as SREBP-1a or SREBP-1c) or SREBP-2. SCAP plays a role in activating SREBPs, thus inhibiting the activity of SCAP may reduce the expression of one or more genes that are regulated by an SREBP. SREBP pathway inhibition may also be determined by assessing gene transcription levels of one or more target genes of SREBP-1 and/or SREBP-2, such as one or more of ACSS2, ALDOC, CYP51A1, DHCR7, ELOVL6, FASN, FDFT1, FDPS, HMGCS1, HSD17B7, IDI1, INSIG1, LDLR, LSS, ME1, PCSK9, PMVK, RDH11, SC5DL, SQLE, STARD4, TM7SF2, PNPLA3, SREBF1, SREBF2, HMGCR, MVD, MVK, ACLY, MSMO1, ACACA, or ACACB. The transcription levels may be assessed, for example, by transcriptomic analysis, including but not limited to q-PCR A reduction in one, two, three, four, five, or more of these genes may indicate inhibition of SREBP activation. This evaluation of endogenous SREBP gene expression may be assessed in cell lines (such as hepatic cell lines) or primary cells (such as primary hepatocytes of mouse, rat, or human origin). In some embodiments, the gene transcription levels of PCSK9 or PNPLA3, or a combination thereof, are evaluated.

Therefore, provided herein are uses and methods of reducing the expression of one or more genes selected from the group consisting of ACSS2, ALDOC, CYP51A1, DHCR7, ELOVL6, FASN, FDFT1, FDPS, HMGCS1, HSD17B7, IDI1, INSIG1, LDLR, LSS, ME1, PCSK9, PMVK, RDHI1, SC5DL, SQLE, STARD4, TM7SF2, PNPLA3, SREBF1, SREBF2, HMGCR, MVD, MVK, ACLY, MSMO1, ACACA, and ACACB, comprising contacting an SREBP or SCAP with a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof. In some embodiments, the expression of PCSK9 is reduced. In other embodiments, the expression of PNPLA3 is reduced. In still further embodiments, both the expression of PCSK9 and PNPLA3 are reduced. In certain embodiments, one or more SREBP is contacted, for example an SREBP-1 (such as SREBP-1a or SREBP-1c) or SREBP-2, or any combinations thereof. In other embodiments, SCAP is contacted. In still further embodiments, one or more of SREBP-1a, SREBP-1c, SREBP-2, and SCAP is contacted. In certain embodiments, inhibition of a component of the SREBP pathway may treat a disorder mediated by an SREBP, such as the disorders as described herein. Thus, in certain embodiments, expression of one or more genes as described above is reduced in a subject in need thereof.

Another method of indirectly detecting SREBP pathway inhibition may include: Serum-starving a hepatic cell line (HepG2) expressing luciferase under the control of the LSS-promoter to induce SREBP activation and increased luciferase expression. The cells may then be treated with a compound, such as a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof. Following treatment, a reduction of luciferase activity reflects inhibition of SREBP activation, and non-cytotoxicity of the compound can be assessed by LDH release.

B. Treating a Disorder

In other aspects, provided herein are uses and methods of treating a disorder in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof. In certain aspects, provided herein are uses and methods of treating a disorder in a subject in need thereof, comprising administering to the subject in need thereof a pharmaceutical composition comprising a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, and a pharmaceutically acceptable excipient. In certain embodiments, the compound is a compound of Formula (X-A), or a pharmaceutically acceptable salt, solvate, tautomer, isotope, or isomer thereof. In other embodiments, the compound is a compound of Formula (X-Ai), or a pharmaceutically acceptable salt, solvate, tautomer, isotope, or isomer thereof. In certain embodiments, the compound is a compound of Formula (X-B), or a pharmaceutically acceptable salt, solvate, tautomer, isotope, or isomer thereof. In still further embodiments, the compound is a compound of Formula (X-Bi), or a pharmaceutically acceptable salt, solvate, tautomer, isotope, or isomer thereof. In certain embodiments, the compound is a compound of Formula (Z-A), or a pharmaceutically acceptable salt, solvate, tautomer, isotope, or isomer thereof. In other embodiments, the compound is a compound of Formula (Z-Ai), or a pharmaceutically acceptable salt, solvate, tautomer, isotope, or isomer thereof. In certain embodiments, the compound is a compound of Formula (Z-B), or a pharmaceutically acceptable salt, solvate, tautomer, isotope, or isomer thereof. In still further embodiments, the compound is a compound of Formula (Z-Bi), or a pharmaceutically acceptable salt, solvate, tautomer, isotope, or isomer thereof. In certain embodiments, the compound is a compound of Formula (I-A), or a pharmaceutically acceptable salt, solvate, tautomer, isotope, or isomer thereof. In other embodiments, the compound is a compound of Formula (I-Ai), or a pharmaceutically acceptable salt, solvate, tautomer, isotope, or isomer thereof. In certain embodiments, the compound is a compound of Formula (I-B), or a pharmaceutically acceptable salt, solvate, tautomer, isotope, or isomer thereof. In still further embodiments, the compound is a compound of Formula (I-Bi), or a pharmaceutically acceptable salt, solvate, tautomer, isotope, or isomer thereof. In some embodiments, the disorder is mediated by an SREBP.

The uses and methods of treatment describe herein may use a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof; or a pharmaceutical composition comprising a compound of Formula (X), (X-A), (X-Ai), (X-B), (X-Bi), (Z), (Z-A), (Z-B), (Z-Ai), (Z-Bi), (I), (I-A), (I-B), (I-Ai), or (I-Bi), or a pharmaceutically acceptable salt, solvate, tautomer, isotope, or isomer thereof, and a pharmaceutically acceptable excipient.

1. Metabolic Disorders

In some embodiments, the disorder is a metabolic disorder, such as a disorder that affects lipid metabolism, cholesterol metabolism, or insulin metabolism. In certain embodiments, the disorder is related to lipid metabolism, cholesterol metabolism, or insulin metabolism, for example, liver disease as a result of the buildup of fat in the liver, or cardiovascular disease.

In some embodiments, the disorder is a liver disease, such as chronic liver disease. In some embodiments, the liver disease is mediated by a component of the SREBP pathway, such as an SREBP or SCAP. In some embodiments, the liver disease is mediated by an SREBP. In certain embodiments, the liver disease is mediated by a downstream gene target of an SREBP, such as PNPLA-3. In other embodiments, the liver disease is mediated by SCAP. Thus, in some aspects, provided herein are uses and methods of treating a liver disease in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. The chronic liver disease may be, for example, primary alcoholic liver disease, nonalcoholic fatty liver disease (NAFLD), or nonalcoholic steatohepatitis (NASH). In some embodiments, the liver disease is liver fat, liver inflammation, or liver fibrosis, or a combination thereof.

In certain embodiments, the liver disease is non-alcoholic fatty liver disease (NAFLD). NAFLD is a group of conditions that are related to fat buildup in the liver. Non-alcoholic steatohepatitis (NASH) is a form of NAFLD which includes liver inflammation. In NASH, the liver inflammation may lead to liver damage and scarring, which can be irreversible, and it can also progress to cirrhosis and liver failure. NAFLD and NASH are associated with metabolic disorders such as obesity, dyslipidemia, insulin resistance, and type 2 diabetes. Other disorders associated with NAFLD and NASH include increased abdominal fat and high blood pressure. In some embodiments, NASH is mediated by a component of the SREBP pathway, such as an SREBP or SCAP.

In other aspects, provided herein are uses and methods of treating NASH in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. Treatment of NASH may include reduction in average liver fat content, which may be evaluated, for example, by magnetic resonance imaging (MRI), magnetic resonance elastography (MRE), ultrasound, or computerized tomography (CT); reduction of the liver enzyme alanine aminotransferase (ALT); reduction of the liver enzyme aspartate aminotransferase (ALT); reduction of liver inflammation as evaluated through histological scoring of liver biopsy; reduction of liver fibrosis as evaluated through histological scoring of liver biopsy; reduction of liver fat content as evaluated through histological scoring of liver biopsy; or any combinations thereof. Treatment of NASH may be evaluated using the NAFLD activity score (NAS); or steatosis, activity, and fibrosis score (SAF); or other NASH diagnostic and/or scoring metrics (such as FIB4 or ELF).

Further provided herein are uses and methods of treating a disorder in a subject in need thereof, wherein the disorder is liver fibrosis associated with NASH, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. In some embodiments, the liver fibrosis is mediated by SREBP. Treatment of liver fibrosis may be evaluated, for example, by magnetic resonance imaging (MRI), magnetic resonance elastography (MRE), ultrasound, or computerized tomography (CT); reduction of the liver enzyme alanine aminotransferase (ALT); reduction of the liver enzyme aspartate aminotransferase (ALT); reduction of liver inflammation and/or fibrosis as evaluated through histological scoring of liver biopsy; or any combinations thereof Further provided herein are uses and methods of treating a disorder in a subject in need thereof, wherein the disorder is fatty liver disease, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. In some embodiments, the fatty liver disease is mediated by SREBP. In certain embodiments, a subject may have fatty liver disease when the fat content of the subject's liver is 5% or greater. In some embodiments, a subject with fatty liver disease has NASH, or liver fibrosis associated with NASH. In certain embodiments, a subject with fatty liver disease has not been diagnosed with NASH or liver fibrosis associated with NASH. Treatment of fatty liver disease may be evaluated, for example, by magnetic resonance imaging (MRI), magnetic resonance elastography (MRE), ultrasound, or computerized tomography (CT); reduction of the liver enzyme alanine aminotransferase (ALT); reduction of the liver enzyme aspartate aminotransferase (ALT); reduction of liver inflammation as evaluated through histological scoring of liver biopsy; reduction of liver fibrosis as evaluated through histological scoring of liver biopsy; reduction of liver fat content as evaluated through histological scoring of liver biopsy; or any combinations thereof.

In some embodiments of the uses and methods of treating liver disease provided herein, such as methods of treating liver fibrosis, fatty liver disease, or NASH, the subject is administered between about 0.01 mg/kg to about 100 mg/kg of compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof, relative to the body mass of the subject. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof is administered to the subject in need thereof. In certain embodiments, the compound or pharmaceutically acceptable salt, solvate, tautomer, isotope, or isomer thereof, is administered as a pharmaceutical composition, as described herein.

Other metabolic disorders which may be treated with the compounds or pharmaceutical compositions described herein may include, for example, insulin resistance, hyperglycemia, diabetes mellitus, dyslipidemia, adiposopathy, obesity, and Metabolic Syndrome. In some embodiments, the metabolic disorder is mediated by a genetic factor. In other embodiments, the metabolic disorder is mediated by one or more environmental factors, such as a diet rich in fat, or a diet rich in sugar, or a combination thereof. In some embodiments, the metabolic disorder is mediated by SREBP. In some embodiments, the diabetes mellitus is type I diabetes. In certain embodiments, the diabetes mellitus is type II diabetes.

Provided herein are uses and methods of treating diabetes in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. Diabetes (also known as diabetes mellitus) refers to a disease or condition that is generally characterized by metabolic defects in production and utilization of glucose which result in the failure to maintain appropriate blood sugar levels in the body. In some embodiments, the diabetes is type II diabetes, which is characterized by insulin resistance, in which insulin loses its ability to exert its biological effects across a broad range of concentrations. In some embodiments, the diabetes is mediated by a component of the SREBP pathway, such as an SREBP or SCAP.

Further provided herein are uses and methods of treating insulin resistance in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. Insulin resistance has been hypothesized to unify the clustering of hypertension, glucose intolerance, hyperinsulinemia, increased levels of triglyceride, decreased HDL cholesterol, and central and overall obesity. "Metabolic Syndrome" refers to a similar clustering of conditions, which may include abdominal obesity, hypertension, high blood sugar, high serum triglycerides (such as elevated fasting serum triglycerides), and low HDL levels, and is associated with a risk of developing cardiovascular disease and/or type II diabetes. Further provided herein are uses and methods of treating Metabolic Syndrome in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. In some embodiments, the Metabolic Syndrome or insulin resistance is mediated by a component of the SREBP pathway, such as an SREBP or SCAP.

In some embodiments of the uses and methods of treating insulin resistance, hyperglycemia, diabetes mellitus, obesity, or Metabolic Syndrome provided herein, the subject is administered between about 0.01 mg/kg to about 100 mg/kg of compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof, relative to the body mass of the subject. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof is administered to the subject in need thereof. In certain embodiments, the compound or pharmaceutically acceptable salt, solvate, tautomer, isotope, or isomer thereof, is administered as a pharmaceutical composition, as described herein.

In other embodiments, the metabolic disorder is dyslipidemia. Thus, in other aspects, provided herein are uses and methods of treating dyslipidemia in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. Dyslipidemia refers to abnormal blood plasma levels of one or more lipids or one or more lipoproteins, or any combinations thereof. Dyslipidemia may include depressed levels or elevated levels of one or more lipids and/or one or more lipoproteins, or a combination of depressed and elevated levels (for example, elevated levels of one type of lipid and depressed levels of another type of lipid and/or lipoprotein). Dyslipidemia may include, but is not limited to, elevated low density lipoprotein cholesterol (LDL), elevated apolipoprotein B, elevated triglycerides (TGs), elevated lipoprotein(a), elevated apolipoprotein A, reduced high density lipoprotein cholesterol (HDL), or reduced apolipoprotein A1, or any combinations thereof. Dyslipidemia, such as abnormal cholesterol or abnormal TG levels, is associated with an increased risk for vascular disease (such as heart attack or stroke), atherosclerosis, and coronary artery disease. In some embodiments of the uses and methods provided herein, the dyslipidemia is hyperlipidemia. Hyperlipidemia refers to the presence of an abnormally elevated level of lipids in the blood, and may include (1) hypercholesterolemia (an elevated cholesterol level); (2) hypertriglyceridemia, (an elevated triglyceride level); and (3) combined hyperlipidemia, (a combination of hypercholesterolemia and hypertriglyceridemia). Dyslipidemia may arise from a combination of genetic predisposition and diet, and may be associated with being overweight, diabetes, or Metabolic Syndrome. Lipid disorders may also arise as the result of certain medications (such as those used for anti-rejection regimens in people who have had organ or tissue transplants). In some embodiments, the dyslipidemia, such as hyperlipidemia, is mediated by a component of the SREBP pathway, such as an SREBP or SCAP. Thus, in some aspects, provided herein are uses and methods of reducing cholesterol levels, modulating cholesterol metabolism, modulating cholesterol catabolism, modulating the absorption of dietary cholesterol, reversing cholesterol transport, or lowering triglycerides in a subject in need thereof, comprising administering to the subject in need thereof a compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient.

In some embodiments of the uses and methods of treating dyslipidemia provided herein, such as reducing cholesterol levels, modulating cholesterol metabolism, modulating cholesterol catabolism, modulating the absorption of dietary cholesterol, reversing cholesterol transport, or lowering triglycerides in a subject in need thereof as provided herein, the subject is administered between about 0.01 mg/kg to about 100 mg/kg of compound of Formula (X), (X-A), (X-Ai), (X-B), (X-Bi), (Z), (Z-A), (Z-B), (Z-Ai), (Z-Bi), (I), (I-A), (I-Ai), (I-B), or (I-Bi), or a pharmaceutically acceptable salt, solvate, tautomer, isotope, or isomer thereof, relative to the body mass of the subject. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof is administered to the subject in need thereof. In certain embodiments, the compound or pharmaceutically acceptable salt, solvate, tautomer, isotope, or isomer thereof, is administered as a pharmaceutical composition, as described herein.

In still other aspects, provided herein are uses and methods of treating adiposopathy in a subject in need thereof, comprising administering to the subject in need thereof a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. In some embodiments, the adiposopathy is associated with Metabolic Syndrome. In some embodiments, the adiposopathy is mediated by a component of the SREBP pathway, such as an SREBP or SCAP.

In certain aspects, provided herein are uses and methods of treating gallstones in a subject in need thereof, comprising administering to the subject in need thereof a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient. Gallstones may be associated with gallbladder inflammation, pancreas inflammation, or liver inflammation. In certain embodiments, the gallstones are cholesterol gallstones, which may form when bile contains a high concentration of cholesterol and not enough bile salts. In some embodiments, the gallstones, which may include cholesterol gallstone disease, is mediated by a component of the SREBP pathway, such as an SREBP or SCAP.

In other embodiments, the disorder is pancreatitis. In yet other embodiments, the disorder is endotoxic shock, systemic inflammation, or xanthoma. In still further embodiments, the disorder is atherosclerosis, coronary artery disease, angina pectoris, carotid artery disease, stroke, or cerebral arteriosclerosis. In certain embodiments, any of the foregoing disorders are mediated by a component of the SREBP pathway, such as an SREBP or SCAP.

In some embodiments of the uses and methods of treating gall stones, pancreatitis, endotoxic shock, systemic inflammation, xanthoma, atherosclerosis, coronary artery disease, angina pectoris, carotid artery disease, stroke, or cerebral arteriosclerosis provided herein, the subject is administered between about 0.01 mg/kg to about 100 mg/kg of compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, relative to the body mass of the subject. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof is administered to the subject in need thereof. In certain embodiments, the compound or pharmaceutically acceptable salt, solvate, tautomer, isotope, or isomer thereof, is administered as a pharmaceutical composition, as described herein.

In some embodiments of any of the above embodiments, the subject is overweight, obese, has insulin resistance, is pre-diabetic or has type II diabetes. In certain embodiments of any of the preceding embodiments, the subject has NASH.

2. Hyperproliferative Disorders

In another embodiment, the disorder is a hyperproliferative disorder. Thus, in some aspects, provided herein are uses and methods of treating a hyperproliferative disorder in a subject in need thereof, comprising administering to the subject in need thereof a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof; or a pharmaceutical composition comprising any of the foregoing and a pharmaceutically acceptable excipient.

As described above, the metabolism of fatty acids, cholesterol, and triglycerides may play a role in hyperproliferative disorders, such as cancer. Often, during transformation of non-cancerous cells to cancerous cell, cell metabolism shifts from catabolic to anabolic processes. Depending on the type of tumor, the tumor cells may synthesize up to 95% of the saturated and mono-unsaturated fatty acids. Some cancers exhibit increased synthesis of fatty acids and other lipids (such as cholesterol), and steroids (such as androgens). Elevated fatty acid synthase (FAS) expression may induce progression to S phase in cancer cells, and inhibition of FAS expression may reduce cell growth and may induce apoptosis. Thus, components of the SREBP pathway may play a role in hyperproliferative disorders.

Hyperproliferative disorders, which are disorders associated with some degree of abnormal cell proliferation, may be benign or malignant. Benign hyperproliferative disorders may include pre-cancerous disorders.

In some embodiments of the uses and methods provided herein, the disorder is a benign hyperproliferative disorder. In some embodiments, the benign hyperproliferative disorder is mediated by a component of the SREBP pathway, such as an SREBP or SCAP. In other embodiments, the disorder is a malignant hyperproliferative disorder. In some embodiments, the malignant hyperproliferative disorder is mediated by a component of the SREBP pathway, such as an SREBP or SCAP.

In some embodiments, the hyperproliferative disorder is breast cancer, liver cancer, ovarian cancer, pancreatic cancer, or prostate cancer.

In some embodiments of the uses and methods of treating a hyperproliferative disorder in a subject in need thereof, as described herein, between about 0.01 mg/kg to about 100 mg/kg. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, relative to the body mass of the subject, is administered to the subject in need thereof. In certain embodiments, the compound or pharmaceutically acceptable salt, solvate, tautomer, isotope, or isomer thereof, is administered as a pharmaceutical composition, as described herein.

III. Dosing and Methods of Administration

The dose of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, administered to a subject in need thereof according to any of the disclosed methods may vary with the particular compound or pharmaceutically acceptable salt, solvate, tautomer, isotope, or isomer thereof; the method of administration; the particular disorder being treated; and the characteristics of the subject (such as weight, sex, and/or age). In some embodiments, the amount of the compound or pharmaceutically acceptable salt, solvate, tautomer, isotope, or isomer thereof is a therapeutically effective amount.

The effective amount of the compound or pharmaceutically acceptable salt, solvate, tautomer, isotope, or isomer thereof, relative to the subject's body mass, may in some embodiments be between about 0.01 mg/kg to about 100 mg/kg. In some embodiments, about 0.7 mg to about 7 g daily, or about 7 mg to about 350 mg daily, or about 350 mg to about 1.75 g daily, or about 1.75 to about 7 g daily of the compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof is administered to a subject in need thereof. In certain embodiments, the compound or pharmaceutically acceptable salt, solvate, tautomer, isotope, or isomer thereof, is administered as a pharmaceutical composition, as described herein.

Any of the uses and methods provided herein may comprise administering to a subject in need therein a pharmaceutical composition that comprises an effective amount of a compound provided herein, such as a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a corresponding amount of a pharmaceutically acceptable salt, solvate, tautomer, isotope, or isomer thereof, and a pharmaceutically acceptable excipient.

The compounds of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof as provided herein, or a pharmaceutical composition comprising any of these and a pharmaceutically acceptable excipient as provided herein, may be administered to a subject via any suitable route, including, for example, intravenous, intramuscular, subcutaneous, oral, or transdermal routes.

In certain aspects, the invention provides a method of treating a disorder in subject in need thereof by parenterally administering to the subject in need thereof an effective amount of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof as provided herein, or a pharmaceutical composition comprising an effective amount of any of the foregoing and a pharmaceutically acceptable excipient as provided herein. In some embodiments, the disorder is a hyperproliferative disorder. In certain embodiments, the hyperproliferative disorder is cancer. In other embodiments, the disorder is fatty liver disease. In certain embodiments, the disorder is NASH. In some embodiments, the route of administration is intravenous, intra-arterial, intramuscular, or subcutaneous. In some embodiments, the route of administration is transdermal.

In some aspects, provided herein are pharmaceutical compositions comprising a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, and a pharmaceutically acceptable excipient, for the use in treating a disorder as described herein. In some embodiments, the disorder is prevented, or the onset delayed, or the development delayed. In some embodiments, the disorder is a hyperproliferative disorder. In certain embodiments, the hyperproliferative disorder is cancer. In some embodiments, the disorder is fatty liver disease. In certain embodiments, the disorder is NASH. In certain embodiments, the composition comprises a pharmaceutical formulation which is present in a one or more unit dosage forms, for example one, two, three, four, or more unit dosage forms.

IV. Kits

Also provided are articles of manufacture comprising a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, or pharmaceutical compositions comprising same, or unit dosages comprising any of these, as described herein in suitable packaging for use in the methods described herein. Suitable packaging may include, for example, vials, vessels, ampules, bottles, jars, flexible packaging, and the like. An article of manufacture may further be sterilized and/or sealed kits.

Further provided herein are kits comprising a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, or a pharmaceutical composition comprising same and a pharmaceutically acceptable excipient. The kits may be used in any of the uses and methods described herein. In some embodiments, the kit further comprises instructions. The kits may be used for any one or more of the uses described herein, and, accordingly, may contain instructions for the treatment of a hyperproliferative disease (such as cancer), fatty liver disease, or NASH. The kits may comprise one or more containers. Each component (if there is more than one component) may be packaged in separate containers or some components may be combined in one container where cross-reactivity and shelf life permit.

The kits may be in unit dosage forms, bulk packages (e.g., multi-dose packages) or subunit doses. For example, kits may be provided that contain sufficient dosages of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, as disclosed herein and/or a second pharmaceutically active compound useful for a disorder detailed herein to provide effective treatment of a subject for an extended period, such as one week, 2 weeks, 3 weeks, 4 weeks, 6 weeks, 8 weeks, 3 months, 4 months, 5 months, 7 months, 8 months, 9 months, or more. Kits may also include multiple unit doses of a compound of Formula (X), (X-A), (X-Ai), (X-B), (X-Bi), (Z), (Z-A), (Z-Ai), (Z-B), (Z-Bi), (I), (I-A), (I-Ai), (I-B), or (I-Bi), or a pharmaceutically acceptable salt, solvate, tautomer, isotope, or isomer thereof, and instructions for use, and be packaged in quantities sufficient for storage and use in pharmacies (e.g., hospital pharmacies or compounding pharmacies).

The kits may optionally include a set of instructions, generally written instructions, although electronic storage media (e.g., magnetic diskette or optical disk) containing instructions are also acceptable, relating to the use of component(s) of the uses and methods as described herein. The instructions included with the kit may include information as to the components and their administration to an individual.

ENUMERATED EMBODIMENTS

Embodiment I-1. A compound of Formula (I):

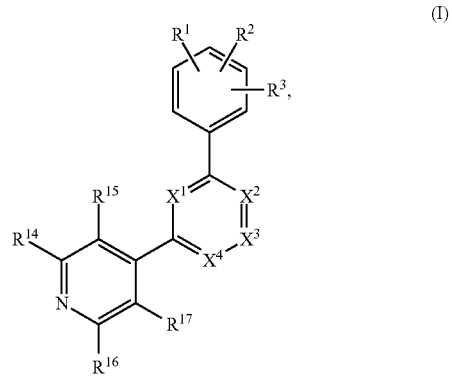

or a pharmaceutically acceptable salt, solvate, tautomer, isotope, or isomer thereof, wherein:

$R^1$ is $-C(O)OR^9$, $-C(O)NR^8R^9$, $-S(O)_2NR^8R^9$, $-NR^{10}C(O)NR^8R^9$, $-NR^{10}C(O)R^9$, $-NR^{10}S(O)_2R^9$, $-OR^{26}$, $-SR^9$, $-S(O)R^9$, $-S(O)_2R^9$, $-NR^8R^9$, or $-NR^{10}C(O)OR^9$, wherein each of $R^8$, $R^9$, and $R^{10}$ is independently selected from the group consisting of hydrogen, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, and heteroaryl-alkyl, $R^{26}$ is $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, or heteroaryl-alkyl, each $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, $(C_{6-10})$aryl, $(C_{6-10})$aryl$(C_{1-10})$alkyl, heteroaryl, and heteroaryl-alkyl is independently unsubstituted or substituted with one or more substituents independently selected from the group consisting of halo, cyano, oxo, $-OR^{19}$, $-C(O)NR^{19}R^{19}$, $-NR^{19}C(O)R^{19}$, $-NR^{19}C$ (O)NR$^{19}$R$^{19}$, —NR$^{19}$R$^{19}$, —S(O)$_2$NR$^{19}$R$^{19}$, —NR$^{19}$S(O)$_2$R$^{19}$, —S(O)$_{n4}$R$^{20}$, —C(O)OR$^{19}$, and —C(O)R$^{20}$,
- each R$^{19}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two R$^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each R$^{20}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, and
- n4 is 0, 1, or 2;

or R$^8$ and R$^9$, together with the nitrogen atom to which they are attached, form a heterocycloalkyl, wherein the heterocycloalkyl is unsubstituted or substituted with 1 to 3 substituents independently selected from the group consisting of halo, cyano, oxo, (C$_{1-10}$)alkyl, (C$_{2-10}$)alkenyl, (C$_{2-10}$)alkynyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, heteroaryl-alkyl, —OR$^{23}$, —C(O)NR$^{23}$R$^{23}$, —NR$^{23}$C(O)R$^{23}$, —NR$^{23}$C(O)OR$^{23}$, —NR$^{23}$C(O)NR$^{23}$R$^{23}$, —NR$^{23}$R$^{23}$, —S(O)$_2$NR$^{23}$R$^{23}$, —NR$^{23}$S(O)$_2$R$^{24}$, —S(O)$_{n6}$R$^{24}$, —C(O)OR$^{23}$, and —C(O)R$^{24}$,
- wherein each R$^{23}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two R$^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each R$^{24}$ is independently (C$_{1-10}$)cycloalkyl, (C$_{3-10}$)cycloalkyl(C$_{1-10}$)alkyl, or heterocycloalkyl, wherein each of the foregoing is independently unsubstituted or substituted with one or more halo, and
- n6 is 0, 1, or 2;

R$^2$ and R$^3$ are independently selected from the group consisting of hydrogen, halo, cyano, (C$_{1-10}$)alkyl, (C$_{3-10}$)cycloalkyl, (C$_{3-10}$)cycloalkyl(C$_{1-10}$)alkyl, —OR$^{25}$, —C(O)NR$^{25}$R$^{25}$, —NR$^{25}$C(O)R$^{25}$, —NR$^{25}$C(O)NR$^{25}$R$^{25}$, —NR$^{25}$R$^{25}$, —S(O)$_2$NR$^{25}$R$^{25}$, —NR$^{25}$S(O)$_2$R$^{25}$, —S(O)$_{n7}$R$^{30}$, —NR$^{25}$C(O)OR$^{25}$R$^{25}$, —C(O)OR$^{25}$, or —C(O)R$^{30}$,
- wherein each (C$_{1-10}$)alkyl, (C$_{3-10}$)cycloalkyl, and (C$_{3-10}$)cycloalkyl(C$_{1-10}$)alkyl is independently unsubstituted or substituted with one or more halo,
- each R$^{25}$ is independently hydrogen (C$_{1-10}$)alkyl, (C$_{3-10}$)cycloalkyl, (C$_{3-10}$)cycloalkyl(C$_{1-10}$)alkyl, or heterocycloalkyl; or two R$^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each R$^{30}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, and
- n7 is 0, 1, or 2;

X$^1$, X$^2$, X$^3$ and X$^4$ are independently CR$^4$ or N, wherein X$^2$, X$^3$ and X$^4$ may not all be N;

when at least one of X$^1$, X$^2$, X$^3$ and X$^4$ is N, each R$^4$ is independently selected from the group consisting of hydrogen, halo, cyano, (C$_{1-10}$)alkyl, (C$_{3-10}$)cycloalkyl, (C$_{3-10}$)cycloalkyl(C$_{1-10}$)alkyl, heterocycloalkyl connected by an annular carbon atom, heterocycloalkyl-alkyl, —OR$^{27}$, —C(O)NR$^{27}$R$^{27}$, —S(O)$_2$NR$^{27}$R$^{27}$, —S(O)$_{n8}$R$^{28}$, —C(O)OR$^{27}$, and —C(O)R$^{28}$,
- wherein each (C$_{1-10}$)alkyl, (C$_{3-10}$)cycloalkyl, (C$_{3-10}$)cycloalkyl(C$_{1-10}$)alkyl, heterocycloalkyl, and heterocycloalkyl-alkyl is independently unsubstituted or substituted with one or more halo,
- each R$^{27}$ is independently hydrogen or (C$_{1-10}$)alkyl, (C$_{3-10}$)cycloalkyl, (C$_{3-10}$)cycloalkyl(C$_{1-10}$)alkyl, or heterocycloalkyl; or two R$^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each R$^{28}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo,
- n8 is 0, 1 or 2; or when each of X$^1$, X$^2$, X$^3$ and X$^4$ is CR$^4$, each R$^4$ is independently selected from the group consisting of hydrogen, halo, cyano, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, —OR$^{27}$, —C(O)NR$^{27}$R$^{27}$, —NRC(O)R$^{27}$, —NR$^{27}$R$^{27}$, —NR$^{27}$S(O)$_2$R$^{27}$, —S(O)$_2$NR$^{27}$R$^{27}$, —S(O)$_{n8}$R$^{28}$, —C(O)OR$^{27}$, and —C(O)R$^{28}$,
- wherein each (C$_{1-10}$)alkyl, (C$_{3-10}$)cycloalkyl, (C$_{3-10}$)cycloalkyl(C$_{1-10}$)alkyl, heterocycloalkyl, and heterocycloalkyl-alkyl is independently unsubstituted or substituted with one or more halo,
- each R$^{27}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two R$^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
- each R$^{28}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, and
- n8 is 0, 1, or 2;

two R$^4$ on adjacent annular carbon atoms together with the carbon atoms to which they are attached may form a carbocyclyl or heterocyclyl,
- wherein the carbocyclyl is unsubstituted or substituted with one or more substituents independently selected from the group consisting of halo, cyano, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, —OR$^{27}$, —C(O)NR$^{27}$R$^{27}$, —NR C(O)R$^{27}$, —NR$^{27}$R$^{27}$, —S(O)$_2$ NR$^{27}$R$^{27}$, —NR$^{27}$S(O)$_2$R$^{27}$, —S(O)$_{n8}$R$^{28}$, and —C(O)R$^{28}$,
- or the heterocyclyl is unsubstituted or substituted with one or more substituents independently selected from the group consisting of halo, cyano, (C$_{1-10}$)alkyl, (C$_{3-10}$)cycloalkyl, (C$_{3-10}$)cycloalkyl(C$_{1-10}$)alkyl, heterocycloalkyl connected by an annular carbon atom, heterocycloalkyl-alkyl, —OR$^{27}$, —C(O)NR$^{27}$R$^{27}$, —S(O)$_2$NR$^{27}$R$^{27}$, —S(O)$_{n8}$R$^{28}$, and —C(O)R$^{28}$,
- each R$^{27}$ is independently hydrogen, (C$_{1-10}$)alkyl, (C$_{3-10}$)cycloalkyl, (C$_{3-10}$)cycloalkyl(C$_{1-10}$)alkyl; or two R$^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and n8 is 0, 1, or 2;

$R^{15}$ and $R^{17}$ are independently hydrogen, halo, alkyl, or —$OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;

$R^{14}$ is $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl connected through an annular carbon atom, heterocycloalkenyl connected through an annular carbon atom, heterocycloalkyl-alkyl, —$OR^5$, —$C(O)NR^5R^5$, —$RC(O)NR^5R^5$, —$S(O)_2NR^5R^5$, —$S(O)_{n1}R^6$, or —$C(O)R^6$;

$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;

the $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl, heterocycloalkenyl, or heterocycloalkyl-alkyl, of $R^{14}$ or $R^{16}$ is independently unsubstituted or substituted with 1 to 3 substituents independently selected from the group consisting of $(C_{1-10})$alkyl, halo, cyano, oxo, —$OR^7$, —$C(O)R^7$, —$C(O)NR^7R^7$, —$NR^7C(O)R^7$, —$NR^7C(O)NR^7R^7$, —$NR^7R^7$, —$S(O)_2NR^7R^7$, —$NR^7S(O)_2R^7$, —$S(O)_{n2}R^{13}$, and —$C(O)R^{13}$;

each $R^5$ is independently hydrogen, $(C_{1-10})$alkyl, or $(C_{3-10})$cycloalkyl; or two $R^5$, together with the nitrogen atom to which they are attached, form a heterocycloalkyl; wherein each alkyl, cycloalkyl, or heterocycloalkyl is independently unsubstituted or substituted with one or more halo;

each $R^6$ is independently $(C_{1-10})$alkyl or $(C_{3-10})$cycloalkyl, wherein each alkyl or cycloalkyl is independently unsubstituted or substituted with one or more halo;

each n1 is independently 0, 1, or 2;

each $R^7$ is independently hydrogen, unsubstituted $(C_{1-10})$alkyl, or $(C_{1-10})$alkyl substituted with one or more halo;

each n2 is independently 0, 1, or 2, and each $R^{13}$ is independently unsubstituted $(C_{1-10})$alkyl or $(C_{1-10})$alkyl substituted with one or more halo;

or $R^{14}$ and $R^{15}$, together with the atoms to which they are attached, form a carbocyclyl or heterocyclyl, wherein the carbocyclyl or heterocyclyl is unsubstituted or substituted with one or two substituents independently selected from the group consisting of halo, cyano, oxo, $(C_{1-10})$alkyl, $(C_{3-10})$cycloalkyl, $(C_{3-10})$cycloalkyl$(C_{1-10})$alkyl, —$OR^{18}$, —$C(O)NR^{18}R^{18}$, —$NR^{18}C(O)R^{18}$, —$NR^{18}C(O)NR^{18}R^{18}$, —$NR^{18}R^{18}$, —$S(O)_2NR^{18}R^{18}$, —$NR^{18}S(O)_2R^{18}$, —$S(O)_{n3}R^{21}$, —$C(O)OR^{18}$, and —$C(O)R^{21}$, wherein each $R^{18}$ is independently hydrogen, $(C_{1-10})$alkyl, or $(C_{3-10})$cycloalkyl; or two $R^{18}$, together with the nitrogen atom to which they are attached, form a heterocycloalkyl; wherein each alkyl, cycloalkyl, or heterocycloalkyl is independently unsubstituted or substituted with one or more halo each $R^{21}$ is independently $(C_{1-10})$alkyl or $(C_{3-10})$cycloalkyl, wherein each alkyl or cycloalkyl is independently unsubstituted or substituted with one or more halo, and each n3 is independently 0, 1, or 2.

Embodiment I-2. The compound of Embodiment I-1, wherein the compound is of Formula (I-A):

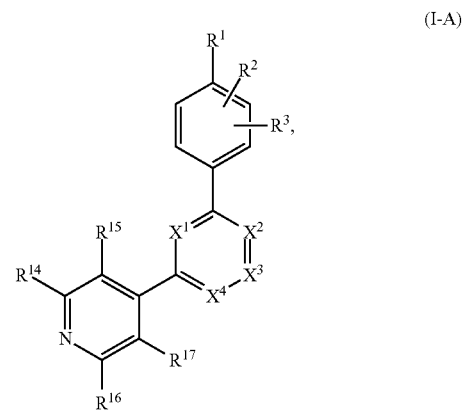

(I-A)

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (I).

Embodiment I-3. The compound of Embodiment I-1, wherein the compound is of Formula (I-B):

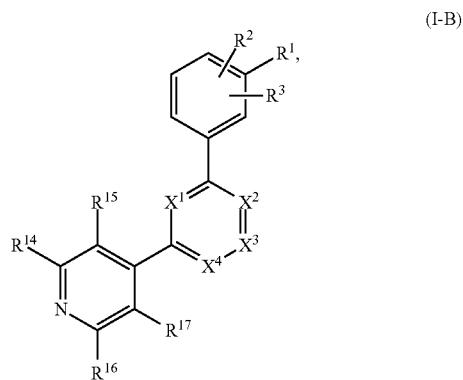

(I-B)

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (I).

Embodiment I-4. The compound of any one of Embodiments I-1 to I-3, or a pharmaceutically acceptable salt, solvate, tautomer, isotope, or isomer thereof, wherein $R^{17}$ is hydrogen.

Embodiment I-5. The compound of any one of Embodiments I-1 to I-4, or a pharmaceutically acceptable salt, solvate, tautomer, isotope, or isomer thereof, wherein $R^1$ is —$C(O)NR^8R^9$, —$S(O)_2NR^8R^9$, —$NR^{10}C(O)NR^8R^9$, —$NR^{10}C(O)R^9$, —$NR^{10}C(O)OR^9$, or —$NR^{10}S(O)_2R^9$.

Embodiment I-6. The compound of any one of Embodiments I-1 to I-5, or a pharmaceutically acceptable salt, solvate, tautomer, isotope, or isomer thereof, wherein $R^1$ is —$NR^{10}C(O)NR^8R^9$.

Embodiment I-7. The compound of any one of Embodiments I-1 to I-5, or a pharmaceutically acceptable salt, solvate, tautomer, isotope, or isomer thereof, wherein $R^1$ is —$NR^{10}C(O)OR^9$.

Embodiment I-8. The compound of any one of Embodiments I-1 to I-5, or a pharmaceutically acceptable salt, solvate, tautomer, isotope, or isomer thereof, wherein $R^1$ is $-NR^{10}S(O)_2R^9$.

Embodiment I-9. The compound of any one of Embodiments I-1 to I-8, or a pharmaceutically acceptable salt, solvate, tautomer, isotope, or isomer thereof, wherein $R^{10}$ is hydrogen.

Embodiment I-10. The compound of any one of Embodiments I-1 to I-5, or a pharmaceutically acceptable salt, solvate, tautomer, isotope, or isomer thereof, wherein $R^1$ is $-C(O)NR^8R^9$, and the $R^8$ and $R^9$ together with the nitrogen to which they are attached form an unsubstituted or substituted heterocycloalkyl.

Embodiment I-11. The compound of anyone of Embodiments I-1 to I-5, or I-10, or a pharmaceutically acceptable salt, solvate, tautomer, isotope, or isomer thereof, wherein $R^1$ is $-C(O)NR^8R^9$, and the $R^8$ and $R^9$ together with the nitrogen to which they are attached form an unsubstituted or substituted piperidinyl.

Embodiment I-12. The compound of Embodiment I-11, or a pharmaceutically acceptable salt, solvate, tautomer, isotope, or isomer thereof, wherein the piperidinyl is substituted with one to three substituents independently selected from the group consisting of $-OR^{23}$, $(C_{1-10})$alkyl, and $-NR^{23}C(O)OR^{23}$.

Embodiment I-13. The compound of anyone of Embodiments I-1 to I-12, or a pharmaceutically acceptable salt, solvate, tautomer, isotope, or isomer thereof, wherein $R^2$ is halo.

Embodiment I-14. The compound of any one of Embodiments I-1 to I-13, or a pharmaceutically acceptable salt, solvate, tautomer, isotope, or isomer thereof, wherein one of $X^1$, $X^2$, $X^3$, and $X^4$ are N.

Embodiment I-15. The compound of anyone of Embodiments I-1 to I-13, or a pharmaceutically acceptable salt, solvate, tautomer, isotope, or isomer thereof, wherein $X^1$, $X^2$, and $X^4$ are $CR^4$, and $X^3$ is N.

Embodiment I-16. The compound of any one of Embodiments I-1 to I-13, or a pharmaceutically acceptable salt, solvate, tautomer, isotope, or isomer thereof, wherein two of $X^1$, $X^2$, $X^3$, and $X^4$ are N.

Embodiment I-17. The compound of anyone of Embodiments I-1 to I-13, or a pharmaceutically acceptable salt, solvate, tautomer, isotope, or isomer thereof, wherein each of $X^1$, $X^2$, $X^3$ and $X^4$ is $CR^4$.

Embodiment I-18. The compound of any one of Embodiments I-1 to I-17, or a pharmaceutically acceptable salt, solvate, tautomer, isotope, or isomer thereof, wherein each $R^4$ is independently selected from the group consisting of hydrogen, halo, cyano, $(C_{1-10})$alkyl, and $-OR^{27}$.

Embodiment I-19. The compound of any one of Embodiments I-1 to I-18, or a pharmaceutically acceptable salt, solvate, tautomer, isotope, or isomer thereof, wherein $R^{14}$ is $(C_{1-10})$alkyl or heterocycloalkyl connected through an annular carbon atom, wherein the alkyl or heterocycloalkyl is unsubstituted or substituted with 1 to 3 substituents selected from the group consisting of $(C_{1-10})$alkyl, halo, $-C(O)OR^7$, and $-OR^5$.

Embodiment I-20. The compound of any one of Embodiments I-1 to I-16, I-18, or I-19, wherein at least one of $X^2$, $X^3$ and $X^4$ is N, and an adjacent annular carbon is bonded to $R^4$, wherein the $R^4$ is independently hydrogen, fluoro, cyano, $(C_{1-10})$alkyl, or $-OR^{27}$.

Embodiment I-21. The compound of any one of Embodiments I-1 to I-20, or a pharmaceutically acceptable salt, solvate, tautomer, isotope, or isomer thereof, wherein $R^3$ is hydrogen.

Embodiment I-22. The compound of any one of Embodiments I-1, I-2, or I-4 to I-21, wherein the compound is of Formula (I-Ai):

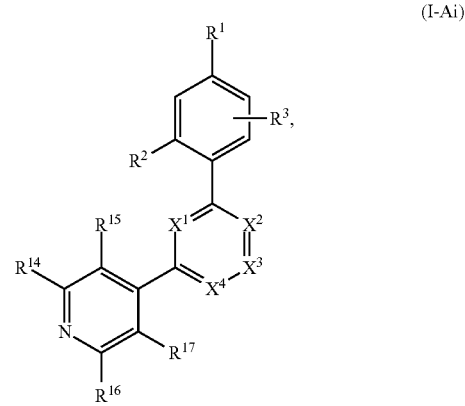

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (I).

Embodiment I-23. The compound of any one of Embodiments I-1 or I-3 to I-21, wherein the compound is of Formula (I-Bi):

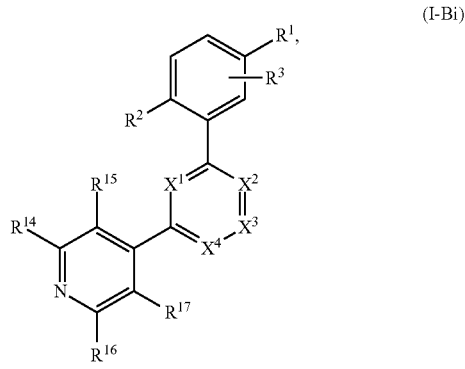

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (I).

Embodiment I-24. The compound of any one of Embodiments I-1, I-2, I-4 to I-7, or I-9 to I-22, selected from the group consisting of:

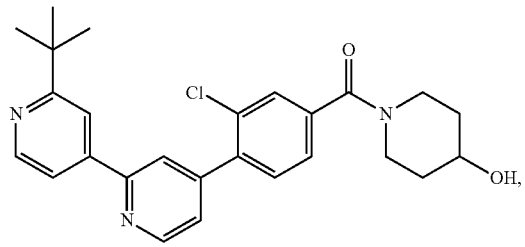

149
-continued
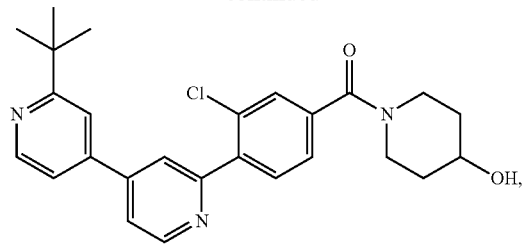
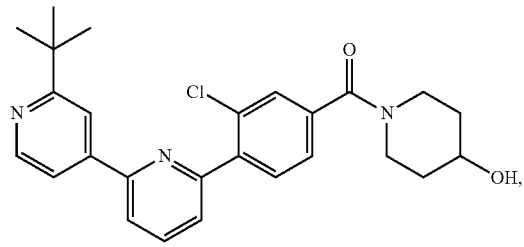
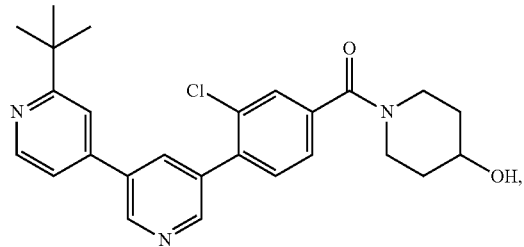
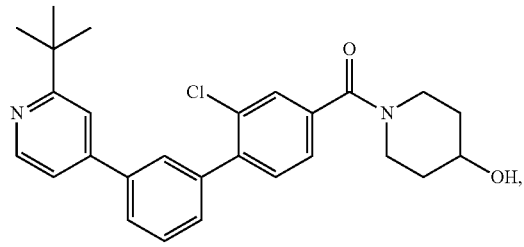
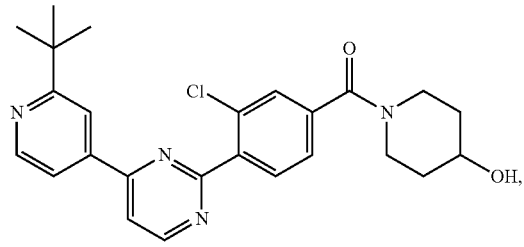
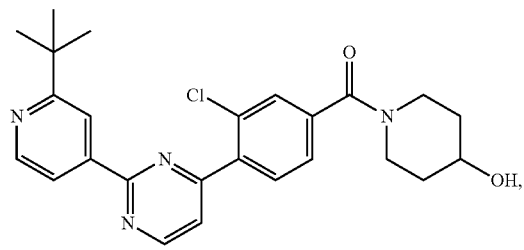
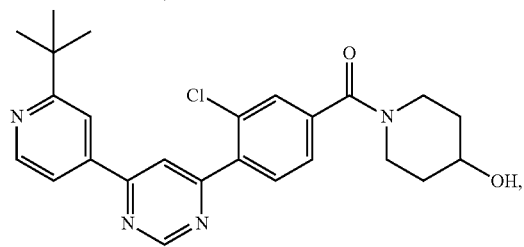
150
-continued
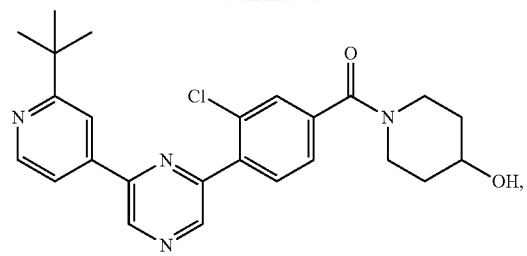
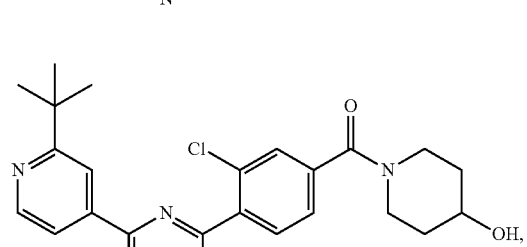
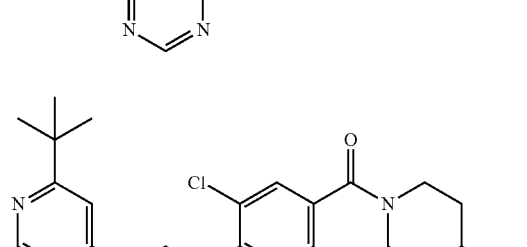
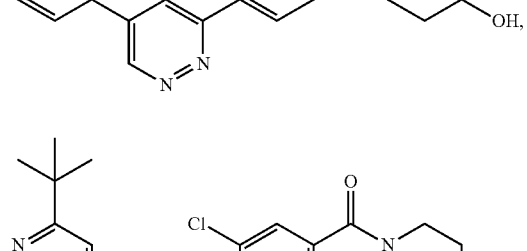
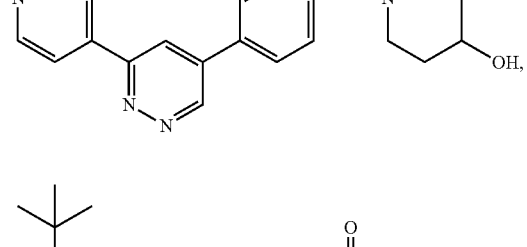
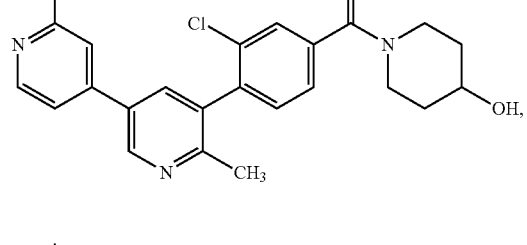
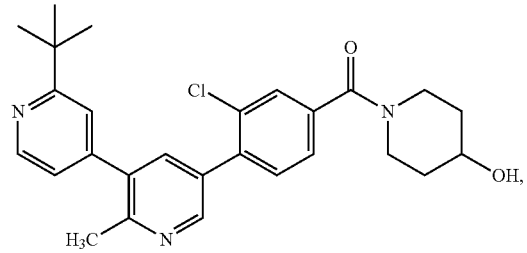

-continued
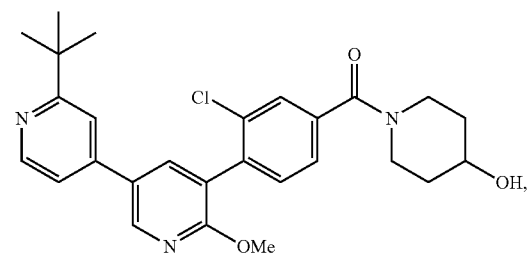
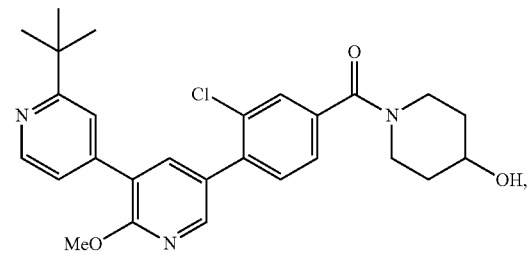
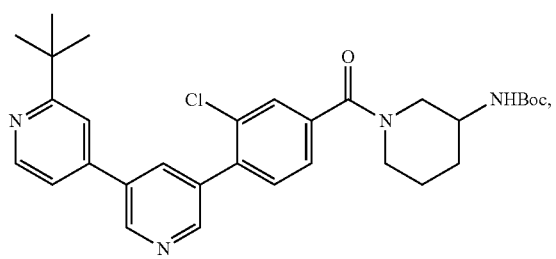
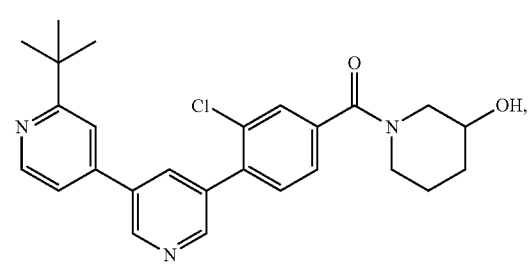
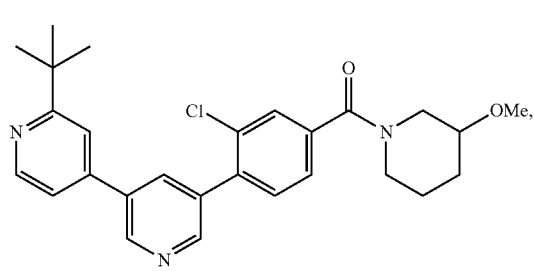
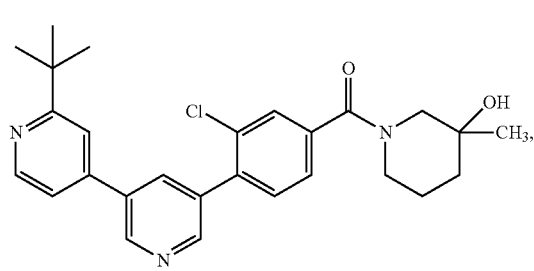
-continued
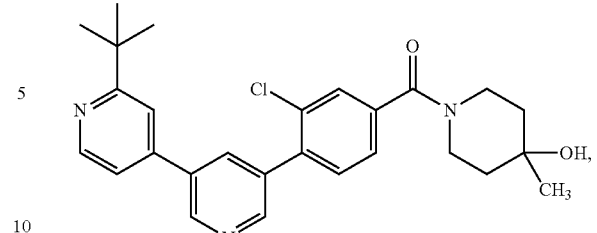
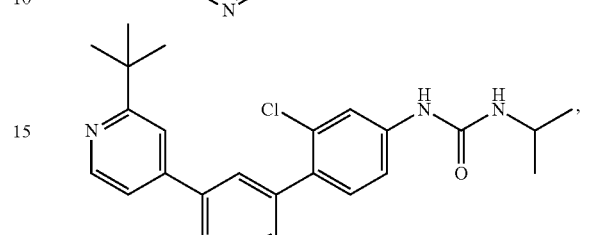
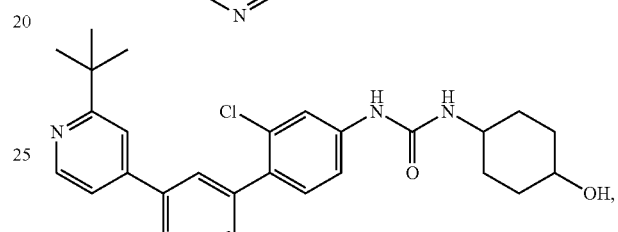
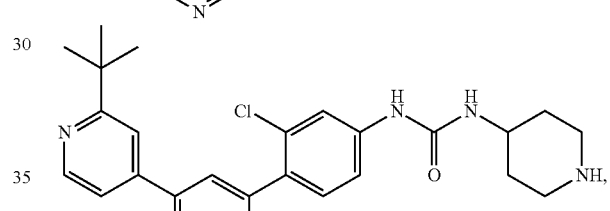
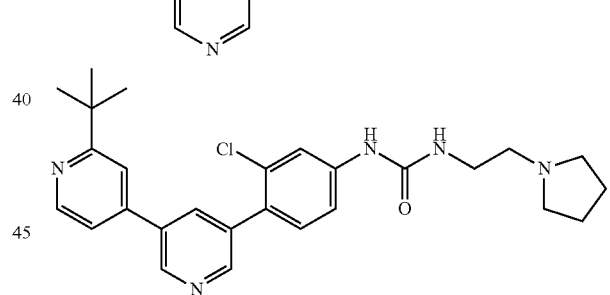
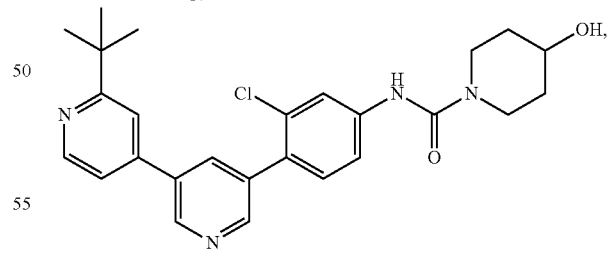
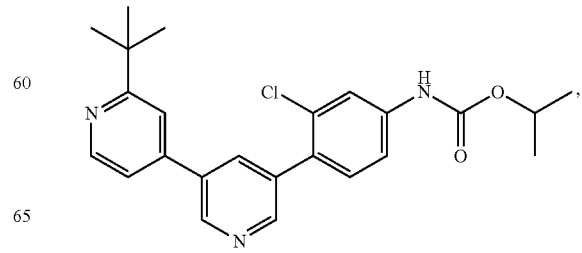

153
-continued
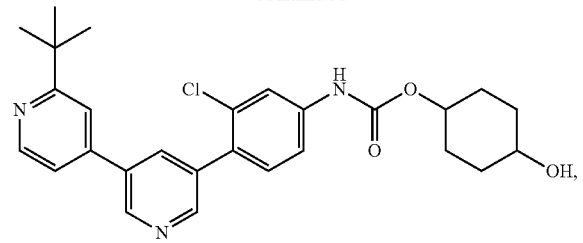
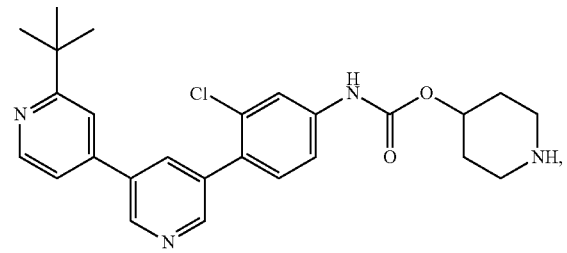
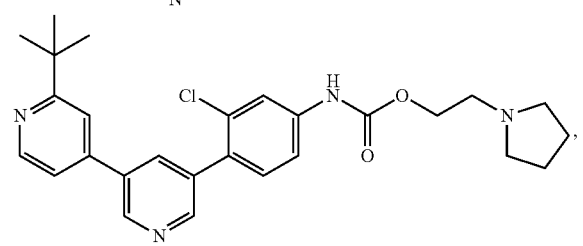
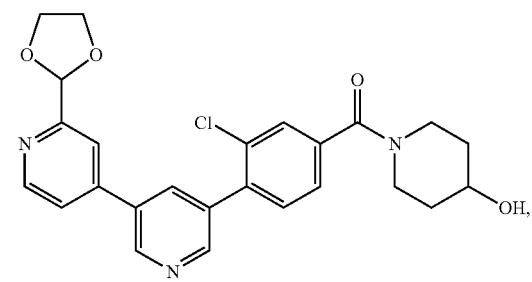
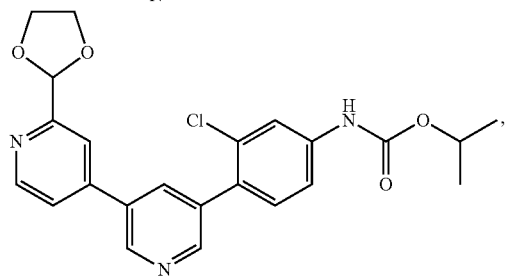
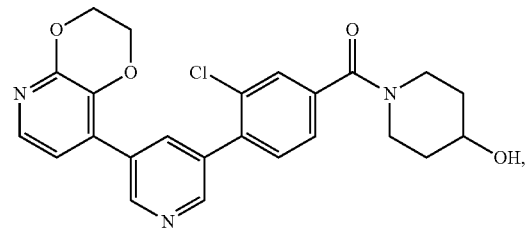
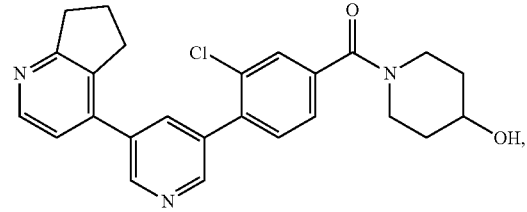
154
-continued
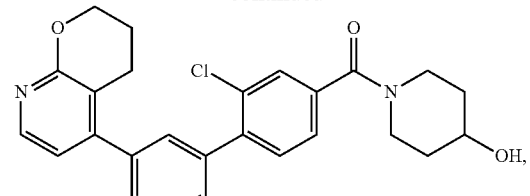
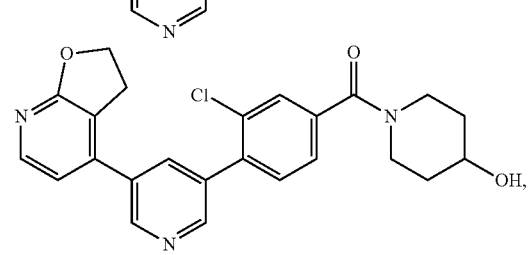
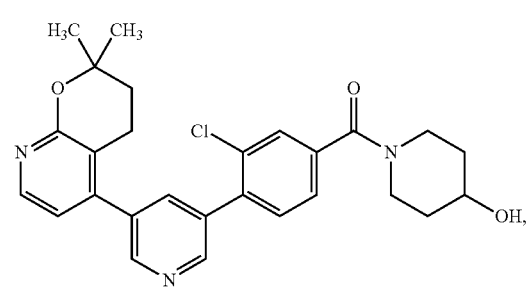
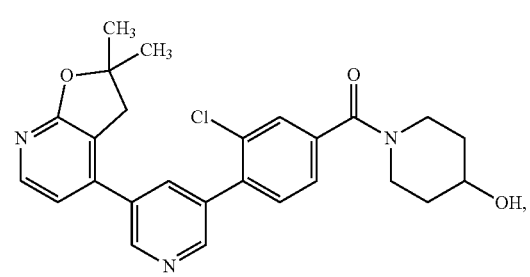
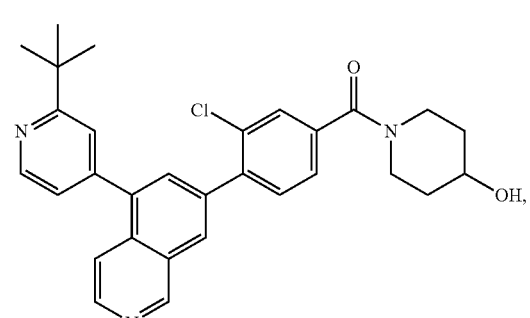
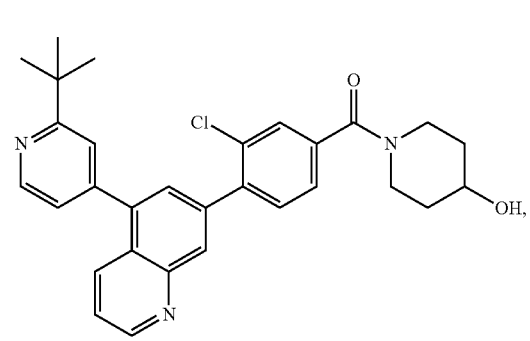

155
-continued
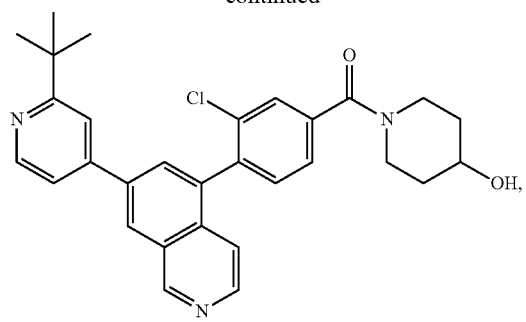
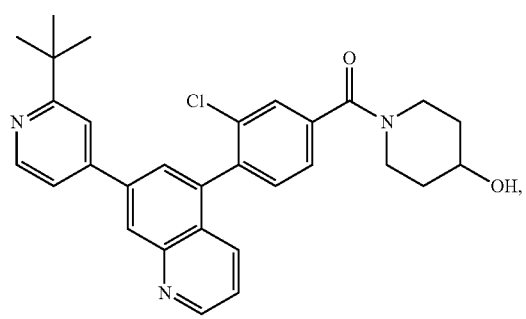
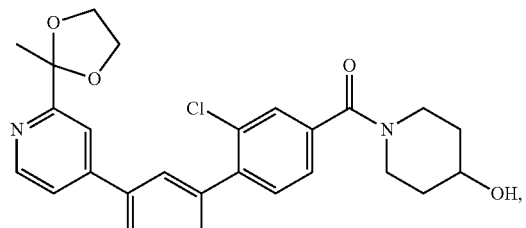
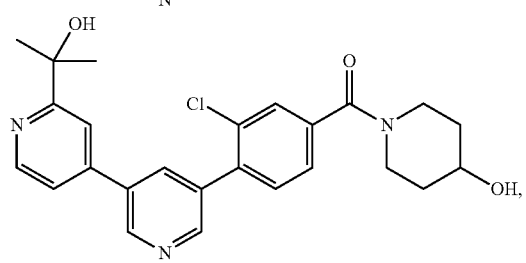
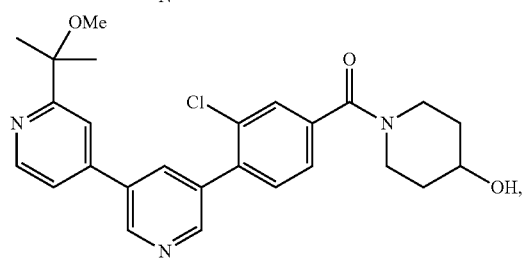
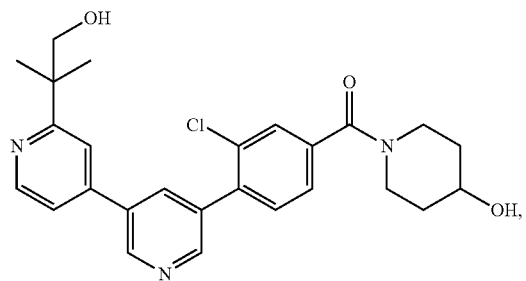
156
-continued
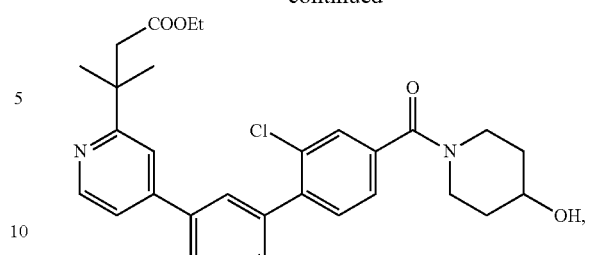
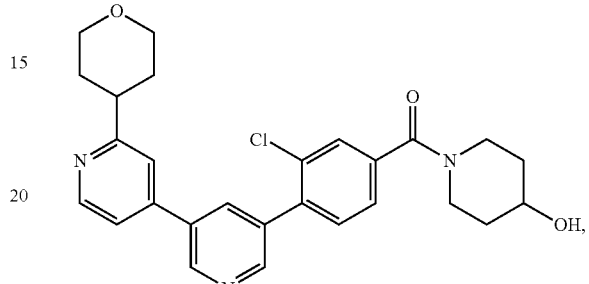
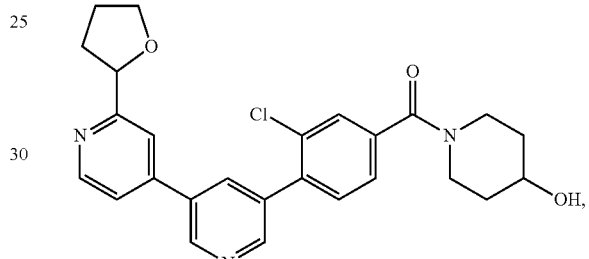
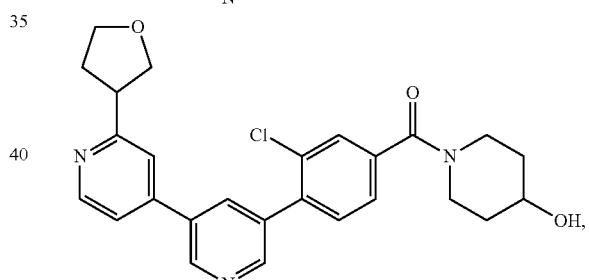
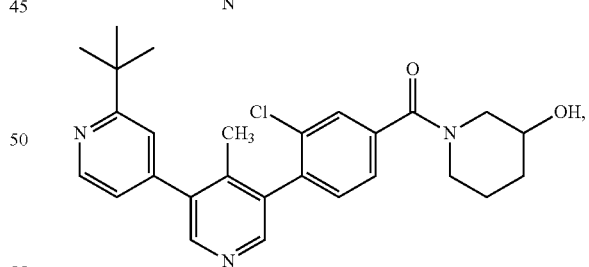
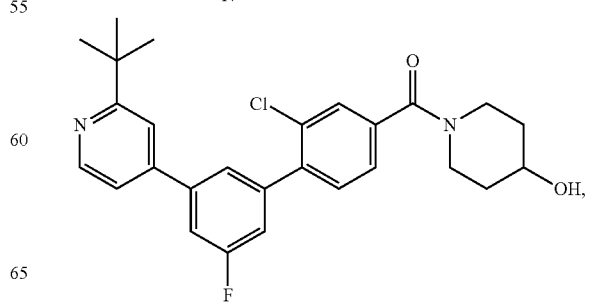

157
-continued
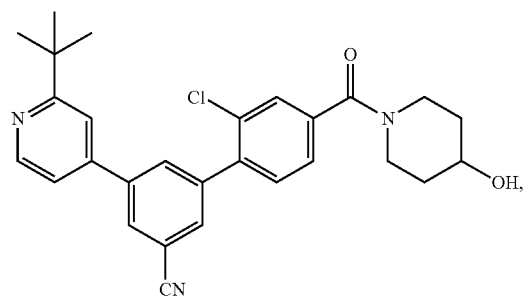
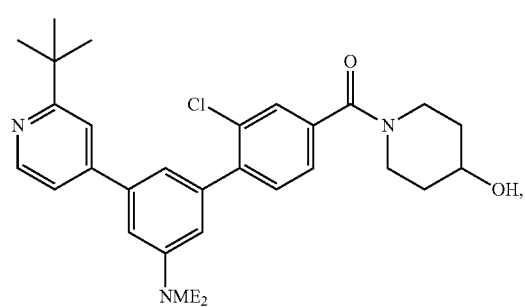
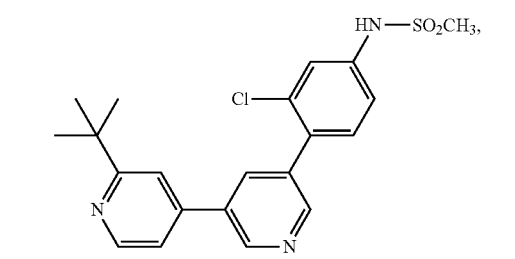
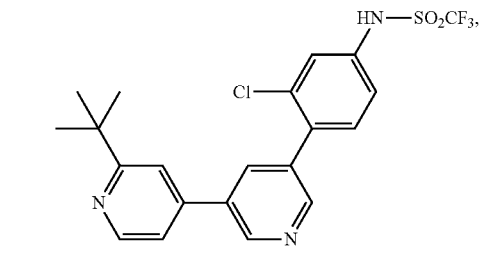
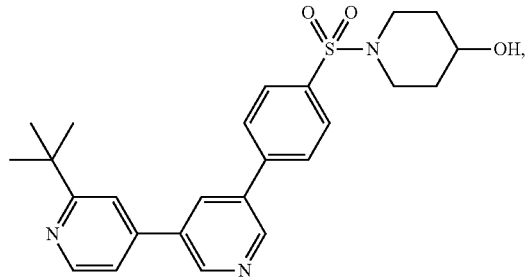
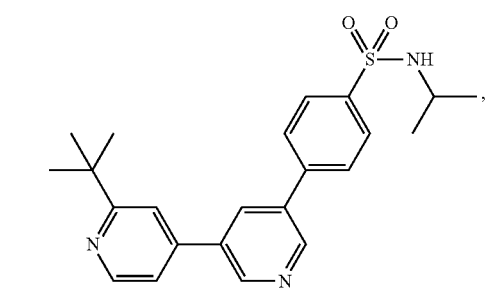
158
-continued
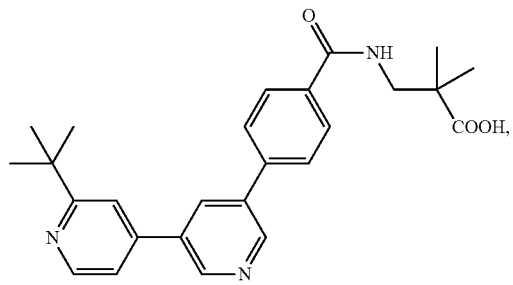
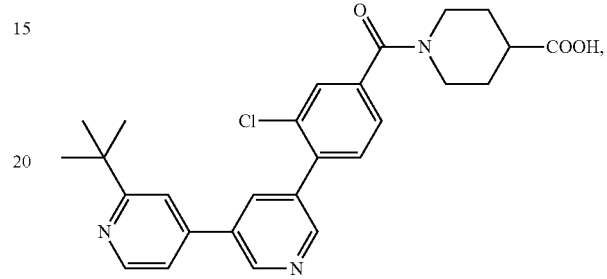
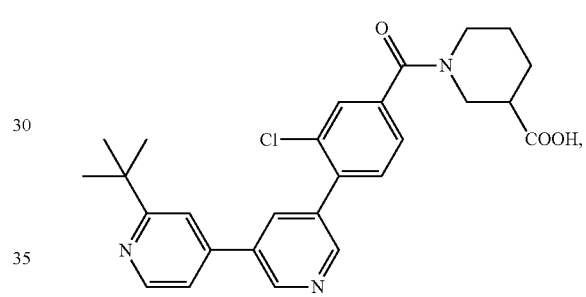
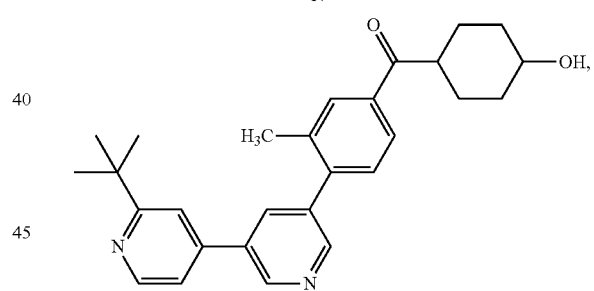
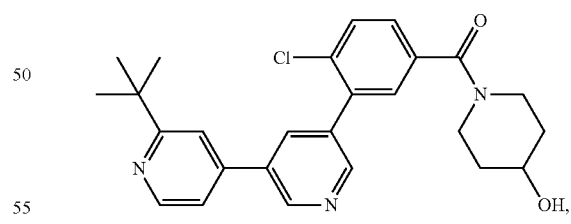
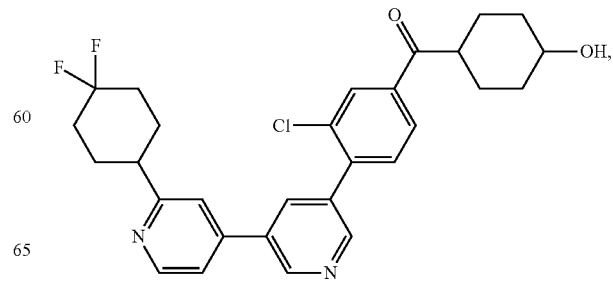

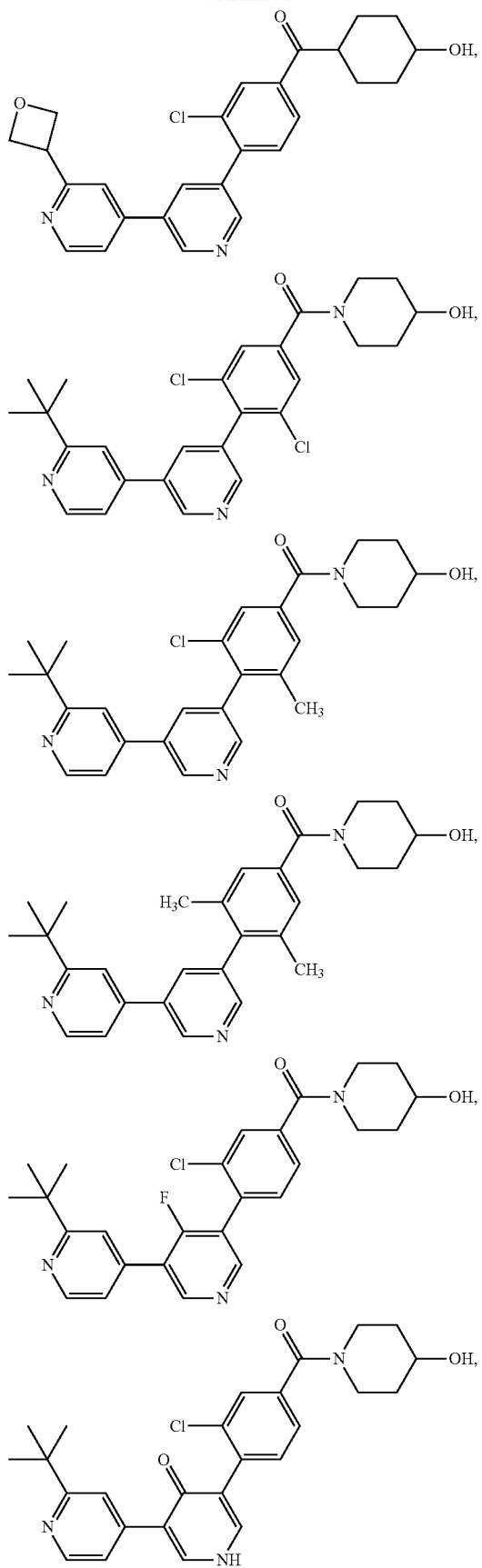

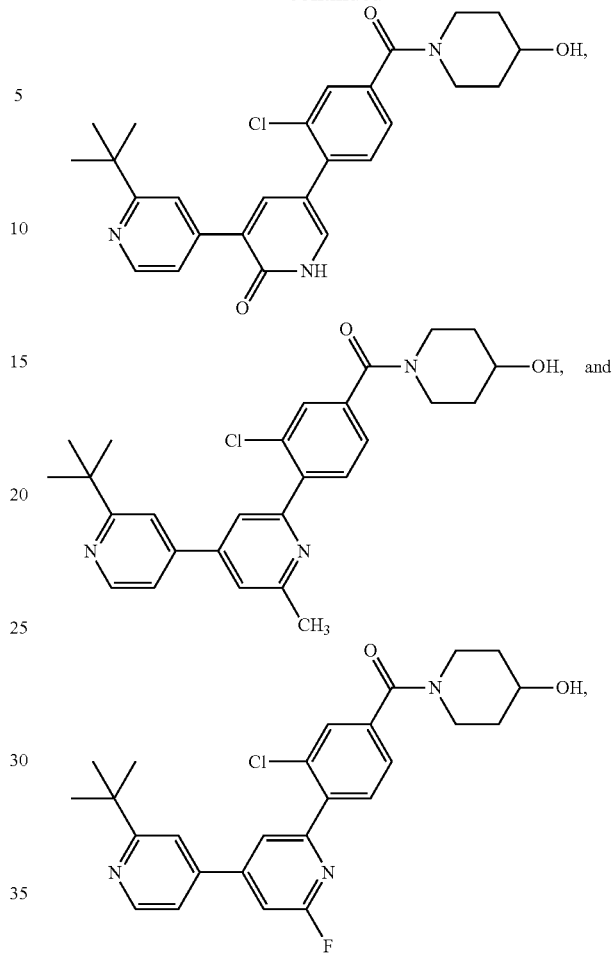

or a pharmaceutically acceptable salt, solvate, tautomer, isotope, or isomer of any of the foregoing.

Embodiment I-25. A pharmaceutical composition, comprising the compound of any one of Embodiments I-1 to I-24, or a pharmaceutically acceptable salt, solvate, tautomer, isotope, or isomer thereof, and a pharmaceutically acceptable excipient.

Embodiment I-26. A method of inhibiting a sterol regulatory element-binding protein (SREBP), comprising contacting the SREBP or contacting an SREBP cleavage activating-protein (SCAP) with a compound of any one of Embodiments I-1 to I-24, or a pharmaceutically acceptable salt, solvate, tautomer, isotope, or isomer thereof, or the pharmaceutical composition of Embodiment I-25.

Embodiment I-27. A method of inhibiting the proteolytic activation of a sterol regulatory element-binding protein (SREBP), comprising contacting an SREBP cleavage activating-protein (SCAP) with a compound of any one of Embodiments I-1 to I-24, or a pharmaceutically acceptable salt, solvate, tautomer, isotope, or isomer thereof, or the pharmaceutical composition of Embodiment I-25.

Embodiment I-28. The method of Embodiment I-26 or I-27, wherein the SREBP is an SREBP-1.

Embodiment I-29. The method of Embodiment I-28, wherein the SREBP-1 is SREBP-1a.

Embodiment I-30. The method of Embodiment I-28, wherein the SREBP-1 is SREBP-1c.

Embodiment I-31. The method of Embodiment I-26 or I-27, wherein the SREBP is SREBP-2.

Embodiment I-32. The method of any one of Embodiments I-26 to I-31, wherein SREBP is inhibited in a subject in need thereof.

Embodiment I-33. The method of any one of Embodiments I-26 to I-32, wherein SCAP is inhibited in a subject in need thereof.

Embodiment I-34. The method of any one of Embodiments I-26 to I-33, wherein the expression of one or more genes selected from the group consisting of ACSS2, ALDOC, CYP51A1, DHCR7, ELOVL6, FASN, FDFT1, FDPS, HMGCS1, HSD17B7, IDI1, INSIG1, LDLR, LSS, ME1, PCSK9, PMVK, RDH11, SC5DL, SQLE, STARD4, TM7SF2, PNPLA3, SREBF1, SREBF2, HMGCR, MVD, MVK, ACLY, MSMO1, ACACA, and ACACB is reduced after contacting the SREBP or SCAP with the compound, or pharmaceutically acceptable salt, solvate, tautomer, isotope, or isomer thereof, or the pharmaceutical composition.

Embodiment I-35. A method of treating a disorder in a subject in need thereof, comprising administering to the subject an effective amount of a compound of any one of Embodiments I-1 to I-24, or a pharmaceutically acceptable salt, solvate, tautomer, isotope, or isomer thereof, or the pharmaceutical composition of Embodiment I-25.

Embodiment I-36. A method of treating a disorder in a subject in need thereof, wherein the disorder is mediated by a sterol regulatory element-binding protein (SREBP), comprising administering to the subject an effective amount of a compound of any one of Embodiments I-1 to I-24, or a pharmaceutically acceptable salt, solvate, tautomer, isotope, or isomer thereof, or the pharmaceutical composition of Embodiment I-25.

Embodiment I-37. The method of Embodiment I-35 or I-36, wherein the disorder is Metabolic Syndrome, type 2 diabetes, obesity, liver disease, insulin resistance, adiposopathy, or dyslipidemia.

Embodiment I-38. The method of Embodiment I-37, wherein the dyslipidemia is hypertriglyceridemia or elevated cholesterol levels.

Embodiment I-39. The method of Embodiment I-37, wherein the liver disease is nonalcoholic steatohepatitis, liver fibrosis, or liver inflammation, or a combination thereof.

Embodiment I-40. The method of Embodiment I-35 or I-36, wherein the disorder is a hyperproliferative disorder.

Embodiment I-41. The method of Embodiment I-40, wherein the hyperproliferative disorder is cancer.

Embodiment I-42. The method of Embodiment I-41, wherein the cancer is breast cancer, liver cancer, ovarian cancer, pancreatic cancer, or prostate cancer.

Embodiment I-43. The method of Embodiment I-35 or I-36, wherein the disorder is endotoxic shock, systemic inflammation, or atherosclerosis.

Embodiment I-44. Use of a compound of any one of Embodiments I-1 to I-24, or a pharmaceutically acceptable salt, solvate, tautomer, isotope, or isomer thereof, in the manufacture of a medicament for use in treating a disorder in a subject in need thereof.

Embodiment I-45. Use of a compound of any one of Embodiments I-1 to I-24, or a pharmaceutically acceptable salt, solvate, tautomer, isotope, or isomer thereof, in the manufacture of a medicament for use in inhibiting a sterol regulatory element-binding protein (SREBP) in a subject in need thereof.

Embodiment I-46. Use of a compound of any one of Embodiments I-1 to I-24, or a pharmaceutically acceptable salt, solvate, tautomer, isotope, or isomer thereof, in the manufacture of a medicament for use in inhibiting the proteolytic activation of a sterol regulatory element-binding protein (SREBP) in a subject in need thereof.

Embodiment I-47. Use of a compound of any one of Embodiments I-1 to I-24, or a pharmaceutically acceptable salt, solvate, tautomer, isotope, or isomer thereof, in the manufacture of a medicament for use in treating a disorder in a subject in need thereof, wherein the disorder is mediated by a sterol regulatory element-binding protein (SREBP).

Embodiment I-48. Use of a compound of any one of Embodiments I-1 to I-24, or a pharmaceutically acceptable salt, solvate, tautomer, isotope, or isomer thereof, or the pharmaceutical composition of Embodiment I-25, for inhibiting a sterol regulatory element-binding protein (SREBP).

Embodiment I-49. Use of a compound of any one of Embodiments I-1 to I-24, or a pharmaceutically acceptable salt, solvate, tautomer, isotope, or isomer thereof, or the pharmaceutical composition of Embodiment I-25, for inhibiting an SREBP cleavage activating protein (SCAP).

Embodiment I-50. The use of any one of Embodiments I-45 to I-49, wherein the SREBP is an SREBP-1.

Embodiment I-51. The method of Embodiment I-50, wherein the SREBP-1 is SREBP-1a.

Embodiment I-52. The method of Embodiment I-50, wherein the SREBP-1 is SREBP-1c.

Embodiment I-53. The use of any one of Embodiments I-45 to I-49, wherein the SREBP is SREBP-2.

Embodiment I-54. The use of any one of Embodiments I-44 to I-53, wherein SREBP is inhibited in a subject in need thereof.

Embodiment I-55. The use of any one of Embodiments I-44 to I-54, wherein SCAP is inhibited in a subject in need thereof.

Embodiment I-56. Use of a compound of any one of Embodiments I-1 to I-24, or a pharmaceutically acceptable salt, solvate, tautomer, isotope, or isomer thereof, or the pharmaceutical composition of Embodiment I-25, for treating a disorder in a subject in need thereof.

Embodiment I-57. Use of a compound of any one of Embodiments I-1 to I-24, or a pharmaceutically acceptable salt, solvate, tautomer, isotope, or isomer thereof, or the pharmaceutical composition of Embodiment I-25, for treating a disorder in a subject in need thereof, wherein the disorder is mediated by a sterol regulatory element-binding protein (SREBP).

Embodiment I-58. The use of Embodiment I-56 or 57, wherein the disorder is Metabolic Syndrome, type 2 diabetes, obesity, liver disease, insulin resistance, adiposopathy, or dyslipidemia.

Embodiment I-59. The use of Embodiment I-58, wherein the dyslipidemia is hypertriglyceridemia or elevated cholesterol levels.

Embodiment I-60. The use of Embodiment I-58, wherein the liver disease is nonalcoholic steatohepatitis, liver fibrosis, or liver inflammation, or a combination thereof.

Embodiment I-61. The use of Embodiment I-56 or I-57, wherein the disorder is a hyperproliferative disorder.

Embodiment I-62. The use of Embodiment I-61, wherein the hyperproliferative disorder is cancer.

Embodiment I-63. The use of Embodiment I-62, wherein the cancer is breast cancer, liver cancer, ovarian cancer, pancreatic cancer, or prostate cancer.

Embodiment I-64. The use of Embodiment I-56 or I-57, wherein the disorder is endotoxic shock, systemic inflammation, or atherosclerosis.

Embodiment I-65. A method of treating non-alcoholic steatohepatitis (NASH) in a subject in need thereof, comprising administering to the subject an effective amount of a compound of any one of Embodiments I-1 to I-24, or a pharmaceutically acceptable salt, solvate, tautomer, isotope, or isomer thereof, or the pharmaceutical composition of Embodiment I-25.

Embodiment I-66. Use of a compound of any one of Embodiments I-1 to I-24, or a pharmaceutically acceptable salt, solvate, tautomer, isotope, or isomer thereof, or the pharmaceutical composition of Embodiment I-25, for treating non-alcoholic steatohepatitis (NASH) in a subject in need thereof.

Embodiment I-67. Use of a compound of any one of Embodiments I-1 to I-24, or a pharmaceutically acceptable salt, solvate, tautomer, isotope, or isomer thereof, or the pharmaceutical composition of Embodiment I-25, in the manufacture of a medicament for use in treating non-alcoholic steatohepatitis (NASH) in a subject in need thereof.

Embodiment I-68. A method of treating a hyperproliferative disorder in a subject in need thereof, comprising administering to the subject an effective amount of a compound of any one of Embodiments I-1 to I-24, or a pharmaceutically acceptable salt, solvate, tautomer, isotope, or isomer thereof, or the pharmaceutical composition of Embodiment I-25.

Embodiment I-69. Use of a compound of any one of Embodiments I-1 to I-24, or a pharmaceutically acceptable salt, solvate, tautomer, isotope, or isomer thereof, or the pharmaceutical composition of Embodiment I-25, for treating a hyperproliferative disorder in a subject in need thereof.

Embodiment I-70. Use of a compound of any one of Embodiments I-1 to I-24, or a pharmaceutically acceptable salt, solvate, tautomer, isotope, or isomer thereof, or the pharmaceutical composition of Embodiment I-25, in the manufacture of a medicament for use in treating a hyperproliferative disorder in a subject in need thereof.

Embodiment I-71. The compound of Embodiment I-1, selected from the group consisting of:

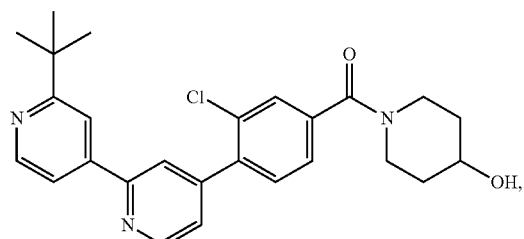

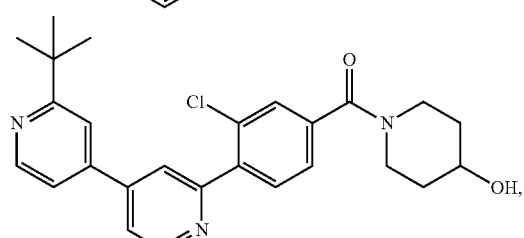

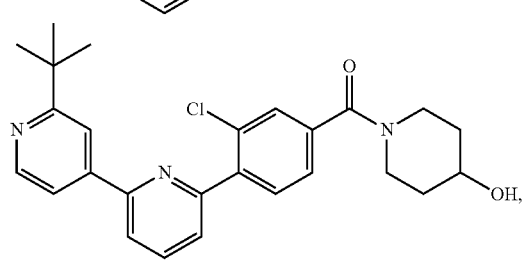

-continued

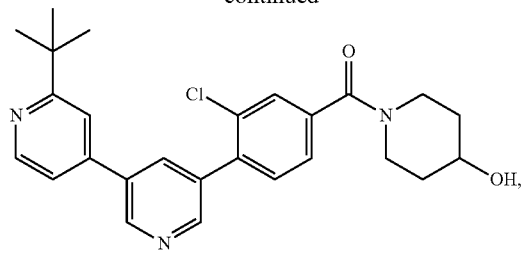

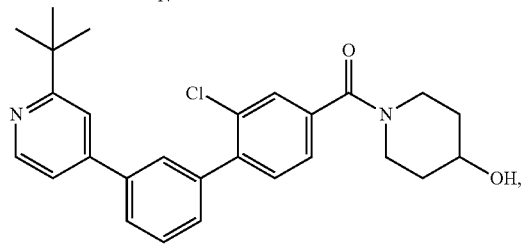

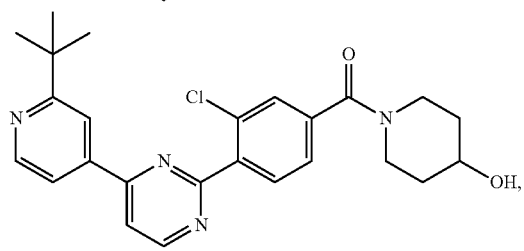

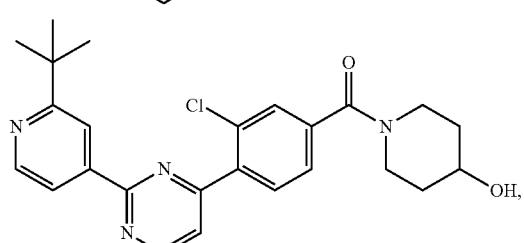

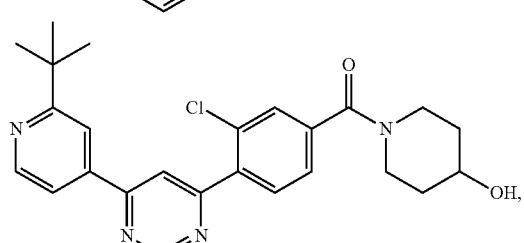

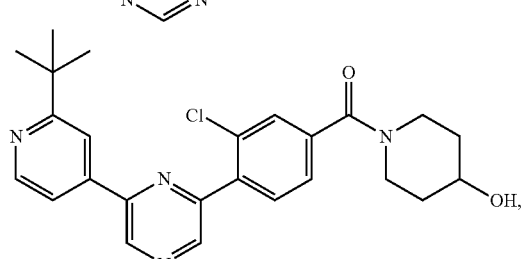

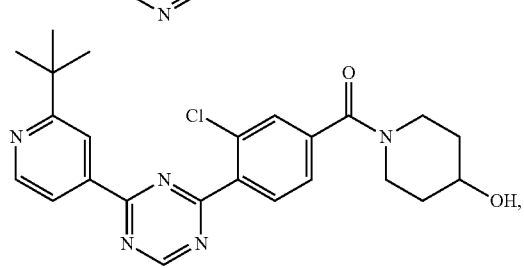

165
-continued
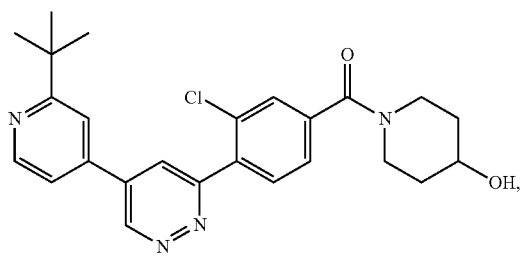
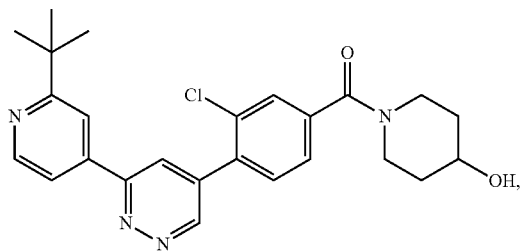
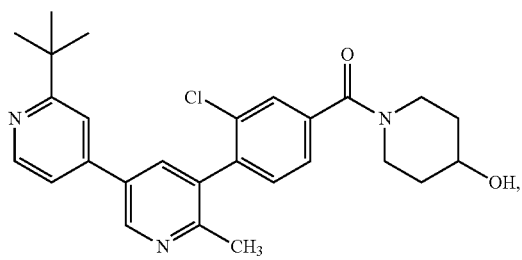
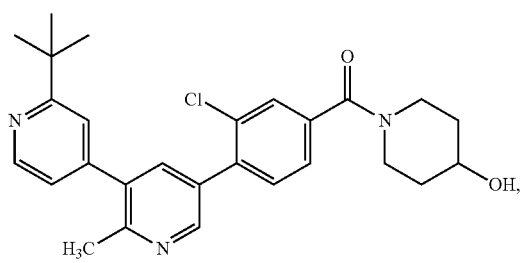
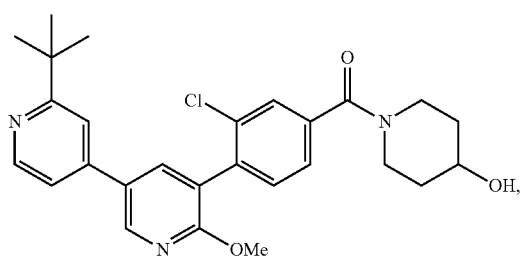
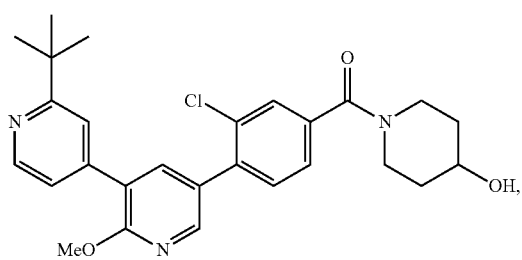
166
-continued
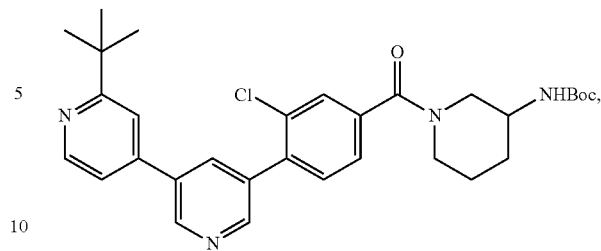
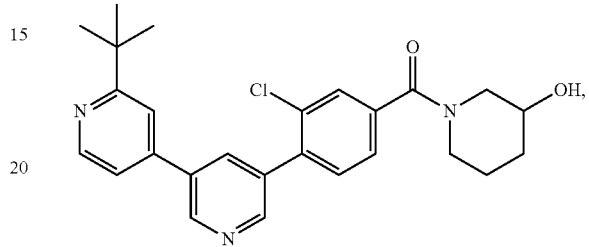
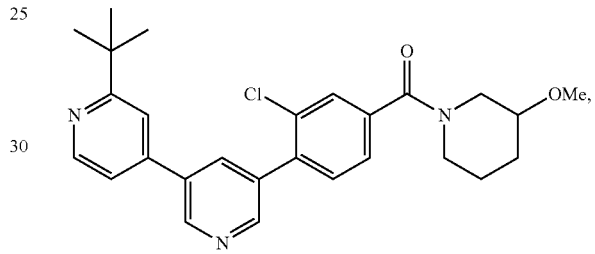
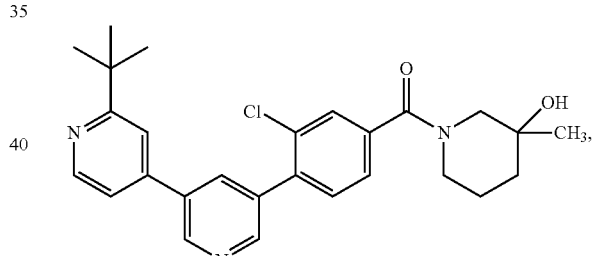
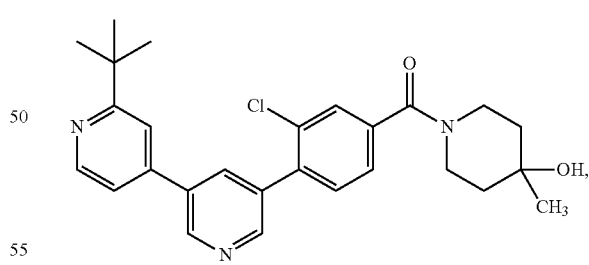
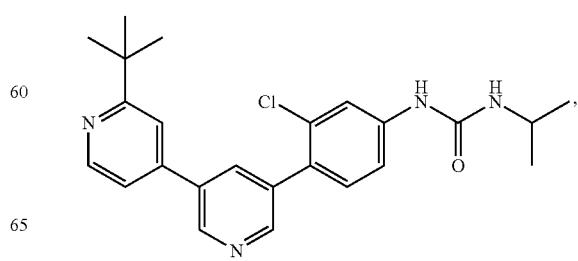

167
-continued
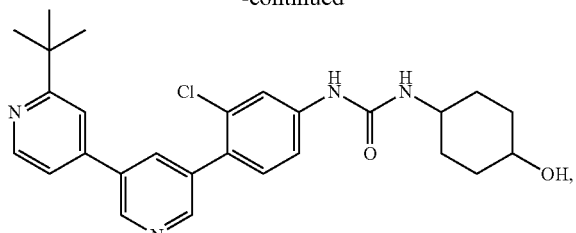
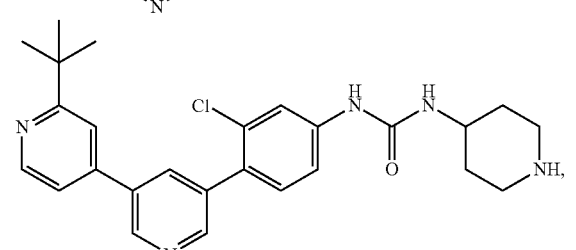
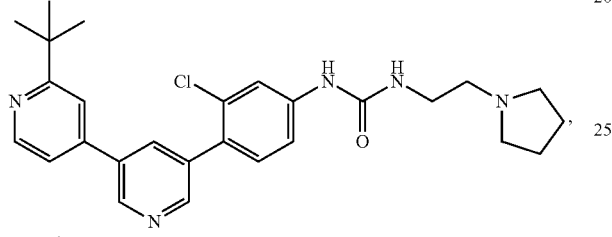
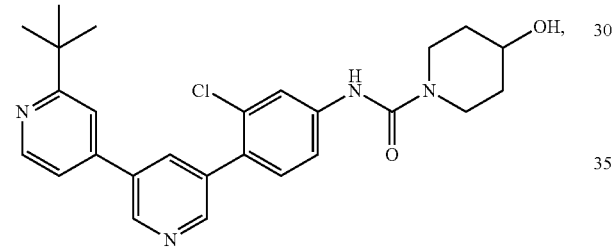
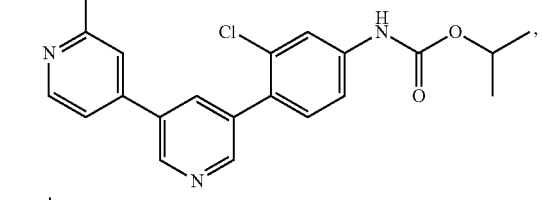
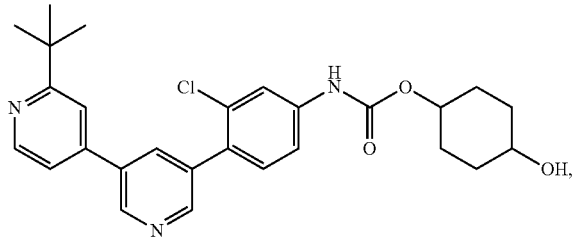
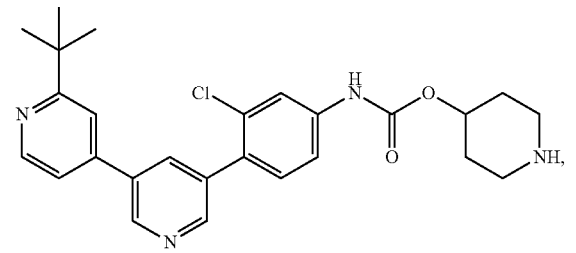
168
-continued
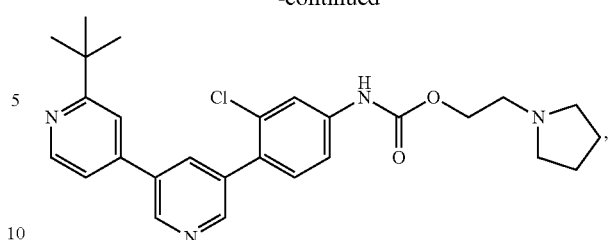
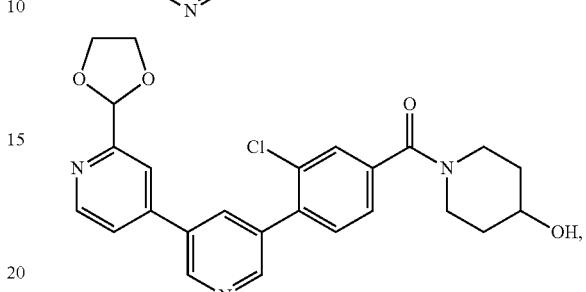
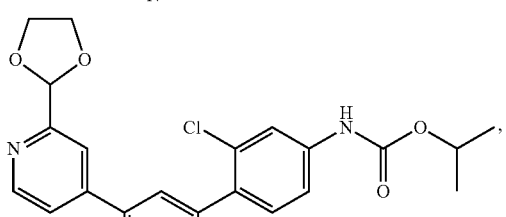
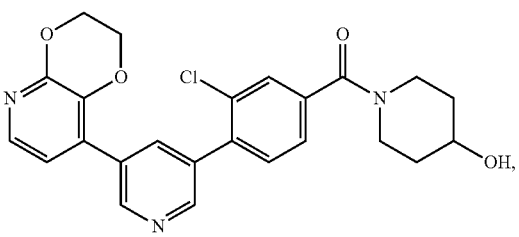
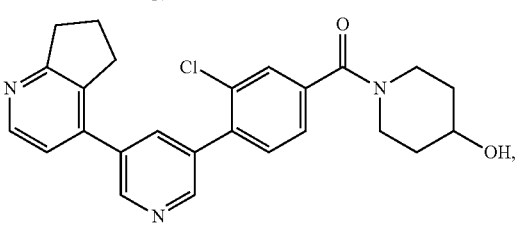
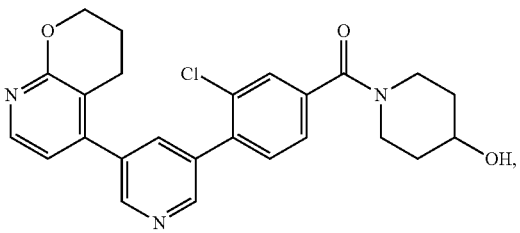
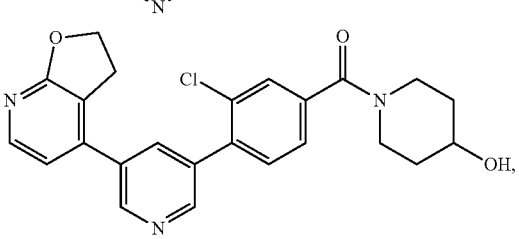

169
-continued
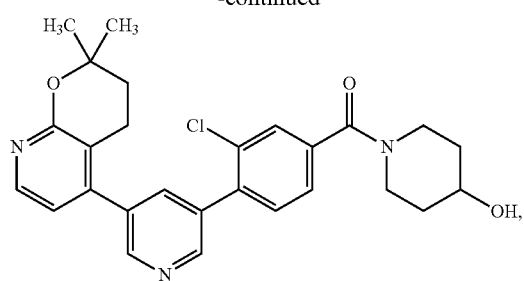
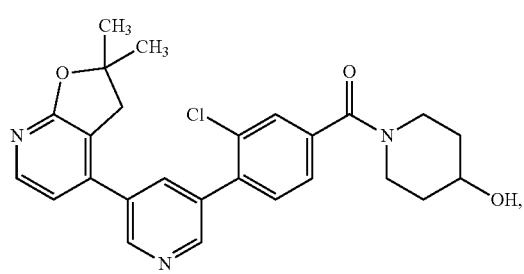
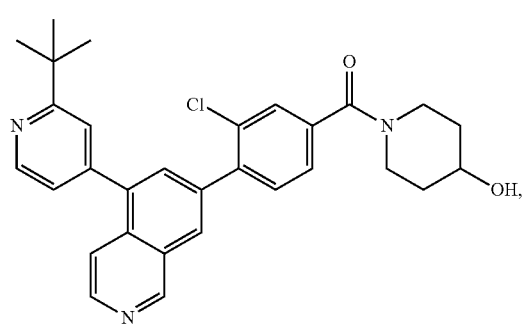
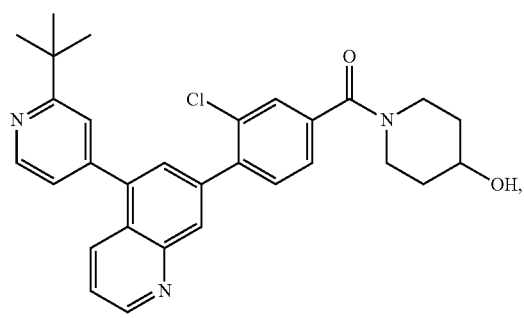
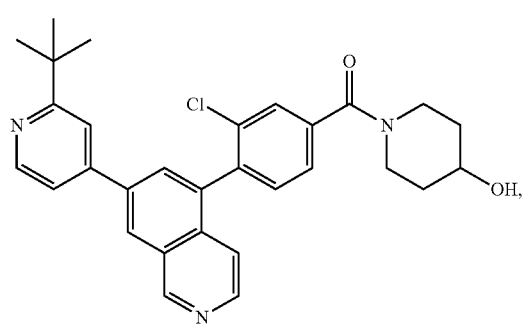
170
-continued
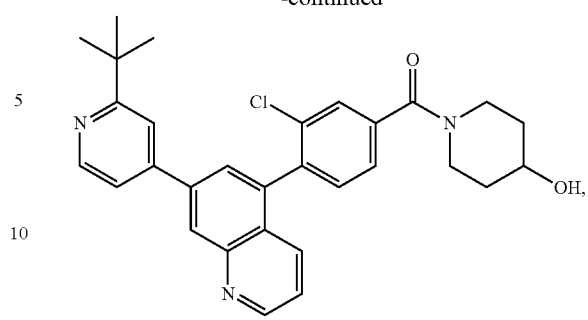
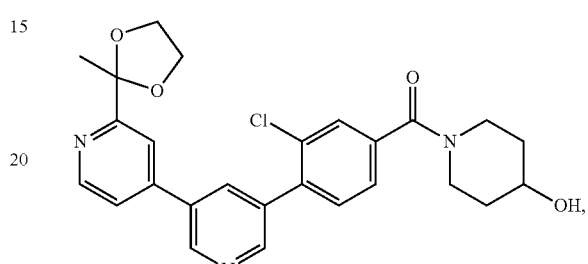
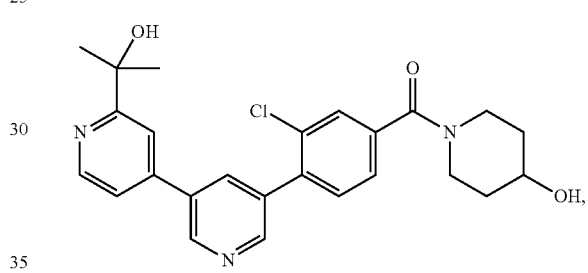
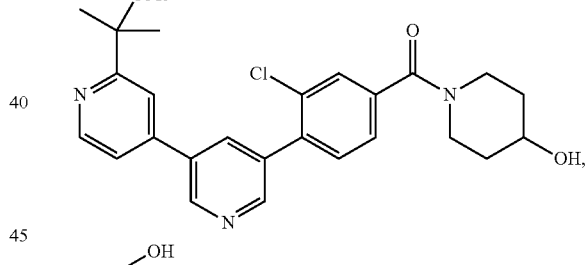
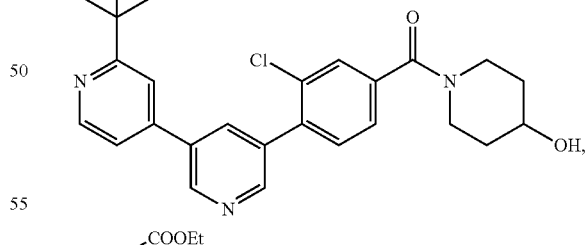
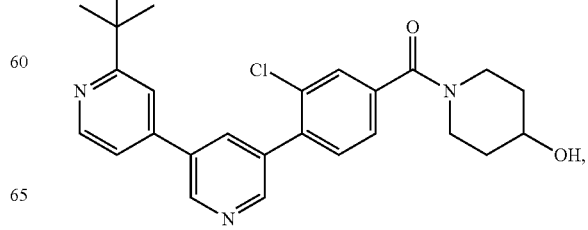

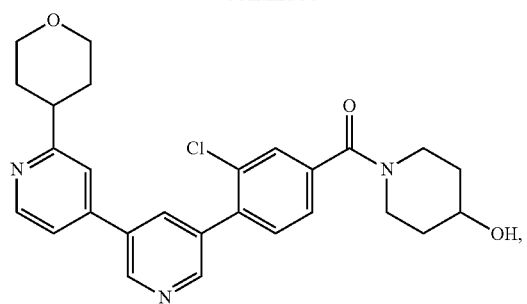
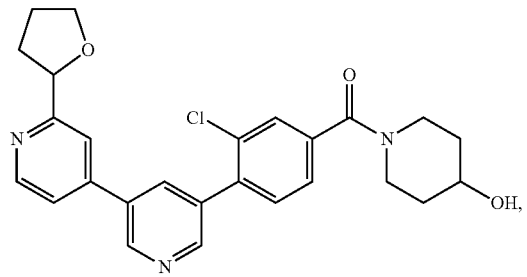
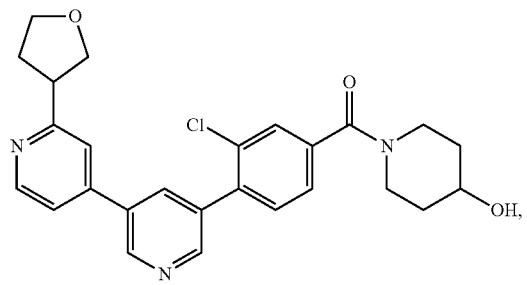
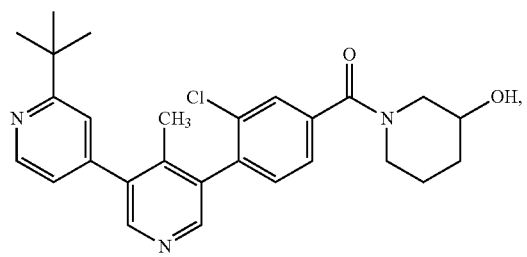
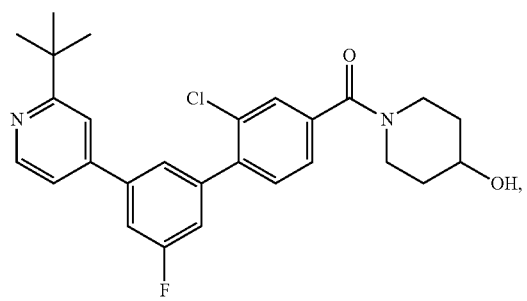
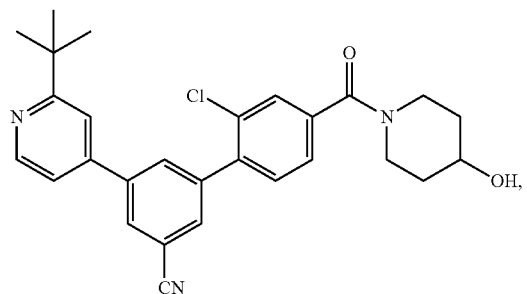
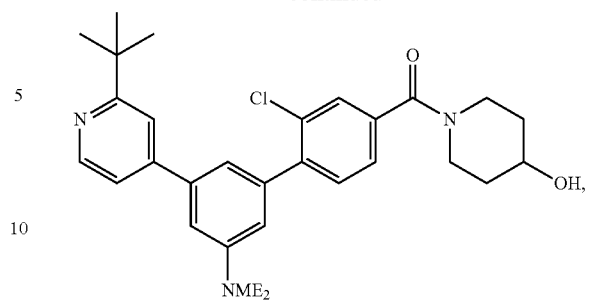
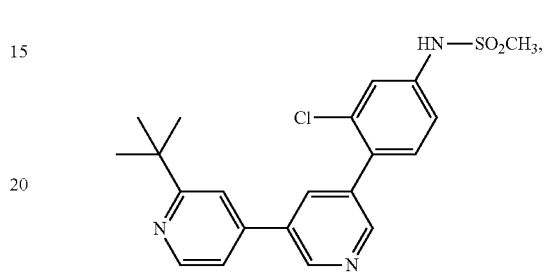
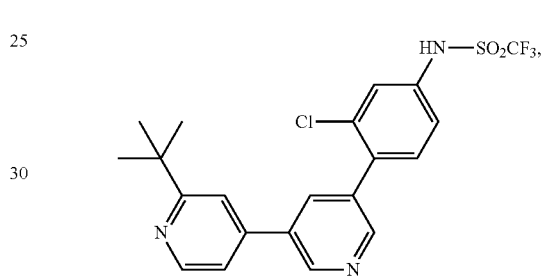
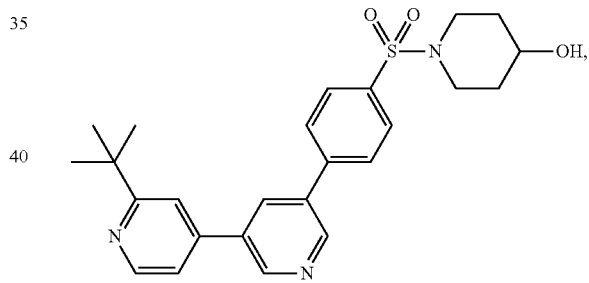
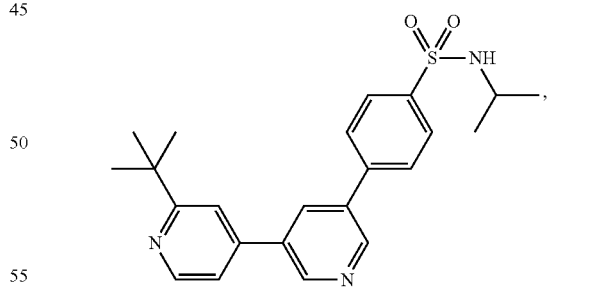
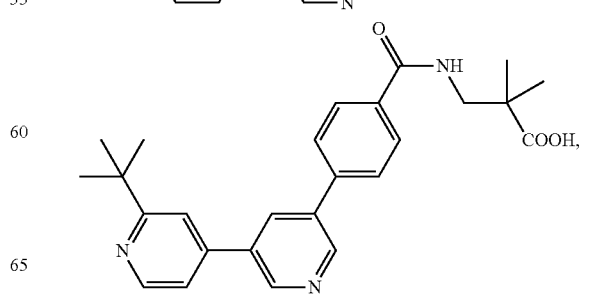

-continued
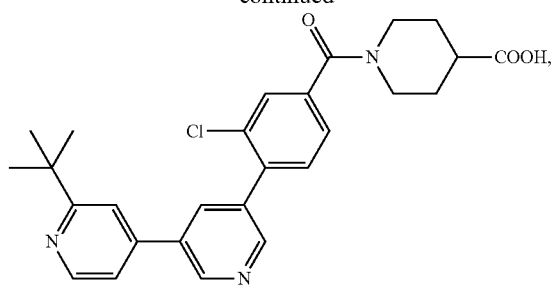
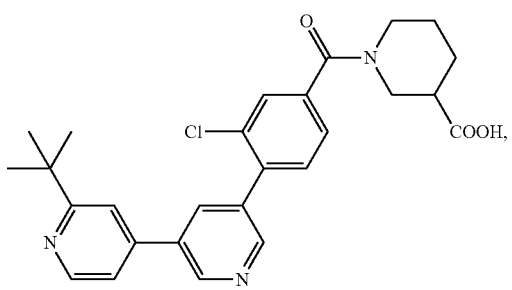
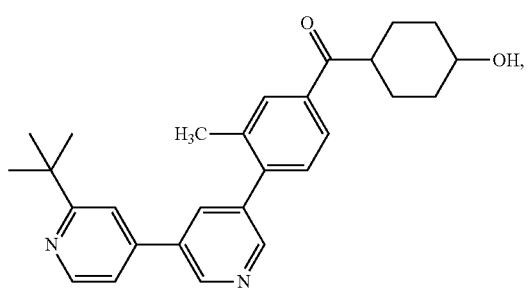
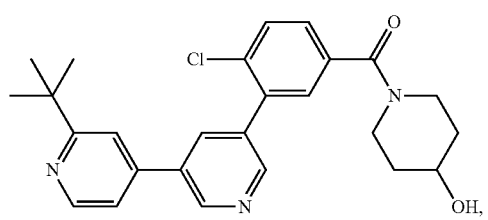
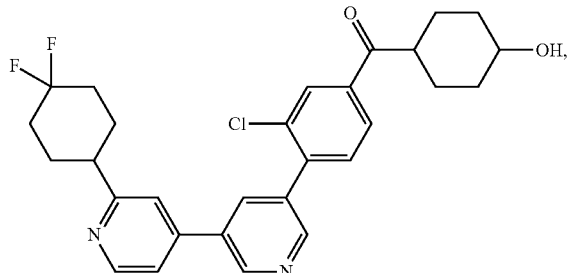
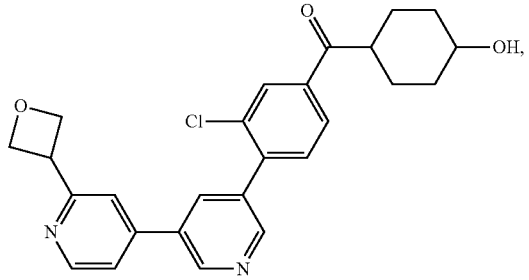
-continued
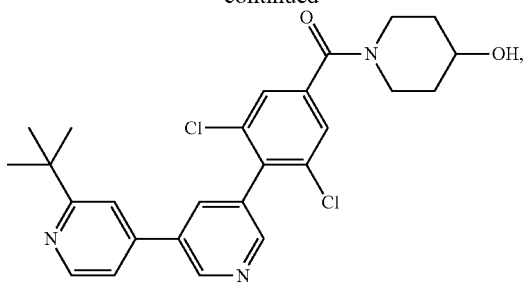
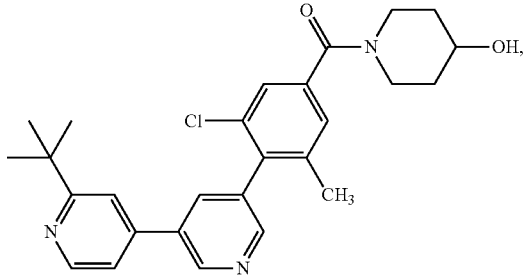
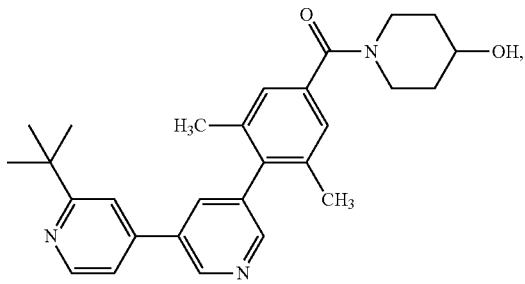
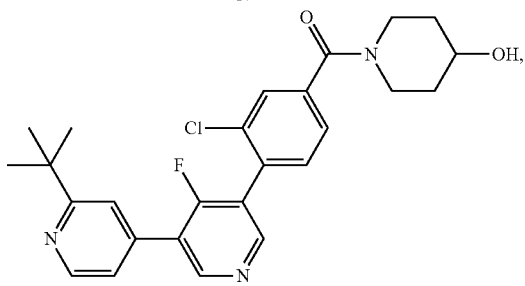
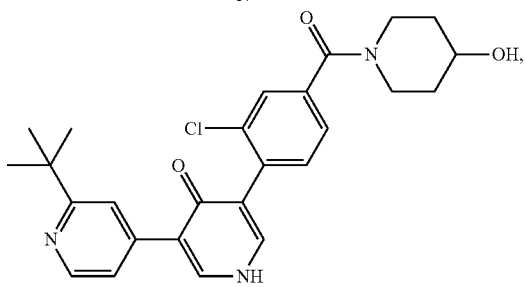
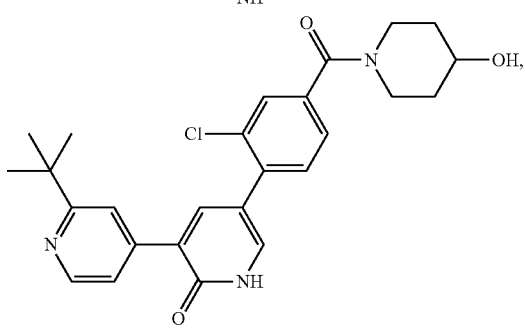

-continued

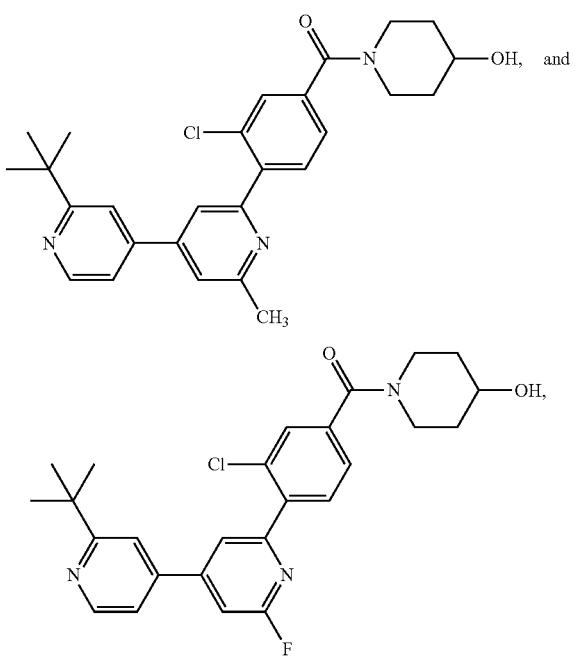

or a pharmaceutically acceptable salt, solvate, tautomer, isotope, or isomer thereof.

Embodiment I-72. The compound of any one of Embodiments I-1 to I-3, I-22, or I-23, or a pharmaceutically acceptable salt, solvate, tautomer, isotope, or isomer thereof, wherein $R^1$ is

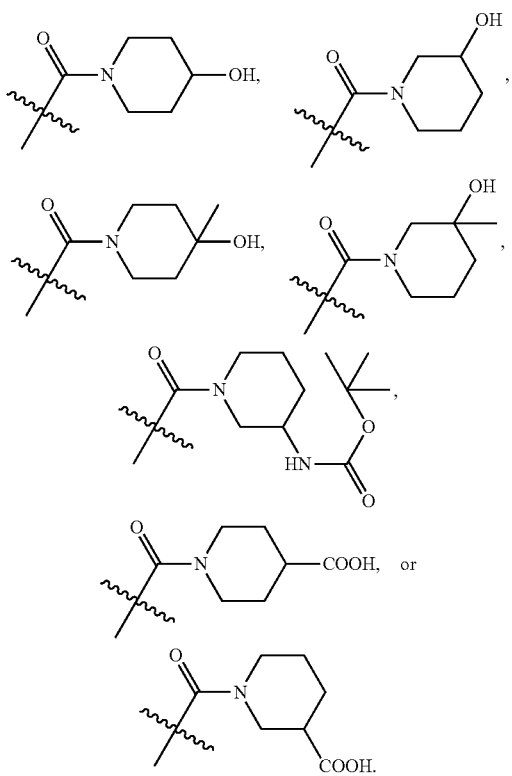

Embodiment I-73. The compound of any one of Embodiments I-1 to I-3, I-22, or I-23, or a pharmaceutically acceptable salt, solvate, tautomer, isotope, or isomer thereof, wherein $R^1$ is

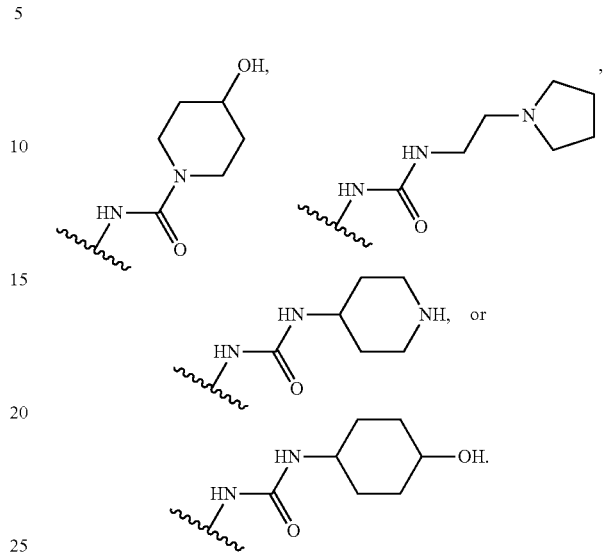

Embodiment I-74. The compound of any one of Embodiments I-1 to I-3, I-22, or I-23, or a pharmaceutically acceptable salt, solvate, tautomer, isotope, or isomer thereof, wherein $R^1$ is

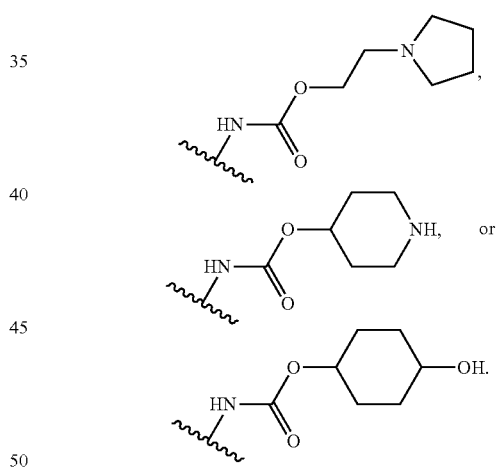

Embodiment I-75. The compound of any one of Embodiments I-1 to I-3, I-22, or I-23, or a pharmaceutically acceptable salt, solvate, tautomer, isotope, or isomer thereof, wherein $R^1$ is

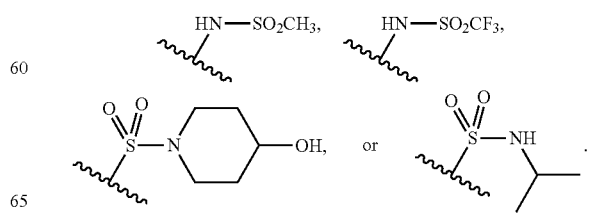

Embodiment I-76. The compound of any one of Embodiments I-1 to I-3, I-22, or I-23, or a pharmaceutically acceptable salt, solvate, tautomer, isotope, or isomer thereof, wherein $R^{14}$ is

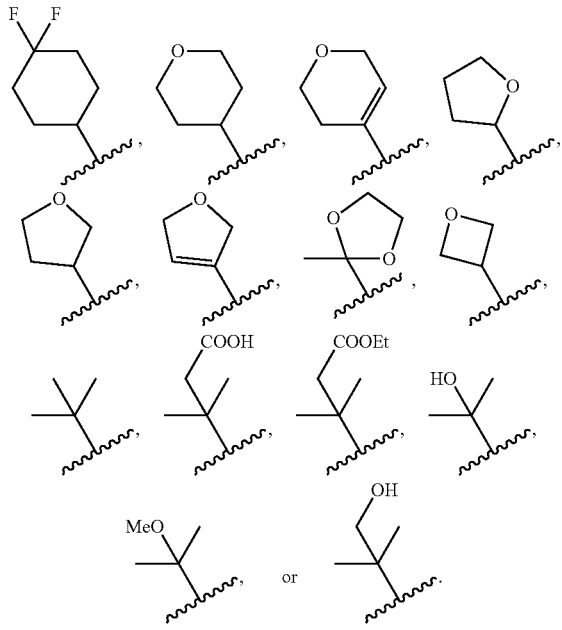

Embodiment I-77. A pharmaceutical composition, comprising a compound of any one of Embodiments I-71 to I-76, or a pharmaceutically acceptable salt, solvate, tautomer, isotope, or isomer thereof, and a pharmaceutically acceptable excipient.

Embodiment II-1. A compound of Formula (Z):

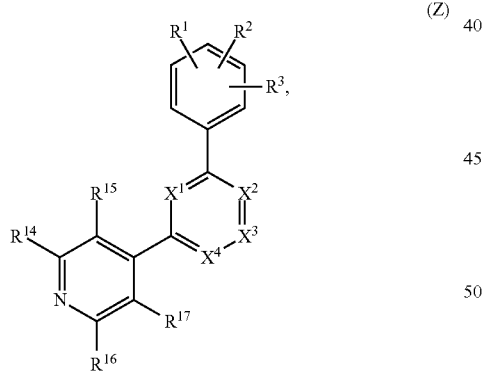

or a pharmaceutically acceptable salt, solvate, tautomer, isotope, or isomer thereof, wherein:

$R^1$ is —C(O)$R^9$, —C(O)N$R^8R^9$, —S(O)$_2$N$R^8R^9$, —N$R^{10}$C(O)N$R^8R^9$, —N$R^{10}$C(O)$R^9$, —N$R^{10}$S(O)$_2R^9$, —O$R^{26}$, —S$R^9$, —S(O)$R^9$, —S(O)$_2R^9$, —N$R^8R^9$, —N$R^{10}$C(O)O$R^9$, —C(O)$R^{26}$, —N$R^{10}$S(O)$_2$N$R^8R^9$, or —C(O)N$R^{10}$S(O)$_2R^9$;

wherein each of $R^8$, $R^9$, and $R^{10}$ is independently selected from the group consisting of hydrogen, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl, $R^{26}$ is (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, or heteroaryl-alkyl, each (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl of $R^8$, $R^9$, $R^{10}$, and $R^{26}$ is independently unsubstituted or substituted with one or more substituents independently selected from the group consisting of halo, cyano, oxo, —O$R^{19}$, —C(O)N$R^{19}R^{19}$, —N$R^{19}$C(O)$R^{19}$, —N$R^{19}$C(O)N$R^{19}R^{19}$, —N$R^{19}R^{19}$, —S(O)$_2$N$R^{19}R^{19}$, —N$R^{19}$S(O)$_2R^{19}$, —S(O)$_{n4}R^{20}$, —C(O)O$R^{19}$, and —C(O)$R^{20}$, each $R^{19}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{20}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, and n4 is 0, 1, or 2;

or $R^8$ and $R^9$, together with the nitrogen atom to which they are attached, form a heterocycloalkyl, wherein the heterocycloalkyl is unsubstituted or substituted with 1 to 3 substituents independently selected from the group consisting of halo, cyano, oxo, (C$_{1-10}$)alkyl, (C$_{2-10}$)alkenyl, (C$_{2-10}$)alkynyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, heteroaryl-alkyl, —O$R^{23}$, —C(O)N$R^{23}R^{23}$, —N$R^{23}$C(O)$R^{23}$, —N$R^{23}$C(O)O$R^{23}$, —N$R^{23}$C(O)N$R^{23}R^{23}$, —N$R^{23}R^{23}$, —S(O)$_2$N$R^{23}R^{23}$, —N$R^{23}$S(O)$_2R^{24}$, —S(O)$_{n6}R^{24}$, —C(O)O$R^{23}$, and —C(O)$R^{24}$, wherein each $R^{23}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{24}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, and n6 is 0, 1, or 2;

$R^2$ and $R^3$ are independently selected from the group consisting of hydrogen, halo, cyano, (C$_{1-10}$)alkyl, (C$_{3-10}$)cycloalkyl, (C$_{3-10}$)cycloalkyl(C$_{1-10}$)alkyl, —O$R^{25}$, —C(O)N$R^{25}R^{25}$, —N$R^{25}$C(O)$R^{25}$, —N$R^{25}$C(O)N$R^{25}R^{25}$, —N$R^{25}R^{25}$, —S(O)$_2$N$R^{25}R^{25}$, —N$R^{25}$S(O)$_2R^{25}$, —S(O)$_{n7}R^{30}$, —N$R^{25}$C(O)O$R^{25}R^{25}$, —C(O)O$R^{25}$, or —C(O)$R^{30}$, wherein each (C$_{1-10}$)alkyl, (C$_{3-10}$)cycloalkyl, and (C$_{3-10}$)cycloalkyl(C$_{1-10}$)alkyl is independently unsubstituted or substituted with one or more halo, and each $R^{25}$ is independently hydrogen (C$_{1-10}$)alkyl, (C$_{3-10}$)cycloalkyl, (C$_{3-10}$)cycloalkyl(C$_{1-10}$)alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{30}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n7 is 0, 1, or 2;

$X^1$, $X^2$, $X^3$ and $X^4$ are independently $CR^4$ or N, wherein $X^2$, $X^3$ and $X^4$ may not all be N;

when at least one of $X^1$, $X^2$, $X^3$ and $X^4$ is N, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, n8 is 0, 1 or 2; or when each of $X^1$, $X^2$, $X^3$ and $X^4$ is $CR^4$, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$NR^{27}S(O)_2R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^{27}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n8 is 0, 1, or 2; or two $R^4$ on adjacent annular carbon atoms together with the carbon atoms to which they are attached may form a carbocyclyl or heterocyclyl, wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$S(O)_2NR^{27}R^{27}$, —$NR^{27}S(O)_2R^{27}$, —$S(O)_{n8}R^{28}$, and —$C(O)R^{28}$, or the heterocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, and —$C(O)R^{28}$, each $R^{27}$ is independently hydrogen, $(C_{1-10})$alkyl, $(C_{3-10})$cycloalkyl, $(C_{3-10})$cycloalkyl$(C_{1-10})$alkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and n8 is 0, 1, or 2;

$R^{15}$ and $R^{17}$ are independently hydrogen, halo, alkyl, or —$OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;

$R^{14}$ is $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl connected through an annular carbon atom, heterocycloalkenyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;

$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;

the $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl, heterocycloalkenyl, or heterocycloalkyl-alkyl, of $R^{14}$ or $R^{16}$ is independently unsubstituted or substituted with 1 to 3 substituents independently selected from the group consisting of $(C_{1-10})$alkyl, halo, cyano, oxo, —$OR^7$, —$C(O)OR^7$, —$C(O)NR^7R^7$, —$NR^7C(O)R^7$, —$NR^7C(O)NR^7R^7$, —$NR^7R^7$, —$S(O)_2NR^7R^7$, —$NR^7S(O)_2R^7$, —$S(O)_{n2}R^{13}$, and —$C(O)R^{13}$;

each $R^5$ is independently hydrogen, $(C_{1-10})$alkyl, or $(C_{3-10})$cycloalkyl; or two $R^5$, together with the nitrogen atom to which they are attached, form a heterocycloalkyl; wherein each alkyl, cycloalkyl, or heterocycloalkyl is independently unsubstituted or substituted with one or more halo;

each $R^6$ is independently $(C_{1-10})$alkyl or $(C_{3-10})$cycloalkyl, wherein each alkyl or cycloalkyl is independently unsubstituted or substituted with one or more halo;

each n1 is independently 0, 1, or 2;

each $R^7$ is independently hydrogen, unsubstituted $(C_{1-10})$alkyl, or $(C_{1-10})$alkyl substituted with one or more halo;

each n2 is independently 0, 1, or 2, and each $R^{13}$ is independently unsubstituted $(C_{1-10})$alkyl or $(C_{1-10})$alkyl substituted with one or more halo;

or $R^{14}$ and $R^{15}$, together with the atoms to which they are attached, form a carbocyclyl or heterocyclyl, wherein the carbocyclyl or heterocyclyl is unsubstituted or substituted with one or two substituents independently selected from the group consisting of halo, cyano, oxo, $(C_{1-10})$alkyl, $(C_{3-10})$cycloalkyl, $(C_{3-10})$cycloalkyl$(C_{1-10})$alkyl, —OR$^{18}$, —C(O)NR$^{18}$R$^{18}$, —NR$^{18}$C(O)R$^{18}$, —NR$^{18}$C(O)NR$^{18}$R$^{18}$, —NR$^{18}$R$^{18}$, —S(O)$_2$NR$^{18}$R$^{18}$, —NR$^{18}$S(O)$_2$R$^{18}$, —S(O)$_{n3}$R$^{21}$, —C(O)OR$^{18}$, and —C(O)R$^{21}$, wherein each R$^{18}$ is independently hydrogen, $(C_{1-10})$alkyl, or $(C_{3-10})$cycloalkyl; or two R$^{18}$, together with the nitrogen atom to which they are attached, form a heterocycloalkyl; wherein each alkyl, cycloalkyl, or heterocycloalkyl is independently unsubstituted or substituted with one or more halo each R$^{21}$ is independently $(C_{1-10})$alkyl or $(C_{3-10})$cycloalkyl, wherein each alkyl or cycloalkyl is independently unsubstituted or substituted with one or more halo, and each n3 is independently 0, 1, or 2.

Embodiment II-2. The compound of Embodiment II-1, or a pharmaceutically acceptable salt, solvate, tautomer, isotope, or isomer thereof, wherein R$^1$ is —C(O)OR$^9$, —C(O)NR$^8$R$^9$, —S(O)$_2$NR$^8$R$^9$, —NR$^{10}$C(O)NR$^8$R$^9$, —NR$^{10}$C(O)R$^9$, —NR$^{10}$S(O)$_2$R$^9$, —OR$^{26}$, —SR$^9$, —S(O)R$^9$, —S(O)$_2$R$^9$, —NR$^8$R$^9$, or —NR$^{10}$C(O)OR$^9$.

Embodiment II-3. The compound of Embodiment II-1 or II-2, wherein the compound is of Formula (Z-A):

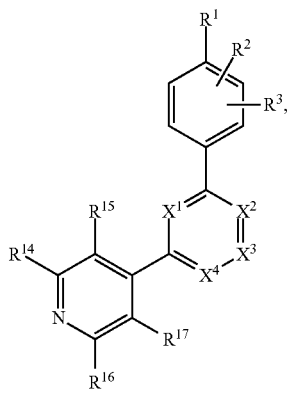

(Z-A)

or a pharmaceutically acceptable salt, solvate, tautomer, isotope, or isomer thereof, wherein R$^1$, R$^2$, R$^3$, R$^{14}$, R$^{15}$, R$^{16}$, R$^{17}$, X$^1$, X$^2$, X$^3$, and X$^4$ are as defined for Formula (Z).

Embodiment II-4. The compound of Embodiment II-1 or II-2, wherein the compound is of Formula (Z-B):

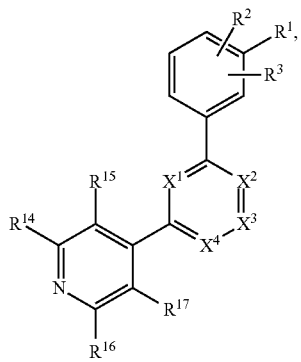

(Z-B)

or a pharmaceutically acceptable salt, solvate, tautomer, isotope, or isomer thereof, wherein R$^1$, R$^2$, R$^3$, R$^{14}$, R$^{15}$, R$^{16}$, R$^{17}$, X$^1$, X$^2$, X$^3$, and X$^4$ are as defined for Formula (Z).

Embodiment II-5. The compound of any one of Embodiments II-1 to II-4, or a pharmaceutically acceptable salt, solvate, tautomer, isotope, or isomer thereof, wherein R$^{17}$ is hydrogen.

Embodiment II-6. The compound of any one of Embodiments II-1, or II-3 to II-5, or a pharmaceutically acceptable salt, solvate, tautomer, isotope, or isomer thereof, wherein R$^1$ is —C(O)OR$^9$, —C(O)NR$^8$R$^9$, —S(O)$_2$NR$^8$R$^9$, —NR$^{10}$S(O)$_2$R$^9$, —NR$^{10}$C(O)OR$^9$, —C(O)R$^{26}$, —NR$^{10}$S(O)$_2$NR$^8$R$^9$, or —C(O)NR$^8$S(O)$_2$R$^9$.

Embodiment II-7. The compound of any one of Embodiments II-1, or II-3 to II-6, or a pharmaceutically acceptable salt, solvate, tautomer, isotope, or isomer thereof, wherein R$^1$ is —C(O)NR$^8$R$^9$, —S(O)$_2$NR$^8$R$^9$, —NR$^{10}$C(O)OR$^9$, —NR$^{10}$S(O)$_2$R$^9$, —C(O)R$^{26}$, or —NR$^{10}$S(O)$_2$NR$^8$R$^9$.

Embodiment II-8. The compound of anyone of Embodiments II-1 to II-7, or a pharmaceutically acceptable salt, solvate, tautomer, isotope, or isomer thereof, wherein R$^1$ is —C(O)NR$^8$R$^9$.

Embodiment II-9. The compound of any one of Embodiments II-1 to II-7, or a pharmaceutically acceptable salt, solvate, tautomer, isotope, or isomer thereof, wherein R$^1$ is —NR$^{10}$C(O)OR$^9$.

Embodiment II-10. The compound of any one of Embodiments II-1 to II-7, or a pharmaceutically acceptable salt, solvate, tautomer, isotope, or isomer thereof, wherein R$^1$ is —NR$^{10}$S(O)$_2$R$^9$.

Embodiment II-11. The compound of any one of Embodiments II-1 to II-10, or a pharmaceutically acceptable salt, solvate, tautomer, isotope, or isomer thereof, wherein R$^{10}$ is hydrogen.

Embodiment II-12. The compound of any one of Embodiments II-1 to II-11, or a pharmaceutically acceptable salt, solvate, tautomer, isotope, or isomer thereof, wherein R$^8$ is hydrogen.

Embodiment II-13. The compound of any one of Embodiments II-1 to II-12, or a pharmaceutically acceptable salt, solvate, tautomer, isotope, or isomer thereof, wherein R$^9$ is hydrogen, $(C_{1-10})$alkyl, or heterocycloalkyl-alkyl.

Embodiment II-14. The compound of any one of Embodiments II-1 to II-7, or a pharmaceutically acceptable salt, solvate, tautomer, isotope, or isomer thereof, wherein R$^1$ is —C(O)NR$^8$R$^9$, and the R$^8$ and R$^9$ together with the nitrogen to which they are attached form an unsubstituted or substituted heterocycloalkyl.

Embodiment II-15. The compound of any one of Embodiments II-1 to II-7, or II-14, or a pharmaceutically acceptable salt, solvate, tautomer, isotope, or isomer thereof, wherein R$^1$ is —C(O)NR$^8$R$^9$, and the R$^8$ and R$^9$ together with the nitrogen to which they are attached form an unsubstituted or substituted piperidinyl.

Embodiment II-16. The compound of Embodiment II-15, or a pharmaceutically acceptable salt, solvate, tautomer, isotope, or isomer thereof, wherein the piperidinyl is substituted with one to three substituents independently selected from the group consisting of —OR$^{23}$, $(C_{1-10})$alkyl, —C(O)OR$^{23}$, and —NR$^{23}$C(O)OR$^{23}$.

Embodiment II-17. The compound of Embodiment II-16, or a pharmaceutically acceptable salt, solvate, tautomer, isotope, or isomer thereof, wherein R$^{23}$ is independently hydrogen or $(C_{1-10})$alkyl.

Embodiment II-18. The compound of anyone of Embodiments II-1 to II-17, or a pharmaceutically acceptable salt, solvate, tautomer, isotope, or isomer thereof, wherein $R^2$ is halo or alkyl.

Embodiment II-19. The compound of any one of Embodiment II-1 to II-18, or a pharmaceutically acceptable salt, solvate, tautomer, isotope, or isomer thereof, wherein one of $X^1$, $X^2$, $X^3$, and $X^4$ is N.

Embodiment II-20. The compound of any one of Embodiments II-1 to II-18, or a pharmaceutically acceptable salt, solvate, tautomer, isotope, or isomer thereof, wherein $X^1$, $X^2$, and $X^4$ are $CR^4$, and $X^3$ is N.

Embodiment II-21. The compound of anyone of Embodiments II-1 to II-18, or a pharmaceutically acceptable salt, solvate, tautomer, isotope, or isomer thereof, wherein two of $X^1$, $X^2$, $X^3$, and $X^4$ are N.

Embodiment II-22. The compound of any one of Embodiments II-1 to II-18, or a pharmaceutically acceptable salt, solvate, tautomer, isotope, or isomer thereof, wherein each of $X^1$, $X^2$, $X^3$ and $X^4$ is $CR^4$.

Embodiment II-23. The compound of any one of Embodiments II-1 to II-22, or a pharmaceutically acceptable salt, solvate, tautomer, isotope, or isomer thereof, wherein each $R^4$ is independently selected from the group consisting of hydrogen, halo, cyano, $(C_{1-10})$alkyl, and $-OR^{27}$.

Embodiment II-24. The compound of any one of Embodiments II-1 to II-22, or a pharmaceutically acceptable salt, solvate, tautomer, isotope, or isomer thereof, wherein $X^1$ is $CR^4$, wherein $R^4$ is hydrogen, halo, or methyl.

Embodiment II-25. The compound of any one of Embodiments II-1 to II-24, or a pharmaceutically acceptable salt, solvate, tautomer, isotope, or isomer thereof, wherein $R^{14}$ is $(C_{1-10})$alkyl or heterocycloalkyl connected through an annular carbon atom, wherein the alkyl or heterocycloalkyl is unsubstituted or substituted with one to three substituents selected from the group consisting of $(C_{1-10})$alkyl, halo, $-C(O)OR^7$, oxo, and $-OR^5$.

Embodiment II-26. The compound of Embodiments II-25, or a or a pharmaceutically acceptable salt, solvate, tautomer, isotope, or isomer thereof, wherein $R^{14}$ is $(C_{1-10})$ alkyl unsubstituted or substituted with one to three substituents selected from the group consisting of $(C_{1-10})$alkyl, halo, $-C(O)OR^7$, oxo, and $-OR^5$.

Embodiment II-27. The compound of any one of Embodiments II-1 to II-26, or a pharmaceutically acceptable salt, solvate, tautomer, isotope, or isomer thereof, wherein $R^{15}$, $R^{16}$, and $R^{17}$ are hydrogen.

Embodiment II-28. The compound of any one of Embodiments II-1 to II-24, or a pharmaceutically acceptable salt, solvate, tautomer, isotope, or isomer thereof, wherein $R^{14}$ and $R^{15}$, together with the atoms to which they are attached, form a heterocyclyl.

Embodiment II-29. The compound of any one of Embodiments II-1 to II-19, or II-25 to II-28, wherein at least one of $X^2$, $X^3$ and $X^4$ is N, and an adjacent annular carbon is bonded to $R^4$, wherein the $R^4$ is independently hydrogen, fluoro, cyano, $(C_{1-10})$alkyl, or $-OR^{27}$.

Embodiment II-30. The compound of any one of Embodiments II-1 to II-29, or a pharmaceutically acceptable salt, solvate, tautomer, isotope, or isomer thereof, wherein $R^3$ is hydrogen.

Embodiment II-31. The compound of any one of Embodiments II-1 to II-29, or a pharmaceutically acceptable salt, solvate, tautomer, isotope, or isomer thereof, wherein $R^3$ is halo or alkyl.

Embodiment II-32. The compound of any one of Embodiments II-1 to II-31, or a pharmaceutically acceptable salt, solvate, tautomer, isotope, or isomer thereof, wherein $R^2$ is halo or alkyl.

Embodiment II-33. The compound of any one of Embodiments II-1 to II-31, or a pharmaceutically acceptable salt, solvate, tautomer, isotope, or isomer thereof, wherein $R^2$ is chloro.

Embodiment II-34. The compound of any one of Embodiments II-1 to II-33, or a pharmaceutically acceptable salt, solvate, tautomer, isotope, or isomer thereof, wherein one or more of $R^4$, $R^5$, $R^8$, $R^9$, $R^{10}$, $R^{14}$, $R^{16}$, $R^{19}$, $R^{20}$, $R^{23}$, $R^{24}$, $R^{25}$, $R^{26}$, $R^{27}$, $R^{28}$, and $R^{30}$ is heterocycloalkyl; or wherein $R^8$ and $R^9$, together with the nitrogen atom to which they are attached, form a heterocycloalkyl; or wherein two $R^{18}$, together with the nitrogen atom to which they are attached; or wherein two $R^{19}$, together with the nitrogen to which they are attached, form a heterocycloalkyl; or wherein two $R^{25}$, together with the nitrogen to which they are attached, form a heterocycloalkyl; or wherein two $R^{27}$, together with the nitrogen to which they are attached, form a heterocycloalkyl; each heterocycloalkyl is independently a 3- to 10-membered heterocycloalkyl.

Embodiment II-35. The compound of any one of Embodiments II-1 to II-34, or a pharmaceutically acceptable salt, solvate, tautomer, isotope, or isomer thereof, wherein when one or more of $R^4$, $R^8$, $R^9$, $R^{10}$, $R^{14}$, $R^{16}$, and $R^{26}$ is heterocycloalkyl-alkyl, each heterocycloalkyl-alkyl is independently (3-10 membered)heterocycloalkyl($C_{1-10}$)alkyl.

Embodiment II-36. The compound of any one of Embodiments II-1 to II-35, or a pharmaceutically acceptable salt, solvate, tautomer, isotope, or isomer thereof, wherein when one or more of $R^8$, $R^9$, $R^{10}$, and $R^{26}$ is heteroaryl, each heteroaryl is independently a 5- to 10-membered heteroaryl.

Embodiment II-37. The compound of any one of Embodiments II-1 to II-36, or a pharmaceutically acceptable salt, solvate, tautomer, isotope, or isomer thereof, wherein when one or more of $R^8$, $R^9$, $R^{10}$, and $R^{26}$ is heteroaryl-alkyl, each heteroaryl-alkyl is independently a (5-10 membered)heteroaryl($C_{1-10}$)alkyl.

Embodiment II-38. The compound of any one of Embodiments II-1 to II-37, or a pharmaceutically acceptable salt, solvate, tautomer, isotope, or isomer thereof, wherein two $R^4$ on adjacent annular carbon atoms together with the carbon atoms to which they are attached form a carbocyclyl; or wherein $R^{14}$ and $R^{15}$ together with the atoms to which they are attached form a carbocyclyl; each carbocyclyl, is independently a $(C_3-C_8)$carbocyclyl.

Embodiment II-39. The compound of any one of Embodiments II-1 to II-38, or a pharmaceutically acceptable salt, solvate, tautomer, isotope, or isomer thereof, wherein two $R^4$ on adjacent annular carbon atoms together with the carbon atoms to which they are attached form a heterocyclyl; or wherein $R^{14}$ and $R^{15}$ together with the atoms to which they are attached form a heterocyclyl; each heterocyclyl is independently a 4- to 8-membered heterocyclyl.

Embodiment II-40. The compound of any one of Embodiments II-1 to II-39, or a pharmaceutically acceptable salt, solvate, tautomer, isotope, or isomer thereof, wherein when $R^{14}$ or $R^{16}$ is heterocycloalkenyl, each heterocycloalkenyl is independently a 3- to 8-membered heterocycloalkenyl.

Embodiment II-41. The compound of any one of Embodiments II-1 to II-3, or II-5 to II-40, wherein the compound is of Formula (Z-Ai):

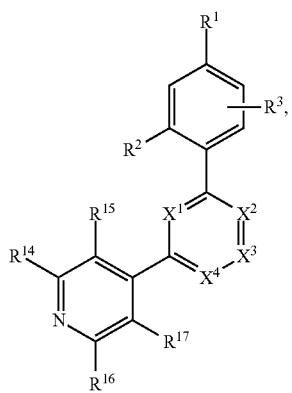

(Z-Ai)

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (Z).

Embodiment II-42. The compound of any one of Embodiments II-1, II-2, or II-4 to II-40, wherein the compound is of Formula (Z-Bi):

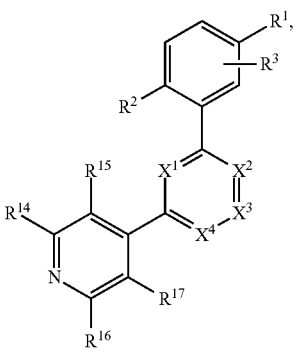

(Z-Bi)

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$ and $X^4$ are as defined for Formula (Z).

Embodiment II-43. The compound of Embodiment II-1, selected from the group consisting of:

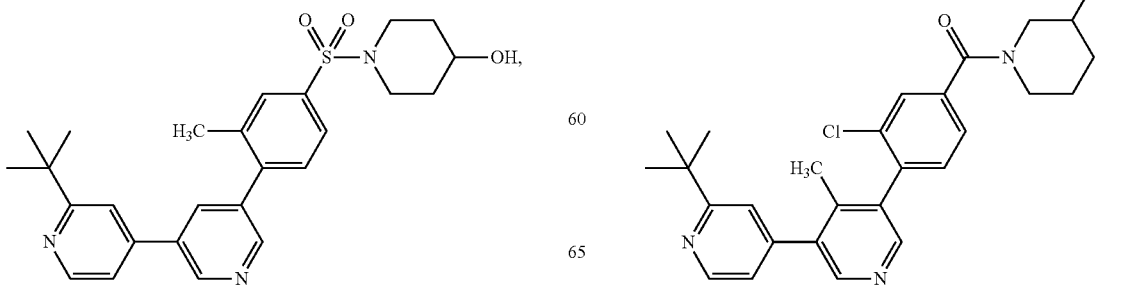

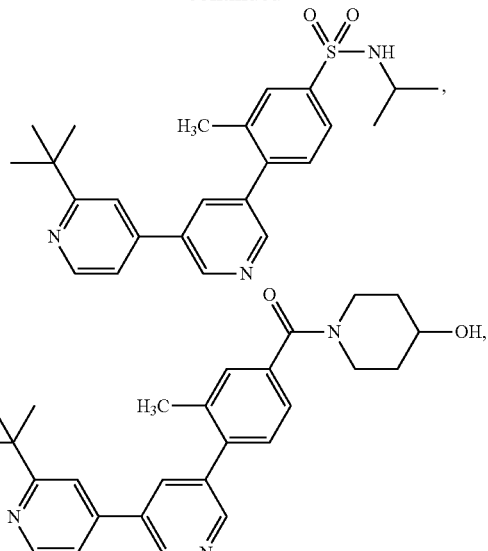

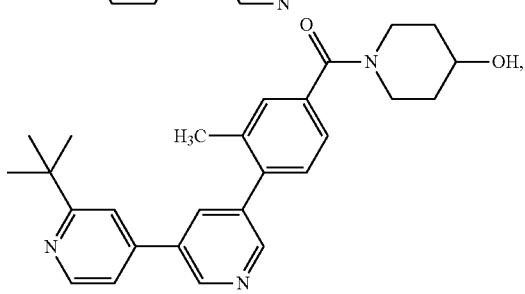

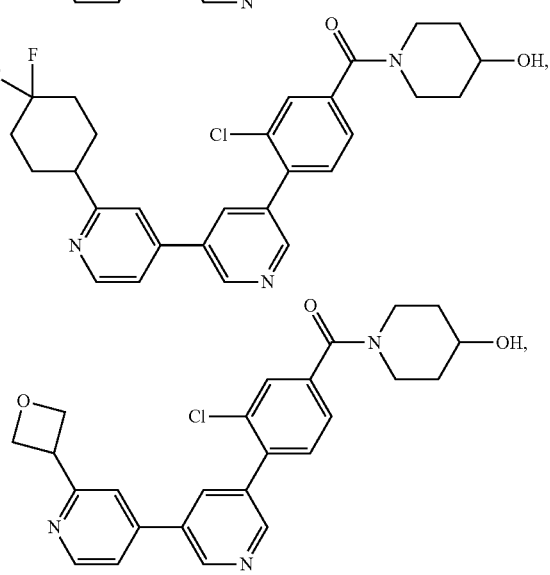

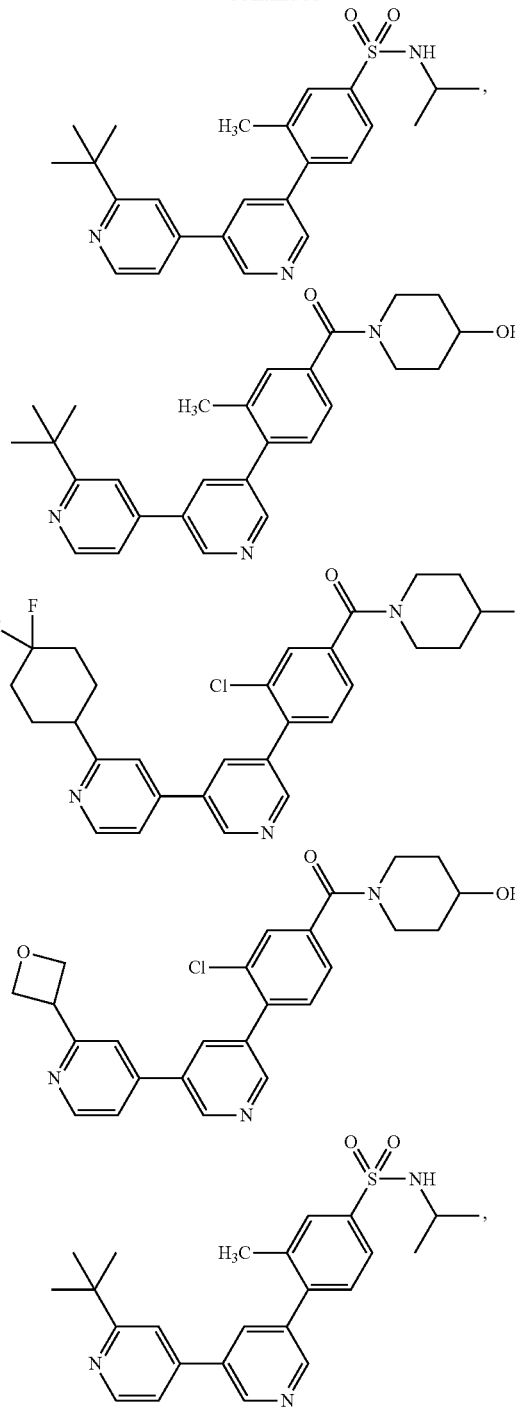

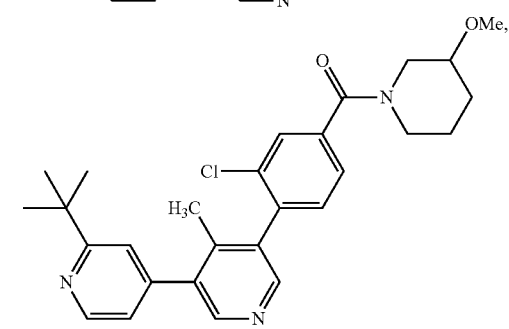

187
-continued
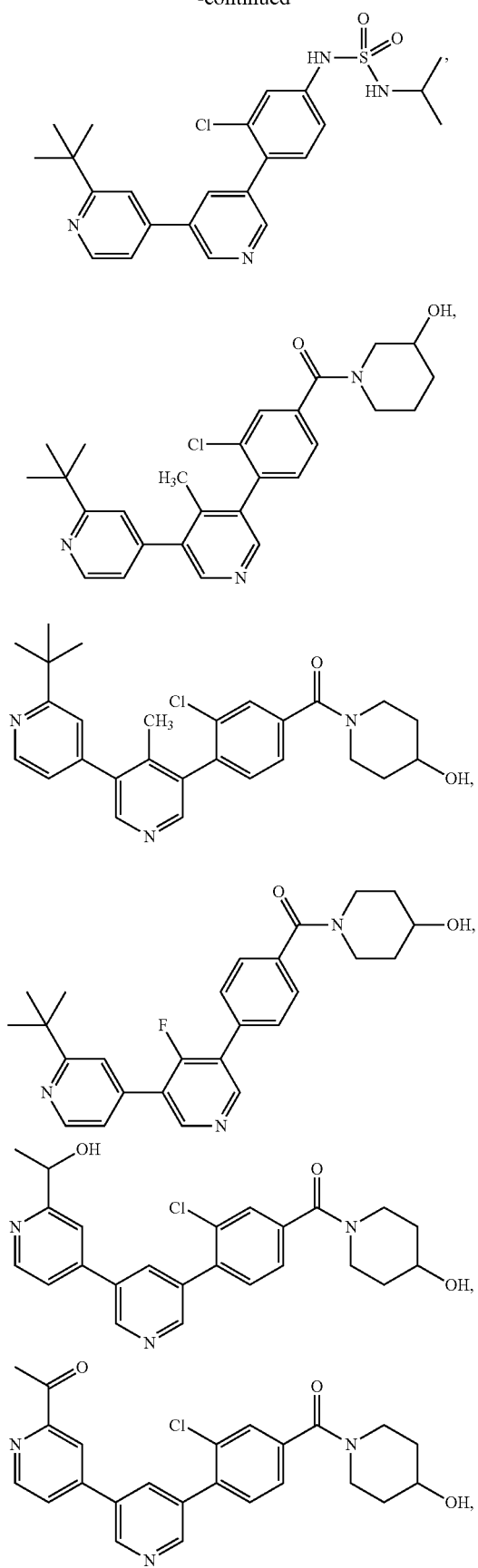
188
-continued
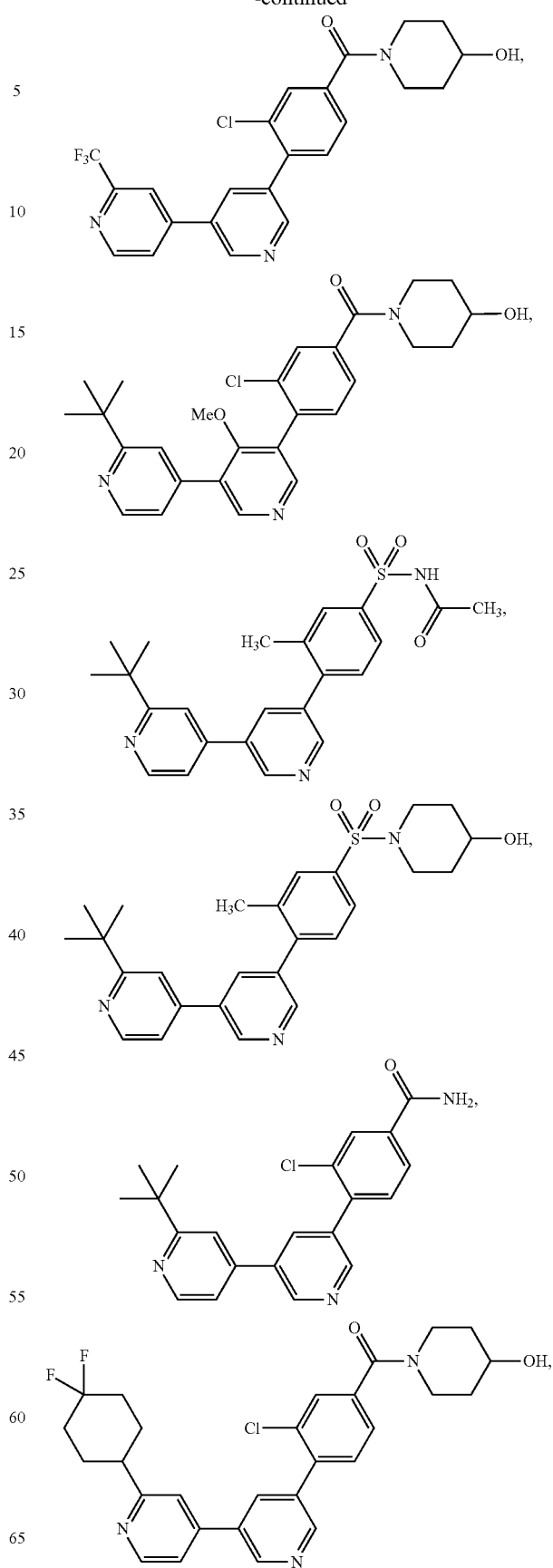

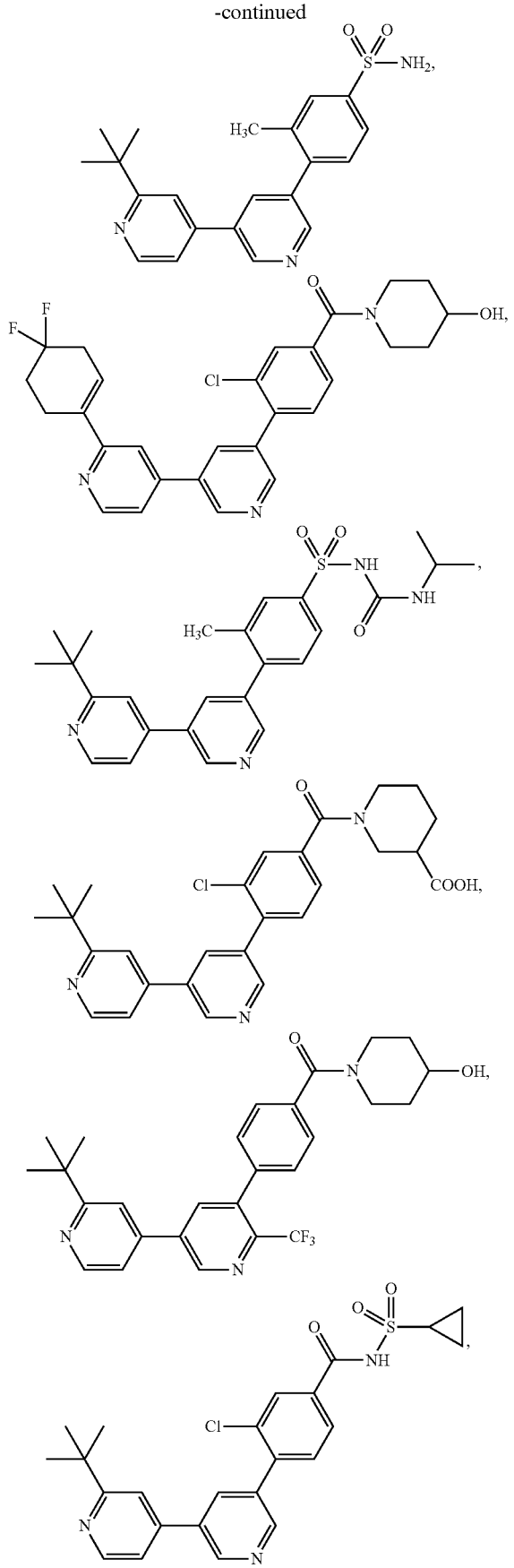
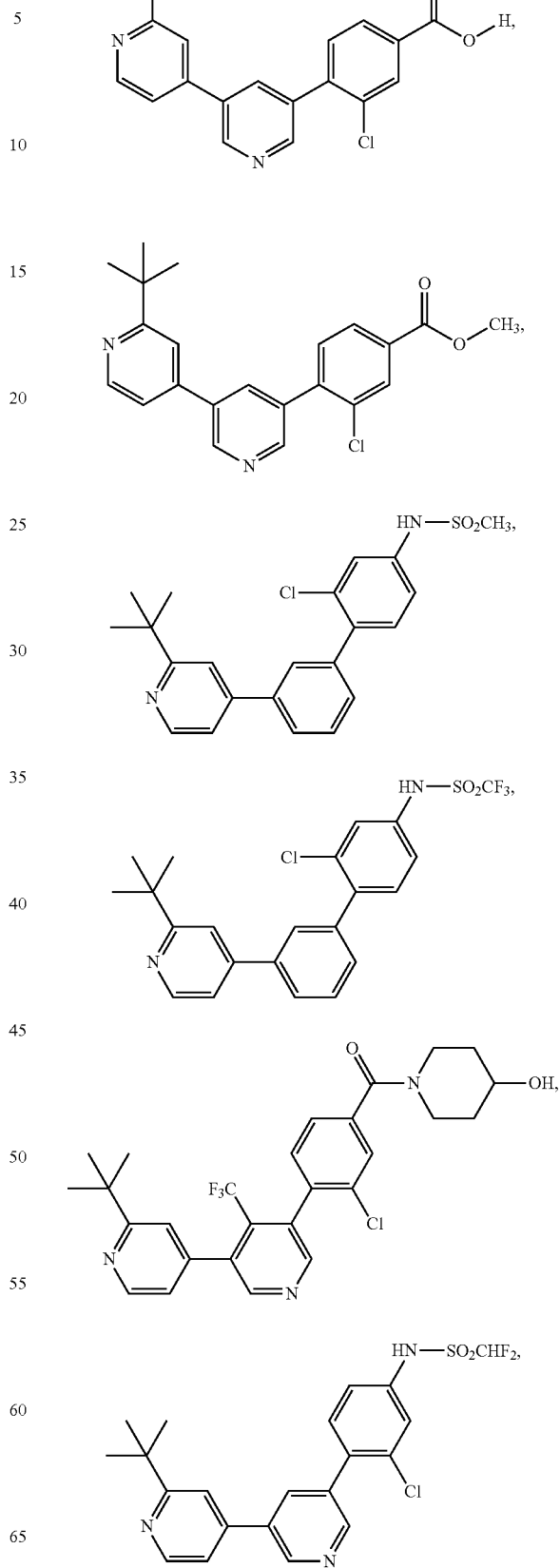

191
-continued
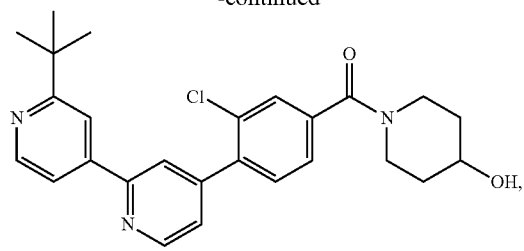
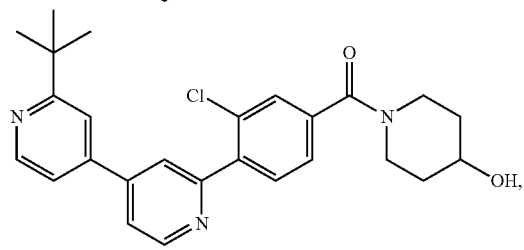
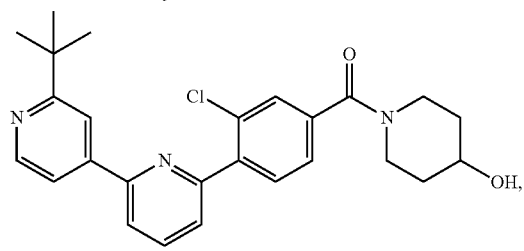
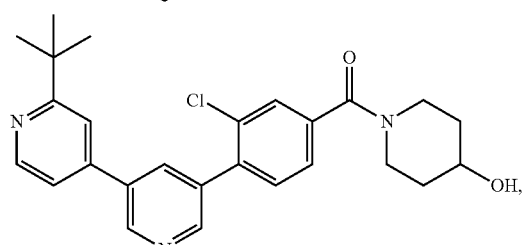
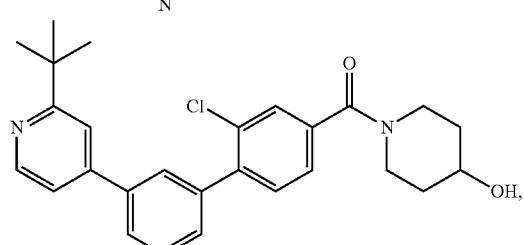
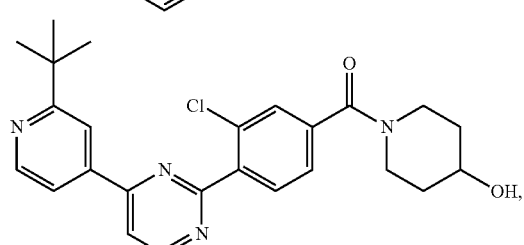
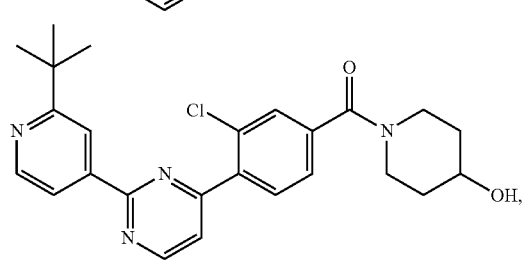
192
-continued
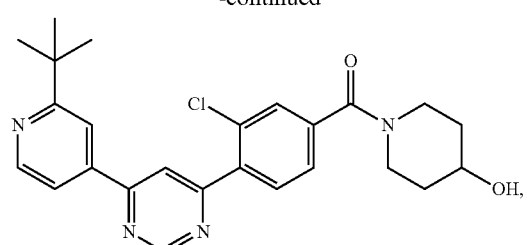
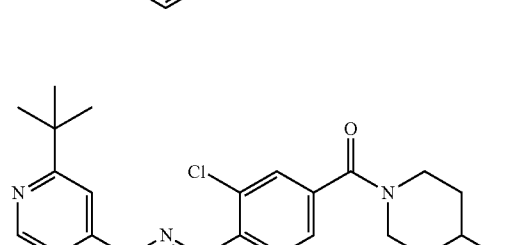
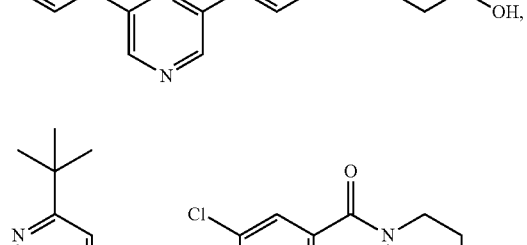
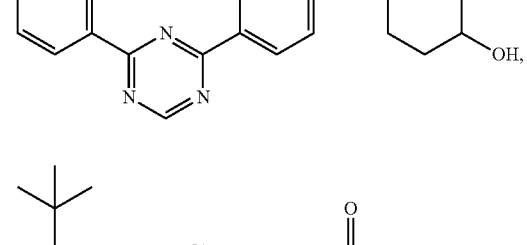
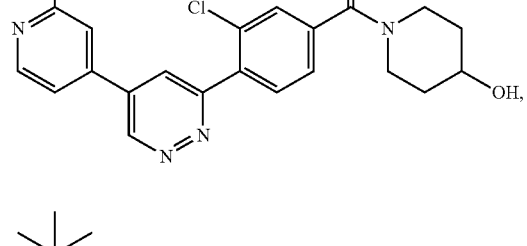
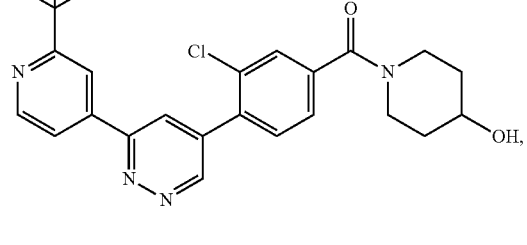
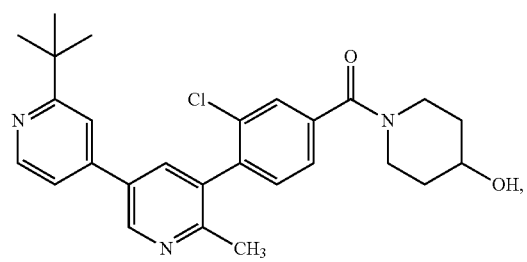

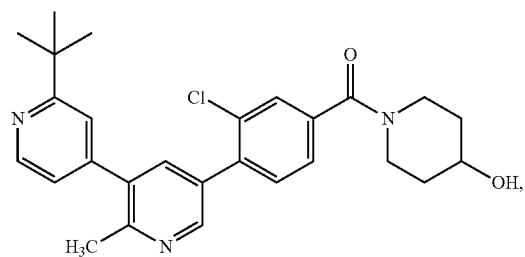
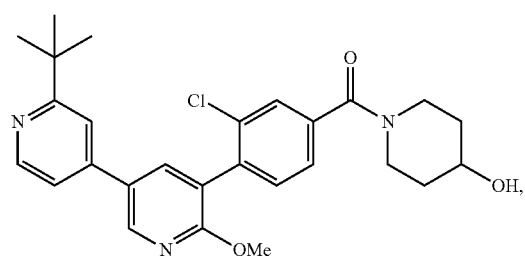
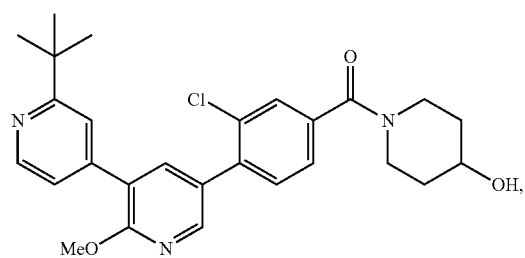
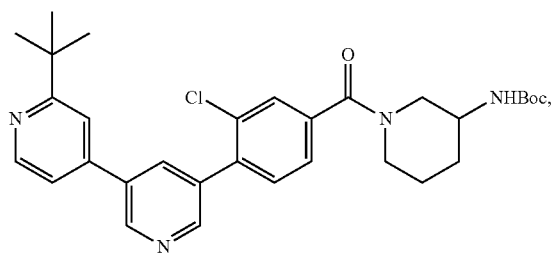
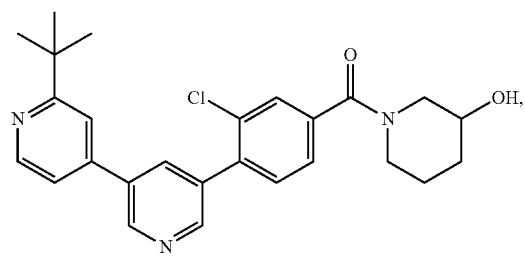
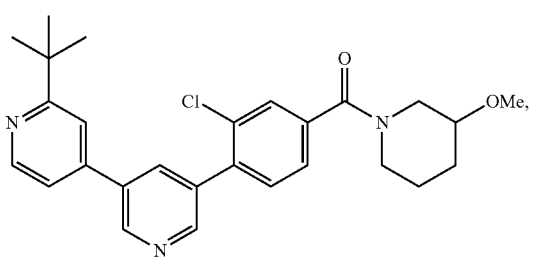
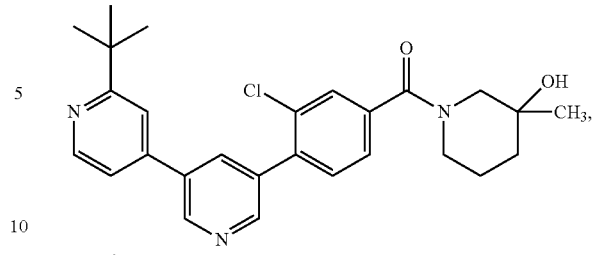
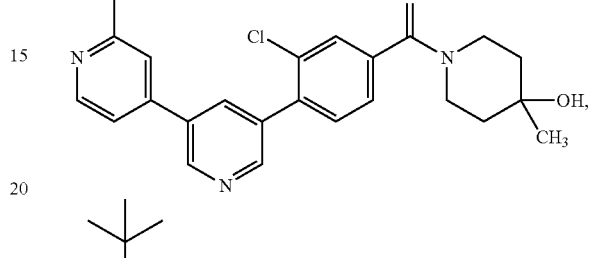
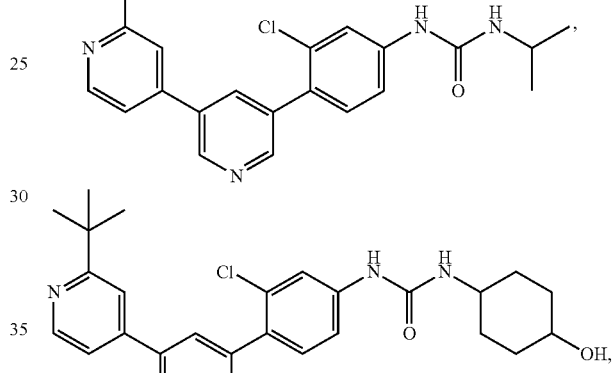
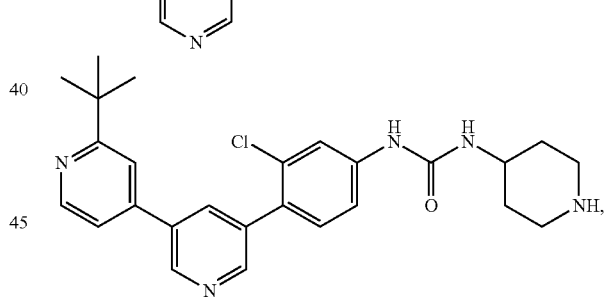
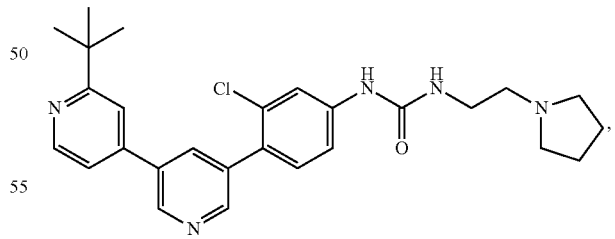
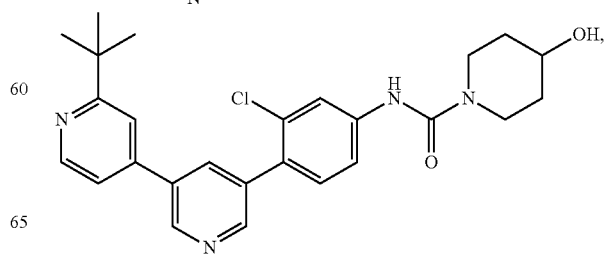

195
-continued
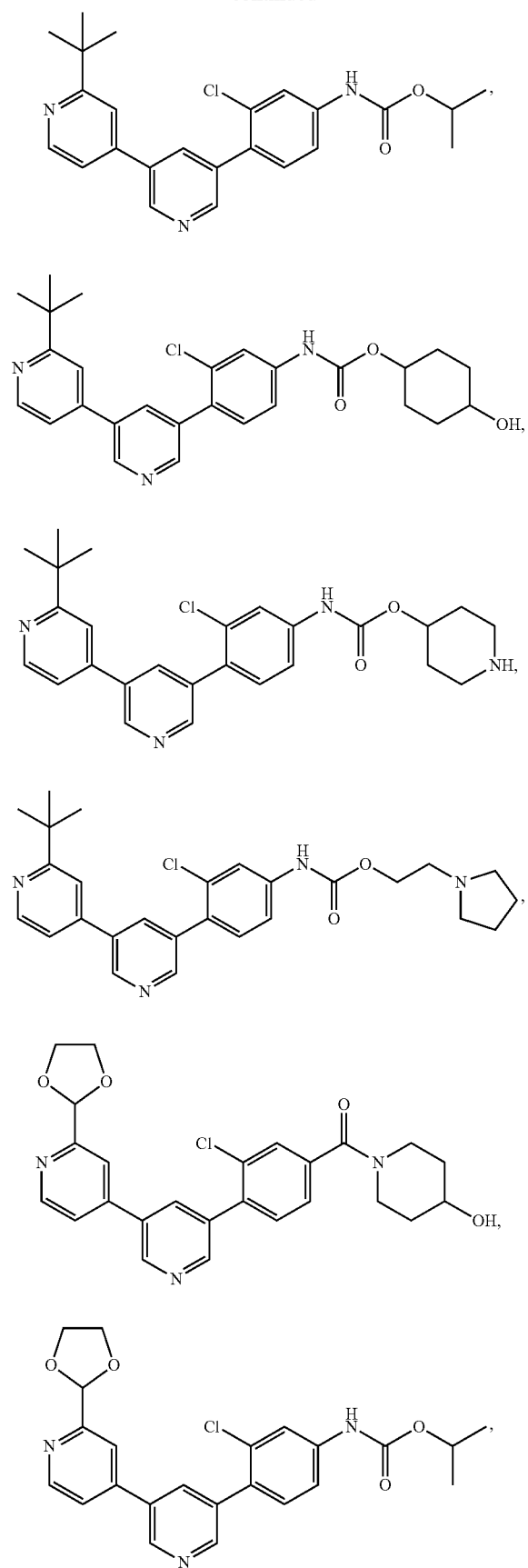
196
-continued
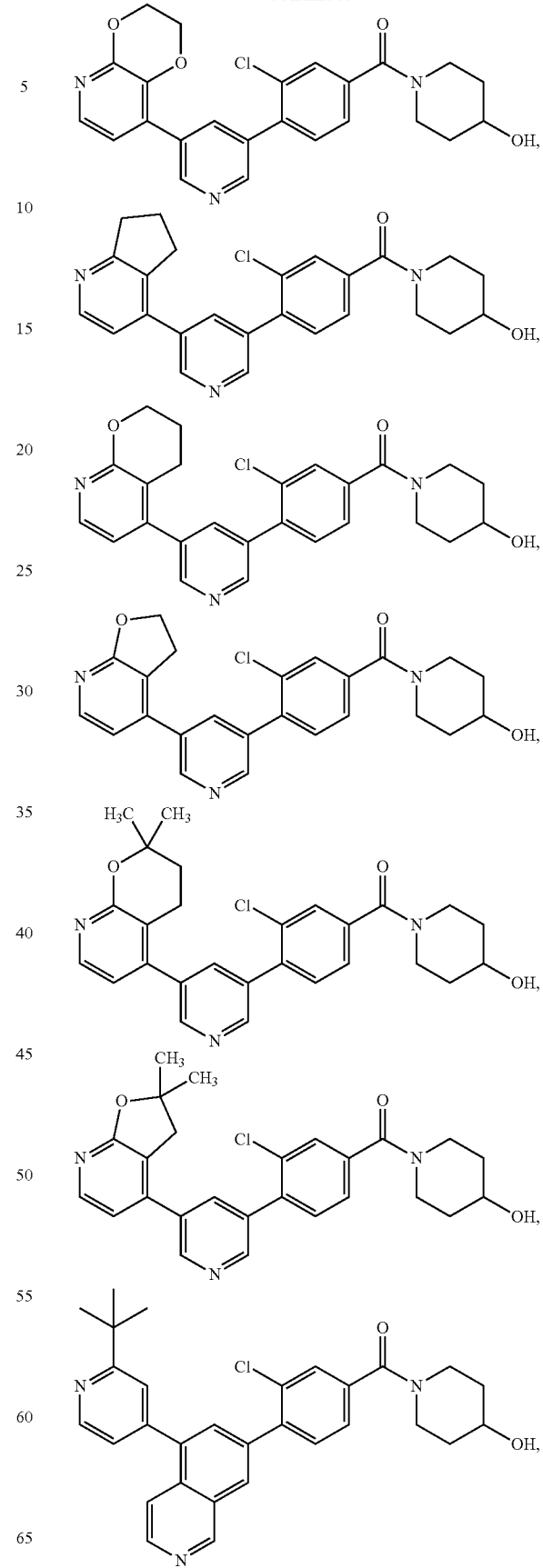

197
-continued
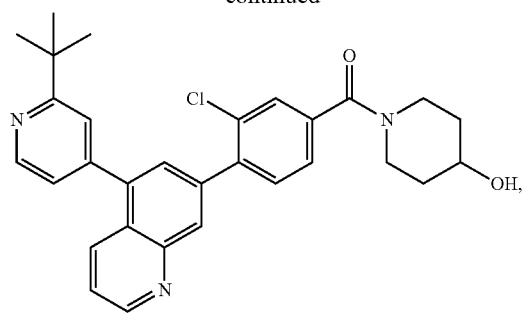
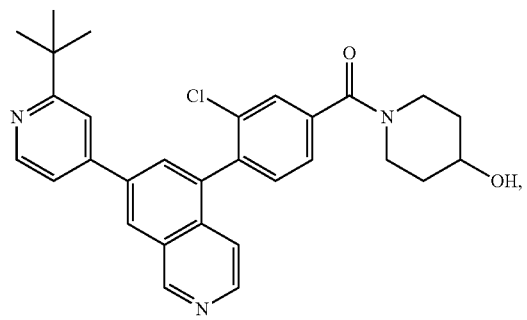
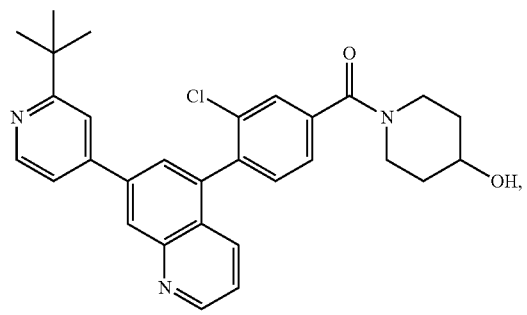
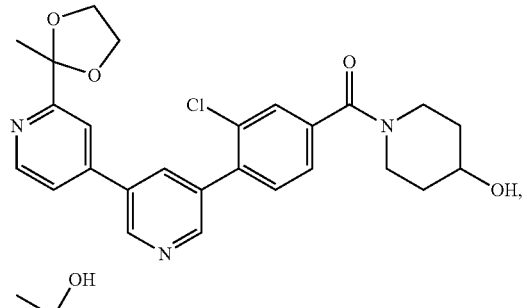
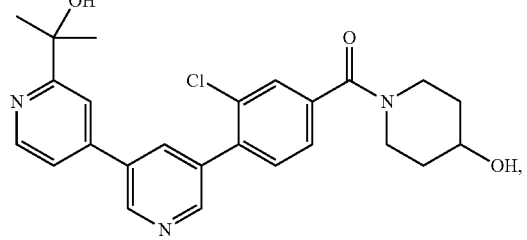
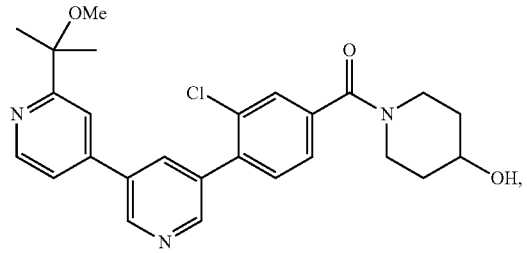
198
-continued
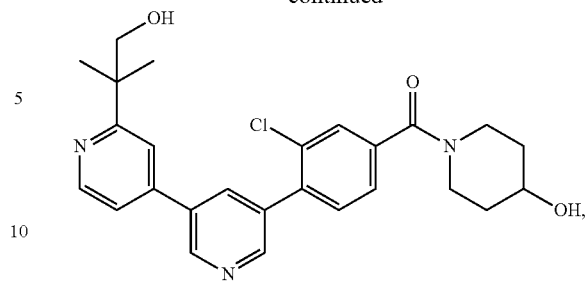
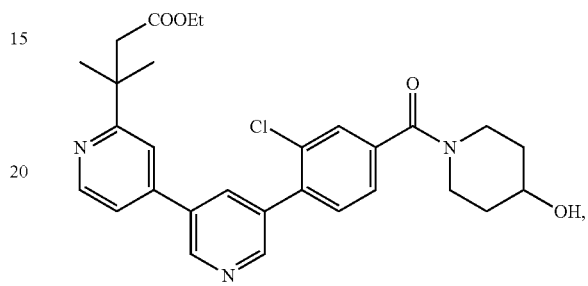
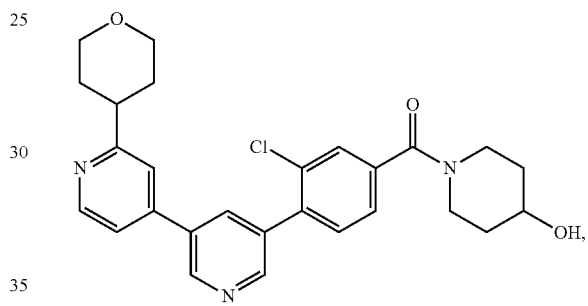
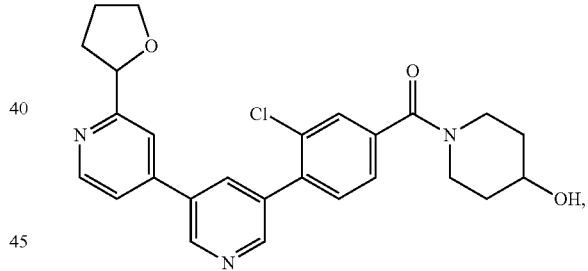
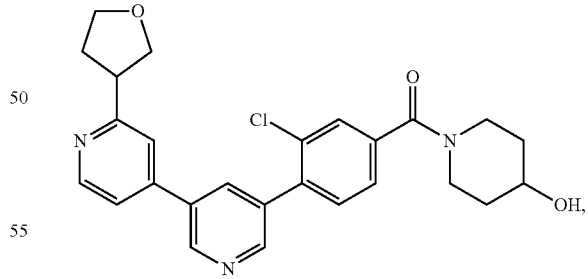
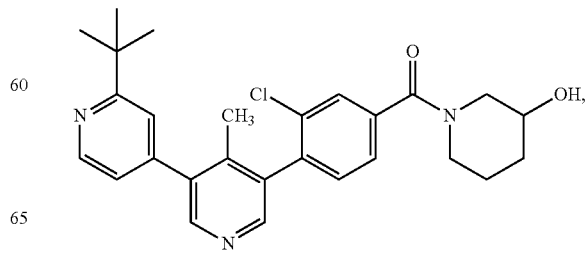

199
-continued
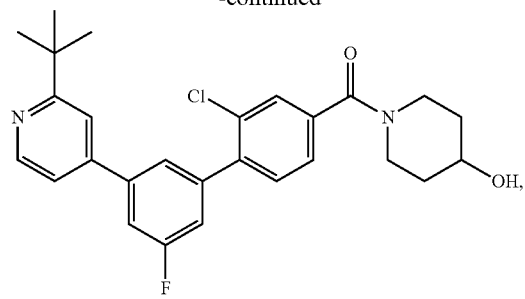
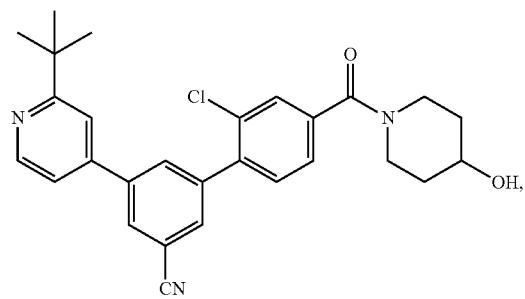
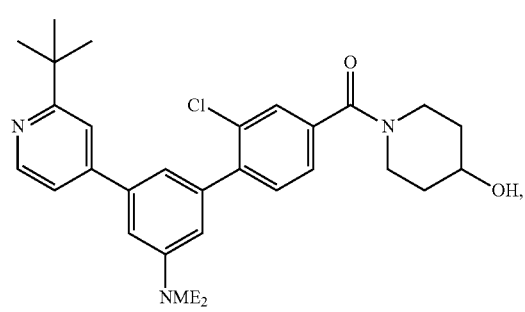
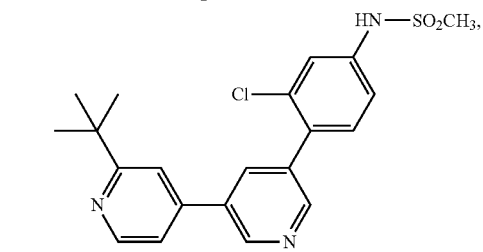
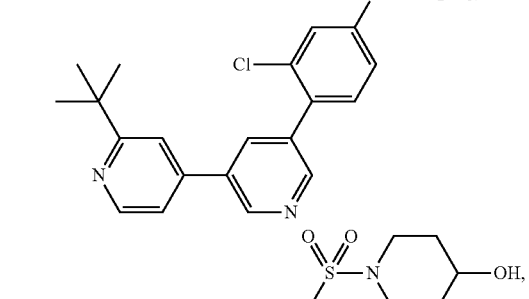
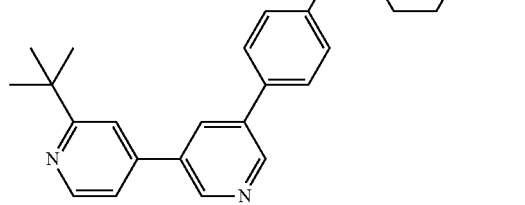
200
-continued
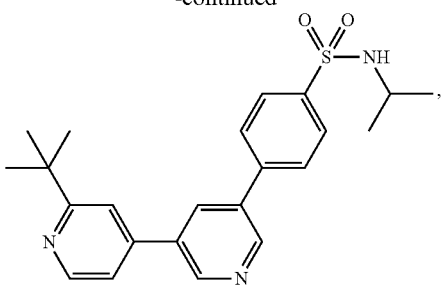
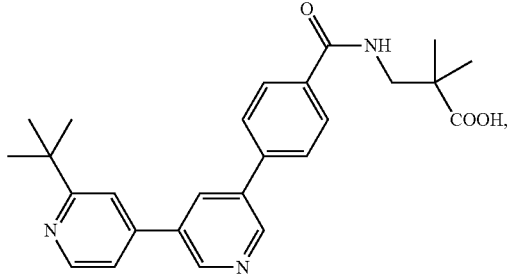
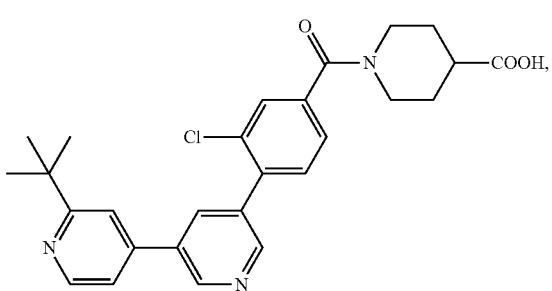
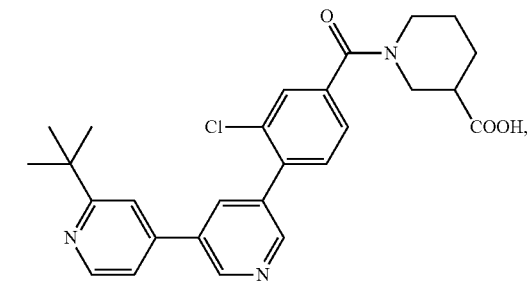
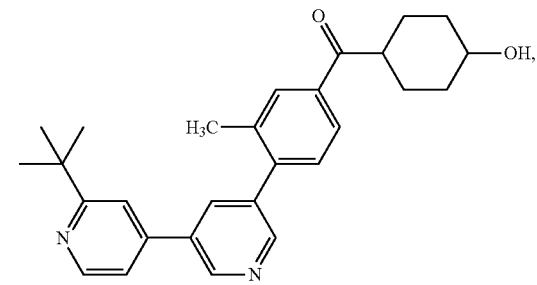
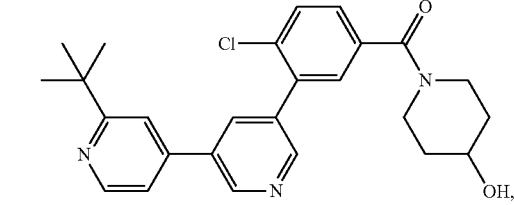

201
-continued
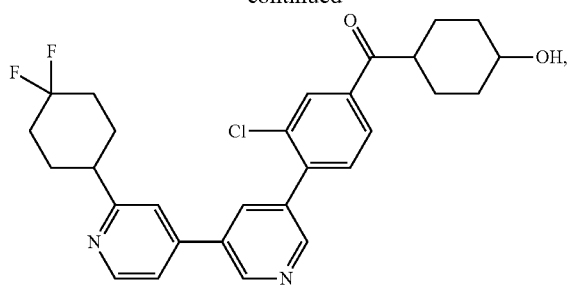
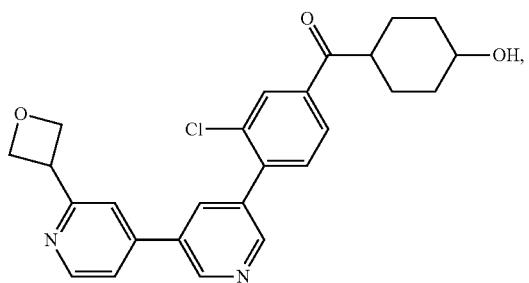
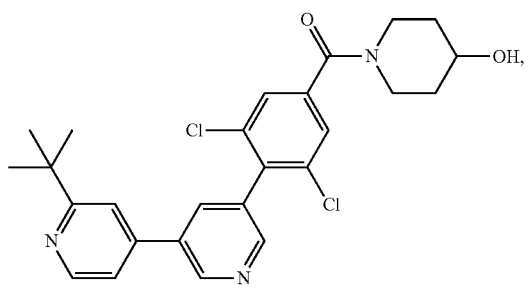
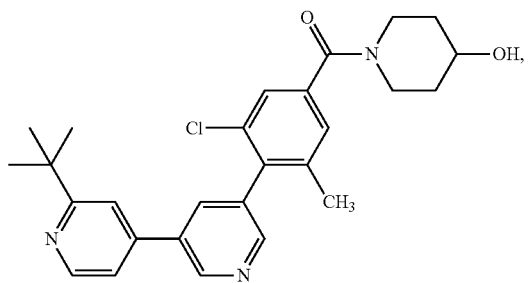
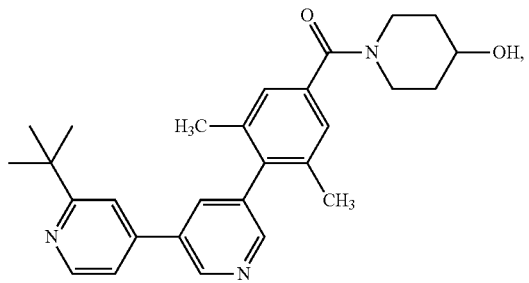
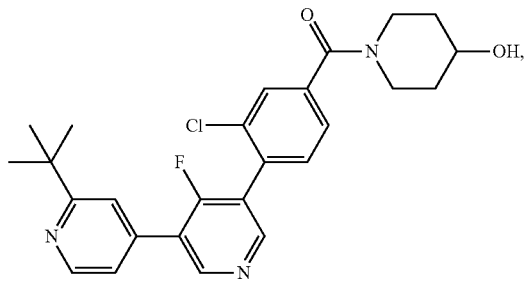
202
-continued
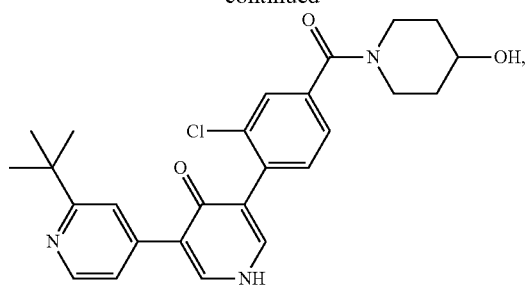
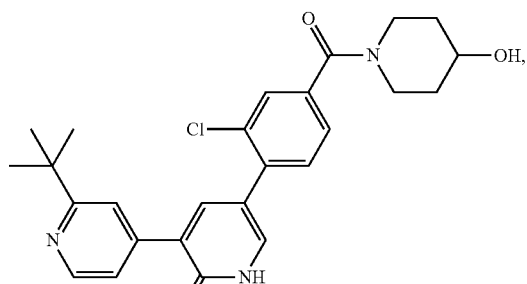
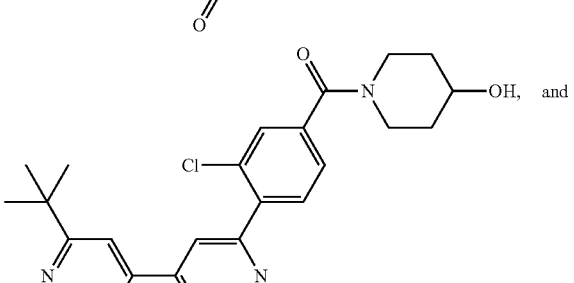
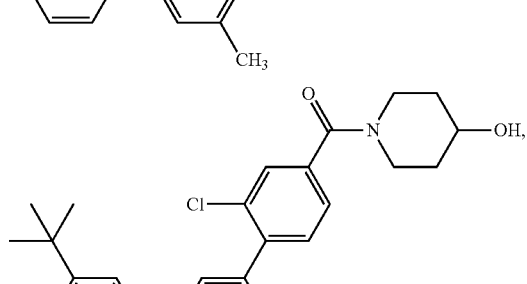
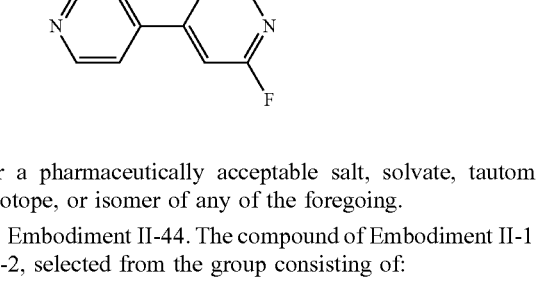
or a pharmaceutically acceptable salt, solvate, tautomer, isotope, or isomer of any of the foregoing.
Embodiment II-44. The compound of Embodiment II-1 or II-2, selected from the group consisting of:
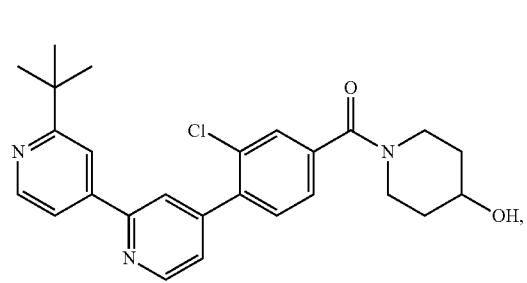

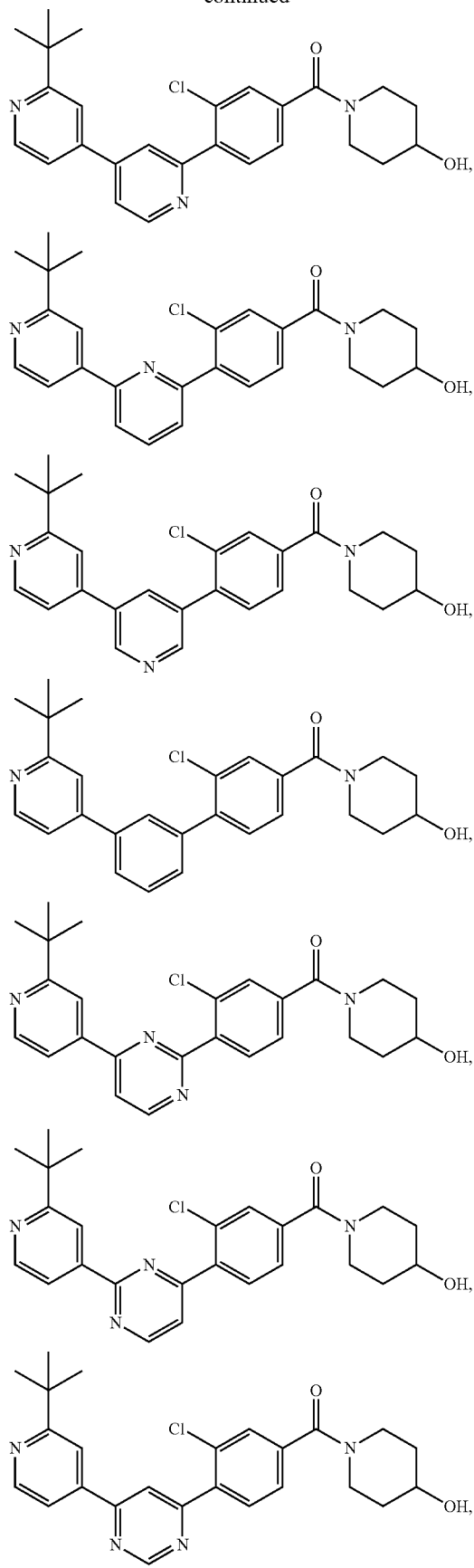
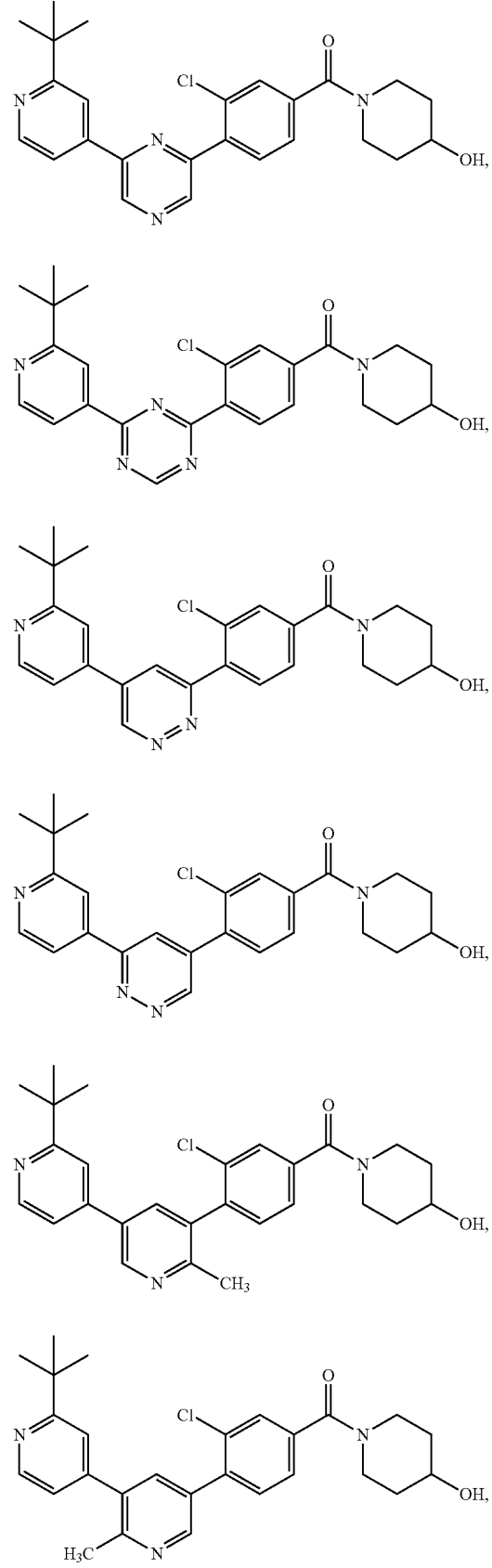 [SMILES: CC(C)(C)c1cc(-c2nccc(-c3ccc(C(=O)N4CCC(O)CC4)cc3Cl)n2)ccn1 ; CC(C)(C)c1cc(-c2cc(-c3ccc(C(=O)N4CCC(O)CC4)cc3Cl)ncn2)ccn1 ; CC(C)(C)c1cc(-c2cncc(-c3ccc(C(=O)N4CCC(O)CC4)cc3Cl)n2)ccn1 ; CC(C)(C)c1cc(-c2ncnc(-c3ccc(C(=O)N4CCC(O)CC4)cc3Cl)n2)ccn1 ; CC(C)(C)c1cc(-c2cnnc(-c3ccc(C(=O)N4CCC(O)CC4)cc3Cl)c2)ccn1 ; CC(C)(C)c1cc(-c2cc(-c3ccc(C(=O)N4CCC(O)CC4)cc3Cl)cnn2)ccn1]

205
-continued
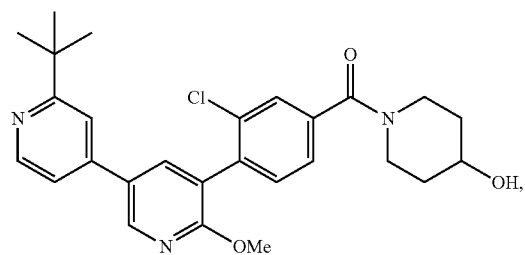
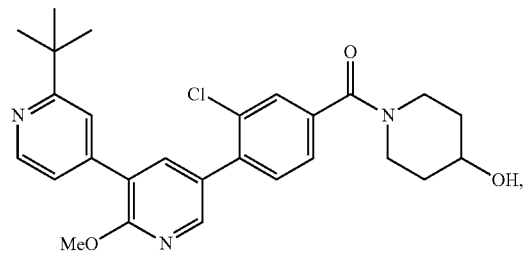
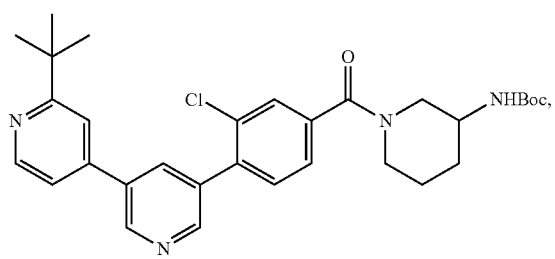
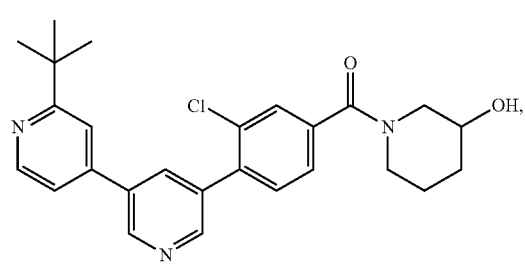
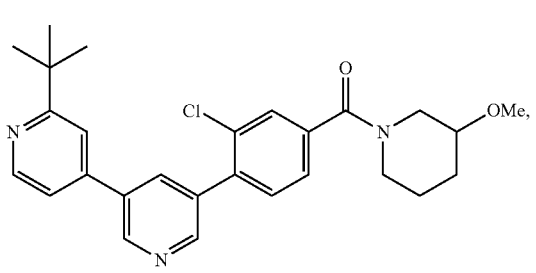
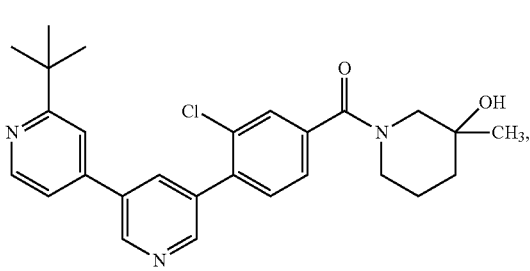
206
-continued
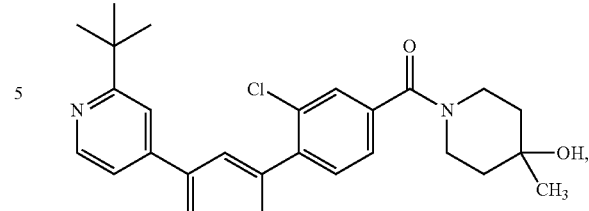
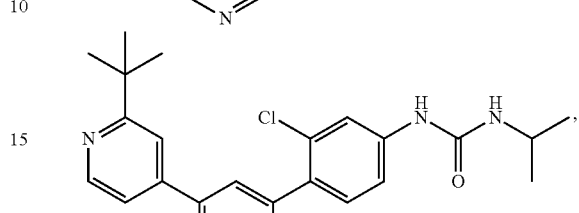
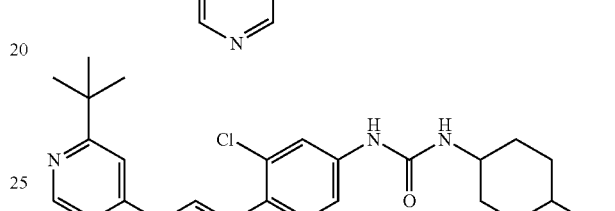
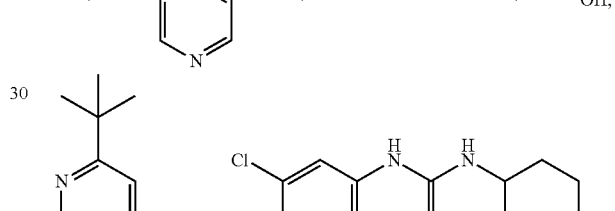
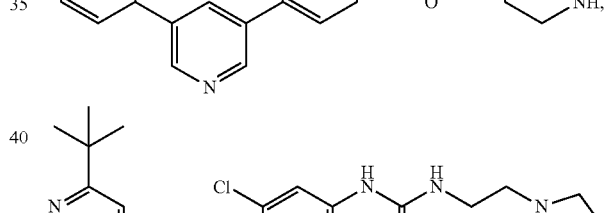
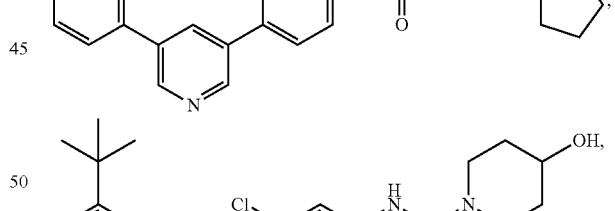
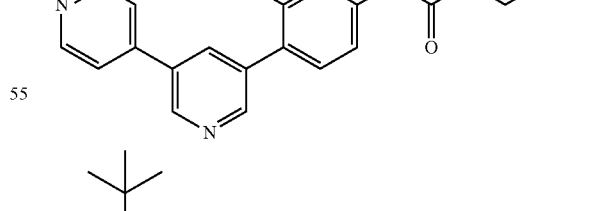
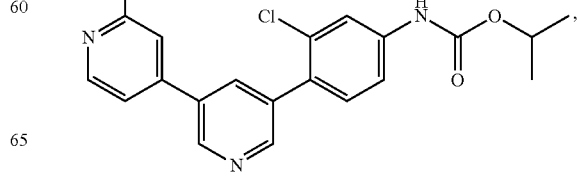

207
-continued
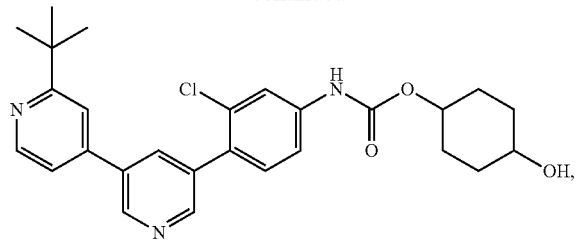
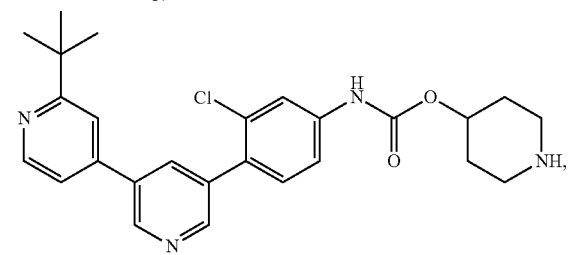
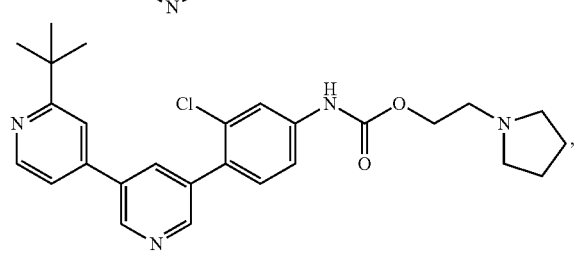
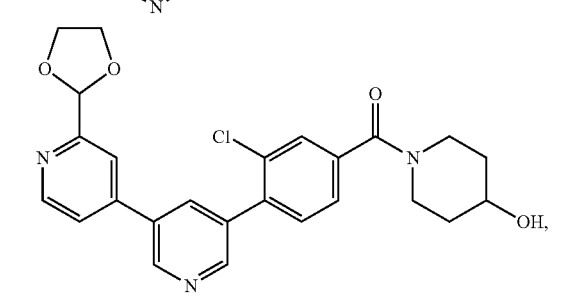
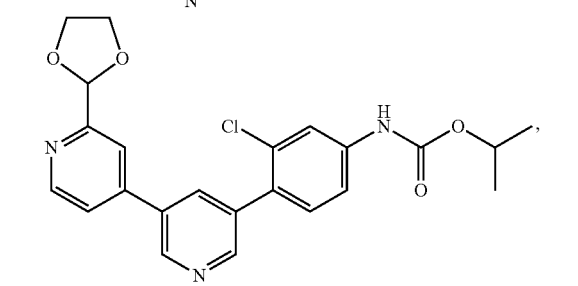
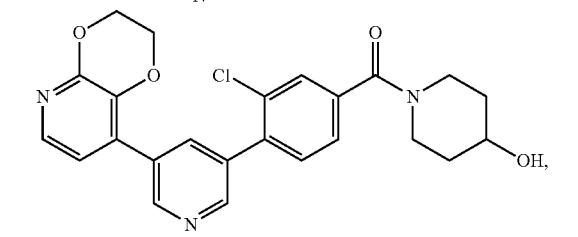
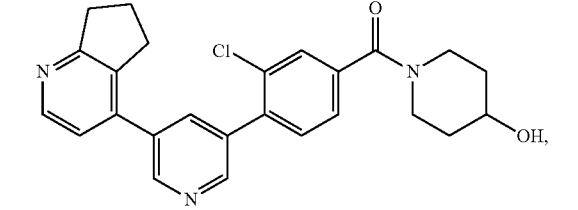
208
-continued
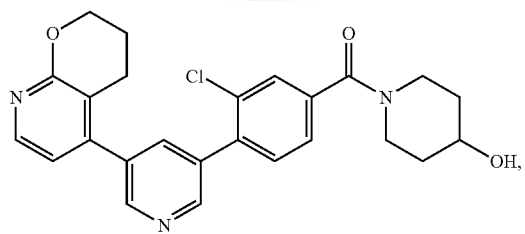
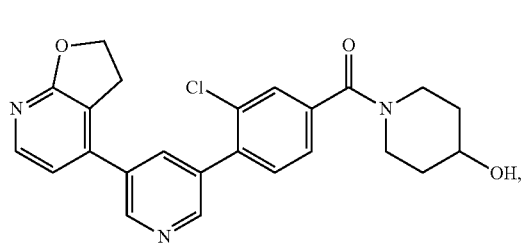
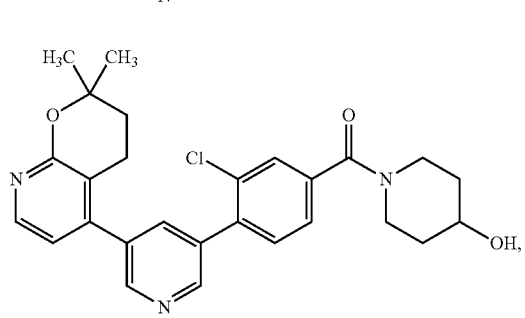
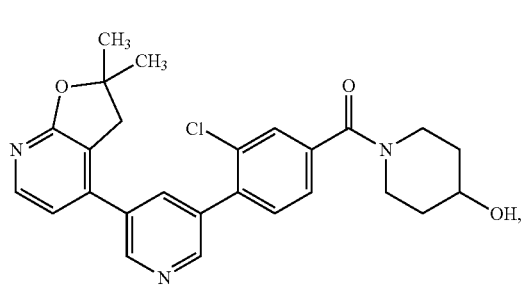
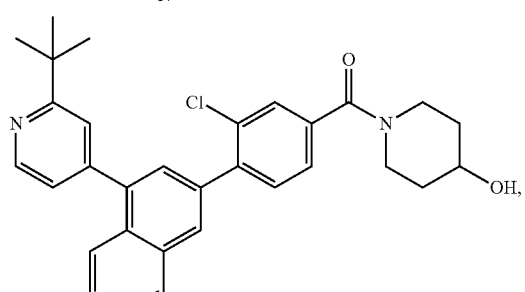
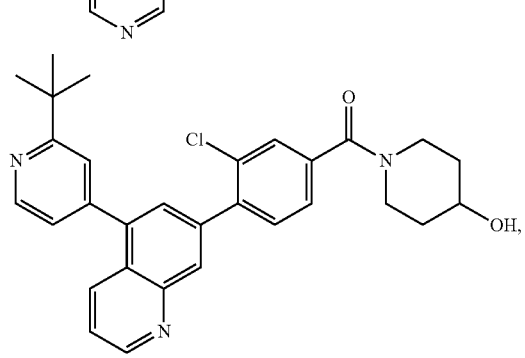

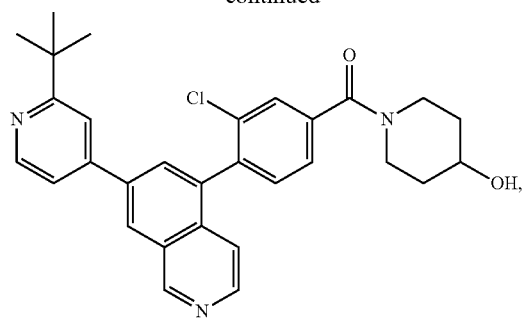
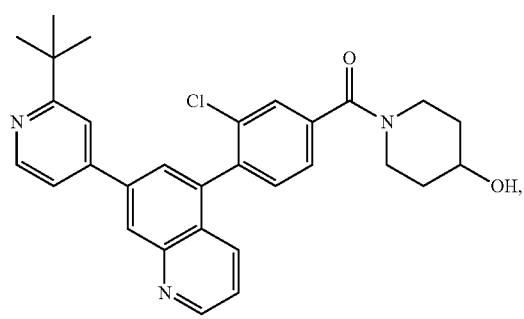
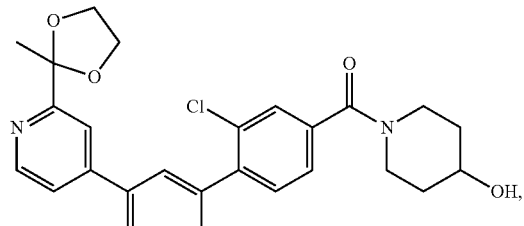
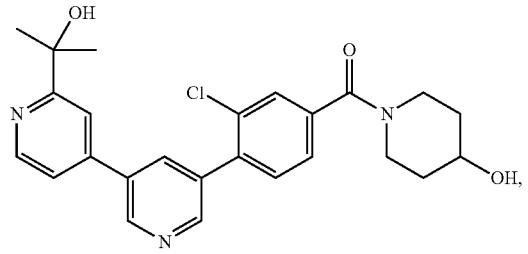
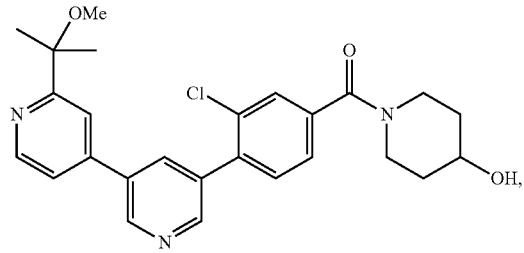
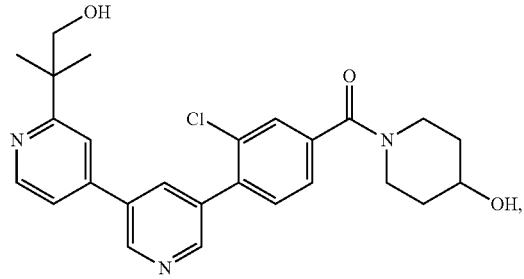
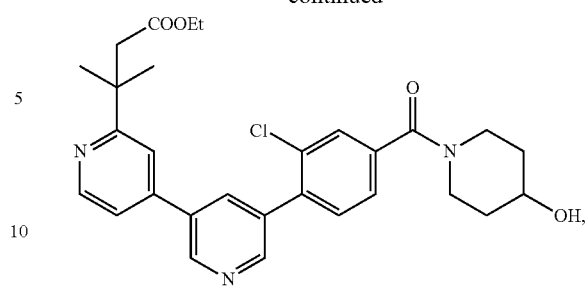

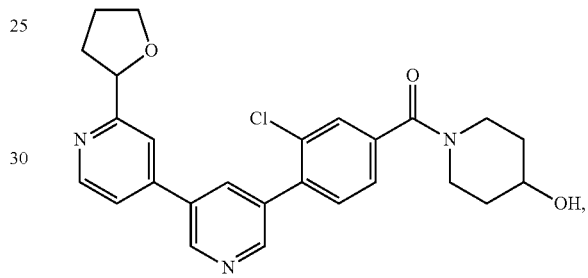
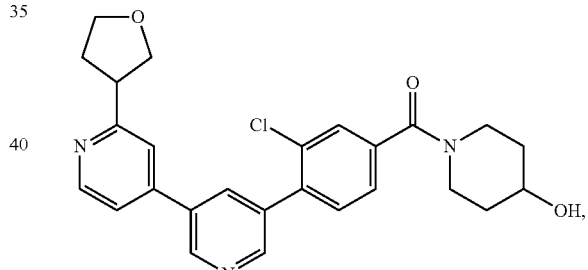
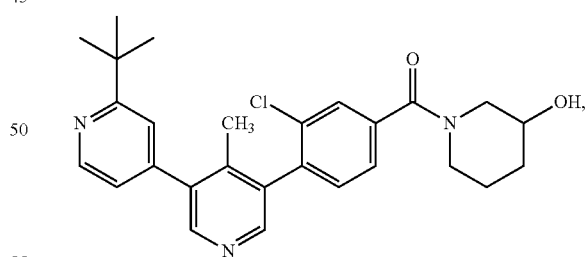
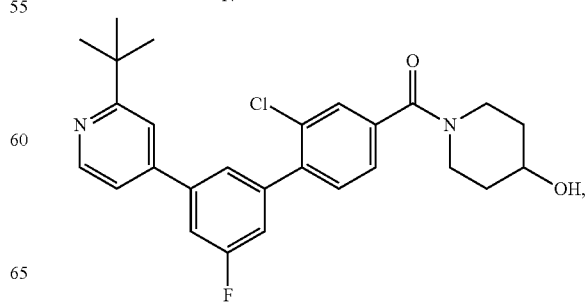

211
-continued
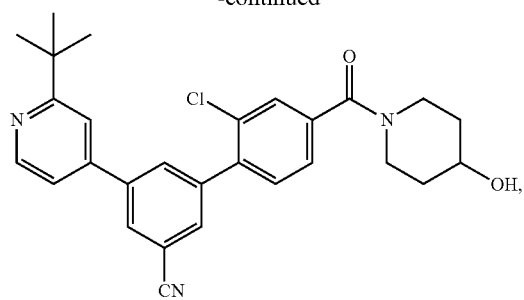
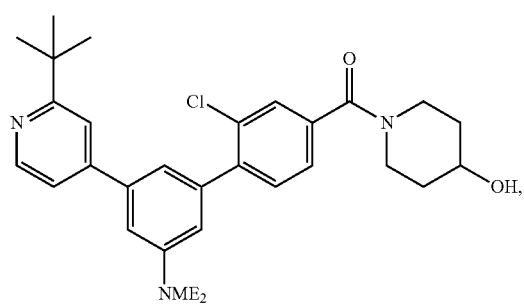
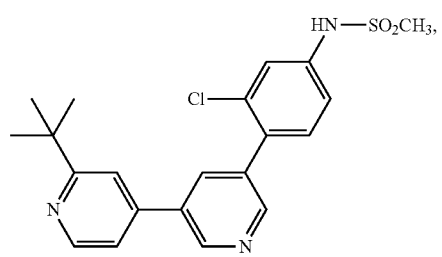
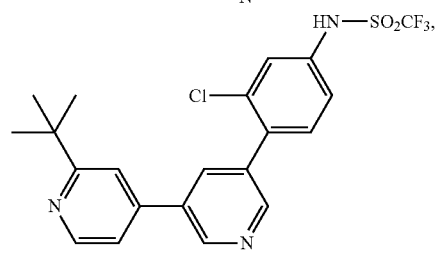
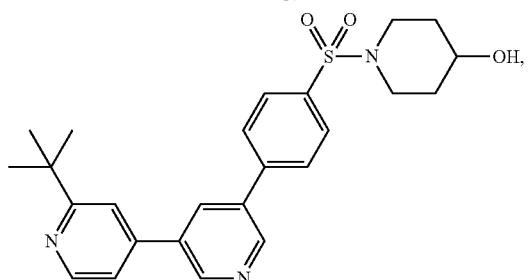
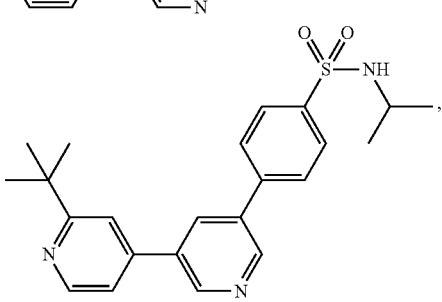
212
-continued
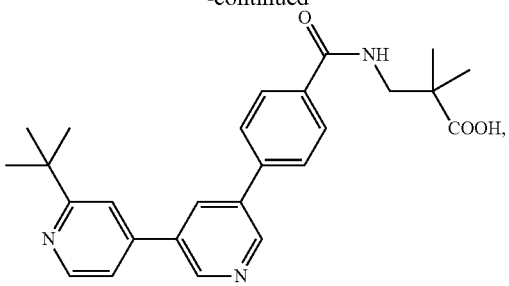
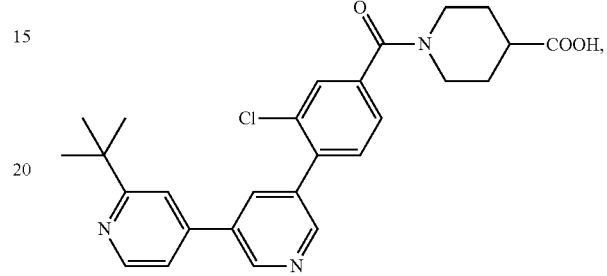
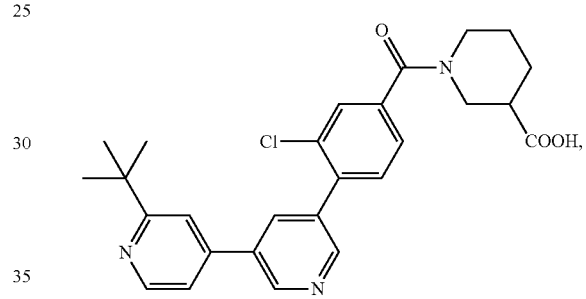
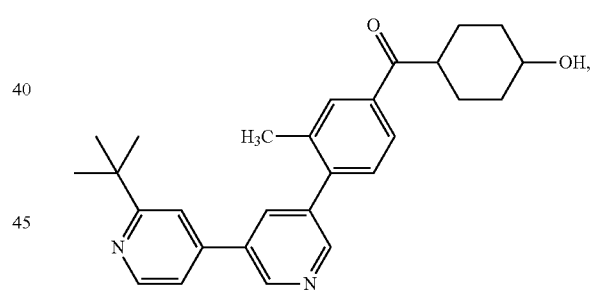
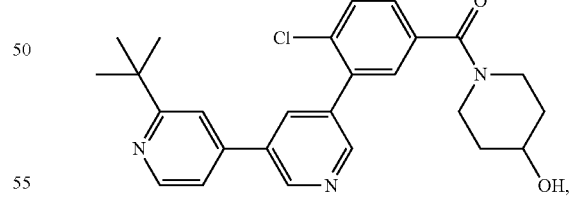
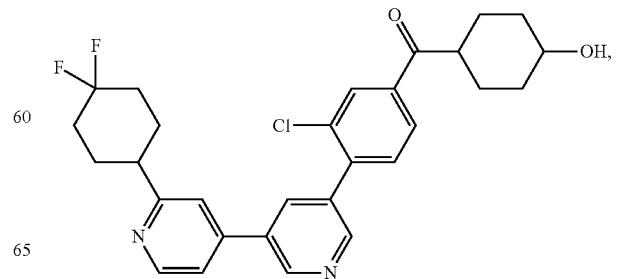

-continued

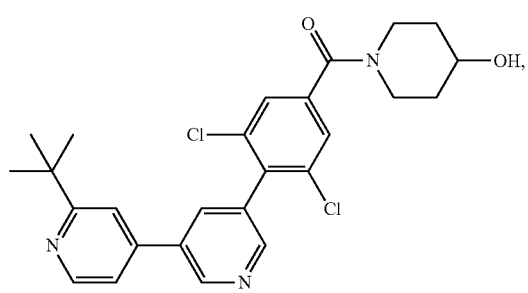
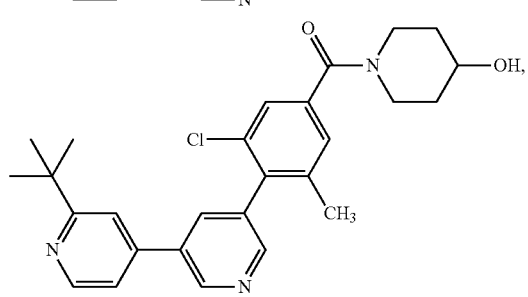
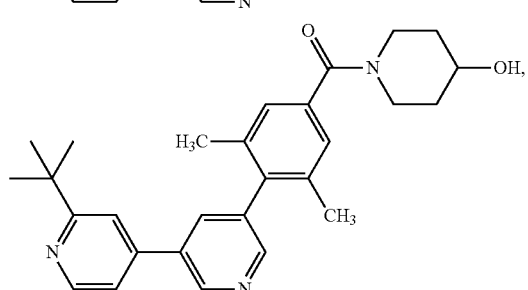
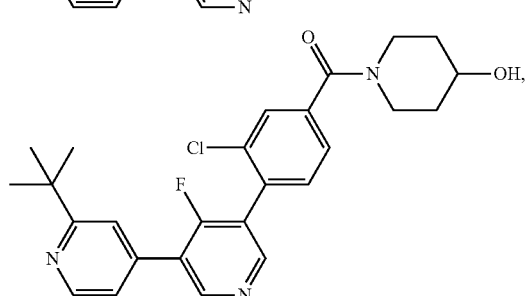
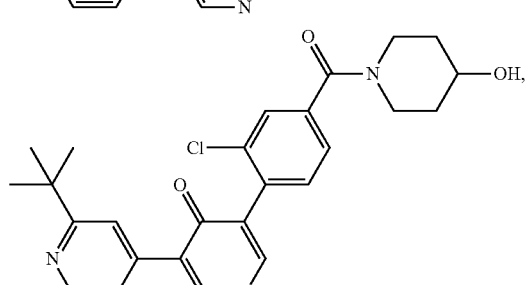
-continued
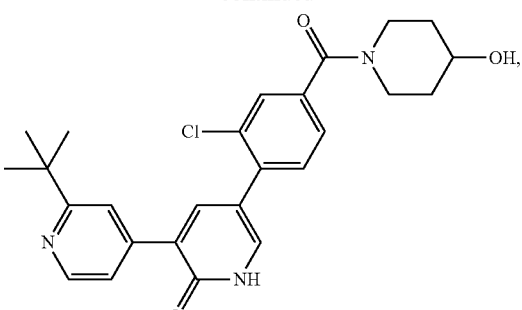
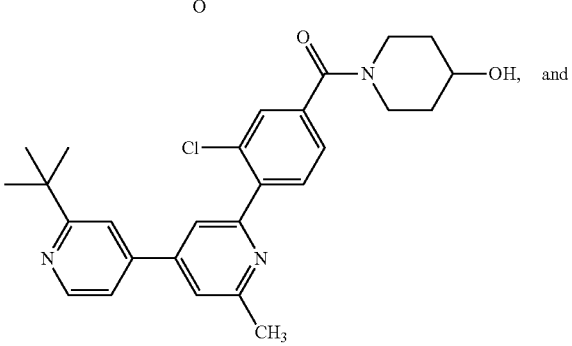
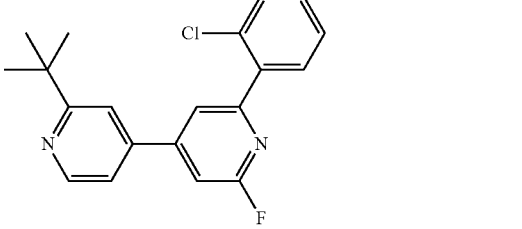
or a pharmaceutically acceptable salt, solvate, tautomer, isotope, or isomer of any of the foregoing.
Embodiment II-45. The compound of Embodiment II-1, selected from the group consisting of:
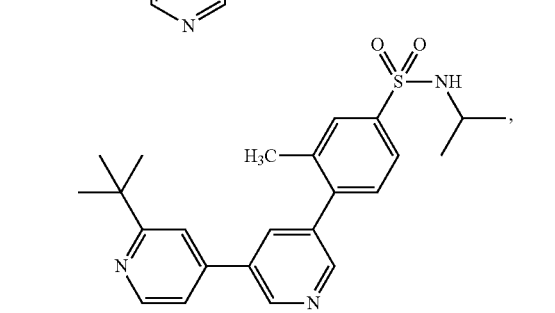

215
-continued
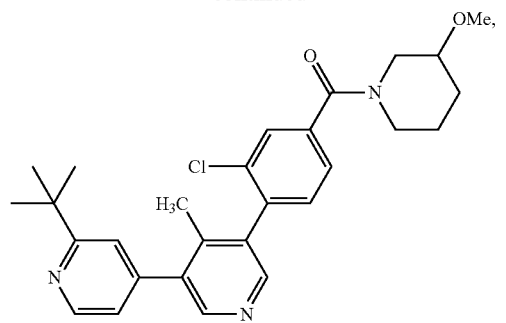
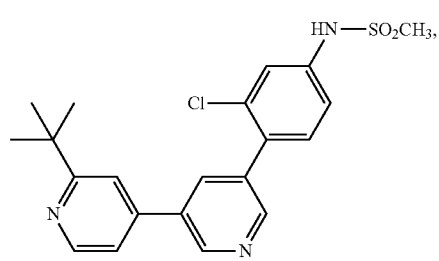
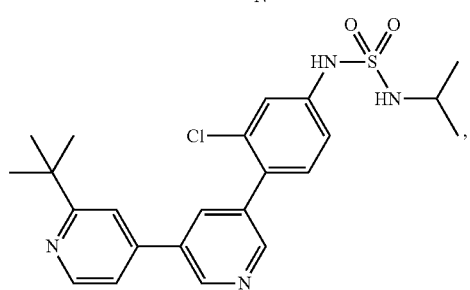
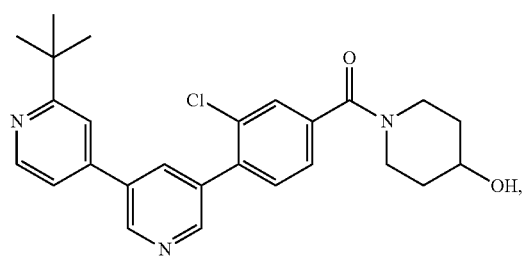
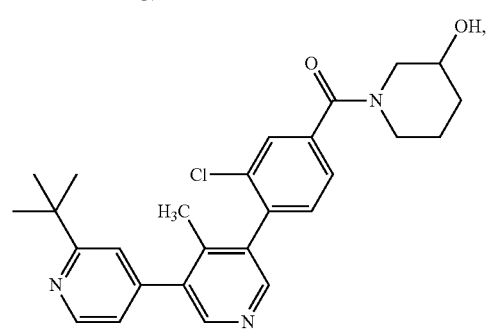
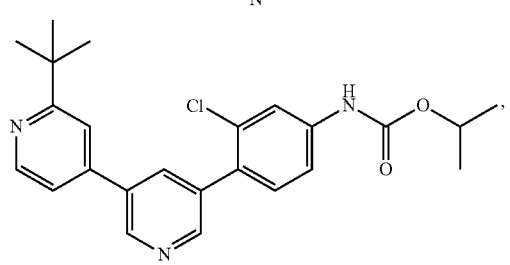
216
-continued
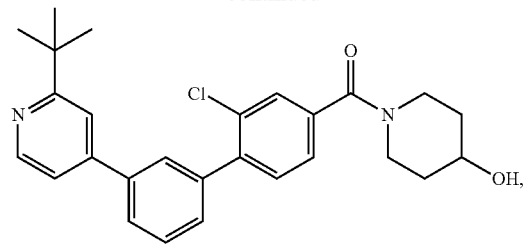
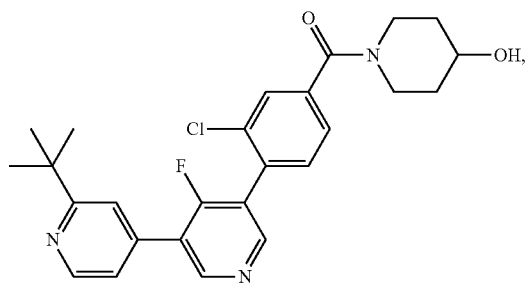
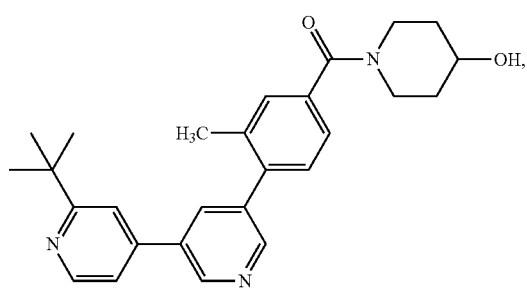
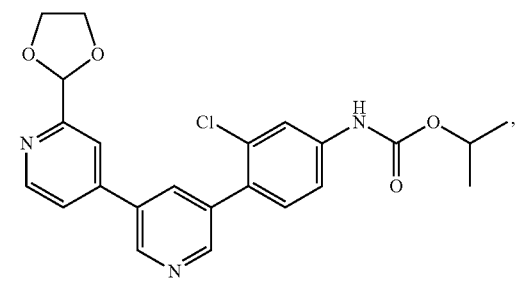
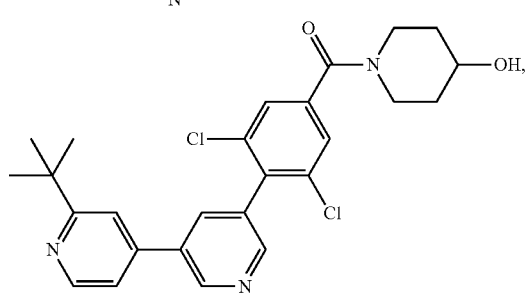
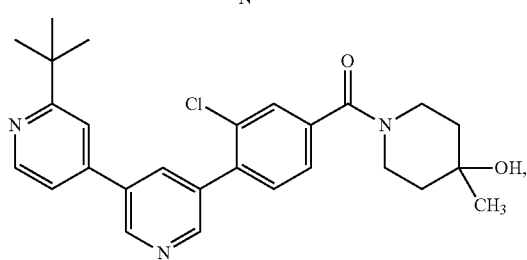

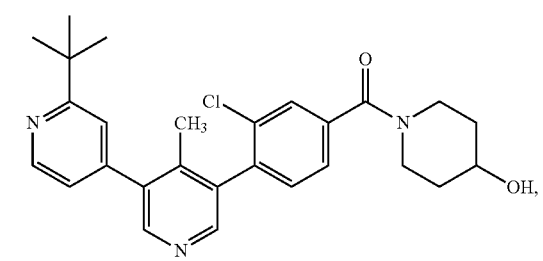
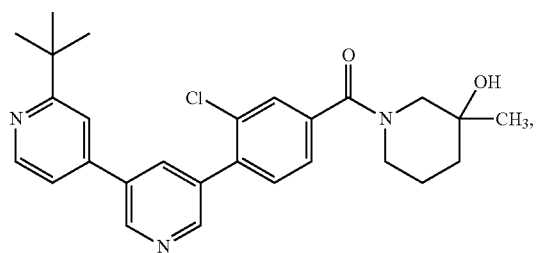
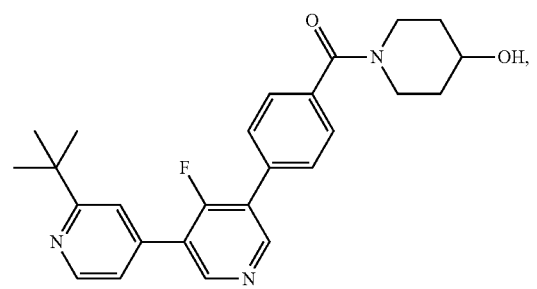
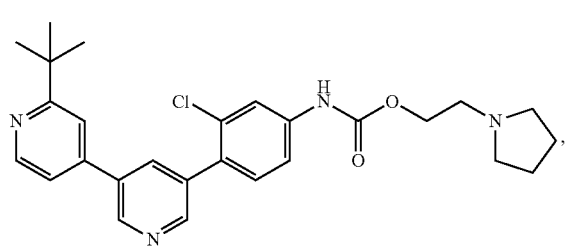
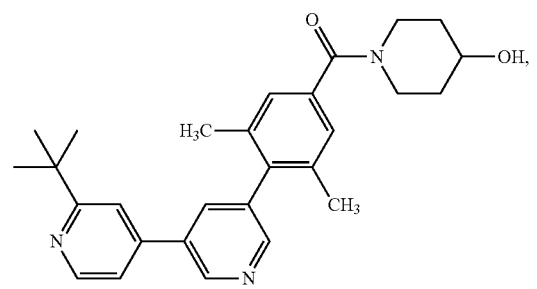
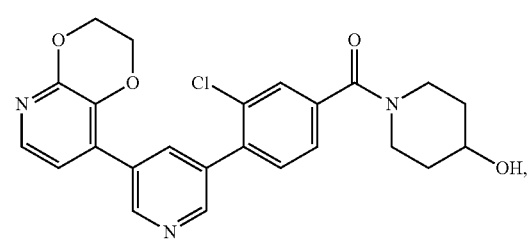
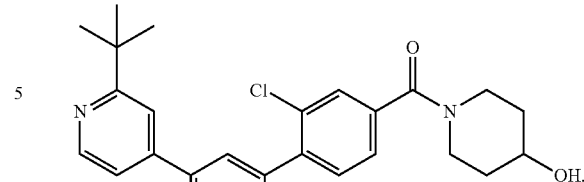
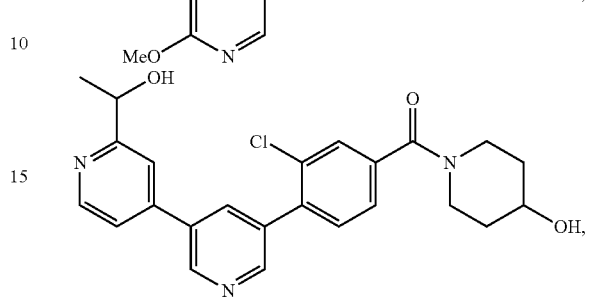
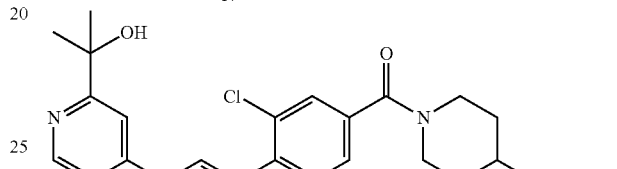
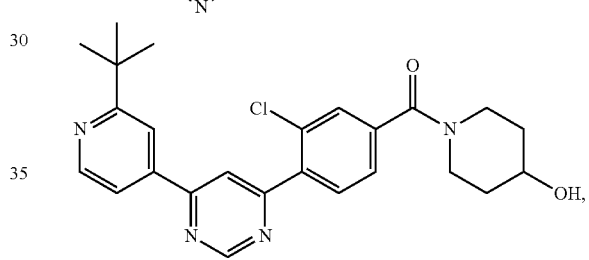
or a pharmaceutically acceptable salt, solvate, tautomer, isotope, or isomer of any of the foregoing.
Embodiment II-46. The compound of Embodiment II-1, selected from the group consisting of:
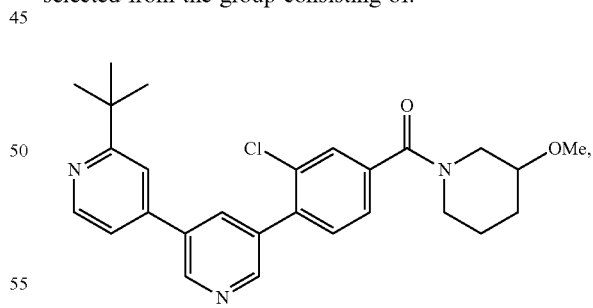
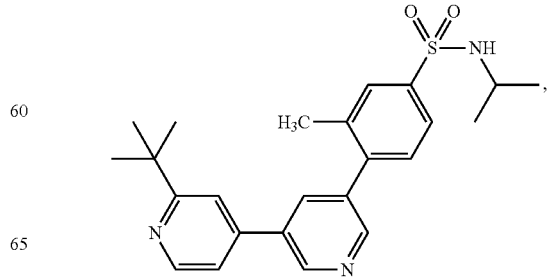

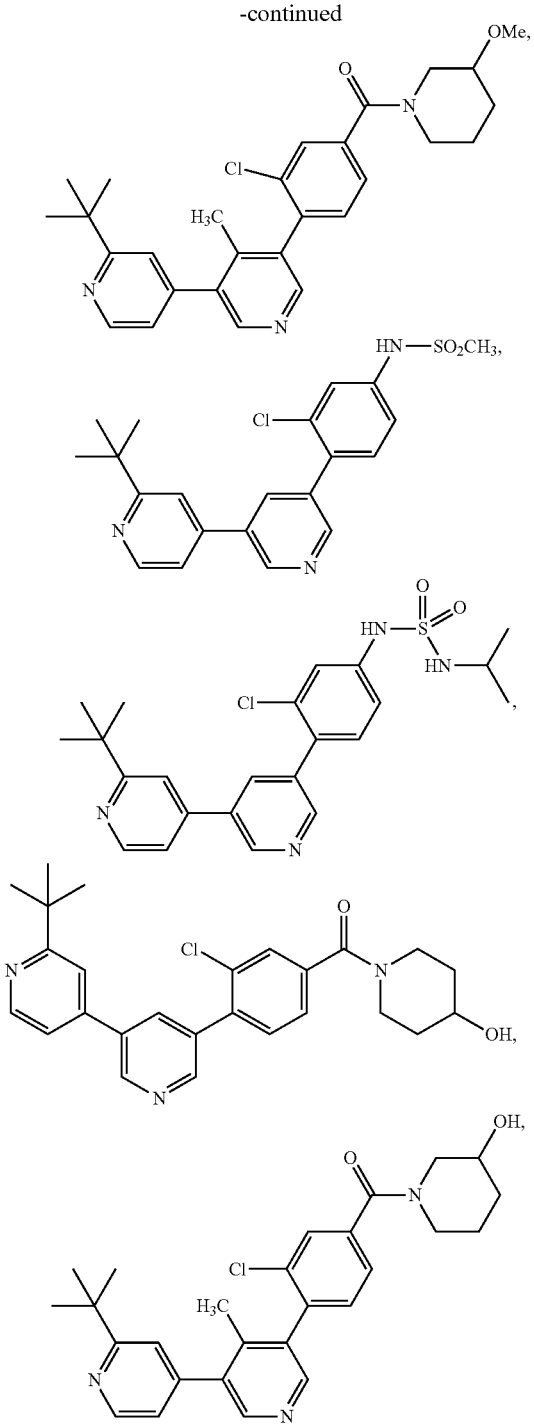

or a pharmaceutically acceptable salt, solvate, tautomer, isotope, or isomer of any of the foregoing.

Embodiment II-47. A pharmaceutical composition, comprising the compound of any one of Embodiments II-1 to II-46, or a pharmaceutically acceptable salt, solvate, tautomer, isotope, or isomer thereof, and a pharmaceutically acceptable excipient.

Embodiment II-48. A method of inhibiting a sterol regulatory element-binding protein (SREBP), comprising contacting the SREBP or contacting an SREBP cleavage activating-protein (SCAP) with a compound of any one of Embodiments II-1 to II-46, or a pharmaceutically acceptable salt, solvate, tautomer, isotope, or isomer thereof, or the pharmaceutical composition of Embodiment II-47.

Embodiment II-49. A method of inhibiting the proteolytic activation of a sterol regulatory element-binding protein (SREBP), comprising contacting an SREBP cleavage activating-protein (SCAP) with a compound of any one of Embodiment II-1 to II-46, or a pharmaceutically acceptable salt, solvate, tautomer, isotope, or isomer thereof, or the pharmaceutical composition of Embodiment II-47.

Embodiment II-50. The method of Embodiment II-48 or II-49, wherein the SREBP is an SREBP-1.

Embodiment II-51. The method of Embodiment II-50, wherein the SREBP-1 is SREBP-1a.

Embodiment II-52. The method of Embodiment II-50, wherein the SREBP-1 is SREBP-1c.

Embodiment II-53. The method of Embodiment II-48 or II-49, wherein the SREBP is SREBP-2.

Embodiment II-54. The method of any one of Embodiments II-48 to II-53, wherein SREBP is inhibited in a subject in need thereof.

Embodiment II-55. The method of any one of Embodiment II-48 to II-54, wherein SCAP is inhibited in a subject in need thereof.

Embodiment II-56. The method of any one of Embodiments II-48 to II-55, wherein the expression of one or more genes selected from the group consisting of ACSS2, ALDOC, CYP51A1, DHCR7, ELOVL6, FASN, FDFT1, FDPS, HMGCS1, HSD17B7, IDI1, INSIG1, LDLR, LSS, MEL PCSK9, PMVK, RDH11, SC5DL, SQLE, STARD4, TM7SF2, PNPLA3, SREBF1, SREBF2, HMGCR, MVD, MVK, ACLY, MSMO1, ACACA, and ACACB is reduced after contacting the SREBP or SCAP with the compound, or pharmaceutically acceptable salt, solvate, tautomer, isotope, or isomer thereof, or the pharmaceutical composition.

Embodiment II-57. A method of treating a disorder in a subject in need thereof, comprising administering to the subject in need thereof an effective amount of a compound of any one of Embodiments II-1 to II-46, or a pharmaceutically acceptable salt, solvate, tautomer, isotope, or isomer thereof, or the pharmaceutical composition of Embodiment II-47.

Embodiment II-58. A method of treating a disorder in a subject in need thereof, wherein the disorder is mediated by a sterol regulatory element-binding protein (SREBP), comprising administering to the subject in need thereof an effective amount of a compound of any one of Embodiments II-1 to II-46, or a pharmaceutically acceptable salt, solvate, tautomer, isotope, or isomer thereof, or the pharmaceutical composition of Embodiment II-47.

Embodiment II-59. The method of Embodiment II-57 or II-58, wherein the disorder is Metabolic Syndrome, type 2 diabetes, obesity, liver disease, insulin resistance, adiposopathy, or dyslipidemia.

Embodiment II-60. The method of Embodiment II-59, wherein the dyslipidemia is hypertriglyceridemia or elevated cholesterol levels.

Embodiment II-61. The method of Embodiment II-59, wherein the liver disease is nonalcoholic steatohepatitis, liver fibrosis, or liver inflammation, or a combination thereof.

Embodiment II-62. The method of Embodiment II-57 or II-58, wherein the disorder is a hyperproliferative disorder.

Embodiment II-63. The method of Embodiment II-62, wherein the hyperproliferative disorder is cancer.

Embodiment II-64. The method of Embodiment II-63, wherein the cancer is breast cancer, liver cancer, ovarian cancer, pancreatic cancer, or prostate cancer.

Embodiment II-65. The method of Embodiment II-57 or II-58, wherein the disorder is endotoxic shock, systemic inflammation, or atherosclerosis.

Embodiment II-66. Use of a compound of any one of Embodiments II-1 to II-46, or a pharmaceutically acceptable salt, solvate, tautomer, isotope, or isomer thereof, in the manufacture of a medicament for use in treating a disorder in a subject in need thereof.

Embodiment II-67. Use of a compound of any one of Embodiments II-1 to II-46, or a pharmaceutically acceptable salt, solvate, tautomer, isotope, or isomer thereof, in the manufacture of a medicament for use in inhibiting a sterol regulatory element-binding protein (SREBP) in a subject in need thereof.

Embodiment II-68. Use of a compound of any one of Embodiments II-1 to II-46, or a pharmaceutically acceptable salt, solvate, tautomer, isotope, or isomer thereof, in the manufacture of a medicament for use in inhibiting the proteolytic activation of a sterol regulatory element-binding protein (SREBP) in a subject in need thereof.

Embodiment II-69. Use of a compound of any one of Embodiments II-1 to II-46, or a pharmaceutically acceptable salt, solvate, tautomer, isotope, or isomer thereof, in the manufacture of a medicament for use in treating a disorder in a subject in need thereof, wherein the disorder is mediated by a sterol regulatory element-binding protein (SREBP).

Embodiment II-70. Use of a compound of any one of Embodiments II-1 to II-46, or a pharmaceutically acceptable salt, solvate, tautomer, isotope, or isomer thereof, or the pharmaceutical composition of Embodiment II-47, for inhibiting a sterol regulatory element-binding protein (SREBP).

Embodiment II-71. Use of a compound of any one of Embodiments II-1 to II-46, or a pharmaceutically acceptable salt, solvate, tautomer, isotope, or isomer thereof, or the pharmaceutical composition of Embodiment II-47, for inhibiting an SREBP cleavage activating protein (SCAP).

Embodiment II-72. The use of any one of Embodiments II-67 to II-71, wherein the SREBP is an SREBP-1.

Embodiment II-73. The use of Embodiment II-72, wherein the SREBP-1 is SREBP-1a.

Embodiment II-74. The use of Embodiment II-72, wherein the SREBP-1 is SREBP-1c.

Embodiment II-75. The use of any one of Embodiments II-67 to II-71, wherein the SREBP is SREBP-2.

Embodiment II-76. The use of any one of Embodiments II-67 to II-71, wherein SREBP is inhibited in a subject in need thereof.

Embodiment II-77. The use of any one of Embodiments II-67 to II-71, wherein SCAP is inhibited in a subject in need thereof.

Embodiment II-78. Use of a compound of any one of Embodiments II-1 to II-46, or a pharmaceutically acceptable salt, solvate, tautomer, isotope, or isomer thereof, or the pharmaceutical composition of Embodiment II-47, for treating a disorder in a subject in need thereof.

Embodiment II-79. Use of a compound of any one of Embodiments II-1 to II-46, or a pharmaceutically acceptable salt, solvate, tautomer, isotope, or isomer thereof, or the pharmaceutical composition of Embodiment II-47, for treating a disorder in a subject in need thereof, wherein the disorder is mediated by a sterol regulatory element-binding protein (SREBP).

Embodiment II-80. The use of Embodiment II-78 or II-79, wherein the disorder is Metabolic Syndrome, type 2 diabetes, obesity, liver disease, insulin resistance, adiposopathy, or dyslipidemia.

Embodiment II-81. The use of Embodiment II-80, wherein the dyslipidemia is hypertriglyceridemia or elevated cholesterol levels.

Embodiment II-82. The use of Embodiment II-80, wherein the liver disease is nonalcoholic steatohepatitis, liver fibrosis, or liver inflammation, or a combination thereof.

Embodiment II-83. The use of Embodiment II-78 or II-79, wherein the disorder is a hyperproliferative disorder.

Embodiment II-84. The use of Embodiment II-83, wherein the hyperproliferative disorder is cancer.

Embodiment II-85. The use of Embodiment II-84, wherein the cancer is breast cancer, liver cancer, ovarian cancer, pancreatic cancer, or prostate cancer.

Embodiment II-86. The use of Embodiment II-78 or II-79, wherein the disorder is endotoxic shock, systemic inflammation, or atherosclerosis.

Embodiment II-87. A method of treating non-alcoholic steatohepatitis (NASH) in a subject in need thereof, comprising administering to the subject in need thereof an effective amount of a compound of any one of Embodiments II-1 to II-46, or a pharmaceutically acceptable salt, solvate, tautomer, isotope, or isomer thereof, or the pharmaceutical composition of Embodiment II-47.

Embodiment II-88. Use of a compound of any one of Embodiments II-1 to II-46, or a pharmaceutically acceptable salt, solvate, tautomer, isotope, or isomer thereof, or the pharmaceutical composition of Embodiment II-47, for treating non-alcoholic steatohepatitis (NASH) in a subject in need thereof.

Embodiment II-89. Use of a compound of any one of Embodiments II-1 to II-46, or a pharmaceutically acceptable salt, solvate, tautomer, isotope, or isomer thereof, in the manufacture of a medicament for use in treating non-alcoholic steatohepatitis (NASH) in a subject in need thereof.

Embodiment II-90. A method of treating a hyperproliferative disorder in a subject in need thereof, comprising administering to the subject in need thereof an effective amount of a compound of any one of Embodiments II-1 to II-46, or a pharmaceutically acceptable salt, solvate, tautomer, isotope, or isomer thereof, or the pharmaceutical composition of Embodiment II-47.

Embodiment II-91. Use of a compound of any one of Embodiments II-1 to II-46, or a pharmaceutically acceptable salt, solvate, tautomer, isotope, or isomer thereof, or the pharmaceutical composition of Embodiment II-47, for treating a hyperproliferative disorder in a subject in need thereof.

Embodiment II-92. Use of a compound of any one of Embodiments II-1 to II-46, or a pharmaceutically acceptable salt, solvate, tautomer, isotope, or isomer thereof, in the manufacture of a medicament for use in treating a hyperproliferative disorder in a subject in need thereof.

Embodiment III-1. A compound of Formula (X):

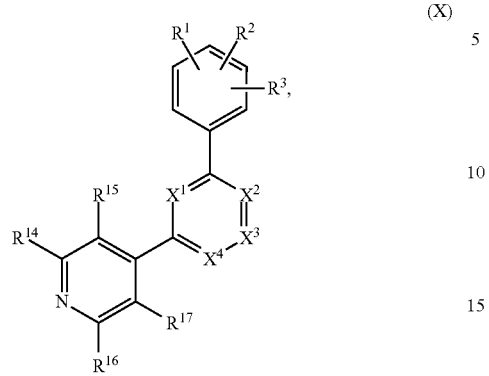

or a pharmaceutically acceptable salt, solvate, tautomer, isotope, or isomer thereof, wherein:

$R^1$ is —C(O)$R^9$, —C(O)N$R^8R^9$, —S(O)$_2$N$R^8R^9$, —N$R^{10}$C(O)N$R^8R^9$, —N$R^{10}$C(O)$R^9$, —N$R^{10}$S(O)$_2R^9$, —O$R^{26}$, —S$R^9$, —S(O)$R^9$, —S(O)$_2R^9$, —N$R^8R^9$, —N$R^{10}$C(O)O$R^9$, —C(O)$R^{26}$, —N$R^{10}$S(O)$_2$N$R^8R^9$, —C(O)N$R^{10}$S(O)$_2R^9$, or —C(O)N$R^{10}$N$R^8R^9$;

wherein each of $R^8$, $R^9$, and $R^{10}$ is independently selected from the group consisting of hydrogen, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl, $R^{26}$ is (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, or heteroaryl-alkyl, each (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl of $R^8$, $R^9$, $R^{10}$, and $R^{26}$ is independently unsubstituted or substituted with one or more substituents independently selected from the group consisting of halo, (C$_{1-10}$)alkyl, (C$_{1-10}$)haloalkyl, cyano, oxo, —O$R^{19}$, —C(O)N$R^{19}R^{19}$, —N$R^{19}$C(O)$R^{19}$, —N$R^{19}$C(O)N$R^{19}R^{19}$, —N$R^{19}R^{19}$, —S(O)$_2$N$R^{19}R^{19}$, —N$R^{19}$S(O)$_2R^{19}$, —S(O)$_{n4}R^{20}$, —C(O)O$R^{19}$, —C(O)$R^{20}$, and —(O$R^{38}$)$_{n15}$O$R^{19}$;

each $R^{19}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{20}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, each $R^{38}$ is independently (C$_{1-10}$)alkylene or (C$_{1-10}$)haloalkylene, each n15 is independently an integer from 1 to 5, and n4 is 0, 1, or 2;

or $R^8$ and $R^9$, together with the nitrogen atom to which they are attached, form a heterocycloalkyl, wherein the heterocycloalkyl is unsubstituted or substituted with one or more substituents independently selected from the group consisting of halo, cyano, oxo, (C$_{1-10}$)alkyl, (C$_{2-10}$)alkenyl, (C$_{2-10}$)alkynyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, heteroaryl-alkyl, —O$R^{23}$, —C(O)N$R^{23}R^{23}$, —N$R^{23}$C(O)$R^{23}$, —N$R^{23}$C(O)O$R^{23}$, —N$R^{23}$C(O)N$R^{23}R^{23}$, —N$R^{23}R^{23}$, —S(O)$_2$N$R^{23}R^{23}$, —N$R^{23}$S(O)$_2R^{24}$, —S(O)$_{n6}R^{24}$, —C(O)O$R^{23}$, —C(O)$R^{24}$, and —(O$R^{39}$)$_{n16}$O$R^{23}$, wherein each alkyl, alkenyl, alkynyl, cycloalkyl, cycloalkyl-alkyl, heterocycloalkyl, heterocycloalkyl-alkyl, aryl, aryl-alkyl, heteroaryl, and heteroaryl-alkyl is independently unsubstituted or substituted with one or more substituents independently selected from the group consisting of halo, oxo, alkyl, haloalkyl, —O$R^{31}$, —C(O)N$R^{31}R^{31}$, —N$R^{31}$C(O)$R^{31}$, —N$R^{31}$C(O)O$R^{31}$, —N$R^{31}$C(O)N$R^{31}R^{31}$, —N$R^{31}$S(O)$_2R^{31}$, and —S(O)$_{n9}R^{31}$, wherein each $R^{31}$ is independently hydrogen, alkyl, or haloalkyl, and each n9 is independently 0, 1, or 2, each $R^{23}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{24}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, each $R^{39}$ is independently (C$_{1-10}$)alkylene or (C$_{1-10}$)haloalkylene, each n16 is independently an integer from 1 to 5, and n6 is 0, 1, or 2;

$R^2$ and $R^3$ are independently selected from the group consisting of hydrogen, halo, cyano, (C$_{1-10}$)alkyl, (C$_{3-10}$)cycloalkyl, (C$_{3-10}$)cycloalkyl(C$_{1-10}$)alkyl, —O$R^{25}$, —C(O)N$R^{25}R^{25}$, —N$R^{25}$C(O)$R^{25}$, —N$R^{25}$C(O)N$R^{25}R^{25}$, —N$R^{25}R^{25}$, —S(O)$_2$N$R^{25}R^{25}$, —N$R^{25}$S(O)$_2R^{25}$, —S(O)$_{n7}R^{30}$, —N$R^{25}$C(O)O$R^{25}R^{25}$, —C(O)O$R^{25}$, and —C(O)$R^{30}$, wherein each (C$_{1-10}$)alkyl, (C$_{3-10}$)cycloalkyl, and (C$_{3-10}$)cycloalkyl(C$_{1-10}$)alkyl is independently unsubstituted or substituted with one or more halo, each $R^{25}$ is independently hydrogen (C$_{1-10}$)alkyl, (C$_{3-10}$)cycloalkyl, (C$_{3-10}$)cycloalkyl(C$_{1-10}$)alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{30}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, and n7 is 0, 1, or 2;

$X^1$, $X^2$, $X^3$ and $X^4$ are independently CR$^4$ or N, wherein $X^2$, $X^3$ and $X^4$ may not all be N;

when at least one of $X^1$, $X^2$, $X^3$ and $X^4$ is N, each $R^4$ is independently selected from the group consisting of hydrogen, halo, cyano, (C$_{1-10}$)alkyl, (C$_{3-10}$)cycloalkyl, (C$_{3-10}$)cycloalkyl(C$_{1-10}$)alkyl, heterocycloalkyl connected by an annular carbon atom, heterocycloalkyl-alkyl, —O$R^{27}$, —C(O)N$R^{27}R^{27}$, —S(O)$_2$N$R^{27}R^{27}$, —S(O)$_{n8}R^{28}$, —C(O)O$R^{27}$, and —C(O)$R^{28}$, wherein each (C$_{1-10}$)alkyl, (C$_{3-10}$)cycloalkyl, (C$_{3-10}$)cycloalkyl(C$_{1-10}$)alkyl, heterocycloalkyl, and heterocycloalkyl-alkyl is independently unsubstituted or substituted with one or more halo,
each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo,
n8 is 0, 1 or 2; or when each of $X^1$, $X^2$, $X^3$ and $X^4$ is $CR^4$, each $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$NR^{27}S(O)_2R^{27}$, —$S(O)_2NR^{27}R^{27}$, —$S(O)_{n8}R^{28}$, —$C(O)OR^{27}$, and —$C(O)R^{28}$,
wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo,
each $R^{27}$ is independently hydrogen, $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and
n8 is 0, 1, or 2; or two $R^4$ on adjacent annular carbon atoms together with the carbon atoms to which they are attached may form a carbocyclyl or heterocyclyl,
wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$S(O)_2NR^{27}R^{27}$, —$NR^{27}S(O)_2R^{27}$, —$S(O)_{n8}R^{28}$ and —$C(O)R^{28}$,
or the heterocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, and —$C(O)R^{28}$,
each $R^{27}$ is independently hydrogen, $(C_{1-10})$alkyl, $(C_{3-10})$cycloalkyl, $(C_{3-10})$cycloalkyl$(C_{1-10})$alkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo,
each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and
n8 is 0, 1, or 2;

$R^{15}$ and $R^{17}$ are independently hydrogen, halo, alkyl, or —$OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;
$R^{14}$ is $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl connected through an annular carbon atom, heterocycloalkenyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;
$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;
wherein the $(C_{1-10})$alkyl, $(C_{1-10})$alkenyl, $(C_{3-10})$cycloalkyl, $(C_{3-10})$cycloalkenyl, $(C_{3-10})$cycloalkyl$(C_{1-10})$alkyl, heterocycloalkyl, heterocycloalkenyl, or heterocycloalkyl-alkyl of $R^{14}$ or $R^{16}$ is independently unsubstituted or substituted with one or more substituents independently selected from the group consisting of $(C_{1-10})$alkyl, cycloalkyl, heterocycloalkyl, halo, cyano, oxo, —$OR^7$, —$C(O)OR^7$, —$C(O)NR^7R^7$, —$NR^7C(O)R^7$, —$NR^7C(O)NR^7R^7$, —$NR^7R^7$, —$S(O)_2NR^7R^7$, —$NR^7S(O)_2R^7$, —$S(O)_{n2}R^{13}$, and —$C(O)R^{13}$;
wherein each alkyl, cycloalkyl, and heterocycloalkyl is independently unsubstituted or substituted with one or more substituents selected from the group consisting of halo, cycloalkyl, halocycloalkyl, heterocycloalkyl, haloheterocycloalkyl, and —$(OR^{33})_{n10}OR^{32}$, wherein each n10 is independently an integer from 0 to 5, each $R^{32}$ is independently hydrogen, $(C_{1-10})$alkyl or $(C_{1-10})$haloalkyl, and each $R^{33}$ is independently $(C_{1-10})$alkylene or $(C_{1-10})$haloalkylene;
each $R^5$ is independently hydrogen, $(C_{1-10})$alkyl, or $(C_{3-10})$cycloalkyl; or two $R^5$, together with the nitrogen atom to which they are attached, form a heterocycloalkyl; wherein each alkyl, cycloalkyl, or heterocycloalkyl is independently unsubstituted or substituted with one or more substituents selected from the group consisting of halo, cyano, oxo, alkyl, haloalkyl, —$C(O)OR^{34}$, —$C(O)NR^{34}R^{34}$, —$NR^{34}C(O)R^{34}$, —$NR^{34}C(O)NR^{34}R^{34}$, —$NR^{34}R^{34}$, —$S(O)_2NR^{34}R^{34}$, —$NR^{34}S(O)_2R^{34}$, —$S(O)_{n1}R^{34}$, —$C(O)R^{34}$, and —$(OR^{35})_{n12}OR^{34}$, wherein each $R^{34}$ is independently hydrogen, $(C_{1-10})$alkyl, or $(C_{1-10})$haloalkyl; each n11 is independently 0, 1, or 2; each n12 is independently an integer from 0 to 5; and each $R^{35}$ is independently $(C_{1-10})$alkylene or $(C_{1-10})$haloalkylene;
each $R^6$ is independently $(C_{1-10})$alkyl or $(C_{3-10})$cycloalkyl, wherein each alkyl or cycloalkyl is independently unsubstituted or substituted with one or more halo;
each n1 is independently 0, 1, or 2;
each $R^7$ is independently hydrogen, unsubstituted $(C_{1-10})$ alkyl, or $(C_{1-10})$alkyl substituted with one or more halo;
each n2 is independently 0, 1, or 2,
and each $R^{13}$ is independently unsubstituted $(C_{1-10})$alkyl or $(C_{1-10})$alkyl substituted with one or more halo;
or $R^{14}$ and $R^{15}$, together with the atoms to which they are attached, form a carbocyclyl or heterocyclyl,
wherein the carbocyclyl or heterocyclyl is unsubstituted or substituted with one or more substituents independently selected from the group consisting of halo, cyano, oxo, $(C_{1-10})$alkyl, $(C_{3-10})$cycloalkyl, $(C_{3-10})$cycloalkyl$(C_{1-10})$alkyl, —$OR^{18}$, —$C(O)NR^{18}R^{18}$, —NR¹⁸C(O)R¹⁸, —NR¹⁸C(O)NR¹⁸R¹⁸, —NR¹⁸R¹⁸, —S(O)₂NR¹⁸R¹⁸, —NR¹⁸S(O)₂R¹⁸, —S(O)$_{n3}$R²¹, —C(O)OR¹⁸, and —C(O)R²¹, wherein each (C$_{1-10}$)alkyl, (C$_{3-10}$)cycloalkyl, and (C$_{3-10}$)cycloalkyl(C$_{1-10}$)alkyl is independently unsubstituted or substituted with one or more substituents independently selected from the group consisting of halo, alkyl, haloalkyl, cyano, oxo, —C(O)OR³⁶, —C(O)NR³⁶R³⁶, —NR³⁶C(O)R³⁶, —NR³⁶C(O)NR³⁶R³⁶, —NR³⁶R³⁶, —S(O)₂NR³⁶R³⁶, —NR³⁶S(O)₂R³⁶, —S(O)$_{n13}$R³⁶, —C(O)R³⁶, and —(OR³⁷)$_{n14}$OR³⁶, wherein each R³⁶ is independently hydrogen, (C$_{1-10}$)alkyl, or (C$_{1-10}$)haloalkyl; each n13 is independently 0, 1, or 2; each n14 is independently an integer from 0 to 5; and each R³⁷ is independently (C$_{1-10}$)alkylene or (C$_{1-10}$)haloalkylene;

wherein each R¹⁸ is independently hydrogen, (C$_{1-10}$)alkyl, or (C$_{3-10}$)cycloalkyl; or two R¹⁸, together with the nitrogen atom to which they are attached, form a heterocycloalkyl; wherein each alkyl, cycloalkyl, or heterocycloalkyl is independently unsubstituted or substituted with one or more halo;

each R²¹ is independently (C$_{1-10}$)alkyl or (C$_{3-10}$)cycloalkyl, wherein each alkyl or cycloalkyl is independently unsubstituted or substituted with one or more halo; and each n3 is independently 0, 1, or 2.

Embodiment III-2. The compound of Embodiment III-1, or a pharmaceutically acceptable salt, solvate, tautomer, isotope, or isomer thereof, wherein R¹ is —C(O)OR⁹, —C(O)NR⁸R⁹, —S(O)₂NR⁸R⁹, —NR¹⁰C(O)NR⁸R⁹, —NR¹⁰C(O)R⁹, —NR¹⁰S(O)₂R⁹, —OR²⁶, —SR⁹, —S(O)R⁹, —S(O)₂R⁹, —NR⁸R⁹, or —NR¹⁰C(O)OR⁹.

Embodiment III-3. The compound of Embodiment III-1 or III-2, wherein the compound is of Formula (X-A):

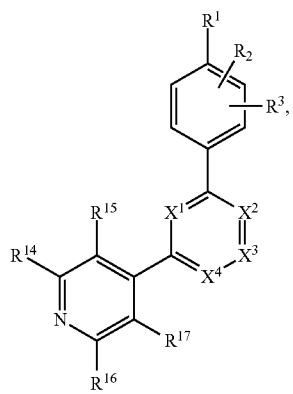

(X-A)

or a pharmaceutically acceptable salt, solvate, tautomer, isotope, or isomer thereof, wherein R¹, R², R³, R¹⁴, R¹⁵, R¹⁶, R¹⁷, X¹, X², X³, and X⁴ are as defined for Formula (X).

Embodiment III-4. The compound of Embodiment III-1 or III-2, wherein the compound is of Formula (X-B):

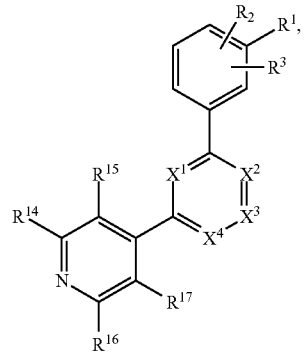

(X-B)

or a pharmaceutically acceptable salt, solvate, tautomer, isotope, or isomer thereof, wherein R¹, R², R³, R¹⁴, R¹⁵, R¹⁶, R¹⁷, X¹, X², X³, and X⁴ are as defined for Formula (X).

Embodiment III-5. The compound of any one of Embodiments III-1 to III-4, or a pharmaceutically acceptable salt, solvate, tautomer, isotope, or isomer thereof, wherein R¹⁷ is hydrogen.

Embodiment III-6. The compound of any one of Embodiments III-1, or III-3 to III-5, or a pharmaceutically acceptable salt, solvate, tautomer, isotope, or isomer thereof, wherein R¹ is —C(O)OR⁹, —C(O)NR⁸R⁹, —S(O)₂NR⁸R⁹, —NR¹⁰C(O)NR⁸R⁹, —NR¹⁰S(O)₂R⁹, —NR¹⁰C(O)OR⁹, —C(O)R²⁶, —NR¹⁰S(O)₂NR⁸R⁹, or —C(O)NR⁸S(O)₂R⁹.

Embodiment III-7. The compound of any one of Embodiments III-1, or III-3 to III-6, or a pharmaceutically acceptable salt, solvate, tautomer, isotope, or isomer thereof, wherein R¹ is —C(O)NR⁸R⁹, —S(O)₂NR⁸R⁹, —NR¹⁰C(O)OR, —NR¹⁰S(O)₂R⁹, or —NR¹⁰S(O)₂NR⁸R⁹.

Embodiment III-8. The compound of any one of Embodiments III-1 to III-7, or a pharmaceutically acceptable salt, solvate, tautomer, isotope, or isomer thereof, wherein R¹ is —C(O)NR⁸R⁹.

Embodiment III-9. The compound of any one of Embodiments III-1 to III-7, or a pharmaceutically acceptable salt, solvate, tautomer, isotope, or isomer thereof, wherein R¹ is —NR¹⁰C(O)OR⁹.

Embodiment III-10. The compound of any one of Embodiment III-1 to 7, or a pharmaceutically acceptable salt, solvate, tautomer, isotope, or isomer thereof, wherein R¹ is —NR¹⁰S(O)₂R⁹.

Embodiment III-11. The compound of any one of Embodiments III-1 to III-10, or a pharmaceutically acceptable salt, solvate, tautomer, isotope, or isomer thereof, wherein R¹⁰ is hydrogen.

Embodiment III-12. The compound of any one of Embodiments III-1 to III-11, or a pharmaceutically acceptable salt, solvate, tautomer, isotope, or isomer thereof, wherein R⁸ is hydrogen.

Embodiment III-13. The compound of any one of Embodiments III-1 to III-12, or a pharmaceutically acceptable salt, solvate, tautomer, isotope, or isomer thereof, wherein R⁹ is hydrogen, (C$_{1-10}$)alkyl, heterocycloalkyl-alkyl, or (C$_{3-10}$)cycloalkyl.

Embodiment III-14. The compound of Embodiment III-13, wherein R⁹ is unsubstituted methyl, ethyl, propyl, or cyclopropyl.

Embodiment III-15. The compound of any one of Embodiments III-1 to III-7, or a pharmaceutically acceptable salt, solvate, tautomer, isotope, or isomer thereof, wherein R¹ is —C(O)NR⁸R⁹, and the R⁸ and R⁹ together with the nitrogen to which they are attached form an unsubstituted or substituted heterocycloalkyl.

Embodiment III-16. The compound of Embodiment III-15, or a pharmaceutically acceptable salt, solvate, tautomer, isotope, or isomer thereof, wherein the heterocycloalkyl is a 4- to 8-membered heterocycloalkyl.

Embodiment III-17. The compound of any one of Embodiments III-1 to III-7, or III-15, or a pharmaceutically acceptable salt, solvate, tautomer, isotope, or isomer thereof, wherein $R^1$ is $-C(O)NR^8R^9$, and the $R^8$ and $R^9$ together with the nitrogen to which they are attached form an unsubstituted or substituted piperidinyl.

Embodiment III-18. The compound of Embodiment III-16 or III-17, or a pharmaceutically acceptable salt, solvate, tautomer, isotope, or isomer thereof, wherein the substituents are independently selected from the group consisting of halo, oxo, $(C_{1-10})$alkyl, $-OR^{23}$, $-C(O)OR^{23}$, and $-NR^{23}C(O)OR^{23}$, wherein each $(C_{1-10})$alkyl is unsubstituted or substituted with $-OR^{31}$.

Embodiment III-19. The compound of Embodiment III-17, or a pharmaceutically acceptable salt, solvate, tautomer, isotope, or isomer thereof, wherein the piperidinyl is substituted with one to three substituents independently selected from the group consisting of $-OR^{23}$, $(C_{1-10})$alkyl, $-C(O)OR^{23}$, and $-NR^{23}C(O)OR^{23}$.

Embodiment III-20. The compound of Embodiment III-19, or a pharmaceutically acceptable salt, solvate, tautomer, isotope, or isomer thereof, wherein $R^{23}$ is independently hydrogen or $(C_{1-10})$alkyl.

Embodiment III-21. The compound of any one of Embodiments III-1 to III-20, or a pharmaceutically acceptable salt, solvate, tautomer, isotope, or isomer thereof, wherein $R^2$ is halo or alkyl.

Embodiment III-22. The compound of any one of Embodiments III-1 to III-21, or a pharmaceutically acceptable salt, solvate, tautomer, isotope, or isomer thereof, wherein one of $X^1$, $X^2$, $X^3$, and $X^4$ is N.

Embodiment III-23. The compound of any one of Embodiments III-1 to III-21, or a pharmaceutically acceptable salt, solvate, tautomer, isotope, or isomer thereof, wherein $X^1$, $X^2$, and $X^4$ are $CR^4$, and $X^3$ is N.

Embodiment III-24. The compound of any one of Embodiments III-1 to III-21, or a pharmaceutically acceptable salt, solvate, tautomer, isotope, or isomer thereof, wherein two of $X^1$, $X^2$, $X^3$, and $X^4$ are N.

Embodiment III-25. The compound of any one of Embodiments III-1 to III-21, or a pharmaceutically acceptable salt, solvate, tautomer, isotope, or isomer thereof, wherein each of $X^1$, $X^2$, $X^3$ and $X^4$ is $CR^4$.

Embodiment III-26. The compound of any one of Embodiments III-1 to III-25, or a pharmaceutically acceptable salt, solvate, tautomer, isotope, or isomer thereof, wherein each $R^4$ is independently selected from the group consisting of hydrogen, halo, cyano, $(C_{1-10})$alkyl, and $-OR^{27}$.

Embodiment III-27. The compound of any one of Embodiments III-1 to III-25, or a pharmaceutically acceptable salt, solvate, tautomer, isotope, or isomer thereof, wherein $X^1$ is $CR^4$, wherein $R^4$ is hydrogen, halo, or methyl.

Embodiment III-28. The compound of any one of Embodiments III-1 to III-27, or a pharmaceutically acceptable salt, solvate, tautomer, isotope, or isomer thereof, wherein $R^{14}$ is $(C_{1-10})$alkyl or heterocycloalkyl connected through an annular carbon atom, wherein the alkyl or heterocycloalkyl is unsubstituted or substituted with one to three substituents selected from the group consisting of $(C_{1-10})$alkyl, halo, $-C(O)OR^7$, oxo, and $-OR^5$.

Embodiment III-29. The compound of Embodiment III-28, or a or a pharmaceutically acceptable salt, solvate, tautomer, isotope, or isomer thereof, wherein $R^{14}$ is $(C_{1-10})$alkyl unsubstituted or substituted with one to three substituents selected from the group consisting of $(C_{1-10})$alkyl, halo, $-C(O)OR^7$, oxo, and $-OR^5$.

Embodiment III-30. The compound of any one of Embodiments III-1 to III-27, or a pharmaceutically acceptable salt, solvate, tautomer, isotope, or isomer thereof, wherein $R^{14}$ is unsubstituted $(C_{3-10})$cycloalkyl or $(C_{3-10})$halocycloalkyl.

Embodiment III-31. The compound of any one of Embodiments III-1 to III-30, or a pharmaceutically acceptable salt, solvate, tautomer, isotope, or isomer thereof, wherein $R^{15}$, $R^{16}$, and $R^{17}$ are hydrogen.

Embodiment III-32. The compound of any one of Embodiments III-1 to III-27, or a pharmaceutically acceptable salt, solvate, tautomer, isotope, or isomer thereof, wherein $R^{14}$ and $R^{15}$, together with the atoms to which they are attached, form a heterocyclyl.

Embodiment III-33. The compound of any one of Embodiments III-1 to III-22, or III-28 to 32, wherein at least one of $X^2$, $X^3$ and $X^4$ is N, and an adjacent annular carbon is bonded to $R^4$, wherein the $R^4$ is independently hydrogen, fluoro, cyano, $(C_{1-10})$alkyl, or $-OR^{27}$.

Embodiment III-34. The compound of any one of Embodiments III-1 to III-33, or a pharmaceutically acceptable salt, solvate, tautomer, isotope, or isomer thereof, wherein $R^3$ is hydrogen.

Embodiment III-35. The compound of any one of Embodiments III-1 to III-33, or a pharmaceutically acceptable salt, solvate, tautomer, isotope, or isomer thereof, wherein $R^3$ is halo or alkyl.

Embodiment III-36. The compound of any one of Embodiments III-1 to III-35, or a pharmaceutically acceptable salt, solvate, tautomer, isotope, or isomer thereof, wherein $R^2$ is halo or alkyl.

Embodiment III-37. The compound of any one of Embodiments III-1 to III-35, or a pharmaceutically acceptable salt, solvate, tautomer, isotope, or isomer thereof, wherein $R^2$ is chloro.

Embodiment III-38. The compound of any one of Embodiments III-1 to III-37, or a pharmaceutically acceptable salt, solvate, tautomer, isotope, or isomer thereof, wherein when one or more of $R^4$, $R^5$, $R^8$, $R^9$, $R^{10}$, $R^{14}$, $R^{16}$, $R^{19}$, $R^{20}$, $R^{23}$, $R^{24}$, $R^{25}$, $R^{26}$, $R^{27}$, $R^{28}$, and $R^{30}$ is heterocycloalkyl; or wherein $R^8$ and $R^9$, together with the nitrogen atom to which they are attached, form a heterocycloalkyl; or wherein two $R^{18}$, together with the nitrogen atom to which they are attached; or wherein two $R^{19}$, together with the nitrogen to which they are attached, form a heterocycloalkyl; or wherein two $R^{25}$, together with the nitrogen to which they are attached, form a heterocycloalkyl; or wherein two $R^{27}$, together with the nitrogen to which they are attached, form a heterocycloalkyl; each heterocycloalkyl is independently a 3- to 10-membered heterocycloalkyl.

Embodiment III-39. The compound of any one of Embodiments III-1 to III-38, or a pharmaceutically acceptable salt, solvate, tautomer, isotope, or isomer thereof, wherein when one or more of $R^4$, $R^8$, $R^9$, $R^{10}$, $R^{14}$, $R^{16}$, and $R^{26}$ is heterocycloalkyl-alkyl, each heterocycloalkyl-alkyl is independently (3-10 membered)heterocycloalkyl$(C_{1-10})$alkyl.

Embodiment III-40. The compound of any one of Embodiments III-1 to III-39, or a pharmaceutically acceptable salt, solvate, tautomer, isotope, or isomer thereof, wherein when one or more of $R^8$, $R^9$, $R^{10}$, and $R^{26}$ is heteroaryl, each heteroaryl is independently a 5- to 10-membered heteroaryl.

Embodiment III-41. The compound of any one of Embodiments III-1 to III-40, or a pharmaceutically acceptable salt, solvate, tautomer, isotope, or isomer thereof, wherein when one or more of $R^8$, $R^9$, $R^{10}$, and $R^{26}$ is heteroaryl-alkyl, each heteroaryl-alkyl is independently a (5-10 membered)heteroaryl($C_{1-10}$)alkyl.

Embodiment III-42. The compound of any one of Embodiments III-1 to III-41, or a pharmaceutically acceptable salt, solvate, tautomer, isotope, or isomer thereof, wherein two $R^4$ on adjacent annular carbon atoms together with the carbon atoms to which they are attached form a carbocyclyl; or wherein $R^{14}$ and $R^{15}$ together with the atoms to which they are attached form a carbocyclyl; each carbocyclyl, is independently a ($C_3$-$C_8$)carbocyclyl.

Embodiment III-43. The compound of any one of Embodiments III-1 to III-42, or a pharmaceutically acceptable salt, solvate, tautomer, isotope, or isomer thereof, wherein two $R^4$ on adjacent annular carbon atoms together with the carbon atoms to which they are attached form a heterocyclyl; or wherein $R^{14}$ and $R^{15}$ together with the atoms to which they are attached form a heterocyclyl; each heterocyclyl is independently a 4- to 8-membered heterocyclyl.

Embodiment III-44. The compound of any one of Embodiments III-1 to III-43, or a pharmaceutically acceptable salt, solvate, tautomer, isotope, or isomer thereof, wherein when $R^{14}$ or $R^{16}$ is heterocycloalkenyl, each heterocycloalkenyl is independently a 3- to 8-membered heterocycloalkenyl.

Embodiment III-45. The compound of any one of Embodiments III-1 to III-3, or III-5 to III-44, wherein the compound is of Formula (X-Ai):

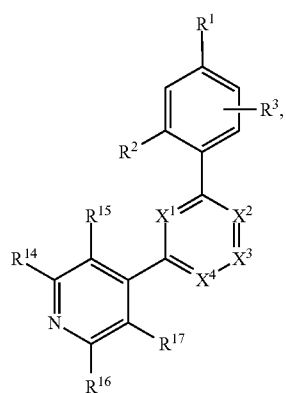

(X-Ai)

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (X).

Embodiment III-46. The compound of any one of Embodiments III-1, III-2, or III-4 to III-44, wherein the compound is of Formula (X-Bi):

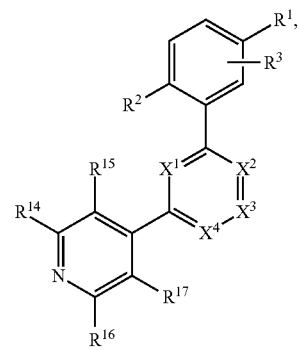

(X-Bi)

or a pharmaceutically acceptable salt, solvate, tautomer, isotope, or isomer thereof, wherein $R^1$, $R^2$, $R^3$, $R^{14}$, $R^{15}$, $R^{16}$, $R^{17}$, $X^1$, $X^2$, $X^3$, and $X^4$ are as defined for Formula (X).

Embodiment III-47. The compound of Embodiment III-1, selected from the group consisting of:

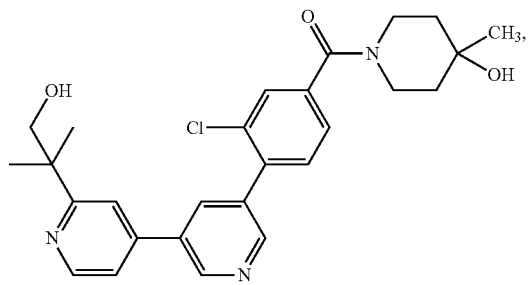

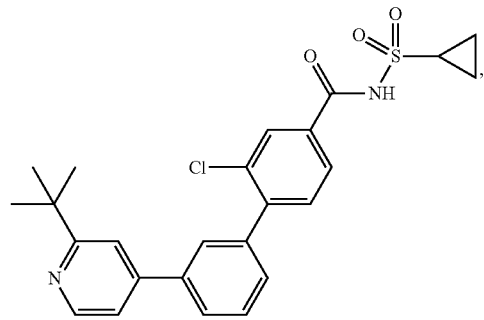

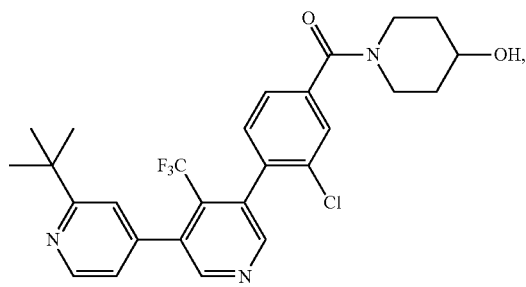

233
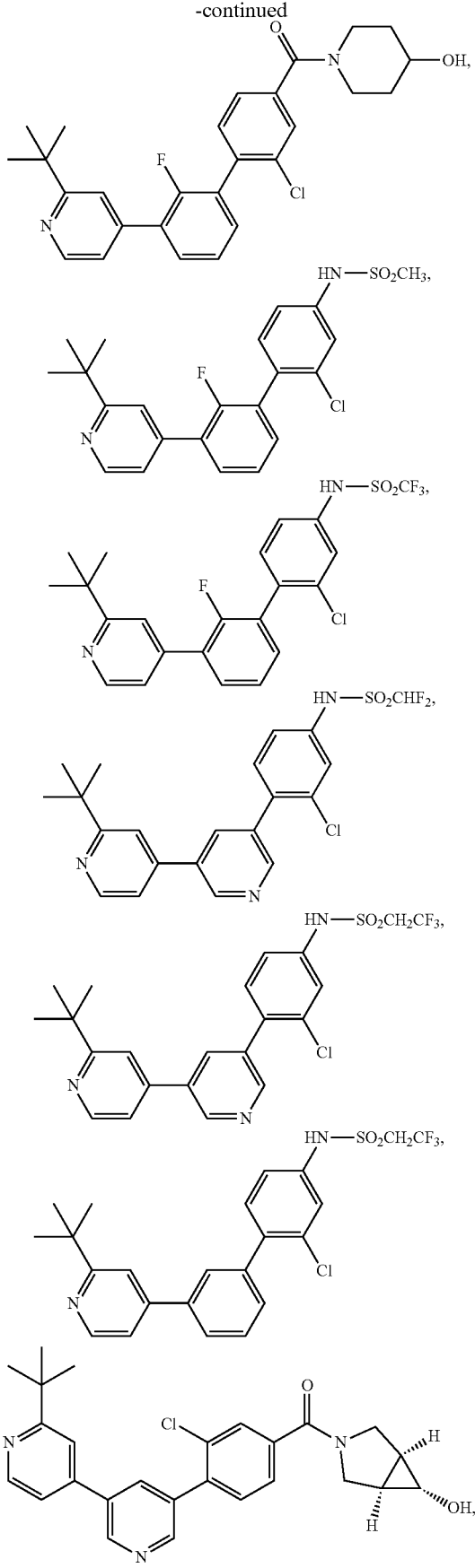
234
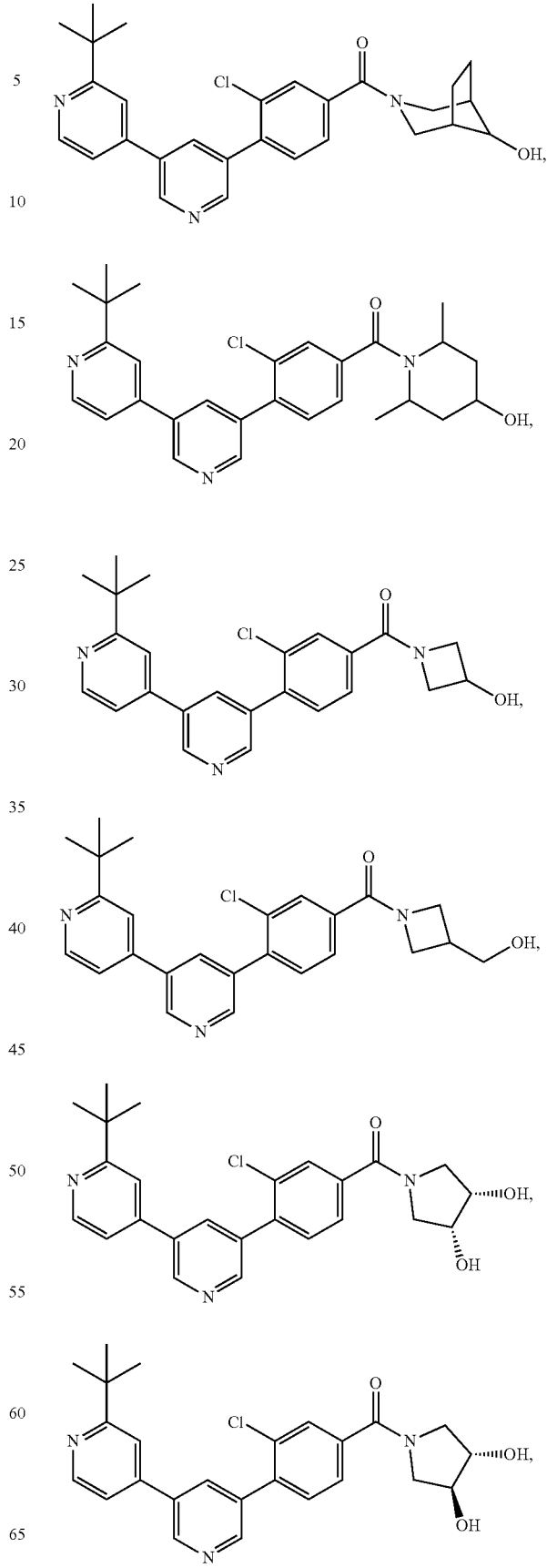

235
-continued
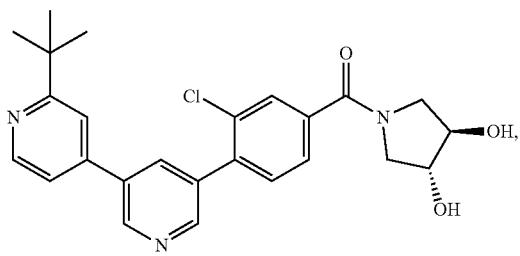
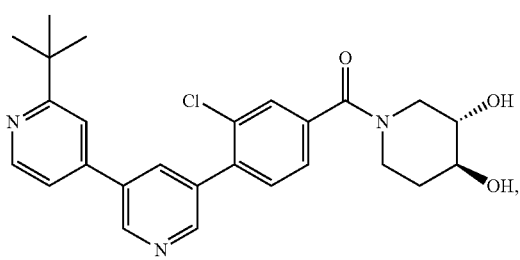
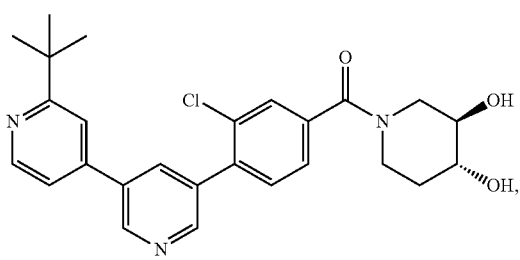
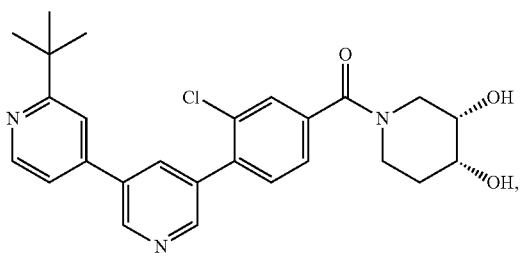
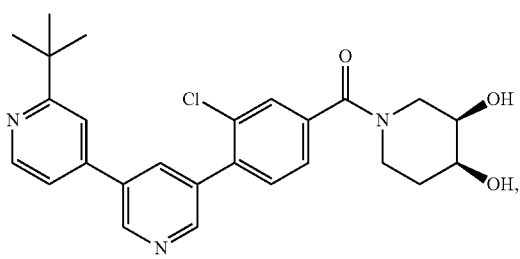
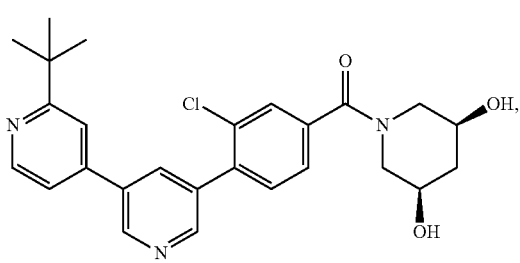
236
-continued
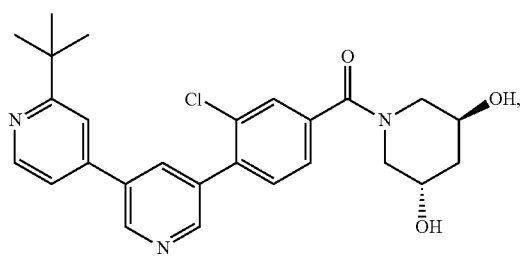
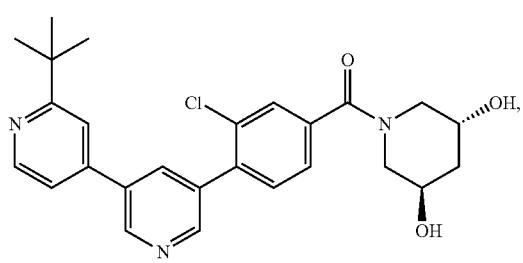
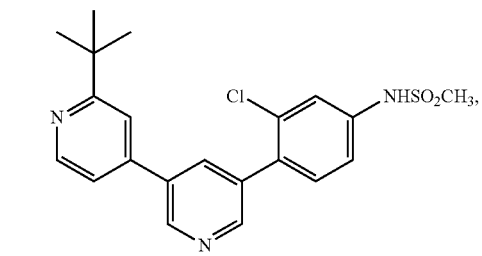
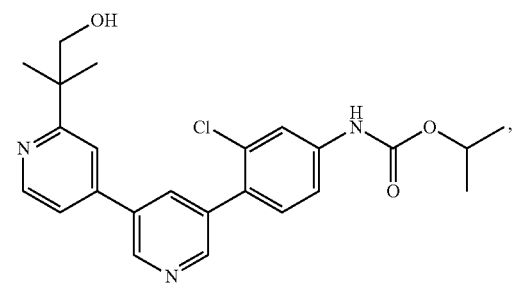
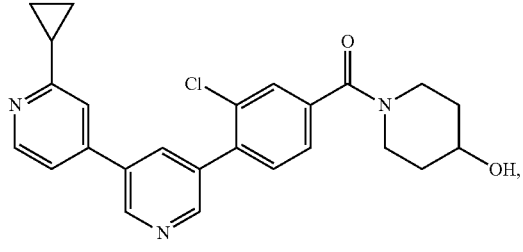
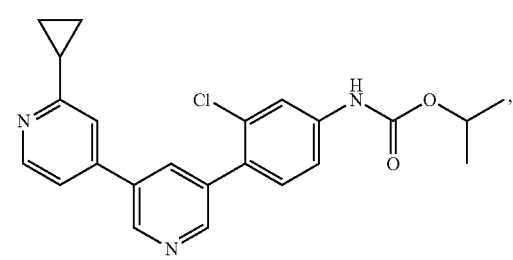

237
-continued
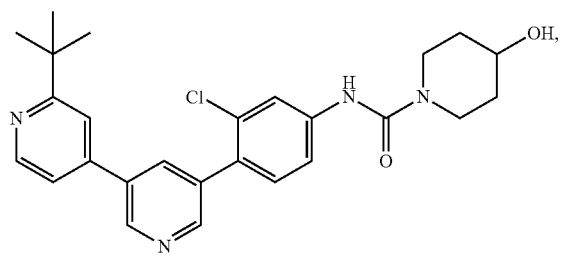
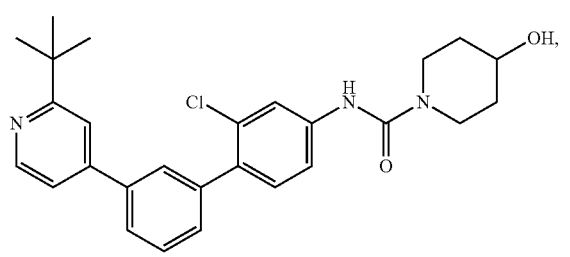
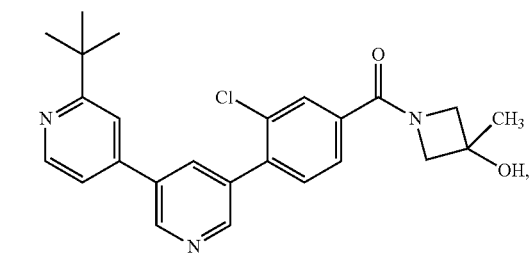
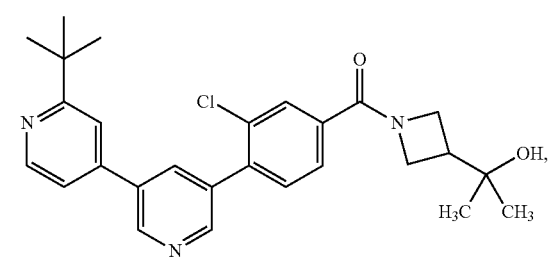
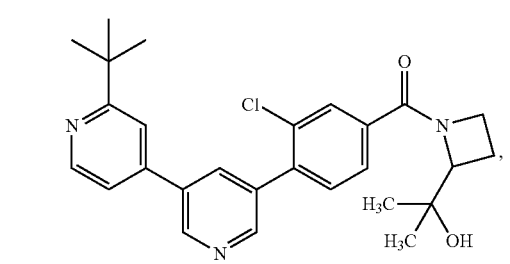
238
-continued
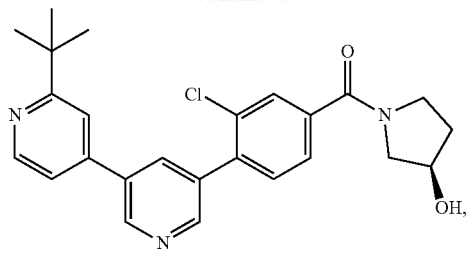
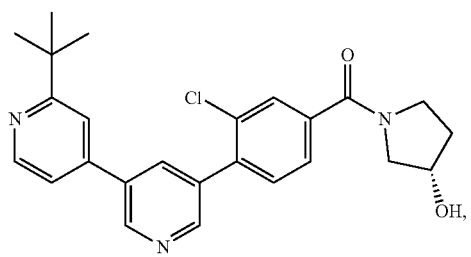
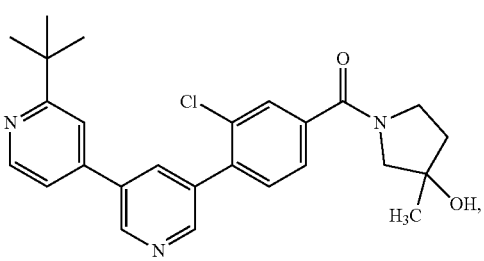
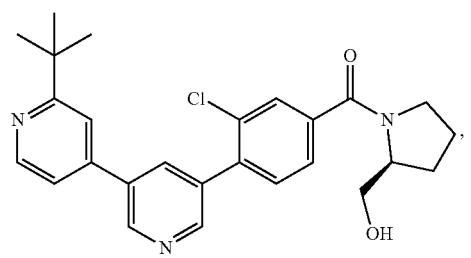
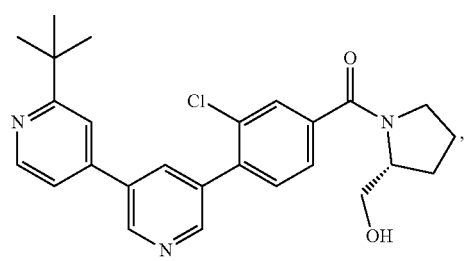
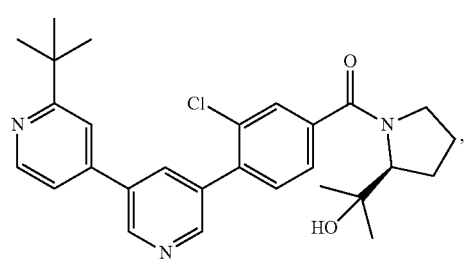

239
-continued
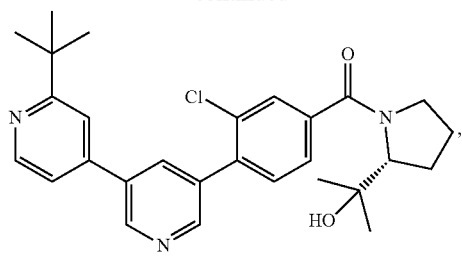
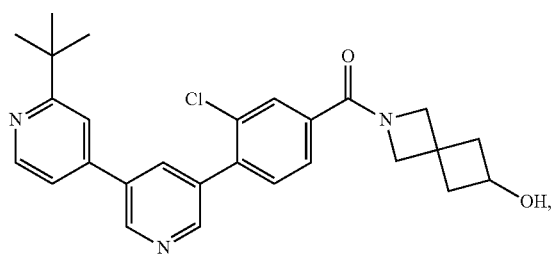
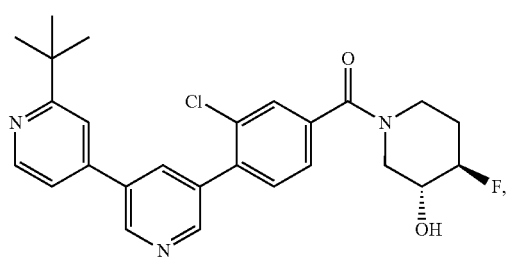
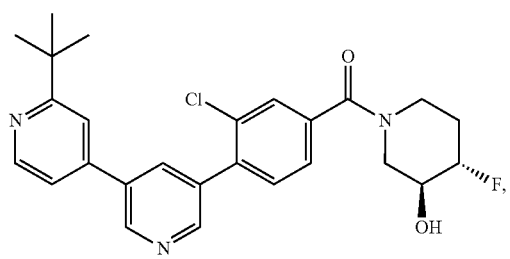
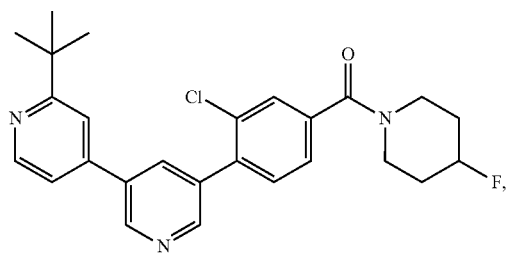
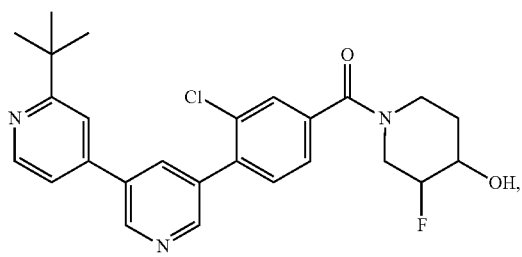
240
-continued
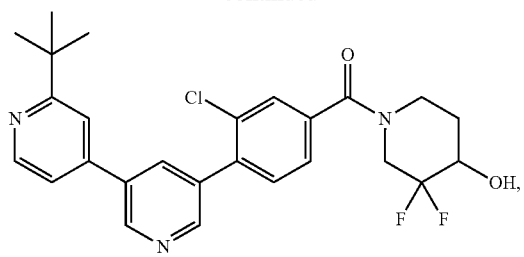
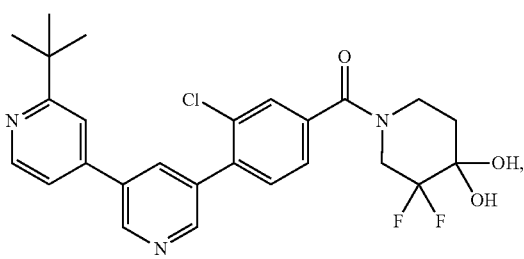
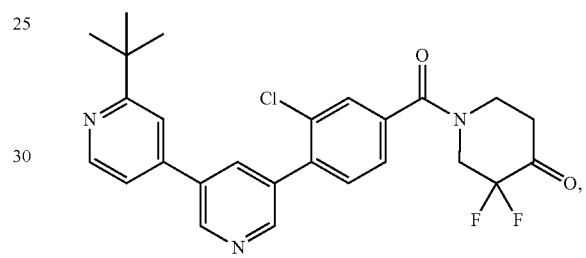
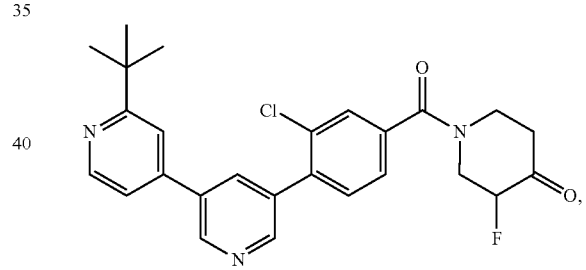
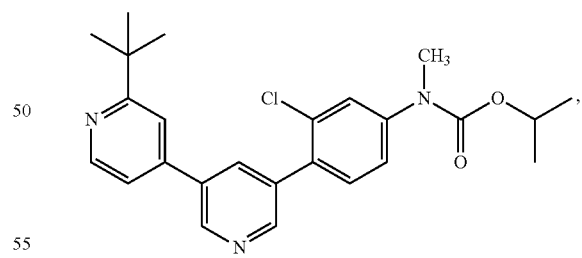
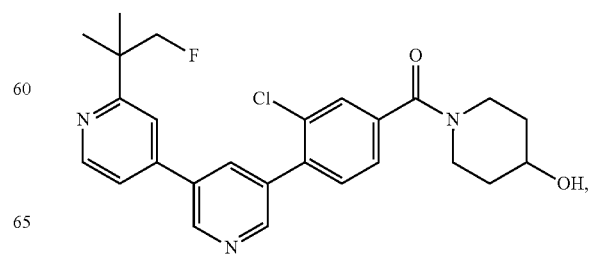

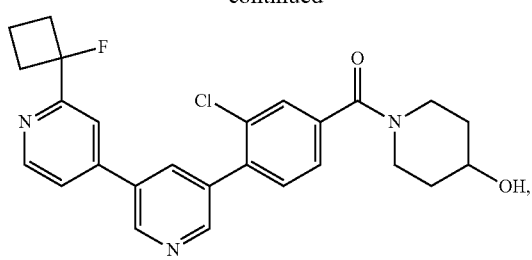
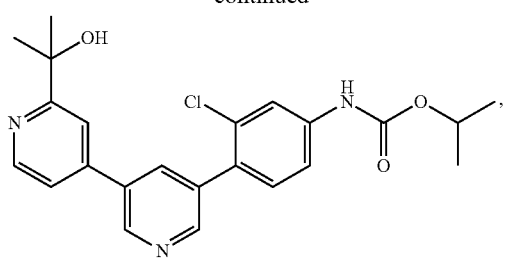
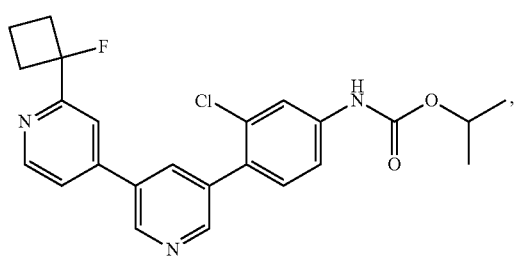
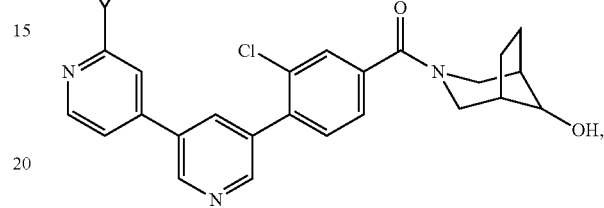
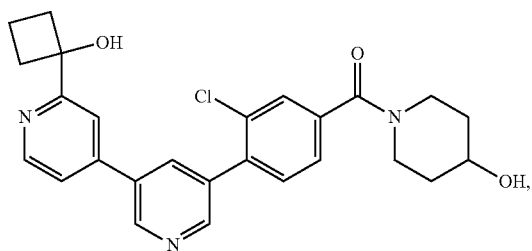
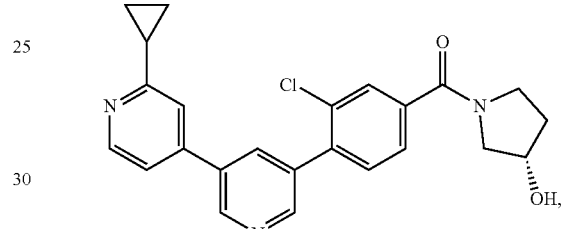
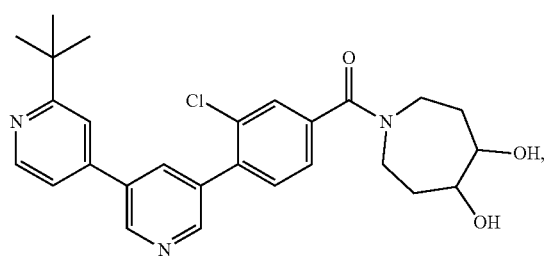
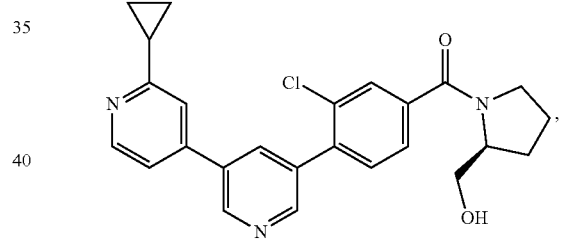
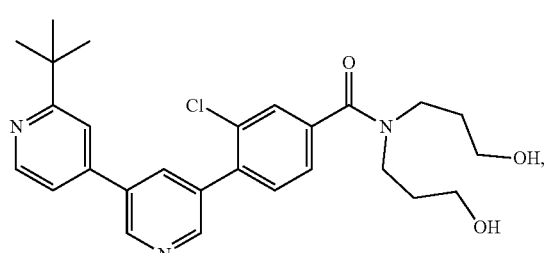
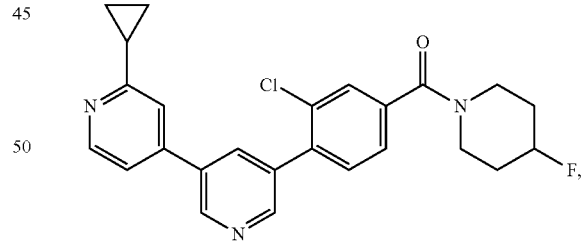
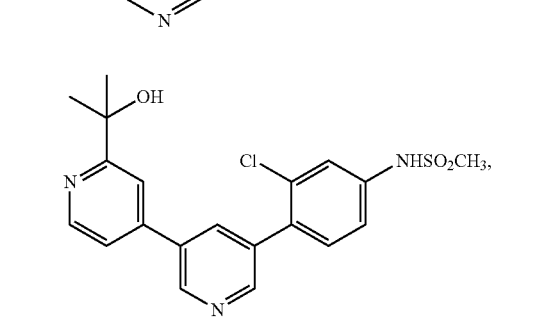
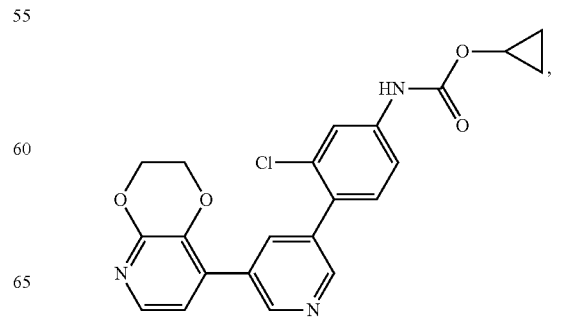

-continued
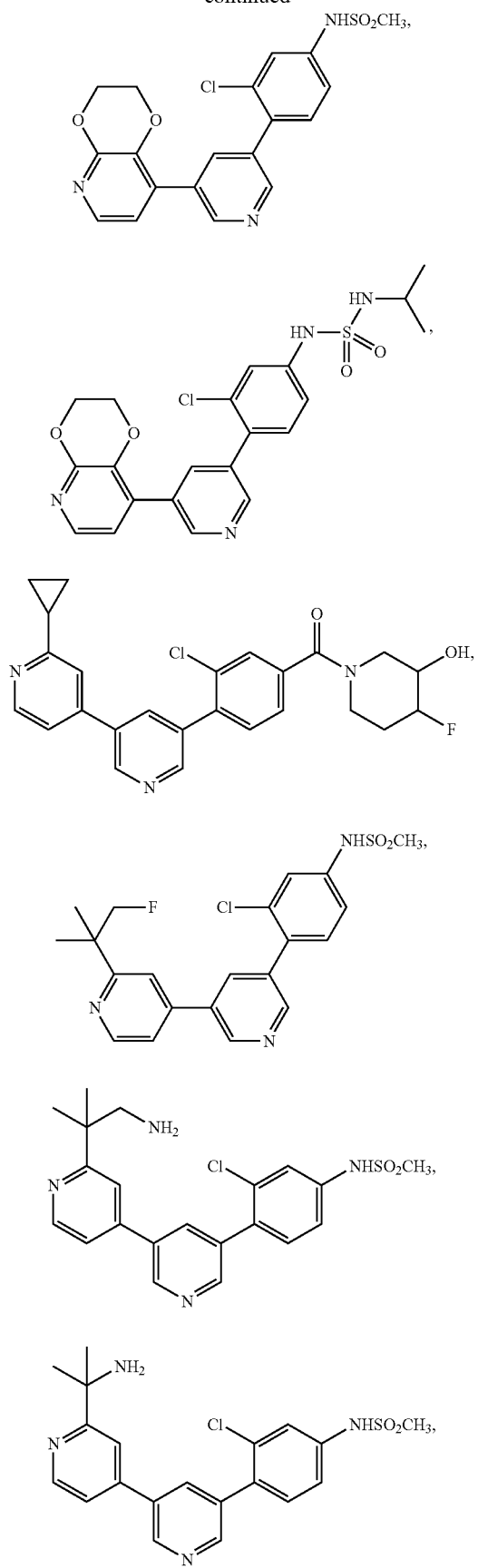
-continued
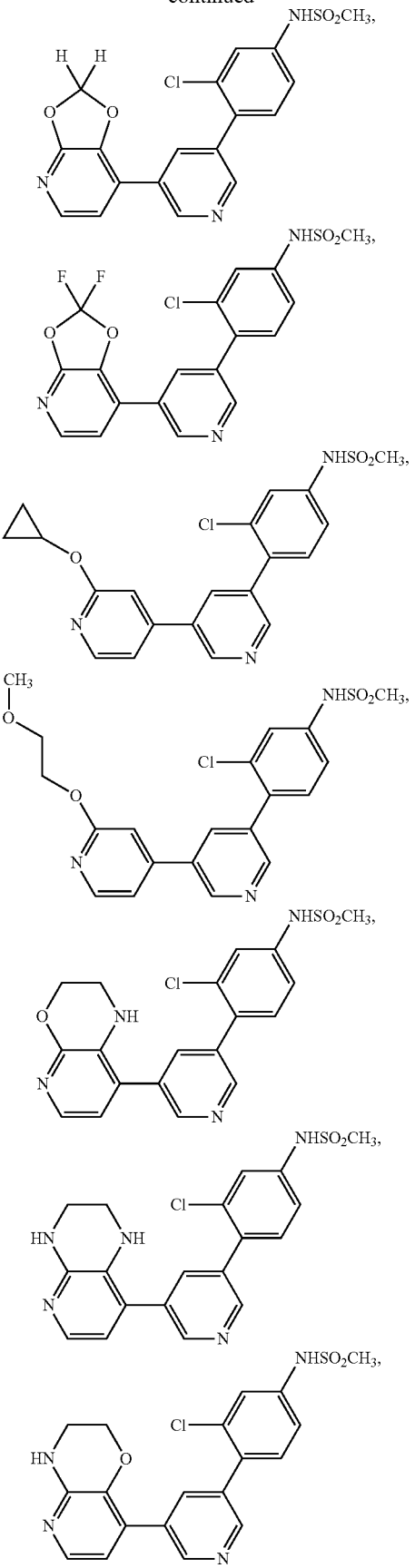

245
-continued
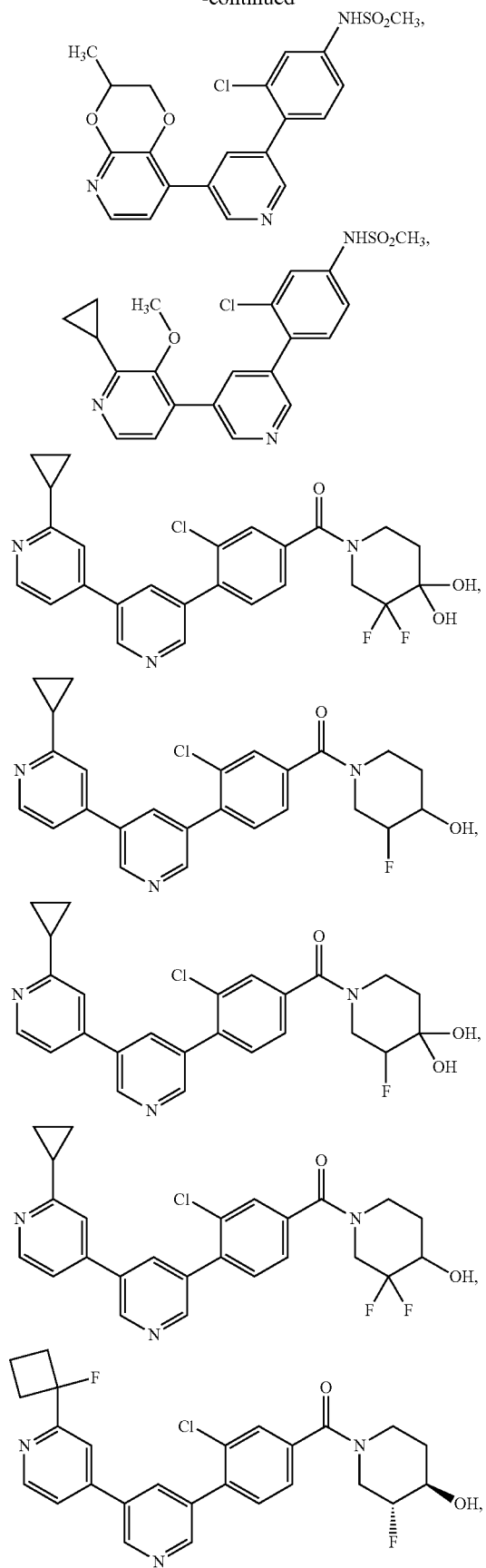
246
-continued
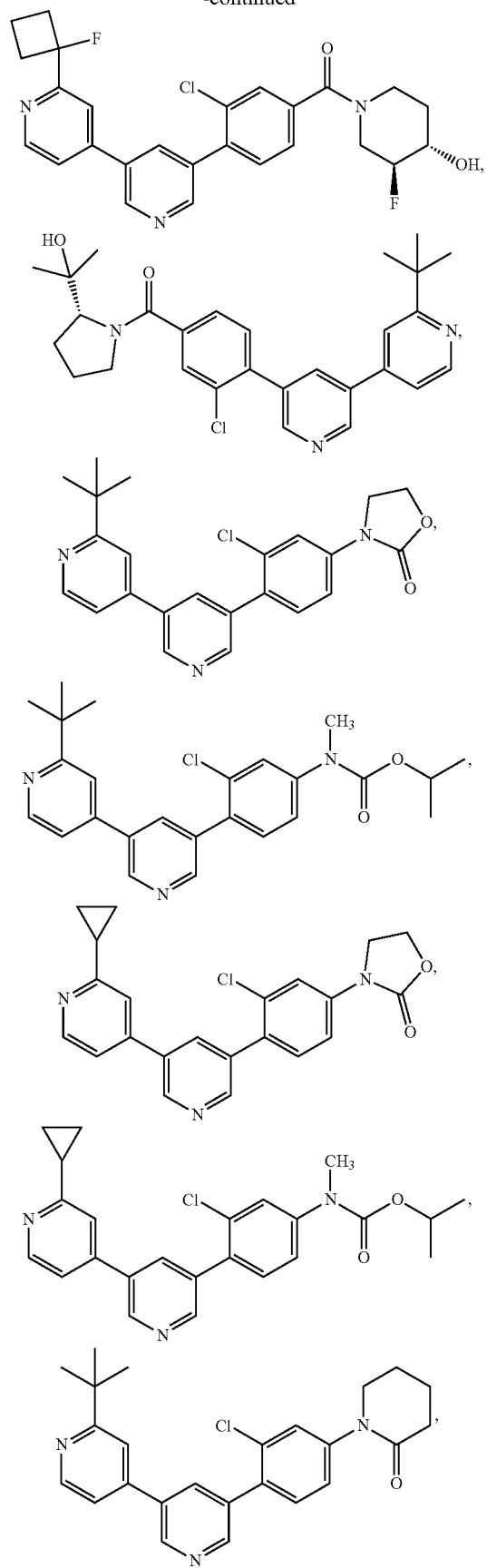

247
-continued
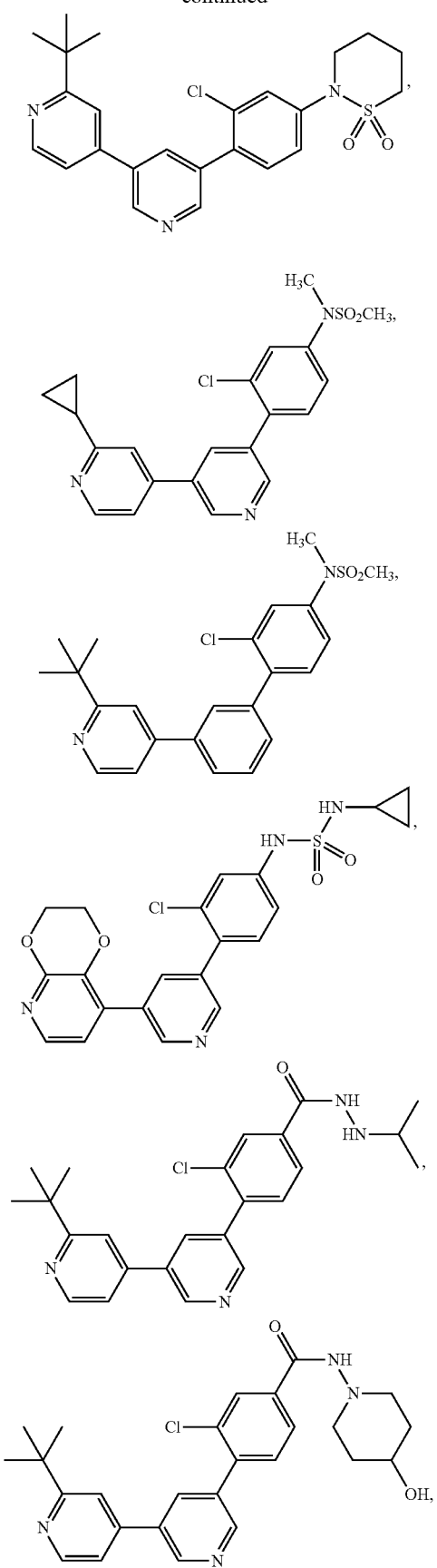
248
-continued
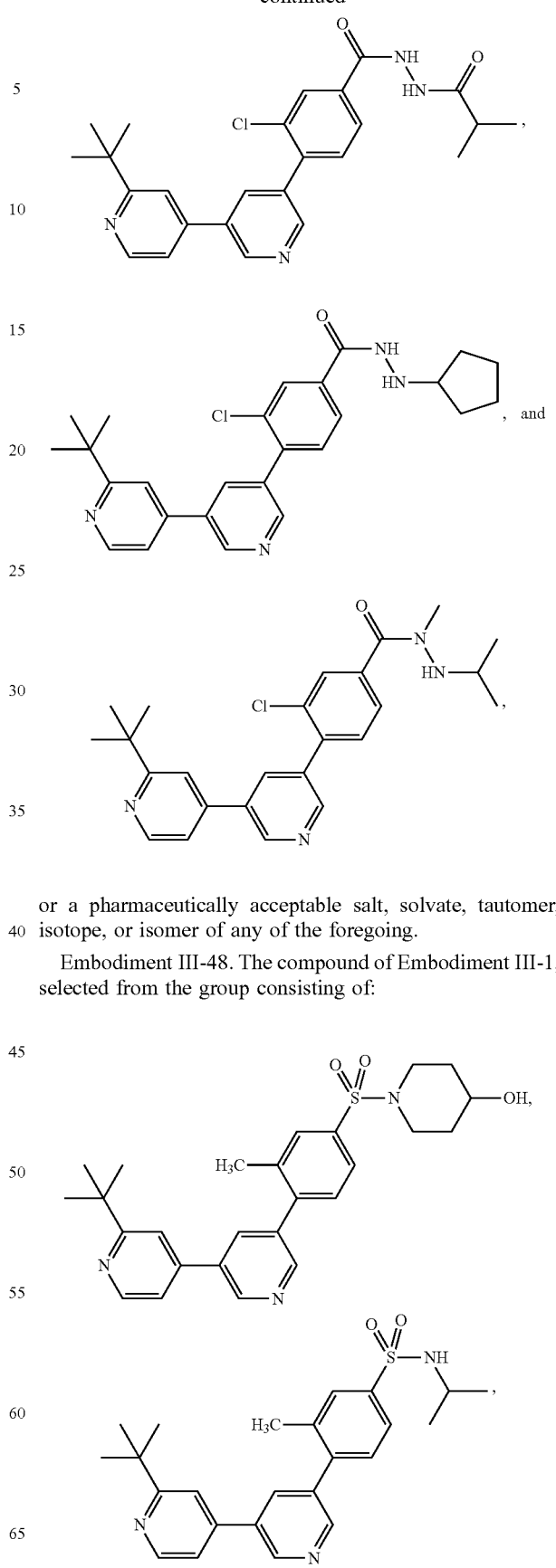
or a pharmaceutically acceptable salt, solvate, tautomer, isotope, or isomer of any of the foregoing.
Embodiment III-48. The compound of Embodiment III-1, selected from the group consisting of:

249
-continued
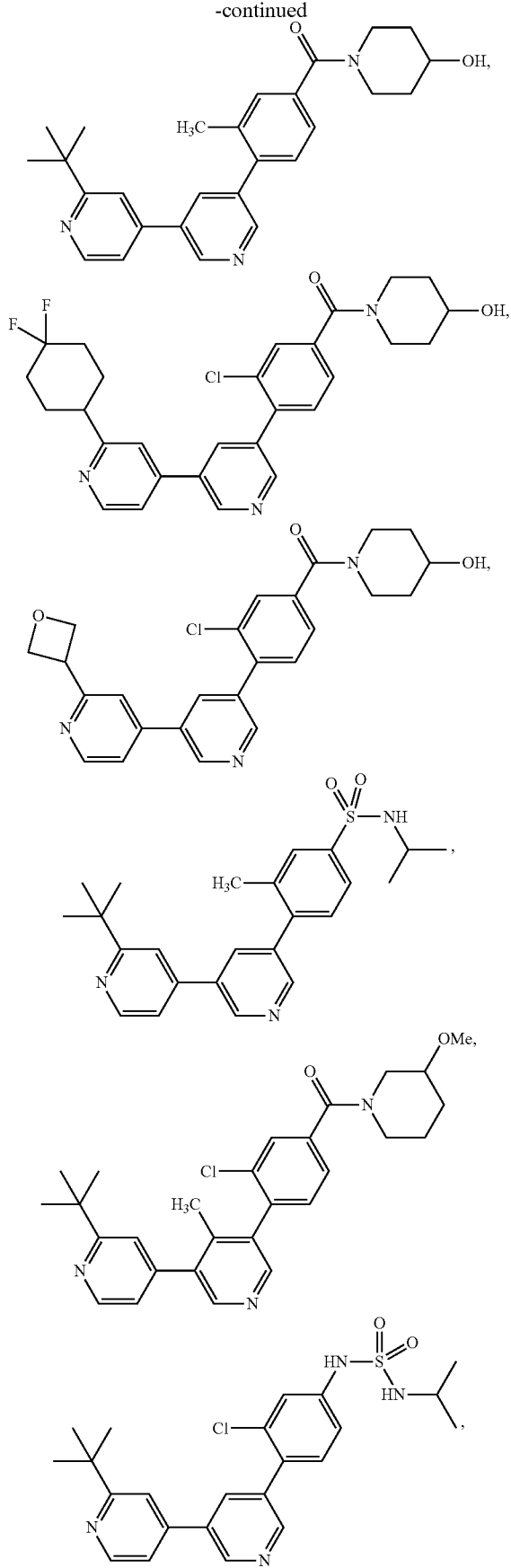
250
-continued
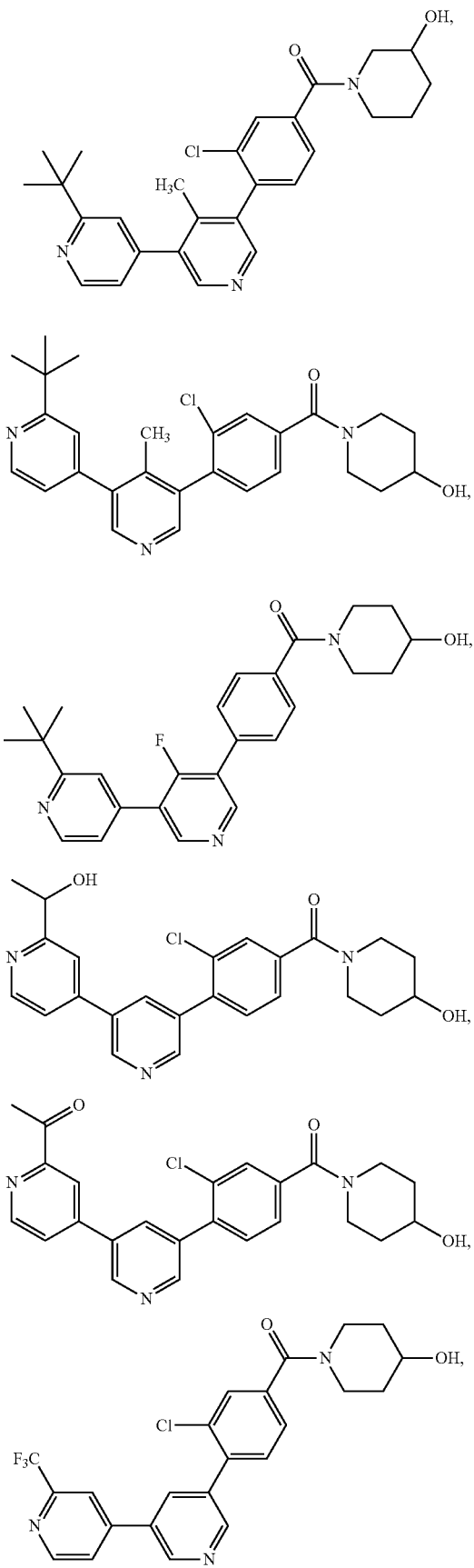

-continued
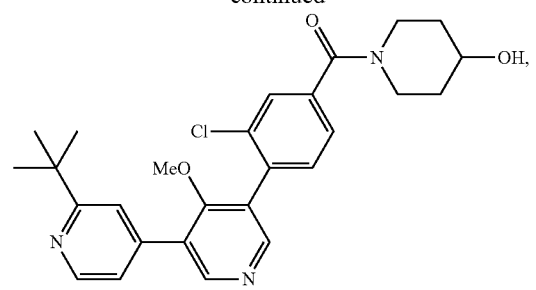
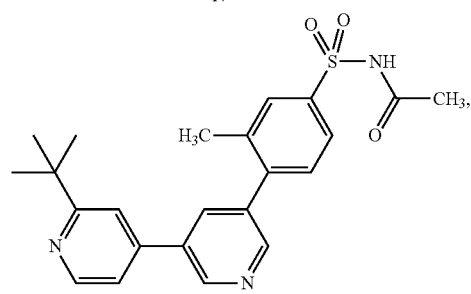
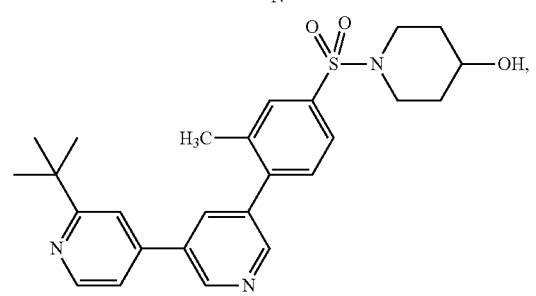
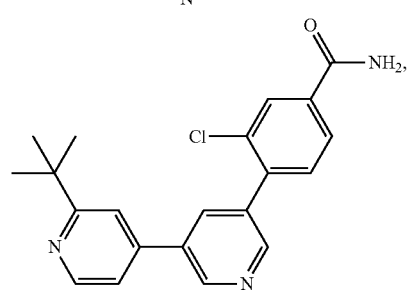
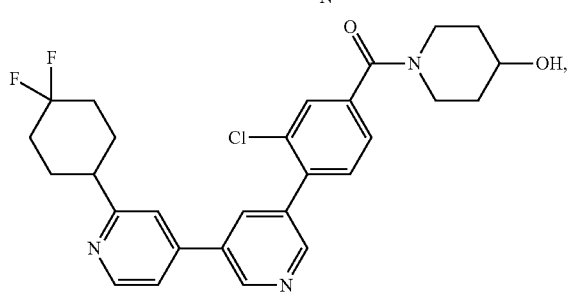
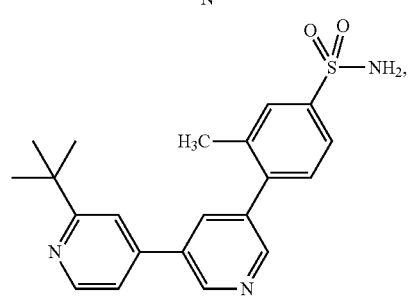
-continued
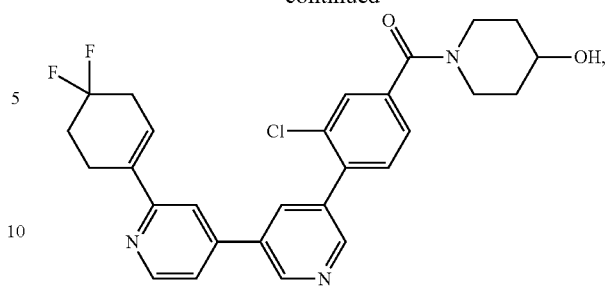
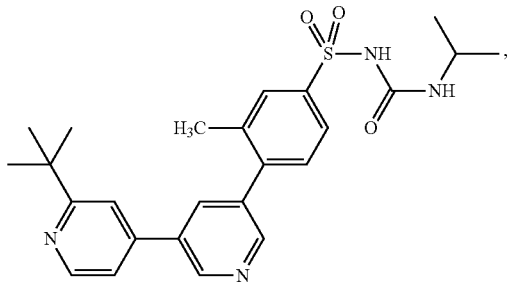
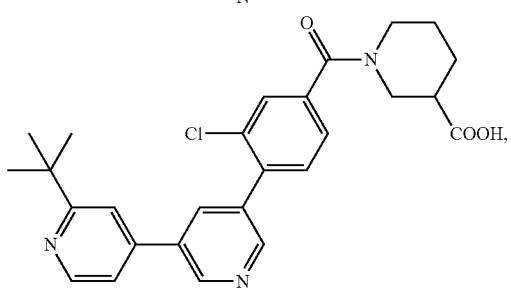
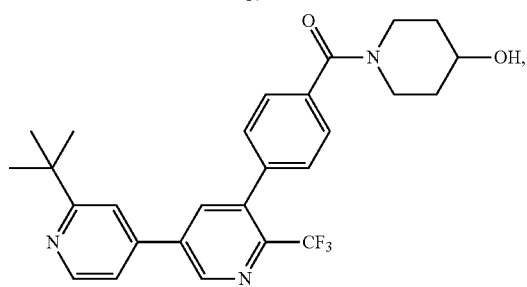
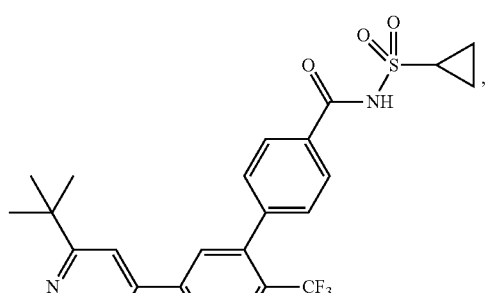
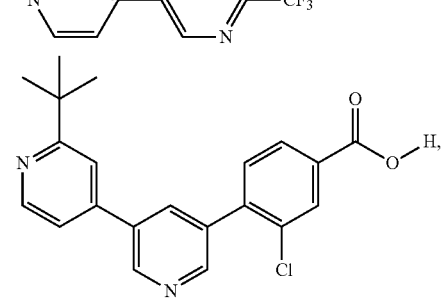

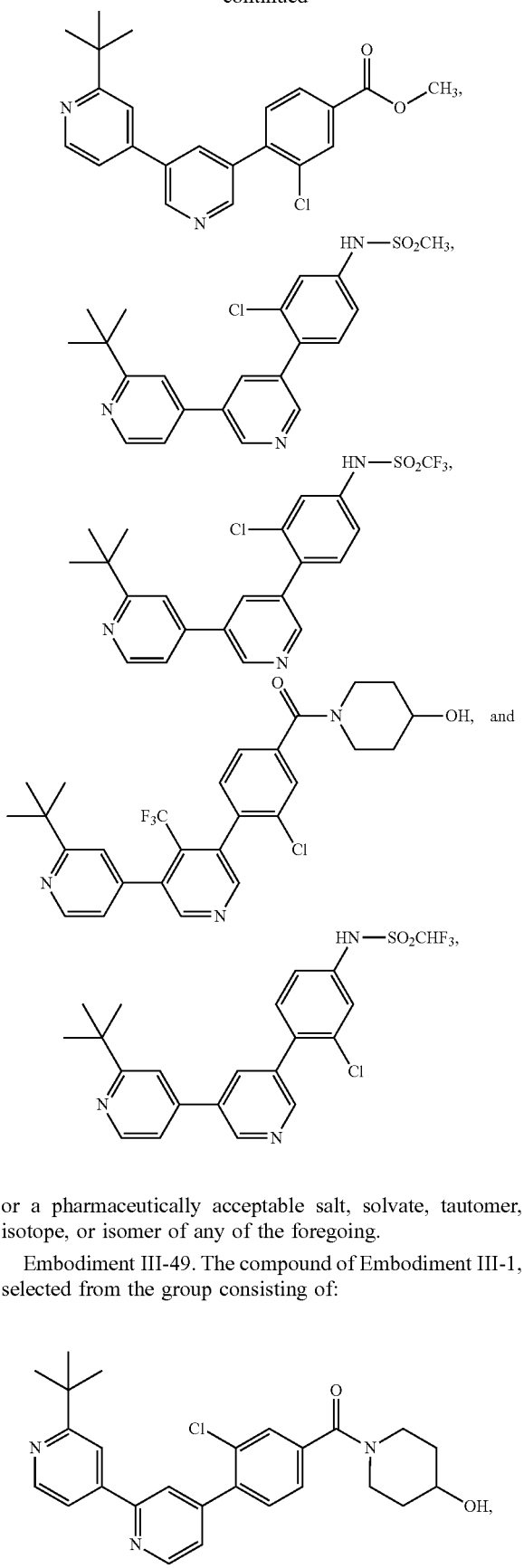
or a pharmaceutically acceptable salt, solvate, tautomer, isotope, or isomer of any of the foregoing.
Embodiment III-49. The compound of Embodiment III-1, selected from the group consisting of:
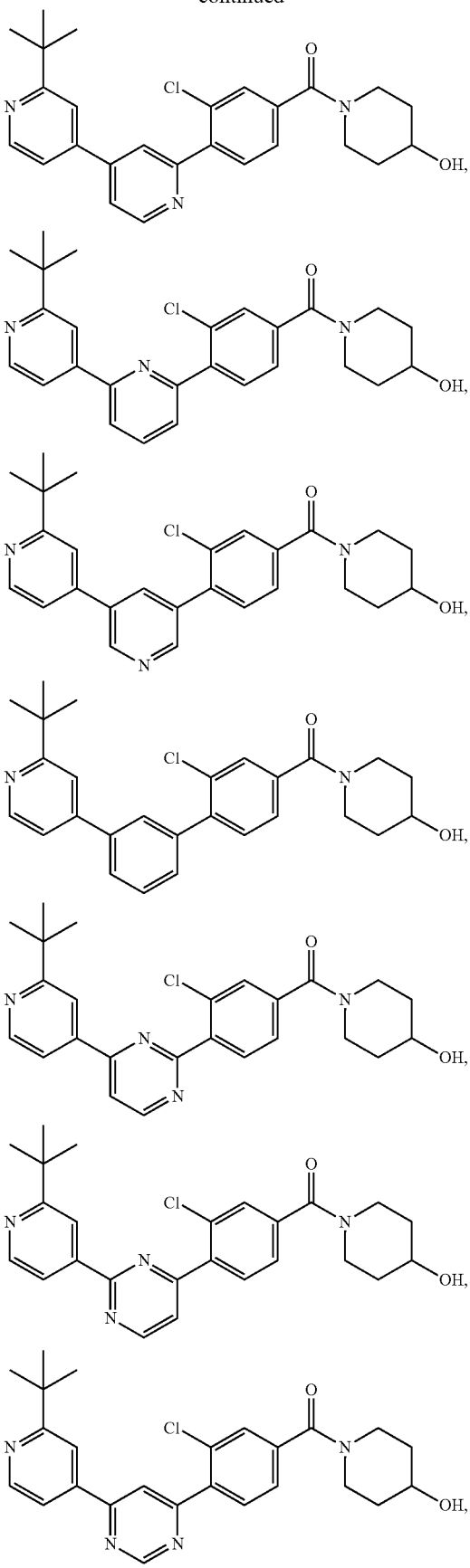

255
-continued
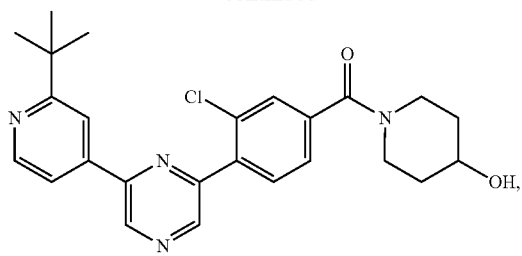
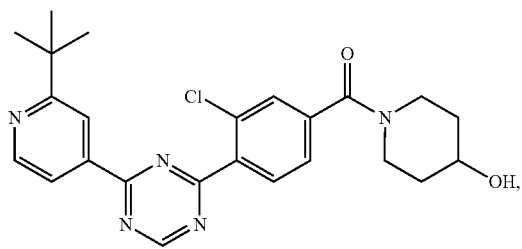
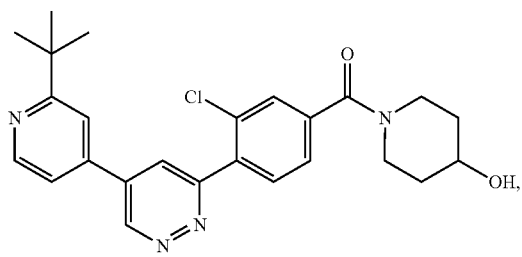
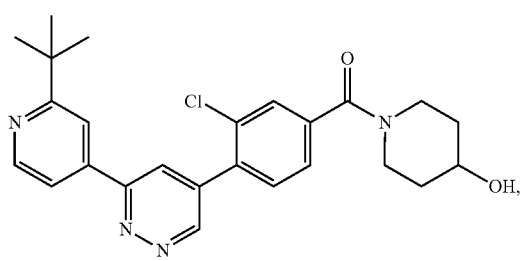
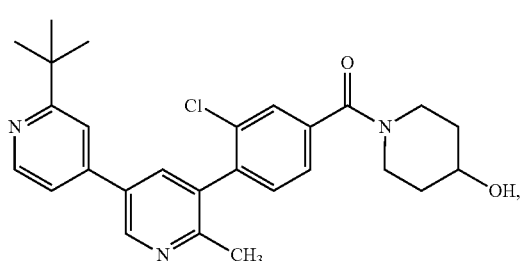
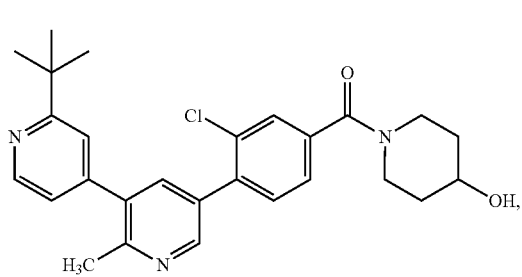
256
-continued
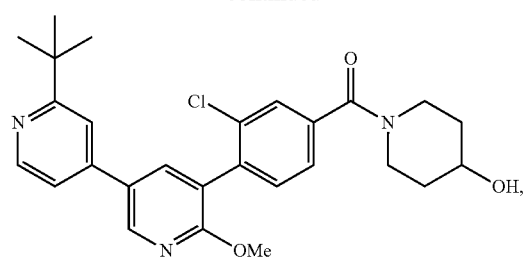
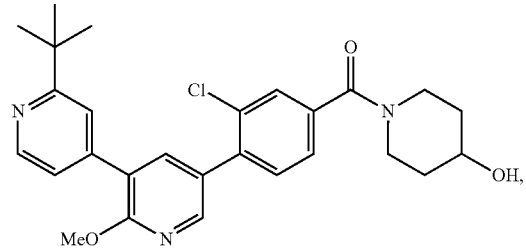
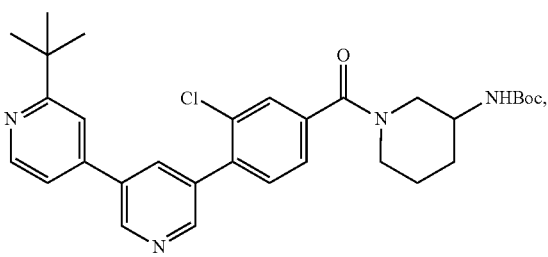
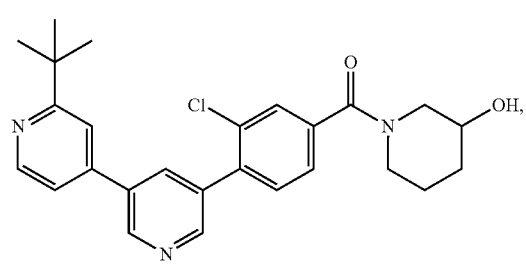
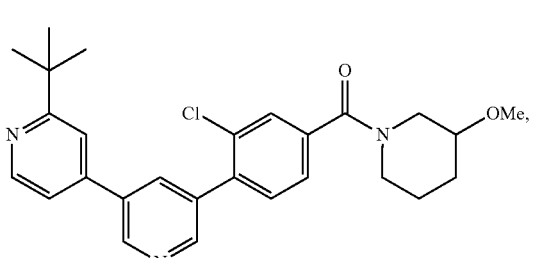
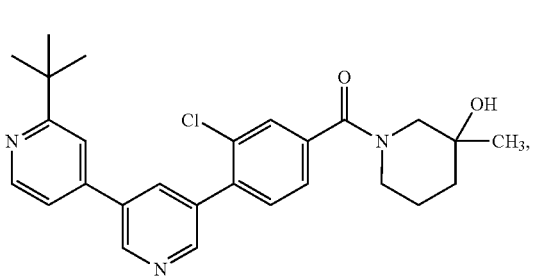

257
-continued
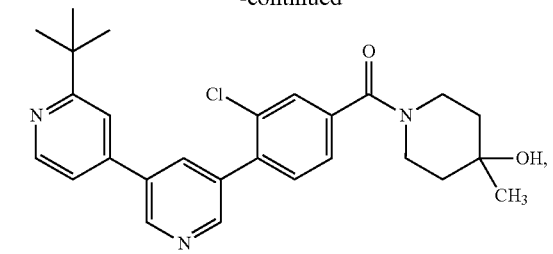
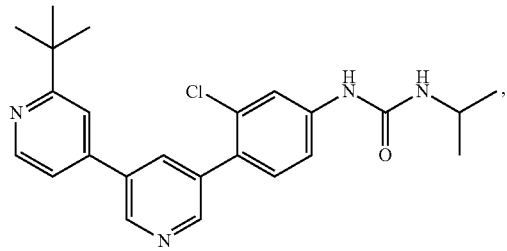
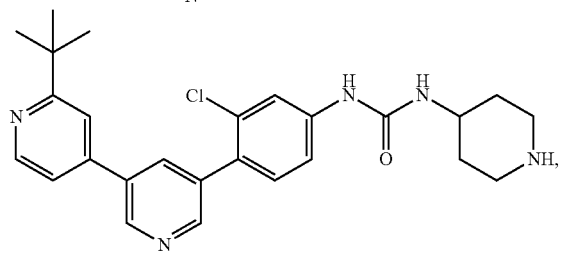
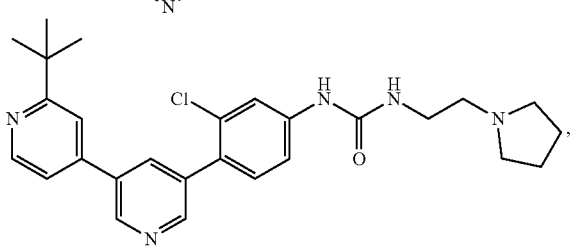
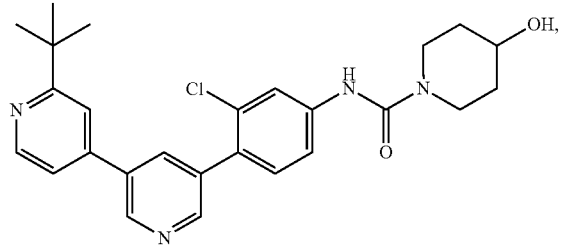
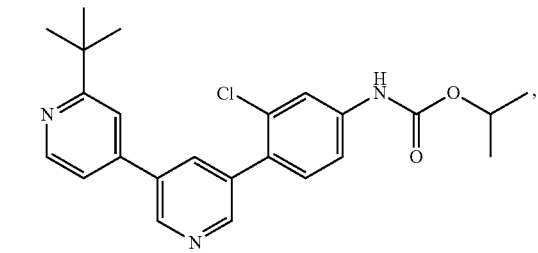
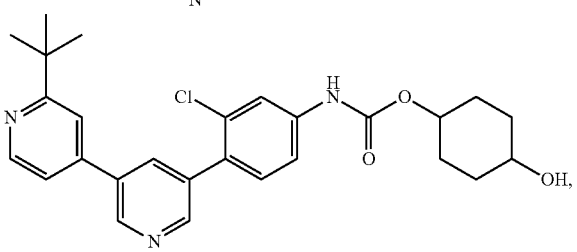
258
-continued
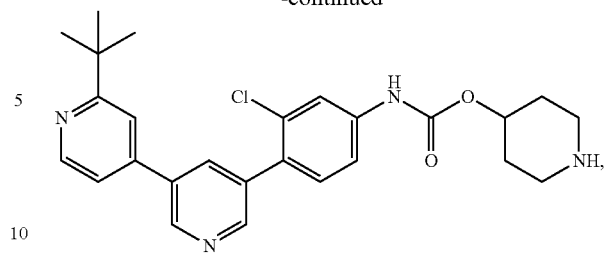
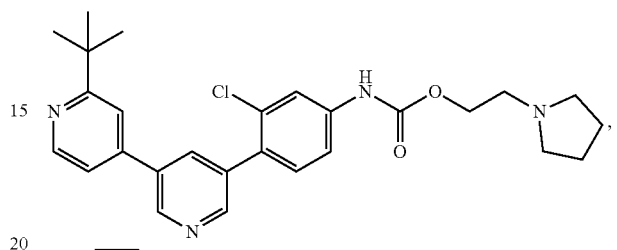
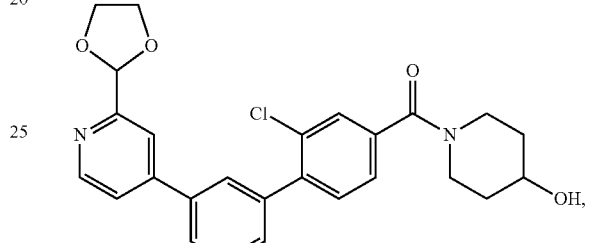
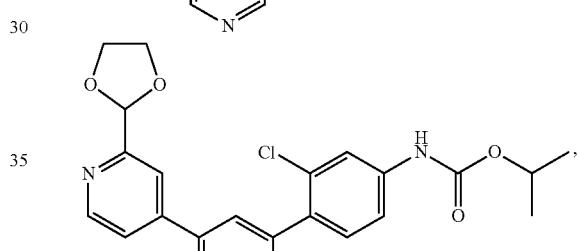
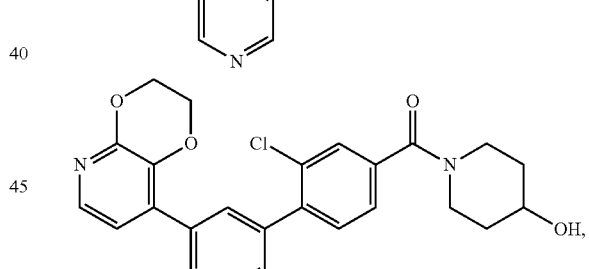
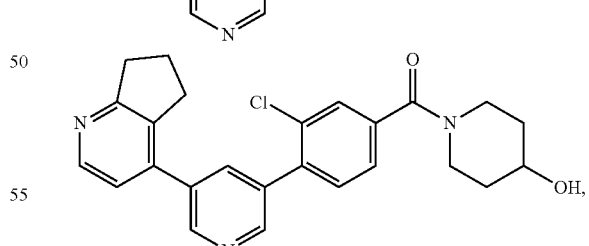
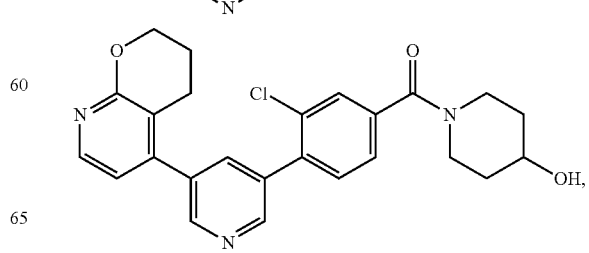

259
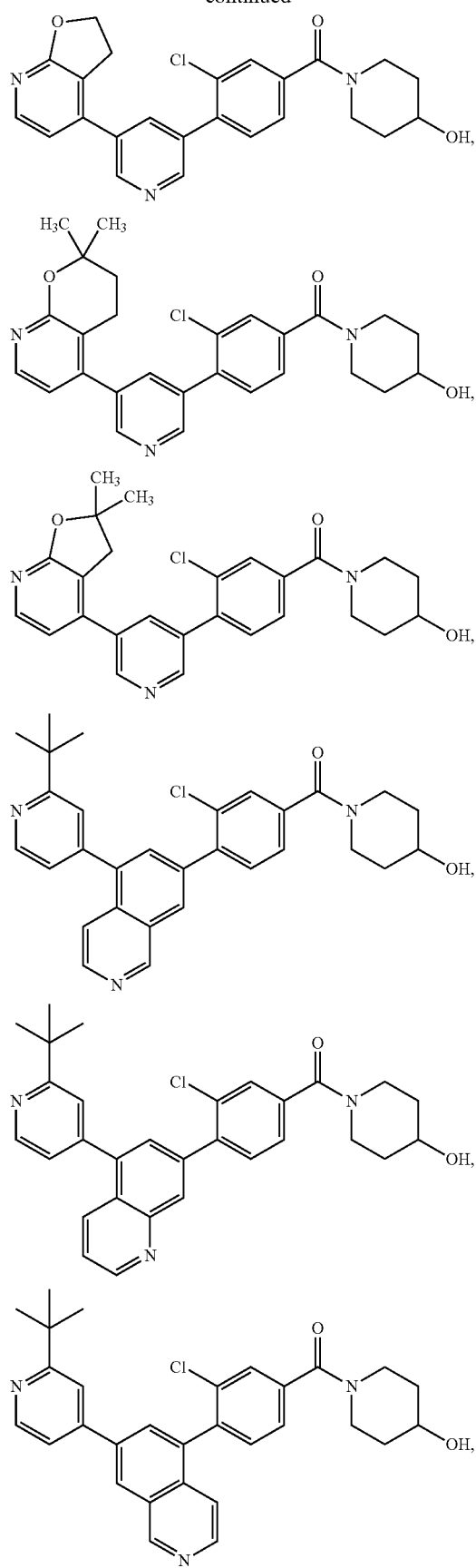
260
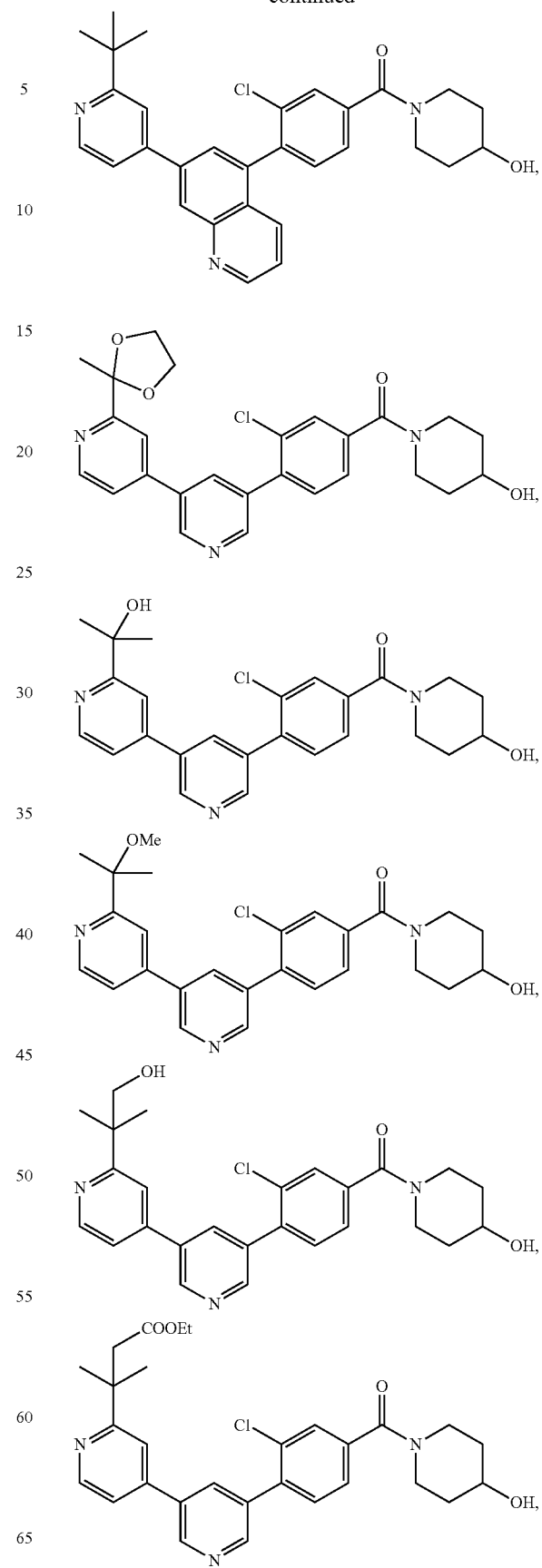

261
-continued
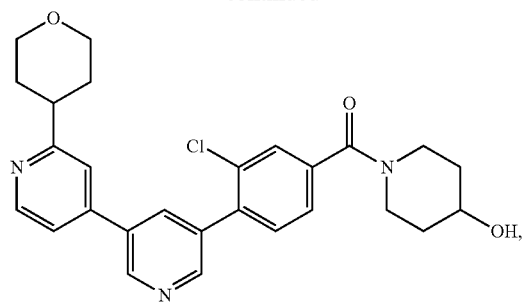
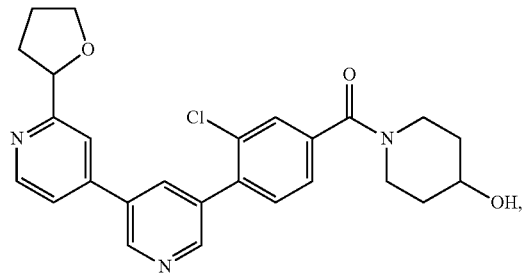
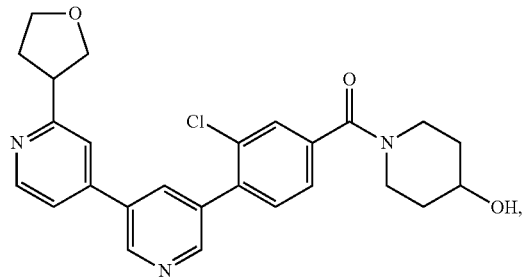
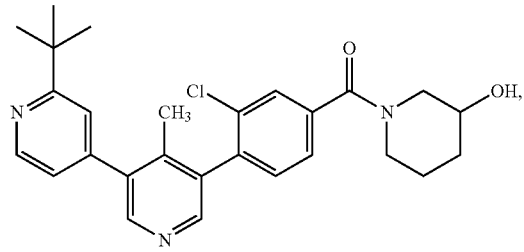
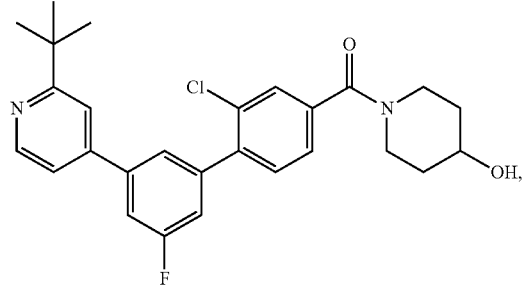
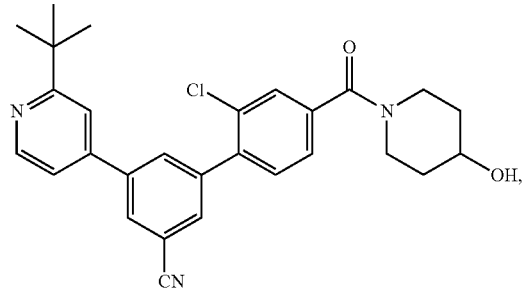
262
-continued
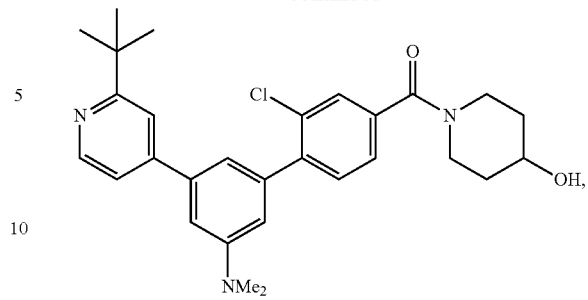
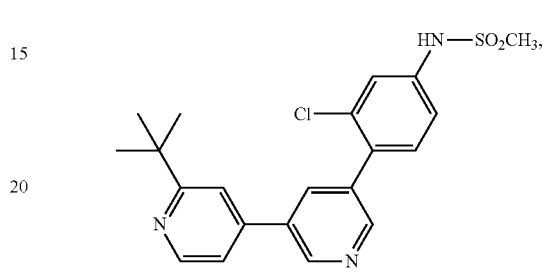
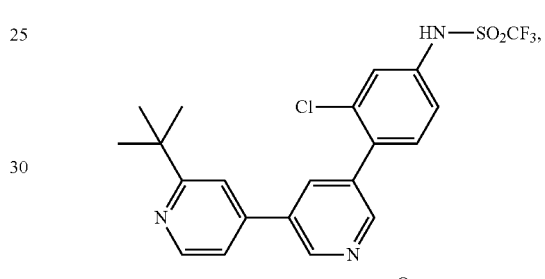
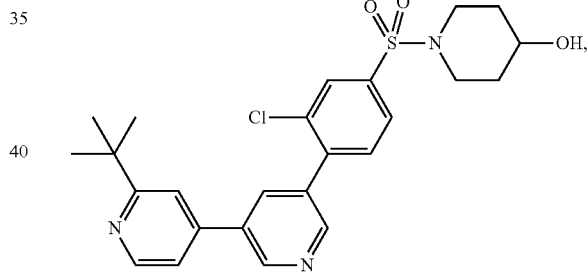
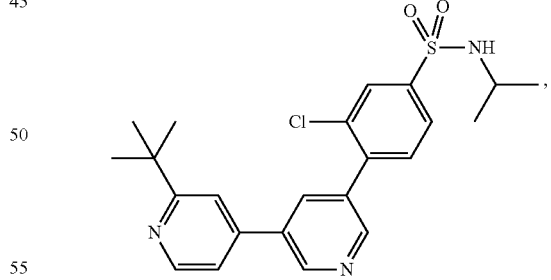
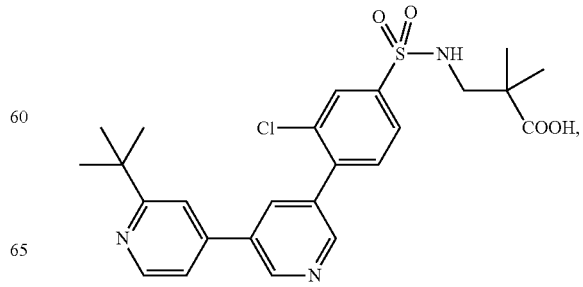

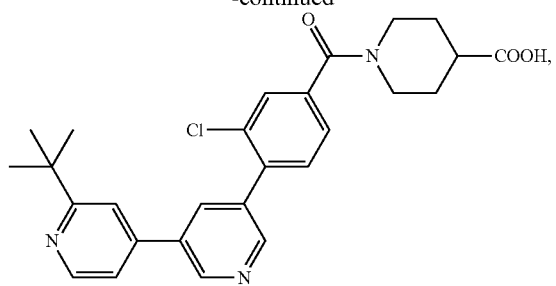
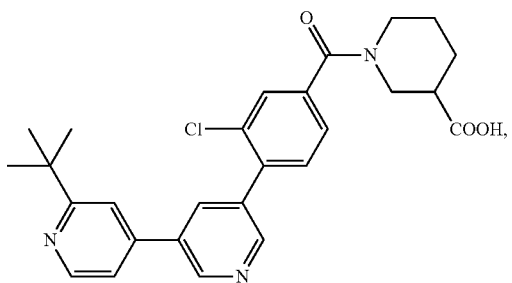
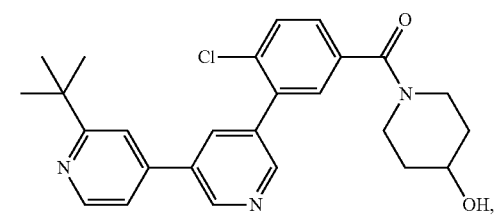
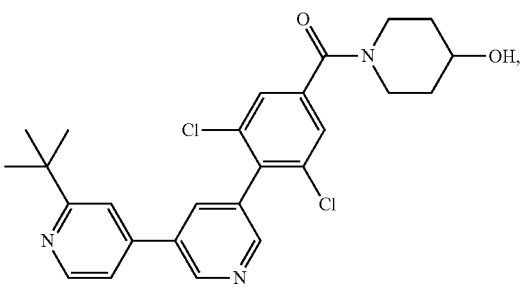
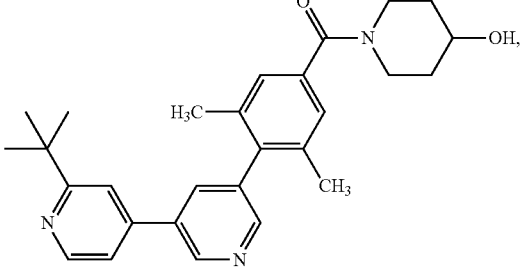
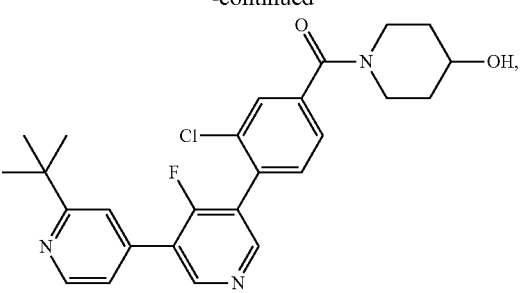
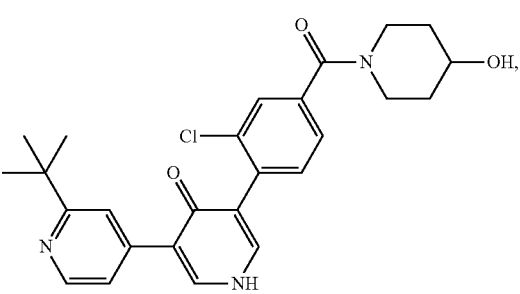
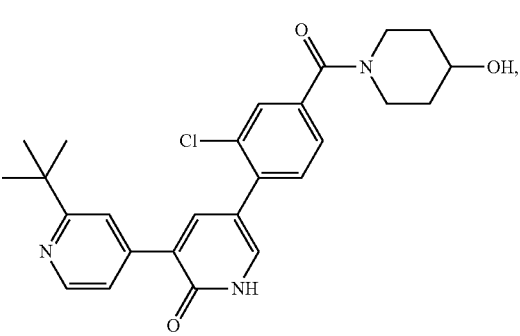
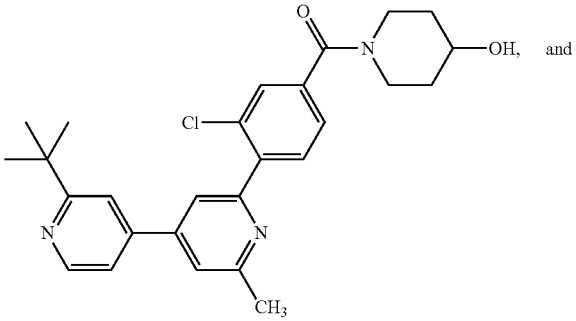
and
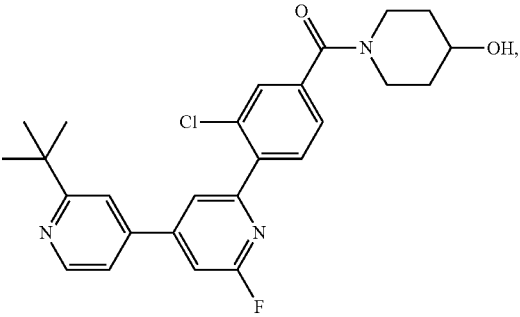 [SMILES: CC(C)(C)c1cc(-c2cc(F)nc(-c3ccc(C(=O)N4CCC(O)CC4)cc3Cl)c2)ccn1]
or a pharmaceutically acceptable salt, solvate, tautomer, isotope, or isomer of any of the foregoing.

Embodiment III-50. The compound of Embodiment III-1, selected from the group consisting of:

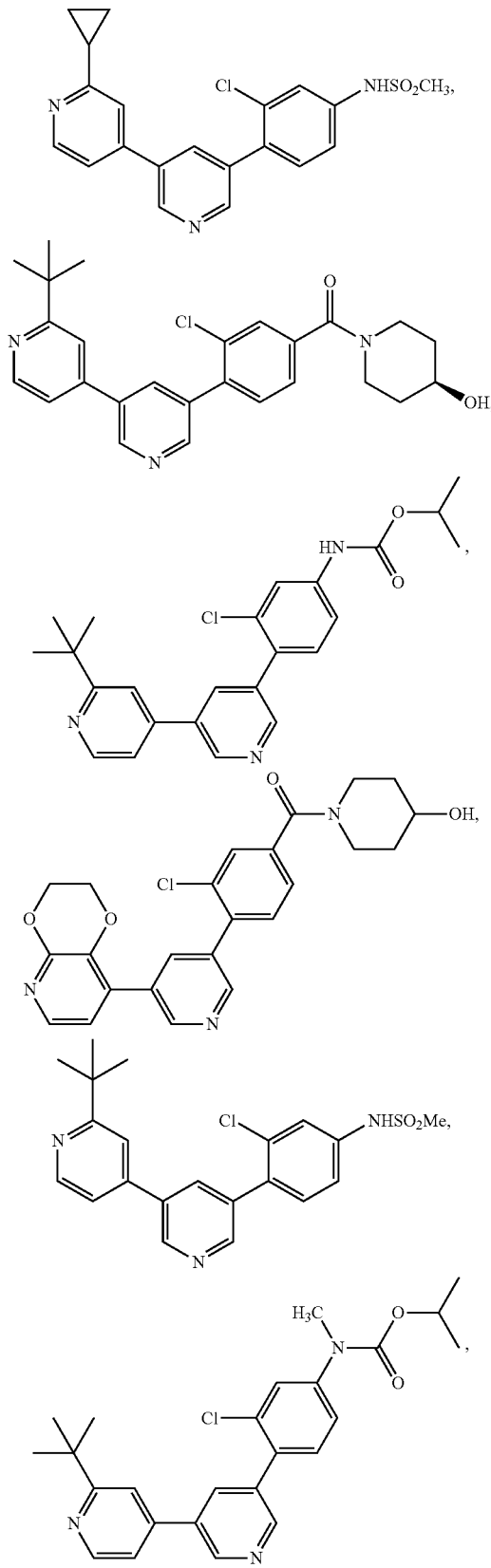

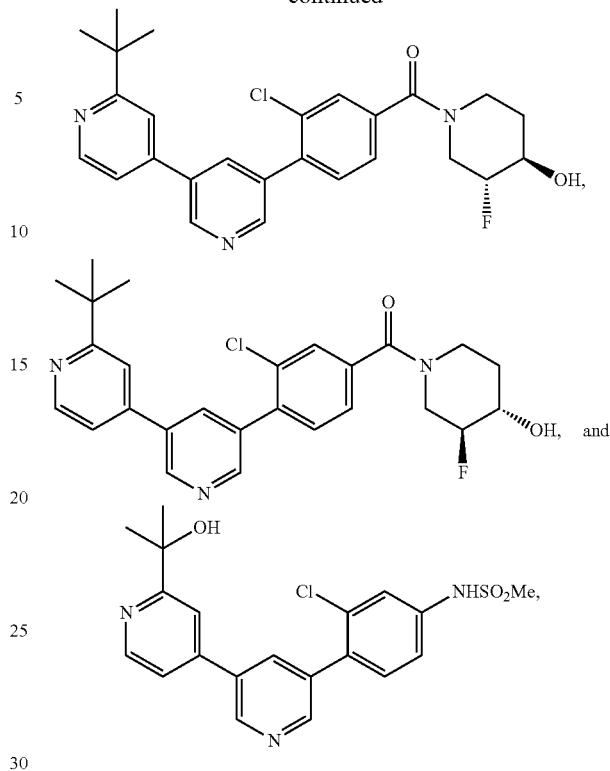

or a pharmaceutically acceptable salt, solvate, tautomer, isotope, or isomer of any of the foregoing.

Embodiment III-51. A pharmaceutical composition, comprising the compound of any one of Embodiments III-1 to III-50, or a pharmaceutically acceptable salt, solvate, tautomer, isotope, or isomer thereof, and a pharmaceutically acceptable excipient.

Embodiment III-52. A method of inhibiting a sterol regulatory element-binding protein (SREBP), comprising contacting the SREBP or contacting an SREBP cleavage activating-protein (SCAP) with a compound of any one of Embodiments III-1 to III-50, or a pharmaceutically acceptable salt, solvate, tautomer, isotope, or isomer thereof, or the pharmaceutical composition of Embodiment III-51.

Embodiment III-53. A method of inhibiting the proteolytic activation of a sterol regulatory element-binding protein (SREBP), comprising contacting an SREBP cleavage activating-protein (SCAP) with a compound of any one of Embodiments III-1 to III-50, or a pharmaceutically acceptable salt, solvate, tautomer, isotope, or isomer thereof, or the pharmaceutical composition of Embodiment III-51.

Embodiment III-54. The method of Embodiment III-52 or III-53, wherein the SREBP is an SREBP-1.

Embodiment III-55. The method of Embodiment III-54, wherein the SREBP-1 is SREBP-1a.

Embodiment III-56. The method of Embodiment III-54, wherein the SREBP-1 is SREBP-1c.

Embodiment III-57. The method of Embodiment III-52 or III-53, wherein the SREBP is SREBP-2.

Embodiment III-58. The method of any one of Embodiments III-52 to III-57, wherein SREBP is inhibited in a subject in need thereof.

Embodiment III-59. The method of any one of Embodiments III-52 to III-58, wherein SCAP is inhibited in a subject in need thereof.

Embodiment III-60. The method of any one of Embodiments III-52 to III-59, wherein the expression of one or more genes selected from the group consisting of ACSS2, ALDOC, CYP51A1, DHCR7, ELOVL6, FASN, FDFT1, FDPS, HMGCS1, HSD17B7, IDI1, INSIG1, LDLR, LSS, ME1, PCSK9, PMVK, RDHI1, SC5DL, SQLE, STARD4, TM7SF2, PNPLA3, SREBF1, SREBF2, HMGCR, MVD, MVK, ACLY, MSMO1, ACACA, and ACACB is reduced after contacting the SREBP or SCAP with the compound, or pharmaceutically acceptable salt, solvate, tautomer, isotope, or isomer thereof, or the pharmaceutical composition.

Embodiment III-61. A method of treating a disorder in a subject in need thereof, comprising administering to the subject in need thereof an effective amount of a compound of any one of Embodiments III-1 to III-50, or a pharmaceutically acceptable salt, solvate, tautomer, isotope, or isomer thereof, or the pharmaceutical composition of Embodiment III-51.

Embodiment III-62. A method of treating a disorder in a subject in need thereof, wherein the disorder is mediated by a sterol regulatory element-binding protein (SREBP), comprising administering to the subject in need thereof an effective amount of a compound of any one of Embodiments III-1 to III-50, or a pharmaceutically acceptable salt, solvate, tautomer, isotope, or isomer thereof, or the pharmaceutical composition of Embodiment III-51.

Embodiment III-63. The method of Embodiment III-61 or III-62, wherein the disorder is Metabolic Syndrome, type 2 diabetes, obesity, liver disease, insulin resistance, adiposopathy, or dyslipidemia.

Embodiment III-64. The method of Embodiment III-63, wherein the dyslipidemia is hypertriglyceridemia or elevated cholesterol levels.

Embodiment III-65. The method of Embodiment III-63, wherein the liver disease is nonalcoholic steatohepatitis, liver fibrosis, or liver inflammation, or a combination thereof.

Embodiment III-66. The method of Embodiment III-61 or III-62, wherein the disorder is a hyperproliferative disorder.

Embodiment III-67. The method of Embodiment III-66, wherein the hyperproliferative disorder is cancer.

Embodiment III-68. The method of Embodiment III-67, wherein the cancer is breast cancer, liver cancer, ovarian cancer, pancreatic cancer, or prostate cancer.

Embodiment III-69. The method of Embodiment III-61 or III-62, wherein the disorder is endotoxic shock, systemic inflammation, or atherosclerosis.

Embodiment III-70. Use of a compound of any one of Embodiments III-1 to III-50, or a pharmaceutically acceptable salt, solvate, tautomer, isotope, or isomer thereof, in the manufacture of a medicament for use in treating a disorder in a subject in need thereof.

Embodiment III-71. Use of a compound of any one of Embodiments III-1 to III-50, or a pharmaceutically acceptable salt, solvate, tautomer, isotope, or isomer thereof, in the manufacture of a medicament for use in inhibiting a sterol regulatory element-binding protein (SREBP) in a subject in need thereof.

Embodiment III-72. Use of a compound of any one of Embodiments III-1 to III-50, or a pharmaceutically acceptable salt, solvate, tautomer, isotope, or isomer thereof, in the manufacture of a medicament for use in inhibiting the proteolytic activation of a sterol regulatory element-binding protein (SREBP) in a subject in need thereof.

Embodiment III-73. Use of a compound of any one of Embodiments III-1 to III-50, or a pharmaceutically acceptable salt, solvate, tautomer, isotope, or isomer thereof, in the manufacture of a medicament for use in treating a disorder in a subject in need thereof, wherein the disorder is mediated by a sterol regulatory element-binding protein (SREBP).

Embodiment III-74. Use of a compound of any one of Embodiments III-1 to III-50, or a pharmaceutically acceptable salt, solvate, tautomer, isotope, or isomer thereof, or the pharmaceutical composition of Embodiment III-51, for inhibiting a sterol regulatory element-binding protein (SREBP).

Embodiment III-75. Use of a compound of any one of Embodiments III-1 to III-50, or a pharmaceutically acceptable salt, solvate, tautomer, isotope, or isomer thereof, or the pharmaceutical composition of Embodiment III-51, for inhibiting an SREBP cleavage activating protein (SCAP).

Embodiment III-76. The use of any one of Embodiments III-71 to III-75, wherein the SREBP is an SREBP-1.

Embodiment III-77. The use of Embodiment III-76, wherein the SREBP-1 is SREBP-1a.

Embodiment III-78. The use of Embodiment III-76, wherein the SREBP-1 is SREBP-1c.

Embodiment III-79. The use of any one of Embodiments III-71 to III-75, wherein the SREBP is SREBP-2.

Embodiment III-80. The use of any one of Embodiments III-71 to III-75, wherein SREBP is inhibited in a subject in need thereof.

Embodiment III-81. The use of any one of Embodiments III-71 to III-75, wherein SCAP is inhibited in a subject in need thereof.

Embodiment III-82. Use of a compound of any one of Embodiments III-1 to III-50, or a pharmaceutically acceptable salt, solvate, tautomer, isotope, or isomer thereof, or the pharmaceutical composition of Embodiment III-51, for treating a disorder in a subject in need thereof.

Embodiment III-83. Use of a compound of any one of Embodiments III-1 to III-50, or a pharmaceutically acceptable salt, solvate, tautomer, isotope, or isomer thereof, or the pharmaceutical composition of Embodiment III-51, for treating a disorder in a subject in need thereof, wherein the disorder is mediated by a sterol regulatory element-binding protein (SREBP).

Embodiment III-84. The use of Embodiment III-82 or III-83, wherein the disorder is Metabolic Syndrome, type 2 diabetes, obesity, liver disease, insulin resistance, adiposopathy, or dyslipidemia.

Embodiment III-85. The use of Embodiment III-84, wherein the dyslipidemia is hypertriglyceridemia or elevated cholesterol levels.

Embodiment III-86. The use of Embodiment III-84, wherein the liver disease is nonalcoholic steatohepatitis, liver fibrosis, or liver inflammation, or a combination thereof.

Embodiment III-87. The use of Embodiment III-82 or III-83, wherein the disorder is a hyperproliferative disorder.

Embodiment III-88. The use of Embodiment III-87, wherein the hyperproliferative disorder is cancer.

Embodiment III-89. The use of Embodiment III-88, wherein the cancer is breast cancer, liver cancer, ovarian cancer, pancreatic cancer, or prostate cancer.

Embodiment III-90. The use of Embodiment III-82 or III-83, wherein the disorder is endotoxic shock, systemic inflammation, or atherosclerosis.

Embodiment III-91. A method of treating non-alcoholic steatohepatitis (NASH) in a subject in need thereof, comprising administering to the subject in need thereof an effective amount of a compound of any one of Embodiments III-1 to III-50, or a pharmaceutically acceptable salt, solvate, tautomer, isotope, or isomer thereof, or the pharmaceutical composition of Embodiment III-51.

Embodiment III-92. Use of a compound of any one of Embodiments III-1 to III-50, or a pharmaceutically acceptable salt, solvate, tautomer, isotope, or isomer thereof, or the pharmaceutical composition of Embodiment III-51, for treating non-alcoholic steatohepatitis (NASH) in a subject in need thereof.

Embodiment III-93. Use of a compound of any one of Embodiments III-1 to III-50, or a pharmaceutically acceptable salt, solvate, tautomer, isotope, or isomer thereof, in the manufacture of a medicament for use in treating non-alcoholic steatohepatitis (NASH) in a subject in need thereof.

Embodiment III-94. A method of treating a hyperproliferative disorder in a subject in need thereof, comprising administering to the subject in need thereof an effective amount of a compound of any one of Embodiments III-1 to III-50, or a pharmaceutically acceptable salt, solvate, tautomer, isotope, or isomer thereof, or the pharmaceutical composition of Embodiment III-51.

Embodiment III-95. Use of a compound of any one of Embodiments III-1 to III-50, or a pharmaceutically acceptable salt, solvate, tautomer, isotope, or isomer thereof, or the pharmaceutical composition of Embodiment III-51, for treating a hyperproliferative disorder in a subject in need thereof.

Embodiment III-96. Use of a compound of any one of Embodiments III-1 to III-50, or a pharmaceutically acceptable salt, solvate, tautomer, isotope, or isomer thereof, in the manufacture of a medicament for use in treating a hyperproliferative disorder in a subject in need thereof.

EXAMPLES

The following Examples are merely illustrative and are not meant to limit any aspects of the present disclosure in any way.

Example 1: Synthesis of (4-(2'-(tert-butyl)-[2,4'-bipyridin]-4-yl)-3-chlorophenyl)(4-hydroxypiperidin-1-yl)methanone (Compound 1)

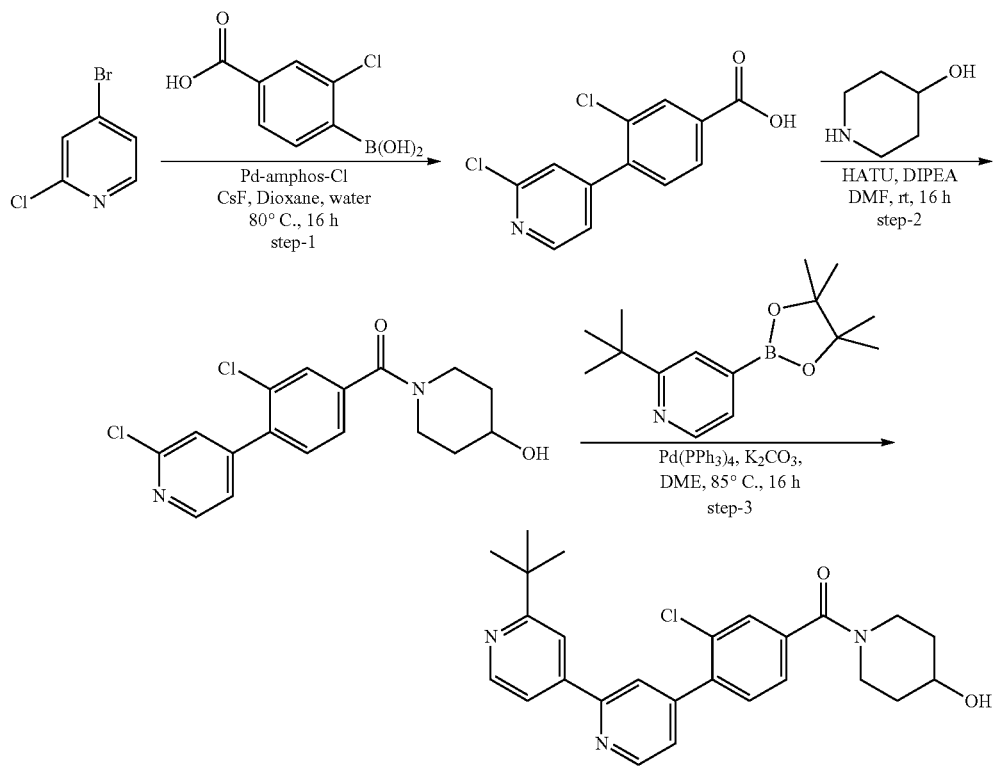

Step 1: Synthesis of 3-chloro-4-(2-chloropyridin-4-yl) benzoic acid. 4-bromo-2-chloropyridine (0.3 g, 1.55 mmol), bromo-3-chloro benzoic acid (0.39 g, 1.94 mmol), cesium fluoride (0.58 g, 0.155 mmol) in water (0.9 mL) and 1,4 dioxane (6 mL) were charged into a 15 mL glass seal tube and purged with argon gas for 30 minutes. To this mixture was added Pd(amphos)$_2$Cl$_2$ (0.109 g, 0.155 mmol) and again the tube was purged with argon gas for 30 minutes. The tube was heated to 80° C. for 16 h, and reaction progress was monitored by TLC and LCMS. When complete, the reaction mixture was cooled to 25-30° C. and ice-cold water was added (10 mL). The obtained solids were filtered and dried. The crude 3-chloro-4-(2-chloropyridin-4-yl)benzoic acid (0.3 g) was taken for the next step without purification.

Step 2: (3-chloro-4-(2-chloropyridin-4-yl)phenyl)(4-hydroxypiperidin-1-yl)methanone. To a stirred solution of the compound from Step 1 (0.3 g, 1.12 mmol) in DMF (6 mL) was added DIPEA (1.95 mL, 11.2 mmol) followed by the addition of HATU (1.7 g, 4.48 mmol) under nitrogen atmosphere. This mixture was stirred for 30 minutes followed by addition of 4-hydroxy piperidine (0.220 g, 2.24 mmol). The reaction was stirred at rt for 16 h. The reaction progress was monitored by TLC and, when complete, the reaction mixture was cooled to 0° C., water (30 mL) was added and the whole extracted with ethyl acetate. The ethyl acetate layer was washed with brine, dried over sodium sulfate, filtered and concentrated. The crude compound was purified by silica gel (230-400 mesh) column chromatography eluting with 0-80% ethyl acetate in pet ether to afford (3-chloro-4-(2-chloropyridin-4-yl)phenyl)(4-hydroxypiperidin-1-yl)methanone (0.158 g, 40%).

Step 3: Synthesis of (4-(2'-(tert-butyl)-[2,4'-bipyridin]-4-yl)-3-chlorophenyl)(4-hydroxypiperidin-1-yl)methanone.

To a stirred solution of (3-chloro-4-(2-chloropyridin-4-yl)phenyl)(4-hydroxypiperidin-1-yl)methanone (0.15 g, 0.427 mmol) in DME (3 mL) was added 2-(tert-butyl)-4-(4,4,5,5-tetramethyl-1,3,2-dioxaborolan-2-yl)pyridine (0.139 g, 0.533 mmol), and $K_2CO_3$ (0.147 g, 1.06 mmol) in water (0.45 mL) at room temperature under argon atmosphere. The combination was purged with argon for 30 minutes and, and after adding palladium tetrakis (0.049 g, 0.0427 mmol), again purged with argon gas for 30 minutes. The mixture was heated to 85° C. for 16 h, and the reaction progress monitored by TLC and LCMS. When the reaction was complete the reaction mixture was cooled to 0° C., water (50 mL) added and the whole was extracted with ethyl acetate. The ethyl acetate layer was washed with brine, dried over sodium sulfate, filtered, and concentrated. The crude compound was purified by preparative HPLC to afford (4-(2'-(tert-butyl)-[2,4'-bipyridin]-4-yl)-3-chlorophenyl)(4-hydroxypiperidin-1-yl)methanone (42 mg, 15%). $^1$H NMR (400 MHz, DMSO-$d_6$): δ 8.83 (d, J=5.6 Hz, 1H), 8.63-8.64 (m, 1H), 8.23 (s, 1H), 8.13 (bs, 1H), 7.90-7.92 (dd, J=2 Hz, J=5.2 Hz, 1H), 7.63-7.65 (m, 2H), 7.59-7.60 (dd, J=1.8 Hz, J=4.8 Hz, 1H), 7.49-7.51 (dd, J=1.6 Hz, J=7.6 Hz, 1H), 4.80 (d, J=4.0 Hz, 1H), 3.95-4.05 (m, 1H), 3.74-3.79 (m, 1H), 3.50-3.56 (m, 1H), 3.16-3.24 (m, 2H), 1.69-1.80 (m, 2H), 1.35-1.42 (m, 11H). LCMS: 98.64% (m/z=450.39 [M+H]).

Example 2: Synthesis of (4-(2'-(tert-butyl)-[4,4'-bipyridin]-2-yl)-3-chlorophenyl)(4-hydroxypiperidin-1-yl)methanone (Compound 2)

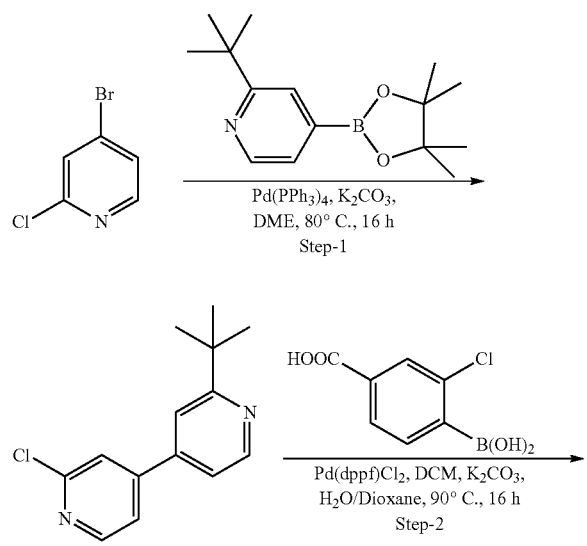

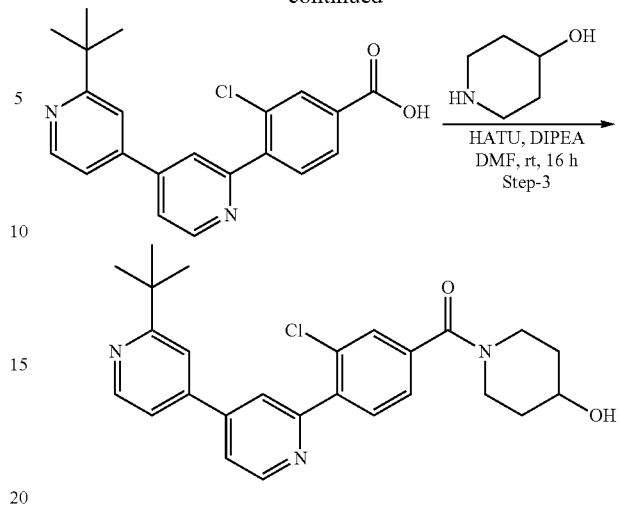

(4-(2'-(tert-butyl)-[4,4'-bipyridin]-2-yl)-3-chlorophenyl)(4-hydroxypiperidin-1-yl)methanone was prepared in a similar fashion to the compound of Example 1, but with the reverse order of the reactions of Step 1 and Step 2. $^1$H NMR (400 MHz, DMSO): δ (ppm): 8.83 (d, J=5.2 Hz, 1H), 8.66 (d, J=5.2 Hz, 1H) 8.10 (bs, 1H), 7.88 (dd, $J_1$=1.6 Hz, $J_2$=5.2 Hz, 1H), 7.83 (s, 1H), 7.72 (d, J=8 Hz, 1H), 7.67 (dd, $J_1$=1.6 Hz, $J_2$=5.2 Hz, 1H), 7.61 (d, J=1.2 Hz, 1H), 7.49 (dd, $J_1$=1.6 Hz, $J_2$=7.6 Hz, 1H), 4.81 (d, J=4 Hz, 1H), 3.99-4.03 (m, 1H), 3.75-3.78 (m, 1H), 3.50-3.55 (m, 1H), 3.25-3.32 (m, 2H), 1.82-1.73 (m, 2H), 1.38 (s, 11H). LCMS 99.99% (m/z=450.47 [M+H]). HPLC purity 99.84%.

Example 3: Synthesis of (4-(2'-(tert-butyl)-[2,4'-bipyridin]-6-yl)-3-chlorophenyl)(4-hydroxypiperidin-1-yl)methanone (Compound 3)

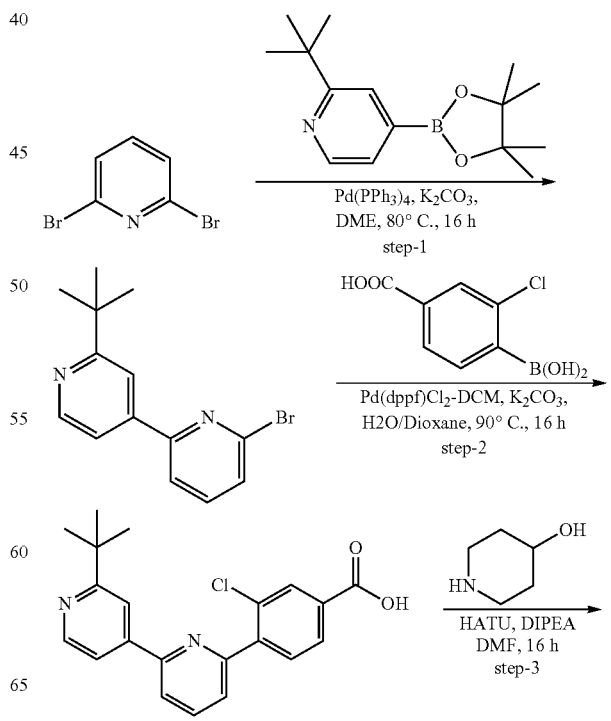

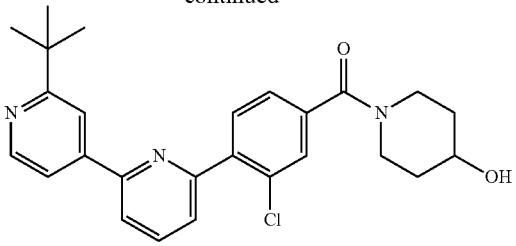

Step 1: Synthesis of 6-bromo-2'-(tert-butyl)-2,4'-bipyridine. 2,6-dibromo-pyridine (0.3 g, 1.27 mmol), 2-tert-butylpyridine-4-boronic acid pinacol ester (0.323 g, 1.14 mmol), and potassium carbonate (0.35 g, 2.53 mmol) in DME (6 mL) were added to a 10 mL glass seal tube and purged with nitrogen gas for 10 minutes. Palladium tetrakis (0.14 6 g, 0.12 mmol) was added and the container was again purged with nitrogen gas for 10 minutes. The container was then heated to 80° C. for 16 h and the reaction monitored by TLC and LCMS. After completion, the reaction mixture was cooled to RT, 5 mL ice cold water was added, and the whole extracted with EtOAc (3×15 mL). The organic extracts were combined, washed with brine (3×10 mL) and dried over anhydrous sodium sulfate. The extract was then concentrated under reduced pressure and the crude product purified by column chromatography using 0-10% EtOAc in hexane as eluent to afford 6-bromo-2'-(tert-butyl)-2,4'-bipyridine (0.210 g, 56.9%) as an off white solid.

Step 2: Synthesis of 4-(2'-(tert-butyl)-[2,4'-bipyridin]-6-yl)-3-chlorobenzoic acid. 6-bromo-2'-(tert-butyl)-2,4'-bipyridine (0.15 g, 0.52 mmol, 1 equiv), 4-carboxy-2-chlorophenylboronic acid (0.156 g, 0.78 mmol, 1.5 equiv) and potassium carbonate (0.143 g, 1.035 mmol, 2 equiv) in dioxane:water (2.5:0.5 mL) were combined in a 10 mL glass seal tube and purged with nitrogen gas for 10 minutes. To the mixture was added Pd(dppf)Cl$_2$-DCM complex (0.049 g, 0.060 mmol) and it was again purged with nitrogen gas for 10 minutes. The mixture was heated to 90° C. for 16 h, and monitored by TLC. After completion, the reaction was cooled, 5 ml water was added, and the pH of the mixture was adjusted by addition of AcOH to pH 6. The resulting mixture was extracted with EtOAc (3×20 mL). The organic extracts were combined, dried over anhydrous sodium sulfate and concentrated under reduced pressure. The crude product was triturated with n-hexane (3×10 mL). This residue was dissolved in diethyl ether (10 mL) and then concentrated under reduced pressure to obtain 0.3 g (crude) of 4-(2'-(tert-butyl)-[2,4'-bipyridin]-6-yl)-3-chlorobenzoic acid, which was used without further purification in the next step.

Step 3: Synthesis of (4-(2'-(tert-butyl)-[2,4'-bipyridin]-6-yl)-3-chlorophenyl)(4-hydroxypiperidin-1-yl)methanone. To a solution of 4-(2'-(tert-butyl)-[2,4'-bipyridin]-6-yl)-3-chlorobenzoic acid from Step 2 (0.2 g, 0.546 mmol, 1 equiv) in DMF (5 mL, 25 vol), was added DIPEA (1 mL, 5.464 equiv.) and HATU (0.83 g, 2.186 mmol, 4.0 equiv). The reaction was stirred for 30 min followed by addition of 4-hydroxy pyridine (0.11 g, 1.092 mmol, 2.0 equiv), and further stirred for 16 h. The progress of the reaction was monitored by TLC. After completion, the mixture was diluted with ethyl acetate and washed with ice-cold water (4×5 mL). The organic layer was separated, dried over anhydrous sodium sulfate, and concentrated under reduced pressure. The crude product obtained was purified by preparative HPLC to afford (4-(2'-(tert-butyl)-[2,4'-bipyridin]-6-yl)-3-chlorophenyl)(4-hydroxypiperidin-1-yl)methanone (0.103 g (27.9% yield)) as an off white solid. The crude product was analyzed by $^1$H-NMR (400 MHz, DMSO), δ (ppm): 8.65 (d, J=5.2 Hz 1H), 8.16 (d, J=7.2 Hz, 1H), 8.11-8.07 (m, 2H), 7.89 (dd, J$_1$=1.6 Hz, J$_2$=4.8 Hz, 1H), 7.77 (t, J=7.2 Hz, 2H), 7.62 (d, J=1.6 Hz, 1H), 7.50 (dd, J$_1$=1.6 Hz, J$_2$=8.0 Hz, 1H), 4.81 (d, J=4 Hz, 1H), 4.00-4.04 (m, 1H), 3.78-3.75 (m, 1H), 3.5-3.53 (m, 1H), 3.15-3.20 (m, 2H), 1.83-1.78 (m, 2H) 1.38 (s, 11H). LCMS 99.81% (m/z 450.44 [M+H]). HPLC purity 98.46%.

Example 4: Synthesis of (4-(2'-(tert-butyl)-[3,4'-bipyridin]-5-yl)-3-chlorophenyl)(4-hydroxypiperidin-1-yl)methanone (Compound 4)

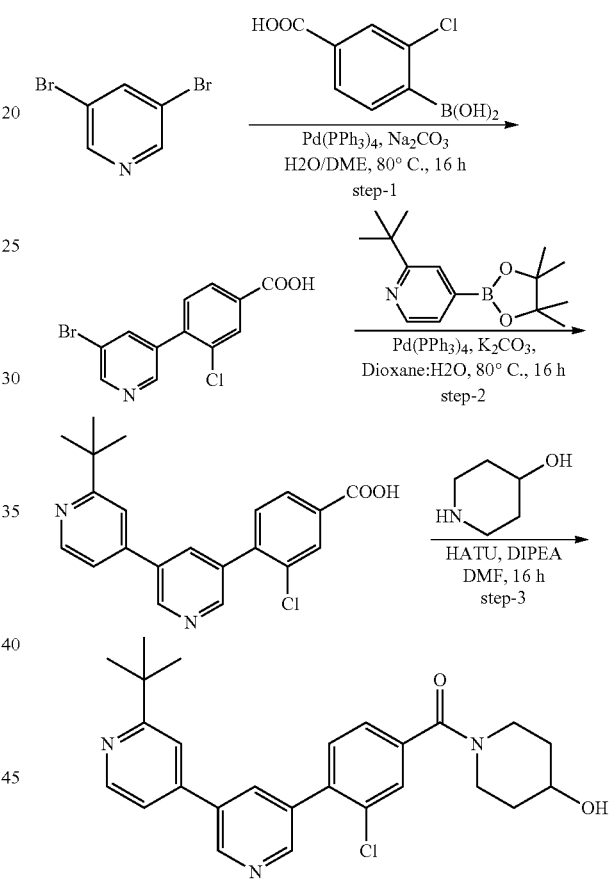

Step 1: Synthesis of 4-(5-bromopyridin-3-yl)-3-chlorobenzoic acid. 3,5-dibromopyridine (0.5 g, 2.11 mmol, 1 equiv), 4-carboxy-2-chlorophenyl boronic acid (0.402 g, 2.00 mmol, 0.95 equiv) and sodium carbonate (0.559 g, 5.28 mmol, 2.5 equiv) in DME-H$_2$O (3.75:1.25 mL) were combined in a 10 mL glass seal tube and purged with nitrogen gas for 10 minutes. After adding palladium tetrakis (0.122 g, 0.105 mmol, 0.05 equiv) the mixture was again purged with nitrogen gas for 10 minutes. The mixture was heated to 80° C. for 16 h and reaction monitored by TLC and LCMS. After completion, the reaction mixture was cooled to RT, 10 mL water was added and the whole was extracted with EtOAc (3×15 mL). The organic extracts were combined and washed with brine (3×10 mL) and dried over anhydrous sodium sulfate. The extract was then concentrated under reduced pressure to give crude 4-(5-bromopyridin-3-yl)-3-chlorobenzoic acid (0.350 g, crude) as a white solid.

Step 2: Synthesis of 4-(2'-(tert-butyl)-[3,4'-bipyridin]-5-yl)-3-chlorobenzoic acid. 4-(5-bromopyridin-3-yl)-3-chlorobenzoic acid (0.150 g, 0.4799 mmol, 1 equiv), 2-tert butyl pyridine 4-boronic acid pinacol ester (0.156 g, 0.5759 mmol, 1.2 equiv) and potassium carbonate (0.133 g, 0.9598 mmol, 2 equiv) in dioxane:water (2.4:0.6 mL) were combined in a 10 mL glass seal tube and purged with nitrogen gas for 10 minutes. After adding palladium tetrakis (0.055 g, 0.0479 mmol, 0.1 equiv), the container was again purged with nitrogen gas for 10 minutes. The mixture was heated to 80° C. for 16 h and the reaction monitored by TLC. After completion, the mixture was cooled, 10 mL water added, and the mixture extracted with EtOAc (3×10 mL). The organic extracts were combined, dried over anhydrous sodium sulfate and concentrated under reduced pressure to obtain 4-(2'-(tert-butyl)-[3,4'-bipyridin]-5-yl)-3-chlorobenzoic acid (0.140 g, crude).

Step 3: Synthesis of (4-(2'-(tert-butyl)-[3,4'-bipyridin]-5-yl)-3-chlorophenyl)(4-hydroxypiperidin-1-yl)methanone. To a solution of 4-(2'-(tert-butyl)-[3,4'-bipyridin]-5-yl)-3-chlorobenzoic acid (0.140 g, 0.3816 mmol, 1 equiv) in DMF (2.8 mL, 20 v), was added DIPEA (0.211 mL, 1.1448 mmol, 3 equiv) and HATU (0.218 g, 0.5724 mmol, 1.5 equiv). The mixture was stirred for 30 minutes, then 4-hydroxy piperidine (0.058 g, 0.5724 mmol, 1.5 equiv) was added and the mixture stirred for 16 h at RT. The progress of the reaction was monitored by TLC. After completion, the mixture was diluted with ethyl acetate and washed with cold water (4×5 mL). The organic layers were separated, combined, dried over anhydrous sodium sulfate and concentrated under reduced pressure. The crude product obtained was purified by preparative HPLC method to afford (4-(2'-(tert-butyl)-[3,4'-bipyridin]-5-yl)-3-chlorophenyl)(4-hydroxypiperidin-1-yl)methanone (0.103 g, 30.23% yield) as an off white solid. $^1$H NMR (400 MHz, DMSO d$_6$): δ (ppm): 9.07 (d, J=2 Hz, 1H), 8.76 (d, J=2 Hz, 1H), 8.63-8.62 (m, 1H), 8.35-8.34 (m, 1H), 7.82 (s, 1H), 7.68-7.64 (m, 3H) 7.50-7.48 (m, 1H), 4.82 (s, 1H), 4.01 (s, 1H), 3.76 (s, 1H), 3.54-3.53 (m, 1H), 3.3-3.2 (m, 2H), 1.80-1.75 (m, 2H), 1.38 (s, 11H); LCMS 99.86% (m/z 450.47 [M+H]). HPLC purity 99.76%.

Example 5: Synthesis of (3'-(2-(tert-butyl)pyridin-4-yl)-2-chloro-[1,1'-biphenyl]-4-yl)(4-hydroxypiperidin-1-yl)methanone (Compound 5)

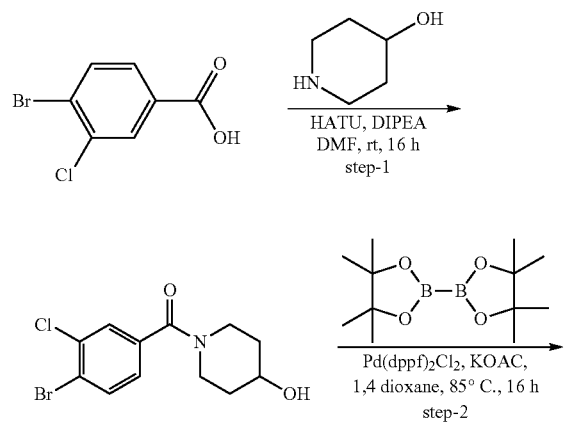

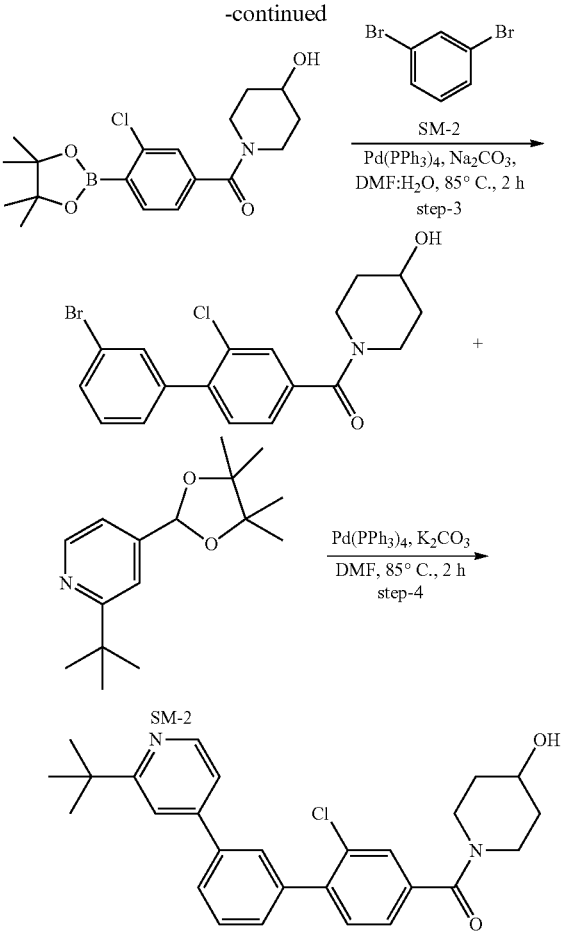

Step 1: Synthesis of (4-bromo-3-chlorophenyl)(4-hydroxypiperidin-1-yl)methanone. To a stirred solution of 3-chloro-4-bromo benzoic acid (2.0 g, 8.49 mmol) in DMF (40 mL) was added DIPEA (15.23 mL, 84.94 mmol) and HATU (12.9 g, 33.97 mmol) under a nitrogen atmosphere with stirring for 30 minutes. Next, 4-hydroxy piperidine (1.71 g, 16.98 mmol) was added, and the mixture stirred at rt for 16 h. The progress of the reaction was monitored by TLC, and when complete it was cooled to 0° C., water (300 mL) was added, and the whole was extracted with ethyl acetate. The combined ethyl acetate layers were washed with brine, dried over sodium sulfate, filtered and concentrated. The crude compound was purified by silica gel column chromatography, eluting with 0-80% ethyl acetate in petroleum ether to give (4-bromo-3-chlorophenyl)(4-hydroxypiperidin-1-yl)methanone (1.1 g, 41%).

Step 2: Synthesis of (3-chloro-4-(4,4,5,5-tetramethyl-1,3,2-dioxaborolan-2-yl)phenyl)(4-hydroxypiperidin-1-yl)methanone. To a stirred solution of (4-bromo-3-chlorophenyl)(4-hydroxypiperidin-1-yl)methanone (0.3 g, 0.943 mmol) in 1,4 dioxane (3 mL) in a glass seal tube was added 4,4,4',4',5,5,5',5'-octamethyl-2,2'-bi(1,3,2-dioxaborolane) (0.299 g, 1.17 mmol), and KOAc (0.231 g, 2.35 mmol) at room temperature under a nitrogen atmosphere. The mixture was purged for 15 min with nitrogen, then Pd(dppf)$_2$Cl$_2$ (0.069 g, 0.094 mmol) was added and the mixture again purged for 10 min with nitrogen. The reaction vial was sealed and subjected to heating at 85° C. for 16 h. The reaction progress was monitored by TLC and, when complete, was cooled to 0° C., water added (50 mL) and the whole extracted with ethyl acetate. The combined ethyl acetate layers were washed with brine, dried over sodium sulfate, filtered and concentrated under reduced pressure to give (3-chloro-4-(4,4,5,5-tetramethyl-1,3,2-dioxaborolan-2-yl)phenyl)(4-hydroxypiperidin-1-yl)methanone as a brown oil that was used in the next step without further purification.

Step 3: Synthesis of (3'-bromo-2-chloro-[1,1'-biphenyl]-4-yl)(4-hydroxypiperidin-1-yl)methanone. To a stirred solution of (3-chloro-4-(4,4,5,5-tetramethyl-1,3,2-dioxaborolan-2-yl)phenyl)(4-hydroxypiperidin-1-yl)methanone (0.387 g, 1.05 mmol) in DMF (2.0 mL) in a microwave vial was added 1,3-dibromobenzene (0.2 g, 0.84 mmol), Na₂CO₃ (0.224 g, 2.11 mmol) in water (0.6 mL) at room temperature under a nitrogen atmosphere. The mixture was purged for 15 min with nitrogen, palladium tetrakis (0.097 g, 0.084 mmol) was added, and the mixture was again purged for 10 min with nitrogen. The reaction vial was sealed and subjected to microwave irradiation at 85° C. for 2 h. The reaction progress was monitored by TLC and when complete it was cooled to 0° C., water (50 mL) added, and the whole was extracted with ethyl acetate. The combined ethyl acetate layers were washed with brine, dried over sodium sulfate, filtered and concentrated. The crude compound was purified by silica gel column chromatography eluting with 5-80% ethyl acetate in petroleum ether to afford (3'-bromo-2-chloro-[1,1'-biphenyl]-4-yl)(4-hydroxypiperidin-1-yl)methanone as an off white solid (50 mg, 15%).

Step 4: Synthesis of (3'-(2-(tert-butyl)pyridin-4-yl)-2-chloro-[1,1'-biphenyl]-4-yl)(4-hydroxypiperidin-1-yl)methanone. To a stirred solution of (3'-bromo-2-chloro-[1,1'-biphenyl]-4-yl)(4-hydroxypiperidin-1-yl)methanone (0.10 g, 0.25 mmol) in DMF (2 mL) in a microwave vial was added 2-(tert-butyl)-4-(4,4,5,5-tetramethyl-1,3-dioxolan-2-yl)pyridine (0.082 g, 0.31 mmol) and K₂CO₃ (0.087 g, 0.634 mmol) at room temperature under a nitrogen atmosphere. The mixture was purged for 15 min with nitrogen, palladium tetrakis (0.029 g, 0.025 mmol) was added and the reaction mixture was again purged for 10 min with nitrogen. The reaction vial was then sealed and subjected to irradiation at 85° C. for 2 h. The reaction progress was monitored by TLC and, when complete, it was cooled to 0° C., water (30 mL) was added and the whole was extracted with ethyl acetate. The combined ethyl acetate layers were washed with brine, dried over sodium sulfate, filtered and concentrated. The crude compound was purified by preparative HPLC to afford (3'-(2-(tert-butyl)pyridin-4-yl)-2-chloro-[1,1'-biphenyl]-4-yl)(4-hydroxypiperidin-1-yl)methanone as an off white solid (9.5 mg, 8%). ¹H NMR (400 MHz, DMSO): δ 8.58-8.57 (m, 1H), 7.85-7.83 (m, 2H), 7.720 (d, J=0.8 Hz, 1H) 7.636-7.545 (m, 5H), 7.46-7.43 (m, 1H) 4.80 (d, J=4 Hz, 1H), 4.01 (d, J=6.4 Hz, 1H), 3.78-3.73 (m, 1H), 3.55-3.53 (m, 1H), 3.23-3.20 (m, 2H), 1.792 (s, 2H), 1.374 (s, 11H). LCMS: 96.44% (m/z=449.38 [M+H]). HPLC: 96.17%.

Example 6: (4-(4-(2-(tert-butyl)pyridin-4-yl)pyrimidin-2-yl)-3-chlorophenyl)(4-hydroxypiperidin-1-yl)methanone (Compound 6)

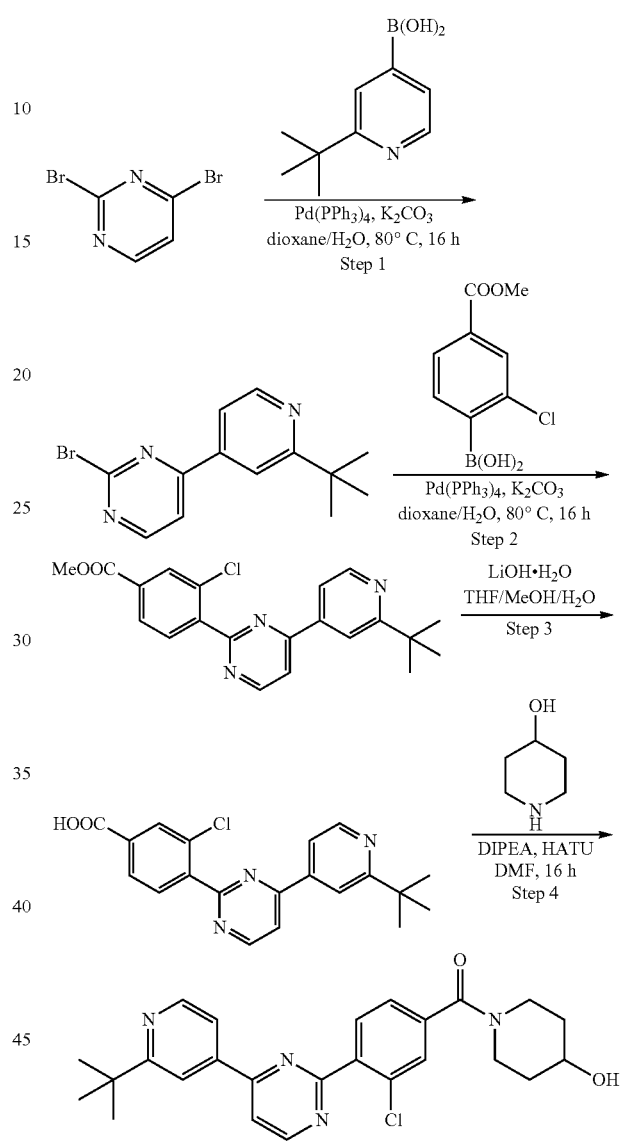

Step 1: Synthesis of 2-bromo-4-(2-(tert-butyl)pyridin-4-yl)pyrimidine. In a glass tube, 2,4-dibromopyrimidine (400 mg, 1.68 mmol) was dissolved in 1,4-dioxane/H₂O (9:1, 10 mL), and (2-(tert-butyl)pyridin-4-yl)boronic acid (270 mg, 1.51 mmol) and K₂CO₃ (695 mg, 5.04 mmol) were added under nitrogen atmosphere. The mixture was purged for 15 minutes with nitrogen, then Pd(PPh₃)₄ (194 mg, 0.16 mmol) was added and the reaction mixture purged for 10 minutes with nitrogen. The tube was sealed and stirred at 80° C. for 16 h. The reaction progress was monitored by TLC. After completion of the reaction, the residue was dissolved in water (10 mL) and extracted with EtOAc (3×20 mL). The organic extracts were combined, dried over anhydrous sodium sulfate and concentrated under reduced pressure to obtain crude material which was purified by column chromatography (Silica 100-200 mesh), eluted with 10% EA in hexanes. Removal of the solvent under reduced pressure gave 2-bromo-4-(2-(tert-butyl)pyridin-4-yl)pyrimidine as a gummy liquid (250 mg, 51%).

Step 2: Synthesis of methyl 4-(4-(2-(tert-butyl)pyridin-4-yl)pyrimidin-2-yl)-3-chlorobenzoate. In a glass tube, 2-bromo-4-(2-(tert-butyl)pyridin-4-yl)pyrimidine (280 mg, 0.85 mmol) was dissolved in 1,4-dioxane/H₂O (9:1, 10 mL), and (2-chloro-4-(methoxycarbonyl)phenyl)boronic acid (138 mg, 0.77 mmol) and K₂CO₃ (354 mg, 2.56 mmol) were added under nitrogen atmosphere. The mixture was purged for 15 minutes with nitrogen, then Pd(PPh₃)₄ (99 mg, 0.08 mmol) was added and the reaction mixture purged for 10 minutes with nitrogen. The tube was sealed and stirred at 80° C. for 16 h. The reaction progress was monitored by TLC. After completion of the reaction, the residue was dissolved in water (10 mL) and extracted with EtOAc (3×20 mL). The organic extracts were combined, dried over anhydrous sodium sulfate and concentrated under reduced pressure to obtain crude material which was purified by column chromatography (Silica 100-200 mesh), eluted with 10% EA in hexanes. Removal of the solvent under reduced pressure gave methyl 4-(4-(2-(tert-butyl)pyridin-4-yl)pyrimidin-2-yl)-3-chlorobenzoate as a gummy liquid (160 mg, 49%). ¹H NMR (400 MHz, DMSO: δ (ppm): 9.01 (d, J=5.2 Hz, 1H), 8.75 (d, J=4.8 Hz, 1H), 8.23 (d, J=1.6 Hz, 1H), 8.21 (s, 1H), 8.05-8.08 (m, 1H), 7.97-7.99 (m, 1H), 7.76-7.80 (m, 2H), 3.97 (s, 3H), 1.44 (s, 9H). LCMS: 94% (M+H=382.23).

Step 3: Synthesis of 4-(4-(2-(tert-butyl)pyridin-4-yl)pyrimidin-2-yl)-3-chlorobenzoic acid. To a stirred solution of methyl 4-(4-(2-(tert-butyl)pyridin-4-yl)pyrimidin-2-yl)-3-chlorobenzoate (160 mg, 0.41 mmol) in THF-MeOH/H₂O (3:3:1, 7 mL) was added LiOH.H₂O (42 mg, 1.25 mmol), and the mixture stirred at rt for 2 h. The reaction progress was monitored by TLC. After completion of reaction, THF was removed under reduced pressure. The residue was dissolved in water (10 mL) and acidified with 1N HCl up to pH 4, then the aqueous layer was extracted with EtOAc (3×15 mL). The organic extracts were combined, dried over anhydrous sodium sulphate and concentrated under reduced pressure to obtain crude 4-(4-(2-(tert-butyl)pyridin-4-yl)pyrimidin-2-yl)-3-chlorobenzoic acid, which was used for the next step without purification.

Step 4: Synthesis of (4-(4-(2-(tert-butyl)pyridin-4-yl)pyrimidin-2-yl)-3-chlorophenyl)(4-hydroxypiperidin-1-yl) methanone. To a stirred solution of 4-(4-(2-(tert-butyl)pyridin-4-yl)pyrimidin-2-yl)-3-chlorobenzoic acid (110 mg, 0.29 mmol) in DMF (5 mL) was added DIPEA (154 mg, 1.19 mmol) followed by the addition of HATU (455 mg, 1.19 mmol). The mixture was stirred for 10 minutes, then 4-hydroxypiperidine (33 mg, 0.32 mmol) was added. The reaction was stirred at rt for 16 h, and reaction progress monitored by TLC. After completion of the reaction, the residue was dissolved in water (10 mL) and extracted with EtOAc (2×15 mL). The organic extracts were combined, dried over anhydrous sodium sulfate, and concentrated under reduced pressure to obtain crude product which was purified by preparative HPLC. Collected fractions were concentrated under reduced pressure to afford (4-(4-(2-(tert-butyl)pyridin-4-yl)pyrimidin-2-yl)-3-chlorophenyl)(4-hydroxypiperidin-1-yl)methanone (0.04 g, 38%) as an off white solid. ¹H NMR (400 MHz, DMSO: δ (ppm): 9.15 (d, J=5.2 Hz), 8.74 (d, J=4.8 Hz, 1H), 8.29 (d, J=5.2 Hz, 1H), 8.23 (s, 1H), 8.01-7.96 (m, 2H), 7.64 (d, J=1.2 Hz, 1H), 7.53-7.50 (m, 1H), 4.81 (d, J=4 Hz, 1H), 3.95-4.00 (br, 1H), 3.75-3.85 (br, 1H), 3.51-3.53 (br, 1H), 3.19-3.21 (br, 2H), 1.77-1.88 (m, 2H), 1.32-1.34 (m, 11H). LCMS: (451.48 [M+H]) 99.44%. HPLC: 96.33%.

Example 7: (4-(2-(2-(tert-butyl)pyridin-4-yl)pyrimidin-4-yl)-3-chlorophenyl)(4-hydroxypiperidin-1-yl)methanone (Compound 7)

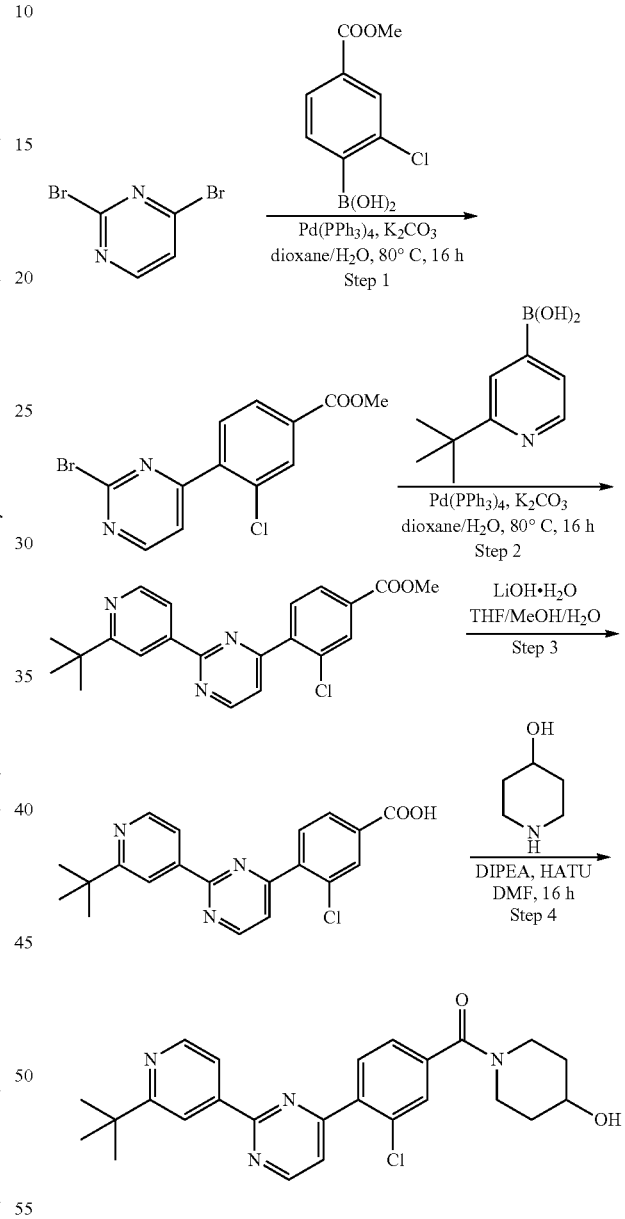

(4-(2-(2-(tert-butyl)pyridin-4-yl)pyrimidin-4-yl)-3-chlorophenyl)(4-hydroxypiperidin-1-yl)methanone was prepared in a similar fashion to the compound of Example 6, but with the reverse order of the reactions of Step 1 and Step 2. ¹H NMR (400 MHz, DMSO: δ (ppm): 9.15 (d, J=5.2 Hz, 1H), 8.75-8.74 (m, 1H), 8.29-8.28 (d, J=5.2 Hz, 1H), 8.24 (br s, 1H), 8.01-7.99 (m, 1H), 7.97 (d, J=7.6 Hz, 1H), 7.64 (m, 1H), 7.53-7.50 (m, 1H), 4.82 (d, J=4 Hz, 1H), 4.00-3.95 (br, 1H), 3.85-3.75 (br, 1H), 3.53-3.51 (br, 1H), 3.21-3.19 (br, 2H), 1.88-1.77 (m, 2H), 1.34-1.32 (m, 11H). LCMS: (451.1 [M+H]) 99.44%. HPLC: 96.33%.

Example 8: (4-(6-(2-(tert-butyl)pyridin-4-yl)pyrimidin-4-yl)-3-chlorophenyl)(4-hydroxypiperidin-1-yl)methanone (Compound 8)

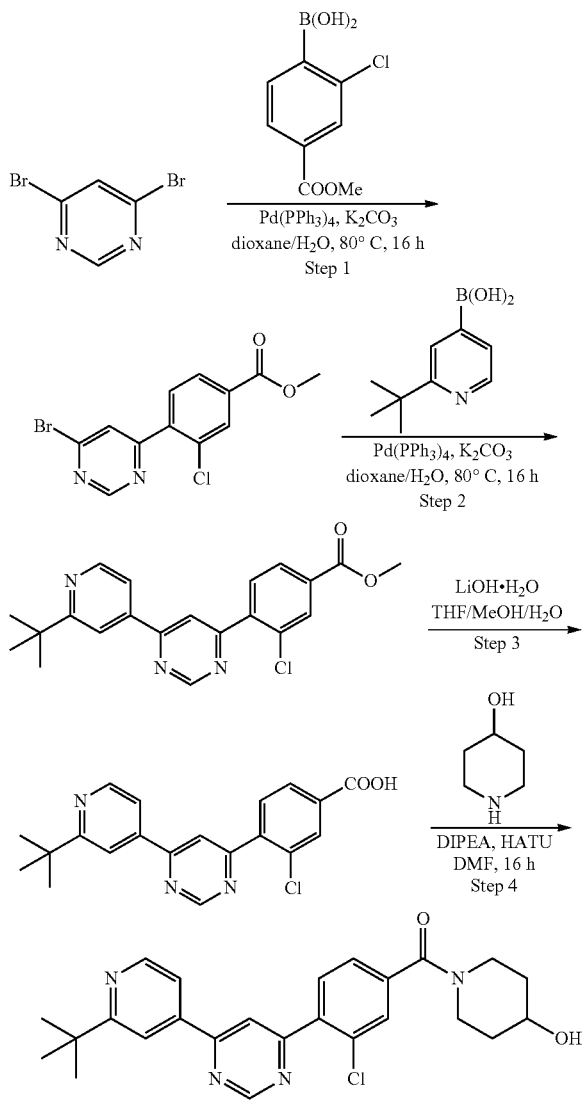

Step 1: Synthesis of methyl 4-(6-bromopyrimidin-4-yl)-3-chlorobenzoate. To a stirred solution of 4,6-dibromopyrimidine (300 mg, 1.261 mmol), (2-chloro-4-(methoxycarbonyl)phenyl)boronic acid (300 mg, 1.513 mmol), potassium carbonate (435 mg, 3.15 mmol) in water (1 mL) and 1,4-dioxane (3 mL) were added in a 15 mL glass sealed tube, which was purged with nitrogen gas for 30 minutes. After adding palladium tetrakis (145 mg, 0.126 mmol) it was again purged with nitrogen gas for 30 minutes and then heated to 80° C. for 16 h. The reaction progress was monitored by TLC and LCMS. After completion of the reaction, the mixture was cooled to 25° C.-30° C., filtered through a Celite® bed, and washed with ethyl acetate (20 mL). The combined organic layers were directly concentrated under reduced pressure to afford crude product which was purified through neutral alumina column chromatography using 0-50% ethyl acetate in petroleum ether as an eluent. Selected fractions were collected and concentrated under reduced pressure to afford methyl 4-(6-bromopyrimidin-4-yl)-3-chlorobenzoate (100 mg) as an off-white solid. $^1$H NMR (400 MHz, CDCl$_3$): 9.09-9.09 (d, J=8.0 Hz, 1H), 8.21-8.21 (d, J=1.6 Hz, 1H), 8.09-8.07 (dd, J=8.0, 8.0 Hz, 1H), 8.00 (d, J=1.2 Hz, 1H), 7.78-7.76 (d, J=8 Hz, 1H), 3.99 (s, 3H).

Step 2: Synthesis of methyl 4-(6-(2-(tert-butyl)pyridin-4-yl)pyrimidin-4-yl)-3-chlorobenzoate. A stirred solution of methyl 4-(6-bromopyrimidin-4-yl)-3-chlorobenzoate (100 mg, 0.305 mmol), (2-(tert-butyl)pyridin-4-yl)boronic acid (54 mg, 0.305 mmol), potassium carbonate (105 mg, 0.763 mmol) in water (1 mL) and 1,4-dioxane (4 mL) in a 15 mL glass seal tube was purged with nitrogen gas for 30 minutes. After adding palladium tetrakis (35 mg, 0.0305 mmol), the reaction mixture was again purged with nitrogen gas for 30 minutes, sealed, and heated at 80° C. for 16 h. The reaction progress was monitored by TLC and LCMS. After completion of reaction, the mixture was cooled to 25° C.-30° C., filtered through a bed of Celite®, and concentrated under reduced pressure to afford crude product. This was purified through neutral alumina column chromatography using 0-50% ethyl acetate in petroleum ether as an eluent to give methyl 4-(6-(2-(tert-butyl)pyridin-4-yl)pyrimidin-4-yl)-3-chlorobenzoate (70 mg, 60%) as a colorless gum.

Step 3: Synthesis of 4-(6-(2-(tert-butyl)pyridin-4-yl)pyrimidin-4-yl)-3-chlorobenzoic acid. To a stirred solution of (70 mg, 0.183 mmol) in methanol:THF:water (3:2:1, 5 mL) was added LiOH.H$_2$O (23 mg, 0.549 mmol), and the mixture was stirred at room temperature for 2 h. The reaction progress was monitored by TLC and LCMS. After completion, the reaction mixture was concentrated under reduced pressure. The crude product was dissolved in water (10 mL) and acidified with citric acid to pH ~5. The water layer was then extracted with ethyl acetate (2×20 mL) and the combined organic layers dried over sodium sulfate and concentrated under reduced pressure to afford 4-(6-(2-(tert-butyl)pyridin-4-yl)pyrimidin-4-yl)-3-chlorobenzoic acid (70 mg) as an off white solid.

Step 4: Synthesis of (4-(6-(2-(tert-butyl)pyridin-4-yl)pyrimidin-4-yl)-3-chlorophenyl)(4-hydroxypiperidin-1-yl)methanone. To a stirred solution of 4-(6-(2-(tert-butyl)pyridin-4-yl)pyrimidin-4-yl)-3-chlorobenzoic acid (70 mg, 0.190 mmol) in DMF (3 mL) and DIPEA (98 mg, 0.761 mmol) was added HATU (289 mg, 0.761 mmol), and the mixture stirred for 15 min at room temperature under nitrogen. 4-hydroxypiperidine (19 mg, 0.190 mmol) was added under nitrogen and the mixture was stirred for 16 h at room temperature. The reaction progress was monitored by TLC and LCMS. After completion, the reaction mixture was diluted with cold water (50 mL) and extracted into EtOAc (2×25 mL). The combined organic layers were washed with ice cold water (50 mL) and dried over sodium sulfate, concentrated under reduced pressure to afford crude product (100 mg) which was purified through neutral alumina column chromatography using 0-100% ethyl acetate in petroleum ether followed by 10% methanol in ethyl acetate as an eluent. Selected fractions were collected and concentrated under reduced pressure to afford (4-(6-(2-(tert-butyl)pyridin-4-yl)pyrimidin-4-yl)-3-chlorophenyl)(4-hydroxypiperidin-1-yl)methanone (58 mg, 40%) as an off white solid. $^1$H NMR (400 MHz, DMSO): δ 9.47-9.47 (m, 1H), 8.74-8.73 (d, J=4.8 Hz, 1H), 8.57 (m, 1H), 8.21 (m, 1H), 8.01-8.00 (dd, J=5.2, 5.2 Hz, 1H), 7.80-7.78 (d, J=8.0 Hz, 1H), 7.67-7.67 (m, 1H), 7.55-7.53 (dd, J=7.6, 7.6 Hz, 1H), 4.81 (d, 1H), 4.0 (bs, 1H), 3.78-3.74 (m, 1H), 3.53-3.48 (m, 1H), 3.21-3.20 (s, 2H), 1.80-1.74 (m, 2H), 1.39 (s, 11H). LCMS: 99.8% (m/z=451.54 [M+H]). HPLC=98.8%.

Example 9: (4-(6-(2-(tert-butyl)pyridin-4-yl)pyrazin-2-yl)-3-chlorophenyl)(4-hydroxypiperidin-1-yl)methanone (Compound 9)

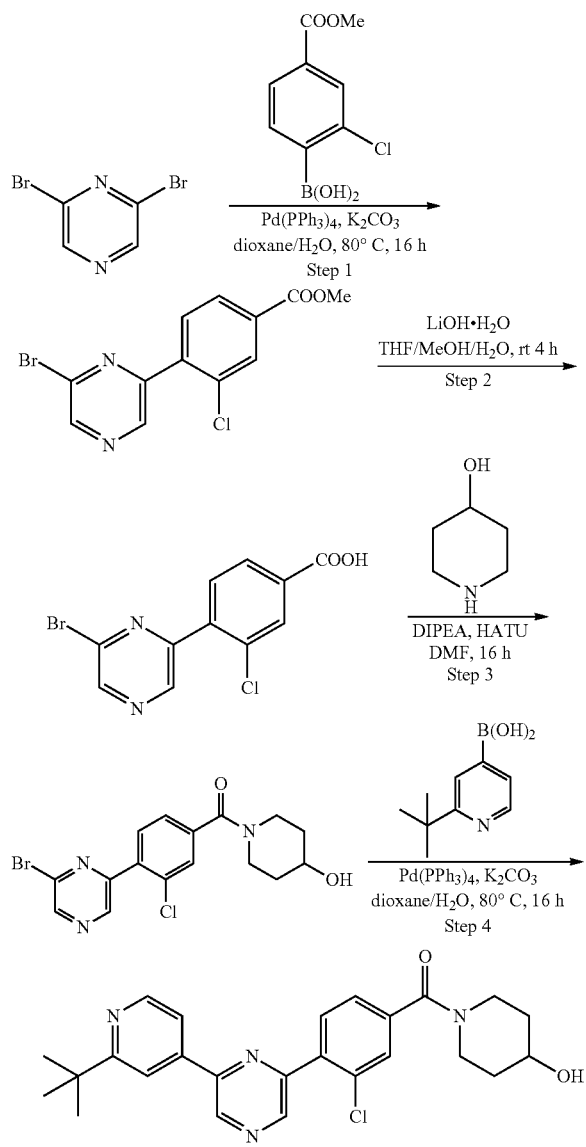

Step 1: Synthesis of methyl 4-(6-bromopyrazin-2-yl)-3-chlorobenzoate. A solution of 2,6-dibromopyrazine (500 mg, 2.1019 mmol), (2-chloro-4-(methoxycarbonyl)phenyl)boronic acid (314 mg, 1.4713 mmol) and potassium carbonate (314 mg, 3.1528 mmol) in 1,4-dioxane/H$_2$O (10:1, 11 mL) was purged with nitrogen gas for 15 minutes. To this mixture was added palladium tetrakis (242.76 mg, 0.21 mmol), and the combination was heated at 80° C. for 16 h. The reaction progress was monitored by TLC. After completion of the reaction, the reaction mixture was filtered through Celite® and concentrated under reduced pressure. The residue was dissolved in water (10 mL) and extracted with EtOAc (3×15 mL). The combined organic extracts were dried over anhydrous sodium sulfate and concentrated under reduced pressure to obtain crude product which was purified by column chromatography (Silica 100-200 mesh), eluting with 25% EtOAc in petroleum ether to give methyl 4-(6-bromopyrazin-2-yl)-3-chlorobenzoate as an off-white solid (220 mg, 32%). LCMS: 93.75% (M+H=327.11). $^1$H NMR (400 MHz, CDCl$_3$: δ (ppm): 8.96 (s, 1H), 8.72 (s, 1H), 8.18 (d, J=1.6 Hz, 1H), 8.06-8.06-8.04 (m, 1H), 7.74 (d, J=8 Hz, 1H), 3.97 (s, 3H).

Step 2: Synthesis of 4-(6-bromopyrazin-2-yl)-3-chlorobenzoic acid. To a stirred solution of methyl 4-(6-bromopyrazin-2-yl)-3-chlorobenzoate (300 mg, 0.613 mmol) in THF/H$_2$O (3:1) (3.7 mL) was added LiOH.H$_2$O (25.7 mg, 0.613 mmol), and the reaction stirred at rt for 4 h. The reaction progress was monitored by TLC. After completion of the reaction, the mixture was concentration under reduced pressure, the residue was dissolved in water (10 mL) and acidified with 1N HCl to pH 3, and the aqueous layer was extracted with EtOAc (3×20 mL). The organic extracts were combined, dried over anhydrous sodium sulfate, and concentrated under reduced pressure to obtain crude 4-(6-bromopyrazin-2-yl)-3-chlorobenzoic acid, which was used for next step without purification (130 mg, 68%).

Step 3: Synthesis of (4-(6-bromopyrazin-2-yl)-3-chlorophenyl)(4-hydroxypiperidin-1-yl)methanone. To a stirred solution of 4-(6-bromopyrazin-2-yl)-3-chlorobenzoic acid (125 mg, 0.40 mmol) in DMF (5 mL) was added DIPEA (0.21 ml, 1.2 mmol) followed by the addition of HATU (608.9 mg, 1.6 mmol), and the mixture stirred for 10 minutes. Then was added piperidin-4-ol (60.69 mg, 0.60 mmol). The reaction mixture was stirred at rt for 16 h and the reaction progress was monitored by TLC. After completion of the reaction, the residue was dissolved in water (10 mL) and extracted with EtOAc (3×15 mL). The organic extracts were combined, dried over anhydrous sodium sulfate, and concentrated under reduced pressure to obtain crude (4-(6-bromopyrazin-2-yl)-3-chlorophenyl)(4-hydroxypiperidin-1-yl)methanone (125 mg, 73%). $^1$H NMR (400 MHz, CDCl3: δ (ppm): 8.94 (s, 1H), 8.71 (s, 1H), 7.70 (d, J=8 Hz, 1H), 7.56 (s, 1H), 7.43-7.41 (dd, J=1.6, 1.6 Hz, 1H), 4.14-4.09 (m, 1H), 3.71-3.68 (s, 1H), 3.46 (s, 1H), 3.17 (s, 1H), 3.16 (s, 1H), 1.81 (s, 1H), 1.75 (s, 1H), 1.30-1.28 (m, 2H), LCMS: 95.20% (M+H=396.19).

Step 4: Synthesis of (4-(6-(2-(tert-butyl)pyridin-4-yl)pyrazin-2-yl)-3-chlorophenyl)(4-hydroxypiperidin-1-yl)methanone. A solution of (4-(6-bromopyrazin-2-yl)-3-chlorophenyl)(4-hydroxypiperidin-1-yl)methanone (125 mg, 0.316 mmol), (2-(tert-butyl)pyridin-4-yl)boronic acid (82.5 mg, 0.316 mmol) and potassium carbonate (87.3 mg, 0.632 mmol) in 1,4-dioxane/H$_2$O (5:1, 6 mL) was purged with nitrogen gas for 15 minutes. To this mixture was added palladium tetrakis (36.55 mg, 0.031 mmol), and the mixture was heated at 80° C. for 16 h. The reaction was monitored by TLC. After completion of the reaction, the reaction mixture was filtered through Celite®, concentrated under reduced pressure, and the residue dissolved in water (10 mL) then extracted with EtOAc (3×15 mL). The organic extracts were combined, dried over anhydrous sodium sulfate and concentrated under reduced pressure to obtain crude product. The crude compound was purified by preparative HPLC. Collected fractions were concentrated under reduced pressure to afford (4-(6-(2-(tert-butyl)pyridin-4-yl)pyrazin-2-yl)-3-chlorophenyl)(4-hydroxypiperidin-1-yl)methanone (16.8 mg, 11.7%) as an off white solid. $^1$H NMR (400 MHz, DMSO: δ (ppm): 9.45 (s, 1H), 9.06 (s, 1H), 8.70 (d, J=5.2 Hz, 1H), 8.16 (s, 1H), 7.97-7.95 (m, 1H), 7.85 (d, J=8 Hz, 1H), 7.68 (d, J=1.6 Hz, 1H), 7.56-7.53 (m, 1H), 4.81 (d, J=4 Hz, 1H), 4.05-4.02 (m, 1H), 3.79-3.74 (m, 1H), 3.52 (br, 1H), 3.22 (br, 2H), 1.81-1.75 (br, 2H), 1.39 (s, 11H). LCMS: 98.89% (M+H=451.42). HPLC: 97.30%.

Example 10: (4-(2'-(tert-butyl)-6-methoxy-[3,4'-bipyridin]-5-yl)-3-chlorophenyl)(4-hydroxypiperidin-1-yl)methanone (Compound 10)

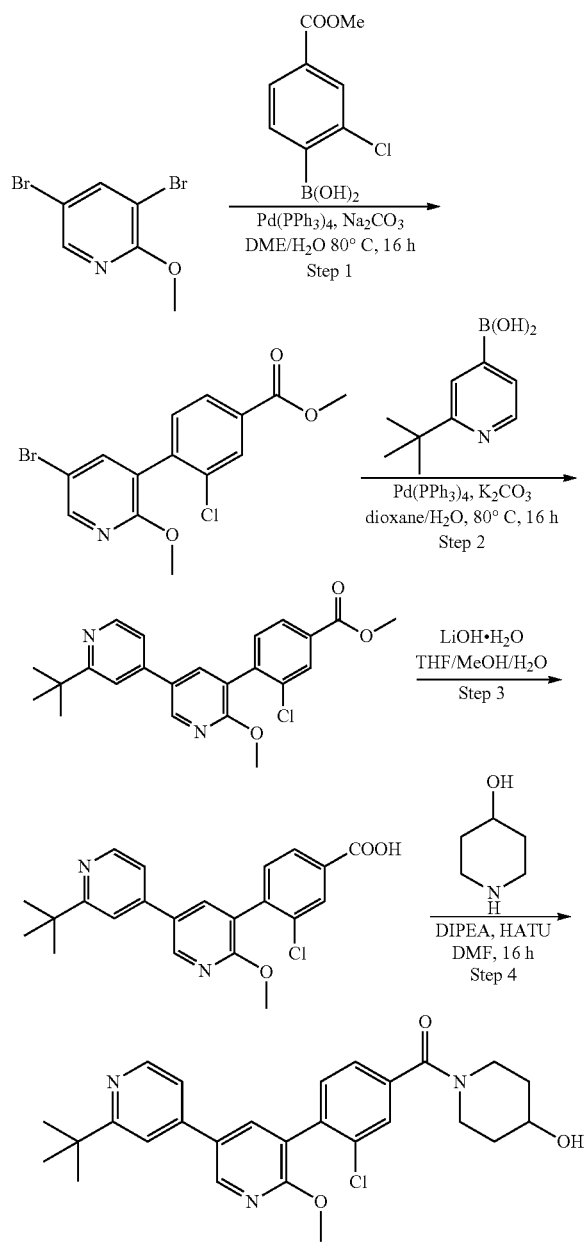

Step 1: Synthesis of methyl 4-(5-bromo-2-methoxypyridin-3-yl)-3-chlorobenzoate. 3,5-dibromo-2-methoxypyridine (300 mg, 1.124 mmol), (2-chloro-4-(methoxycarbonyl)phenyl)boronic acid (289 mg, 1.348 mmol), sodium carbonate (297 mg, 2.801 mmol), water (1 mL) and DME (3 mL) were combined in a 15 mL glass sealed tube and purged with nitrogen gas for 30 minutes. After adding palladium tetrakis (130 mg, 0.112 mmol), the mixture was again purged with nitrogen gas for 30 minutes and then heated to 80° C. for 16 h. The reaction progress was monitored by TLC and LCMS. After completion of the reaction, it was cooled to 25° C.-30° C., filtered through a bed of Celite®, and washed with ethyl acetate (20 mL). The combined organic layers were concentrated under reduced pressure to afford crude product, which was purified through neutral alumina column chromatography using 0-30% ethyl acetate in petroleum ether as an eluent. Selected fractions were collected and concentrated under reduced pressure to afford methyl 4-(5-bromo-2-methoxypyridin-3-yl)-3-chlorobenzoate (200 mg) as an off-white solid. $^1$H NMR (400 MHz, CDCl$_3$): δ 8.27-8.27 (d, J=2.4 Hz, 1H), 8.14-8.13 (d, J=1.6 Hz, 1H), 7.98-7.96 (dd, J=8.0, 8.0 Hz, 1H), 7.62-7.61 (d, J=2.4 Hz, 1H), 7.37-7.35 (d, J=8.0 Hz, 1H), 3.95 (s, 3H), 3.9 (s, 3H). LCMS: 98% (m/z=356.16 [M+H]).

Step 2: Synthesis of methyl 4-(2'-(tert-butyl)-6-methoxy-[3,4'-bipyridin]-5-yl)-3-chlorobenzoate. Methyl 4-(2'-(tert-butyl)-6-methoxy-[3,4'-bipyridin]-5-yl)-3-chlorobenzoate (200 mg, 0.563 mmol), (2-(tert-butyl)pyridin-4-yl)boronic acid (147 mg, 0.563 mmol), potassium carbonate (194 mg, 1.408 mmol) in water (1 mL) and 1,4-dioxane (4 mL) were charged in 15 mL glass seal tube and purged with nitrogen gas for 30 minutes. After adding palladium tetrakis (65 mg, 0.0563 mmol), the mixture was again purged with nitrogen gas for 30 minutes, and then heated to 80° C. for 16 h. The reaction progress was monitored by TLC and LCMS. After completion of the reaction, it was cooled 25° C.-30° C., filtered through a bed of Celite®, and extracted with ethyl acetate (15 mL). The combined organic layers were concentrated under reduced pressure to afford crude product, which was purified through neutral alumina column chromatography using 0-50% ethyl acetate in petroleum ether. Selected fractions were collected and concentrated under reduced pressure to afford methyl 4-(2'-(tert-butyl)-6-methoxy-[3,4'-bipyridin]-5-yl)-3-chlorobenzoate (70 mg) as a colorless gum. $^1$H-NMR (400 MHz, DMSO-D6): δ 8.63-8.61 (m, 1H), 8.52-8.52 (d, J=2.4 Hz, 1H), 8.18-8.17 (d, J=1.6 Hz, 1H), 8.02-7.99 (m, 1H), 7.77-7.76 (d, J=2.4 Hz, 1H), 7.50-7.50 (m, 1H), 7.45-7.43 (d, J=8 Hz, 1H), 7.26 (m, 1H), 3.99 (s, 3H), 3.96 (s, 3H), 1.41 (s, 9H). LCMS: 80.63% (m/z=411.1 [M+H]).

Step 3: Synthesis of 4-(2'-(tert-butyl)-6-methoxy-[3,4'-bipyridin]-5-yl)-3-chlorobenzoic acid. To a stirred solution of 4-(2'-(tert-butyl)-6-methoxy-[3,4'-bipyridin]-5-yl)-3-chlorobenzoic acid (240 mg, 0.585 mmol) in methanol:THF:water (3:2:1, 5 mL) was added LiOH.H$_2$O (73 mg, 1.755 mmol), and the mixture was stirred at room temperature for 2 h. The reaction progress was monitored by TLC and LCMS. After completion of the reaction, it was concentrated under reduced pressure, dissolved in water (10 mL) and acidified with citric acid up to pH ~5. The aqueous layer was extracted with ethyl acetate (2×20 mL), and the combined organic layers were collected and dried over sodium sulfate and concentrated under reduced pressure to afford 4-(2'-(tert-butyl)-6-methoxy-[3,4'-bipyridin]-5-yl)-3-chlorobenzoic acid (200 mg) as an off white solid.

Step 4: Synthesis of (4-(2'-(tert-butyl)-6-methoxy-[3,4'-bipyridin]-5-yl)-3-chlorophenyl)(4-hydroxypiperidin-1-yl)methanone. To a stirred solution of 4-(2'-(tert-buty)-6-methoxy-[3,4'-bipyridin]-5-yl)-3-chlorobenzoic acid (200 mg, 0.505 mmol) in DMF (2 mL) and DIPEA (261 mg, 2.02 mmol) was added HATU (768 mg, 2.02 mmol), and the mixture was stirred for 15 min at room temperature under nitrogen. Then 4-hydroxypiperidine (51 mg, 0.505 mmol) was added under nitrogen. The mixture was stirred for 16 h at room temperature and the reaction progress was monitored by TLC and LCMS. After completion of reaction, it was diluted with cold water (25 mL) and extracted with ethyl acetate (2×20 mL). The combined organic layers were washed with ice cold water (50 mL) and dried over sodium sulfate, then concentrated under reduced pressure to afford crude (100 mg) product which was purified through neutral alumina column chromatography using 0-100% ethyl acetate in petroleum ether followed by 10% methanol in ethyl acetate as an eluent. Selected fractions were collected and concentrated under reduced pressure to afford (4-(2'-(tert-butyl)-6-methoxy-[3,4'-bipyridin]-5-yl)(4-hydroxypiperidin-1-yl)methanone (58 mg) as an off white solid. $^1$H-NMR (400 MHz, DMSO): δ 8.73-8.73 (d, J=2.4 Hz, 1H), 8.56-8.55 (d, J=5.2 Hz, 1H), 8.18-8.17 (d, J=2.4 Hz, 1H), 7.75-7.74 (m, 1H), 7.59-7.58 (d, J=1.6 Hz, 1H), 7.58-7.57 (d, J=1.6 Hz, 1H), 7.55-7.53 (d, J=8.0 Hz, 1H), 7.44-7.44 (dd, J=8.0, 8.0 Hz, 1H), 4.82 (bs, 1H), 4.0 (s, 1H), 3.92 (s, 3H), 3.76-3.74 (m, 1H), 3.54 (s, 1H), 3.23 (m, 2H), 1.77-1.54 (m, 2H), 1.362 (s, 11H). LCMS: 99.21% (m/z=480.2 [M+H]). HPLC=99.71%.

Example 11: 1-(4-(2'-(tert-butyl)-[3,4'-bipyridin]-5-yl)-3-chlorophenyl)-3-isopropylurea (Compound 11)

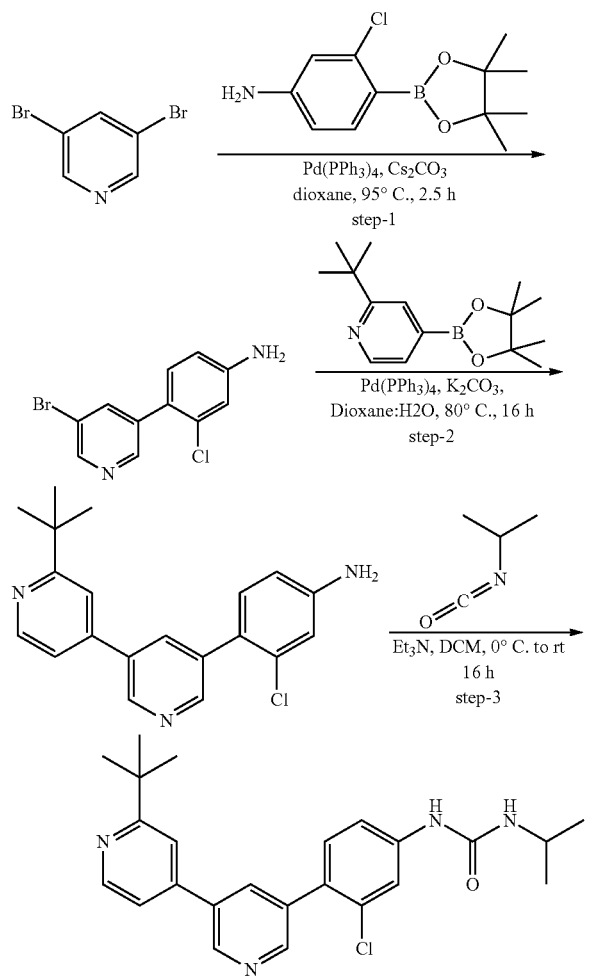

Step 1: Synthesis of 4-(5-bromopyridin-3-yl)-3-chloroaniline. 3,5-dibromo-pyridine (0.300 g, 1.266 mmol), 3-chloro-4-(4,4,5,5-teteramethyl-1,3,2-dioxaborolan-2-yl) aniline (0.291 g, 1.139 mmol) and cesium carbonate (0.824 g, 2.532 mmol) in dioxane (6 mL) were combined in a 10 mL glass seal tube and purged with nitrogen gas for 10 minutes. After adding palladium tetrakis (0.146 g, 0.126 mmol), the mixture was again purged with nitrogen gas for 10 min, then heated to 95° C. for 2.5 h. The reaction was monitored by TLC and LCMS. After completion, the reaction mixture was cooled to RT, then 10 mL water added and the mixture extracted with ethyl acetate (3×15 mL). The organic extracts were combined and were washed with brine (3×10 mL), dried over anhydrous sodium sulfate, and concentrated under reduced pressure to give crude product which was purified by silica gel column chromatography eluting with (0-15% EtOAc in hexane). The product fractions were combined and concentrated to give 4-(5-bromopyridin-3-yl)-3-chloroaniline (0.250 g, 69.63%) as off white solid. $^1$H-NMR (400 MHz, DMSO d$_6$): δ (ppm): 8.63 (1H, J=2.4, d), 8.55 (1H, J=2.0 Hz, d), 8.03 (1H, J=2.0 Hz, t), 7.15-7.13 (1H, J=8.0 Hz, t), 6.73 (1H, J=2.0 Hz, d), 6.62-6.60 (1H, m), 5.68 (2H, s), 5.68 (2H, s); LCMS: 98.62% (m/z=285.0 [M+H]).

Step 2: Synthesis of 4-(2'-(tert-butyl)-[3,4'-bipyridin]-5-yl)-3-chloroaniline. 4-(5-bromopyridin-3-yl)-3-chloroaniline (0.250 g, 0.881 mmol), 2-tert butyl pyridine 4-boronic acid pinacol ester (0.276 g, 1.058 mmol) and potassium carbonate (0.244 g, 1.762 mmol) in dioxane:water (4:1 mL) were combined in a 10 mL glass seal tube and purged with nitrogen gas for 10 minutes. After adding palladium tetrakis (0.101 g, 0.088 mmol), and again purging with nitrogen for 10 minutes, the mixture was heated to 80° C. for 16 h. The reaction was monitored by TLC. After completion, it was cooled, water (10 mL) added and the whole extracted with ethyl acetate (3×10 mL). The extracts were combined, dried over anhydrous sodium sulfate and concentrated under reduced pressure to give crude product which was purified on silica column chromatography eluting with (0-35% ethyl acetate in hexane) to give 4-(2'-(tert-butyl)-[3,4'-bipyridin]-5-yl)-3-chloroaniline (0.250 g, 83.89%) as white solid. $^1$H-NMR (400 MHz, DMSO d$_6$): δ (ppm): 8.91 (1H, J=2.4, d), 8.65 (s, 1H), 8.64 (s, 1H), 8.15 (1H, s), 7.78 (1H, J=0.08, d), 7.6 (m, 1H), 7.23 (1H, J=8.0 Hz, d), 6.76 (1H, J=2.0 Hz, d), 6.7 (s, 1H), 5.64 (2H, s), 1.37 (9H, s). LCMS: 96.96% (m/z [M+H=338.29]).

Step 3: Synthesis of 1-(4-(2'-(tert-butyl)-[3,4'-bipyridin]-5-yl)-3-chlorophenyl)-3-isopropylurea. To a solution of 4-(2'-(tert-butyl)-[3,4'-bipyridin]-5-yl)-3-chloroaniline (0.100 g, 0.296 mmol) in DCM (4 mL, 20 v), was added triethylamine (0.44 g, 0.444 mmol) and 2-isocyanatopropane (0.038 g, 0.444 mmol) at 0° C. The reaction was stirred for 16 h at RT and monitored by TLC. After completion, the reaction mass was diluted with DCM and washed with brine solution (2×5 mL). The organic layer was separated, dried over anhydrous sodium sulfate and concentrated under reduced pressure to give crude product that was purified by preparative HPLC to afford 1-(4-(2'-(tert-butyl)-[3,4'-bipyridin]-5-yl)-3-chlorophenyl)-3-isopropylurea (0.070 g, 56.00% yield) as an off white solid. $^1$H-NMR (400 MHz, DMSO d$_6$): δ (ppm): 8.98 (1H, J=2.4, d), 8.69 (1H, J=2.0 Hz, d), 8.66 (1H, s), 8.61 (1H, J=4.8 Hz, d), 8.24-8.233 (1H, J=2.0, t), 7.84 (1H, J=2.0 Hz, d), 7.80 (1H, J=0.8 Hz, d), 7.64-7.62 (1H, m), 7.46-7.44 (1H, J=8.4 Hz, d), 7.35-7.32 (1H, m), 6.17-6.15 (1H, J=7.8 Hz, d), 3.80-3.73 (1H, m), 1.37 (9H, s), 1.10 (6H, d). LCMS: 99.56% (m/z 423.40 [M+H]). HPLC: purity 99.79%.

Example 12: (4-(2'-(1,3-dioxolan-2-yl)-[3,4'-bipyridin]-5-yl)-3-chlorophenyl)(4-hydroxypiperidin-1-yl)methanone (Compound 12)

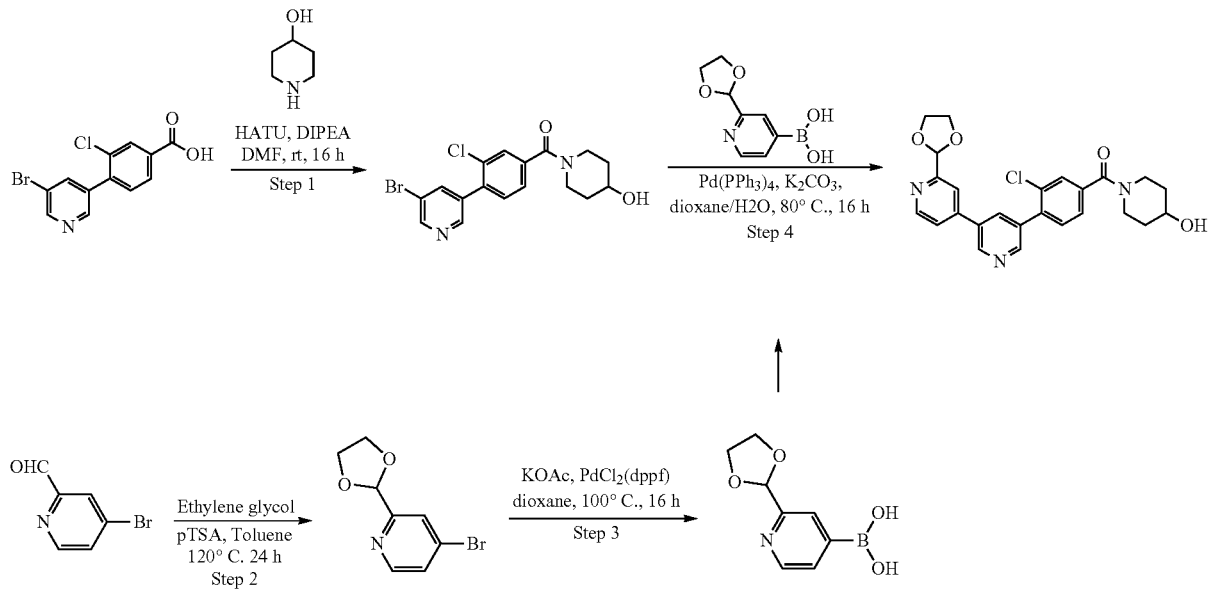

Step 1: (4-(5-bromopyridin-3-yl)-3-chlorophenyl)(4-hydroxypiperidin-1-yl)methanone. To a stirred solution of 4-(5-bromopyridin-3-yl)-3-chlorobenzoic acid as prepared in Example 4 (0.3 g, 1.2 mmol) in DMF (5 mL) was added DIPEA (0.49 g, 3.8 mmol) followed by the addition of HATU (0.73 g, 1.9 mmol). This mixture was stirred for 10 min, then 4-hydroxypiperidine (0.143 g, 1.4 mmol) was added and the mixture stirred at rt for 16 h and monitored by TLC. After completion of the reaction, it was dissolved in water (10 mL) and extracted with ethyl acetate (2×15 mL). The extracts were combined, dried over anhydrous sodium sulfate and concentrated under reduced pressure to obtain crude (4-(5-bromopyridin-3-yl)-3-chlorophenyl)(4-hydroxypiperidin-1-yl)methanone (0.2 g), which was used in step 4 without further purification.

Step 2: Synthesis of 4-bromo-2-(1,3-dioxolan-2-yl)pyridine. To a stirred solution of 4-bromopicolinaldehyde in toluene was added ethylene glycol (2.25 g, 32.5 mmol) and PTSA (0.245 g, 0.075 mmol), and the mixture was heated under reflux for 24 h. The progress of the reaction was monitored by LCMS and TLC. At completion, the reaction mixture was concentrated and partitioned between ethyl acetate and water to give crude product which was purified by flash chromatography eluting with 20% ethyl acetate and petroleum ether to give 4-bromo-2-(1,3-dioxolan-2-yl)pyridine (2.5 g) as a pale yellow liquid. $^1$H-NMR (400 MHz, CDCl$_3$: δ (ppm): 8.43 (d, J=5.2 Hz, 1H), 7.72 (d, J=2 Hz, 1H), 7.47-7.45 (dd, J=2 Hz, 1H), 5.83 (s, 1H), 4.18-4.06 (m, 4H).

Step 3: Synthesis of (2-(1,3-dioxolan-2-yl)pyridin-4-yl)boronic acid. In a glass tube was combined 4-bromo-2-(1,3-dioxolan-2-yl)pyridine (1.0 g, 4.3 mmol) in 1,4-dioxane (15 mL), 4,4,4',4',5,5,5',5'-octamethyl-2,2'-bi(1,3,2-dioxaborolane) (2.20 g, 8.6 mmol), and KOAc (1.2 g, 13.11 mmol) under a nitrogen atmosphere. The mixture was purged for 15 min with nitrogen, then Pd(dppf)Cl$_2$ (0.354 g, 0.43 mmol) was added and the mixture purged again for 10 min with nitrogen. The mixture was sealed in the glass tube and stirred at 80° C. for 16 h, and reaction progress monitored by TLC. After completion of the reaction, the residue was dissolved in water (10 mL) and extracted with EtOAc (3×20 mL). The organic extracts were combined, dried over anhydrous sodium sulfate, and concentrated under reduced pressure to obtained crude product, which was purified by column chromatography (Florisil® 60-120 mesh), eluting with 50% ethyl acetate in hexanes. The product fractions were concentrated under reduced pressure to obtain (2-(1,3-dioxolan-2-yl)pyridin-4-yl)boronic acid as a dark brown semi solid (1 g).

Step 4: Synthesis of (4-(2'-(1,3-dioxolan-2-yl)-[3,4'-bipyridin]-5-yl)-3-chlorophenyl)(4-hydroxypiperidin-1-yl)methanone. (4-(5-bromopyridin-3-yl)-3-chlorophenyl)(4-hydroxypiperidin-1-yl)methanone (0.2 g, 0.5 mmol) was dissolved in 1,4-dioxane (20 mL) and (2-(1,3-dioxolan-2-yl)pyridin-4-yl)boronic acid (0.098 g, 0.5 mmol) and K$_2$CO$_3$ (0.211 g, 1.5 mmol) were added under a nitrogen atmosphere. The mixture was purged for 15 min with nitrogen, then Pd(PPh$_3$)$_4$ (0.058 g, 0.05 mmol) was added and the mixture purged again for 10 min with nitrogen. The reaction vessel was sealed and the reaction stirred at 80° C. for 16 h, with reaction progress monitored by TLC. After completion of the reaction, the residue was dissolved in water (10 mL) and extracted with ethyl acetate (3×20 mL). The organic extracts were combined, dried over anhydrous sodium sulfate, and concentrated under reduced pressure to give crude product, which was purified by preparative HPLC. The product fractions were combined and lyophilized to give (4-(2'-(1,3-dioxolan-2-yl)-[3,4'-bipyridin]-5-yl)-3-chlorophenyl)(4-hydroxypiperidin-1-yl)methanone (62 mg) as an off-white solid. $^1$H-NMR (400 MHz, DMSO: δ (ppm): 9.8 (d, J=2.0 Hz, 1H), 8.79 (d, J=2.0 Hz, 1H), 8.68 (d, J=5.2 Hz, 1H), 7.93-7.89 (m, 2H), 7.69-7.65 (m, 2H), 7.50-7.40 (m, 1H), 5.82 (s, 1H), 4.82 (s, 1H), 4.19-4.1 (m, 2H), 4.04-3.96 (m, 3H), 3.96-3.70 (m, 1H), 3.7 (m, 1H), 3.50 (br 1H), 3.20 (br, 2H), 1.80-1.74 (br, 2H), 1.39-1.33 (br, 2H). LCMS: (466.39 [M+H]) 98.38%. HPLC: 97.78%.

Example 13: tert-butyl (1-(4-(2'-(tert-butyl)-[3,4'-bipyridin]-5-yl)-3-chlorobenzoyl)piperidin-3-yl)carbamate (Compound 13)

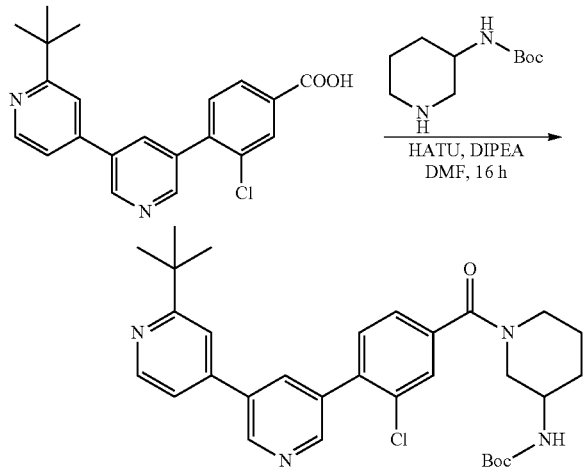

To a stirred solution of 4-(2'-(tert-butyl)-[3,4'-bipyridin]-5-yl)-3-chlorobenzoic acid (100 mg, 0.4098 mmol) as prepared in Example 4 in DMF (1 mL) was added tert-butyl piperidin-3-ylcarbamate (123 mg, 0.614 mmol), HATU (622.8 mg, 1.639 mmol) and DIPEA (158.8 mg, 1.229 mmol), and the mixture stirred at RT for 16 h. The reaction was monitored by TLC. After completion, the reaction mixture was quenched with ice cold water and extracted with ethyl acetate. The organic layer was dried with anhydrous sodium sulfate, filtered and concentrated under reduced pressure to obtain crude compound (150 mg), which was purified by preparative HPLC. Selected fractions were concentrated under reduced pressure and lyophilized to afford tert-butyl (1-(4-(2'-(tert-butyl)-[3,4'-bipyridin]-5-yl)-3-chlorobenzoyl)piperidin-3-yl)carbamate (48 mg) as an off white solid. $^1$H-NMR (400 MHz, DMSO d$_6$): δ (ppm): 9.06 (d, J=2.0 Hz 1H), 8.74 (br s, 1H), 8.62 (d, J=5.2 Hz, 1H), 8.34 (br s, 1H), 7.82 (s, 1H), 7.68-7.64 (m, 3H) 7.52-7.40 (m, 1H), 7.01 (br s, 1H), 3.92-3.70 (m, 2H), 3.43 (br s, 1H), 3.15-3.10 (m, 1H), 1.80-1.76 (m, 2H), 1.51-1.47 (m, 2H) 1.38-1.36 (m, 20H). LCMS: 99.46% (m/z=549.49 [M+H]). HPLC: 99.84%.

Example 14: (4-(2'-(tert-butyl)-[3,4'-bipyridin]-5-yl)-3-chlorophenyl)(3-hydroxypiperidin-1-yl)methanone (Compound 14)

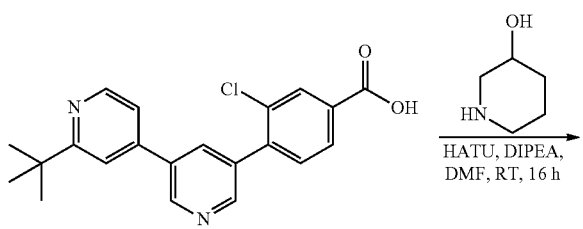

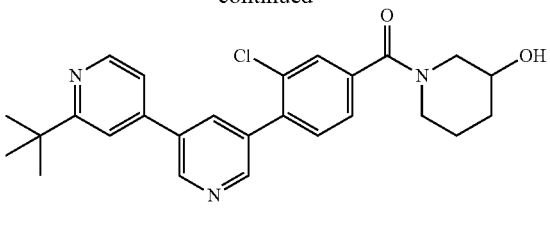

To a stirred solution of 4-(2'-(tert-butyl)-[3,4'-bipyridin]-5-yl)-3-chlorobenzoic acid (100 mg, 0.4098 mmol) in DMF (1 mL) was added HATU (622.8 mg, 1.639 mmol) and DIPEA (158.8 mg, 1.229 mmol), and the mixture stirred for 10 min. Then piperidin-3-ol (62 mg, 0.614 mmol) was added, and the reaction was stirred at RT for 16 h. After completion of the reaction (as determined by TLC), the reaction mixture was quenched with ice cold water and extracted with ethyl acetate. The organic layer was dried with anhydrous sodium sulfate, filtered and concentrated under reduced pressure to obtain crude compound (150 mg), which was purified by preparative HPLC. Compound fractions were concentrated under reduced pressure and lyophilized to afford (4-(2'-(tert-butyl)-[3,4'-bipyridin]-5-yl)-3-chlorophenyl)(3-hydroxypiperidin-1-yl)methanone.
$^1$H-NMR (400 MHz, DMSO d$_6$): δ (ppm): 9.07 (d, J=2.0 Hz 1H), 8.76 (d, J=2 Hz 1H), 8.63-8.62 (m, 1H), 8.35-8.34 (m, 1H), 7.83-7.82 (m, 1H), 7.68-7.64 (m, 3H) 7.52-7.50 (m, 1H), 5.01-4.90 (m, 1H), 3.89-3.32 (m, 4H), 3.10-2.89 (m, 1H), 1.81-1.43 (m, 2H), 1.38-1.36 (m, 11H). LCMS: 98.92%. HPLC: 98.81% (m/z=450.1 [M+H]).

Example 15: (4-(2'-(tert-butyl)-[3,4'-bipyridin]-5-yl)-3-chlorophenyl)(3-methoxypiperidin-1-yl)methanone (Compound 15)

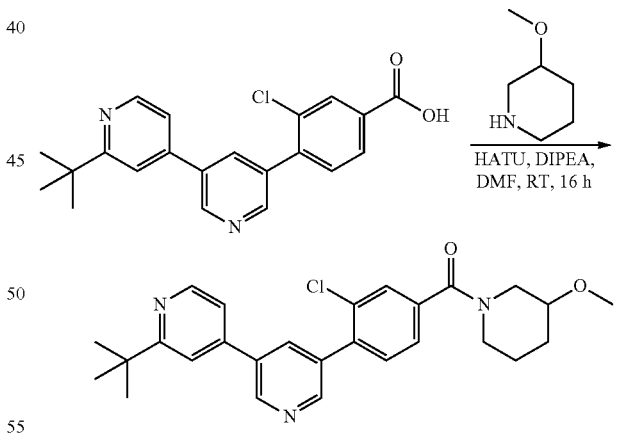

To a stirred solution of 4-(2'-(tert-butyl)-[3,4'-bipyridin]-5-yl)-3-chlorobenzoic acid (100 mg, 0.4098 mmol) in DMF (1 mL) was added HATU (622.8 mg, 1.639 mmol) and DIPEA (158.8 mg, 1.229 mmol), and the mixture stirred for 10 min. Then 3-methoxypiperidine (71 mg, 0.614 mmol) was added, and the reaction stirred at RT for 16 h. After completion of the reaction (as determined by TLC), the reaction mixture was quenched with ice cold water and extracted with ethyl acetate. The organic layer was dried with anhydrous sodium sulfate, filtered, and concentrated under reduced pressure to obtain crude product (150 mg), which was purified by preparative HPLC. Fractions containing the product were combined and concentrated under reduced pressure and lyophilized to afford (4-(2'-(tert-butyl)-[3,4'-bipyridin]-5-yl)-3-chlorophenyl)(3-methoxypiperidin-1-yl. $^1$H-NMR (400 MHz, DMSO d$_6$): δ (ppm): 9.07 (d, J=2.4 Hz 1H), 8.76 (d, J=2 Hz 1H), 8.63-8.62 (m, 1H), 8.36-8.35 (m, 1H), 7.83-7.82 (m, 1H), 7.68-7.62 (m, 3H) 7.49 (m, 1H), 3.95-3.75 (m, 1H), 3.34 (m, 4H), 3.15 (m, 3H), 1.90-1.70 (m, 3H), 1.38 (s, 10H). LCMS: 99.56%. HPLC: 99.83% (m/z=464.2 [M+H]).

Example 16: isopropyl (4-(2'-(tert-butyl)-[3,4'-bipyridin]-5-yl)-3-chlorophenyl)carbamate (Compound 16)

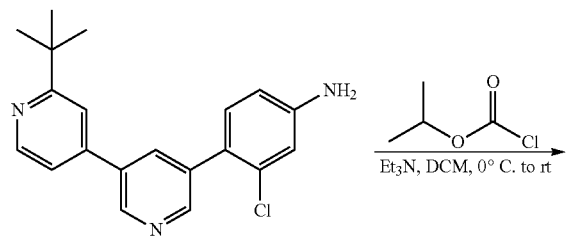

To a solution of 4-(2'-(tert-butyl)-[3,4'-bipyridin]-5-yl)-3-chloroaniline (0.100 g, 0.296 mmol) in DCM (4 mL, 20 v), was added triethylamine (0.44 g, 0.444 mmol) and isopropyl chloroformate (0.054 g, 0.444 mmol) at 0° C. The reaction was then stirred for 16 h at RT. After completion (as determined by TLC), the mixture was diluted with DCM and washed with brine solution (2×5 mL). The organic layers were separated, combined, dried over anhydrous sodium sulfate and concentrated under reduced pressure to get a crude product which was purified by preparative HPLC to afford isopropyl (4-(2'-(tert-butyl)-[3,4'-bipyridin]-5-yl)-3-chlorophenyl)carbamate (0.031 g, 24.60% yield) as an off-white solid. $^1$H-NMR (400 MHz, DMSO d$_6$): δ (ppm): 9.94 (1H, s), 9.00 (1H, J=2.4 Hz, d), 8.70 (1H, J=2.0, s), 8.62-8.61 (1H, m), 8.25 (1H, t), 7.80 (1H, J=0.08 Hz, d), 7.64-7.42 (1H, m), 7.52 (2H, J=1.2 d), 4.95-4.89 (1H, m), 1.37 (9H, s), 1.29-1.27 (6H, d). LCMS: 99.55% (m/z 424.1 [M+H]). HPLC purity 99.12%.

Example 17: (4-(2'-(tert-butyl)-6-methyl-[3,4'-bipyridin]-5-yl)-3-chlorophenyl)(4-hydroxypiperidin-1-yl)methanone (Compound 17)

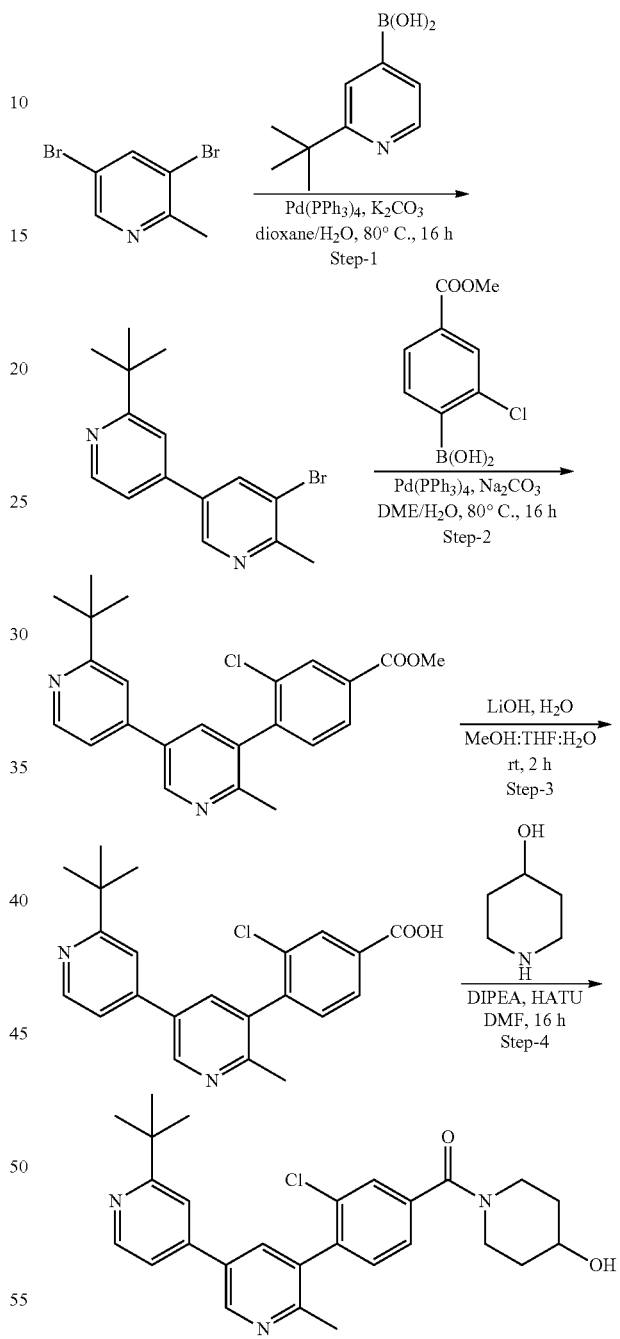

Step 1: Synthesis of 5-bromo-2'-(tert-butyl)-6-methyl-3,4'-bipyridine. In a 48 mL glass seal tube was combined 3,5-dibromo-2-methylpyridine (200 mg, 0.80 mmol), (2-(tert-butyl)pyridin-4-yl)boronic acid (158 mg, 0.88 mmol), and potassium carbonate (277 mg, 2.00 mmol) in water (1 mL) and 1,4-dioxane (10 mL) which was purged with argon gas for 30 min. After adding palladium tetrakis (92 mg, 0.08 mmol), the mixture was again purged with argon gas for 30 min, then the tube was sealed and heated to 80° C. for 16 h.

After completion of reaction (as determined by TLC), the mixture was cooled to 25° C.-30° C., filtered through a Celite® bed, and extracted with ethyl acetate (20 mL). The combined organic layers were concentrated under reduced pressure to afford crude product (500 mg) which was purified with neutral alumina column chromatography using 0-30% ethyl acetate in petroleum ether as an eluent. Selected fractions were collected and concentrated under reduced pressure to afford 5-bromo-2'-(tert-butyl)-6-methyl-3,4'-bipyridine (200 mg) as an off-white solid. $^1$H-NMR (400 MHz, CDCl$_3$): δ 8.67-8.64 (m, 2H), 8.03-8.03 (d, J=2.0 Hz, 1H), 7.47 (m, 1H), 7.27-7.26 (m, 1H), 2.73 (s, 3H), 1.43 (s, 9H).

Step 2: Synthesis of (2-chloro-4-(methoxycarbonyl)phenyl)boronic. Into a 15 mL glass seal tube was combined 5-bromo-2'-(tert-butyl)-6-methyl-3,4'-bipyridine (200 mg, 0.657 mmol), (2-chloro-4-(methoxycarbonyl)phenyl)boronic acid (168 mg, 0.789 mmol), potassium carbonate (226 mg, 1.64 mmol), water (1 mL), and 1,4-dioxane (10 mL), and the mixture purged with argon gas for 30 min. After adding palladium tetrakis (75 mg, 0.065 mmol), the mixture was again purged with argon gas for 30 min, then heated to 80° C. for 16 h. After completion of the reaction (as determined by TLC), the mixture was cooled 25° C.-30° C., filtered through a Celite® bed, and extracted with ethyl acetate. The combined organic layers were concentrated under reduced pressure to afford crude product (300 mg), which was purified with neutral alumina column chromatography using 0-50% ethyl acetate in petroleum ether as an eluent. Selected fractions were collected and concentrated under reduced pressure to afford (2-chloro-4-(methoxycarbonyl)phenyl)boronic acid (150 mg) as a pale yellow gum.

Step 3: Synthesis of 4-(2'-(tert-butyl)-6-methyl-[3,4'-bipyridin]-5-yl)-3-chlorobenzoic acid. To a stirred solution of (2-chloro-4-(methoxycarbonyl)phenyl)boronic acid (150 mg, 0.585 mmol) in methanol:THF:water (3:2:1, 5 mL) was added LiOH.H$_2$O (48 mg, 1.14 mmol), and the mixture stirred at room temperature for 2 h. After completion of the reaction, the mixture was concentrated under reduced pressure. The crude material was dissolved in water (10 mL) and acidified with citric acid up to pH ~5. Then the product was extracted into ethyl acetate (2×20 mL). The combined organic layers were dried over sodium sulfate and concentrated under reduced pressure to afford product (140 mg) as an off white solid which was used in the next step without further purification.

Step 4: Synthesis of (4-(2'-(tert-butyl)-6-methyl-[3,4'-bipyridin]-5-yl)-3-chlorophenyl)(4-hydroxypiperidin-1-yl)methanone. To a stirred solution of 4-(2'-(tert-butyl)-6-methyl-[3,4'-bipyridin]-5-yl)-3-chlorobenzoic acid (140 mg, 0.368 mmol) in DMF (3 mL) and DIPEA (0.264 mL, 1.47 mmol) was added HATU (559 mg, 1.47 mmol) and the mixture was stirred for 15 min at room temperature under argon. Then 4-hydroxypiperidine (44 mg, 0.442 mmol) was added under argon. The mixture was stirred for 16 h at room temperature. After completion of the reaction (as determined by TLC), the mixture was diluted with cold water (25 mL) and the product was extracted into ethyl acetate (2×20 mL). The combined ethyl acetate layers were washed with ice cold water (50 mL) and dried over sodium sulfate, then concentrated under reduced pressure to afford crude product which was purified by preparative HPLC to afford (4-(2'-(tert-butyl)-6-methyl-[3,4'-bipyridin]-5-yl)-3-chlorophenyl)(4-hydroxypiperidin-1-yl)methanone (54 mg) as an off white solid. $^1$H-NMR (400 MHz, DMSO): 8.97-8.96 (d, J=2.4 Hz, 1H), 8.59-8.58 (d, J=5.2 Hz, 1H), 8.10-8.09 (d, J=2.4 Hz, 1H), 7.77 (m, 1H), 7.64-7.60 (m, 2H), 7.54-7.52 (m, 1H), 7.48-7.46 (m, 1H), 4.82-4.81 (d, J=3.6 Hz, 1H), 4.00 (bs, 1H), 3.79-3.75 (m, 1H), 3.57-3.55 (m, 1H), 3.32 (m, 2H), 2.33 (s, 3H), 1.79 (m, 2H), 1.4 (m, 2H), 1.36 (s, 9H). LCMS: 98.59% (m/z=464.55 [M+H]). HPLC: 98.83%.

Example 18: (4-(2'-(tert-butyl)-2-methyl-[3,4'-bipyridin]-5-yl)-3-chlorophenyl)(4-hydroxypiperidin-1-yl)methanone (Compound 18)

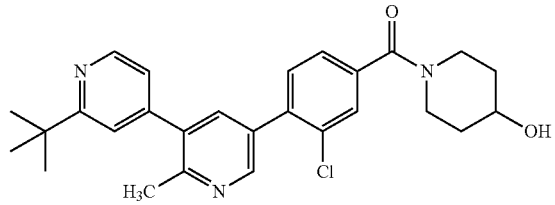 [SMILES: Cc1ncc(-c2ccc(C(=O)N3CCC(O)CC3)cc2Cl)cc1-c1ccnc(C(C)(C)C)c1]

This compound was prepared by a series of reactions similar to those shown in Example 17. $^1$H-NMR (400 MHz, DMSO-D6): δ 8.63-8.60 (m, 2H), 8.56-8.55 (d, J=2.0 Hz, 1H), 7.63-7.61 (m, 2H), 7.54-7.53 (m, 1H), 7.46-7.44 (dd, J=7.6 Hz, J=8 Hz, 1H), 4.81-4.80 (d, J=4 Hz, 1H), 4.02-3.99 (s, 1H), 3.78-3.73 (m, 1H), 3.50 (bs, 1H), 3.32-3.18 (b, 2H), 2.53-2.49 (m, 3H), 1.79-1.73 (m, 2H), 1.36 (s, 11H). LCMS: 97.82% (m/z=464.54 [M+H]). HPLC: 99.59%.

Example 19: (4-(2'-(tert-butyl)-2-methoxy-[3,4'-bipyridin]-5-yl)-3-chlorophenyl)(4-hydroxypiperidin-1-yl)methanone (Compound 19)

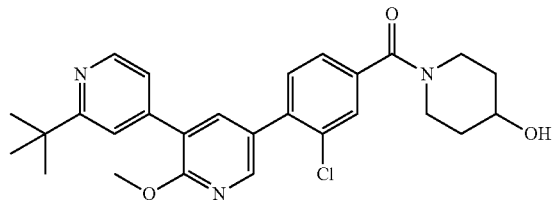 [SMILES: COc1ncc(-c2ccc(C(=O)N3CCC(O)CC3)cc2Cl)cc1-c1ccnc(C(C)(C)C)c1]

This compound was prepared by a series of reactions similar to those shown in Example 17. $^1$H-NMR (400 MHz, DMSO): δ 8.57-8.56 (d, J=5.2 Hz, 5.2 Hz, 1H), 8.36-8.35 (d, J=2.4 Hz, 1H), 8.03-8.02 (d, J=2.4 Hz, 1H), 7.65-7.60 (m, 3H), 7.48-7.43 (m, 2H), 4.81-4.80 (d, J=3.6 Hz, 1H), 4.01 (m, 1H), 3.97 (s, 3H), 3.77-3.74 (m, 1H), 3.53-3.51 (m, 1H), 3.20-3.19 (m, 2H), 1.82-1.75 (m, 2H), 1.37 (m, 2H), 1.35 (s, 9H). LCMS: 99.52% (m/z=480.1 [M+H]). HPLC: 99.15%.

Example 20: Isopropyl (4-(2'-(1,3-dioxolan-2-yl)-[3,4'-bipyridin]-5-yl)-3-chlorophenyl)carbamate (Compound 20)

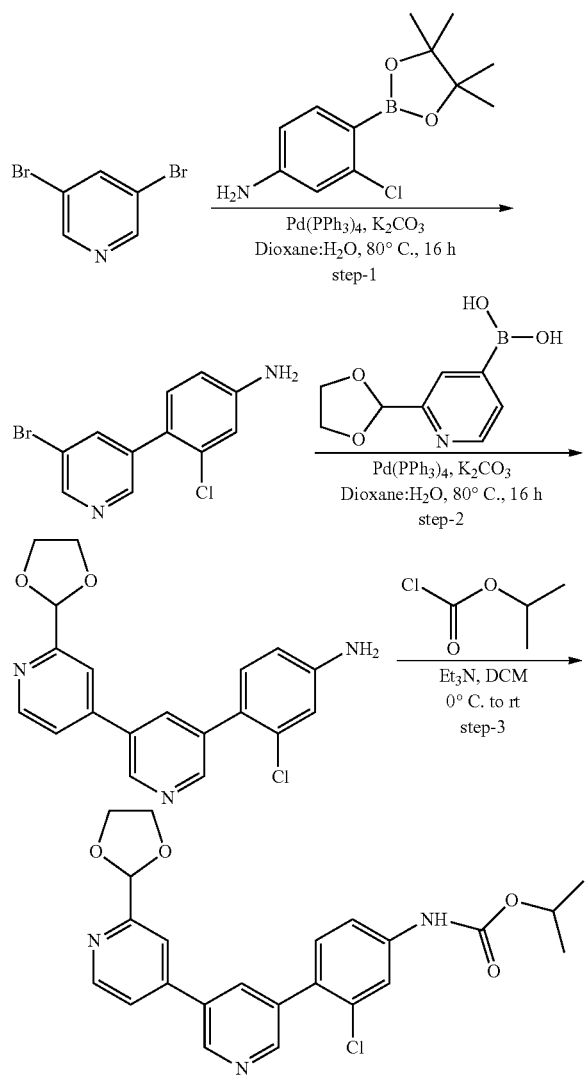

Step 1: Synthesis of 4-(5-bromopyridin-3-yl)-3-chloroaniline. 3,5-dibromopyridine (1.0 g, 4.22 mmol), 3-chloro-4-(4,4,5,5-teteramethyl-1,3,2-dioxaborolan-2-yl)aniline (0.96 g, 3.78 mmol) and potassium carbonate (1.75 g, 12.66 mmol) in dioxane (25 mL) were combined in a 50 mL glass seal tube and purged with nitrogen gas for 10 min. Tetrakis palladium (0.48 g, 0.422 mmol) was added and the mixture was again purged with nitrogen gas for 10 min, then heated to 80° C. for 16 h. After completion of the reaction (as determined by TLC), the reaction mixture was cooled to RT, 10 mL water added, and the mixture extracted with ethyl acetate (3×15 mL). The organic extracts were combined, washed with brine (3×10 mL) and dried over anhydrous sodium sulfate. The solution was concentrated under reduced pressure and purified by flash column chromatography (silica gel 100-200 mesh) using 20% ethyl acetate and hexane used as an eluent. Selected fractions were collected and concentrated to give 4-(5-bromopyridin-3-yl)-3-chloroaniline (0.350 g, 97%) as an off white solid.

Step 2: Synthesis of 4-(2'-(1,3-dioxolan-2-yl)-[3,4'-bipyridin]-1-yl)-3-chloroaniline. 4-(5-bromopyridin-3-yl)-3-chloroaniline (0.350 g, 1.23 mmol), (2-(1,3-dioxolan-2-yl)pyridin-4-yl)boronic acid (0.36 g, 1.85 mmol) and potassium carbonate (0.51 g, 3.78 mmol) in dioxane:water (30 mL, 4:1) were combined in a 50 mL glass seal tube and purged with nitrogen gas for 10 minutes. Palladium tetrakis (0.14 g, 0.123 mmol) was added and the mixture again purged with nitrogen gas for 10 minutes. The reaction mass was heated to 80° C. for 16 h. After completion of the reaction (as determined by TLC), the mixture was cooled, water (10 mL) was added, and the mixture was extracted with ethyl acetate (3×10 mL). The organic extracts were combined, dried over anhydrous sodium sulfate, and concentrated under reduced pressure to obtain crude product, which was purified by column chromatography (silica gel 230-400) using MeOH/DCM as the mobile phase. Selected fractions containing the product were combined and concentrated to give 4-(2'-(1,3-dioxolan-2-yl)-[3,4'-bipyridin]-5-yl)-3-chloroaniline (0.200 g, 83.89%) as a yellow solid.

Step 3: Synthesis of isopropyl (4-(2'-(1,3-dioxolan-2-yl)-[3,4'-bipyridin]-5-yl)-3-chlorophenyl)carbamate. To a solution of 4-(2'-(1,3-dioxolan-2-yl)-[3,4'-bipyridin]-5-yl)-3-chloroaniline (0.200 g, 0.56 mmol) in DCM (10 mL, 20 v) was added triethylamine (0.17 g, 1.69 mmol) and isopropylchloroformate (0.1 g, 0.84 mmol) at 0° C. The reaction was stirred for 16 h at RT. After completion, the reaction mass was diluted with DCM and washed with brine solution (2×5 mL). The combined organic layers were separated, dried over anhydrous sodium sulfate and concentrated under reduced pressure to get crude product which was purified by preparative HPLC to afford isopropyl (4-(2'-(1,3-dioxolan-2-yl)-[3,4'-bipyridin]-5-yl)-3-chlorophenyl)carbamate (0.034 g, 24.60% yield) as an off white solid. $^1$H-NMR (400 MHz, DMSO $d_6$): δ (ppm): 8.94 (1H, s), 8.70 (1H, J=2.0 Hz, d), 8.66 (1H, J=5.2 Hz, d), 8.26 (1H, J=2 Hz, t), 7.95 (1H, 1.2 Hz, s), 7.82-7.79 (2H, m), 7.51-7.48 (1H, m), 7.44-7.42 (d, J=8.4 Hz, 1H), 5.86 (1H, s), 5.0-4.97 (1H, m), 4.21-4.15 (2H, m), 4.09-4.06 (2H, m), 1.31 (6H, J=6.4 Hz, d). LCMS: 99.18% (m/z 440.1 [M+H]). HPLC: purity 97.64%.

Example 21: Synthesis of (4-(2'-(tert-butyl)-[3,4'-bipyridin]-5-yl)-3-chlorophenyl)(4-hydroxy-4-methylpiperidin-1-yl)methanone (Compound 21)

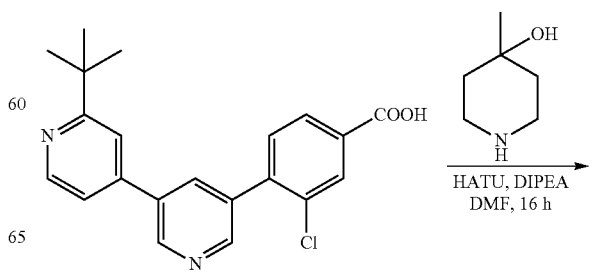

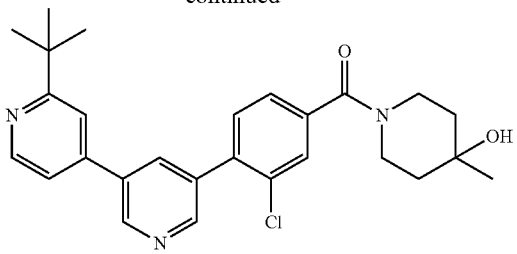

To a stirred solution of 4-(2'-(tert-butyl)-[3,4'-bipyridin]-5-yl)-3-chlorobenzoic acid (100 mg, 0.4098 mmol) in DMF (1 ml) was added HATU (622.8 mg, 1.639 mmol) and DIPEA (158.8 mg, 1.229 mmol). After stirring for 10 min, 4-methylpiperidin-4-ol (71 mg, 0.614 mmol) was added, and the reaction then stirred at RT for 16 h. The reaction mixture was quenched with ice cold water and extracted with EtOAc. The organic layer was dried with anhydrous sodium sulfate, filtered, and concentrated under reduced pressure to obtain crude product, which was purified by preparative HPLC. Compound fractions were combined, concentrated under reduced pressure, and lyophilized to afford (4-(2'-(tert-butyl)-[3,4'-bipyridin]-5-yl)-3-chlorophenyl)(4-hydroxy-4-methylpiperidin-1-yl)methanone as an off white solid (35 mg). $^1$H-NMR (400 MHz, DMSO d$_6$): δ (ppm): δ 9.07 (d, J=2.00 Hz, 1H), 8.76 (d, J=2.40 Hz, 1H), 8.63 (dd, J=0.80, 5.20 Hz, 1H), 8.35 (t, J=2.40 Hz, 1H), 7.83 (d, J=0.80 Hz, 1H), 7.68-7.63 (m, 3H), 7.49 (dd, J=1.60, 7.60 Hz, 1H), 4.45 (s, 1H), 4.09-4.12 (m, 1H), 3.34-3.37 (br, 3H), 1.60-1.40 (br, 4H), 1.38 (s, 9H), 1.19 (s, 3H). LCMS: 99.16% (m/z=464.2 [M+H]). HPLC 98.86%.

Example 22: Synthesis of (4-(2'-(tert-butyl)-[3,4'-bipyridin]-5-yl)-3-chlorophenyl)(3-hydroxy-3-methylpiperidin-1-yl)methanone (Compound 22)

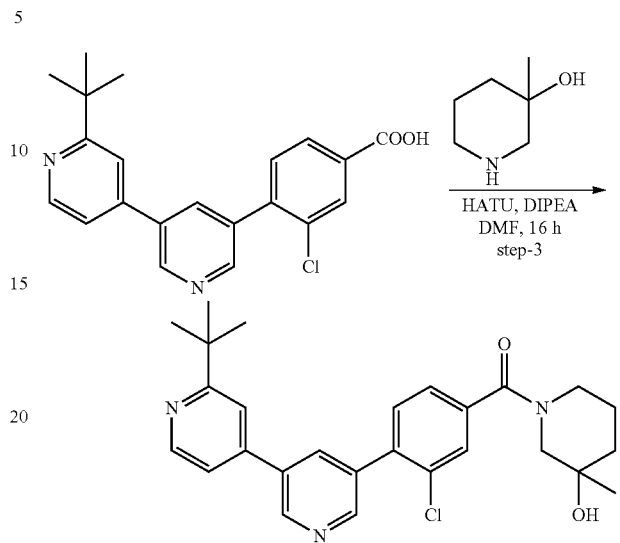

This compound was prepared by a reaction similar to that described in Example 21. $^1$H-NMR 400 MHz, DMSO-d$_6$: δ 9.07 (d, J=2.00 Hz, 1H), 8.77 (d, J=2.00 Hz, 1H), 8.63 (d, J=5.20 Hz, 1H), 8.35 (t, J=2.40 Hz, 1H), 7.83 (s, 1H), 7.67-7.65 (m, 3H), 7.50-7.51 (m, 1H), 4.60-4.61 (m, 1H), 4.00-4.03 (m, 1H), 3.60-3.63 (m, 1H), 3.15-3.05 (m, 2H), 1.85-1.60 (m, 1H), 1.60-1.45 (m, 3H), 1.38 (s, 9H), 1.19 (s, 3H). LCMS: 99.33% (m/z=464.52 [M+H]). HPLC: 97.15%.

Example 23: Synthesis of 2-(pyrrolidin-1-yl)ethyl (4-(2'-(tert-butyl)-[3,4'-bipyridin]-5-yl)-3-chlorophenyl)carbamate (Compound 23)

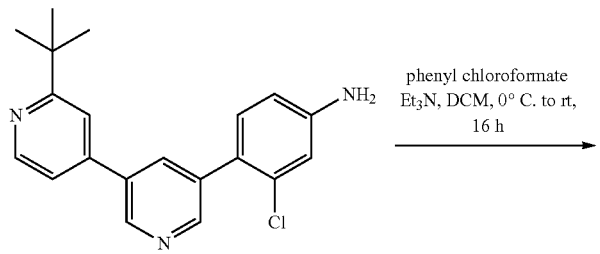

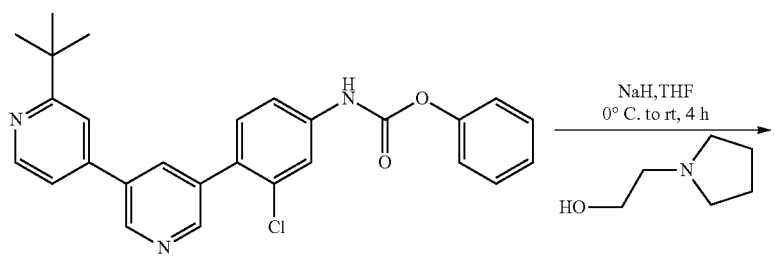

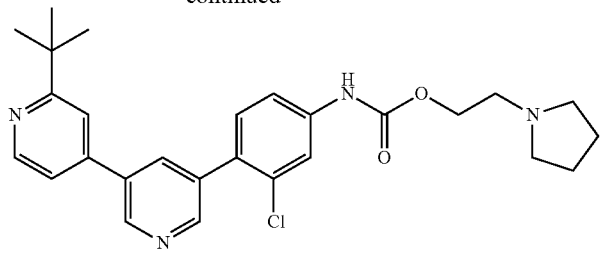

To a solution of 4-(2'-(tert-butyl)-[3,4'-bipyridin]-5-yl)-3-chloroaniline (250 mg, 0.74 mmol) and Et$_3$N (150 mg, 1.48 mmol) in DCM (5 mL) at 0° C. was added phenyl chloroformate (116 mg, 0.81 mmol). After stirring at rt for 16 h, the reaction was diluted with water 10 mL and extracted with EtOAc (3×10 mL). The organic extracts were combined, dried over anhydrous sodium sulfate, and concentrated under reduced pressure to give crude product, which was purified by flash column chromatography (100-200 mesh) using 20% EtOAc and hexane as eluent to give phenyl (4-(2'-(tert-butyl)-[3,4'-bipyridin]-5-yl)-3-chlorophenyl)carbamate as a gummy solid (180 mg, 44%). To a solution of this compound (24 mg, 0.18 mmol) in THF (5 mL), was added NaH (10 mg, 0.18 mmol), and the mixture was stirred for 10 min. Then, 2-(pyrrolidin-1-yl)ethan-1-ol (70 mg, 0.15 mmol) was added at 0° C. and allowed to come to RT for 4 h. The reaction mass was diluted with water (10 mL) and extracted with EtOAc (3×10 mL). The extracts were combined, dried over anhydrous sodium sulfate, and concentrated under reduced pressure to give crude product which was purified by preparative HPLC method to afford 2-(pyrrolidin-1-yl)ethyl(4-(2'-(tert-butyl)-[3,4'-bipyridin]-5-yl)-3-chlorophenyl)carbamate as an off white solid (25 mg, 27%). $^1$H-NMR 400 MHz, DMSO-d$_6$: δ 8.89 (d, J=2.40 Hz, 1H), 8.68 (d, J=2.00 Hz, 1H), 8.60 (d, J=5.20 Hz, 1H), 8.23 (t, J=2.00 Hz, 1H), 7.82 (d, J=2.00 Hz, 1H), 7.77 (d, J=0.80 Hz, 1H), 7.57 (dd, J=2.00, 5.20 Hz, 1H), 7.51 (dd, J=2.00, 8.40 Hz, 1H), 7.44 (d, J=8.40 Hz, 1H), 4.32 (t, J=5.60 Hz, 2H), 2.85 (t, J=5.60 Hz, 2H), 2.68 (b s, 4H), 1.83-1.86 (m, 4H), 1.44 (s, 9H). LCMS 97.00% (m/z 479.2 [M+H]). HPLC purity 97.14%.

Example 24: Synthesis of 4-hydroxycyclohexyl (4-(2'-(tert-butyl)-[3,4'-bipyridin]-5-yl)-3-chlorophenyl)carbamate (Compound 24)

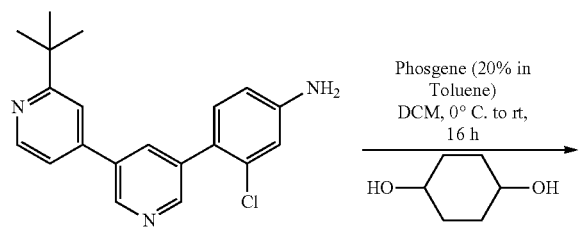

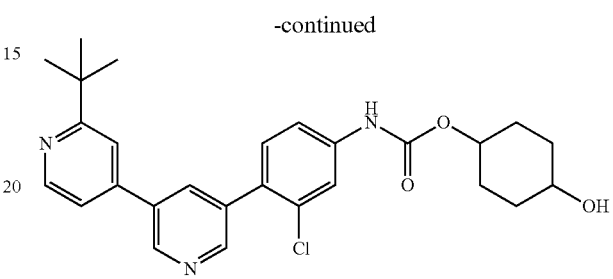

To a solution of 4-(2'-(tert-butyl)-[3,4'-bipyridin]-5-yl)-3-chloroaniline (103.4 mg, 0.89 mmol) in DCM (20 mL), phosgene (20% in toluene) was added (0.1 ml, 0.89 mmol), and the mixture stirred for 30 min at RT. Cyclohexane-1,4-diol (103.4 mg, 0.89 mmol) was added to this mixture at 0° C. and the mixture stirred for 16 h at RT. Evaporation of the solvents under reduced pressure gave a crude product, which was purified by preparative HPLC to afford 4-hydroxycyclohexyl (4-(2'-(tert-butyl)-[3,4'-bipyridin]-5-yl)-3-chlorophenyl)carbamate as an off white solid (20 mg, 8%). $^1$H-NMR 400 MHz, DMSO-d6: δ 9.95 (s, 1H), 9.00 (s, 1H), 8.70 (s, 1H), 8.62 (s, 1H), 8.25 (s, 1H), 7.80 (s, 2H), 7.63 (d, J=5.20 Hz, 1H), 7.53-7.53 (m, 2H), 4.73-4.53 (m, 2H), 3.65-3.45 (m, 1H), 2.01-1.90 (m, 1H), 1.83-1.73 (m, 2H), 1.70-1.55 (m, 3H), 1.45-1.60 (m, 2H), 1.38 (s, 9H); LCMS (98.48%, m/z=480.42 [M+H]). Compound is a mixture of cis, trans isomers. HPLC: 66.14+33.07, LCMS: 53.18+45.30.

Example 25: Synthesis of (3-chloro-4-(5-(6,7-dihydro-5H-cyclopenta[b]pyridin-4-yl)pyridin-3-yl)phenyl)(4-hydroxypiperidin-1-yl)methanone (Compound 25)

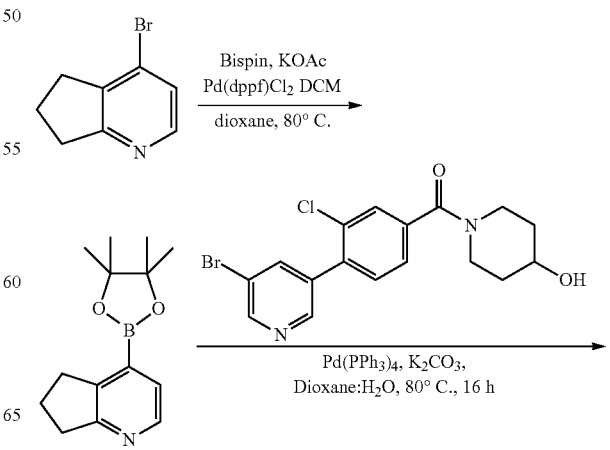

-continued

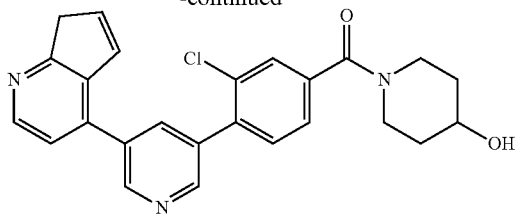

To a stirred solution of 4-bromo-6,7-dihydro-5H-cyclopenta[b]pyridine (0.4 g, 2.01 mmol) in dioxane (4.0 mL) was added bis-pinacalatodiborane (0.76 g, 3.02 mmol) and AcOK (0.59 g, 6.03 mmol) at RT under a nitrogen atmosphere. The mixture was purged for 15 minutes with nitrogen, followed by addition of Pd(dppf)$_2$Cl$_2$ (0.015 g, 0.201 mmol), and the reaction mixture again purged for 10 minutes with nitrogen. The reaction tube was sealed and stirred at 100° C. for 12 h. Then the reaction mixture was cooled to 25° C., water was added (20 mL), and the product was extracted with ethyl acetate. The organic layer was washed with brine, dried over sodium sulfate, filtered and concentrated to give crude 4-(4,4,5,5-tetramethyl-1,3,2-dioxaborolan-2-yl)-6,7-dihydro-5H-cyclopenta[b]pyridine which was taken for next step without purification.

To a stirred solution of this material (0.102 g, 0.41 mmol, 1.0 eq) in dioxane:water (1.5 mL), was added (4-(5-bromopyridin-3-yl)-3-chlorophenyl)(4-hydroxypiperidin-1-yl)methanone (0.15 g, 0.37 mmol, 1.1 eq) and K$_2$CO$_3$ (0.154 g, 1.118 mmol, 3.0 eq), and the mixture was purged for 15 min with nitrogen. Then palladium tetrakis (0.042 g, 0.037 mmol, 0.1 eq) was added and the mixture was again purged for 10 min with nitrogen. The reaction tube was sealed and stirred at 80° C. for 16 h. Then the reaction mixture was diluted with water (10 mL) and extracted with EtOAc (3×10 mL). The organic extracts were combined, dried over anhydrous sodium sulfate, and concentrated under reduced pressure to obtain crude product, which was purified by preparative HPLC. Fractions containing the product were combined and concentrated under reduced pressure to afford (3-chloro-4-(5-(6,7-dihydro-5H-cyclopenta[b]pyridin-4-yl)pyridin-3-yl)phenyl)(4-hydroxypiperidin-1-yl)methanone as a white solid. $^1$H-NMR (400 MHz, DMSO): δ 8.85 (d, J=6.0 Hz, 1H), 8.74 (d, J=2.0 Hz, 1H), 8.42 (d, J=5.2 Hz, 8.13 (t, J=2.4 Hz, 1H), 7.65-7.63 (m, 2H), 7.49-7.47 (m, 1H), 7.37 (d, J=5.2 Hz 1H), 4.81 (d, J=3.6 Hz, 1H), 3.99 (s, 1H), 3.78-3.73 (m, 1H), 3.50 (m, 1H), 3.31-3.21 (m, 2H), 3.10 (t, J=7.2 Hz, 4H), 2.99-(t, J=7.6 Hz, 2H), 2.11-2.04 (m, 2H), 1.81-1.23 (m, 4H). HPLC: 99.03%, LCMS: 96.39% (m/z=434.46 [M+H]$^+$).

Example 26: Synthesis of (3'-(2-(tert-butyl)pyridin-4-yl)-2-chloro-5'-fluoro-[1,1'-biphenyl]-4-yl)(4-hydroxypiperidin-1-yl)methanone (Compound 26)

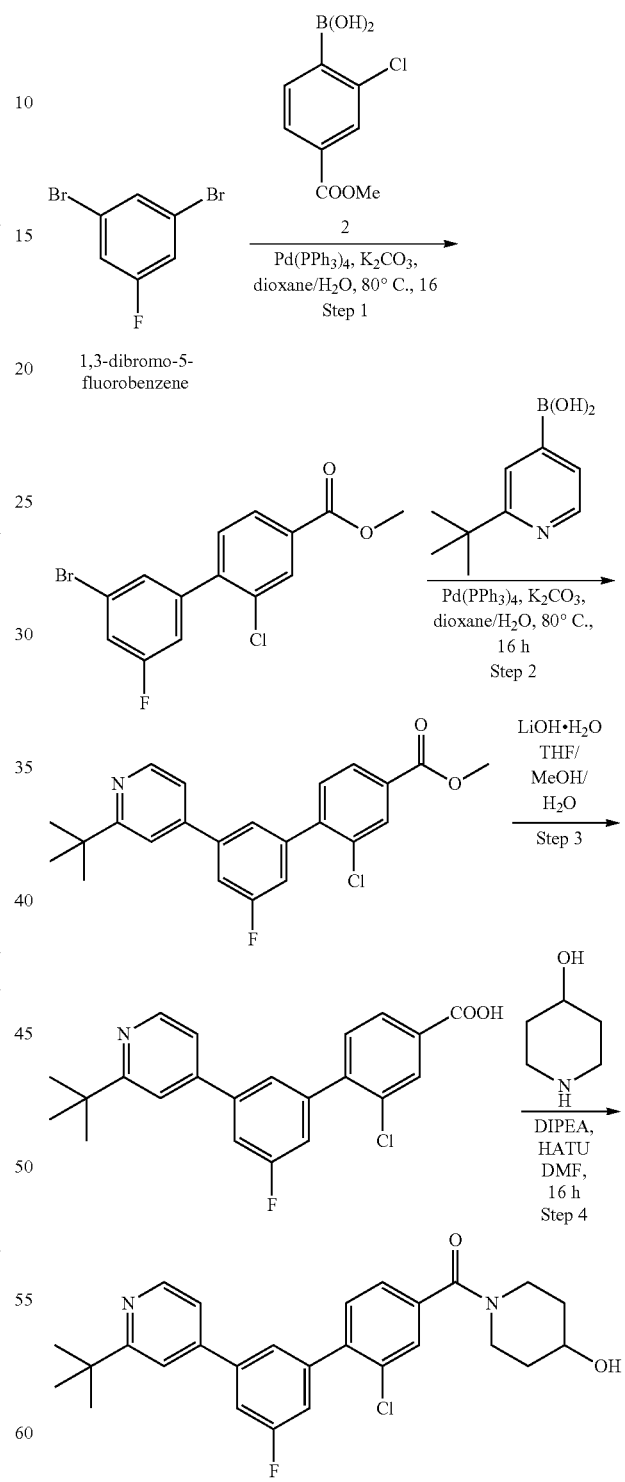

Step 1: Methyl 3'-bromo-2-chloro-5'-fluoro-[1,1'-biphenyl]-4-carboxylate. A stirred mixture of 1,3-dibromo-5-fluorobenzene (400 mg, 1.575 mmol), (2-chloro-4-(methoxycarbonyl)phenyl)boronic acid (338 mg, 1.575 mmol) and potassium carbonate (544 mg, 3.937 mmol) in water (1 mL) and 1,4-dioxane (10 mL) in 40 mL glass seal tube was purged with nitrogen gas for 30 minutes. After adding palladium tetrakis (182 mg, 0.157 mmol), the reaction mixture was again purged with nitrogen gas for 30 minutes, the tube was sealed, and the reaction heated to 80° C. for 16 h. The reaction mixture was then cooled to RT and filtered through a Celite® bed and washed with ethyl acetate (20 mL). The combined organic layers were concentrated under reduced pressure to afford crude product, which was purified using neutral alumina column chromatography with 0-30% ethyl acetate in petroleum ether as an eluent. Selected fractions were collected and concentrated under reduced pressure to afford methyl 3'-bromo-2-chloro-5'-fluoro-[1,1'-biphenyl]-4-carboxylate (300 mg) as an off-white solid.

Step 2: Methyl 3'-(2-(tert-butyl)pyridin-4-yl)-2-chloro-5'-fluoro-[1,1'-biphenyl]-4-carboxylate. A stirred mixture of the product from Step 1 (300 mg, 0.873 mmol), (2-(tert-butyl)pyridin-4-yl)boronic acid (172 mg, 0.873 mmol), potassium carbonate (302 mg, 2.182 mmol) in water (2 mL) and 1,4-dioxane (8 mL) in a 40 mL glass seal tube was purged with nitrogen gas for 30 minutes. After adding palladium tetrakis (101 mg, 0.0873 mmol), the reaction mixture was again purged with nitrogen gas for 30 minutes, then the tube was sealed and heated to 80° C. for 16 h. Then the reaction mixture was cooled to RT and filtered through a Celite® bed and washed with ethyl acetate (25 mL). The combined organic layers were concentrated under reduced pressure to afford crude product, which was purified through neutral alumina column chromatography using 0-50% ethyl acetate in petroleum ether as an eluent. Selected fractions were collected and concentrated under reduced pressure to afford methyl 3'-(2-(tert-butyl)pyridin-4-yl)-2-chloro-5'-fluoro-[1,1'-biphenyl]-4-carboxylate (290 mg) as a colorless gummy material.

Step 3: 3'-(2-(tert-butyl)pyridin-4-yl)-2-chloro-5'-fluoro-[1,1'-biphenyl]-4-carboxylic acid. To a stirred mixture of the product from Step 2 (330 mg, 0.829 mmol) in THF:methanol:water (20 mL:10 mL:5 mL) was added LiOH.H$_2$O (105 mg, 2.488 mmol), and the mixture was stirred at room temperature for 2 h. The reaction mixture was concentrated under reduced pressure and dissolved in water (10 mL), then acidified with citric acid to pH ~5. The aqueous layer was extracted with ethyl acetate (2×20 mL), and the combined ethyl acetate layers were dried over sodium sulfate and concentrated under reduced pressure to afford 3'-(2-(tert-butyl)pyridin-4-yl)-2-chloro-5'-fluoro-[1,1'-biphenyl]-4-carboxylic acid (310 mg) as an off white solid.

Step 4: (3'-(2-(tert-butyl)pyridin-4-yl)-2-chloro-5'-fluoro-[1,1'-biphenyl]-4-yl)(4-hydroxypiperidin-1-yl)methanone. To a stirred mixture of the product from Step 3 (310 mg, 0.807 mmol) in DMF (3 mL) and DIPEA (0.688 mL, 3.230 mmol), was added HATU (1.507 g, 3.230 mmol), and the mixture was stirred for 15 min at RT under nitrogen. 4-hydroxypiperidine (100 mg, 0.807 mmol) was then added under nitrogen and the mixture was stirred for 16 h at RT. The reaction mixture was diluted with cold water (50 mL) and the product was extracted into EtOAc (2×25 mL). The combined organic layers were washed with ice cold water (50 mL), dried over sodium sulfate, and concentrated under reduced pressure to afford crude product which was purified through preparative HPLC to afford (3'-(2-(tert-butyl)pyridin-4-yl)-2-chloro-5'-fluoro-[1,1'-biphenyl]-4-yl)(4-hydroxypiperidin-1-yl)methanone (26 mg) as an off white solid. $^1$H-NMR (400 MHz, DMSO-d6): δ 8.59-8.58 (m, 1H), 7.78-7.72 (m, 3H), 7.62-7.58 (m, 3H), 7.46-7.42 (m, 2H), 4.79 (bs, 1H), 4.02-3.99 (bs, 1H), 3.77-3.75 (m, 1H), 3.62- 3.60 (bs, 1H), 3.20 (m, 2H), 1.77-1.75 (bs, 2H), 1.38 (m, 2H), 1.37 (s, 9H). LCMS: 99.7% (m/z=467.36 [M+H]). HPLC: 98.81%.

Example 27: Synthesis of 5-(2-(tert-butyl)pyridin-4-yl)-2'-chloro-4'-(4-hydroxypiperidine-1-carbonyl)-[1,1'-biphenyl]-3-carbonitrile (Compound 27)

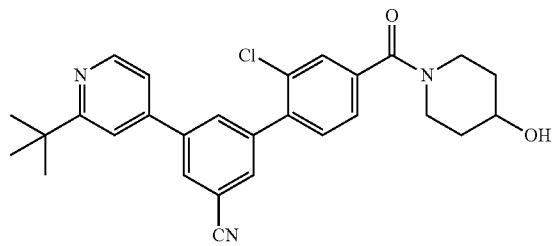 [SMILES: CC(C)(C)c1cc(-c2cc(C#N)cc(-c3ccc(C(=O)N4CCC(O)CC4)cc3Cl)c2)ccn1]

This compound was prepared using 3,5-dibromobenzonitrile in a series of reactions similar to that shown in Example 26 to give 5-(2-(tert-butyl)pyridin-4-yl)-2'-chloro-4'-(4-hydroxypiperidine-1-carbonyl)-[1,1'-biphenyl]-3-carbonitrile. $^1$H-NMR (400 MHz, DMSO-d6: δ 8.62 (d, J=5.20 Hz, 1H), 8.42 (t, J=1.60 Hz, 1H), 8.24 (t, J=1.60 Hz, 1H), 8.06 (s, 1H), 7.84 (d, J=0.80 Hz, 1H), 7.63-7.66 (m, 3H), 7.48 (dd, J=1.60, 8.00 Hz, 1H), 4.82 (d, J=3.60 Hz, 1H), 4.00 (br s, 1H), 3.74-3.76 (m, 1H), 3.53 (br s, 1H), 3.22 (br s, 2H), 1.78 (br, 2H), 1.39 (br s, 11H). LCMS: 99.57% (m/z=474.1 [M+H]); HPLC 99.67%.

Example 28: Synthesis of (3'-(2-(tert-butyl)pyridin-4-yl)-2-chloro-5'-(dimethylamino)-[1,1'-biphenyl]-4-yl)(4-hydroxypiperidin-1-yl)methanone (Compound 28)

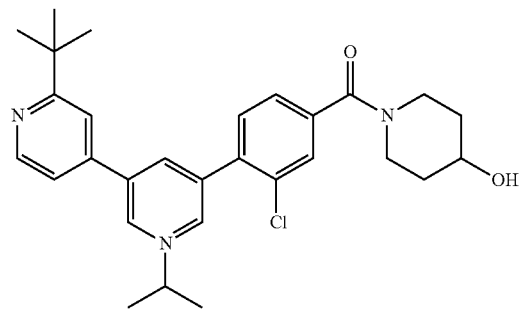

This compound was prepared using 3,5-dibromo-N,N-dimethylaniline in a series of reactions similar to that shown in Example 26 to give (3'-(2-(tert-butyl)pyridin-4-yl)-2-chloro-5'-(dimethylamino)-[1,1'-biphenyl]-4-yl)(4-hydroxypiperidin-1-yl)methanone. $^1$H-NMR: (400 MHz, DMSO): δ (ppm): 8.56-8.54 (dd, J=0.4 Hz, J=1.6 Hz, 1H), 7.64 (d, J=0.6 Hz, 1H), 7.56-7.55 (dd, J=2.0 Hz, J=2.0 Hz, 2H), 7.51-7.49 (dd, J=1.6 Hz, J=1.6 Hz, 1H), 7.42-7.40 (dd, J=1.6 Hz, J=1.6 Hz, 1H), 7.04-7.02 (m, 2H), 6.82-6.81 (dd, J=1.2 Hz, J=1.2 Hz, 1H), 4.80 (d, J=4.0 Hz, 1H), 3.99 (bs, 1H), 3.78-3.73 (m, 1H), 3.56 (bs, 1H), 3.24-3.23 (bs, 2H), 3.01 (s, 6H), 1.78-1.75 (bs, 2H), 1.40 (s, 9H). LCMS: (492.55 [M+H]) 99.30%, HPLC: 98.71%.

Example 29: (4-(2'-(tert-butyl)-4-methyl-[3,4'-bipyridin]-5-yl)-3-chlorophenyl)(4-hydroxypiperidin-1-yl)methanone (Compound 29)

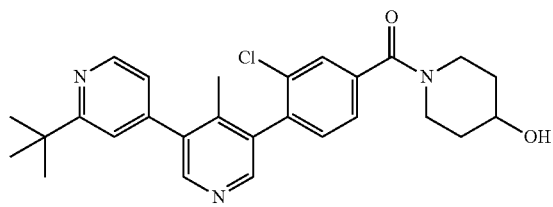 [SMILES: Cc1c(-c2ccnc(C(C)(C)C)c2)cncc1-c1ccc(C(=O)N2CCC(O)CC2)cc1Cl]

This compound was prepared using 3,5-dibromo-4-methylpyridine in a similar series of reactions to that shown in Example 26 to give (4-(2'-(tert-butyl)-4-methyl-[3,4'-bipyridin]-5-yl)-3-chlorophenyl)(4-hydroxypiperidin-1-yl)methanone. $^1$H-NMR (400 MHz, DMSO-d6: δ 8.63 (dd, J=0.80, 5.20 Hz, 1H), 8.50 (s, 1H), 8.41 (s, 1H), 7.64 (d, J=1.20 Hz, 1H), 7.46-7.47 (m, 3H), 7.32 (dd, J=1.60, 4.80 Hz, 1H), 4.82 (s, 1H), 4.02 (br, 1H), 3.76 (br, 1H), 3.54-3.50 (br, 1H), 3.36-3.28 (br, 2H), 2.03 (s, 3H), 1.78 (br, 2H), 1.39 (br s, 11H); LCMS 98% (m/z=464.54 [M+H]); HPLC 99.04%.

Example 30: Synthesis of Additional Compounds

The compounds listed in Table 1 are prepared. Some of these compounds are prepared using the synthetic routes and procedures described above.

TABLE 1

| Structure | Name |
|---|---|
| 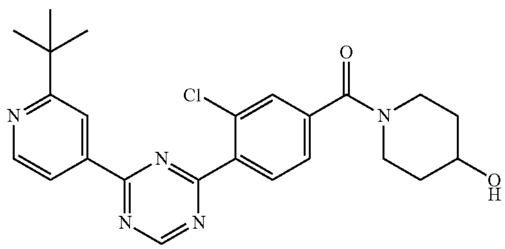 | (4-(4-(2-(tert-butyl)pyridin-4-yl)-1,3,5-triazin-2-yl)-3-chlorophenyl)(4-hydroxypiperidin-1-yl)methanone |
| Compound 30-1 |  |
| 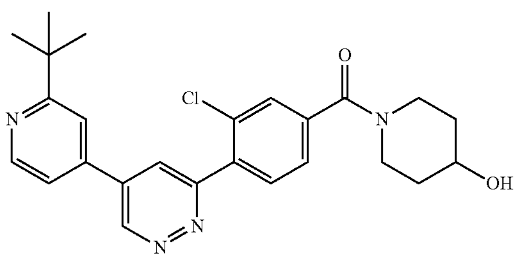 | (4-(5-(2-(tert-butyl)pyridin-4-yl)pyridazin-3-yl)-3-chlorophenyl)(4-hydroxypiperidin-1-yl)methanone |
| Compound 30-2 |  |
| 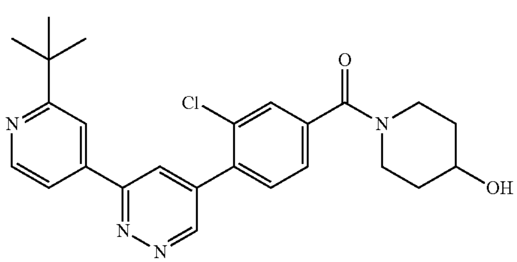 | (4-(6-(2-(tert-butyl)pyridin-4-yl)pyridazin-4-yl)-3-chlorophenyl)(4-hydroxypiperidin-1-yl)methanone |
| Compound 30-3 |  |

TABLE 1-continued

Additional compounds.

| Structure | Name |
|---|---|
| Compound 30-4 | 1-(4-(2'-(tert-butyl)-[3,4'-bipyridin]-5-yl)-3-chlorophenyl)-3-(4-hydroxycyclohexyl)urea |
| Compound 30-5 | 1-(4-(2'-(tert-butyl)-[3,4'-bipyridin]-5-yl)-3-chlorophenyl)-3-(piperidin-4-yl)urea |
| Compound 30-6 | 1-(4-(2'-(tert-butyl)-[3,4'-bipyridin]-5-yl)-3-chlorophenyl)-3-(2-(pyrrolidin-1-yl)ethyl)urea |
| Compound 30-7 | N-(4-(2'-(tert-butyl)-[3,4'-bipyridin]-5-yl)-3-chlorophenyl)-4-hydroxypiperidine-1-carboxamide |
| Compound 30-8 | piperidin-4-yl (4-(2'-(tert-butyl)-[3,4'-bipyridin]-5-yl)-3-chlorophenyl)carbamate |

TABLE 1-continued

Additional compounds.

| Structure | Name |
|---|---|
| Compound 30-9 | (3-chloro-4-(5-(2,3-dihydro-[1,4]dioxino[2,3-b]pyridin-8-yl)pyridin-3-yl)phenyl)(4-hydroxypiperidin-1-yl)methanone |
| Compound 30-10 | (3-chloro-4-(5-(3,4-dihydro-2H-pyrano[2,3-b]pyridin-5-yl)pyridin-3-yl)phenyl)(4-hydroxypiperidin-1-yl)methanone |
| Compound 30-11 | (3-chloro-4-(5-(2,3-dihydrofuro[2,3-b]pyridin-4-yl)pyridin-3-yl)phenyl)(4-hydroxypiperidin-1-yl)methanone |
| Compound 30-12 | (3-chloro-4-(5-(2,2-dimethyl-3,4-dihydro-2H-pyrano[2,3-b]pyridin-5-yl)pyridin-3-yl)phenyl)(4-hydroxypiperidin-1-yl)methanone |
| Compound 30-13 | (3-chloro-4-(5-(2,2-dimethyl-2,3-dihydrofuro[2,3-b]pyridin-4-yl)pyridin-3-yl)phenyl)(4-hydroxypiperidin-1-yl)methanone |

TABLE 1-continued

Additional compounds.

| Structure | Name |
|---|---|
| Compound 30-14 | (4-(5-(2-(tert-butyl)pyridin-4-yl)isoquinolin-7-yl)-3-chlorophenyl)(4-hydroxypiperidin-1-yl)methanone |
| Compound 30-15 | (4-(5-(2-(tert-butyl)pyridin-4-yl)quinolin-7-yl)-3-chlorophenyl)(4-hydroxypiperidin-1-yl)methanone |
| Compound 30-16 | (4-(7-(2-(tert-butyl)pyridin-4-yl)isoquinolin-5-yl)-3-chlorophenyl)(4-hydroxypiperidin-1-yl)methanone |
| Compound 30-17 | (4-(7-(2-(tert-butyl)pyridin-4-yl)quinolin-5-yl)-3-chlorophenyl)(4-hydroxypiperidin-1-yl)methanone |

TABLE 1-continued

Additional compounds.

| Structure | Name |
|---|---|
| Compound 30-18 | (3-chloro-4-(2'-(2-methyl-1,3-dioxolan-2-yl)-[3,4'-bipyridin]-5-yl)phenyl)(4-hydroxypiperidin-1-yl)methanone |
| Compound 30-19 | (3-chloro-4-(2'-(2-hydroxypropan-2-yl)-[3,4'-bipyridin]-5-yl)phenyl)(4-hydroxypiperidin-1-yl)methanone |
| Compound 30-20 | (3-chloro-4-(2'-(2-methoxypropan-2-yl)-[3,4'-bipyridin]-5-yl)phenyl)(4-hydroxypiperidin-1-yl)methanone |
| Compound 30-21 | (3-chloro-4-(2'-(1-hydroxy-2-methylpropan-2-yl)-[3,4'-bipyridin]-5-yl)phenyl)(4-hydroxypiperidin-1-yl)methanone |
| Compound 30-22 | ethyl 3-(5-(2-chloro-4-(4-hydroxypiperidine-1-carbonyl)phenyl)-[3,4'-bipyridin]-2'-yl)-3-methylbutanoate |

TABLE 1-continued

Additional compounds.

| Structure | Name |
|---|---|
| Compound 30-23 | (3-chloro-4-(2'-(tetrahydro-2H-pyran-4-yl)-[3,4'-bipyridin]-5-yl)phenyl)(4-hydroxypiperidin-1-yl)methanone |
| Compound 30-24 | (3-chloro-4-(2'-(tetrahydrofuran-2-yl)-[3,4'-bipyridin]-5-yl)phenyl)(4-hydroxypiperidin-1-yl)methanone |
| Compound 30-25 | (3-chloro-4-(2'-(tetrahydrofuran-2-yl)-[3,4'-bipyridin]-5-yl)phenyl)(4-hydroxypiperidin-1-yl)methanone |
| Compound 30-26 | (4-(2'-(tert-butyl)-4-methyl-[3,4'-bipyridin]-5-yl)-3-chlorophenyl)(3-hydroxypiperidin-1-yl)methanone |

Example 31: Reporter Screening Assay

This assay was used to evaluate the effect on transcriptional activity SREBP of the compounds synthesized according to Examples 1-16, 20, and 22, using an SRE-luciferase reporter construct. On day 1, 10,000 cells were seeded in a 96 well (white) plate as per the plate map in Growth media without antibiotics. Cells were incubated at 37° C. for 8 hours. After 8 hours, cells were washed with DPBS for complete removal of FBS. DPBS was completely removed and Growth media was replaced with phenol free treatment medium (90 µl) with different FBS concentrations. The cells were then incubated at 37° C. for 24 hours with varying doses (0.01 uM to 10 uM) of compounds. Then a Luciferase assay was performed.

Reagents for performing Luciferase assay were stored at −20° C. To a tube of lyophilized assay substrate was added 1 mL Substrate Solvent and mixed well. The Substrate tube after reconstitution was covered with aluminum foil so as to keep it protected from light. The assay buffer was thawed to room temperature. To 20 mL Assay Buffer was added 200 μL of reconstituted 100× Substrate and mixed well. The reconstituted substrate as well as the assay solution (buffer+substrate) was protected from light throughout the procedure by keeping it covered with aluminum foil.

Using a multi-channel pipette, 100 μL Assay Solution (buffer+substrate) was added directly to each sample well in Plate 1, which was incubated for 30 min (plate was covered with aluminum foil). After 30 min incubation, the plate was read for total luminescence. Each well was read for 2 seconds in a plate luminometer. (Microplate reader Envision Microplate reader from Perkin Elmer). Precaution was taken to incubate plate exactly for 30 min prior to reading on the plate reader.

Materials: SREBPv1 Reporter cell line: HepG2—#32251. Growth Medium: MEM (Corning 10-010), 10% FBS, 1% GlutaMax (Invitrogen Catalog #35050061), μg/ml Puromycin (Invitrogen Catalog #A1113803) and 1% Penicillin-Streptomycin (Pen-Strep). Treatment Media: Phenol-free MEM (Invitrogen Catalog #51200-038) and 1% GlutaMax (Invitrogen Catalog #35050061). Luciferase Assay: Light-Switch Luciferase Assay Kit (Catalog #32032). LDH assay: Pierce LDH Cytotoxicity Assay Kit (Catalog #SD249616).

The transcriptional activity results for the compounds of Examples 1-16, 20, and 22 are shown in Table 2 below.

TABLE 2

| Results of Reporter Screening | |
|---|---|
| Compound of Example # | Reporter Screening IC50 (nM) Activity Range |
| 1 | ++ |
| 2 | +++ |
| 3 | ++ |
| 4 | ++++ |
| 5 | ++++ |
| 6 | ++ |
| 7 | ++ |
| 8 | ++ |
| 9 | ++ |
| 10 | + |
| 11 | ++ |
| 12 | ++ |

TABLE 2-continued

| Results of Reporter Screening | |
|---|---|
| Compound of Example # | Reporter Screening IC50 (nM) Activity Range |
| 13 | +++ |
| 14 | ++++ |
| 15 | ++++ |
| 16 | +++ |
| 20 | +++ |
| 22 | +++ |

+ IC50 ≤ 3000 nM
++ IC50 ≤ 1000 nM
+++ IC50 ≤ 500 nM
++++ IC50 ≤ 100 nM

Example 32: In Vivo Activity Assay

The in vivo effect of compounds described herein, for example the compounds of Examples 1-30, or 33-52, or pharmaceutically acceptable salt, solvate, tautomer, isotope, or isomer thereof, may be assessed using the ob/ob mouse model. The ob/ob mouse is a well characterized model of obesity, fatty liver, and diabetes, which are exhibited due to a mutation in the ob gene, which encodes for leptin.

Compounds produced according to Examples 1-30 as described above, are administered by the oral route once or twice daily for 4 weeks in male ob/ob mice. Body weight and food and water intake are assessed daily, and improvements in glucose control are assessed by plasma glucose and insulin measurement. Upon completion of the test period, terminal blood samples are taken and analyzed for triglyceride, cholesterol (total, HDL-C and LDL-C), blood urea nitrogen (BUN), alanine aminotransferase (ALT), and aspartate aminotransferase (AST) levels. Liver and fat pad weights are determined and liver tissue is processed for histological determination of NASH activity scores (NAS: ballooning, inflammation, steatosis and fibrosis). Liver levels of triglycerides, cholesterol, and non-esterified fatty acids (NEFA) are also determined.

Example 33: 4-(2'-(tert-butyl)-[3,4'-bipyridin]-5-yl)-N-isopropyl-3-methylbenzenesulfonamide (Compound Z-814)

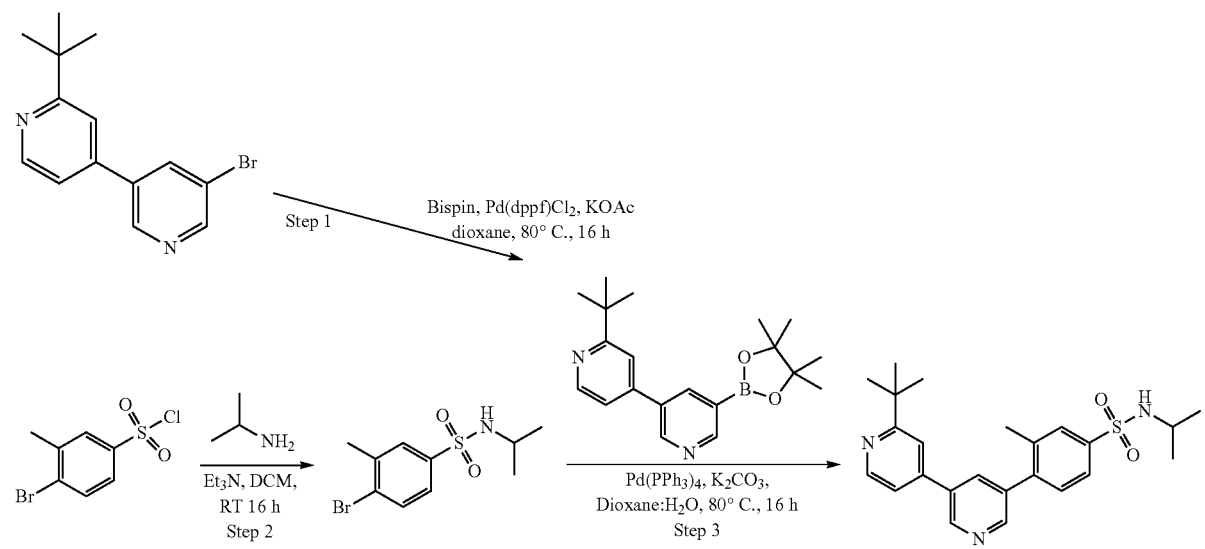

Step 1—2'-(tert-butyl)-5-(4,4,5,5-tetramethyl-1,3,2-dioxaborolan-2-yl)-3,4'-bipyridine: To a stirred solution of 5-bromo-2'-(tert-butyl)-3,4'-bipyridine (250.0 mg, 0.862 mmol), Bispin (328.4 mg, 1.29 mmol), and KOAc (254 mg 2.58 mmol) in dioxane (10.0 V) was added Pd(dppf)Cl$_2$ (63.07 mg, 0.0862 mmol) at 25° C., and the reaction mass degassed for 15 mins, then stirred for 16 h at 80° C. On completion of reaction (monitored by TLC), the reaction mass was concentrated under reduced pressure, the obtained residue was dissolved in ethyl acetate (50 mL), washed with water (20 mL), brine, dried over sodium sulfate, filtered and concentrated. The crude compound was purified by Florisil® column chromatography eluting with 0-30% ethyl acetate in petroleum ether to afford 2'-(tert-butyl)-5-(4,4,5,5-tetramethyl-1,3,2-dioxaborolan-2-yl)-3,4'-bipyridine as a light brown gummy solid (430 mg).

Step 2—4-bromo-N-isopropyl-3-methylbenzenesulfonamide: To a stirred solution of 2-aminopropane (48.54 mg, 0.8212 mmol) in DCM (10.0 mL) was added Et$_3$N (83.428 mg, 0.82115 mmol) at 0° C. under nitrogen atmosphere. The reaction mass was stirred at 0° C. for 20 min, followed by addition of 4-bromo-3-methylbenzenesulfonyl chloride (200.0 mg, 0.7425 mmol) dissolved in DCM at 0° C. The reaction mass was stirred for 16 h at 25° C. After completion of the reaction (monitored by TLC), the reaction mixture was cooled to 25° C., water added (25 mL), and the product was extracted into dichloromethane. The organic layer was washed with brine and the organic layer dried over sodium sulfate, filtered and concentrated to give 4-bromo-N-isopropyl-3-methylbenzenesulfonamide as a light yellow solid (0.200 g) which was used in the next step without purification.

Step 3—4-(2'-(tert-butyl)-[3,4'-bipyridin]-5-yl)-N-isopropyl-3-methylbenzenesulfonamide: To a stirred solution of the product from Step 2 (120.0 mg, 0.4123 mmol) in dioxane:H$_2$O (10.0 V) was added the product of Step 1 (167.0 mg 0.4948 mmol) and K$_2$CO$_3$ (171.06 mg, 1.236 mmol) at room temperature under nitrogen atmosphere. The reaction mass was degassed for 15 minutes with nitrogen gas followed by the addition of Pd(PPh$_3$)$_4$ (23.81 mg, 0.0206 mmol), and the mixture again degassed for 15 minutes with nitrogen, then sealed in a glass tube and stirred at 80° C. for 16 h. After completion of the reaction (monitored by TLC), the reaction mixture was cooled to 25° C., water added (25 mL), and the product extracted into ethyl acetate. The organic layer was washed with brine, dried over sodium sulfate, filtered and concentrated. The crude compound was purified with reverse phase chromatography with ammonium acetate in water and methanol as mobile phase (5% MeOH in DCM) to give 4-(2'-(tert-butyl)-[3,4'-bipyridin]-5-yl)-N-isopropyl-3-methylbenzenesulfonamide as an off white solid (75.0 mg). $^1$H NMR (400 MHz, DMSO): δ 9.06 (d, J=2.40 Hz, 1H), 8.70 (d, J=2.00 Hz, 1H), 8.62 (dd, J=0.40, 5.20 Hz, 1H), 8.30 (t, J=2.00 Hz, 1H), 7.82 (dd, J=1.60, 8.00 Hz, 2H), 7.67-7.67 (m, 1H), 7.65 (t, J=1.60 Hz, 2H), 7.58 (d, J=8.00 Hz, 1H), 3.28-3.28 (m, 1H), 2.37 (s, 3H), 1.38 (s, 9H), 1.02 (d, J=6.40 Hz, 6H). LCMS: 99.12% (m/z=424.21 [M+1].

Example 34: 1-((4-(2'-(tert-butyl)-[3,4'-bipyridin]-5-yl)-3-methylphenyl)sulfonyl)piperidin-4-ol (Compound Z-813)

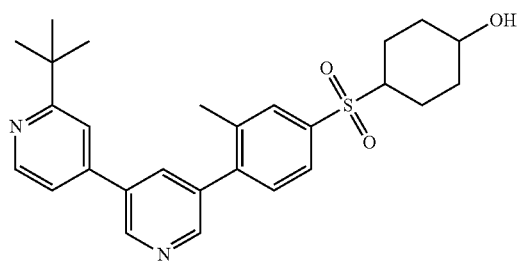 [SMILES: Cc1cc(S(=O)(=O)C2CCC(O)CC2)ccc1-c1cncc(-c2ccnc(C(C)(C)C)c2)c1]

1-((4-(2'-(tert-butyl)-[3,4'-bipyridin]-5-yl)-3-methylphenyl)sulfonyl)piperidin-4-ol was prepared from 2'-(tert-butyl)-5-(4,4,5,5-tetramethyl-1,3,2-dioxaborolan-2-yl)-3,4'-bipyridine, 4-bromo-3-methylbenzenesulfonyl chloride and 4-hydroxypiperidine using a similar series of reactions as described in Example 33 to give a white solid. 1H NMR (400 MHz, DMSO) δ 9.07 (d, J=2.40 Hz, 1H), 8.71 (d, J=2.00 Hz, 1H), 8.62 (dd, J=0.40, 5.20 Hz, 1H), 8.33 (t, J=2.00 Hz, 1H), 7.83 (d, J=0.80 Hz, 1H), 7.75 (s, 1H), 7.62-7.64 (m, 3H), 4.71 (d, J=3.60 Hz, 1H), 3.59-3.60 (m, 1H), 3.14-3.16 (m, 2H), 2.84-2.84 (m, 2H), 2.40 (s, 3H), 1.76-1.77 (m, 2H), 1.50-1.51 (m, 2H), 1.48 (s, 9H); LCMS: 99.24% (m/z=466.40 [M+1]).

Example 35: N-((4-(2'-(tert-butyl)-[3,4'-bipyridin]-5-yl)-3-methylphenyl)sulfonyl)acetamide (Compound Z-831)

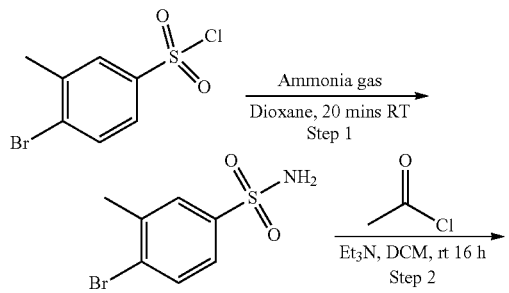

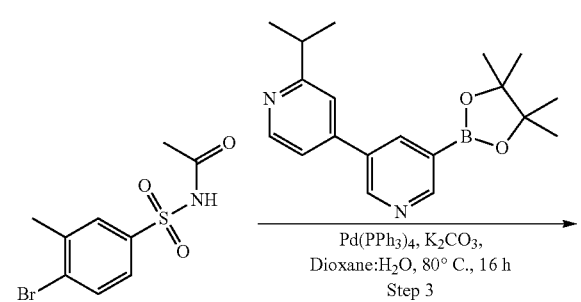

323

-continued

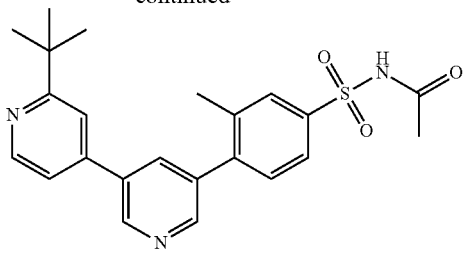

N-((4-(2'-(tert-butyl)-[3,4'-bipyridin]-5-yl)-3-methylphenyl)sulfonyl)acetamide was prepared using a similar series of reactions as described in Example 33 to give an off white solid (75 mg). 1H NMR (400 MHz, DMSO): δ 9.07 (d, J=2.40 Hz, 1H), 8.70 (d, J=2.00 Hz, 1H), 8.62 (d, J=4.80 Hz, 1H), 8.30 (t, J=2.00 Hz, 1H), 7.85 (d, J=16.40 Hz, 1H), 7.82 (s, 2H), 7.66 (dd, J=2.00, 5.20 Hz, 1H), 7.59 (d, J=8.00 Hz, 1H), 2.37 (s, 3H), 1.93 (s, 3H), 1.38 (s, 9H); LCMS: 99.12% (m/z=424.21 [M+1]).

Example 36: 4-(2'-(tert-butyl)-[3,4'-bipyridin]-5-yl)-N-(isopropylcarbamoyl)-3-methylbenzenesulfonamide (Compound Z-832)

324

4-(2'-(tert-butyl)-[3,4'-bipyridin]-5-yl)-N-(isopropylcarbamoyl)-3-methylbenzenesulfonamide was prepared using a similar series of reactions as described in Example 33, to produce an off white solid (14 mg). 1H NMR (400 MHz, DMSO δ 9.04 (d, J=2.40 Hz, 1H), 8.68 (d, J=2.00 Hz, 1H), 8.61 (d, J=5.20 Hz, 1H), 8.27 (t, J=2.00 Hz, 1H), 7.82 (d, J=0.40 Hz, 1H), 7.75 (t, J=8.00 Hz, 2H), 7.66 (dd, J=1.60, 4.80 Hz, 1H), 7.45 (d, J=7.60 Hz, 1H), 5.97 (s, 1H), 3.55-3.57 (m, 1H), 2.33 (s, 3H), 1.38 (s, 9H), 0.99 (d, J=6.80 Hz, 6H); LCMS: 99.12% (m/z=467.1 [M+1].

Example 37: 4-(2'-(tert-butyl)-[3,4'-bipyridin]-5-yl)-3-methylbenzenesulfonamide (Compound Z-830)

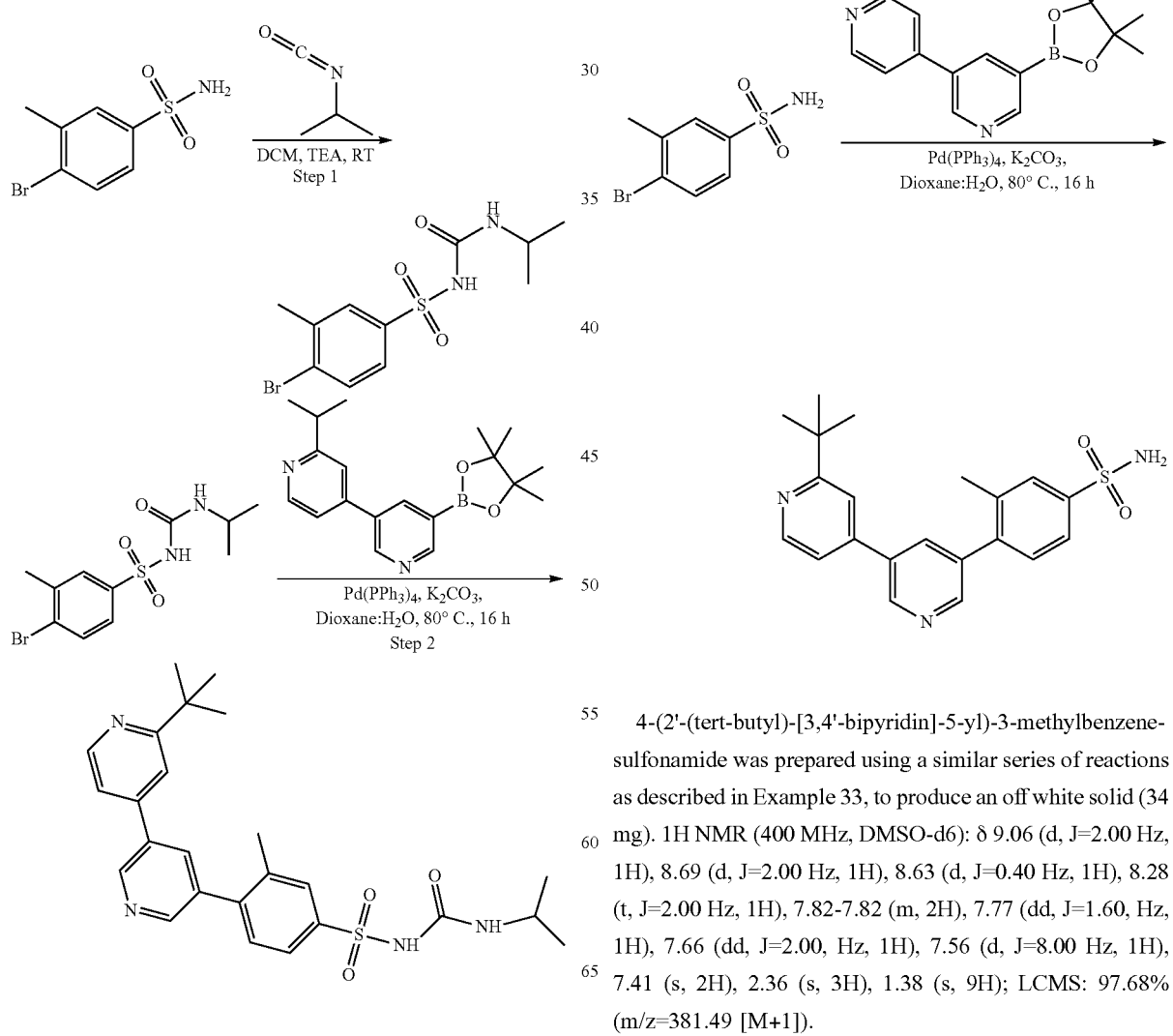

4-(2'-(tert-butyl)-[3,4'-bipyridin]-5-yl)-3-methylbenzenesulfonamide was prepared using a similar series of reactions as described in Example 33, to produce an off white solid (34 mg). 1H NMR (400 MHz, DMSO-d6): δ 9.06 (d, J=2.00 Hz, 1H), 8.69 (d, J=2.00 Hz, 1H), 8.63 (d, J=0.40 Hz, 1H), 8.28 (t, J=2.00 Hz, 1H), 7.82-7.82 (m, 2H), 7.77 (dd, J=1.60, Hz, 1H), 7.66 (dd, J=2.00, Hz, 1H), 7.56 (d, J=8.00 Hz, 1H), 7.41 (s, 2H), 2.36 (s, 3H), 1.38 (s, 9H); LCMS: 97.68% (m/z=381.49 [M+1]).

Example 38: (3-chloro-4-(2'-(4,4-difluorocyclohex-1-en-1-yl)-[3,4'-bipyridin]-5-yl)phenyl)(4-hydroxypiperidin-1-yl)methanone (Compound Z-824)

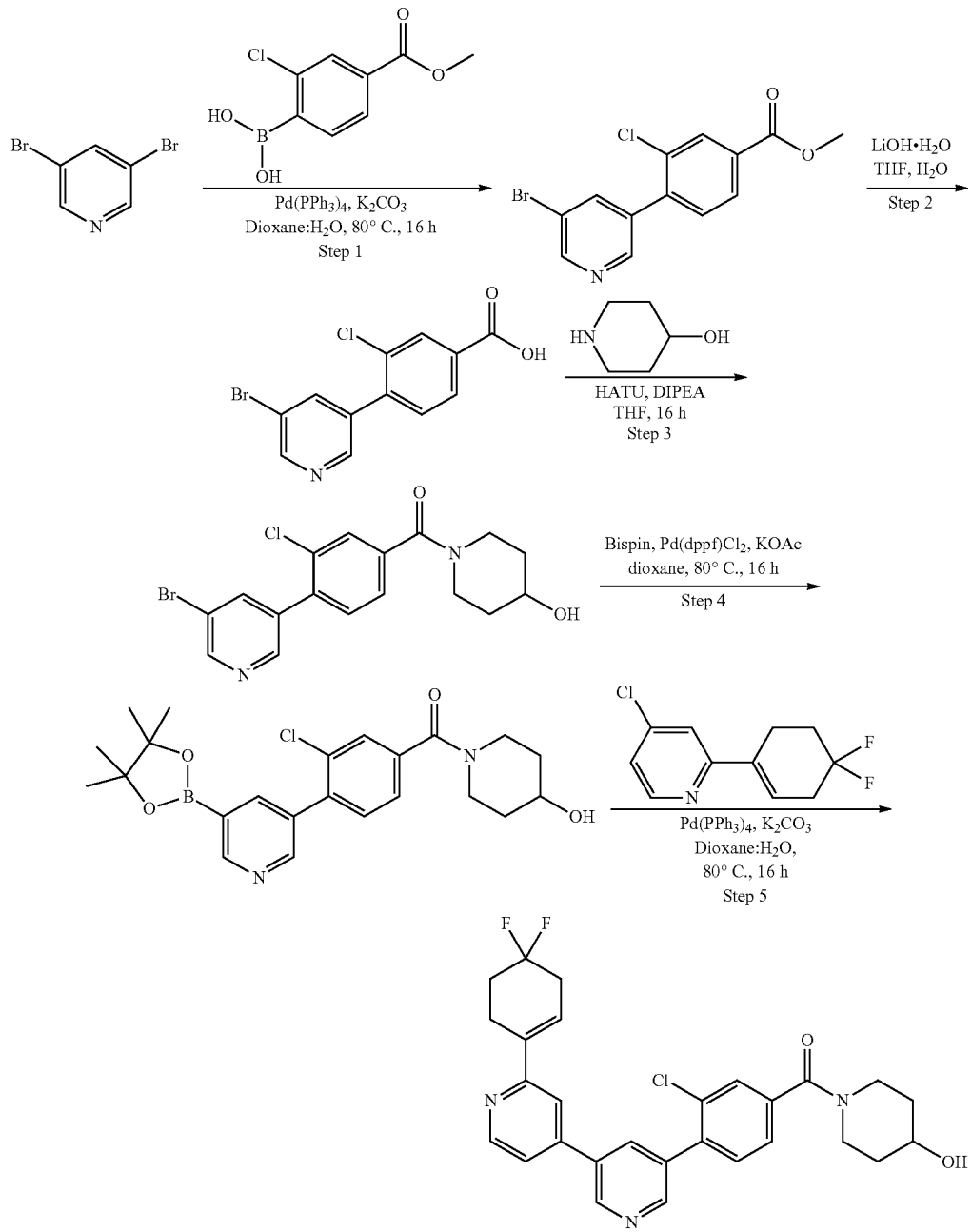

4-chloro-2-(4,4-difluorocyclohex-1-en-1-yl)pyridine—A solution of 2-bromo-4-chloropyridine (0.300 g), 2-(4,4-difluorocyclohex-1-en-1-yl)-4,4,5,5-tetramethyl-1,3,2-dioxaborolane (0.418 g) and cesium carbonate (1.52 g) in dioxane (20 mL) was charged in a 20 mL glass seal tube and purged with nitrogen gas for 10 minutes. After adding Pd(dppf)Cl$_2$ (0.108 g) it was again purged with nitrogen gas for 10 minutes. The reaction mass was heated to 80° C. for 16 h and then cooled to RT and evaporated to dryness under reduced pressure. 5 ml water was added to the residue and the product was extracted into EtOAc (3×15 mL). The extracts were combined, washed with brine (3×10 mL), dried over anhydrous sodium sulfate, filtered and concentrated under reduced pressure to get crude product which was purified by column chromatography to give 4-chloro-2-(4,4-difluorocyclohex-1-en-1-yl)pyridine (0.350 g, 97.76%) as a colorless liquid. $^1$H NMR 400 MHz, CDCl$_3$ 400 MHz, DMSO-d6: δ 8.45 (d, J=0.40 Hz, 1H), 7.35 (d, J=52.00 Hz, 1H), 7.17 (d, J=2.00 Hz, 1H), 6.53 (d, J=1.20 Hz, 1H), 2.80-2.65 (m, 4H), 2.23-2.10 (m, 2H); LCMS: 97.88% (m/z=229.9 [M+H]).

Step 1: methyl 4-(5-bromopyridin-3-yl)-3-chlorobenzoate—3,5-dibromopyridine (6.0 g), (2-chloro-4-(methoxycarbonyl)phenyl)boronic acid (4.87 g) and potassium carbonate (10.5 g) in dioxane-H$_2$O (60:12 mL) were charged in 100 mL glass seal tube and purged with nitrogen gas for 10 minutes. After adding palladium tetrakis (2.98 g) it was again purged with nitrogen gas for 10 minutes. The reaction mass was heated to 80° C. for 16 h, cooled to RT and 50 mL water was added and extracted with EtOAc (3×25 mL). The combined extracts were washed with brine (3×10 mL) and dried over anhydrous sodium sulfate. The solution was concentrated under reduced pressure to give methyl 4-(5-bromopyridin-3-yl)-3-chlorobenzoate (4.2 g, 50.90%) as a white solid.

Step 2: 4-(5-bromopyridin-3-yl)-3-chlorobenzoic acid—To a solution of methyl 4-(5-bromopyridin-3-yl)-3-chlorobenzoate (4.2 g) in THF:Water (42:4.2 mL) was added LiOH.H$_2$O (1.6 g) and the reaction mass was stirred at RT for 3 h. The reaction mass was then evaporated, diluted with water, acidified with dil. HCl to (pH 4) and the product extracted into DCM (3×25 mL). Organic layer was washed with brine solution (2×15 mL) dried over anhydrous sodium sulfate and concentrated under reduced pressure to afford 4-(5-bromopyridin-3-yl)-3-chlorobenzoic acid, 3.8 g (94.52%) as an off white solid.

Step 3: (4-(5-bromopyridin-3-yl)-3-chlorophenyl)(4-hydroxypiperidin-1-yl)methanone—To a solution of 4-(5-bromopyridin-3-yl)-3-chlorobenzoic acid (3.8 g) in THF (76 mL), was added DIPEA (0.651 mL) and HATU (6.0 g). The reaction was stirred for 30 minutes, then added 4-hydroxy piperidine (1.6 g) and stirred for 16 h at RT. The reaction mass was diluted with ethyl acetate and washed with cold water (4×5 mL). The organic layer was separated, dried over anhydrous sodium sulfate and concentrated under reduced pressure to give crude product which was purified by column chromatography to afford (4-(5-bromopyridin-3-yl)-3-chlorophenyl)(4-hydroxypiperidin-1-yl)methanone (3.8 g, 79.33% yield) as an off white solid. $^1$H NMR 400 MHz, DMSO-d6: δ 8.78 (s, 1H), 8.67 (d, J=2.00 Hz, 1H), 8.23 (d, J=2.00 Hz, 1H), 7.61 (d, J=8.00 Hz, 1H), 7.47-7.48 (m, 2H), 7.45 (d, J=1.20 Hz, 1H), 4.81 (d, J=4.0 Hz, 1H), 4.05-3.95 (br s, 1H), 3.78-3.73 (m, 1H), 3.60-3.50 (m, 1H), 3.17 (d, J=5.2 Hz, 2H), 1.76 (d, J=26.00 Hz, 2H), 1.34-1.37 (m, 2H); LCMS: 98.86% (m/z 395.0 [M+H]).

Step 4: (3-chloro-4-(5-(4,4,5,5-tetramethyl-1,3,2-dioxaborolan-2-yl)pyridin-3-yl)phenyl)(4-hydroxypiperidin-1-yl)methanone—A solution of (4-(5-bromopyridin-3-yl)-3-chlorophenyl)(4-hydroxypiperidin-1-yl)methanone (1.0 g), bispin (1.28 g) and potassium acetate (0.62 g) in dioxane (45 mL) were charged in a 50 mL glass seal tube and purged with nitrogen gas for 10 minutes. After adding Pd(dppf)Cl$_2$ (0.018 g, 0.025 mmol) it was again purged with nitrogen gas for 10 minutes and the reaction mass was heated to 80° C. for 16 h. After completion (monitored by TLC), the reaction mixture was cooled to RT and evaporated under reduced pressure. 25 ml water was added to the residue and the product was extracted into EtOAc (3×25 mL). The combined extracts were washed with brine (3×10 mL), dried over anhydrous sodium sulfate, filtered and concentrated under reduced pressure to give crude product which was purified by passing through a Florisil® column to (3-chloro-4-(5-(4,4,5,5-tetramethyl-1,3,2-dioxaborolan-2-yl)pyridin-3-yl)phenyl)(4-hydroxypiperidin-1-yl)methanone (1.80 g, crude) as a black-brown semi-solid.

Step 5: (3-chloro-4-(2'-(4,4-difluorocyclohex-1-en-1-yl)-[3,4'-bipyridin]-5-yl)phenyl)(4-hydroxypiperidin-1-yl)methanone—A solution of 4-chloro-2-(4,4-difluorocyclohex-1-en-1-yl)pyridine (0.250 g), (3-chloro-4-(5-(4,4,5,5-tetramethyl-1,3,2-dioxaborolan-2-yl)pyridin-3-yl)phenyl)(4-hydroxypiperidin-1-yl)methanone (0.589 g) and potassium carbonate (0.3 g, 2.18 mmol) in dioxane-water (7.5:1 mL) were charged in a 20 mL glass seal tube and purged with nitrogen gas for 10 minutes. After adding palladium tetrakis (0.126 g) it was again purged with nitrogen gas for 10 minutes and the reaction mass was heated to 80° C. for 16 h. The reaction mixture was cooled to RT and evaporated under reduced pressure. 5 ml of water was added to the residue and the product was extracted into EtOAc (3×15 mL). The combined extracts were washed with brine (3×10 mL), dried over anhydrous sodium sulfate and concentrated under reduced pressure to give crude product which was purified by column chromatography to give (3-chloro-4-(2'-(4,4-difluorocyclohex-1-en-1-yl)-[3,4'-bipyridin]-5-yl)phenyl)(4-hydroxypiperidin-1-yl)methanone (0.190 g, 53.82%) as a white solid. $^1$H NMR 400 MHz, DMSO-d6: δ 9.13 (d, J=2.40 Hz, 1H), 8.80 (d, J=2.00 Hz, 1H), 8.78 (d, J=2.00 Hz, 1H), 8.66 (d, J=5.20 Hz, 1H), 8.43 (t, J=2.40 Hz, 1H), 8.03 (s, 1H), 7.77 (dd, J=1.60, 5.00 Hz, 1H), 7.57-7.55 (m, 1H), 7.50 (dd, J=1.60, 8.00 Hz, 1H), 6.77 (s, 1H), 4.81 (d, J=4.0 Hz, 1H), 4.00 (br s, 1H), 3.79-3.75 (m, 1H), 3.60-3.50 (br s, 1H), 3.27-3.10 (br s, 2H), 2.90-2.78 (m, 4H), 2.28-2.10 (m, 2H), 1.85-1.60 (m, 2H), 1.45-1.30 (br s, 2H); LCMS: 99.03% (m/z=510.0 [M+H]); HPLC: purity 98.33%.

Example 39: (3-chloro-4-(2'-(4,4-difluorocyclohexyl)-[3,4'-bipyridin]-5-yl)phenyl)(4-hydroxypiperidin-1-yl)methanone (Compound Z-834)

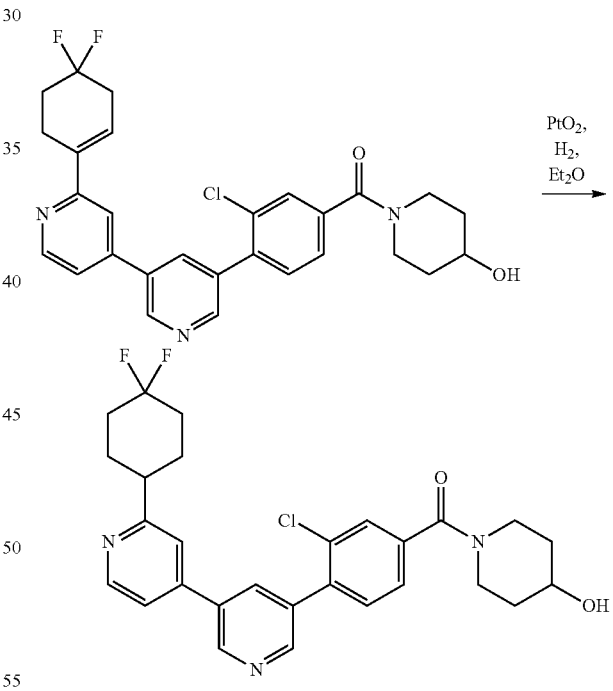

To a stirred solution of (3-chloro-4-(2'-(4,4-difluorocyclohex-1-en-1-yl)-[3,4'-bipyridin]-5-yl)phenyl)(4-hydroxypiperidin-1-yl)methanone (0.150 g) in EtOAc (6 mL), was added PtO$_2$ (0.030 g). The reaction was stirred under H$_2$ balloon pressure at RT for 16 h. After completion (LCMS), the reaction mixture was filtered through a Celite® pad and the pad was washed with methanol. The filtrate and washings were combined, concentrated under reduced pressure to give (3-chloro-4-(2'-(4,4-difluorocyclohexyl)-[3,4'-bipyridin]-5-yl)phenyl)(4-hydroxypiperidin-1-yl)methanone (0.072 g, 48.0%) as a white solid. $^1$H NMR 400 MHz, DMSO-d6: δ 9.08 (d, J=2.00 Hz, 1H), 8.77 (d, J=2.00 Hz, 1H), 8.62 (d, J=5.20 Hz, 1H), 8.37 (t, J=2.40 Hz, 1H), 7.79 (s, 1H), 7.71 (dd, J=1.60, 5.20 Hz, 1H), 7.66 (dd, J=1.60, 6.20 Hz, 1H), 7.49 (dd, J=1.60, 7.60 Hz, 1H), 4.81 (d, J=3.6 Hz, 1H), 4.05-3.95 (br s, 1H), 3.80-3.70 (m, 1H), 3.55-3.45 (m, 1H), 3.28-3.15 (m, 2H), 2.94 (t, J=2.80 Hz, 1H), 2.20-1.70 (br m, 10H), 1.50-1.30 (m, 2H); LCMS: 99.01% (m/z=512.5 [M+H]), HPLC: purity 98.01%.

Example 40: Compounds Z-803, Z-811, Z-812

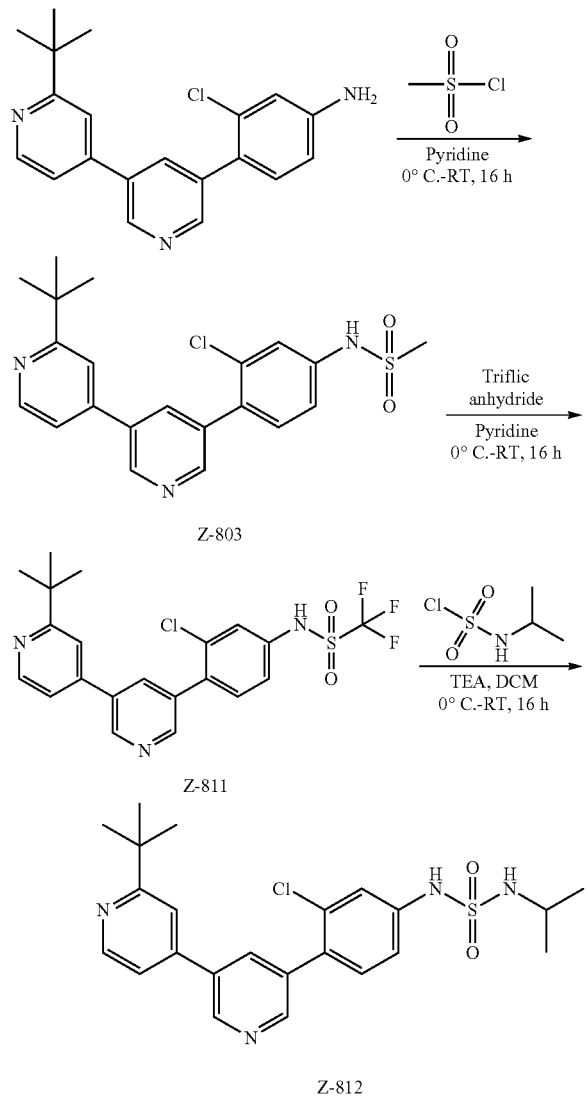

Z-803

Z-811

Z-812

To a stirred solution of 4-(2'-(tert-butyl)-[3,4'-bipyridin]-5-yl)-3-chloroaniline (0.200 g, 0.593 mmol, 1.0 eq) in pyridine (2 mL) was added methanesulfonyl chloride (0.200 mL) at 0° C. The reaction mixture was stirred at RT for 16 h. The pyridine was then evaporated under reduced pressure, and the residue purified by Prep. HPLC to give N-(4-(2'-(tert-butyl)-[3,4'-bipyridin]-5-yl)-3-chlorophenyl)methanesulfonamide. 1H NMR (400 MHz, DMSO: δ (ppm): 10.20 (s, 1H), 9.02 (d, J=2.0 Hz, 1H), 8.71 (d, J=2.0 Hz, 1H), 8.63-8.61 (dd, J=0.8 Hz, J=0.4 Hz, 1H), 8.27-8.26 (t, J=2.0 Hz, 1H), 7.80 (d, J=0.8 Hz, 1H), 7.64-7.62 (dd, J=1.6 Hz, J=1.6 Hz, 1H), 7.59-7.54 (dd, J=8.4 Hz, J=7.2 Hz, 1H), 7.42 (d, J=2.4 Hz, 1H), 7.32-7.30 (dd, J=2.4 Hz, J=2.4 Hz, 1H), 3.11 (s, 3H), 1.37 (s, 9H); LCMS: 96.65% (416.1 [M+H]).

N-(4-(2'-(tert-butyl)-[3,4'-bipyridin]-5-yl)-3-chlorophenyl)-1,1,1-trifluoromethanesulfonamide was prepared in a similar fashion using triflic anhydride. 1H NMR (400 MHz, DMSO: δ (ppm): 10.20 (s, 1H), 9.02 (d, J=2.0 Hz, 1H), 8.71 (d, J=2.0 Hz, 1H), 8.63-8.61 (dd, J=0.8 Hz, J=0.4 Hz, 1H), 8.27-8.26 (t, J=2.0 Hz, 1H), 7.80 (d, J=0.8 Hz, 1H), 7.64-7.62 (dd, J=1.6 Hz, J=1.6 Hz, 1H), 7.59-7.54 (dd, J=8.4 Hz, J=7.2 Hz, 1H), 7.42 (d, J=2.4 Hz, 1H), 7.32-7.30 (dd, J=2.4 Hz, J=2.4 Hz, 1H), 3.11 (s, 3H), 1.37 (s, 9H); LCMS: 96.65% (416.1 [M+H].

N-(4-(2'-(tert-butyl)-[3,4'-bipyridin]-5-yl)-3-chlorophenyl)-isopropylsulfamoyl urea was prepared in a similar fashion using isopropylsulfamoyl chloride. 1H NMR (400 MHz, DMSO: δ (ppm): 10.08 (s, 1H), 9.00 (d, J=2.4 Hz, 1H), 8.70 (d, J=2.0 Hz, 1H), 8.62-8.61 (dd, J=0.8 Hz, J=0.8 Hz, 1H), 8.25-8.24 (t, J=2.0 Hz, 1H), 7.80 (d, J=0.4 Hz, 1H), 7.72 (d, J=7.6 Hz, 1H), 7.64-7.62 (dd, J=1.6 Hz, J=1.6 Hz, 1H), 7.52 (d, J=8.4 Hz, 1H), 7.38 (d, J=2.4 Hz, 1H), 7.23-7.20 (dd, J=24 Hz, J=2.4 Hz, 1H), 3.39-3.36 (m, 1H), 1.37 (s, 9H), 1.05 (d, J=6.4 Hz, 6H); LCMS: 98.66% (459.63 [M+H]).

Example 41: Compounds Z-804 and Z-823

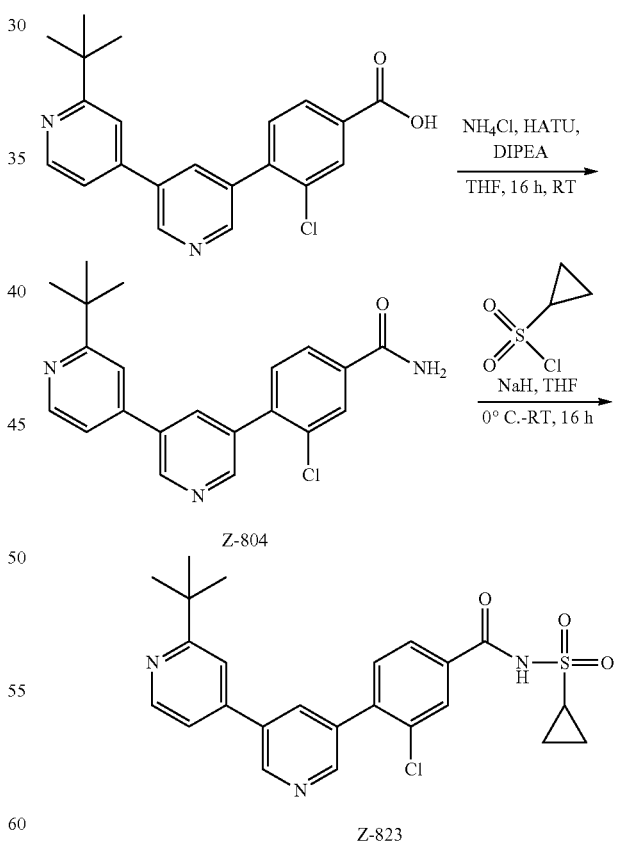

Z-804

Z-823

Step 1: 4-(2'-(tert-butyl)-[3,4'-bipyridin]-5-yl)-3-chlorobenzamide—To a solution of 4-(2'-(tert-butyl)-[3,4'-bipyridin]-5-yl)-3-chlorobenzoic acid (0.200 g, 0.546 mmol) in THF was added DIPEA (0.211 g, 1.638 mmol) and HATU (0.415 g, 1.092 mmol) and the reaction mass was stirred for 20 min. NH₄Cl (0.058 g, 1.092 mmol) was added and stirred at RT for 16 h. The reaction mass was then evaporated under reduced pressure, diluted with water and extracted into DCM (3×25 mL). The organic layer was washed with saturated NaHCO₃ solution (2×15 mL), brine solution (2×15 mL), dried over anhydrous sodium sulfate and concentrated under reduced pressure to give a crude product which was purified by column chromatography to give 4-(2'-(tert-butyl)-[3,4'-bipyridin]-5-yl)-3-chlorobenzamide (0.190 g, 95.2%) as an off white solid. ¹H NMR (400 MHz, DMSO d₆): δ 9.07 (d, J=2.00 Hz, 1H), 8.77 (d, J=2.00 Hz, 1H), 8.63 (d, J=0.40 Hz, 1H), 8.35 (t, J=2.40 Hz, 1H), 8.20 (s, 1H), 8.12 (d, J=2.00 Hz, 1H), 7.98 (dd, J=1.60, 8.00 Hz, 1H), 3.47-3.73 (m, 8H) 7.72 (d, J=8.00 Hz, 1H), 7.66 (dd, J=2.00, 5.00 Hz, 1H), 7.62 (s, 1H), 1.38 (s, 9H); LCMS 99.87% (m/z 366.1 [M+H]).

Step 2: To a stirred solution of 4-(2'-(tert-butyl)-[3,4'-bipyridin]-5-yl)-3-chlorobenzamide (0.100 g, 0.274 mmol) in THF (3 mL) was added NaH (0.013 g, 0.548 mmol) at 0° C. and the reaction mass was stirred at same temperature for 1 h. Then isopropylsulfonyl chloride (0.057 g, 0.411 mmol) was added and stirred for 16 h at RT. The reaction was then quenched with MeOH (5 mL) with ice cooling and the solvent was evaporated under reduced pressure. The residue was diluted with water and the product was extracted into DCM (3×25 mL). The organic layer was washed with brine solution (2×15 mL), dried over anhydrous sodium sulfate and concentrated under reduced pressure to give crude product which was purified by prep. HPLC to give 4-(2'-(tert-butyl)-[3,4'-bipyridin]-5-yl)-3-chloro-N-(cyclopropylsulfonyl)benzamide (0.022 g 17.0%) as an off white solid. ¹H NMR (400 MHz, DMSO d₆): δ 12.38 (s, 1H), 9.09 (d, J=2.00 Hz, 1H), 8.78 (d, J=2.00 Hz, 1H), 8.64 (d, J=5.20 Hz, 1H), 8.36 (t, J=2.00 Hz, 1H), 8.21 (d, J=1.60 Hz, 1H), 8.04 (dd, J=2.00, 8.00 Hz, 1H), 7.79 (d, J=8.00 Hz, 1H), 7.67 (dd, J=1.60, 5.20 Hz, 1H), 3.13-3.14 (m, 1H), 1.38 (s, 9H), 1.12-1.13 (m, 4H); LCMS: 99.1% (m/z 470.0 [M+H]).

Example 42: (4-(2'-(tert-butyl)-4-fluoro-[3,4'-bipyridin]-5-yl)-3-chlorophenyl)(4-hydroxypiperidin-1-yl)methanone (Compound Z-855)

(4-(2'-(tert-butyl)-4-fluoro-[3,4'-bipyridin]-5-yl)-3-chlorophenyl)(4-hydroxypiperidin-1-yl)methanone was prepared following the general procedures described in Example 4, to produce the product as an off white solid. ¹H NMR (400 MHz, DMSO-d6: δ 8.93 (d, J=9.60 Hz, 1H), 8.66-8.66 (m, 2H), 7.68-7.66 (m, 3H), 7.52-7.50 (m, 2H), 4.82 (d, J=4.00 Hz, 1H), 3.99-4.01 (m, 1H), 3.74-3.75 (m, 1H), 3.51 (br s, 1H), 3.21-3.19 (m, 2H), 1.75-1.80 (m, 2H), 1.37 (br s, 11H); LCMS: 98% (m/z=468.54 [M+H]).

Example 43: (4-(2'-(tert-butyl)-4-fluoro-[3,4'-bipyridin]-5-yl)phenyl)(4-hydroxypiperidin-1-yl)methanone (Compound Z-866)

(4-(2'-(tert-butyl)-4-fluoro-[3,4'-bipyridin]-5-yl)phenyl) (4-hydroxypiperidin-1-yl)methanone was prepared following the general procedures described in Example 4, to produce the product as an off white solid. ¹H NMR (400 MHz, DMSO-d6: δ 8.81-8.82 (m, 2H), 8.64-8.66 (m, 1H), 7.73-7.75 (m, 3H), 7.51-7.53 (m, 3H), 4.81 (d, J=4.00 Hz, 1H), 4.02-4.05 (m, 1H), 3.73-3.74 (m, 1H), 3.60-3.50 (m, 1H), 3.19-3.22 (m, 2H), 1.74-1.77 (m, 2H), 1.37 (br s, 11H); LCMS: (m/z=434.1 [M+H]. Mp 100-104° C.

Example 44: (4-(2'-(tert-butyl)-4-methoxy-[3,4'-bipyridin]-5-yl)-3-chlorophenyl)(4-hydroxypiperidin-1-yl)methanone (Compound Z-840)

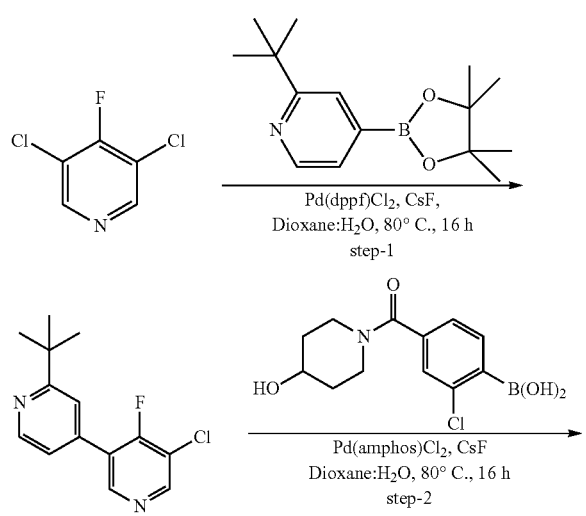

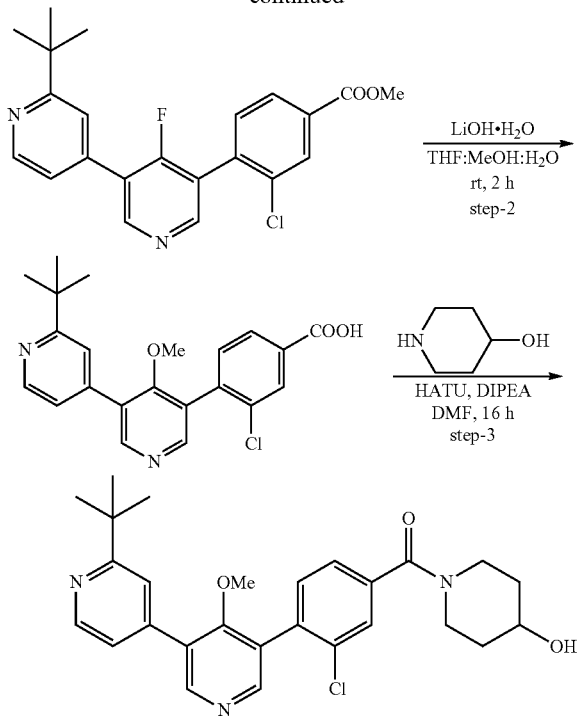

Step 1: methyl 4-(2'-(tert-butyl)-4-fluor-[3,4'-bipyridin]-5-yl)-3-chlorobenzoate—2'-(tert-butyl)-5-chloro-4-fluoro-3,4'-bipyridine (190 mg, 0.719 mmol) was dissolved in 1,4-dioxane (9 mL) and water (1 mL) and (2-chloro-4-(methoxycarbonyl)phenyl)boronic acid (231 mg, 1.079 mmol) and CsF (327 mg, 2.15 mmol) were added under a nitrogen atmosphere. The reaction mass was purged for 15 minutes with nitrogen, Pd(amphos)Cl$_2$ (50 mg, 0.071 mmol) was added and the reaction mixture was again purged for 10 minutes with nitrogen. The reaction tube was sealed and stirred at 80° C. for 16 h. After completion of the reaction, the solvent was evaporated and the residue was diluted with water (10 mL) and extracted into EtOAc (3×20 mL). The combined extracts were dried over anhydrous sodium sulfate and concentrated under reduced pressure to obtain crude methyl 4-(2'-(tert-butyl)-4-fluoro-[3,4'-bipyridin]-5-yl)-3-chlorobenzoate. $^1$H NMR (400 MHz, DMSO-d$_6$): δ 8.96 (d, J=9.60 Hz, 1H), 8.64-8.64 (m, 2H), 8.14 (d, J=1.60 Hz, 1H), 8.05-8.06 (m, 1H), 7.80 (d, J=8.00 Hz, 1H), 7.64-7.70 (m, 1H), 7.45-7.46 (m, 1H), 3.92 (s, 3H), 1.36 (s, 9H); LCMS: (m/z=399 [M+H]).

Step 2: 4-(2'-(tert-butyl)-4-methoxy-[3,4'-bipyridin]-5-yl)-3-chlorobenzoic acid—To a solution of methyl 4-(2'-(tert-butyl)-4-fluoro-[3,4'-bipyridin]-5-yl)-3-chlorobenzoate (200 mg, 2.57 mmol) in THF:MeOH:H$_2$O (6 mL), was added LiOH.H$_2$O (200 mg, 4.87 mmol) and the reaction mixture was stirred at RT for 2 h. After completion of the reaction (monitored by TLC), the solvent was evaporated and the residue was acidified with 1N hydrochloric acid to pH=4, then the product extracted into EtOAc (20 mL). The organic layer was dried over anhydrous sodium sulfate and concentrated under reduced pressure to afford 4-(2'-(tert-butyl)-4-methoxy-[3,4'-bipyridin]-5-yl)-3-chlorobenzoic acid as white solid. $^1$H NMR (400 MHz, DMSO-d$_6$): δ 13.44 (br s, 1H), 8.62-8.63 (m, 2H), 8.45 (s, 1H), 8.09 (d, J=1.60 Hz, 1H), 7.99-8.00 (m, 1H), 7.67 (d, J=8.00 Hz, 1H), 7.62 (s, 1H), 7.42-7.44 (m, 1H), 2.50 (s, 3H), 1.37 (s, 9H); LCMS 89.5% (m/z=395 [M−H]).

Step 3: (4-(2'-(tert-butyl)-4-methoxy-[3,4'-bipyridin]-5-yl)-3-chlorophenyl)(4-hydroxypiperidin-1-yl)methanone—To a solution of 4-(2'-(tert-butyl)-4-methoxy-[3,4'-bipyridin]-5-yl)-3-chlorobenzoic acid (120 mg, 0.3125 mmol) in THF (6 mL, 20 v), was added DIPEA (160 mL, 1.242 mmol) and HATU (356 mg, 0.936 mmol). The reaction was stirred for 30 minutes, then 4-hydroxy piperidine (63 mg, 0.623 mmol) was added and the reaction mixture was stirred for 16 h at RT. After completion (monitored by TLC), the reaction mass was diluted with ethyl acetate and washed with cold water (4×5 mL). The organic layer was dried over anhydrous sodium sulfate and concentrated under reduced pressure. The crude product obtained was purified by Prep. HPLC to afford (4-(2'-(tert-butyl)-4-methoxy-[3,4'-bipyridin]-5-yl)-3-chlorophenyl)(4-hydroxypiperidin-1-yl)methanone as off white solid (18 mg). $^1$H NMR (400 MHz, DMSO-d6): δ 8.62-8.63 (m, 2H), 8.45 (s, 1H), 7.64 (d, J=1.20 Hz, 1H), 7.58-7.64 (m, 3H), 7.47 (dd, J=1.60, 7.60 Hz, 1H), 7.43 (dd, J=1.60, 5.20 Hz, 1H), 4.81 (d, J=4.00 Hz, 1H), 4.00 (br s, 1H), 3.74-3.75 (m, 1H), 3.60 (br s, 1H), 3.32 (br s, 3H), 3.21-3.15 (m, 2H), 1.85-1.65 (m, 2H), 1.37 (br s, 11H); LCMS: (m/z=480 [M+H]). Mp 105-109° C.

Example 45: (3-chloro-4-(2'-(1-hydroxy-2-methyl-propan-2-yl)-[3,4'-bipyridin]-5-yl)phenyl)(4-hydroxypiperidin-1-yl)methanone (Compound Z-856)

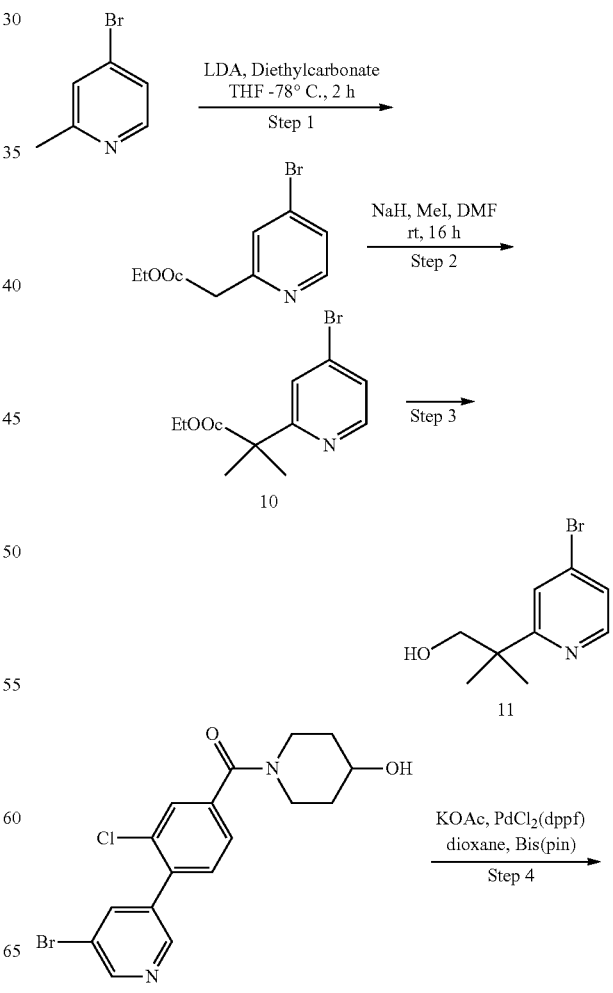

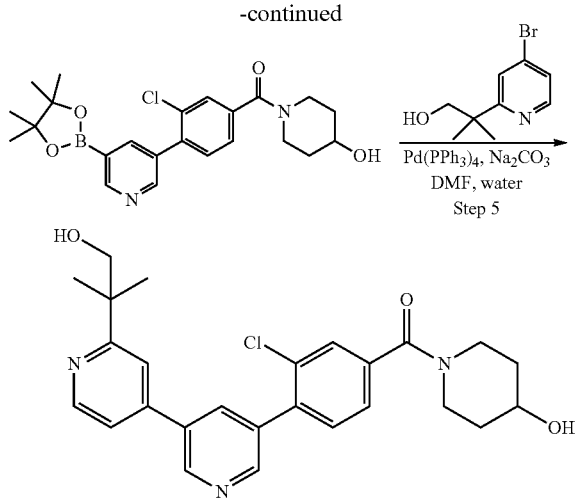

Step 1: ethyl 2-(4-bromopyridin-2-yl)acetate—To a stirred solution of 4-bromo-2-methylpyridine (1.2 g, 4.93 mmol, 1.0 eq) in THF (15 mL), was added diethyl carbonate (0.698 mL, 5.92 mmol, 1.2 eq) and the mixture stirred at −78° C. under nitrogen atmosphere. LDA(2M) (2.96 mL, 5.92 mmol) was added dropwise over 15 min and the reaction was stirred at −78° C. for 2 h. The reaction was then quenched with saturated sodium chloride solution and the product extracted with EtOAc (2×50 mL). The combined organic layers were washed with brine (50 mL), dried over anhydrous sodium sulfate and concentrated under reduced pressure, to give a crude compound, which was purified by column chromatography to give ethyl 2-(4-bromopyridin-2-yl)acetate (0.500 g, 30%) as a pale yellow liquid.

Step 2: ethyl 2-(4-bromopyridin-2-yl)-2-methylpropanoate—To a stirred solution of ethyl 2-(4-bromopyridin-2-yl)acetate (0.5 g, 2.05 mmol, 1.0 eq) in DMF (5 mL) at 0° C. under nitrogen atmosphere was added NaH (60%) (0.246 g, 6.10 mmol, 3 eq). The reaction mass was stirred at rt for 30 mins, then cooled to 0° C. followed by the addition of methyl iodide (1.486 g, 10.25 mmol, 5.0 eq) under nitrogen atmosphere and stirred at RT for 16 h. The DMF was removed under reduced pressure, water (10 mL) was added and the product extracted into EtOAc (3×15 mL). The combined organic extracts were dried over anhydrous sodium sulfate and concentrated under reduced pressure to give a crude product which was purified by column chromatography to give ethyl 2-(4-bromopyridin-2-yl)-2-methylpropanoate (0.140 g, 25%) as a pale yellow liquid.

Step 3: 2-(4-bromopyridin-2-yl)-2-methylpropan-1-ol—To a stirred solution of ethyl 2-(4-bromopyridin-2-yl)-2-methylpropanoate (600 mg, 2.2 mmol, 1 eq) in THF (10 mL) under nitrogen atmosphere, at 0° C., was added 1M $BH_3$.THF (3.3 mL, 3.31 mmol) dropwise. The mixture was stirred at room temperature for 16 h and then quenched with methanol (10 mL) and concentrated under reduced pressure to afford crude product which was diluted with water and extracted into ethyl acetate. The ethyl acetate layer was dried over sodium sulfate and concentrated under reduced pressure to afford 2-(4-bromopyridin-2-yl)-2-methylpropan-1-ol (280 mg) as a pale yellow liquid.

Step 4: (3-chloro-4-(5-(4,4,5,5-tetramethyl-1,3,2-dioxaborolan-2-yl)pyridin-3-yl)phenyl)(4-hydroxypiperidin-1-yl)methanone—In glass seal tube, a solution of (4-(5-bromopyridin-3-yl)-3-chlorophenyl)(4-hydroxypiperidin-1-yl)methanone (0.2 g, 0.5 mmol), Bis(pin) (0.193 g, 1.0 mmol) and potassium acetate (0.147 g, 1.5 mmol) in 1,4-dioxane (10 mL) was purged with nitrogen gas for 15 minutes. After adding $PdCl_2$ (dppf) (0.036 g, 0.05 mmol) it was again purged with nitrogen gas for 5 minutes and the reaction mass was stirred at 80° C. for 16 h. After completion of the reaction (monitored by TLC), the mixture was cooled to RT and filtered through a Celite® bed and washed with ethyl acetate (2×50 mL). The combined organic layers were concentrated under reduced pressure to give crude product which was purified by column chromatography on Florisil® (60-120) to give (3-chloro-4-(5-(4,4,5,5-tetramethyl-1,3,2-dioxaborolan-2-yl)pyridin-3-yl)phenyl)(4-hydroxypiperidin-1-yl)methanone as a brown gummy solid.

Step 5: (3-chloro-4-(2'-(1-hydroxy-2-methylpropan-2-yl)-[3,4'-bipyridin]-5-yl)phenyl)(4-hydroxypiperidin-1-yl)methanone—To a stirred solution of (3-chloro-4-(5-(4,4,5,5-tetramethyl-1,3,2-dioxaborolan-2-yl)pyridin-3-yl)phenyl)(4-hydroxypiperidin-1-yl)methanone (0.19 g, 0.43 mmol) in 1,4-dioxane (8 mL) and $H_2O$ (2 mL) in a glass tube was added 2-(4-bromopyridin-2-yl)-2-methylpropan-1-ol (0.1 g, 0.43 mmol) and $K_2CO_3$ (0.178 g, 1.29 mmol). The reaction mixture was purged for 15 minutes with nitrogen and $Pd(PPh_3)_4$ (0.05 g, 0.043 mmol) was added and the mixture again purged for 10 minutes with nitrogen. The reaction mixture was stirred at 80° C. for 16 h. After completion (monitored by TLC), the solvent was evaporated and water was added (50 mL) and the product extracted into EtOAc (3×45 mL). The combined extracts were dried over anhydrous sodium sulfate and concentrated under reduced pressure to give the crude compound which was purified by prep-HPLC to give (3-chloro-4-(2'-(1-hydroxy-2-methylpropan-2-yl)-[3,4'-bipyridin]-5-yl)phenyl)(4-hydroxypiperidin-1-yl)methanone (33 mg) as a white solid. $^1$H NMR (400 MHz, DMSO-d6): δ 9.06 (d, J=2.40 Hz, 1H), 8.76 (d, J=2.00 Hz, 1H), 8.63 (d, J=5.20 Hz, 1H), 8.33 (t, J=2.40 Hz, 1H), 7.79 (s, 1H), 7.68-7.65 (m, 3H), 7.49 (dd, J=1.60, J=9.2, 1H), 4.82 (d, J=4.00 Hz, 1H), 4.67 (t, J=5.2 Hz, 1H), 4.04 (br s, 1H), 3.79-3.74 (m, 1H), 3.63-3.61 (m, 3H), 3.25-3.15 (br s, 2H), 1.85-1.70 (m, 2H), 1.40-1.30 (br s, 8H); LCMS: 97.97% (M+H=466.59).

Example 46: (4-(2'-(tert-butyl)-6-(trifluoromethyl)-[3,4'-bipyridin]-5-yl)phenyl)(4-hydroxypiperidin-1-yl)methanone (Compound Z-865)

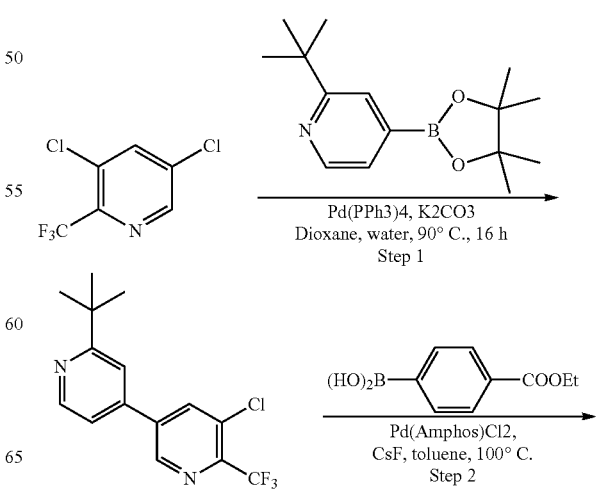

337

-continued

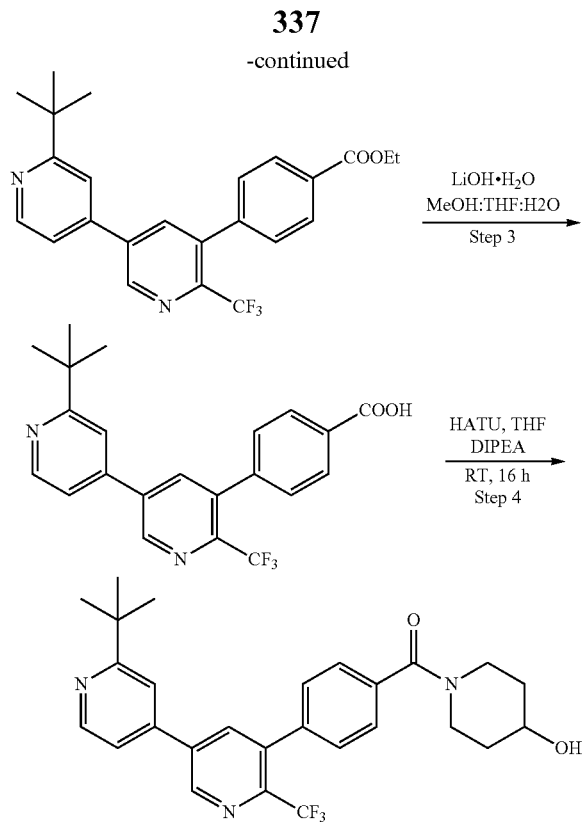

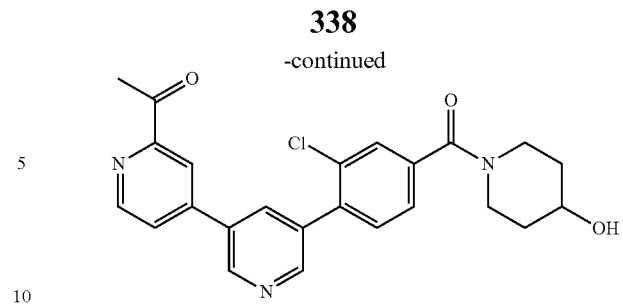

(4-(2'-(tert-butyl)-6-(trifluoromethyl)-[3,4'-bipyridin]-5-yl)phenyl)(4-hydroxypiperidin-1-yl)methanone was prepared from 3,5-dichloro-2-(trifluoromethyl)pyridine was prepared following the general procedures described in Example 4, to produce the product as an off white solid. 1H NMR (400 MHz, DMSO-d6): δ 9.21 (d, J=2.00 Hz, 1H), 8.66 (dd, J=0.40, 5.20 Hz, 1H), 8.40 (d, J=1.60 Hz, 1H), 7.89 (s, 1H), 7.72 (dd, J=1.60, 5.00 Hz, 1H), 7.54-7.49 (m, 4H), 4.81 (d, J=3.60 Hz, 1H), 4.02 (br s, 1H), 3.78-3.73 (m, 1H), 3.60-3.50 (m, 1H), 3.23-3.21 (m, 2H), 1.85-1.70 (m, 2H), 1.38 (s, 11H); LCMS: 98.43% (m/z 484.65 [M+H]).

Example 47: 1-(5-(2-chloro-4-(4-hydroxypiperidine-1-carbonyl)phenyl)-[3,4'-bipyridin]-2'-yl)ethan-1-one (Compound Z-797)

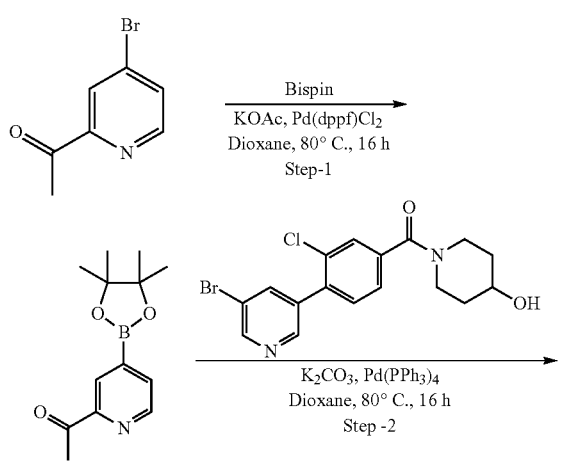

338

-continued

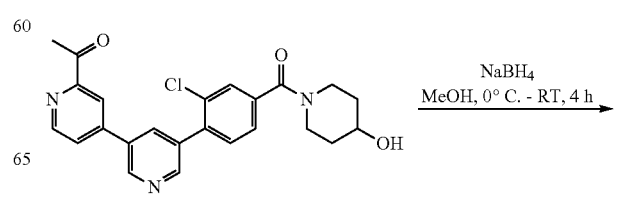

Step 1: 1-(4-(4,4,5,5-tetramethyl-1,3,2-dioxaborolan-2-yl)pyridin-2-yl)ethan-1-one—To a stirred solution of 1-(4-bromopyridin-2-yl)ethan-1-one (200 mg, 1 mmol) and Bispin (379 mg, 1.5 mmol) in dioxane, in a glass seal tube, was added KOAc (294 mg, 3.0 mmol) and the reaction mass was purged for 15 minutes with nitrogen. Then PdCl$_2$(dppf) (77 mg, 0.1 mmol) was added and the reaction mixture was again purged for 10 min with nitrogen. The reaction tube was sealed and stirred at 80° C. for 16 h. The reaction mass was cooled and filtered through Celite®, and the filtrate was concentrated under reduced pressure to obtain crude residue. The residue was suspended in diethyl ether (2×10 mL) and the ether layer was separated, dried over anhydrous sodium sulfate and concentrated under reduced pressure to obtain 1-(4-(4,4,5,5-tetramethyl-1,3,2-dioxaborolan-2-yl)pyridin-2-yl)ethan-1-one (0.300 g) as a brown gummy liquid.

Step 2: 1-(5-(2-chloro-4-(4-hydroxypiperidine-1-carbonyl)phenyl)-[3,4'-bipyridin]-2'-yl)ethan-1-one—To a stirred solution of the product of Step 1 (260 mg, 1.05 mmol) and (4-(5-bromopyridin-3-yl)-3-chlorophenyl)(4-hydroxypiperidin-1-yl)methanone (415 mg, 1.05 mmol) in dioxane: water (5 mL:1 mL), in a glass seal tube, was added K$_2$CO$_3$ (435 mg, 3.15 mmol) at room temperature under nitrogen atmosphere. The reaction mass was purged for 15 minutes with nitrogen, then Pd(PPh$_3$)$_4$ (121 mg, 0.105 mmol) was added and the reaction mixture was again purged for 10 minutes with nitrogen. The reaction tube was sealed and stirred at 80° C. for 16 h. After completion, the residue was diluted with water (10 mL) and extracted into EtOAc (3×15 mL). The combined extracts were dried over anhydrous sodium sulfate and concentrated under reduced pressure to obtain crude product which was purified by Prep. HPLC to give 1-(5-(2-chloro-4-(4-hydroxypiperidine-1-carbonyl)phenyl)-[3,4'-bipyridin]-2'-yl)ethan-1-one (80 mg, 18%) as a white solid. 1H NMR (400 MHz, DMSO: δ (ppm): 9.13 (d, J=2.00 Hz, 1H), 8.86 (dd, J=0.40, 5.20 Hz, 1H), 8.81 (d, J=2.00 Hz, 1H), 8.43 (t, J=2.40 Hz, 1H), 8.36 (t, J=0.40 Hz, 1H), 8.17 (dd, J=2.00, 5.00 Hz, 1H), 7.69 (d, J=8.00 Hz, 1H), 7.65 (d, J=1.60 Hz, 1H), 7.50 (dd, J=1.60, 7.60 Hz, 1H), 4.82 (d, J=4.00 Hz, 1H), 4.01 (br s, 1H), 3.74-3.79 (m, 1H), 3.51-3.55 (m, 1H), 3.32 (br s, 2H), 2.70 (s, 3H), 1.76-1.81 (m, 2H), 1.36-1.38 (m, 2H); LCMS: 98.89% (436.2 [M+H]).

Example 48: (3-chloro-4-(2'-(1-hydroxyethyl)-[3,4'-bipyridin]-5-yl)phenyl)(4-hydroxypiperidin-1-yl)methanone (Compound Z-798)

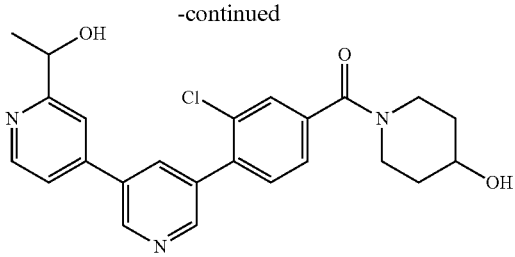

To a stirred solution of 1-(5-(2-chloro-4-(4-hydroxypiperidine-1-carbonyl)phenyl)-[3,4'-bipyridin]-2'-yl)ethan-1-one (150 mg, 0.436 mmol) in methanol (10 mL), at 0° C. was added NaBH₄ (26 mg, 0.68 mmol). The reaction mixture was stirred at RT for 4 h. After completion, the reaction was quenched with aqueous HCl and extracted into EtOAc (3×15 mL). The combined extracts were dried over anhydrous sodium sulfate and concentrated under reduced pressure to obtain crude product which was purified by preparative HPLC to give (3-chloro-4-(2'-(1-hydroxyethyl)-[3,4'-bipyridin]-5-yl)phenyl)(4-hydroxypiperidin-1-yl)methanone (75 mg, 50%) as a white solid. ¹H NMR (400 MHz, DMSO: δ (ppm): 9.05 (d, J=2.00 Hz, 1H), 8.78 (d, J=2.00 Hz, 1H), 8.62-8.60 (m, 1H), 8.31 (t, J=2.00 Hz, 1H), 7.91 (d, J=1.60 Hz, 1H), 7.73 (dd, J=1.60, 5.20 Hz, 1H), 7.65-7.63 (m, 1H), 7.49-7.47 (m, 2H), 5.40 (dd, J=4.80, Hz, 1H), 4.82-4.81 (m, 1H), 4.00 (br s, 1H), 3.80-3.70 (m, 1H), 3.55-3.50 (m, 1H), 3.22-3.21 (m, 2H), 1.80-1.75 (m, 3H), 1.44-1.42 (m, 5H); LCMS: 98.91% (438.42 [M+H]).

Example 49: (3-chloro-4-(2'-(2-hydroxypropan-2-yl)-[3,4'-bipyridin]-5-yl)phenyl)(4-hydroxypiperidin-1-yl)methanone (Compound Z-796)

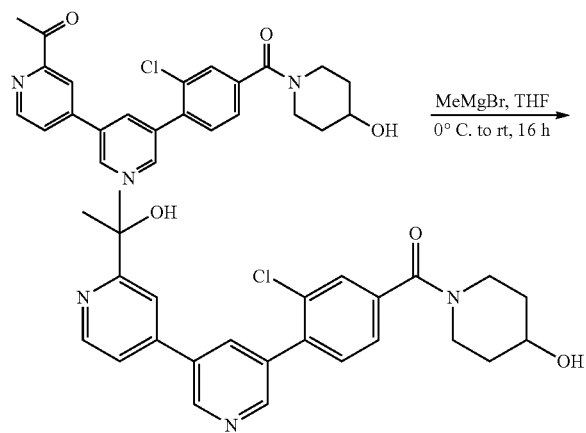

To a stirred solution 1-(5-(2-chloro-4-(4-hydroxypiperidine-1-carbonyl)phenyl)-[3,4'-bipyridin]-2'-yl)ethan-1-one (190 mg, 0.436 mmol) in diethyl ether (10 mL), MeMgBr (3M in DEE) (0.580 mL, 1.746 mmol) was added at 0° C. The reaction mixture was stirred at RT for 16 h. After completion of reaction, the reaction mixture was quenched with ammonium chloride solution (10 mL) and extracted into EtOAc (3×15 mL). The combined extracts were dried over anhydrous sodium sulfate and concentrated under reduced pressure to obtain crude product which was purified by preparative HPLC to afford (3-chloro-4-(2'-(2-hydroxypropan-2-yl)-[3,4'-bipyridin]-5-yl)phenyl)(4-hydroxypiperidin-1-yl)methanone. 1H NMR (400 MHz, DMSO: δ (ppm): 9.04 (d, J=2.4 Hz, 1H), 8.77 (d, J=2.4 Hz, 1H), 8.62-8.60 (dd, J=0.4 Hz, J=0.8 Hz, 1H), 8.30-8.28 (t, J=2.0 Hz, 1H), 8.03 (d, J=1.2 Hz, 1H), 7.71-7.65 (m, 3H), 7.50-7.48 (dd, J=1.6 Hz, J=1.6 Hz, 1H), 5.29 (s, 1H), 4.80 (d, J=4.0 Hz, 1H), 4.00 (bs, 1H), 3.79-3.74 (m, 1H), 3.54-3.50 (m, 1H), 3.31 (bs, 2H), 1.80-1.75 (bs, 2H), 1.49-1.35 (bs, 8H); LCMS: 97.54% (452.1 [M+H].

Example 50: (3-chloro-4-(2'-(2-methoxypropan-2-yl)-[3,4'-bipyridin]-5-yl)phenyl)(4-hydroxypiperidin-1-yl)methanone (Compound Z-799)

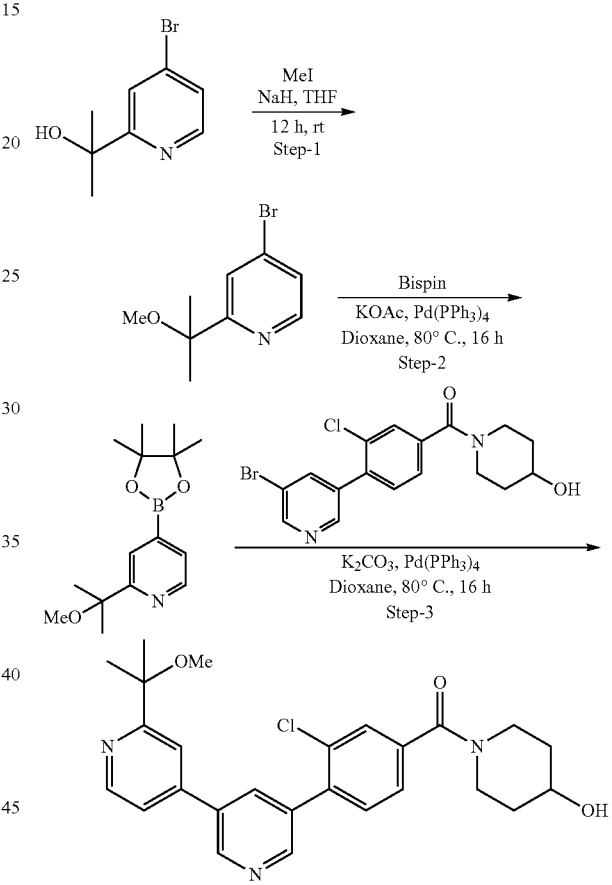

Step 1: 4-bromo-2-(2-methoxyproxan-2-yl)pyridine—To a stirred solution of 2-(4-bromopyridin-2-yl)propan-2-ol (200 mg, 0.92 mmol) in THF (5 mL), was added NaH 56% (130 mg, 2.77 mmol), the mixture stirred at RT for 30 min, then MeI (667 mg, 4.62 mmol) was added and the mixture stirred at RT for 12 h. After completion, the THF was removed under reduced pressure and the residue was dissolved in EtOAc and washed with water (3×15 mL). The organic layer was dried over anhydrous sodium sulfate and concentrated under reduced pressure to obtain crude product which was purified by column chromatography (Silica 60-120 mesh) to afford 4-bromo-2-(2-methoxypropan-2-yl)pyridine (180 mg, 84%) as a pale yellow liquid. ¹H NMR (400 MHz, CDCl₃: δ 8.37 (dd, J=0.40, 5.20 Hz, 1H), 7.74 (dd, J=0.80, 1.80 Hz, 1H), 7.33 (dd, J=2.00, 5.20 Hz, 1H), 3.20 (s, 3H), 1.54 (s, 6H); LCMS: 98.70% (M+H=232.0).

Step 2: 2-(2-methoxypropan-2-yl)-4-(4,4,5,5-tetramethyl-1,3,2-dioxaborolan-2-yl)pyridine—To a stirred solution of 4-bromo-2-(2-methoxypropan-2-yl)pyridine (180 mg, 0.78 mmol) and Bispin (397 mg, 1.56 mmol) in dioxane in a glass tube, was added KOAc (230 mg, 2.37 mmol) and the reaction mass was purged for 15 min with nitrogen. Then PdCl$_2$(dppf) (57 mg, 0.078 mmol) was added and the reaction mixture again purged for 10 min with nitrogen. The reaction tube was sealed and stirred at 80° C. for 16 h. The reaction mass was cooled, filtered through Celite®, and the filtrate concentrated under reduced pressure to obtain crude product. This was diluted with diethyl ether (2×10 mL), then the ether layer was decanted off, dried over anhydrous sodium sulfate and concentrated under reduced pressure to obtain 2-(2-methoxypropan-2-yl)-4-(4,4,5,5-tetramethyl-1,3,2-dioxaborolan-2-yl)pyridine (0.500 g) as a brown gummy liquid.

Step 3: (3-chloro-4-(2'-(2-methoxypropan-2-yl)-[3,4'-bipyridin]-5-yl)phenyl)(4-hydroxypiperidin-1-yl)methanone—To a stirred solution of (4-(5-bromopyridin-3-yl)-3-chlorophenyl)(4-hydroxypiperidin-1-yl)methanone (200 mg, 0.505 mmol) and the product of Step 2 above (181 mg, 0.65 mmol) in dioxane:water (5 mL:1 mL) in a glass tube, was added K$_2$CO$_3$ (174 mg, 1.263 mmol) at room temperature under a nitrogen atmosphere. The reaction mass was purged for 15 minutes with nitrogen and then palladium tetrakis (58 mg, 0.050 mmol) was added and the reaction mixture was again purged for 10 minutes with nitrogen. The reaction tube was sealed and stirred at 80° C. for 16 h. After completion, the residue was diluted with water (10 mL) and the product extracted into EtOAc (3×15 mL). The combined extracts were dried over anhydrous sodium sulfate and concentrated under reduced pressure to obtain crude product which was purified by Prep.HPLC to afford (3-chloro-4-(2'-(2-methoxypropan-2-yl)-[3,4'-bipyridin]-5-yl)phenyl)(4-hydroxypiperidin-1-yl)methanone (35 mg, 10%) as a white solid. 1H NMR (400 MHz, DMSO: δ (ppm): 400 MHz, DMSO-d6: δ 9.06 (d, J=2.00 Hz, 1H), 8.78 (d, J=2.40 Hz, 1H), 8.65 (dd, J=0.40, 5.00 Hz, 1H), 8.34 (t, J=2.00 Hz, 1H), 7.90 (d, J=0.80 Hz, 1H), 7.75 (d, J=1.60 Hz, 1H), 7.68 (d, J=8.00 Hz, 1H), 7.65 (d, J=1.20 Hz, 1H), 7.49 (dd, J=1.60, 8.00 Hz, 1H), 4.81 (d, J=3.6 Hz, 1H), 4.06-3.96 (m, 1H), 3.77-3.74 (m, 1H), 3.61-3.59 (m, 1H), 3.32-3.22 (br, 2H), 3.11 (s, 3H), 1.80-1.75 (br, 2H), 1.52 (s, 6H), 1.40-1.36 (br, 2H); LCMS: 97.99% (466.2 [M+H].

Example 51: (4-(7-(2-(tert-butyl)pyridin-4-yl)isoquinolin-5-yl)-3-chlorophenyl)(4-hydroxypiperidin-1-yl)methanone (Compound Z-828) and (4-(5-(2-(tert-butyl)pyridin-4-yl)isoquinolin-7-yl)-3-chlorophenyl)(4-hydroxypiperidin-1-yl)methanone (Compound Z-829)

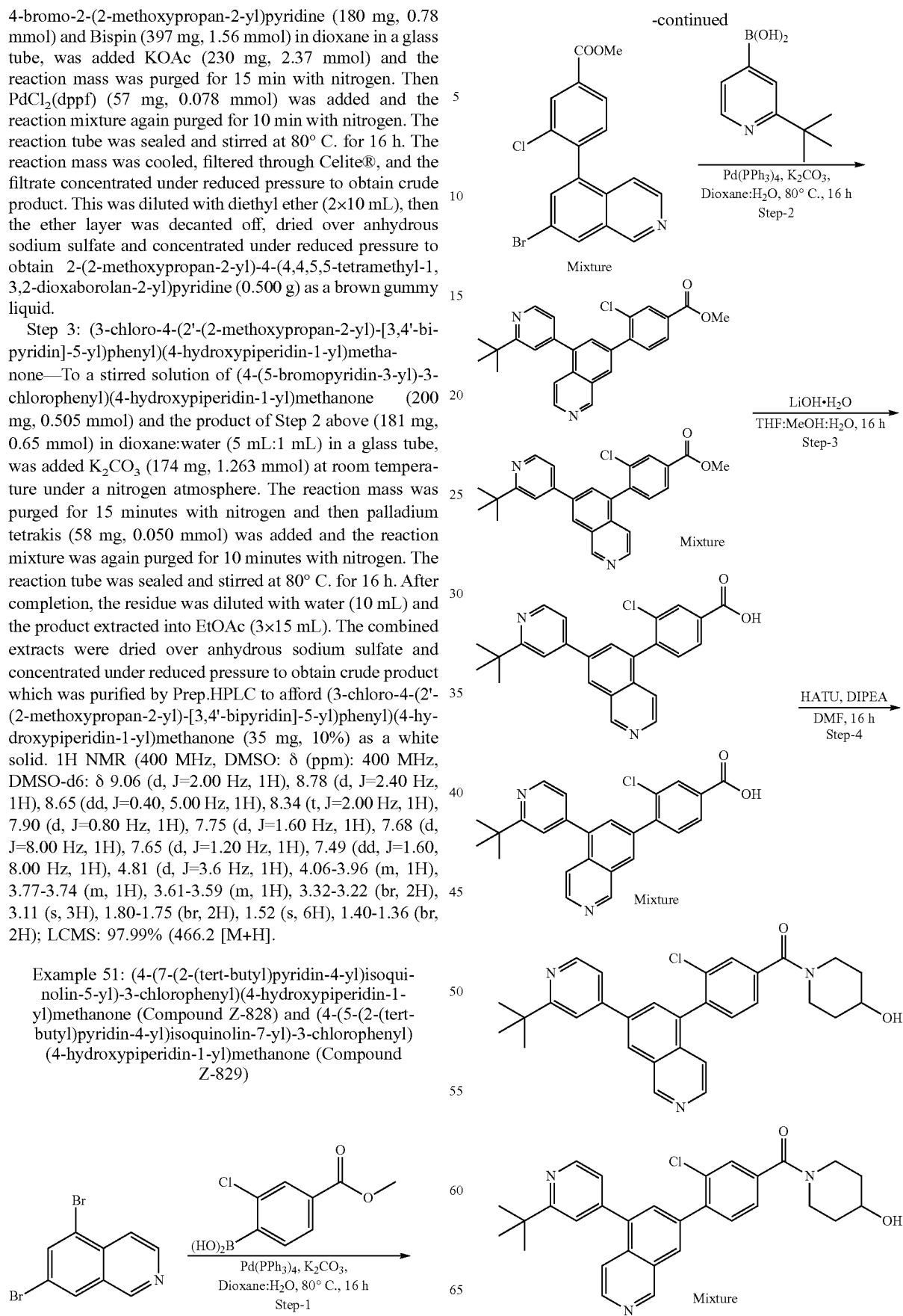

Step 1: A stirred solution of 5,7-dibromoisoquinoline (500 mg, 1.724 mmol), (2-chloro-4-(methoxycarbonyl)phenyl) boronic acid (336 mg, 1.568 mmol), potassium carbonate (201 mg, 4.356 mmol) in water (1 mL) and 1,4-dioxane (10 mL) in a 15 mL glass seal tube was purged with nitrogen gas for 30 minutes. After adding palladium tetrakis (201 mg, 0.174 mmol) it was again purged with nitrogen gas for 30 minutes and then heated to 80° C. for 16 h. The reaction, mixture was cooled to 25° C.-30° C., filtered through a Celite® bed and washed with ethyl acetate (50 mL). The combined organic layers were concentrated under reduced pressure to afford crude product which was purified by column chromatography on neutral alumina to afford a mixture of regioisomers (900 mg) as an off-white solid which was used in the next reaction.

Step 2: A stirred solution of the product of Step 1 (650 mg, 1.725 mmol), (2-(tert-butyl)pyridin-4-yl)boronic acid (492 mg, 2.07 mmol) and potassium carbonate (596 mg, 4.314 mmol) in water (1 mL) and 1,4-dioxane (4 mL) in a 15 mL glass seal tube was purged with nitrogen gas for 30 minutes. After adding palladium tetrakis (199 mg, 0.172 mmol) it was again purged with nitrogen gas for 30 minutes and then heated to 80° C. for 16 h. The mixture was cooled to 25° C.-30° C., filtered through a Celite® bed and washed with ethyl acetate (15 mL). The combined organic layers were concentrated under reduced pressure to afford crude which was purified by column chromatography on neutral alumina to give product (680 mg) as a mixture of regioisomers (680 mg) as a pale yellow gum.

Step 3: The product from Step 2 was dissolved in methanol:THF:water (3:2:1) (10 mL), then LiOH.H$_2$O (199 mg, 4.744 mmol) was added and the mixture was stirred at room temperature for 2 h. After completion of the reaction, the mixture was concentrated under reduced pressure and residue dissolved in water (20 mL) and washed with ethyl acetate (2×20 mL) to remove impurities. Water layer was acidified with citric acid until pH~5 and extracted with ethyl acetate (2×25 mL). The combined ethyl acetate layers were dried over sodium sulfate and concentrated under reduced pressure to afford the product as a mixture of regioisomers (400 mg) as an off white solid.

Step 4: The product from Step 3 was dissolved in in DMF (10 mL), then DIPEA (496 mg, 3.837 mmol) and HATU (1094 mg, 2.877 mmol) was added and the mixture was stirred for 15 min at room temperature under nitrogen. Then 4-hydroxypiperidine (146 mg, 1.439 mmol) was added under nitrogen. The mixture was stirred for 16 h at room temperature. After completion of the reaction, the mixture was diluted with water (100 mL) and the product was extracted into EtOAc (2×30 mL). The combined EtOAc layers were washed with water (50 mL), dried over sodium sulfate and concentrated under reduced pressure to afford crude product which was purified by prep. HPLC to give the product (240 mg) as a mixture of regioisomers as an off white solid. This mixture of regioisomers was separated through SFC. The first eluting peak gave (4-(7-(2-(tert-butyl)pyridin-4-yl)isoquinolin-5-yl)-3-chlorophenyl)(4-hydroxypiperidin-1-yl)methanone (30 mg) as an off white solid as determined by appropriate NOE $^1$H NMR experiments. $^1$H NMR (400 MHz, DMSO): δ 9.53-9.53 (s, 1H), 8.74 (m, 1H), 8.65-8.64 (dd, J=4.8 Hz, J=5.2 Hz, 1H), 8.53-8.52 (d, J=6.0 Hz, 1H), 8.21-8.20 (d, J=1.6 Hz, 1H), 7.92 (s, 1H), 7.74-7.72 (dd, J=5.2 Hz, J=5.2 Hz, 1H), 7.69-7.69 (d, J=1.6 Hz, 1H), 7.62-7.60 (d, J=8.0 Hz, 1H), 7.54-7.52 (dd, J=7.6 Hz, J=7.6 Hz, 1H), 7.32-7.30 (d, J=6.0 Hz, 1H), 4.83-4.82 (d, J=4.0 Hz, 1H), 4.04 (bs, 1H), 3.81-3.76 (m, 1H), 3.64 (bs, 1H), 3.25-3.24 (m, 2H), 1.81 (bs, 2H), 1.49-1.42 (bs, 2H), 1.40 (s, 9H) LCMS: 99.48% (m/z=500.52 [M+H]).

The second eluting peak gave (4-(5-(2-(tert-butyl)pyridin-4-yl)isoquinolin-7-yl)-3-chlorophenyl)(4-hydroxypiperidin-1-yl)methanone (87 mg) as an off white solid as determined by appropriate NOE $^1$H NMR experiments. $^1$H NMR (400 MHz, DMSO): δ 9.50 (s, 1H), 8.70-8.69 (dd, J=4.8 Hz, J=5.2 Hz, 1H), 8.60-8.58 (d, J=6.0 Hz, 1H), 8.37 (s, 1H), 7.93-7.92 (d, J=2.0 Hz, 1H), 7.74-7.71 (m, 2H), 7.65-7.65 (d, J=1.6 Hz, 1H), 7.61-7.61 (s, 1H), 7.51-7.49 (dd, J=7.6 Hz, J=7.6 Hz, 1H), 7.46-7.44 (dd, J=4.8 Hz, J=4.8 Hz, 1H), 4.82-4.81 (d, J=4.0 Hz, 1H), 4.01 (bs, 1H), 3.79-3.74 (m, 1H), 3.54-3.50 (bs, 1H), 3.20 (bs, 2H), 1.80

Example 52: Effect of Compounds on Gene Expression and In Vitro ADME Properties

Gene Expression: The effect of selected compounds described herein on the gene expression of HepG2 cells was evaluated. HepG2 cells (P2) were seeded in 24 well plate (80,000 cells/well) for RNA extraction and in a 96 well plate (10,000 cells/well) for Cell Titer Glow (CTG). The media used was DMEM and contained 10% FBS. Each compound was evaluated at 500 Mm for 48 hours. Two biological replicates per experimental group were evaluated for RNA. For gene analysis, RNA was harvested with RNEasy kit and 20-100 ng used to synthesize cDNA with random primers. Quantitative PCR was performed on 1 pg to 100 ng cDNA for the following genes: ACACA, ACLY, FASN, LSS, PNPLA3. Gene expression levels were normalized with housekeeping gene, β-Actin, and relative expression levels determined using ΔΔCT method comparing treated to mock or vehicle treated cells as a baseline. "Total" gene expression refers to the average of the values of the 5 genes listed above. The results from this evaluation are presented in Table 3.

The ADME properties of kinetic solubility, half-life in human liver microsomes, and half-life in mouse liver microsomes for selected compounds were also evaluated. The results are presented in Table 3.

Kinetic Solubility Procedure: A 10 mM stock solution of a compound was prepared in DMSO, then 4 µL of the stock was added to a deep well plate containing 396 µL of pH 7.4 buffer. The sample plate was vortexed at 800 rpm for 24 h on thermomixer at room temperature. The plate was sealed well during the incubation process. The DMSO content in the sample was 1.0%. The concentration of the evaluated compound in the final incubation was 100 µM. At the end of the incubation period, the sample plate was centrifuged at 4000 rpm for 10 min and analyzed in LC-UV against a calibration curve (CC). Values <10 µg/mL=Low; 10 to 60 µg/mL=Medium; >60 µg/mL=High.

Half-life Human Microsomes: Compounds were evaluated for stability in human liver microsomes. A 10 mM stock solution of the compound being evaluated was prepared in DMSO and diluted with water:acetonitrile (1:1) to a concentration of 1 mM. A working concentration of 100 µM was prepared by further dilution with water:acetonitrile (1:1). To make the preincubation mixture, 2.5 µL of the diluted compound was combined with 75 µL of human liver microsomes at 3.33 mg/mL, and 85 µL of 100 mM potassium phosphate buffer, and this mixture was pre-incubated for 10 min at 37° C. To make the 60 minute mixture without cofactor, 32.5 µL of the preincubation mixture was combined with 17.5 µL of 100 mM potassium phosphate buffer and incubated for 60 min at 37° C. To make the 0 min sample with cofactor (NADPH), 16.25 µL of the preincubation mixture was combined with 200 µL of acetonitrile containing internal standard and 8.75 µL of cofactor (NADPH). To make the incubation mixture, 62 µL of cofactor (2.85 mM) was combined with the remaining incubation mixture, and incubated for 60 min at 37° C. To prepare the sample mixture to be evaluated, 25 µL incubation mixture was combined with 200 µL of acetonitrile containing internal standard and vortexed for 5 min at 1200 rpm, then centrifuged for 10 min at 4000 rpm. The supernatant was diluted 2 fold with water and injected on LC-MS/MS. The sample mixture was evaluated by LC-MS/MS using 10 mM ammonium acetate with 0.1% FA as the aqueous mobile phase, and methanol as the organic mobile phase.

Half-life Mouse Microsomes: Compounds were evaluated in mouse liver microsomes following a similar procedure as described above for human liver microsomes. A similar procedure could be used to evaluate compounds in rat liver microsomes.

TABLE 3

Entries A-F are effect of compounds on gene expression of HepG2 cells.

| Molecule Name | A | B | C | D | E | F | G | H | I |
|---|---|---|---|---|---|---|---|---|---|
| Z-866 | ++ | ++ | ++ | ++ | ++ | ++ | 126 | 82.6 | MEDIUM |
| Z-865 | + | + | + | + | + | + | | | |
| Z-856 | + | + | + | + | + | + | | | |
| Z-855 | ++ | ++ | ++ | ++ | +++ | ++ | 9.52 | 39.2 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-854 | + | + | + | + | + | + | | | |
| Z-848 | + | + | + | + | + | + | | | |
| Z-840 | + | + | + | ++ | + | + | | | |
| Z-834 | + | + | + | + | + | + | | | |

TABLE 3-continued

Entries A-F are effect of compounds on gene expression of HepG2 cells.

| Molecule Name | A | B | C | D | E | F | G | H | I |
| --- | --- | --- | --- | --- | --- | --- | --- | --- | --- |
| Z-832 | + | + | + | + | + | + | | | |
| Z-831 | + | + | + | + | + | + | | | |
| Z-830 | + | + | + | + | + | + | | | |
| Z-827 | ++ | ++ | ++ | ++ | ++ | ++ | | | |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-826 | ++ | ++ | ++ | ++ | +++ | ++ | | | |
| Z-824 | + | + | + | + | + | + | | | |
| Z-823 | + | + | + | + | + | + | | | |
| Z-818 | + | + | + | + | + | + | 2.62 | 1860 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-817 | ++ | ++ | ++ | + | +++ | ++ | 13.9 | 213 | MEDIUM |
| Z-816 | + | + | + | + | + | + | | | |
| Z-814 | ++ | ++ | ++ | +++ | +++ | ++ | 1.69 | 177 | MEDIUM |
| Z-813 | + | + | + | + | + | + | | | |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-812 | ++ | ++ | ++ | +++ | +++ | ++ | 27.3 | 178 | MEDIUM |
| Z-811 | + | + | + | + | + | + | | | |
| Z-808 | ++ | ++ | ++ | +++ | +++ | ++ | | | |
| Z-807 | ++ | ++ | ++ | +++ | +++ | ++ | 11.3 | 25.5 | LOW |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-804 | + | + | + | + | + | + | | | |
| Z-803 | ++ | ++ | +++ | +++ | +++ | ++ | 19.8 | 59.6 | LOW |
| Z-833 | + | + | + | + | + | + | 2.98 | 9.75 | MEDIUM |
| Z-829 | + | + | + | + | + | + | 11.4 | 33.8 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-828 | + | + | + | + | + | + | 119 | 108 | MEDIUM |
| Z-815 | + | + | + | + | + | + | | | |
| Z-806 | + | ++ | ++ | ++ | ++ | ++ | | | |
| Z-805 | + | + | + | + | + | + | 1.78 | 1090 | LOW |
| Z-799 | ++ | + | + | + | + | + | | | |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-798 | ++ | + | ++ | + | + | + | | | |
| Z-797 | + | + | + | + | + | + | | | |
| Z-796 | ++ | ++ | ++ | ++ | + | ++ | 541 | 2920 | MEDIUM |
| Z-795 | ++ | + | + | + | + | + | 9.74 | 101 | MEDIUM |
| Z-794 | ++ | + | + | + | + | + | 19 | 10.2 | LOW |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-793 | + | + | + | + | + | + | 2.07 | 19.3 | LOW |
| Z-790 | ++ | ++ | ++ | ++ | ++ | ++ | 3.21 | 19.5 | MEDIUM |
| Z-789 | ++ | + | + | + | + | + | 20.7 | 13.6 | LOW |
| Z-788 | ++ | + | + | + | + | + | 16.1 | 119 | LOW |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-787 | + | + | + | + | ++ | + | 74.6 | 13.6 | LOW |
| Z-786 | + | + | + | + | ++ | + | 9.79 | 27.4 | MEDIUM |
| Z-785 | + | + | + | + | + | + | 31.3 | 120 | LOW |
| Z-784 | ++ | + | + | ++ | +++ | ++ | 5.81 | 11.4 | MEDIUM |
| Z-782 | + | + | + | + | + | + | | | |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-781 | + | + | + | + | + | + | | | |
| Z-780 | ++ | ++ | ++ | ++ | +++ | ++ | 13 | 30.3 | MEDIUM |
| Z-776 | ++ | ++ | ++ | ++ | ++ | ++ | 53.2 | 14.4 | MEDIUM |
| Z-775 | ++ | ++ | ++ | ++ | +++ | ++ | 13.5 | 19.2 | LOW |
| Z-774 | ++ | ++ | ++ | ++ | +++ | ++ | 69.9 | 222 | LOW |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-773 | ++ | ++ | + | + | + | ++ | 16.1 | 38.5 | MEDIUM |
| Z-772 | + | + | + | + | + | + | 7.8 | 41.7 | MEDIUM |
| Z-770 | ++ | ++ | +++ | +++ | +++ | +++ | 2.02 | 8.98 | MEDIUM |
| Z-757 | + | + | + | ++ | ++ | + | 20.3 | 68.2 | MEDIUM |
| Z-744 | ++ | ++ | ++ | +++ | +++ | ++ | 46.5 | 89.9 | LOW |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| Z-725 | ++ | ++ | ++ | +++ | +++ | ++ | 61.2 | 80.1 | MEDIUM |
| X-9001 | | | | | | | 20.5 | 68.3 | LOW |
| X-9000 | | | | | | | 9.94 | 16.4 | LOW |
| X-8999 | | | | | | | 7.28 | 12.4 | MEDIUM |
| X-8998 | | | | | | | 16.2 | 66.7 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8997 | | | | | | | 39.2 | 87.2 | MEDIUM |
| X-8996 | | | | | | | 21.3 | 42.4 | MEDIUM |
| X-8995 | | | | | | | 27.7 | 120 | MEDIUM |
| X-8994 | | | | | | | 37.4 | 104 | LOW |
| X-8993 | | | | | | | 120 | 120 | LOW |

TABLE 3-continued

| Entries A-F are effect of compounds on gene expression of HepG2 cells. | | | | | | | | | |
|---|---|---|---|---|---|---|---|---|---|
| Molecule Name | A | B | C | D | E | F | G | H | I |
| X-8988 | + | + | + | + | + | + | 116 | 120 | LOW |
| X-8985 | ++ | ++ | ++ | ++ | +++ | ++ | 55.9 | 97.9 | LOW |
| X-8984 | ++ | ++ | ++ | +++ | +++ | ++ | 41.3 | 77.5 | MEDIUM |
| X-8983 | ++ | ++ | ++ | + | +++ | ++ | 11.2 | 1.94 | MEDIUM |
| X-8982 | ++ | ++ | ++ | +++ | +++ | ++ | 14 | 64.3 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8981 | ++ | ++ | ++ | +++ | +++ | ++ | 16.8 | 27.4 | MEDIUM |
| X-8978 (Trans) | ++ | ++ | ++ | +++ | +++ | ++ | 120 | 98.5 | MEDIUM |
| X-8977 | ++ | ++ | ++ | +++ | +++ | ++ | 6.33 | 47.8 | MEDIUM |
| X-8976 | ++ | ++ | +++ | +++ | +++ | +++ | 43.7 | 32.5 | MEDIUM |
| X-8974 | + | ++ | ++ | ++ | ++ | ++ | 76.7 | 120 | MEDIUM |

TABLE 3-continued

| Entries A-F are effect of compounds on gene expression of HepG2 cells. | | | | | | | | | |
|---|---|---|---|---|---|---|---|---|---|
| Molecule Name | A | B | C | D | E | F | G | H | I |
| X-8972 | + | + | + | + | + | + | 9.51 | 40.4 | MEDIUM |
| X-8970 | ++ | ++ | ++ | +++ | +++ | ++ | 32.3 | 54.4 | MEDIUM |
| X-8968 | ++ | ++ | ++ | +++ | +++ | ++ | 28.1 | 88.6 | MEDIUM |
| X-8960 | ++ | ++ | ++ | +++ | +++ | ++ | 12.2 | 21.7 | MEDIUM |
| X-8959 | ++ | ++ | ++ | +++ | +++ | ++ | 59 | 38.3 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8958 | + | ++ | + | ++ | ++ | ++ | 7.35 | 12.4 | MEDIUM |
| X-8957 | ++ | ++ | ++ | +++ | +++ | ++ | 112 | 86.7 | LOW |
| X-8956 | + | ++ | ++ | ++ | ++ | ++ | 120 | 81.1 | LOW |
| X-8955 | ++ | ++ | +++ | +++ | +++ | ++ | 63.6 | 105 | LOW |
| X-8954 | + | ++ | + | + | ++ | + | 1.79 | 120 | MEDIUM |

TABLE 3-continued

Entries A-F are effect of compounds on gene expression of HepG2 cells.

| Molecule Name | A | B | C | D | E | F | G | H | I |
| --- | --- | --- | --- | --- | --- | --- | --- | --- | --- |
| X-8953 | ++ | ++ | ++ | +++ | +++ | ++ | 10.1 | 32 | MEDIUM |
| X-8952 | ++ | ++ | ++ | +++ | +++ | ++ | 5.52 | 28.6 | MEDIUM |
| X-8951 | ++ | ++ | ++ | ++ | ++ | ++ | 12.9 | 28 | MEDIUM |
| X-8950 | ++ | ++ | ++ | +++ | +++ | ++ | 14.4 | 38.7 | MEDIUM |
| X-8949 | ++ | ++ | ++ | ++ | ++ | ++ | 5.01 | 31.5 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8948 | + | ++ | ++ | ++ | ++ | ++ | 6.72 | 39.8 | MEDIUM |
| X-8942 | ++ | ++ | ++ | +++ | +++ | ++ | 11 | 11 | LOW |
| X-8938 | + | + | ++ | +++ | ++ | ++ | 3.17 | 20 | MEDIUM |
| X-8928 | + | + | + | + | + | + | 19.6 | >120 | LOW |
| X-8927 | ++ | ++ | ++ | +++ | +++ | ++ | 36.5 | 54.9 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8924 | + | + | + | + | + | + | 6.03 | >120 | LOW |
| X-8917 (Trans) | + | + | + | + | + | + | 21.8 | 66.5 | MEDIUM |
| X-8915 | + | + | + | ++ | ++ | + | 10 | 63.6 | MEDIUM |
| X-8910 | ++ | ++ | ++ | ++ | +++ | ++ | 6.5 | >120 | LOW |
| X-8908 | ++ | ++ | ++ | +++ | +++ | ++ | 21.5 | 87.8 | LOW |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8906 (Cis) | + | + | + | + | + | + | 21.4 | 56.5 | MEDIUM |
| X-8905 | ++ | ++ | ++ | +++ | +++ | ++ | 15.4 | 21.3 | LOW |
| X-8904 (Trans) | + | + | + | + | + | + | 29.4 | 75.6 | MEDIUM |
| X-8892 | + | + | + | + | + | + | 27.1 | 36.2 | MEDIUM |
| X-8891 | + | ++ | ++ | ++ | ++ | ++ | 1.74 | 26.5 | MEDIUM |

TABLE 3-continued

Entries A-F are effect of compounds on gene expression of HepG2 cells.

| Molecule Name | A | B | C | D | E | F | G | H | I |
|---|---|---|---|---|---|---|---|---|---|
| X-8890 | + | ++ | ++ | ++ | ++ | ++ | 2.01 | 38.3 | MEDIUM |
| X-8937 | + | + | + | + | + | + | 0.54 | 81.3 | MEDIUM |
| X-8886 | | | | | | | | | |
| X-8885 | | | | | | | | | |
| Z-883 | ++ | ++ | ++ | ++ | ++ | ++ | 90.8 | 110 | LOW |

TABLE 3-continued

| Entries A-F are effect of compounds on gene expression of HepG2 cells. | | | | | | | | | |
|---|---|---|---|---|---|---|---|---|---|
| Molecule Name | A | B | C | D | E | F | G | H | I |
| X-8936 | + | ++ | + | ++ | + | + | 16.4 | 206 | LOW |
| X-8935 | + | ++ | ++ | ++ | ++ | ++ | 16.3 | 40.3 | LOW |
| X-8934 | + | + | + | + | + | + | 12.1 | 66.7 | MEDIUM |
| X-8925 | + | + | + | + | + | + | >120 | >120 | LOW |
| X-8919 | + | + | + | + | + | + | 72.1 | 400 | LOW |

A: ACACA; B: ACLY; C: FASN; D: LSS; E: PNPLA3; F: Total. For gene expression at the tested dose, 0-0.309 = +++, 0.31-0.7509 = ++, >0.751 = +. Entry G is the half-life human liver microsomes (min). Entry H is the half-life of mouse liver microsomes (min). Entry I is kinetic solubility class.

Example 53: Additional Gene Expression Testing

The effect of Compound Z-725 on expression of the genes ACACA, ACACB, ACLY, ACSS1, ACSS2, ELOVL6, FASN, HMGCR, LSS, MVK, PNPLA3, SREBP1, SREBP2, SCAP, SCD, and MVD was evaluated, following the procedure described in Example 52. The results are presented in Table 4 below.

TABLE 4

| Effect of Compound Z-725 on gene expression. | | | | | | | |
|---|---|---|---|---|---|---|---|
| Compound Z-725—500 nM, 48 hrs | | | | | | | |
| ACACA | ACACB | ACLY | ACSS1 | ACSS2 | ELOVL6 | FASN | HMGCR |
| 0.43992 | 0.54723 | 0.35049 | 0.28384 | 0.47918 | 0.44324 | 0.29567 | 0.09282 |
| LSS | MVK | PNPLA3 | SREBP1 | SREBP2 | SCAP | SCD | MVD |
| 0.2412 | 0.05926 | 0.09989 | 0.54894 | 0.78602 | 1.31158 | 0.20089 | 0.1984 |

Example 54: Western Blotting of SREBP Processing

Figure 4:
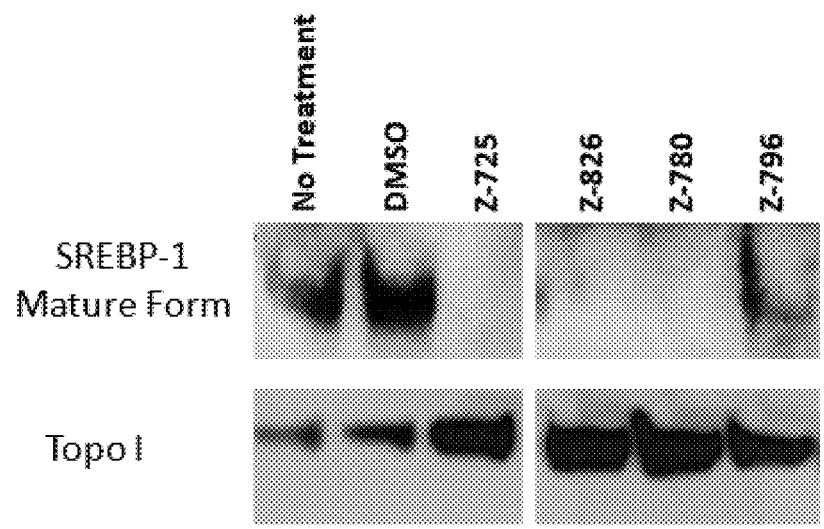
FIG. 4 is an image of Western blot analysis of the effect compounds Z-725, Z-826, Z-780, and Z-796 had on SREBP processing and activation in HepG2 cells. Topoisomerase I was used as a loading control.

The effect of selected compounds on SREBP processing and activation was evaluated in HepG2 cells via Western blotting. Cells were seeded at a density of $8e^6$ in 150 mm plate in DMEM (Dulbecco's modified Eagle's medium) supplemented with 10% (V/V) heat-inactivated FBS (fetal bovine serum), penicillin G (100 units/ml) and gentamycin (0.2 mg/ml). After overnight incubation, they were washed twice in PBS, and then DMEM media with 0% FBS with 500 nM of compound was added to the plate. Cells were incubated at 37° C. After 48 hours, the cells were washed and lysed to obtain cytoplasmic and nuclear extracts for Western blotting to measure SREBP expression along with topoisomerase I as loading control. The Western blot analysis of compounds Z-725, Z-826, Z-780, and Z-796 is shown in FIG. 4.

Example 55: Adipocyte Differentiation and Oil Red-O Staining

The effect of compound Z-725 (Compound 1) on adipocyte differentiation in human pre-adipocyte and 3T3-L1 cells was evaluated.

Human Pre-Adipocyte differentiation: Cells were thawed and seeded at 40,625 cells/cm$^2$ in pre-adipocyte media (ZenBio) as per manufacturer's direction. The cells were allowed to reach confluence for 48 hours, and media switched to Adipocyte Differentiation Media (ZenBio) for 7 days. The media was then switched to Adipocyte Maintenance Media (ZenBio) for additional 7 days. The compound Z-725 was added to the cells for day 1-7 during differentiation (set I), or day 7-14 during maturation (set II). Cells were then stained with oil red-O as described below.

NIH 3T3-L1 cell differentiation: Cells were thawed into Pre-Adipocyte Media (ZenBio) and grown to 80-85% confluence. Cells were seeded 50,000 cells/well into 96-wp in Pre-Adipocyte Media (ZenBio) and allowed to reach confluence for 48-72 hours. They were grown an additional 48 hours after reaching confluence, then the media was changed to Differentiation Media (Zen Bio) and incubated for 72 hours. The media was changed to Adipocyte Differentiation Media (ZenBio) using 150 microliters/well in 96-wp for 72 hours, then media was removed and replaced with 150 microliters of Adipocyte Maintenance Media for an additional 8-14 days, feeding cells every 2-3 days. Compound Z-725 was added to the cells for day 3-6 during differentiation (set I), or day 7-14 during maturation (set II). Cells were then stained with oil red-O as described below.

Figure 2:
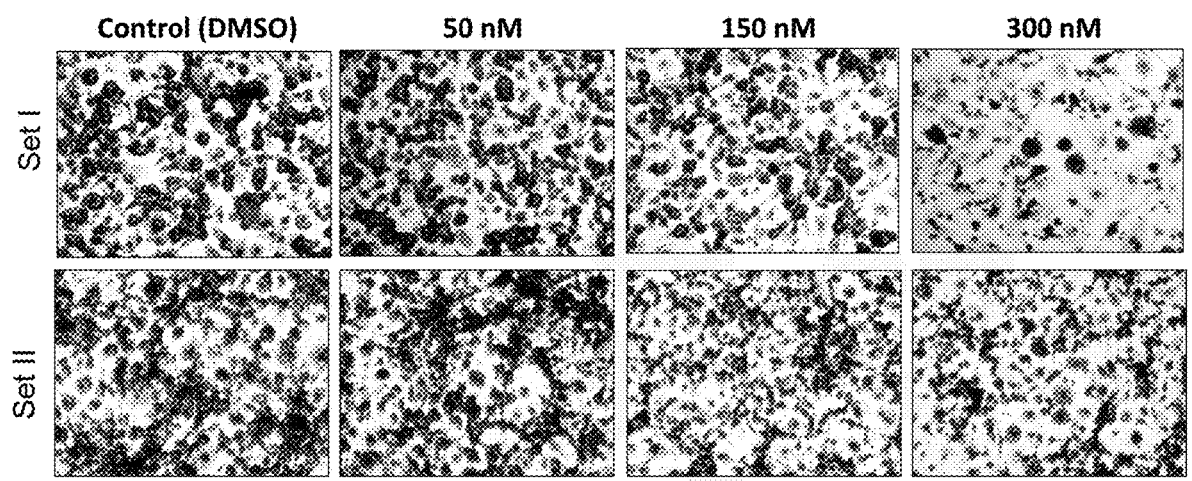
FIG. 2 is an image of differentiated 3T3 L1 cells stained with oil red-O, after being in the presence of compound Z-725 (also known as Compound 4).
Figure 3:
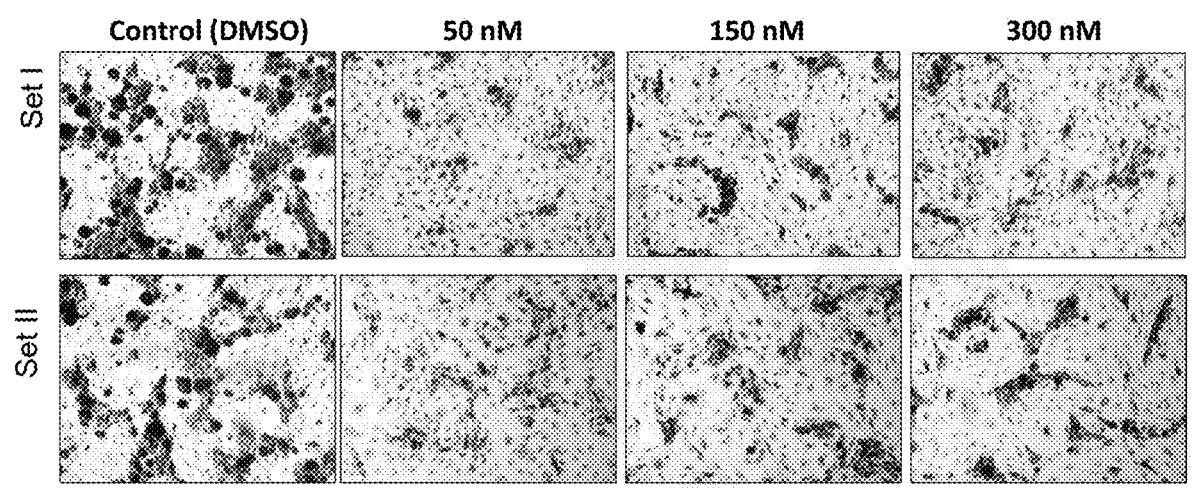
FIG. 3 is an image of differentiated human pre-adipocyte cells stained with oil red-O, after being in the presence of compound Z-725.

Oil Red-O staining: After maturation, the cells were washed, then fixed in 10% Formalin for 30-60 minutes. The formalin was removed, the cells were washed in water twice, and then the cells were incubated in 60% isopropanol for 5 minutes. The isopropanol was removed and Oil Red-O solution added for 20 minutes with gentle rotation of plate. The stain was removed, the cells washed twice with water, and Hematoxylin added for 1 minute. The cells were washed twice with water and air dried, then images were acquired. FIG. 2 depicts images taken of the 3T3-L1 cells, and FIG. 3 depicts the images taken of human pre-adipocyte cells.

Example 56: Log D of Compounds

The Log D of selected compounds was evaluated by octanol/aqueous buffer partitioning. 500 μL of organic phase (1-octanol) was added to each well of a 2 mL deep well plate, followed by 500 μL of buffer and 15 μL of test compound in DMSO (0.15 mM). The plate was vortexed for 10 seconds and incubated at room temperature for 1 hr on a plate shaker at 200 rpm. After incubation, the samples were allowed to equilibrate for 20 min and then centrifuged at 4000 rpm for 30 min for complete phase separation. The distribution of test compound in buffer and octanol phase was analyzed by HPLC-UV. Log D=Log (Area of Octanol/Area of Buffer). The results are presented in Table 5 below.

TABLE 5

| Log D pH 7.4 Values for select compounds. | |
|---|---|
| Compound | LogD |
| Z-725 | 3.56 |
| Z-744 | 4.12 |
| Z-774 | 4.12 |
| Z-780 | 3.76 |
| Z-796 | 2.08 |
| Z-803 | 3.84 |
| Z-806 | 1.98 |
| Z-817 | 3.36 |

Example 57: Evaluation of In Vivo Pharmacokinetic Properties of Compounds

The in vivo pharmacokinetic properties of compounds by both intravenous and oral administration were evaluated in male Sprague Dawley rats or C57BL/6J mice.

Animals were housed in cages with clean bedding. Certified rodent diet was provided. Water was available ad libitum. Environmental controls for the animal room were set to maintain a temperature of 22° C. to 25° C., humidity of 40-70% RH, and a 12-hour light/12-hour dark cycle. Normal healthy animals certified by the attending veterinarian were selected and acclimatized for minimum three days prior to initiation of study.

Surgical Procedure for Jugular Vein Cannulation of Rats: Rats were anaesthetized with a single dose of ketamine 50 mg/kg i.p.+xylazine 6 mg/kg i.p. The right jugular vein was exposed, a loose ligature was placed caudally, and the cranial end of vein was ligated. A small incision was made between the ligatures into which the catheter (polyethylene 50 tubing of internal diameter 0.58 mm and outer diameter 0.96 mm) was inserted. The catheter was secured in place by tying the loose ligature around the catheterized vessel. A small incision was made in the scapular region to serve as the exit site of the catheter. The catheter was subcutaneously tunneled and exteriorized through scapular incision. A stay suture was placed in the scapular area. Patency was tested, and catheter was filled with a locking solution (heparinized saline) and sealed with a stainless steel plug. The incision was then sutured with sterile suturing material. Anti-septic solution was applied to the sutured site and animal was placed back in the home cage.

To evaluate pharmacokinetic properties of intravenous delivery, male Sprague Dawley rats were administered 2.00 mg compound/kg animal weight through the tail vein. The concentration of the compound in the plasma of the animals was evaluated at 0.083, 0.25, 0.5, 1, 2, 4, 8, 12 and 24 hr by taking blood samples from the cannulated jugular vein. For the C5Bl/6J mice, blood samples were collected through a capillary, guided in retro-orbital plexus.

To evaluate pharmacokinetic properties of oral delivery, rats (male Sprague Dawley rats) or mice (C5Bl/6J) were administered 10 mg compound/kg animal weight by mouth. The concentration of compound in the plasma of the animals was evaluated at 0.25, 0.5, 1, 2, 4, 6, 8, 12 and 24 hr by taking blood samples from the cannulated jugular vein (rats) or through a capillary, guided in retro-orbital plexus (mice).

The results of evaluation in rats are shown in Table 6 below, and the results in mice are shown in Table 7.

TABLE 6

Evaluation of in vivo pharmacokinetic properties in rats by intravenous delivery (IV) and by oral delivery (PO).

| | Intravenous Delivery (IV) | | | | Oral Administration (PO) | | | | |
|---|---|---|---|---|---|---|---|---|---|
| Cmpd. | Dose | T1/2 (h) | AUC0-last | CL | Vd (L/Kg) | Dose | Tmax (h) | T1/2 (h) | AUC0-last | % F |
| Z-866 | 2 | 0.91 | 1072 | 31.7 | 2.54 | 10 | 0.5 | 0.69 | 151 | 2.8 |
| Z-826 | 2 | 3.19 | 3100 | 10.7 | 2.97 | 10 | 1 | 3.05 | 5387 | 35 |
| Z-817 | 2 | 3.11 | 6346 | 5.24 | 1.41 | 10 | 0.33 | 2.56 | 3992 | 13 |
| Z-812 | 2 | 1.87 | 605 | 53.5 | 8.65 | 10 | 0.33 | 1.35 | 18 | 0.65 |
| Z-806 | 2 | 2.03 | 2626 | 12.8 | 2.26 | 10 | 0.33 | 2.5 | 272 | 2.1 |
| Z-803 | 2 | 4.86 | 6162 | 5.2 | 2.18 | 10 | 3.33 | 4.37 | 2585 | 8.3 |
| Z-796 | 2 | 3.08 | 3805 | 8.78 | 2.37 | 10 | 0.667 | 3.22 | 7142 | 38 |
| Z-780 | 2 | 1.14 | 2032 | 16.7 | 1.64 | 10 | 0.75 | 0.92 | 2989 | 29 |
| Z-774 | 2 | 5.92 | 2101 | 15.7 | 7.97 | 10 | 0.333 | 3.74 | 604 | 5.8 |
| Z-744 | 2 | 1.91 | 2538 | 13.1 | 2.16 | 10 | 2 | 2.35 | 1058 | 8.6 |
| Z-725 | 2 | 1.53 | 1107 | 30.1 | 4.02 | 10 | 1.67 | 5.1 | 1307 | 24 |

Dose (both IV and PO): mg/kg. CL (IV): mL/Min/Kg. $AUC_{0\text{-}last}$ (both IV and PO): ng*hour/L. Vd=volume of distribution. CL=clearance. % F=Bioavailability of oral delivery.

TABLE 7

Evaluation of in vivo pharmacokinetic properties in mice by intravenous delivery (IV) and by oral delivery (PO).

| | Intravenous Delivery (IV) | | | | Oral Administration (PO) | | | | |
|---|---|---|---|---|---|---|---|---|---|
| Cmpd. | Dose | T1/2 (h) | AUC0-last | CL | Vd (L/Kg) | Dose | Tmax (h) | T1/2 (h) | AUC0-last | % F |
| Z-826 | 2 | 3.24 | 3928 | 8.45 | 2.37 | 10 | 0.25 | 6.2 | 15000 | 82 |
| Z-812 | 2 | 1.12 | 1149 | 28.6 | 2.78 | 10 | 0.25 | 4.21 | 2995 | 52 |
| Z-806 | 2 | 4.89 | 1541 | 21 | 8.91 | 3 | 0.25 | 3.51 | 1369 | 58 |
| Z-780 | 2 | 2.02 | 913 | 36.3 | 6.33 | 10 | 0.25 | 1.24 | 1508 | 33 |
| Z-774 | 2 | 5.31 | 1777 | 18.5 | 8.51 | 10 | 0.5 | 6.79 | 1381 | 16 |
| Z-725 | 2 | 3.39 | 1900 | 17.5 | 5.13 | 10 | 1 | 4.72 | 5398 | 58 |

Dose (both IV and PO): mg/kg.
CL (IV): mL/min/kg.
AUC0-last (both IV and PO): ng*hour/L.
Vd = volume of distribution.
CL = clearance.
% F = Bioavailability of oral delivery.

Example 58: Evaluation of Compounds on Liver Gene Expression in Mice

The pharmacodynamic properties of selected compounds were evaluated in mice. The animals were housed in cages with clean bedding, and maintained and monitored for good health in accordance with Test Facility SOPs and at the discretion of the laboratory animal veterinarian. Certified rodent diet was provided. Food and water was available ad libitum. Environmental controls for the animal room were set to maintain a temperature of 22° C. to 25° C., humidity of 40-70% RH, and a 12-hour light/2-hour dark cycle. Normal healthy animals certified by the attending veterinarian were selected and acclimatized for minimum three days prior to initiation of study. Animals were identified with body markings.

Aliquots of the compounds being evaluated were weighed and triturated with 0.5% methylcellulose (with the addition of 5% N-methyl pyrrolidone when required to remove clumping, as for Z-806) to an appropriate dose concentration. Vials were labeled with the information about study number, test item, concentration and date of preparation. A description of appearance of formulation was recorded (e.g., color, turbidity, etc.). The composition of formulation vehicle was recorded. An aliquot of each dose solution was taken before the dosing began and after dosing was finished, and stored at approximately −20° C. or below for subsequent analysis. The animals were dosed orally through oral gavage needle, and time of dosing was recorded.

After dosing, the mice were anesthetized using gaseous anesthesia. Blood samples were collected through a capillary, guided in retro-orbital plexus, at 6 h or at 24 h. Approximately 100 uL of blood was collected from each mouse, in pre-labeled tubes. The collected blood was stored on ice prior to centrifugation. Blood samples were then centrifuged within 1 hour of collection to separate plasma. Centrifugation was conducted at 2500×g for 15 minutes at 4° C. The plasma was separated and transferred to pre-labeled micro-centrifuge tubes and promptly frozen at −80±10° C. until bioanalysis. The results from this analysis are provided in Table 8 below.

Liver Collection at 6 h or 24 h: Immediately after blood withdrawal for pharmacokinetic evaluation (at 6 or at 24 h), liver tissue was collected without perfusion. Animals were euthanized using carbon dioxide gas in a $CO_2$ chamber. The whole blood was drained by cutting the both side jugular vein and abdominal aorta. The liver was separated out. All the liver samples were divided in two parts. The first part (200 mg approx.) was snap frozen using liquid nitrogen as soon as possible. These samples were immediately transferred to −80° C. for storage. The remaining part was weighed and used for bioanalysis. The results from this analysis are provided in Table 8 below.

RNA Processing and Gene Expression Analysis: Liver Tissue RNA was harvested with the RNEasy kit and 20-100 ng used to synthesize cDNA with random primers following the manufacturer's protocol. Quantitative PCR was performed on 1 pg to 100 ng cDNA for the following genes: ACACA, ACLY, FASN, LSS, PNPLA3. Gene expression levels were determined using $\Delta\Delta CT$ method comparing treated to vehicle treated samples as a baseline, and fold change calculated. The average value for all 5 genes above was averaged and termed to Total Fold Change The results from this evaluation are presented in Table 8.

TABLE 8

Effect of compounds provided herein on the liver Total Fold Change of gene expression at 6 and 24 hours after oral administration.

| Compound | Dose | Time (0 h) | Total Gene FC Time (6 h) | Total Gene FC Time (24 h) | Plasma ng/mL (6 h) | Plasma ng/mL (24 h) | Liver ng/mg (6 h) | Liver ng/mg 24 h |
|---|---|---|---|---|---|---|---|---|
| Vehicle | N/A | 1.00 | ++ | + | N/A | N/A | N/A | N/A |
| Vehicle | N/A | 1.00 | + | + | N/A | N/A | N/A | N/A |
| Z-725 | 10 mpk | 1.00 | +++ | + | <100 | <100 | 100-1000 | 100-1000 |
| Z-725 | 30 mpk | 1.00 | +++ | + | 100-1000 | <100 | 100-1000 | <100 |
| Z-774 | 30 mpk | 1.00 | ++ | +++ | 100-1000 | 100-1000 | >1000 | >1000 |
| Z-796 | 30 mpk | 1.00 | + | + | 100-1000 | <100 | >1000 | <100 |
| Z-744 | 30 mpk | 1.00 | ++ | + | 100-1000 | 100-1000 | >1000 | >1000 |
| Z-817 | 30 mpk | 1.00 | + | + | <100 | <100 | 100-1000 | <100 |
| Z-826 | 30 mpk | 1.00 | + | ++ | >1000 | 100-1000 | >1000 | >1000 |
| Z-780 | 30 mpk | 1.00 | + | ++ | 100-1000 | <100 | >1000 | >100 |
| Z-806 | 30 mpk | 1.00 | ++ | +++ | >1000 | >1000 | >1000 | >1000 |

Gene Expression at tested noted dosage.
Vehicle = 0.5% Methylcellulose.
Ratings: 0-0.509 = +++, 0.51-0.7509 = ++, >0.751 = +.
N/A = Not Applicable Example 57: (4-(2'-(tert-butyl)-[3,4'-bipyridin]-5-yl)-3-chlorophenyl)(6-hydroxy-3-azabicyclo[3.1.0]hexan-3-yl)methanone (X-8938)

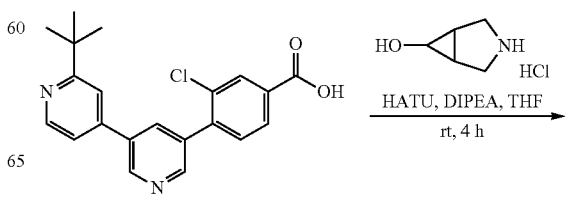

401
-continued

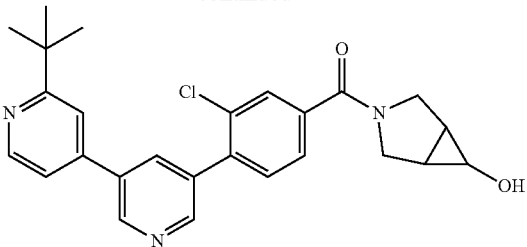

To a solution of 4-(2'-(tert-butyl)-[3,4'-bipyridin]-5-yl)-3-chlorobenzoic acid (100 mg, 0.27 mmol) in THF (10 mL) was added DIPEA (0.25 mL, 1.36 mmol) and HATU (155 mg, 0.41 mmol). The reaction mixture was stirred for 10 minutes, then 3-azabicyclo[3.1.0]hexan-6-ol (56 mg, 0.41 mmol) was added and stirred for 4 h. After completion, the reaction mass was diluted with ethyl acetate and washed with cold water (4×5 mL). Organic layer was separated, dried over anhydrous sodium sulfate and concentrated under reduced pressure to give crude product which was purified by prep HPLC to give (4-(2'-(tert-butyl)-[3,4'-bipyridin]-5-yl)-3-chlorophenyl)(6-hydroxy-3-azabicyclo[3.1.0]hexan-3-yl)methanone as an off white solid (30 mg). $^1$H NMR (400 MHz, DMSO-d6): δ 9.07 (d, J=2.40 Hz, 1H), 8.75 (d, J=2.00 Hz, 1H), 8.63 (d, J=5.20 Hz, 1H), 8.34 (t, J=2.00 Hz, 1H), 7.83 (s, 1H), 7.71 (d, J=1.20 Hz, 1H), 7.66-7.65 (m, 2H), 7.56-7.54 (m, 1H), 5.44 (d, J=1.60 Hz, 1H), 3.84 (d, J=12.00 Hz, 1H), 3.69-3.65 (m, 1H), 3.49-3.45 (m, 1H), 3.42-3.32 (m, 1H), 3.01 (d, J=1.20 Hz, 1H), 1.64 (d, J=3.60 Hz, 2H), 1.38 (s, 9H); LCMS: 99.38% (m/z=448.1 [M+H]).

The following compounds were prepared in a similar fashion:

| Compound | Characterization |
|---|---|
| (4-(2'-(tert-butyl)-[3,4'-bipyridin]-5-yl)-3-chlorophenyl)(3-hydroxy-3-methylpyrrolidin-1-yl)methanone (X-8951) | $^1$H NMR (400 MHz, DMSO-d6): δ 9.01 (d, J = 1.60 Hz, 1H), 8.76 (s, 1H), 8.63 (d, J = 5.20, Hz, 1H), 8.35 (d, J = 2.40 Hz, 1H), 7.83 (s, 1H), 7.75 (d, J = 8.00 Hz, 1H), 7.70-7.58 (m, 3H), 4.87 (d, J = 32.00 Hz, 1H), 3.70-3.45 (m, 3H), 3.26 (d, J = 10.80 Hz, 1H), 1.87-1.81 (m, 2H), 1.38 (s, 9H), 1.31 (d, J = 35.20 Hz, 3H)<br>LCMS: 98.79% (m/z = 450.0 [M + H]). |
| (4-(2'-(tert-butyl)-[3,4'-bipyridin]-5-yl)-3-chlorophenyl)(6-hydroxy-2-azaspiro[3.3]heptan-2-yl)methanone (X-8954) | $^1$H NMR (400 MHz, DMSO-d6): δ 9.07 (d, J = 2.00 Hz, 1H), 8.75 (d, J = 2.00 Hz, 1H), 8.63 (d, J = 5.20 Hz, 1H), 8.34 (s, 1H), 7.82 (s, 2H), 7.72-7.65 (m, 3H), 5.05 (d, J = 6.00 Hz, 1H), 4.33 (d, J = 20.40 Hz, 2H), 3.97-3.96 (m, 3H), 2.50-2.40 (m, 2H), 2.05-1.95 (m, 2H), 1.38 (s, 9H)<br>LCMS: 99.51% (m/z = 462.40 [M + H]) |
| (4-(2'-(tert-butyl)-[3,4'-bipyridin]-5-yl)-3-chlorophenyl)(3-hydroxy-3-methylazetidin-1-yl)methanone (X-8848) | $^1$H NMR (400 MHz, DMSO-d6): δ 9.07 (d, J = 2.00 Hz, 1H), 8.76 (d, J = 2.00 Hz, 1H), 8.63 (d, J = 5.20 Hz, 1H), 8.35 (t, J = 2.40 Hz, 1H), 7.84-7.82 (m, 2H), 7.73-7.65 (m, 3H), 5.72 (s, 1H), 4.23 (d, J = 8.80 Hz, 1H), 4.16 (d, J = 8.40 Hz, 1H), 3.94 (q, J = 10.00 Hz, 2H), 1.42 (s, 3H), 1.38 (s, 9H)<br>LCMS: 99.57% (m/z = 436.38 [M + H]) |

| Compound | Characterization |
|---|---|
| (4-(2'-(tert-butyl)-[3,4'-bipyridin]-5-yl)-3-chlorophenyl)((1R,5S)-8-hydroxy-3-azabicyclo[3.2.1]octan-3-yl)methanone (X-8905) | $^1$H NMR (400 MHz, DMSO-d6): δ 9.07 (d, J = 2.40 Hz, 1H), 8.76 (d, J = 2.40 Hz, 1H), 8.62 (dd, J = 0.40 Hz, 5.2 Hz, 1H), 8.36-8.33 (m, 1H), 7.83 (s, 1H), 7.68-7.62 (m, 3H), 7.47 (dd, J = 1.60 Hz, 7.60 Hz, 1H), 5.20 (d, J = 3.2 Hz, 1H), 4.15-4.05 (m, 1H), 3.90-3.85 (m, 1H), 3.75-3.65 (m, 1H), 3.35-3.25 (m, 1H), 3.15-3.05 (m, 1H), 2.05-1.95 (br s, 1H), 1.85-1.80 (br s, 1H), 1.70-1.60 (m, 2H), 1.55-1.48 (m, 1H), 1.38 (s, 9H), 1.38-1.36 (m, 1H) LCMS: 99.82% (m/z = 476.47 [M + H]). |
| (4-(2'-(tert-butyl)-[3,4'-bipyridin]-5-yl)-3-chlorophenyl)(3-(hydroxymethyl)azetidin-1-yl)methanone (X-8891) | $^1$H NMR (400 MHz, DMSO-d6): δ 9.07 (d, J = 2.00 Hz, 1H), 8.76 (d, J = 2.00 Hz, 1H), 8.63 (dd, J = 0.80 Hz, 5.20 Hz, 1H), 8.35 (t, J = 2.00 Hz, 1H), 7.83 (m, 2H), 7.75-768 (m, 2H), 7.66 (dd, J = 1.6 Hz, 5.20 Hz, 1H), 4.81 (t, J = 5.60 Hz, 1H), 4.39 (dd, J = 8.40 Hz, 1H), 4.10-4.05 (m, 2H), 3.85-3.75 (m, 1H), 3.56 (t, J = 5.60 Hz, 2H), 2.80-2.70 (m, 1H), 1.38 (s, 9H) LCMS: 97.66% (m/z = 436.35 [M + H]) |
| (4-(2'-(tert-butyl)-[3,4'-bipyridin]-5-yl)-3-chlorophenyl)(3-hydroxyazetidin-1-yl)methanone (X-8890) | $^1$H NMR (400 MHz, DMSO-d6): δ 9.07 (d, J = 2.40 Hz, 1H), 8.76 (d, J = 2.00 Hz, 1H), 8.63 (dd, J = 0.80 Hz, 5.20 Hz, 1H), 8.35 (t, J = 2.40 Hz, 1H), 7.83 (s, 2H), 7.73-7.68 (m, 2H), 7.66 (dd, J = 1.60 Hz, 5.20 Hz, 1H), 5.79 (d, J = 5.6 Hz, 1H), 4.60-4.45 (m, 2H), 4.35-4.25 (m, 1H), 4.15-4.05 (m, 1H), 3.85-3.75 (m, 1H), 1.38 (s, 9H) LCMS: 99.54% (m/z = 422.56 [M + H]) |
| (4-(2'-(tert-butyl)-[3,4'-bipyridin]-5-yl)-3-chlorophenyl)(-3,4-dihydroxypiperidin-1-yl)methanone (cis; X-8906) | $^1$H NMR (400 MHz, DMSO-d6): δ 9.07 (d, J = 2.40 Hz, 1H), 8.77 (d, J = 2.00 Hz, 1H), 8.63 (d, J = 1H), 8.36 (t, J = 2.40 Hz, 1H), 7.84 (d, J = 0.80 Hz, 1H), 7.70-7.63 (m, 3H), 7.58-7.47 (m, 1H), 4.85-4.65 (m, 2H), 3.95-3.45 (m, 4H) 3.30-3.15 (m, 2H) 1.80-1.55 (m, 2H), 1.39 (s, 9H) LCMS: 99.41% (m/z = 466.58 [M + H]) |

-continued

| Compound | Characterization |
|---|---|
| 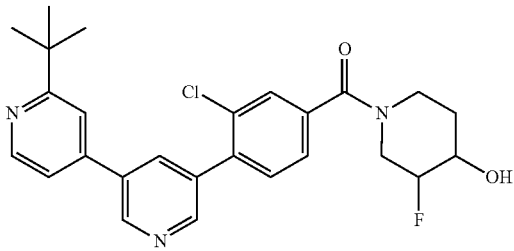<br>(4-(2'-(tert-butyl)-[3,4'-bipyridin]-5-yl)-3-chlorophenyl)(3-fluoro-4-hydroxypiperidin-1-yl)methanone (trans; X-8978) | LCMS: (m/z = 468.0 [M + H]) |

Example 58: Isopropyl (3-chloro-4-(2'-cyclopropyl-[3,4'-bipyridin]-5-yl)phenyl)carbamate (X-8956)

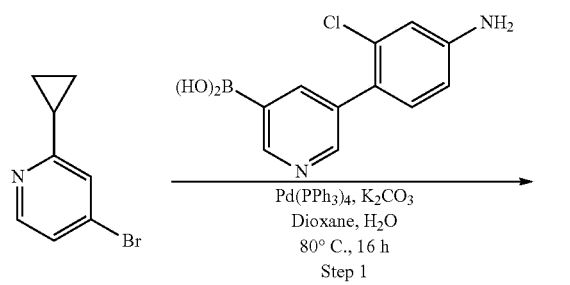

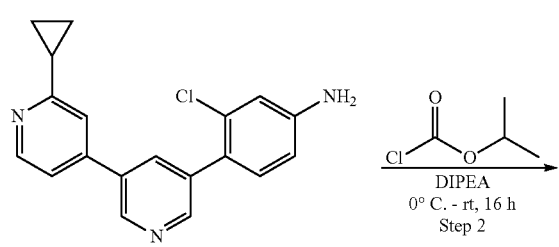

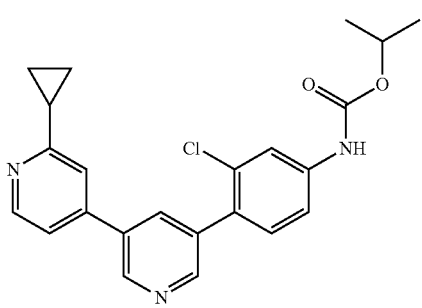

Step 1: 3-chloro-4-(2'-cyclopropyl-[3,4'-bipyridin]-5-yl) aniline. A stirred solution of 4-bromo-2-cyclopropylpyridine (350 mg, 1.76 mmol), (5-(4-amino-2-chlorophenyl)pyridin-3-yl)boronic acid (526 mg, 2.12 mmol) and potassium carbonate (730 mg, 5.30 mmol) in 1,4-dioxane (5.6 mL) and water (1.4 mL) was purged with nitrogen gas for 15 minutes. After adding palladium Pd(PPh$_3$)$_4$ (200 mg, 0.17 mmol), the reaction mass was again purged with nitrogen for 10 min and was heated to 80° C. for 16 h. After completion of the reaction, the solvent was evaporated under reduced pressure and the crude compound was purified by column chromatography (neutral alumina), eluted with 30% EtOAc in pet ether, collected fraction was concentrated under reduced pressure to obtain 3-chloro-4-(2'-cyclopropyl-[3,4'-bipyridin]-5-yl)aniline (0.500 g, 88%) as a gum.

Step 2: isopropyl (3-chloro-4-(2'-cyclopropyl-[3,4'-bipyridin]-5-yl)phenyl)carbamate. To a stirred solution of 3-chloro-4-(2'-cyclopropyl-[3,4'-bipyridin]-5-yl)aniline (200 mg, 0.62 mmol) in pyridine, was added isopropyl carbonochloridate (85 mg, 0.70 mmol) dropwise at 0° C. The reaction mass was slowly allowed to RT and stirred for 24 h. After completion, the reaction was quenched with water (10 mL) and extracted with DCM (3×10 mL). The extracts were combined, dried over anhydrous sodium sulfate and concentrated under reduced pressure. The obtained crude product was purified by column chromatography (neutral alumina), eluted with 5% MeOH in DCM to afford isopropyl (3-chloro-4-(2'-cyclopropyl-[3,4'-bipyridin]-5-yl)phenyl)carbamate as an off white solid. $^1$H NMR (400 MHz, DMSO-d6): δ 10.20 (s, 1H), 9.03 (d, J=2.00 Hz, 1H), 8.72 (d, J=2.00 Hz, 1H), 8.50 (d, J=5.20 Hz, 1H), 8.26 (t, J=2.00 Hz, 1H), 7.76 (d, J=0.80 Hz, 1H), 7.60-7.57 (m, 2H), 7.43 (d, J=2.40 Hz, 1H), 7.33-7.30 (dd, J=2.40 Hz, 8.40 Hz, 1H), 3.12 (s, 3H), 2.22-2.16 (m, 1H), 0.99-0.97 (m, 4H); LCMS: 98.75% (400.26 [M+H]$^+$).

The following compounds were prepared in a similar manner.

| Compound | Characterization |
|---|---|
| 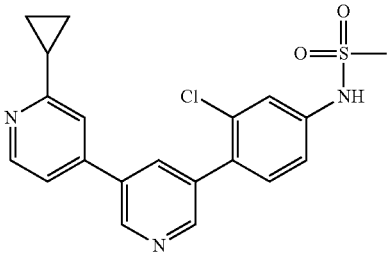<br>N-(3-chloro-4-(2'-cyclopropyl-[3,4'-bipyridin]-5-yl)phenyl)methanesulfonamide (X-8957) | $^1$H NMR (400 MHz, DMSO-d6): δ 10.20 (s, 1H), 9.03 (d, J = 2.00 Hz, 1H), 8.72 (d, J = 2.00 Hz, 1H, 8.50 (d, J = 5.20 Hz, 1H), 8.26 (t, J = 2.00 Hz, 1H), 7.76 (d, J = 0.80 Hz, 1H), 7.60-7.57 (m, 2H), 7.43 (d, J = 2.40 Hz, 1H), 7.33-7.30 (dd, J = 2.40 Hz, 8.40 Hz, 1H), 3.12 (s, 3H), 2.22-2.16 (m, 1H), 0.99-0.97 (m, 4H)<br>LCMS: 98.75% (400.26 [M + H]$^+$) |
| 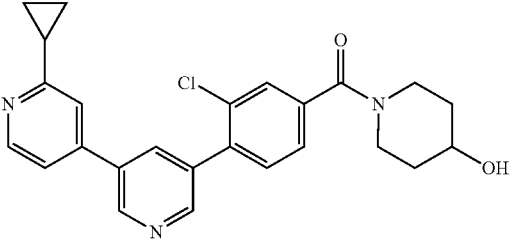<br>(3-chloro-4-(2'-cyclopropyl-[3,4'-bipyridin]-5-yl)phenyl)(4-hydroxypiperidin-1-yl)methanone (X-8927) | LCMS: (434.1 [M + H]$^+$) |
| 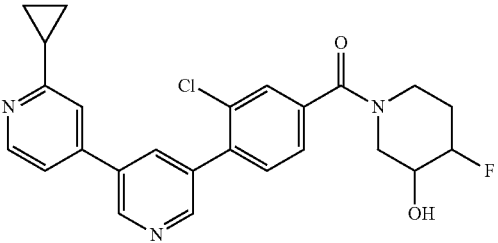<br>(3-chloro-4-(2'-cyclopropyl-[3,4'-bipyridin]-5-yl)phenyl)(4-fluoro-3-hydroxypiperidin-1-yl)methanone (X-9001) | $^1$H NMR (400 MHz, DMSO-d6): δ 9.08 (d, J = 2.40 Hz, 1H), 8.77 (d, J = 2.00 Hz, 1H), 8.50 (d, J = 5.20 Hz, 1H), 8.34 (t, J = 2.00 Hz, 1H), 7.78 (d, J = 0.80 Hz, 1H), 7.71 (s, 1H), 7.68 (d, J = 7.60 Hz, 1H), 7.60-7.59 (m, 1H), 7.58-7.50 (m, 1H), 5.60-5.50 (m, 1H), 4.65-4.45 (m, 1H), 4.20-3.75 (m, 1H), 3.70-3.40 (m, 3H), 3.10-2.95 (m, 1H), 2.75-2.00 (m, 2H), 1.80-1.65 (br s, 1H), 1.03-0.95 (m, 4H)<br>LCMS: 99.64% (452.38 [M + H]$^+$) |
| 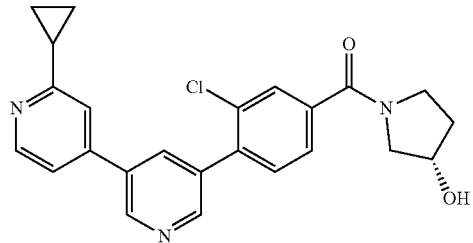<br>(S)-(3-chloro-4-(2'-cyclopropyl-[3,4'-bipyridin]-5-yl)phenyl)(3-hydroxypiperidin-1-yl)methanone (X-8997) | LCMS: (420.34 [M + H]$^+$) |

-continued
| Compound | Characterization |
|---|---|
| 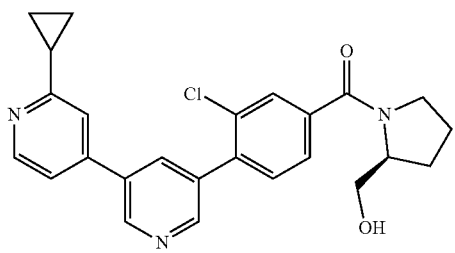<br>(S)-(3-chloro-4-(2'-cyclopropyl-[3,4'-bipyridin]-5-yl)phenyl)(2-(hydroxymethyl)pyrrolidin-1-yl)methanone (X-8998) | LCMS: (434.0 [M + H]$^+$) |
| 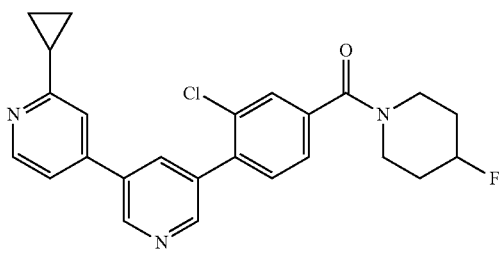<br>(3-chloro-4-(2'-cyclopropyl-[3,4'-bipyridin]-5-yl)phenyl)(4-fluoropiperidin-1-yl)methanone (X-8999) | LCMS: (436.0 [M + H]$^+$) |
| 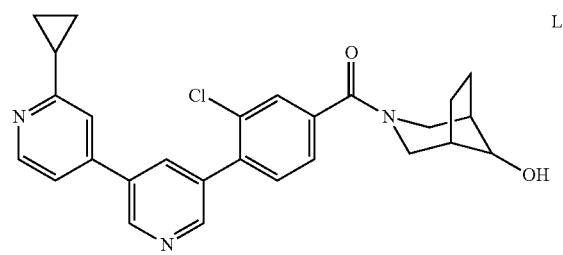<br>(3-chloro-4-(2'-cyclopropyl-[3,4'-bipyridin]-5-yl)phenyl)((1R,5S)-8-hydroxy-3-azabicyclo[3.2.1]octan-3-yl)methanone (X-8996) | LCMS: (460.54 [M + H]$^+$) |

Example 59: N-(3'-(2-(tert-butyl)pyridin-4-yl)-2-chloro-[1,1'-biphenyl]-4-yl)methanesulfonamide (Z-883)

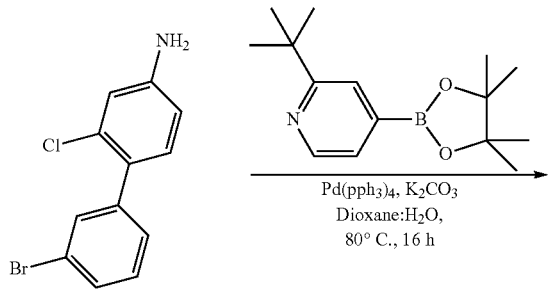

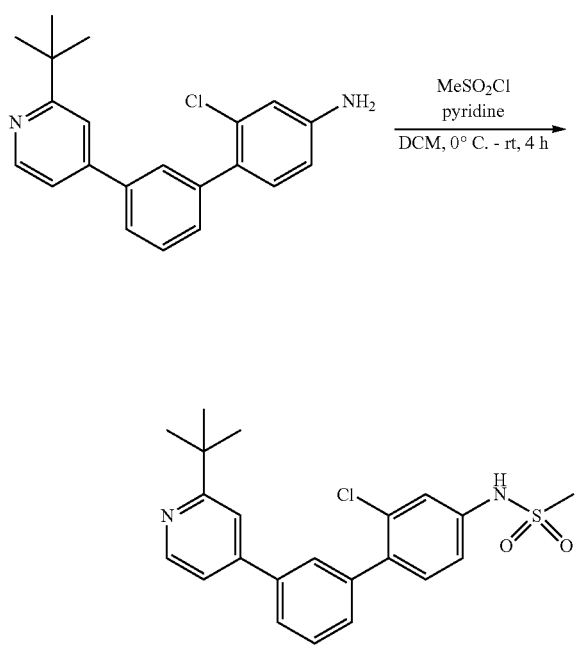

Step 1: 3'-(2-(tert-butyl)pyridin-4-yl)-2-chloro-[1,1'-biphenyl]-4-amine. In a glass tube was taken 3'-bromo-2-chloro-[1,1'-biphenyl]-4-amine (0.36 g, 1.27 mmol) in 1,4-dioxane and water (10 mL). To it was added 2-(tert-butyl)-4-(4,4,5,5-tetramethyl-1,3,2-dioxaborolan-2-yl)pyridine (0.332 g, 1.27 mmol) and $K_2CO_3$ (0.526 g, 3.81 mmol). The reaction mixture was purged for 15 minutes with nitrogen and then added Pd(pph$_3$)$_4$ (147 mg, 0.13 mmol) and purged again for 10 minutes with nitrogen. The reaction was sealed and stirred at 80° C. for 16 h. After completion of the reaction, the reaction mixture was filtered through Celite® bed and the cake was washed with ethyl acetate. Filtrate and washings were combined and concentrated. The residue was dissolved in water (20 mL) and extracted with ethyl acetate (3×30 mL). Organic layer was dried over anhydrous sodium sulfate and concentrated under reduced pressure to obtain crude which was purified by column chromatography to give 3'-(2-(tert-butyl)pyridin-4-yl)-2-chloro-[1,1'-biphenyl]-4-amine as yellow solid.

Step 2: N-(3'-(2-(tert-butyl)pyridin-4-yl)-2-chloro-[1,1'-biphenyl]-4-yl)methanesulfonamide. To 3'-(2-(tert-butyl)pyridin-4-yl)-2-chloro-[1,1'-biphenyl]-4-amine (124 mg, 0.369 mmol) in DCM (10 mL) was added pyridine (0.06 mL, 0.738 mmol) and methanesulfonyl chloride (0.043 mL, 0.55 mmol). The reaction mixture was stirred at rt for 4 h. After completion of the reaction, reaction mixture was diluted with DCM (10 mL) and washed with water (2×10 mL). The organic layer was dried over anhydrous sodium sulfate and concentrated under reduced pressure to obtain crude material which was purified by prep HPLC to afford N-(3'-(2-(tert-butyl)pyridin-4-yl)-2-chloro-[1,1'-biphenyl]-4-yl)methanesulfonamide as a white solid. $^1$H NMR (400 MHz, DMSO-d6: δ 10.12 (s, 1H), 8.58-8.57 (d, J=5.2 Hz, 1H), 7.81-7.78 (m, 2H), 7.69 (s, 1H), 7.62-7.58 (t, J=7.6 Hz, 1H), 7.54-7.49 (m, 3H), 7.38 (m, 1H), 7.29-7.26 (dd, J=8.4 Hz and 2.0 Hz, 1H), 3.09 (s, 3H), 1.37 (s, 9H); LCMS: 99.02% (m/z=415.0) [M+H$^+$].

The following compound was synthesized in a similar manner:

| Compound | Characterization |
| --- | --- |
| N-(3'-(2-tert-butyl)pyridin-4-yl)-2-chloro-[1,1'-biphenyl]-4-yl)-1,1,1-trifluoromethanesulfonamide (Z-884) | $^1$H NMR (400 MHz, DMSO-d6: δ 8.62-8.61 (d, J = 5.60 Hz, 1H), 7.85-7.83 (m, 3H), 7.73-7.65 (br s, 1H), 7.63-7.59 (t, J = 7.6 Hz, 1H), 7.56-7.54 (m, 1H), 7.42-7.40 (d, J = 8.4 Hz, 1H), 7.31 (s, 1H), 7.19-7.16 (dd, J = 8.4 Hz, 1.6 Hz, 1H), 1.40 (s, 9H) LCMS: 99.47% (m/z = 469.33) [M + H$^+$] |

Example 60: (3-chloro-4-(5-(2,3-dihydro-[1,4]dioxino[2,3-b]pyridin-8-yl)pyridin-3-yl)phenyl)(4-hydroxypiperidin-1-yl)methanone (Z-806)

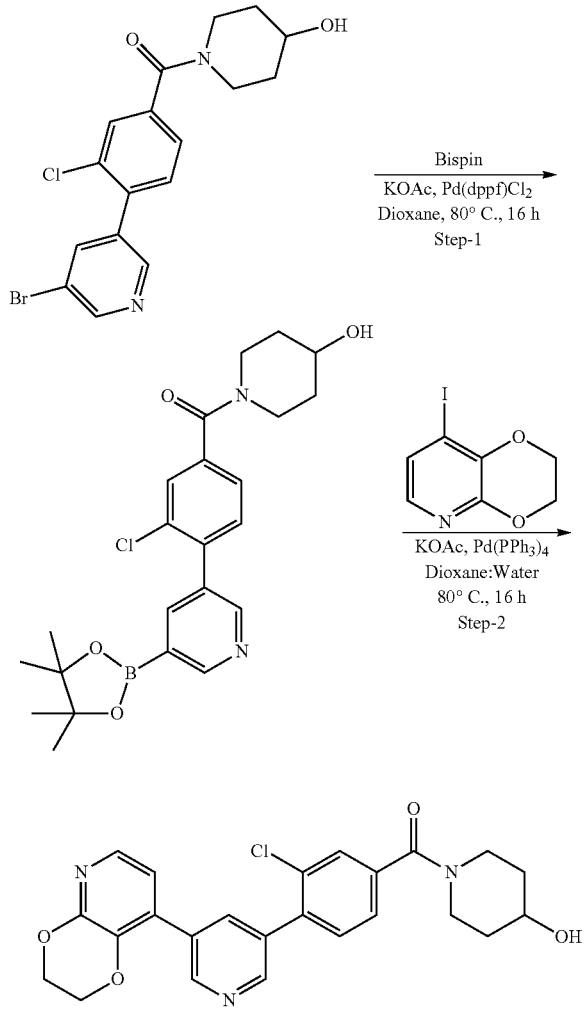

Step 1: (3-chloro-4-(5-(4,4,5,5-tetramethyl-1,3,2-dioxaborolan-2-yl)pyridin-3-yl)phenyl)(4-hydroxypiperidin-1-yl) methanone. To a stirred solution of (4-(5-bromopyridin-3-yl)-3-chlorophenyl)(4-hydroxypiperidin-1-yl)methanone (0.100 g, 0.259 mmol, 1.0 eq) and Bispin (0.128 g, 0.508 mmol, and 2.0 eq) in dioxane (2 mL), in a glass tube was added KOAc (0.062 g, 0.635 mmol, 2.5 eq) and the reaction mass was purged for 15 minutes with nitrogen and then added PdCl$_2$ (dppf) (0.020 g, 0.025 mmol, 0.1 eq) and again purged for 10 minutes with nitrogen. The reaction tube sealed and stirred at 80° C. for 16 h and then filtered through Celite® and concentrated under reduced pressure to obtain a residue which was washed with diethyl ether and n-pentane. The combined organic layers were dried over anhydrous sodium sulfate and concentrated under reduced pressure to obtain (3-chloro-4-(5-(4,4,5,5-tetramethyl-1,3,2-dioxaborolan-2-yl)pyridin-3-yl)phenyl)(4-hydroxypiperidin-1-yl)methanone (0.150 g) as a brown gum.

Step 2: (3-chloro-4-(5-(2,3-dihydro-[1,4]dioxino[2,3-b]pyridin-8-yl)pyridin-3-yl)phenyl)(4-hydroxypiperidin-1-yl) methanone. To a stirred solution of the product from Step 1 (0.100 g, 0.277 mmol, 1.0 eq) and 8-iodo-2,3-dihydro-[1,4]dioxino[2,3-b]pyridine (0.090 g, 0.332 mmol, 1.2 eq) in a glass tube in dioxane:water (3 mL:1 mL), was added K$_2$CO$_3$ (0.095 g, 0.095 mmol, 2.5 eq) at room temperature under nitrogen atmosphere. The reaction mass was purged for 15 min with nitrogen then added palladium tetrakis (0.032 g, 0.027 mmol, 0.1 eq) and again purged for 10 min with nitrogen. The reaction tube was sealed and stirred at 80° C. for 16 h. After completion, the residue was dissolved in water (8 mL) and extracted with EtOAc (3×10 mL). The extracts were combined, dried over anhydrous sodium sulfate and concentrated under reduced pressure to obtain crude product which was purified by preparative. HPLC to give (3-chloro-4-(5-(2,3-dihydro-[1,4]dioxino[2,3-b]pyridin-8-yl)pyridin-3-yl)phenyl)(4-hydroxypiperidin-1-yl)methanone (0.040 g, 32%) as a white solid. $^1$H NMR (400 MHz, DMSO: δ (ppm); δ 8.88 (d, J=2.00 Hz, 1H), 8.71 (d, J=2.00 Hz, 1H), 8.15 (t, J=2.00 Hz, 1H), 7.85 (d, J=4.80 Hz, 1H), 7.64-7.62 (m, 2H), 7.48 (dd, J=1.60, 8.00 Hz, 1H), 7.19 (d, J=5.20 Hz, 1H), 4.81 (d, J=−4.00 Hz, 1H), 4.46-4.45 (m, 2H), 4.31-430 (m, 2H), 3.99 (bs, 1H), 3.75-3.74 (m, 1H), 3.53-3.52 (m, 1H), 3.22-3.22 (m, 2H), 1.78 (bs, 2H), 1.39 (bs, 2H); LCMS: 99.24% (452.41 [M+H]).

Example 61: Preparation of Compounds from 3-chloro-4-(5-(2,3-dihydro-[1,4]dioxino[2,3-b]pyridin-8-yl)pyridin-3-yl)aniline

| Compounds | Characterization |
|---|---|
| Cyclopropyl (3-chloro-4-(5-(2,3-dihydro-[1,4]dioxino[2,3-b]pyridin-8-yl)pyridin-3-yl)phenyl)carbamate (X-9000) | LCMS: (423.29[M + H]) Mp 219-223° C. |

-continued

| Compounds | Characterization |
|---|---|
| N-(3-chloro-4-(5-(2,3-dihydro-[1,4]dioxino[2,3-b]pyridin-8-yl)pyridin-3-yl)phenyl)methanesulfonamide (X-8994) | LCMS: (418.24[M + H])<br>Mp 216-220° C. |
| (X-9003) | LCMS: (459.25[M + H])<br>Mp 192-196° C. |

Example 62: Isopropyl (3-chloro-4-(2'-(1-hydroxy-2-methylpropan-2-yl)-[3,4'-bipyridin]-5-yl)phenyl)carbamate (X-8908)

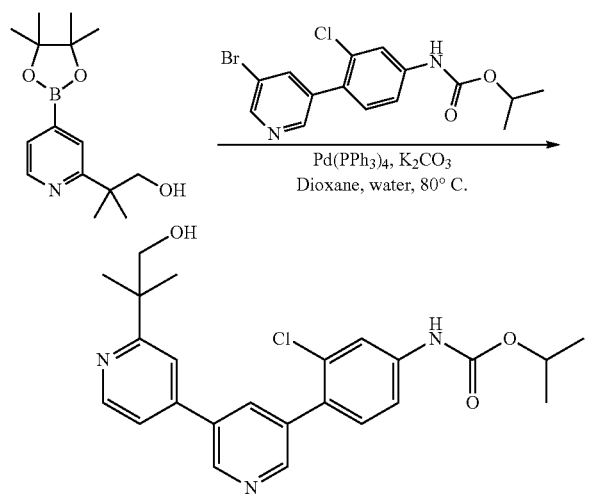

A stirred solution of isopropyl (4-(5-bromopyridin-3-yl)-3-chlorophenyl)carbamate (110 mg, 0.2989 mmol), 2-methyl-2-(4-(4,4,5,5-tetramethyl-1,3,2-dioxaborolan-2-yl)pyridin-2-yl)propan-1-ol (65.0 mg, 0.3288 mmol) and potassium carbonate (124.30 mg, 0.8967 mmol) in a mixture of water (0.3 mL) and 1,4-dioxane (1.2 ml) in a 15 mL glass seal tube was purged with nitrogen gas for 15 min. After adding palladium tetrakis (34.52 mg, 0.0289 mmol) the mixture was again purged with nitrogen gas for 15 min, then the tube sealed and heated at 80° C. for 16 h. After completion, the reaction mixture was cooled to rt and filtered through Celite® bed and washed with ethyl acetate (20 mL). The combined filtrate and washings were concentrated under reduced pressure to afford crude (220 mg) which was purified by preparative HPLC to give isopropyl (3-chloro-4-(2'-(1-hydroxy-2-methylpropan-2-yl)-[3,4'-bipyridin]-5-yl)phenyl)carbamate (33 mg, 26.5%) as an off white solid. $^1$H NMR (400 MHz, DMSO-$d_6$): δ 9.94 (s, 1H), 8.99 (d, J=2.00 Hz, 1H), 8.70 (d, J=2.00 Hz, 1H), 8.62 (d, J=4.80 Hz, 1H), 8.23 (t, J=2.00 Hz, 1H), 7.80 (s, 1H), 7.76 (d, J=0.80 Hz, 1H), 7.64-7.62 (m, 1H), 7.55-7.50 (m, 2H), 4.96-4.88 (m, 1H), 4.67 (t, J=5.60 Hz, 1H), 3.61 (d, J=5.60 Hz, 2H), 1.31 (s, 6H), 1.28 (d, J=6.40 Hz, 6H); LCMS: 99.20% (m/z=440.00 [M+H]).

The following compounds were prepared in a similar manner:

| Compound | Characterization |
|---|---|
| N-(3-chloro-4-(2'-(1-hydroxy-2-methylpropan-2-yl)-[3,4'-bipyridin]-5-yl)phenyl)methanesulfonamide (X-8910) | $^1$H NMR (400 MHz, DMSO-d6): δ 10.21 (s, 1H), 9.00 (d, J = 2.00 Hz, 1H), 8.71 (d, J = 2.00 Hz, 1H), 8.62 (d, J = 5.20 Hz, 1H), 8.24 (t, J = 2.00 Hz, 1H), 7.76 (d, J = 0.80 Hz, 1H), 7.65-7.62 (m, 1H), 7.56 (d, J = 8.40 Hz, 1H), 7.40 (d, J = 2.00 Hz, 1H), 7.30-7.27 (m, 1H), 4.67 (t, J = 5.60 Hz, 1H), 3.62 (d, J = 5.20 Hz, 2H), 3.09 (s, 3H), 1.31 (s, 6H)<br>LCMS: 99.07% (m/z = 432.32[M + H]). |

Example 63: Preparation of Additional Compounds

The following compounds were prepared following procedures described herein.

| Compound | Characterization |
|---|---|
| (3-chloro-4-(2'-(trifluoromethyl)-[3,4'-bipyridin]-5-yl)phenyl)(4-hydroxypiperidin-1-yl)methanone-(Z-854) | LCMS: (462.39[M + H])<br>Mp 97-101° C. |
| (3-chloro-4-(2'-(1-hydroxy-2-methylpropan-2-yl)-[3,4'-bipyridin]-5-yl)phenyl)(4-hydroxy-4-methylpiperidin-1-yl)methanone-(X-8915) | LCMS: (480.1[M + H])<br>Mp 104-108° C. |

-continued

| Compound | Characterization |
|---|---|
| 3'-(2-(tert-butyl)pyridin-4-yl)-2-chloro-N-(cyclopropylsulfonyl)-[1,1'-biphenyl]-4-carboxamide (X-8934) | LCMS: (469.0[M + H])<br>Mp 115-119° C. |
| (4-(2'-(tert-butyl)-4-(trifluoromethyl)-[3,4'-bipyridin]-5-yl)-3-chlorophenyl)(4-hydroxypiperidin-1-yl)methanone (X-8885) | LCMS: (518.67[M + H])<br>Mp 188-192° C. |
| (3'-(2-(tert-butyl)pyridin-4-yl)-2-chloro-2'-fluoro-[1,1'-biphenyl]-4-yl)(4-hydroxypiperidin-1-yl)methanone (X-8935) | LCMS: (467.36[M + H])<br>Mp 104-108° C. |
| N-(3'-(2-(tert-butyl)pyridin-4-yl)-2-chloro-2'-fluoro-[1,1'-biphenyl]-4-yl)methanesulfonamide (X-8936) | LCMS: (433.0[M + H])<br>Mp 94-98° C. |

-continued

| Compound | Characterization |
|---|---|
| 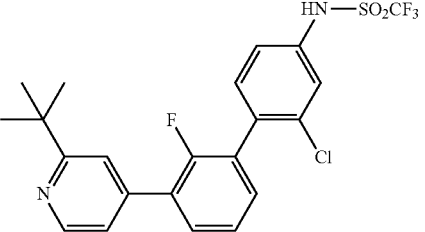<br>N-(3'-(2-(tert-butyl)pyridin-4-yl)-2-chloro-2'-fluoro-[1,1'-biphenyl]-4-yl)-1,1,1-trifluoromethanesulfonamide (X-8937) | LCMS: (487.0[M + H])<br>Mp 108-112° C. |
| 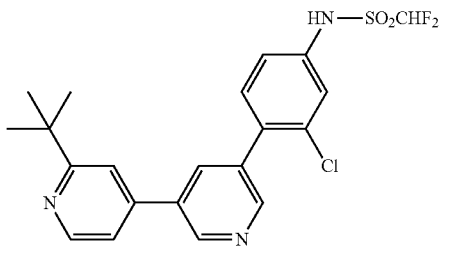<br>N-(4-(2'-(tert-butyl)-[3,4'-bipyridin]-5-yl)-3-chlorophenyl)-1,1-difluoromethanesulfonamide (X-8886) | LCMS: (452.51[M + H])<br>Mp 250-254° C. |
| 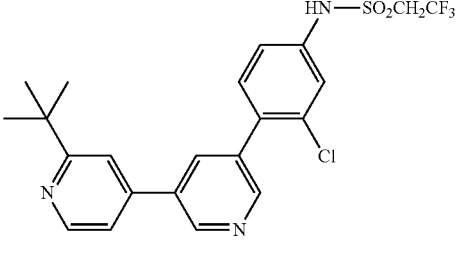<br>N-(4-(2'-(tert-butyl)-[3,4'-bipyridin]-5-yl)-3-chlorophenyl)-2,2,2-trifluoroethane-1-sulfonamide (X-8924) | LCMS: (484.0[M + H])<br>Mp 102-106° C. |
| 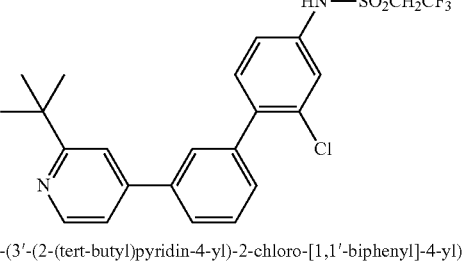<br>N-(3'-(2-(tert-butyl)pyridin-4-yl)-2-chloro-[1,1'-biphenyl]-4-yl)-2,2,2-trifluoroethane-1-sulfonamide (X-8925) | LCMS: (483.0[M + H])<br>Mp 89-93° C. |
| 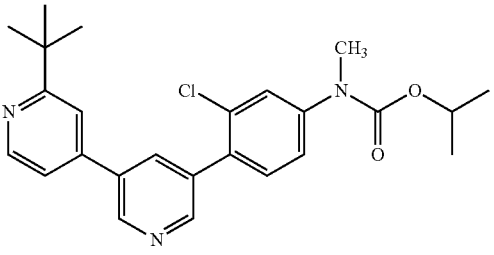<br>isopropyl (4-(2'-(tert-butyl)-[3,4'-bipyridin]-5-yl)-3-chlorophenyl)(methyl)carbamate (X-8955) | LCMS: (438.1[M + H]) |

-continued

| Compound | Characterization |
|---|---|
| (3-chloro-4-(2'-(1-fluoro-2-methylpropan-2-yl)-[3,4'-bipyridin]-5-yl)phenyl)(4-hydroxypiperidin-1-yl)methanone (X-8984) | LCMS: (468.1[M + H]) Mp 116-120° C. |
| (3-chloro-4-(2'-(1-fluorocyclobutyl)-[3,4'-bipyridin]-5-yl)phenyl)(4-hydroxypiperidin-1-yl)methanone (X-8970) | LCMS: (466.39[M + H]) Mp 111-115° C. |
| isopropyl (3-chloro-4-(2'-(1-fluorocyclobutyl)-[3,4'-bipyridin]-5-yl)phenyl)carbamate (X-8985) | LCMS: (440.0[M + H]) Mp 159-163° C. |
| (3-chloro-4-(2'-(1-hydroxycyclobutyl)-[3,4'-bipyridin]-5-yl)phenyl)(4-hydroxypiperidin-1-yl)methanone (X-8974) | LCMS: (464.33[M + H]) Mp 129-133° C. |
| N-(3-chloro-4-(2'-(2-hydroxypropan-2-yl)-[3,4'-bipyridin]-5-yl)phenyl)methanesulfonamide (X-8988) | LCMS: (418.0[M + H]) Mp 224-228° C. |

| Compound | Characterization |
|---|---|
| 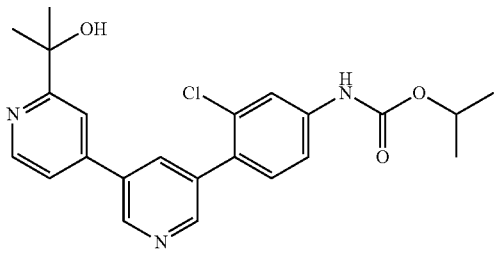<br>isopropyl (3-chloro-4-(2'-(2-hydroxypropan-2-yl)-[3,4'-bipyridin]-5-yl)phenyl)carbamate (X-8993) | LCMS: (426.35[M + H])<br>Mp 87-91° C. |
| 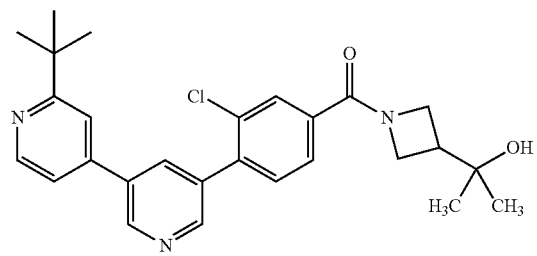<br>(4-(2'-(tert-butyl)-[3,4'-bipyridin]-5-yl)-3-chlorophenyl)(3-(2-hydroxypropan-2-yl)azetidin-1-yl)methanone (X-8958) | LCMS: (464.1[M + H])<br>Mp 91-94° C. |
| 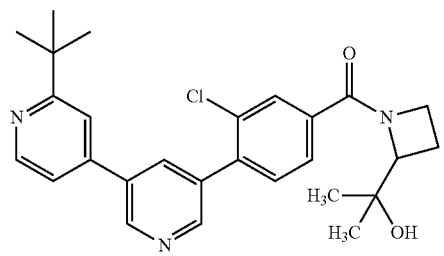<br>(4-(2'-(tert-butyl)-[3,4'-bipyridin]-5-yl)-3-chlorophenyl)(2-(2-hydroxypropan-2-yl)azetidin-1-yl)methanone (X-8959) | LCMS: (464.42[M + H])<br>Mp 80-84° C. |
| 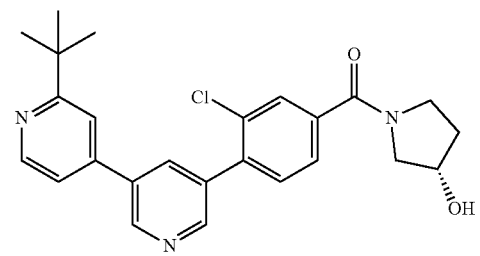<br>(S)-(4-(2'-(tert-butyl)-[3,4'-bipyridin]-5-yl)-3-chlorophenyl)(3-hydroxyprrolidin-1-yl)methanone (X-8950) | LCMS: (436.0[M + H])<br>Mp 101-105° C. |

| Compound | Characterization |
|---|---|
| 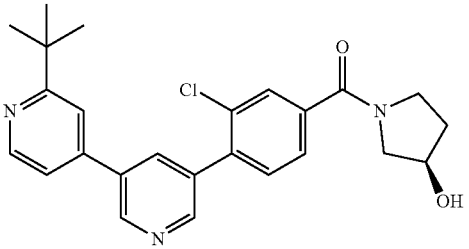<br>(R)-(4-(2'-(tert-butyl)-[3,4'-bipyridin]-5-yl)-3-chlorophenyl)(3-hydroxyprrolidin-1-yl)methanone (X-8949) | LCMS: (436.0[M + H])<br>Mp 111-115° C. |
| 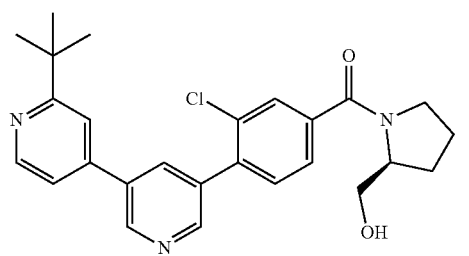<br>(S)-(4-(2'-(tert-butyl)-[3,4'-bipyridin]-5-yl)-3-chlorophenyl)(2-(hydroxymethyl)pyrrolidin-1-yl)methanone (X-8952) | LCMS: (450.1[M + H])<br>Mp 85-89° C. |
| 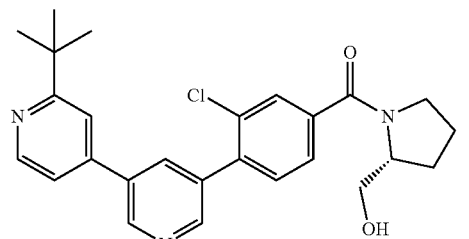<br>(R)-(4-(2'-(tert-butyl)-[3,4'-bipyridin]-5-yl)-3-chlorophenyl)(2-(hydroxymethyl)pyrrolidin-1-yl)methanone (X-8953) | LCMS: (450.0[M + H])<br>Mp 91-95° C. |
| 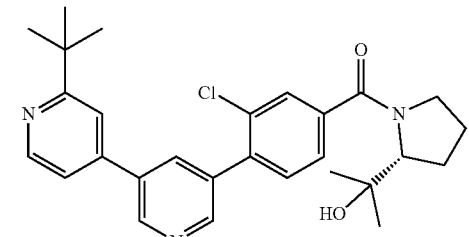<br>(R)-(4-(2'-(tert-butyl)-[3,4'-bipyridin]-5-yl)-3-chlorophenyl)(2-(2-hydroxypropan-2-yl)pyrrolidin-1-yl)methanone (X-8982) | LCMS: (478.1[M + H])<br>Mp 94-98° C. |
| 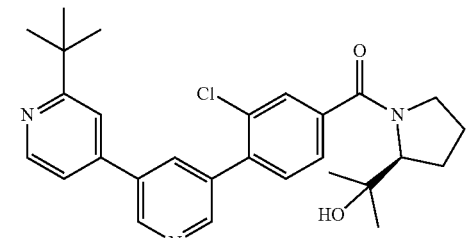<br>(S)-(4-(2'-(tert-butyl)-[3,4'-bipyridin]-5-yl)-3-chlorophenyl)(2-(2-hydroxypropan-2-yl)pyrrolidin-1-yl)methanone (X-8981) | LCMS: (478.1[M + H])<br>Mp 91-95° C. |

-continued

| Compound | Characterization |
|---|---|
| 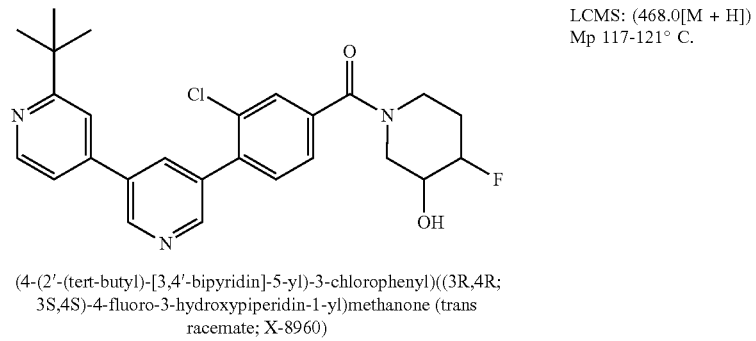<br>(4-(2'-(tert-butyl)-[3,4'-bipyridin]-5-yl)-3-chlorophenyl)((3R,4R;<br>3S,4S)-4-fluoro-3-hydroxypiperidin-1-yl)methanone (trans<br>racemate; X-8960) | LCMS: (468.0[M + H])<br>Mp 117-121° C. |
| 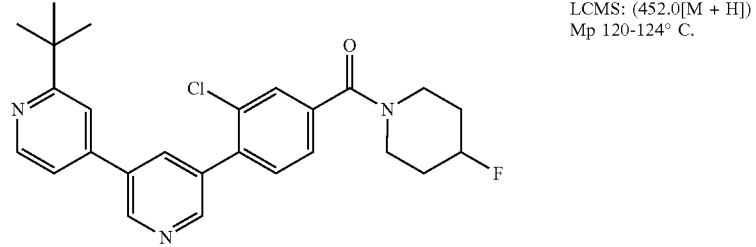<br>(4-(2'-(tert-butyl)-[3,4'-bipyridin]-5-yl)-3-chlorophenyl)(4-<br>fluoropiperidin-1-yl)methanone (X-8942) | LCMS: (452.0[M + H])<br>Mp 120-124° C. |
| 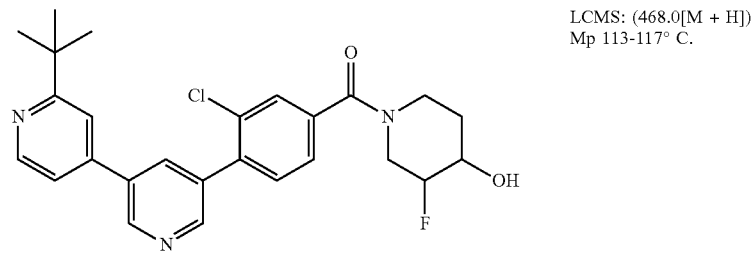<br>(4-(2'-(tert-butyl)-[3,4'-bipyridin]-5-yl)-3-chlorophenyl)(3-fluoro-4-<br>hydroxypiperidin-1-yl)methanone (X-8978) | LCMS: (468.0[M + H])<br>Mp 113-117° C. |
| 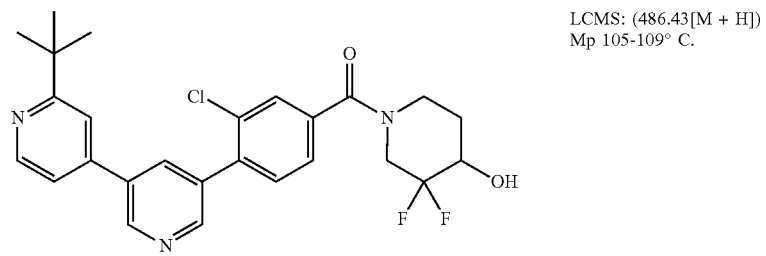<br>(4-(2'-(tert-butyl)-[3,4'-bipyridin]-5-yl)-3-chlorophenyl)(3,3-<br>difluoro-4-hydroxypiperidin-1-yl)methanone (X-8968) | LCMS: (486.43[M + H])<br>Mp 105-109° C. |

-continued

| Compound | Characterization |
|---|---|
| (4-(2'-(tert-butyl)-[3,4'-bipyridin]-5-yl)-3-chlorophenyl)(3,3-difluoro-4,4-dihydroxypiperidin-1-yl)methanone (X-8976) | LCMS: (502.39[M + H])<br>Mp 104-108° C. |
| 1-(4-(2'-(tert-butyl)-[3,4'-bipyridin]-5-yl)-3-chlorophenyl)-3-fluoropiperidin-4-one (X-8983) | LCMS: (484.1[M + H])<br>Mp 100-104° C. |
| N-(4-(5-([1,3]dioxolo[4,5-b]pyridin-7-yl)pyridin-3-yl)-3-chlorophenyl)methanesulfonamide | LCMS: (402.0[M + H])<br>Mp 125-129° C. |
| N-(3-chloro-4-(2'-(2-methoxyethoxy)-[3,4'-bipyridin]-5-yl)phenyl)methanesulfonamide | LCMS: (432.0[M + H])<br>Mp 142-146° C. |
| N-(4-(2'-(tert-butyl)-[3,4'-bipyridin]-5-yl)-3-chlorophenyl)-4-hydroxypiperidine-1-carboxamide (X-8919) | LCMS: (465.0[M + H])<br>Mp 114-118° C. |

| Compound | Characterization |
|---|---|
| 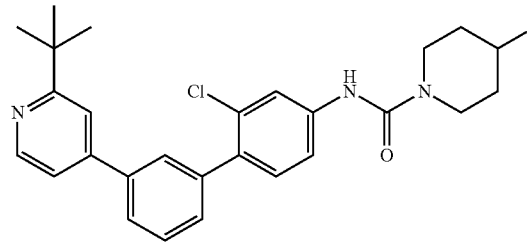 N-(3'-(2-(tert-butyl)pyridin-4-yl)-2-chloro-[1,1'-biphenyl]-4-yl)-4-hydroxypiperidine-1-carboxamide (X-8919) | LCMS: (464.1[M + H]) Mp 130-134° C. |

What is claimed is:

1. A compound of Formula (X-A):

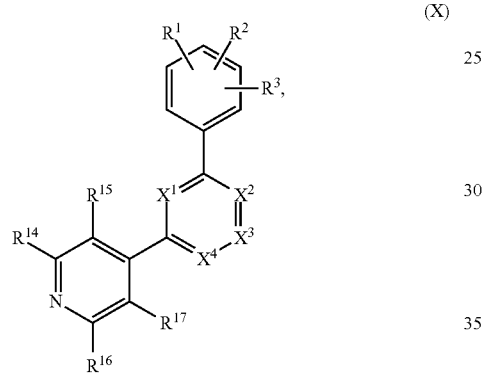

or a pharmaceutically acceptable salt, solvate, or isotope thereof, wherein:

$R^1$ is —C(O)O$R^9$, —C(O)N$R^8R^9$, —S(O)$_2$N$R^8R^9$, —N$R^{10}$C(O)N$R^8R^9$, —N$R^{10}$C(O)$R^9$, —N$R^{10}$S(O)$_2$$R^9$, —O$R^{26}$, —S$R^9$, —S(O)$R^9$, —S(O)$_2R^9$, —N$R^8R^9$, —N$R^{10}$C(O)O$R^9$, —C(O)$R^{26}$, —N$R^{10}$S(O)$_2$N$R^8R^9$, —C(O)N$R^{10}$S(O)$_2R^9$, or —C(O)N$R^{10}$N$R^8R^9$;

wherein each of $R^8$, $R^9$, and $R^{10}$ is independently selected from the group consisting of hydrogen, (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl, $R^{26}$ is (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, or heteroaryl-alkyl, each (C$_{1-10}$)alkyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, and heteroaryl-alkyl of $R^1$, $R^9$, $R^{10}$, and $R^{26}$ is independently unsubstituted or substituted with one or more substituents independently selected from the group consisting of halo, (C$_{1-10}$)alkyl, (C$_{1-10}$)haloalkyl, cyano, oxo, —O$R^{19}$, —C(O)N$R^{19}R^{19}$, —N$R^{19}$C(O)$R^{19}$, —N$R^{19}$C(O)N$R^{19}R^{19}$, —N$R^{19}R^{19}$, —S(O)$_2$N$R^{19}R^{19}$, —N$R^{19}$S(O)$_2R^{19}$, —S(O)$_{n4}R^{20}$, —C(O)O$R^{19}$, —C(O)$R^{20}$, and —(O$R^{38}$)$_{n15}$O$R^{19}$, each $R^{19}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{19}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{20}$ is independently (C$_{1-10}$)alkyl, (C$_{3-10}$)cycloalkyl, (C$_{3-10}$)cycloalkyl(C$_{1-10}$)alkyl, or heterocycloalkyl, wherein each of the foregoing is independently unsubstituted or substituted with one or more halo, each $R^{38}$ is independently (C$_{1-10}$)alkylene or (C$_{1-10}$)haloalkylene, each n15 is independently an integer from 1 to 5, and n4 is 0, 1, or 2;

or $R^8$ and $R^9$, together with the nitrogen atom to which they are attached, form a heterocycloalkyl, wherein the heterocycloalkyl is unsubstituted or substituted with one or more substituents independently selected from the group consisting of halo, cyano, oxo, (C$_{1-10}$)alkyl, (C$_{2-10}$)alkenyl, (C$_{2-10}$)alkynyl, (C$_{3-10}$)cycloalkyl, (C$_{3-10}$)cycloalkyl(C$_{1-10}$)alkyl, heterocycloalkyl, heterocycloalkyl-alkyl, (C$_{6-10}$)aryl, (C$_{6-10}$)aryl(C$_{1-10}$)alkyl, heteroaryl, heteroaryl-alkyl, —O$R^{23}$, —C(O)N$R^{23}R^{23}$, —N$R^{23}$C(O)$R^{23}$, —N$R^{23}$C(O)O$R^{23}$, —N$R^{23}$C(O)N$R^{23}R^{23}$, —N$R^{23}R^{23}$, —S(O)$_2$N$R^{23}R^{23}$—N$R^{23}$S(O)$_2R^{24}$, —S(O)$_{n6}R^{24}$, —C(O)O$R^{23}$, —C(O)$R^{24}$, and —(O$R^{39}$)$_{n16}$O$R^{23}$, wherein each alkyl, alkenyl, alkynyl, cycloalkyl, cycloalkyl-alkyl, heterocycloalkyl, heterocycloalkyl-alkyl, aryl, aryl-alkyl, heteroaryl, and heteroaryl-alkyl is independently unsubstituted or substituted with one or more substituents independently selected from the group consisting of halo, oxo, alkyl, haloalkyl, —O$R^{31}$, —C(O)N$R^{31}R^{31}$, —N$R^{31}$C(O)$R^{31}$, —N$R^{31}$C(O)O$R^{31}$, —N$R^{31}$C(O)N$R^{31}R^{31}$, —N$R^{31}$S(O)$_2R^{31}$, and —S(O)$_{n9}R^{31}$, wherein each $R^{31}$ is independently hydrogen, alkyl, or haloalkyl, and each n9 is independently 0, 1, or 2, each $R^{23}$ is independently hydrogen, (C$_{1-10}$)alkyl, (C$_{3-10}$)cycloalkyl, (C$_{3-10}$)cycloalkyl(C$_{1-10}$)alkyl, or heterocycloalkyl; or two $R^{23}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{24}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, each $R^{39}$ is independently $(C_{1-10})$alkylene or $(C_{1-10})$haloalkylene, each n16 is independently an integer from 1 to 5, and n6 is 0, 1, or 2;

$R^2$ and $R^3$ are independently selected from the group consisting of hydrogen, halo, cyano, $(C_{1-10})$alkyl, $(C_{3-10})$cycloalkyl, $(C_{3-10})$cycloalkyl$(C_{1-10})$alkyl, —$OR^{25}$, —$C(O)NR^{25}R^{25}$, —$NR^{25}C(O)R^{25}$, —$NR^{25}C(O)NR^{25}R^{25}$, —$NR^{25}R^{25}$, —$S(O)_2NR^{25}R^{25}$, —$NR^{25}S(O)_2R^{25}$, —$S(O)_{n7}R^{30}$, —$NR^{25}C(O)OR^{25}R^{25}$, —$C(O)OR^{25}$, and —$C(O)R^{30}$, wherein each $(C_{1-10})$alkyl, $(C_{3-10})$cycloalkyl, and $(C_{3-10})$cycloalkyl$(C_{1-10})$alkyl is independently unsubstituted or substituted with one or more halo, each $R^{25}$ is independently hydrogen $(C_{1-10})$alkyl, $(C_{3-10})$cycloalkyl, $(C_{3-10})$cycloalkyl$(C_{1-10})$alkyl, or heterocycloalkyl; or two $R^{25}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{30}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, and n7 is 0, 1, or 2;

$X^1$, $X^2$, $X^3$ and $X^4$ are independently $CR^4$ or N, wherein one of $X^1$, $X^2$, $X^3$, and $X^4$ is N; and $R^4$ is independently selected from the group consisting of hydrogen, halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, —$C(O)OR^{27}$, and —$C(O)R^{28}$, wherein each $(C_{1-10})$alkyl, $(C_{3-10})$cycloalkyl, $(C_{3-10})$cycloalkyl$(C_{1-10})$alkyl, heterocycloalkyl, and heterocycloalkyl-alkyl is independently unsubstituted or substituted with one or more halo, each $R^{27}$ is independently hydrogen or $(C_{1-10})$alkyl, $(C_{3-10})$cycloalkyl, $(C_{3-10})$cycloalkyl$(C_{1-10})$alkyl, or heterocycloalkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, or heterocycloalkyl, wherein each of the foregoing is independently unsubstituted or substituted with one or more halo, n8 is 0, 1 or 2; or two $R^4$ on adjacent annular carbon atoms together with the carbon atoms to which they are attached may form a carbocyclyl or heterocyclyl, wherein the carbocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl, heterocycloalkyl-alkyl, —$OR^{27}$, —$C(O)NR^{27}R^{27}$, —$NR^{27}C(O)R^{27}$, —$NR^{27}R^{27}$, —$S(O)_2NR^{27}R^{27}$, —$NR^{27}S(O)_2R^{27}$, —$S(O)_{n8}R^{28}$, and —$C(O)R^{28}$, or the heterocyclyl is unsubstituted or substituted with one or more substituents independently selected from the group consisting of halo, cyano, $(C_{1-10})$alkyl, $(C_{3-10})$cycloalkyl, $(C_{3-10})$cycloalkyl$(C_{1-10})$alkyl, heterocycloalkyl connected by an annular carbon atom, heterocycloalkyl-alkyl, —$OR^{27}$, —$C(O)NR^{27}R^{27}$, —$S(O)_2NR^{27}R^{27}$, —$S(O)_{n8}R^{28}$, and —$C(O)R^{28}$, each $R^{27}$ is independently hydrogen, $(C_{1-10})$alkyl, $(C_{3-10})$cycloalkyl, $(C_{3-10})$cycloalkyl$(C_{1-10})$alkyl; or two $R^{27}$, together with the nitrogen atom to which they are attached, form a heterocycloalkyl; wherein each of the foregoing alkyl, cycloalkyl, or heterocycloalkyl moieties is independently unsubstituted or substituted with one or more halo, each $R^{28}$ is independently $(C_{1-10})$alkyl, $(C_{3-10})$cycloalkyl, $(C_{3-10})$cycloalkyl$(C_{1-10})$alkyl, wherein each of the foregoing is independently unsubstituted or substituted with one or more halo, and n8 is 0, 1, or 2;

$R^{15}$ and $R^{17}$ are independently hydrogen, halo, alkyl, or —$OR^{29}$, wherein each $R^{29}$ is independently hydrogen, $(C_{1-10})$alkyl, $(C_{3-10})$cycloalkyl, or $(C_{3-10})$cycloalkyl$(C_{1-10})$alkyl, and each alkyl or cycloalkyl in $R^{15}$ or $R^{17}$, if present, is independently unsubstituted or substituted with one or more halo;

$R^{14}$ is $(C_{1-10})$alkyl, unsubstituted $(C_{3-10})$cycloalkyl or $(C_{3-10})$halocycloalkyl, or —$OR^5$;

wherein $(C_{1-10})$alkyl is unsubstituted or substituted with one to three substituents selected from the group consisting of $(C_{1-10})$alkyl, halo, —$C(O)OR^7$, oxo, and —$OR^5$;

$R^{16}$ is hydrogen, fluoro, $(C_{1-10})$alkyl, $(C_{3-10})$cycloalkyl, $(C_{3-10})$cycloalkyl$(C_{1-10})$alkyl, heterocycloalkyl connected through an annular carbon atom, heterocycloalkyl-alkyl, —$OR^5$, —$C(O)NR^5R^5$, —$R^5C(O)NR^5R^5$, —$S(O)_2NR^5R^5$, —$S(O)_{n1}R^6$, or —$C(O)R^6$;

wherein the $(C_{1-10})$alkyl, $(C_{3-10})$cycloalkyl, $(C_{3-10})$cycloalkyl$(C_{1-10})$alkyl, heterocycloalkyl, or heterocycloalkyl-alkyl of $R^{16}$ is independently unsubstituted or substituted with one or more substituents independently selected from the group consisting of $(C_{1-10})$alkyl, cycloalkyl, heterocycloalkyl, halo, cyano, oxo, —$OR^7$, —$C(O)OR^7$, —$C(O)NR^7R^7$, —$NR^7C(O)R^7$, —$NR^7C(O)NR^7R^7$, —$NR^7R^7$, —$S(O)_2NR^7R^7$, —$NR^7S(O)_2R^7$, —$S(O)_{n2}R^{13}$, and —$C(O)R^{13}$;

wherein each alkyl, cycloalkyl, and heterocycloalkyl is independently unsubstituted or substituted with one or more substituents selected from the group consisting of halo, cycloalkyl, halocycloalkyl, heterocycloalkyl, haloheterocycloalkyl, and —$(OR^{33})^{n10}OR^{32}$, wherein each n10 is independently an integer from 0 to 5, each $R^{32}$ is independently hydrogen, $(C_{1-10})$alkyl or $(C_{1-10})$haloalkyl, and each $R^{33}$ is independently $(C_{1-10})$alkylene or $(C_{1-10})$haloalkylene;

each $R^5$ is independently hydrogen, $(C_{1-10})$alkyl, or $(C_{3-10})$cycloalkyl; or two $R^5$, together with the nitrogen atom to which they are attached, form a heterocycloalkyl; wherein each alkyl, cycloalkyl, or heterocycloalkyl is independently unsubstituted or substituted with one or more substituents selected from the group consisting of halo, cyano, oxo, alkyl, haloalkyl, —C(O)OR$^{34}$, —C(O)NR$^{34}$R$^{34}$, —NR$^{34}$C(O)R$^{34}$, —NR$^{34}$C(O)NR$^{34}$R$^{34}$, —NR$^{34}$R$^{34}$, —S(O)$_2$NR$^{34}$R$^{34}$, —NR$^{34}$S(O)$_2$R$^{34}$, —S(O)$_{n11}$R$^{34}$, —C(O)R$^{34}$, and —(OR$^{35}$)$_{n12}$OR$^{34}$, wherein each R$^{34}$ is independently hydrogen, (C$_{1-10}$)alkyl, or (C$_{1-10}$)haloalkyl; each n11 is independently 0, 1, or 2; each n12 is independently an integer from 0 to 5; and each R$^{35}$ is independently (C$_{1-10}$)alkylene or (C$_{1-10}$)haloalkylene;

each R$^6$ is independently (C$_{1-10}$)alkyl or (C$_{3-10}$)cycloalkyl, wherein each alkyl or cycloalkyl is independently unsubstituted or substituted with one or more halo;

each n1 is independently 0, 1, or 2;

each R$^7$ is independently hydrogen, unsubstituted (C$_{1-10}$) alkyl, or (C$_{1-10}$)alkyl substituted with one or more halo;

each n2 is independently 0, 1, or 2, and each R$^{13}$ is independently unsubstituted (C$_{1-10}$)alkyl or (C$_{1-10}$)alkyl substituted with one or more halo;

or R$^{14}$ and R$^{15}$, together with the atoms to which they are attached, form a carbocyclyl or heterocyclyl, wherein the heterocyclyl is unsubstituted or substituted with one or more substituents independently selected from the group consisting of halo, cyano, oxo, (C$_{1-10}$)alkyl, (C$_{3-10}$)cycloalkyl, (C$_{3-10}$)cycloalkyl(C$_{1-10}$)alkyl, —OR$^{18}$, —C(O)NR$^{18}$R$^{18}$, —NR$^{18}$C(O)R$^{18}$, —NR$^{18}$C(O)NR$^{18}$R$^{18}$, —NR$^{18}$R$^{18}$, —S(O)$_2$NR$^{18}$R$^{18}$, —NR$^{18}$S(O)$_2$R$^{18}$, —S(O)$_{n3}$R$^{21}$, —C(O)OR$^{18}$, and —C(O)R$^{21}$, wherein each (C$_{1-10}$)alkyl, (C$_{3-10}$)cycloalkyl, and (C$_{3-10}$)cycloalkyl(C$_{1-10}$)alkyl is independently unsubstituted or substituted with one or more substituents independently selected from the group consisting of halo, alkyl, haloalkyl, cyano, oxo, —C(O)OR$^{36}$, —C(O)NR$^{36}$R$^{36}$, —NR$^{36}$C(O)R$^{36}$, —NR$^{36}$C(O)NR$^{36}$R$^{36}$, —NR$^{36}$R$^{36}$, —S(O)$_2$NR$^{36}$R$^{36}$, —NR$^{36}$S(O)$_2$R$^{36}$, —S(O)$_{n13}$R$^{36}$, —C(O)R$^{36}$, and —(OR$^{37}$)$_{n14}$OR$^{36}$, wherein each R$^{36}$ is independently hydrogen, (C$_{1-10}$)alkyl, or (C$_{1-10}$)haloalkyl; each n13 is independently 0, 1, or 2; each n14 is independently an integer from 0 to 5; and each R$^{37}$ is independently (C$_{1-10}$)alkylene or (C$_{1-10}$)haloalkylene;

wherein each R$^{18}$ is independently hydrogen, (C$_{1-10}$)alkyl, or (C$_{3-10}$)cycloalkyl; or two R$^{18}$, together with the nitrogen atom to which they are attached, form a heterocycloalkyl; wherein each alkyl, cycloalkyl, or heterocycloalkyl is independently unsubstituted or substituted with one or more halo;

each R$^{21}$ is independently (C$_{1-10}$)alkyl or (C$_{3-10}$)cycloalkyl, wherein each alkyl or cycloalkyl is independently unsubstituted or substituted with one or more halo; and each n3 is independently 0, 1, or 2.

2. The compound of claim 1, or a pharmaceutically acceptable salt, solvate, or isotope thereof, wherein R$^1$ is —C(O)NR$^8$R$^9$, —S(O)$_2$NR$^8$R$^9$, —NR$^{10}$C(O)OR$^9$, —NR$^{10}$S(O)$_2$R$^9$, or —NR$^{10}$S(O)$_2$NR$^8$R$^9$.

3. The compound of claim 1, or a pharmaceutically acceptable salt, solvate, or isotope thereof, wherein R$^1$ is —C(O)NR$^8$R$^9$, —NR$^{10}$C(O)OR$^9$, or —NR$^{10}$S(O)$_2$R$^9$.

4. The compound of claim 1, or a pharmaceutically acceptable salt, solvate, or isotope thereof, wherein R$^8$ is hydrogen.

5. The compound of claim 1, or a pharmaceutically acceptable salt, solvate, or isotope thereof, wherein R$^9$ is hydrogen, (C$_{1-10}$)alkyl, (C$_{3-10}$)cycloalkyl, or heterocycloalkyl-alkyl.

6. The compound of claim 1, or a pharmaceutically acceptable salt, solvate, or isotope thereof, wherein R$^1$ is —C(O)NR$^8$R$^9$, and the R$^8$ and R$^9$ together with the nitrogen to which they are attached form an unsubstituted or substituted heterocycloalkyl.

7. The compound of claim 6, or a pharmaceutically acceptable salt, solvate, or isotope thereof, wherein the heterocycloalkyl is substituted and the substituents are independently selected from the group consisting of halo, oxo, (C$_{1-10}$)alkyl, —OR$^{23}$, —C(O)OR$^{23}$, and —NR$^{23}$C(O)OR$^{23}$, wherein each (C$_{1-10}$)alkyl is unsubstituted or substituted with —OR$^{31}$.

8. The compound of claim 1, or a pharmaceutically acceptable salt, solvate, or isotope thereof, wherein R$^2$ is chloro or methyl.

9. The compound of claim 1, or a pharmaceutically acceptable salt, solvate, or isotope thereof, wherein X$^1$, X$^2$, and X$^4$ are CR$^4$, and X$^3$ is N.

10. The compound of claim 1, or a pharmaceutically acceptable salt, solvate, or isotope thereof, wherein R$^{15}$, R$^{16}$, and R$^{17}$ are hydrogen.

11. The compound of claim 1, selected from the group consisting of:

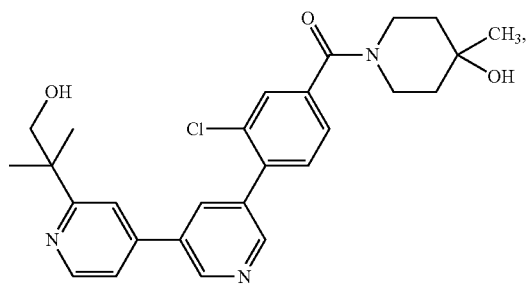

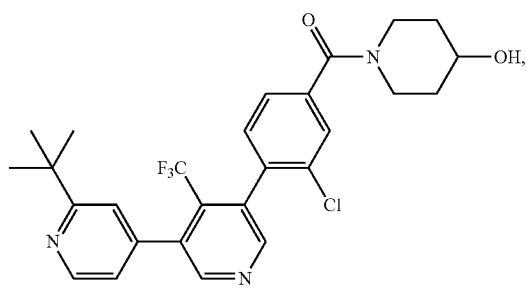

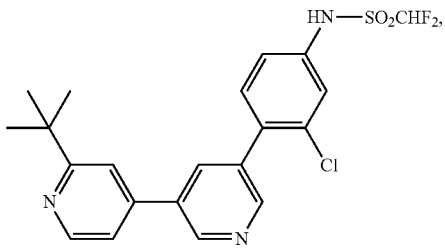

439
-continued
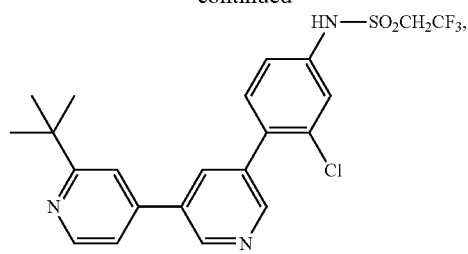
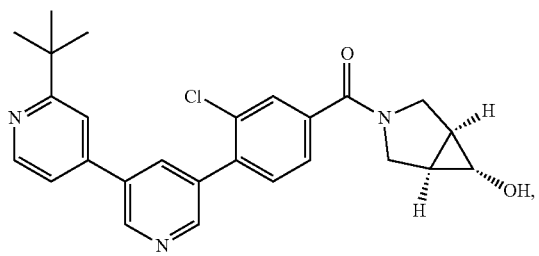
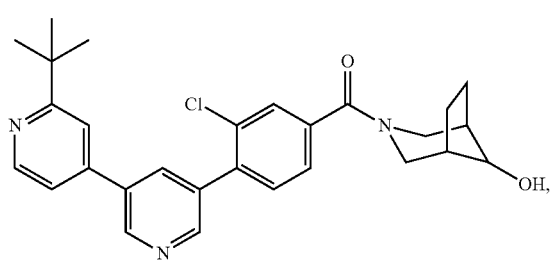
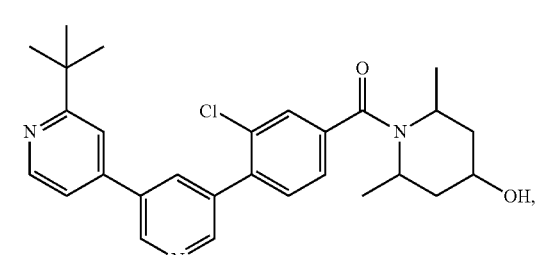
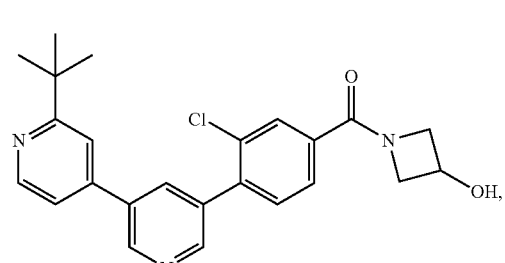
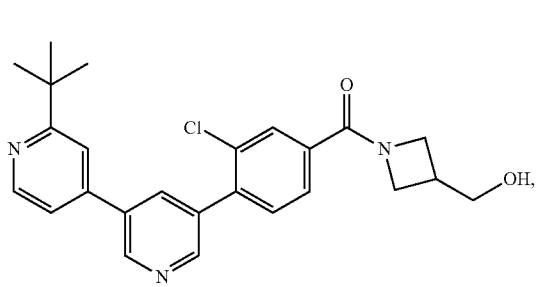
440
-continued
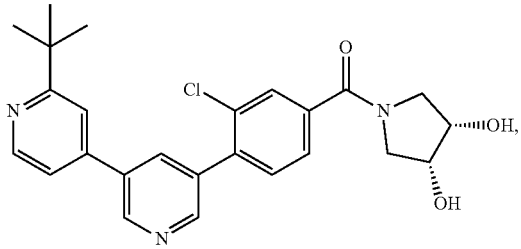
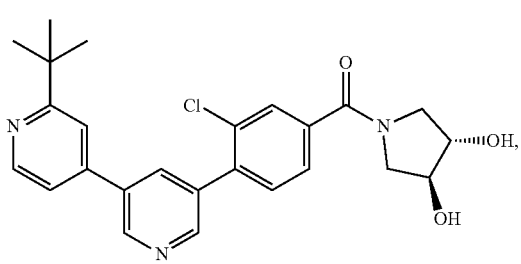
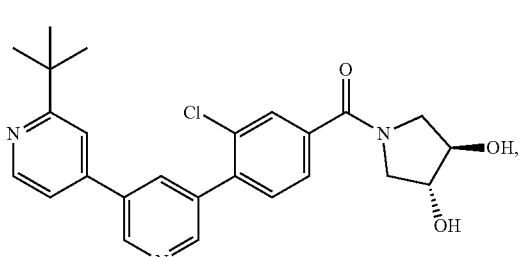
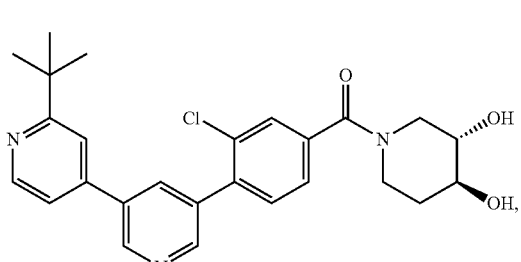
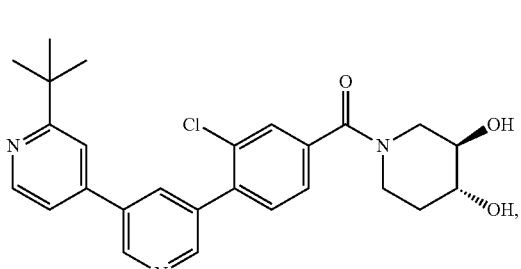
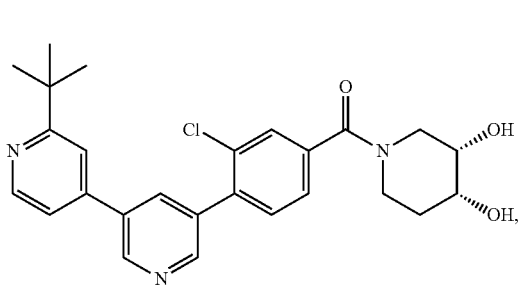

441
-continued
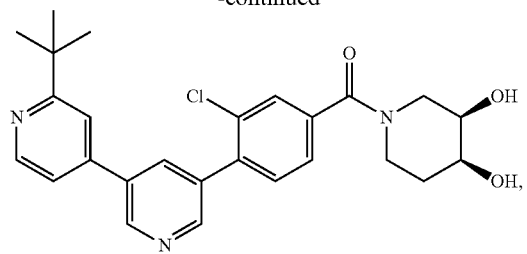
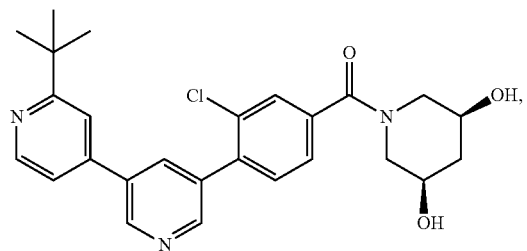
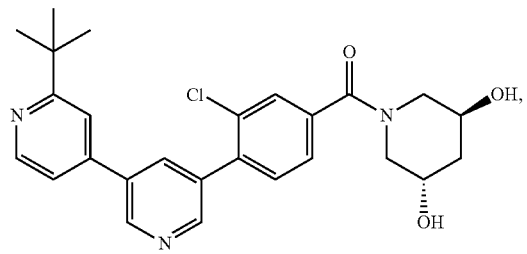
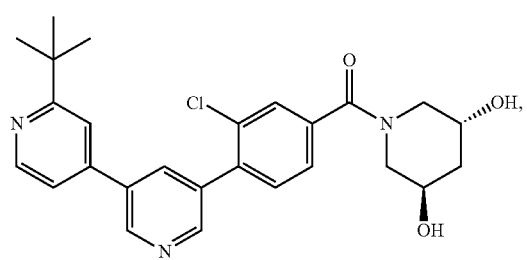
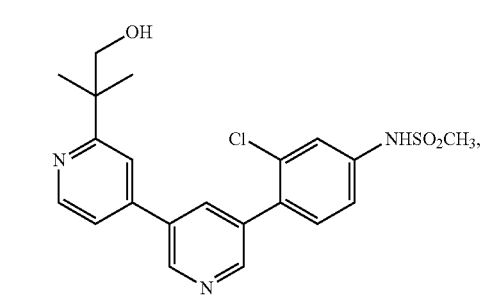
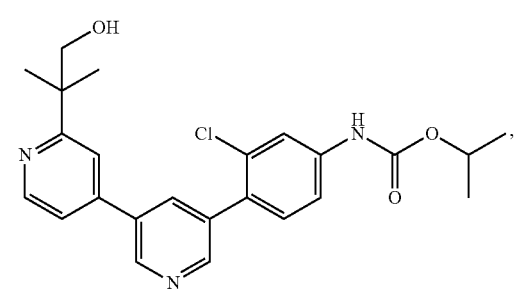
442
-continued
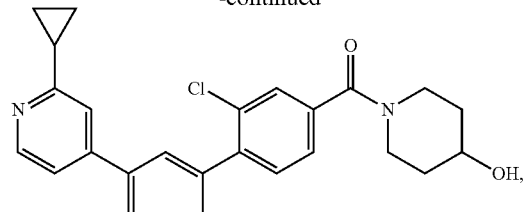
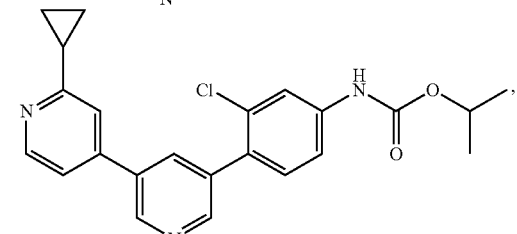
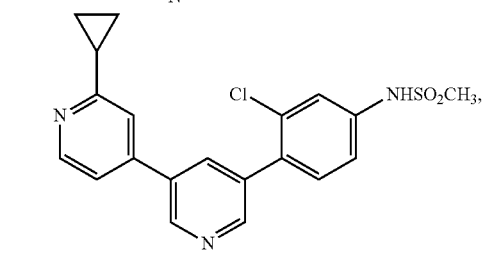
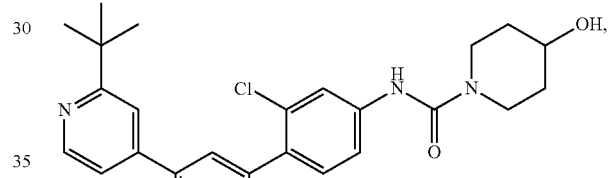
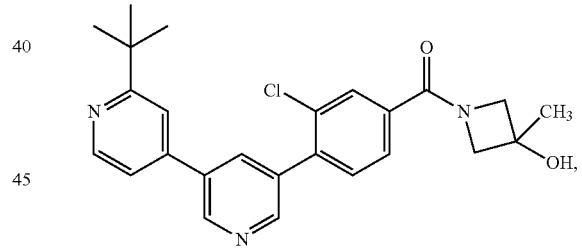
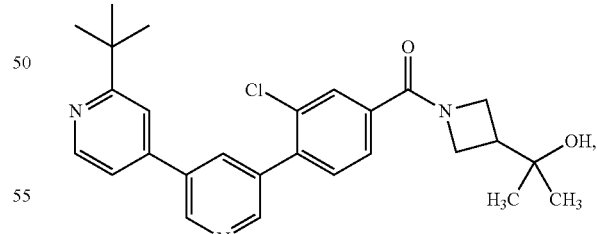
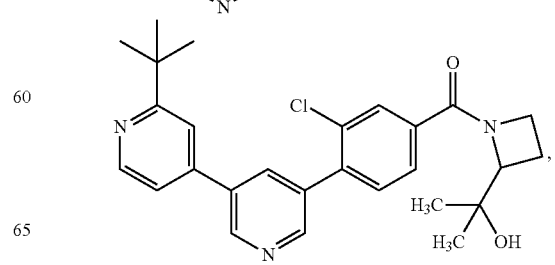

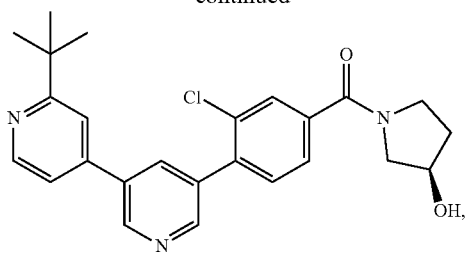
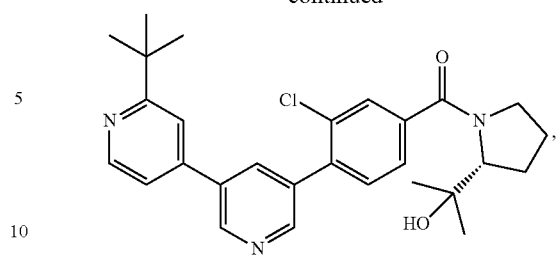

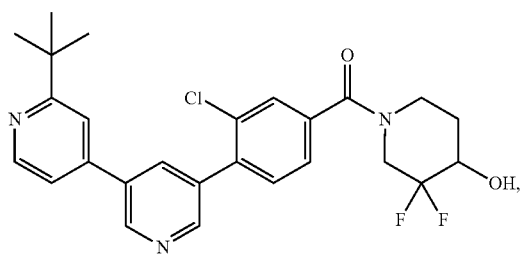
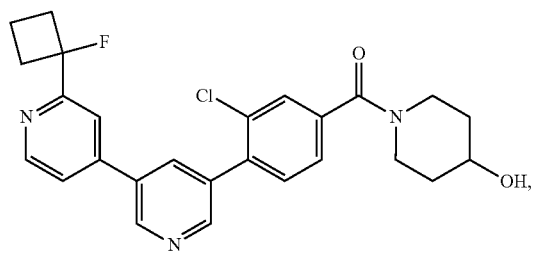
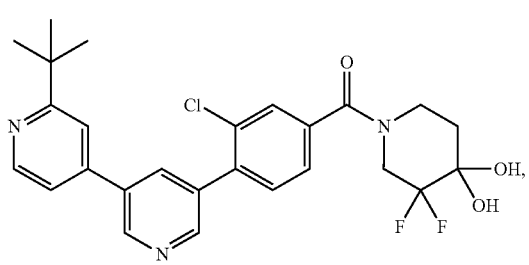
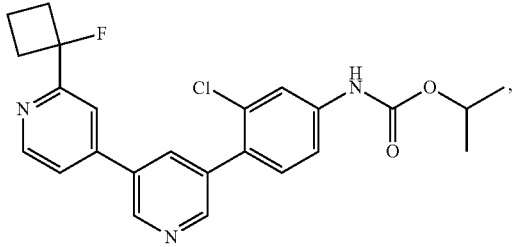
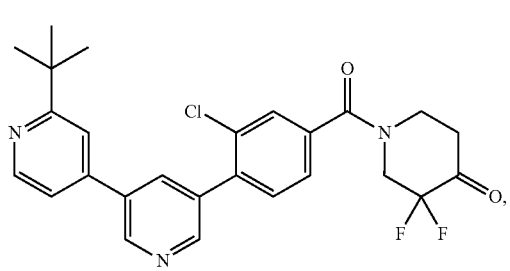
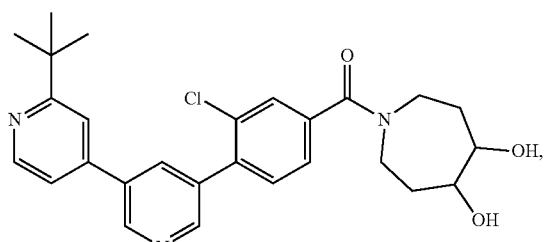
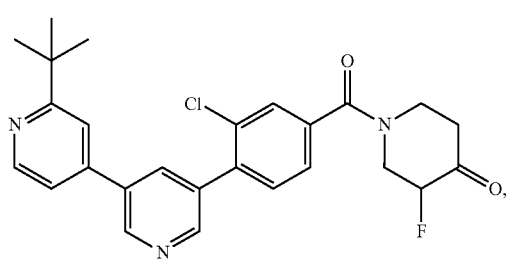
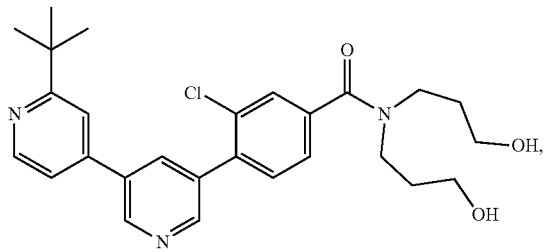
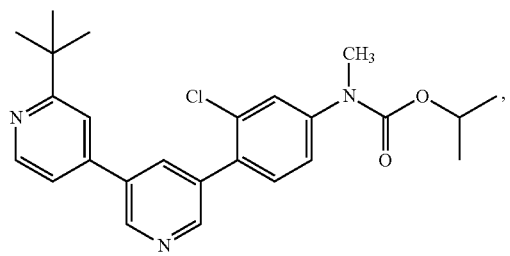
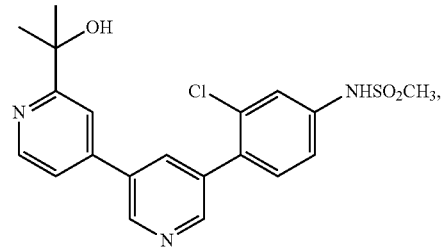
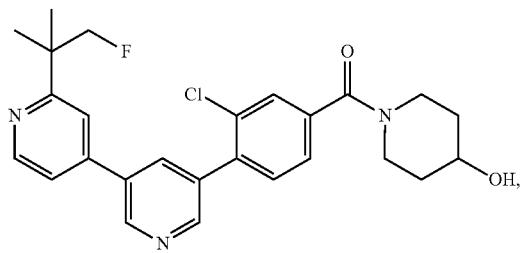
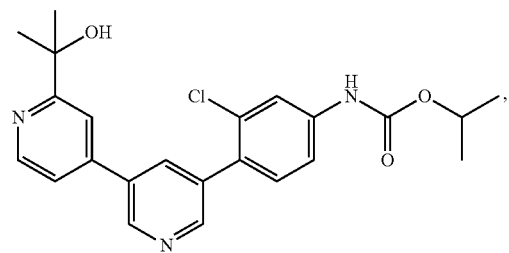

447
-continued
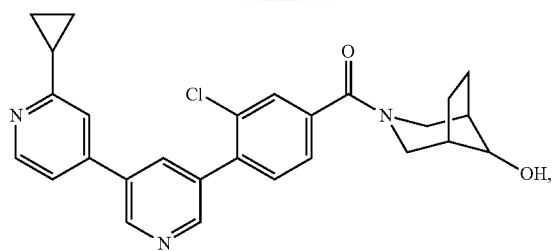
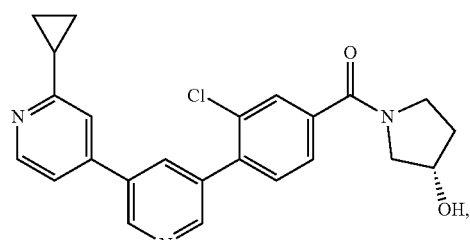
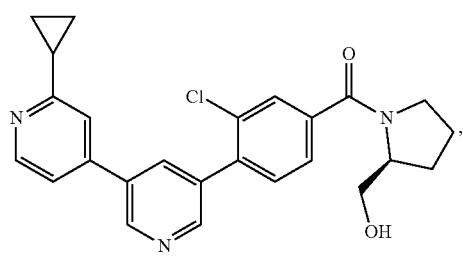
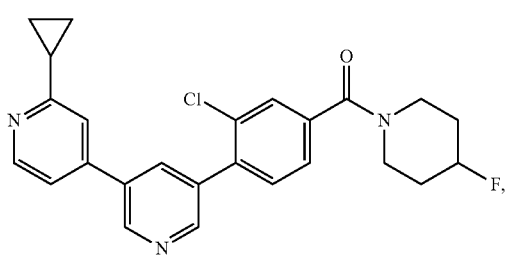
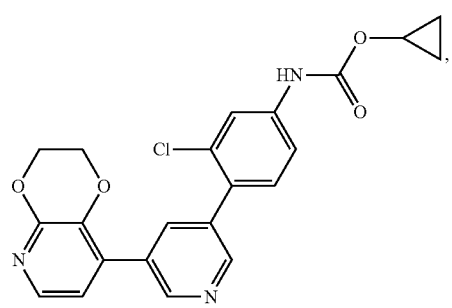
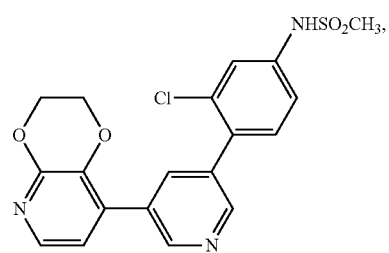
448
-continued
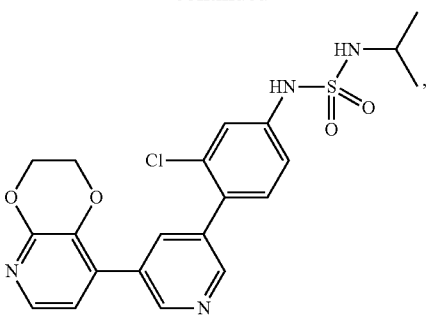
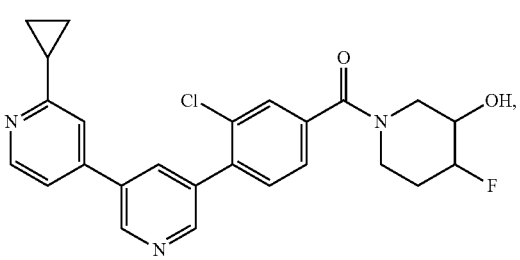
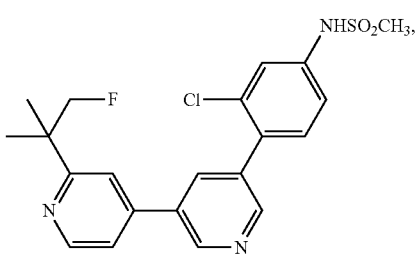
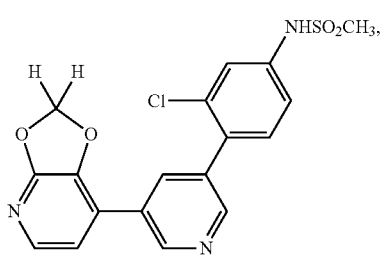
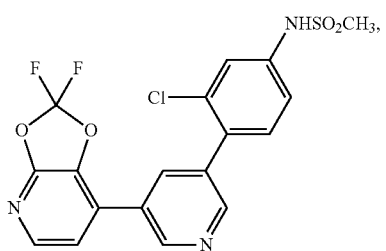
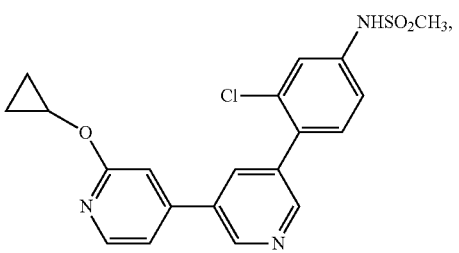

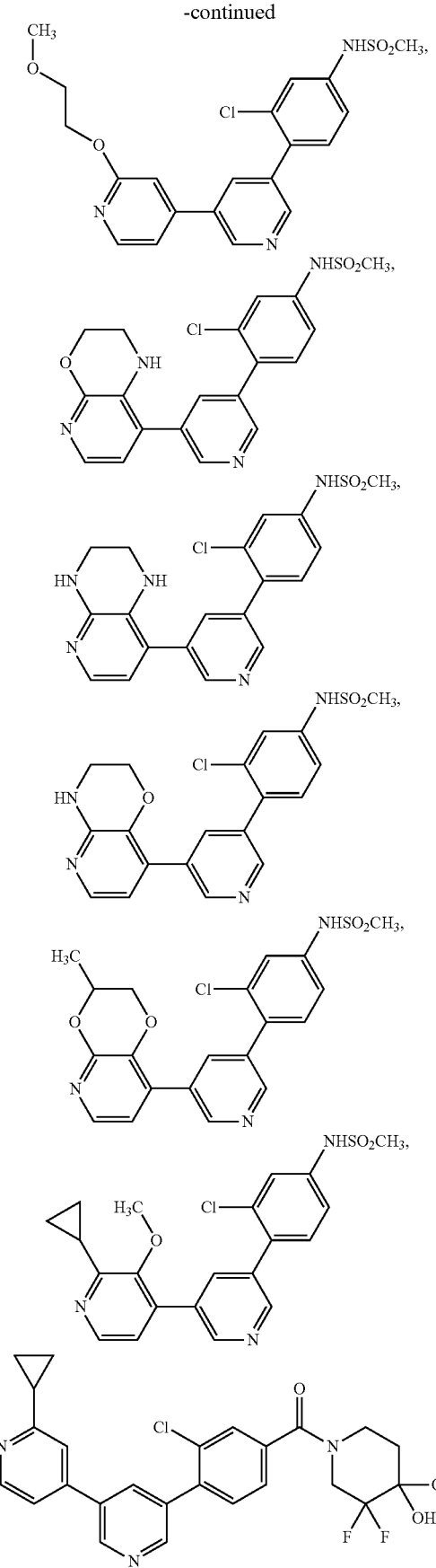
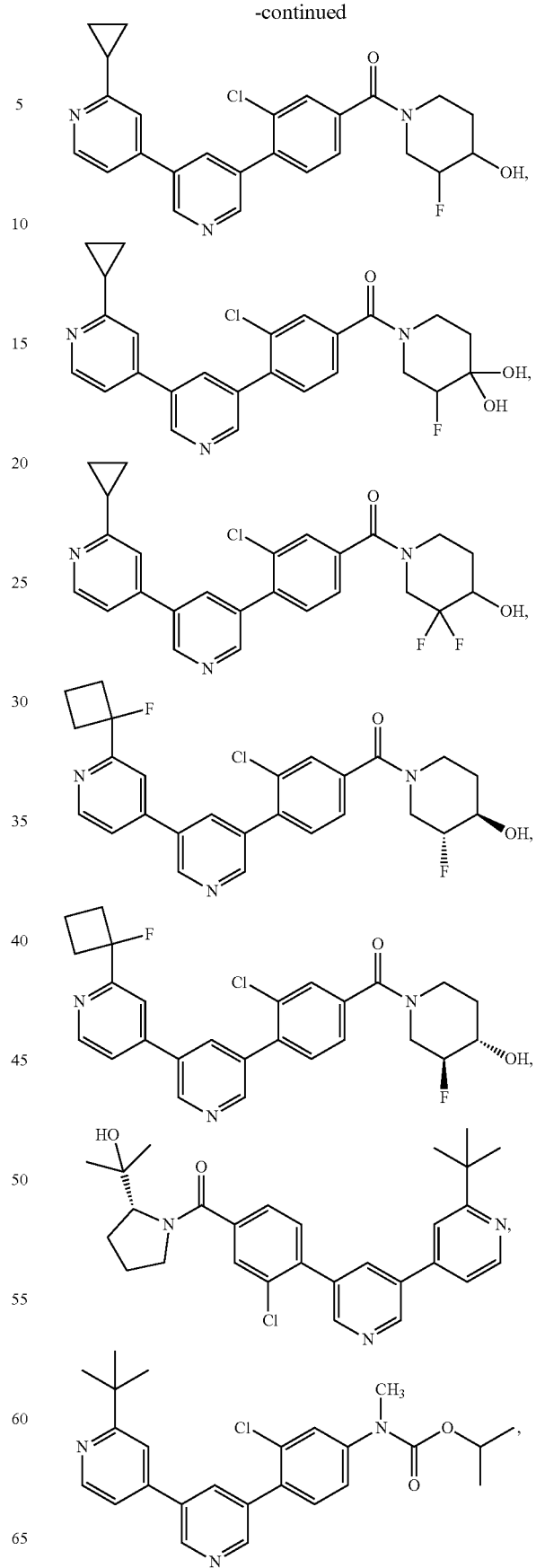

451
-continued
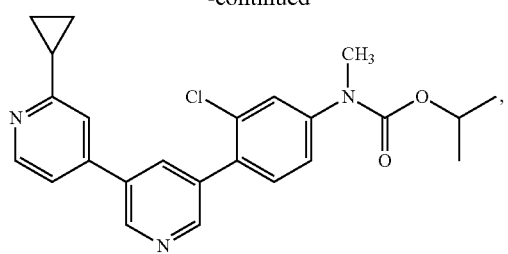
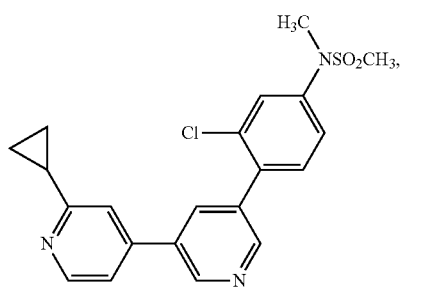
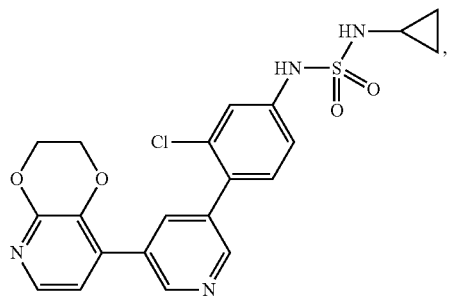
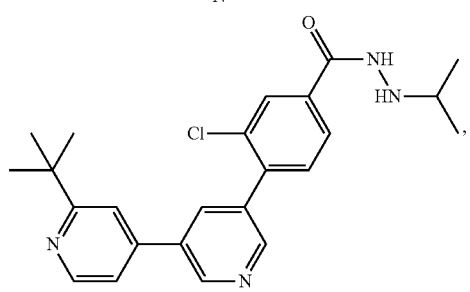
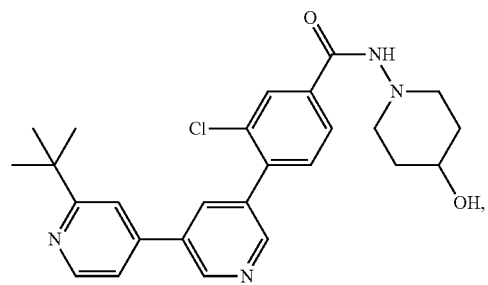
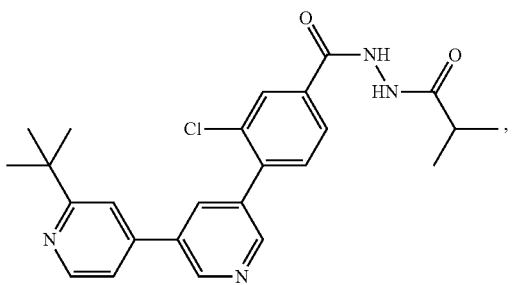
452
-continued
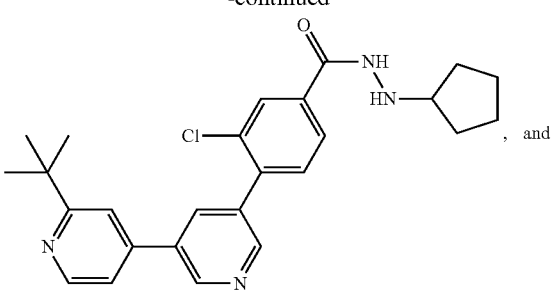
, and
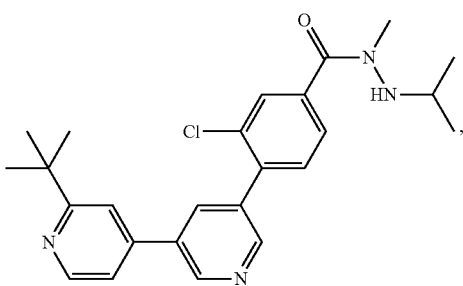
or a pharmaceutically acceptable salt, solvate, or isotope of any of the foregoing.
12. The compound of claim 1, selected from the group consisting of:
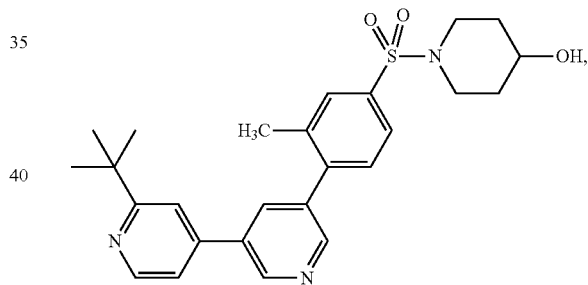
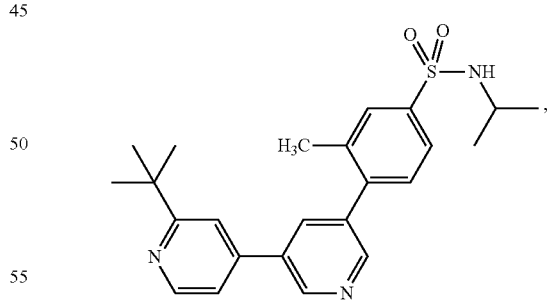
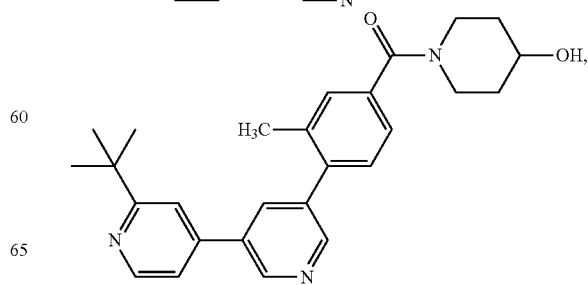

453
-continued
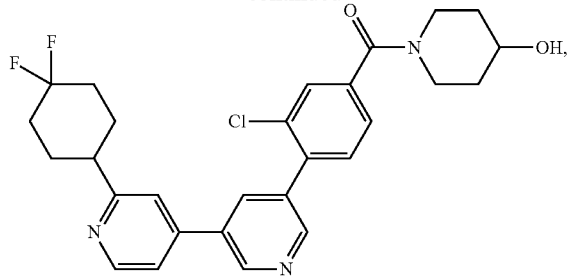
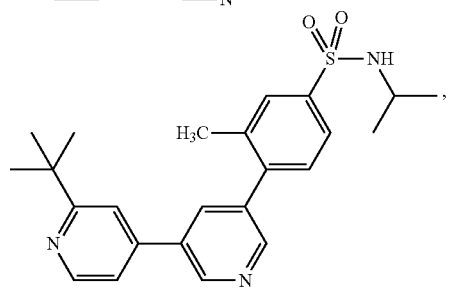
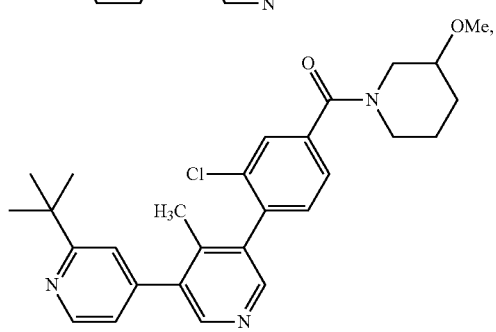
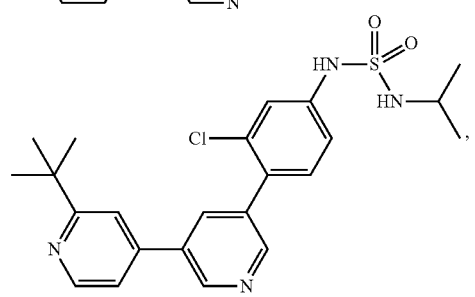
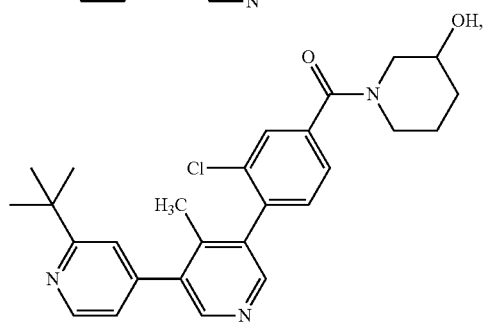
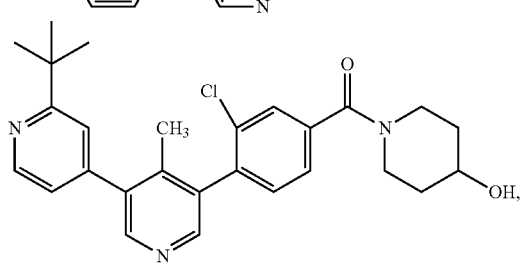
454
-continued
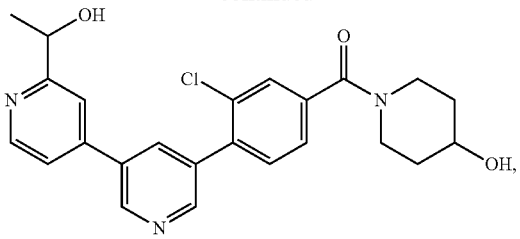
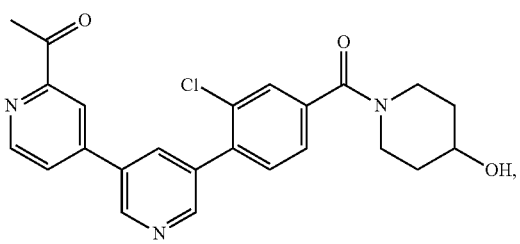
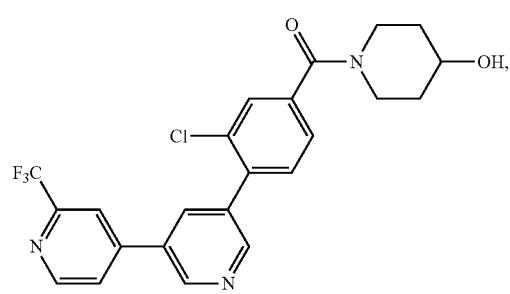
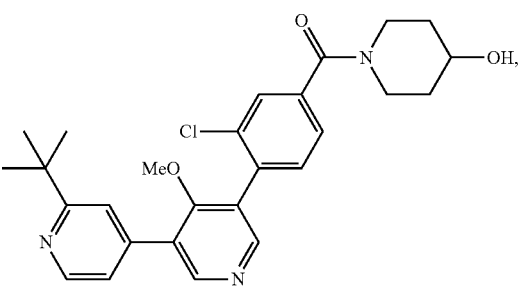
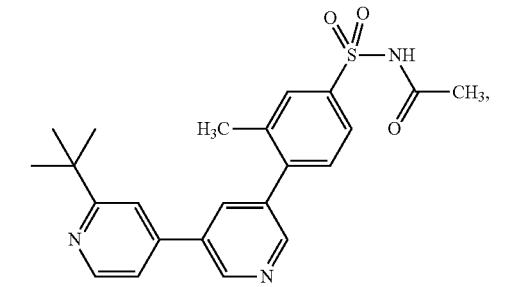
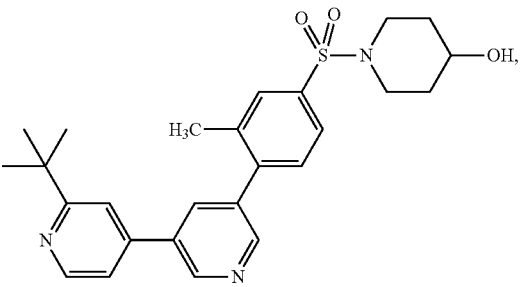

455
-continued
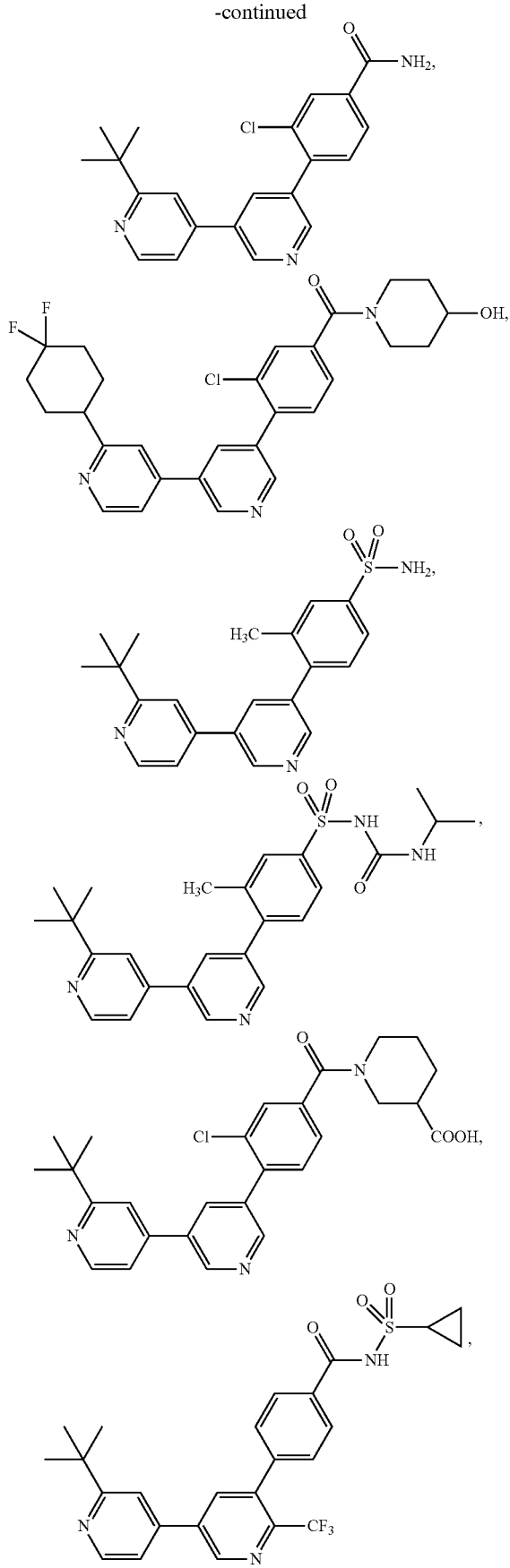
456
-continued
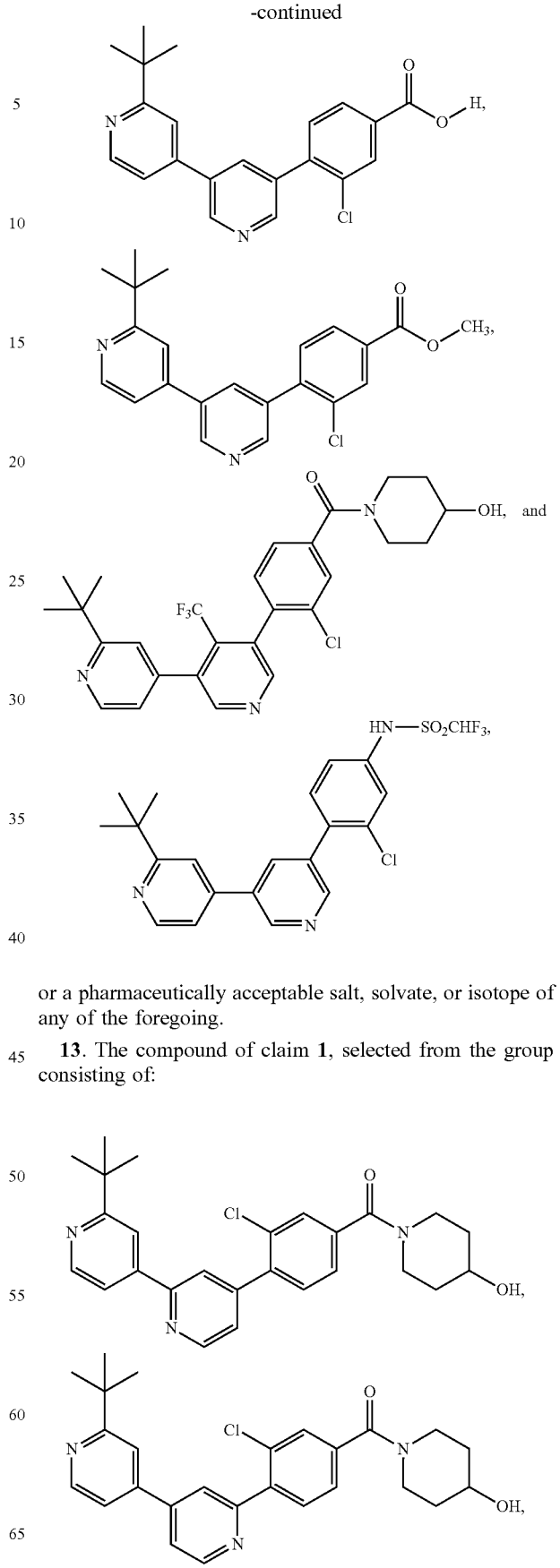
or a pharmaceutically acceptable salt, solvate, or isotope of any of the foregoing.
13. The compound of claim 1, selected from the group consisting of:

457
-continued
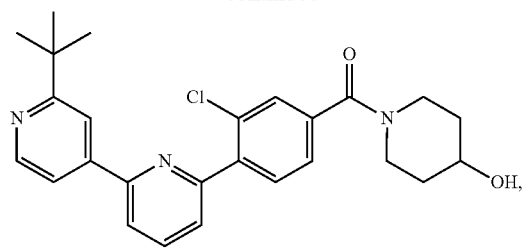
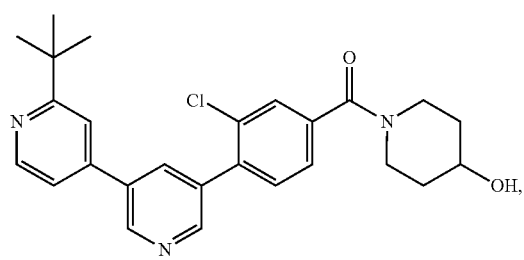
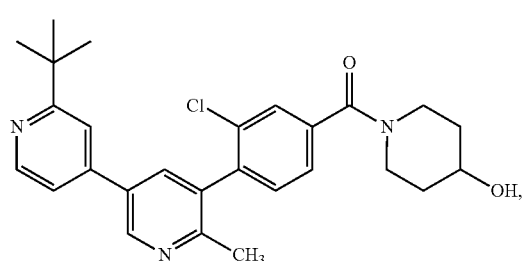
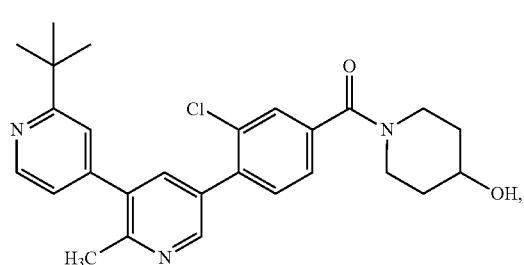
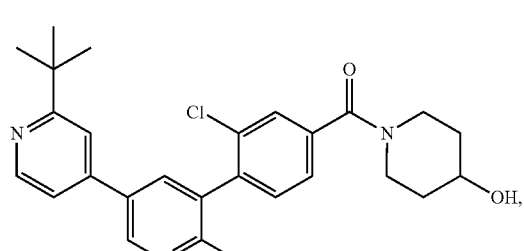
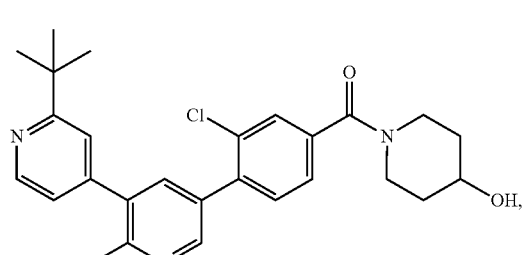
458
-continued
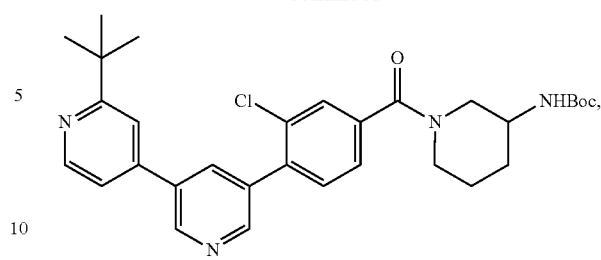
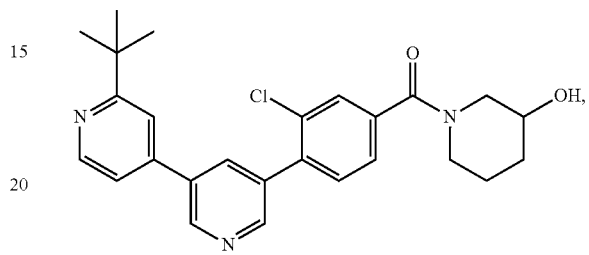
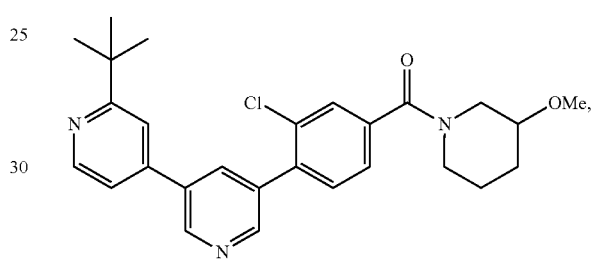
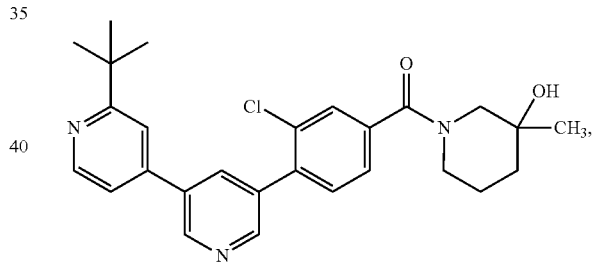
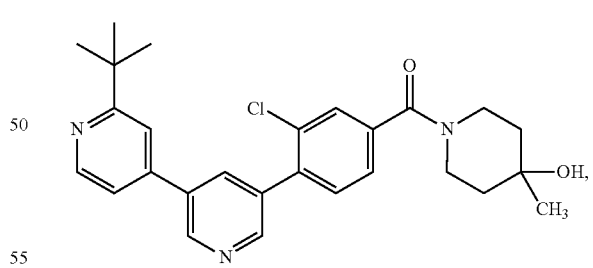
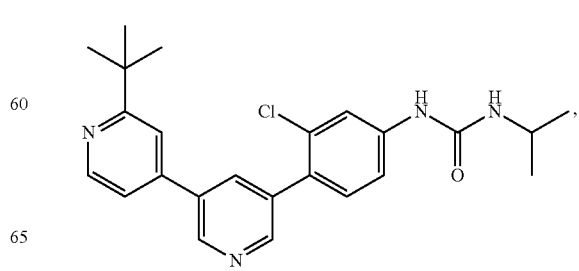

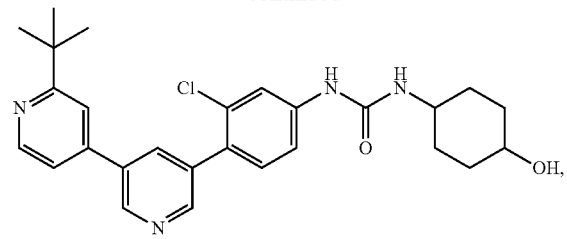
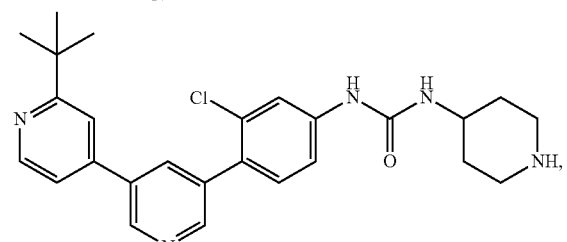
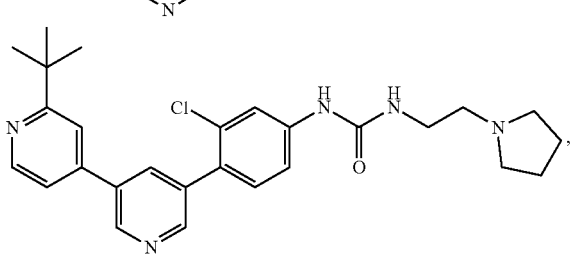
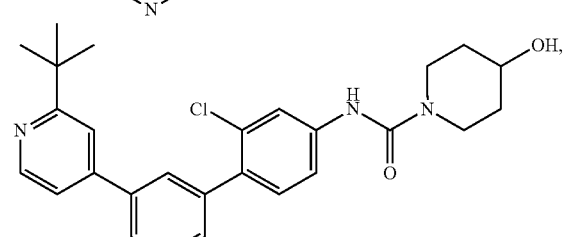
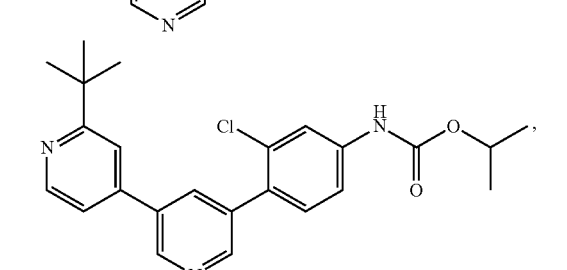
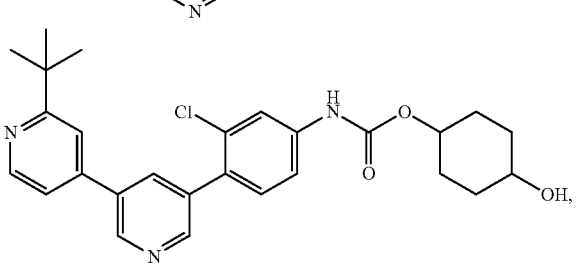
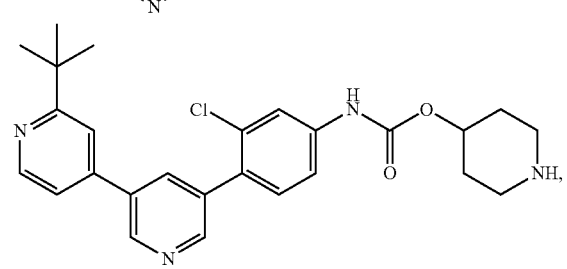
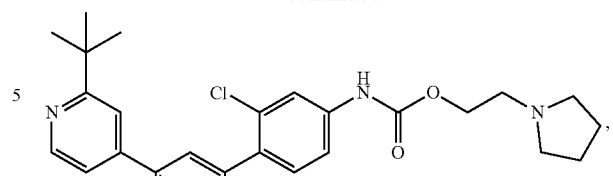
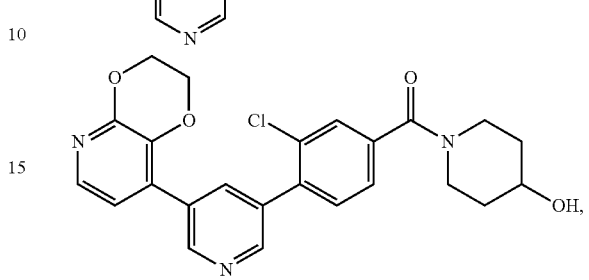
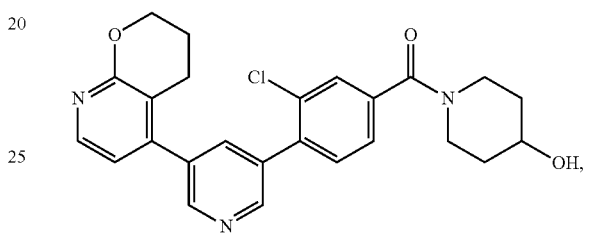
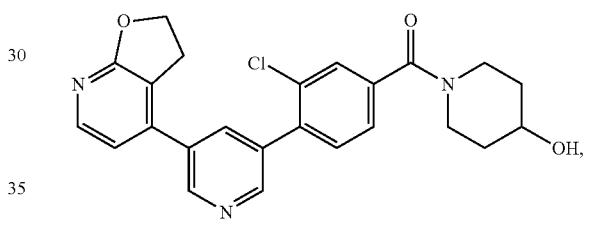
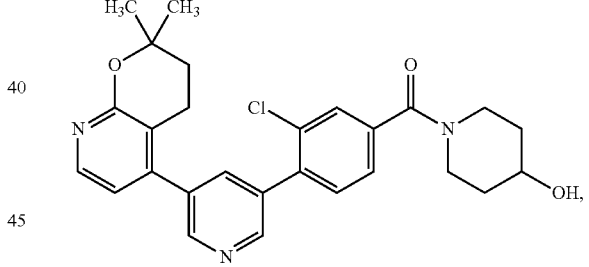
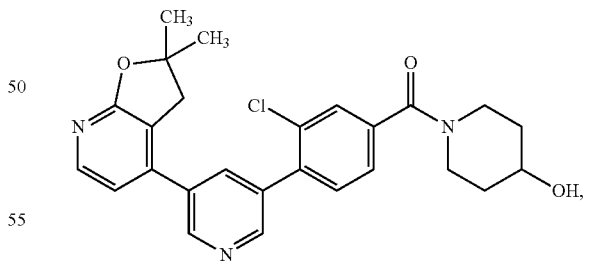
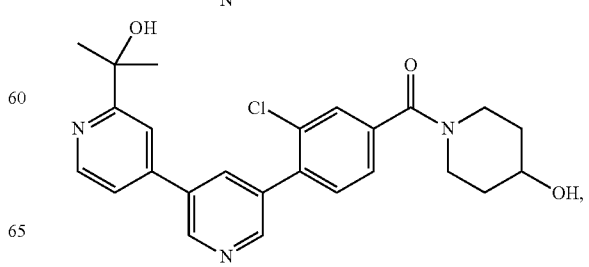

-continued
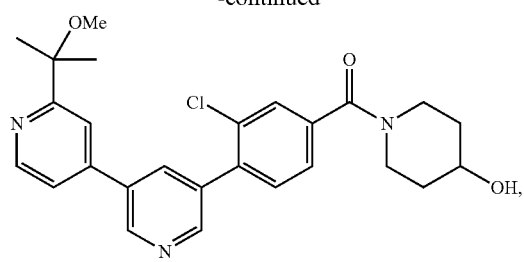
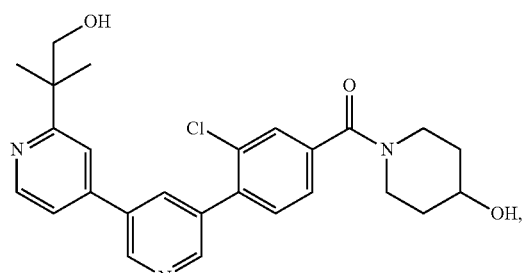
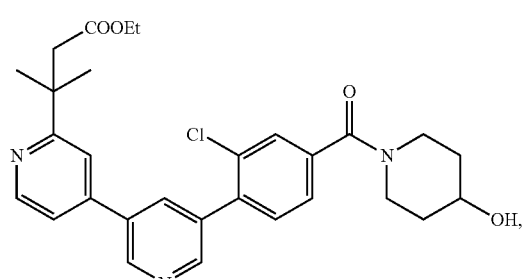
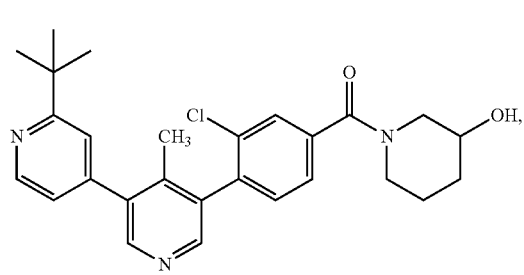
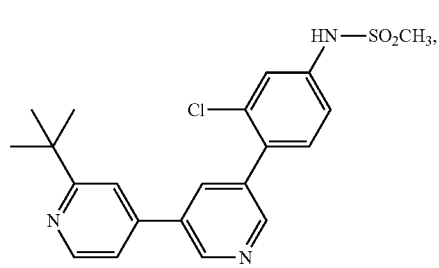
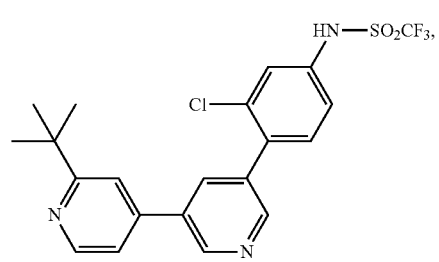
-continued
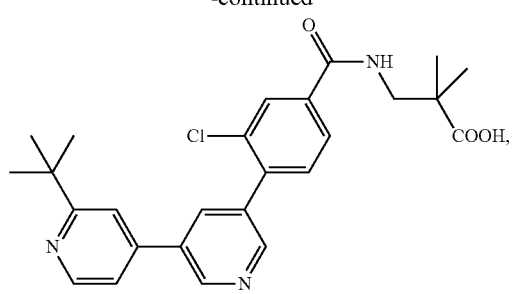
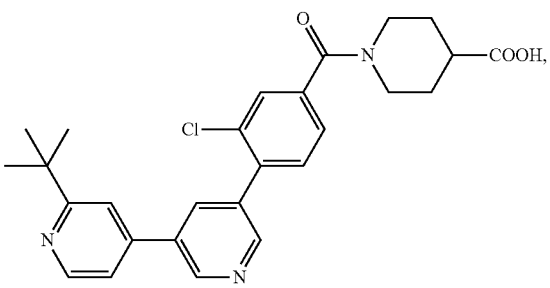
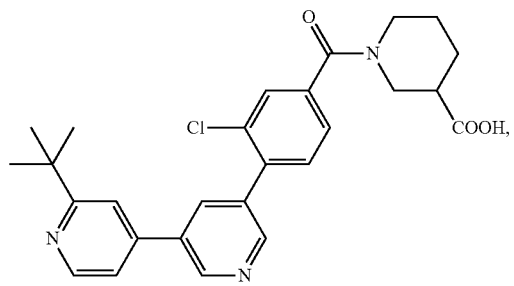
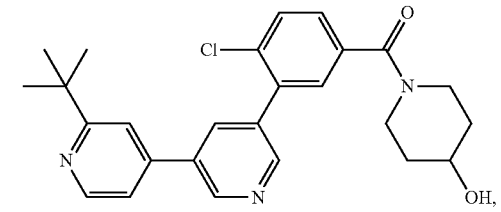
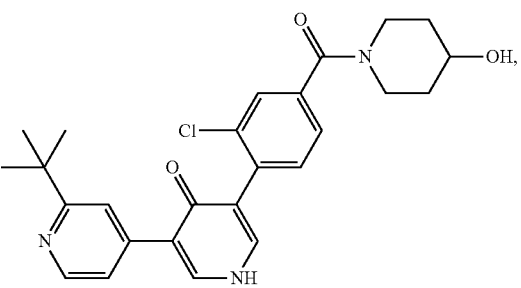
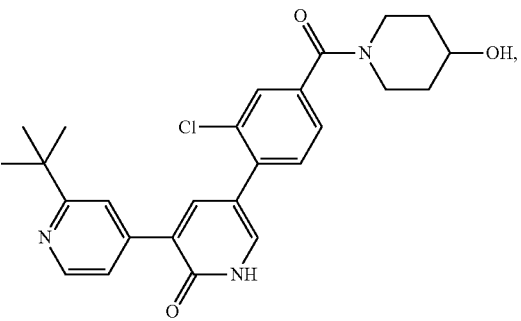

463
-continued
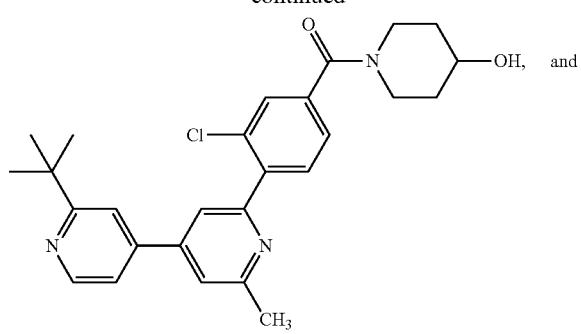
and
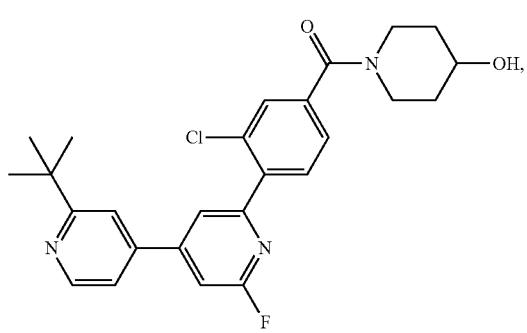 [SMILES: CC(C)(C)c1cc(-c2cc(F)nc(-c3ccc(C(=O)N4CCC(O)CC4)cc3Cl)c2)ccn1]
or a pharmaceutically acceptable salt, solvate, or isotope of any of the foregoing.
14. The compound of claim 1, selected from the group consisting of:
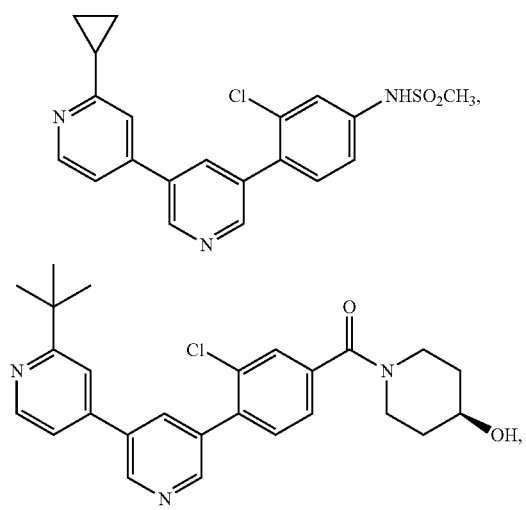
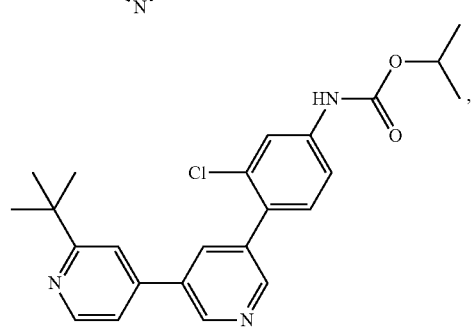
464
-continued
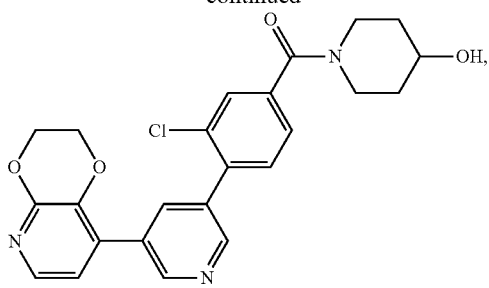
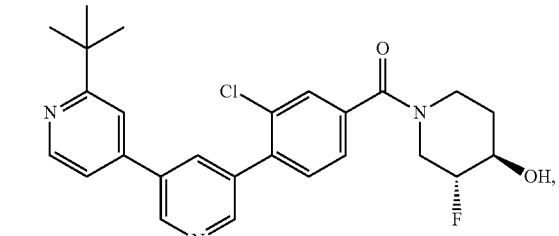
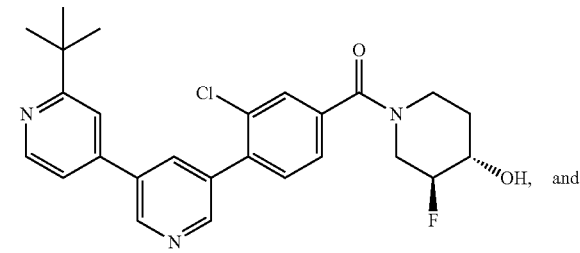
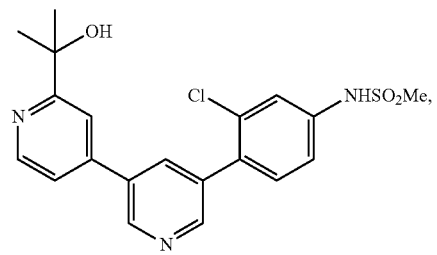
or a pharmaceutically acceptable salt, solvate, or isotope of any of the foregoing.

15. The compound of claim 1, which is

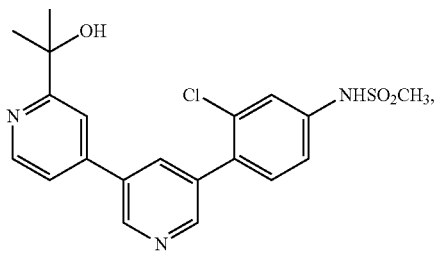

or a pharmaceutically acceptable salt, solvate, or isotope of any of the foregoing.

16. The compound of claim 1, which is

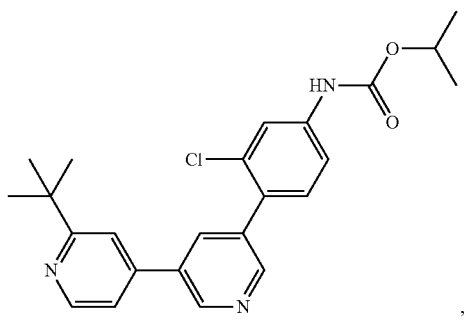 [SMILES: CC(C)OC(=O)Nc1ccc(-c2cncc(-c3ccnc(C(C)(C)C)c3)c2)c(Cl)c1]

or a pharmaceutically acceptable salt, solvate, or isotope of any of the foregoing.

17. A pharmaceutical composition, comprising the compound of claim 1, or a pharmaceutically acceptable salt, solvate, or isotope thereof, and a pharmaceutically acceptable excipient.

18. A method of inhibiting a sterol regulatory element-binding protein (SREBP), comprising contacting the SREBP or contacting an SREBP cleavage activating-protein (SCAP) with a compound of claim 1, or a pharmaceutically acceptable salt, solvate, or isotope thereof.

19. A method of inhibiting the proteolytic activation of a sterol regulatory element-binding protein (SREBP), comprising contacting an SREBP cleavage activating-protein (SCAP) with a compound of claim 1 or a pharmaceutically acceptable salt, solvate, or isotope thereof.

20. A method of treating a disorder in a subject in need thereof, wherein the disorder is Metabolic Syndrome, type 2 diabetes, obesity, liver disease, insulin resistance, adiposopathy, or dyslipidemia, endotoxic shock, systemic inflammation, atherosclerosis, non-alcoholic steatohepatitis (NASH), or a hyperproliferative disorder mediated by a sterol regulatory element-binding protein (SREBP), comprising administering to the subject in need thereof an effective amount of a compound of claim 1, or a pharmaceutically acceptable salt, solvate, or isotope thereof.

* * * * *